US011535835B1

(12) United States Patent
Oakes et al.

(10) Patent No.: US 11,535,835 B1
(45) Date of Patent: *Dec. 27, 2022

(54) COMPOSITIONS AND METHODS FOR THE TARGETING OF RHODOPSIN

(71) Applicant: Scribe Therapeutics Inc., Alameda, CA (US)

(72) Inventors: Benjamin Oakes, El Cerrito, CA (US); Hannah Spinner, Boston, MA (US); Sarah Denny, San Francisco, CA (US); Brett T. Staahl, Tiburon, CA (US); Kian Taylor, Atlanta, GA (US); Katherine Baney, Berkeley, CA (US); Isabel Colin, Oakland, CA (US); Maroof Adil, Davis, CA (US); Cole Urnes, Los Angeles, CA (US); Sean Higgins, Alameda, CA (US)

(73) Assignee: Scribe Therapeutics Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,681

(22) Filed: Sep. 23, 2021

Related U.S. Application Data

(63) Continuation of application No. PCT/US2020/063477, filed on Dec. 4, 2020.

(60) Provisional application No. 62/945,044, filed on Dec. 6, 2019.

(51) Int. Cl.
| | | |
|---|---|---|
| *C12N 9/22* | (2006.01) | |
| *C12N 15/11* | (2006.01) | |
| *A61K 48/00* | (2006.01) | |
| *A61P 27/02* | (2006.01) | |
| *A61K 38/00* | (2006.01) | |

(52) U.S. Cl.
CPC ............. *C12N 9/22* (2013.01); *A61K 48/005* (2013.01); *A61P 27/02* (2018.01); *C12N 15/11* (2013.01); *A61K 38/00* (2013.01); *C12N 2310/20* (2017.05)

(58) Field of Classification Search
CPC ....... C12N 9/22; C12N 2310/20; A61K 38/00
See application file for complete search history.

(56) References Cited

U.S. PATENT DOCUMENTS

| | | | |
|---|---|---|---|
| 5,173,414 A | 12/1992 | Lebkowski et al. | |
| 5,405,783 A | 4/1995 | Pirrung et al. | |
| 5,412,087 A | 5/1995 | Mcgall et al. | |
| 5,445,934 A | 8/1995 | Fodor et al. | |
| 5,695,937 A | 12/1997 | Kinzler et al. | |
| 2016/0324987 A1 | 11/2016 | Wang et al. | |
| 2017/0233756 A1 | 8/2017 | Begemann et al. | |
| 2017/0369870 A1 | 12/2017 | Gill et al. | |
| 2018/0250370 A1* | 9/2018 | Bartsevich ............. | C12N 15/52 |
| 2018/0258424 A1 | 9/2018 | Greenberg et al. | |
| 2019/0153440 A1 | 5/2019 | Kantardzhieva et al. | |
| 2019/0153441 A1* | 5/2019 | Kantardzhieva ..... | C12N 15/907 |
| 2022/0081681 A1 | 3/2022 | Oakes et al. | |

FOREIGN PATENT DOCUMENTS

| | | | |
|---|---|---|---|
| WO | WO-2010/075303 A1 | 7/2010 | |
| WO | WO-2012/068627 A1 | 5/2012 | |
| WO | WO-2016/191684 A1 | 12/2016 | |
| WO | WO-2017/068077 A1 | 4/2017 | |
| WO | WO-2017/147345 A1 | 8/2017 | |
| WO | WO-2017/176529 A1 | 10/2017 | |
| WO | WO-2018/009562 A1 | 1/2018 | |
| WO | WO-2018/064371 A1 | 4/2018 | |
| WO | WO-2018/195555 A1 | 10/2018 | |
| WO | WO-2019/102381 A1 | 5/2019 | |
| WO | WO-2019/183630 A2 | 9/2019 | |
| WO | WO-2020/023529 A1 | 1/2020 | |
| WO | WO-2020/041456 A1 | 2/2020 | |
| WO | WO-2020/247882 A1 | 12/2020 | |
| WO | WO-2020247882 A1 * | 12/2020 | ............... C12N 9/22 |
| WO | WO-2021/113763 A1 | 6/2021 | |
| WO | WO-2022/120095 A1 | 6/2022 | |

OTHER PUBLICATIONS

Yin et al. Partial DNA-guided Cas9 enables genome editing with reduced off-target activity. Nature Chemical Biology, vol. 14, pp. 311-316, p. 1/1 of Online Methods, and pp. 1/14-14/14 of Supplementary Information, Jan. 29, 2018. (Year: 2018).*

Moon et al. Improving CRISPR genome editing by engineering guide RNAs. Trends in Biotechnology, vol. 37, No. 8, pp. 870-881, Mar. 4, 2019. (Year: 2019).*

Giannelli et al. Human Molecular Genetics, vol. 27, No. 5, pp. 761-779, and pp. 1/13-13/13 of Supplementary Text and Figures, Dec. 21, 2017. (Year: 2017).*

Fowler et al. Measuring the activity of protein variants on a large scale using deep mutational scanning. Nature Protocols, vol. 9, No. 9, pp. 2267-2284, 2014. (Year: 2014).*

Aguilera, T.A. et al. (2009). "Systemic in vivo distribution of activatable cell penetrating peptides is superior to that of cell penetrating peptides," Integr. Biol. (Camb) 1(5-6):31-381.

Altschul, S.F. et al. (1990). "Basic local alignment search tool," J. Mol. Biol. 215:403-410.

Athanasiou, D. et al. (2018). "The molecular and cellular basis of rhodopsin retinitis pigmentosa reveals potential strategies for therapy," Prog. Retin. Eye Res. 62:1-23.

(Continued)

*Primary Examiner* — Jennifer Dunston
(74) *Attorney, Agent, or Firm* — Cooley LLP

(57) ABSTRACT

Provided herein are Class 2 Type V CRISPR:gNA systems comprising Class 2 Type V CRISPR polypeptides (e.g. CasX), guide nucleic acids (gNA), and optionally donor template nucleic acids useful in the modification of a RHO gene. The systems are also useful for introduction into cells, for example eukaryotic cells having mutations in the rhodopsin protein. Also provided are methods of using such systems to modify cells having such mutations and utility in methods of treatment of a subject with a RHO-related disease, such as retinitis pigmentosa.

26 Claims, 41 Drawing Sheets

Specification includes a Sequence Listing.

(56) References Cited

OTHER PUBLICATIONS

Burstein, D. et al. (2 017). "New CRISPR-Cas systems from uncultivated microbes," Nature 542:237-241.
Chadderton, N. et al. (2009), "Improved Retinal Function in a Mouse Model of Dominant Retinitis Pigmentosa Following AAV-delivered Gene Therapy," Mol. Ther. 17:593-599.
Chen, B. et al. (2003). "Influence of histidine on the stability and physical properties of a fully human antibody in aqueous and solid forms," Pharm. Res. 20:1952-1960.
Chinchore, Y. et al. (2009). "Accumulation of Rhodopsin in Late Endosomes Triggers Photoreceptor Cell Degeneration," PLoS Genetics 5:e1000377.
Dejneka, N.S. et al. (2001). "Gene therapy and retinitis pigmentosa: advances and future challenges," Bio Essays 23:662.
Dryja, T.P et al. (2000). "Novel Rhodopsin Mutations Gly114Val and Gln184Pro in Dominant Retinitis 33 Pigmentosa," Invest Opthalmol Vis Sci 41:3124.
Foust, K.D. et al. (2013). "Therapeutic AAV9-mediated suppression of mutant RHO slows disease progression and extends survival in models of inherited ALS," Mol Ther. 21:2148.
GenBank Accession No. NM_000539.2 (2008). *Homo sapiens* rhodopsin (opsin 2, rod pigment) 35 (retinitis pigmentosa 4, autosomal dominant) (RHO), mRNA, 3 total pages.
Ghiriando, R. et al. (1999). "Glycosylation of human IgG-Fc: influences on structure revealed by 36 differential scanning microcalorimetry," Immunol Letters 68:47-52.
Giannelli, S.G. et al. (2018). "Cas9/sgRNA selective targeting of the P23H Rhodopsin mutant allele for treating retinitis pigmentosa by intravitreal AAV9.PHP.B-based delivery," Human Mol. Genetics 27:761-779.
Goto, Y. et al. (1995). "Functional Abnormalities in Transfenic Mice Expressing a Mutant Rhodopsin Gene," Invest Opthalmol Vis Sci 36:62.
Hargrave, P.A. et al. (1992). "Rhodopsin and phototransduction: a model system for G protein-linked receptors," FASEB J. 6:2323.
Hermonat, P.L. et al. (1984), "Use of adeno-associated virus as a mammalian DNA cloning vector: 40 Transduction of neomycin resistance into mammalian tissue culture cells," PNAS 81:6466-6470.
HGNC: 10012 (2021). Gene Symbol Report. HGNC data for RHO, 4 total pages.
International Search Report dated May 7. 2021, for PCT Application No. PCT/US2020/063477, filed on Dec. 4, 2020, 7 pages.
Kotin, R.M. (1994). "Prospects for the use of adeno-associated virus as a vector for human gene 43 therapy," Human Gene Therapy 5:793-801.
Latella, M.C. et al. (2016). "In vivo Editing of the Human Mutant Rhodopsin Gene by Electroporation of Plasmid-based CRISPR/Cas9 in the Mouse Retina," Mol. Ther.—Nucl. Acids 5:0389, 12 total pages.
Li, P. et al. (2018). "Allele-Specific CRISPR-Cas9 Genome Editing of the Single-Base P23H Mutation for Rhodopsin-Associated Dominant Retinitis Pigmentosa," The CRISPR Journal 1:55-64.
Liu, J-J. et al. (2019). "CasX enzymes comprise a distinct family of RNA-guided genome editors," Nature 566:218-223.
Liu, X. et al. (1996). "Structure and function in rhodopsin: Correct folding and misfolding in two point mutants in the intradiscai domain of rhodopsin identified in retinitis pigmentosa," PNAS 93:4554.
Murray, A. et al. (2002). "Epitope Affinity Chromatography and Biophysical Studies of Monoclonal Antibodies and Recombinant Antibody Fragments," J. Chromatogr Sci 40:343-349.

Nathans, J. et al., (1986). "Molecular genetics of inherited variation in human color vision," Science 232:203.
Nathans, J. et al. (1984). "Isolation and nucleotide sequence of the gene encoding 50 human rhodopsin," PNAS 81:4851.
Noguchi, H. et al. (2003). "PDX-1 protein containing its own antennapedia-like protein transduction domain can transduce pancreatic duct and islet cells," Diabetes 52:1732-1737.
Olsson, J.E et al., (1992). "Transgenic Mice with a Rhodopsin Mutation (Pro23His): A Mouse Model of Autosomal Dominant Retinitis Pigmentosa," Neuron 9:815-830.
Phillips, M.J. et al. (2014). "Modeling Human Retinal Development with Patient-Specific induced Pluripotent Stem Cells Reveals Multiple Roles for Visual System Homeobox 2," Stem Cells 32:1480-1492.
Sakami, S. et al. (2011). "Probing mechanisms of photoreceptor degeneration in a new mouse model of the common form of autosomal dominant retinitis pigmentosa due to P23H opsin mutations," J. Biol. Chem. 286:10551-10567.
Samulski, R.J. et al., (1989). "Helper-Free Stocks of Recombinant Adeno-Associated Viruses: Normal Integration Does Not Require Viral Gene Expression," J. Virol. 63:03822-3828.
Smith, T.F. et al. (1981). "Comparison of biosequences," Adv. Apol. Math. 2:482-489.
Trapani, I. et al. (2018). "Seeing the Light after 25 Years of Retinal Gene Therapy," Trends in Mol. Med. 24:669-681.
Tratschin, J-D. et al. (1985). "Adeno-Associated Virus Vector for High-Frequency Integration, 58, Expression, and Rescue of Genes in Mammalian Cells," Mol. Cell. Biol. 5:3251-3260.
Tratschin, J-D. et al. (1984). "A Human Parvovirus, Adeno-Associated Virus, as a Eucaryotic Vector: Transient Expression and Encapsidation of the Procaryotic Gene for Chloramphenicol Acetyltransferase," Mol. Cell. Biol. 4:2072-2081.
Tréhin, R. et al. (2004). "Cellular uptake but iow permeation of human calcitonin-derived cell penetrating peptides and Tat(47-57) through well-differentiated epithelial models," Pharm. Res. 21:1248-1256.
Tucker, B.A. et al. (2011). "Transplantation of Adult Mouse iPS Cell-Derived Photoreceptor Precursors 61 Restores Retinal Structure and Function in Degenerative Mice," PLoS One 6:e18992.
Wender, P.A. et al. (2000). "The design, synthesis, and evaluation of molecules that enable or 82 enhance cellular uptake: peptoid molecular transporters," PNAS 97:13003-13008.
Written Opinion of the International Searching Authority dated May 7, 2021, for PCT Application Number PCT/US2020/063477, filed on Dec. 4, 2020, 12 pages.
Zender, L. et al. (Jun. 2002). "VP22-mediated intercellular transport of p53 in hepatoma cells in vitro and in vivo," Cancer Gene Ther. 9:489-496.
Zhang, J. et al. (Jun. 1997). "PowerBLAST: a new network BLAST application for interactive or automated sequence analysis and annotation," Genome Res. 7:649-656.
Zhong, X. et al. (2014). "Generation of three-dimensional retinal tissue with functional photoreceptors from human IPSCs," Nat. Commun. 5:4047.
Liu, J.J. et al. CasX enzymes comprise a distinct family of RNA-guided genome editors, Nature 568:E8-E10. (Author correction: published online Apr. 3, 2019).
Qi, L.S. et al. (Feb. 2013). "Repurposing CRISPR as an RNA-guided platform for sequencespecific control of gene expression," Cell 152:1173-1183.
Yang, H. et al. (May 2019). "CasX: a new and small CRISPR gene-editing protein, " Cell Res. 29:345-346. Published online Apr. 16, 2019.

* cited by examiner

COMPOSITIONS AND METHODS FOR THE TARGETING OF RHODOPSIN

CROSS REFERENCE TO RELATED APPLICATIONS

This application is a continuation of International Patent Application No. PCT/US2020/063477, filed on Dec. 4, 2020, which claims priority to and the benefit of U.S. Provisional Patent Application No. 62/945,044, filed on Dec. 6, 2019, the contents of each of which are incorporated herein by reference in their entirety.

INCORPORATION BY REFERENCE OF SEQUENCE LISTING

This application contains a Sequence Listing which has been submitted in ASCII format via EFS-WEB and is hereby incorporated by reference in its entirety. Said ASCII copy, created on Jul. 26, 2022 is named SCRB_018_01US_2ndSubSeqList_ST25.txt and is 6.70 MB in size.

BACKGROUND

Retinitis pigmentosa (RP) is a progressive neurodegenerative disorder, which affects 1 in 3,000 individuals (Chinchore, Y. et al. Accumulation of Rhodopsin in Late Endosomes Triggers Photoreceptor Cell Degeneration. PLoS Genetics. 5(2): e1000377 (2009)). The disorder begins with death of rod photoreceptor cells, which are the only cells in the retina to express rhodopsin. The loss of rod photoreceptor cells in the retina eventually leads to loss of cone cells; the mainstay of human vision.

Rhodopsin is the visual pigment of photoreceptors in retinal rods. Rhodopsin is a G-coupled receptor, which comprises almost 50% of the total protein content of rod outer segments and 80% of that of discs (Hargrave P A, et al. Rhodopsin and phototransduction: a model system for G protein-linked receptors. FASEB J. 6(6):2323 (1992)). Rhodopsin, which has 348-amino acids with 7 transmembrane domains, a luminal N-terminus and a cytoplasmic C-terminus, mediates vision in dim light and absorbs maximally at 495 nm. (Nathans, J., et al. Molecular genetics of inherited variation in human color vision. Science 232: 203 (1986)). Over 150 distinct mutations in the light-sensing molecule rhodopsin are known to cause autosomal dominant retinitis pigmentosa (adRP) and most are missense mutations affecting single amino acid residues in the rhodopsin protein (Athanasiou, D., et al. The molecular and cellular basis of rhodopsin retinitis pigmentosa reveals potential strategies for therapy. Prog Retin Eye Res. 62; 1 (2018)). Mutations in rhodopsin are also associated with dominant congenital stationary night blindness (adCSNB) and, less frequently, recessive RP (arRP). Recessive RP is usually associated with loss of rhodopsin function, whereas the dominant conditions are a consequence of gain of function and/or dominant negative activity. Several of these mutations are listed in Table 3. These mutations affect rhodopsin transport to the outer segments of rod photoreceptor cells, rhodopsin folding, and rhodopsin endocytosis. Mutations in the human rhodopsin that affect its folding, trafficking and activity are the most commonly encountered causes of retinal degeneration in patients afflicted with RP. Due to their improper folding, class II mutants are labeled with ubiquitin and are destined for degradation by the ubiquitin proteasome system (UPS). Because of the large protein load, the degradation machinery is overwhelmed, which results in a failure to clear other misfolded proteins and leads to cell toxicity. A single base-substitution mutation in position 23 of the rhodopsin gene (RHO), in which proline is changed to histidine (Pro23His or P23H), accounts for 25% to 40% of all cases of adRP in North America (Dejneka N S, Bennett J. Gene therapy and retinitis pigmentosa: advances and future challenges. BioEssays. 23:662 (2001)).

The advent of CRISPR/Cas systems and the programmable nature of these systems has facilitated their use as a versatile technology for genomic manipulation and engineering. Particular CRISPR proteins are particularly well suited for such manipulation. For example CasX, has a compact size, offering ease of delivery, and the nucleotide sequence encoding the protein is relatively short, an advantage for its incorporation into viral vectors for delivery into a cell.

As the treatment options for RP remain inadequate, there is a critical need for developing safe and permanent treatments for this disorder. Provided herein are compositions and methods for targeting rhodopsin mutations to the address this need.

SUMMARY

The present disclosure provides compositions of modified Class 2, Type V CRISPR proteins and guide nucleic acids used in the editing of rhodopsin (RHO) gene target nucleic acid sequences having one or more mutations. The Class 2, Type V CRISPR proteins and guide nucleic acids can be modified for passive entry into target cells. The Class 2, Type V CRISPR proteins and guide nucleic acids are useful in a variety of methods for target nucleic acid modification, which methods are also provided.

In one aspect, the present disclosure relates to Class 2 Type V CRISPR protein and guide nucleic acid systems (e.g. CasX:gNA system) and methods used to alter a target nucleic acid comprising the RHO gene in cells. In some embodiments of the disclosure, the system has utility in modifying RHO target nucleic acid sequence in a population of cells to correct or compensate for the one or more mutations of the RHO gene in the cells of the population, including, but not limited to the mutations of Table 4A. In other embodiments, the system has utility in modifying RHO target nucleic acid sequence in a subject.

In some embodiments, the Class 2 Type V:gNA system gNA is a gRNA, or a gDNA, or a chimera of RNA and DNA, and may be a single-molecule gNA or a dual-molecule gNA. In other embodiments, the system gNA has a targeting sequence complementary to a target nucleic acid sequence comprising a region within the RHO gene or that comprises a sequence having at least about 50%, at least about 60%, at least about 70%, at least about 80%, at least about 85%, at least about 90%, or at least about 95%, or 100% sequence identity to a sequence selected from the group consisting of SEQ ID NOS:328-346, 367-376, 382-2100 and 2286-27274. In some embodiments the gNA has a targeting sequence consisting of a sequence selected from the group consisting of SEQ ID NOS: 328-346, 367-376, 382-2100 and 2286-27274. In some embodiments, the targeting sequence of the gNA is complementary to a sequence within or proximal to an exon of exons 1 to 5 of the RHO gene. In another embodiment, the targeting sequence of the gNA is complementary to a sequence within or proximal to an intron of the RHO gene. In another embodiment, the targeting sequence of the gNA is complementary to a sequence within or proximal to an intron-exon junction of the RHO gene. In another embodiment, the targeting sequence of the gNA is complementary to a sequence within or proximal to a regulatory element of the RHO gene. In another embodiment, the targeting sequence of the gNA is complementary to a sequence within or proximal to an intergenic region of the RHO gene. The gNA can comprise a targeting sequence comprising 14 to 30 consecutive nucleotides. In other embodiments, the targeting sequence of the gNA consists of 20 nucleotides. In other embodiments, the targeting sequence consists of 19 nucleotides. In other embodiments, the targeting sequence consists of 18 nucleotides. In other embodiments, the targeting sequence consists of 17 nucleotides. In other embodiments, the targeting sequence consists of 16 nucleotides. In other embodiments, the targeting sequence consists of 15 nucleotides. In a particular embodiment, the targeting sequence comprises a sequence of AAGUGGCUGCGUACCACACC (SEQ ID NO: 382).

In some embodiments, the gNA has a scaffold comprising a sequence selected from the group consisting of sequences of SEQ ID NOS; 4-16, or a sequence having at least about 50%, at least about 60%, at least about 70%, at least about 80%, at least about 90%, at least about 95%, at least about 96%, at least about 97%, at least about 98%, or at least about 99% sequence identity thereto. In other embodiments, the CasX:gNA system gNA variant has a scaffold comprising a sequence selected from the group consisting of sequences of SEQ ID NOS: 2201-2285, or a sequence having at least about 50%, at least about 60%, at least about 70%, at least about 80%, at least about 90%, at least about 95%, at least about 96%, at least about 97%, at least about 98%, at least about 99% sequence identity thereto. In some embodiments, the CasX:gNA system gNA variant has a scaffold consisting of a sequence selected from the group consisting of sequences of SEQ ID NOS: 2201-2285.

In some embodiments, the Class 2 Type V CRISPR protein comprises a reference CasX sequence comprising any one of SEQ ID NOS: 1-3 or a CasX variant sequence SEQ ID NOS: 49-160, 237-239, 243-246, 251-263 or 273-281 as set forth in Tables 3, 6, 7, 8, and 10, or a sequence having at least about 50%, at least about 60%, at least about 70%, at least about 80%, or at least about 90%, or at least about 95%, or at least about 96%, or at least about 97%, or at least about 98%, or at least about 99% sequence identity thereto. In these embodiments, a CasX variant exhibits one or more improved characteristics relative to the reference CasX protein. In some embodiments, the CasX protein has binding affinity for a protospacer adjacent motif (PAM) sequence selected from the group consisting of TTC, ATC, GTC, and CTC. In some embodiments, the CasX protein has binding affinity for the PAM sequence that is at least 1.5-fold greater compared to the binding affinity of any one of the CasX proteins of SEQ ID NOS: 1-3 for the PAM sequences selected from the group consisting of TTC, ATC, GTC, and CTC.

In some embodiments of the Class 2 Type V CRISPR: gNA system, the CRISPR molecule and the gNA molecule are associated together in a ribonuclear protein complex (RNP). In a particular embodiment, the RNP comprising a CasX variant and the gNA variant exhibits greater editing efficiency and/or binding of a target sequence in the target DNA when any one of the PAM sequences TTC, ATC, GTC, or CTC is located 1 nucleotide 5' to the non-target strand sequence having identity with the targeting sequence of the gNA in a cellular assay system compared to the editing efficiency and/or binding of an RNP comprising a reference CasX protein and a reference gNA in a comparable assay system.

In some embodiments, the system further comprises a donor template comprising a nucleic acid comprising at least a portion of a wild-type RHO gene sequence, wherein the RHO gene portion is selected from the group consisting of a RHO exon, a RHO intron, a RHO intron-exon junction, a RHO regulatory element, or combinations thereof, wherein the donor template is inserted by homology-directed repair (HDR) or homology-independent targeted integration (HITI) to correct or compensate for the mutation in the RHO gene, such that a functional rhodopsin protein can be expressed. In other embodiments, the donor template comprises a nucleic acid sequence having one or more mutations relative to the wild-type RHO gene sequence such that, upon insertion, the RHO gene is knocked-down or knocked-out. In some cases the donor sequence is a single-stranded DNA template or a single stranded RNA template. In other cases, the donor template is a double-stranded DNA template.

In another aspect, the disclosure relates to nucleic acids encoding the systems of any of the embodiments described herein, as well as vectors comprising the nucleic acids. In some embodiments, the vector is selected from the group consisting of a retroviral vector, a lentiviral vector, an adenoviral vector, an adeno-associated viral (AAV) vector, a herpes simplex virus (HSV) vector, a plasmid, a minicircle, a nanoplasmid, and an RNA vector. In other embodiments, the vector is a virus-like particle (VLP) comprising one or more components of a gag polyprotein and an RNP of a CasX and gNA of any of the embodiments described herein and, optionally, a donor template nucleic acid.

In another aspect, the disclosure provides a method of modifying a RHO target nucleic acid sequence in a population of cells, wherein said method comprises introducing into the cells of the population: a) a composition comprising the Class 2 Type V:gNA system of any of the embodiments disclosed herein; b) the nucleic acid of any of the embodiments disclosed herein; c) the vector of any of the embodiments disclosed herein; d) the VLP of any of the embodiments disclosed herein; or e) a combination of two or more of the foregoing wherein the RHO target nucleic acid sequence of the cells targeted by the first gNA is modified by the Class 2 Type V CRISPR protein (e.g. CasX). In some embodiments of the method, the method comprises introducing into the cells of the population a second gNA or a nucleic acid encoding the second gNA, wherein the second gNA has a targeting sequence complementary to a different or overlapping portion of the RHO target nucleic acid compared to the first gNA, resulting in an additional break in the RHO target nucleic acid of the cells of the population. In some embodiments of the method, the modifying comprises introducing an insertion, deletion, substitution, duplication, or inversion of one or more nucleotides in the target nucleic acid sequence as compared to the genomic sequence, wherein the modifying results in a correction of or compensation for the mutation of the RHO gene in the cells of the population. As used herein, "compensation" means that the sequence of the target nucleic acid is modified such that, while not being identical to a wild-type genomic sequence, a functional rhodopsin protein is nevertheless able to be expressed from the modified gene. In some cases, the method further comprises contacting the target nucleic acid with a donor template nucleic acid of any of the embodiments disclosed herein, wherein insertion of the donor template results in a correction of the RHO gene in the cells of the population such that a functional rhodopsin protein is expressed in the cells of the population. In some cases, the modification results in expression of a functional rhodopsin protein that is increased by at least about 10%, at least about 20%, at least about 30%, at least about 40%, at least about 50%, at least about 60%, at least about 70%, at least about 80%, or at least about 90% in comparison to a cell where the RHO gene has not been modified. The cells of the population to be modified by the methods of the embodiments are eukaryotic. In some embodiments of the method, the eukaryotic cells for modification are selected from the group consisting of rodent cells, mouse cells, rat cells, and non-human primate cells. In other embodiments of the method, the eukaryotic cells for modification are human cells. In some embodiments of the method, the eukaryotic cells for modification are selected from the group consisting of a rod photoreceptor cell, a retinal progenitor cell, a pluripotent stem cell (iPSC), fibroblasts, and Müller glial cells. In some embodiments of the method, the modifying of the RHO gene target nucleic acid sequence of the population of cells occurs in vitro or ex vivo. The present disclosure provided populations of such cells modified by the foregoing methods. In one embodiment, the modified cells of the population can be administered to one or both eyes of the subject having a RHO-related disease, using a therapeutically effective amount of the cells. In other embodiments of the method, the modifying of the RHO gene target nucleic acid sequence of the population of cells occurs in vivo in a subject, wherein the subject is selected from the group consisting of a rodent, a mouse, a rat, a non-human primate, and a human.

In other embodiments, the present disclosure provides methods of treating a RHO-related disease (e.g., retinitis pigmentosa) in a subject in need thereof, comprising modifying a RHO gene having one or more mutations in eye retinal cells of the subject, the modifying comprising contacting said cells with a therapeutically effective dose of: i) a composition comprising a CasX and gNA of any of the embodiments disclosed herein and, optionally, a donor template; ii) a nucleic acid encoding the composition of (i); a vector selected from the group consisting of a retroviral vector, a lentiviral vector, an adenoviral vector, an adeno-associated viral (AAV) vector, a herpes simplex virus (HSV) vector, a plasmid, a minicircle, a nanoplasmid, a DNA vector, and an RNA vector, and comprising a nucleic acid of (ii); iii) a VLP comprising the composition of (i); or iv) combinations of two or more of (i)-(iii), wherein the RHO gene of the cells targeted by the first gNA is modified by the CasX protein (and, optionally, the donor template) such that the mutation of the RHO gene is corrected or compensated for and a functional rhodopsin protein is expressed. In other embodiments of the method of treating a RHO-related disease in a subject, the RHO gene is knocked-down or knocked-out such that the expression of non-functional rhodopsin protein is reduced or eliminated. In some embodiments, the subject is selected from the group consisting of a rodent, a mouse, a rat, a non-human primate, and a human. In some embodiments, the therapeutically effective dose is administered to the subject by a route of administration selected from intraocular, intravitreal, subretinal, or suprachoroidal injection or implantation, or combinations thereof. In some embodiments, the method results in improvement in one or more clinically-relevant endpoints selected from the group consisting of mean change or mean rate of change in: 1) best corrected visual acuity (BCVA); 2) visual field sensitivity (including analysis of hill of vision volumes); 3) retinal sensitivity measured by full-field stimulus testing (FST); 4) multiluminance mobility tests; 5) electrophysiological measures of retinal function; 6) optical coherence tomography (OCT) documenting the rate of photoreceptor loss; and 7) hypo- or hyperfluorescent lesion size on fundus autofluorescence; 8) color vision; 9) contrast sensitivity; 10) gaze tracking; 11) light aversion; 12) macular sensitivity.

In another aspect, the present disclosure provides kits comprising the nucleic acids, vectors, Class 2 Type V CRISPR proteins, gNAs and gene editing pairs described herein.

In another aspect, provided herein are compositions comprising gene editing pairs, or compositions of vectors comprising or encoding gene editing pairs for use as a medicament for the treatment of a subject having a RHO-related disease.

In another aspect, provided herein are Class 2 Type V CRISPR:gNA systems, compositions comprising Class 2 Type V CRISPR:gNA systems, vectors comprising or encoding Class 2 Type V CRISPR:gNA systems, VLP comprising Class 2 Type V CRISPR:gNA systems, or populations of cells edited using the Class 2 Type V CRISPR:gNA systems for use as a medicament for the treatment of a RHO-related disease.

In another aspect, provided herein are Class 2 Type V CRISPR:gNA systems, composition comprising Class 2 Type V CRISPR:gNA systems, or vectors comprising or encoding Class 2 Type V CRISPR:gNA systems, VLP comprising Class 2 Type V CRISPR:gNA systems, populations of cells edited using the Class 2 Type V CRISPR:gNA systems, for use in a method of treatment of a RHO-related disease in a subject in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. The contents of PCT/US2020/036505, filed on Jun. 5, 2020, and the contents of U.S. Provisional Patent Application No. 63/121,196, filed on Dec. 3, 2020, both which disclose CasX variants and gNA variants, are hereby incorporated by reference in their entireties.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 26 shows the improvement in editing efficiency of a CasX sgRNA variant of SEQ ID NO:5 versus the reference of SEQ ID NO:4 across 10 targets. When averaged across 10 targets, the editing efficiency of sgRNA SEQ ID NO:5 improved 176% compared to SEQ ID NO:4.

FIG. 41 *a-c*) to visualized retinal layers and stained with HA-tag (bottom row, FIG. 41 *d-f*) antibody to detect CasX expression in photoreceptors (ONL) and other retinal layers (INL;GCL). Legends: ONL=Outer nuclear layer; INL=Inner nuclear layer, GCL=Ganglion cell layer.

DETAILED DESCRIPTION

Figure 1:
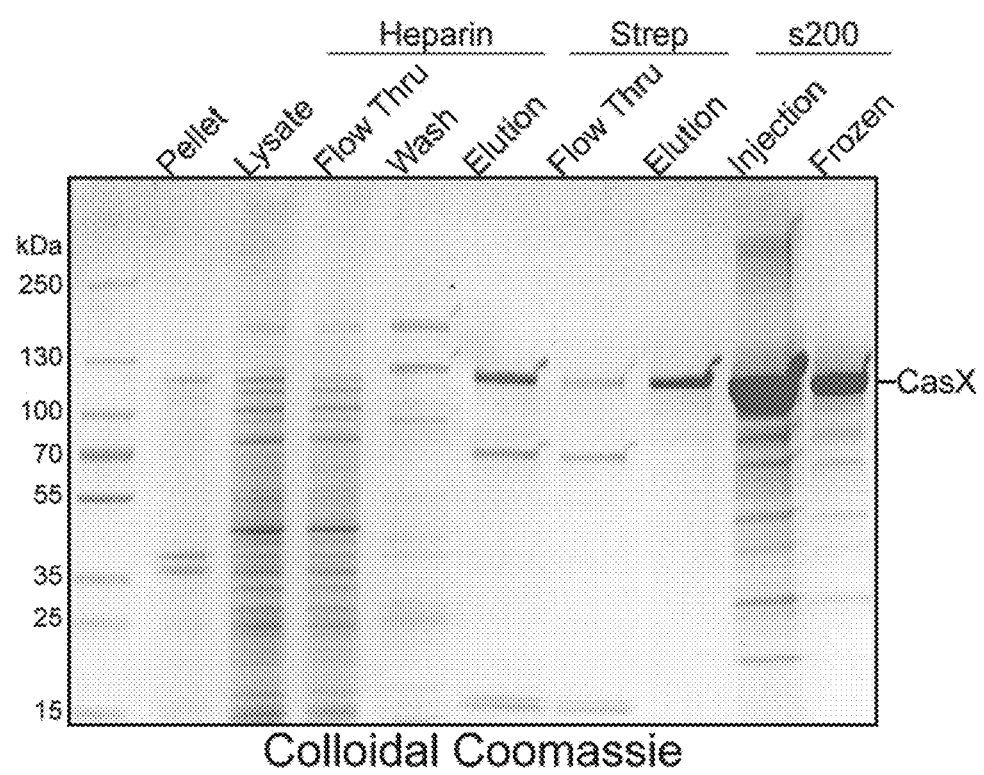
FIG. 1 shows an SDS-PAGE gel of StX2 purification fractions visualized by colloidal Coomassie staining, as described in Example 1.

While exemplary embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

"Hybridizable" or "complementary" are used interchangeably to mean that a nucleic acid (e.g., RNA, DNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. It is understood that the sequence of a polynucleotide need not be 100% complementary to that of its target nucleic acid sequence to be specifically hybridizable; it can have at least about 70%, at least about 80%, or at least about 90%, or at least about 95% sequence identity and still hybridize to the target nucleic acid sequence. Moreover, a polynucleotide may hybridize over one or more segments such that intervening or adjacent segments are not involved in the hybridization event (e.g., a loop structure or hairpin structure, a 'bulge', and the like).

A "gene," for the purposes of the present disclosure, includes a DNA region encoding a gene product (e.g., a protein. RNA), as well as all DNA regions which regulate the production of the gene product, whether or not such regulatory sequences are adjacent to coding and/or transcribed sequences. Accordingly, a gene may include regulatory element sequences including, but not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Coding sequences encode a gene product upon transcription or transcription and translation; the coding sequences of the disclosure may comprise fragments and need not contain a full-length open reading frame. A gene can include both the strand that is transcribed as well as the complementary strand containing the anticodons.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

The term "regulatory element" is used interchangeably herein with the term "regulatory sequence," and is intended to include promoters, enhancers, and other expression regulatory elements (e.g. transcription termination signals, such as polyadenylation signals and poly-U sequences). Exemplary regulatory elements include a transcription promoter such as, but not limited to, CMV. CMV+intron A, SV40, RSV, HIV-Ltr, elongation factor 1 alpha (EF1α), MMLV-ltr, internal ribosome entry site (IRES) or P2A peptide to permit translation of multiple genes from a single transcript, metallothionein, a transcription enhancer element, a transcription termination signal, polyadenylation sequences, sequences for optimization of initiation of translation, and translation termination sequences. In the case of systems utilized for exon skipping, regulatory elements include exonic splicing enhancers. It will be understood that the choice of the appropriate regulatory element will depend on the encoded component to be expressed (e.g., protein or RNA) or whether the nucleic acid comprises multiple components that require different polymerases or are not intended to be expressed as a fusion protein.

The term "promoter" refers to a DNA sequence that contains an RNA polymerase binding site, transcription start site, TATA box, and/or B recognition element and assists or promotes the transcription and expression of an associated transcribable polynucleotide sequence and/or gene (or transgene). A promoter can be synthetically produced or can be derived from a known or naturally occurring promoter sequence or another promoter sequence. A promoter can be proximal or distal to the gene to be transcribed. A promoter can also include a chimeric promoter comprising a combination of two or more heterologous sequences to confer certain properties. A promoter of the present disclosure can include variants of promoter sequences that are similar in composition, but not identical to, other promoter sequence(s) known or provided herein. A promoter can be classified according to criteria relating to the pattern of expression of an associated coding or transcribable sequence or gene operably linked to the promoter, such as constitutive, developmental, tissue-specific, inducible, etc.

The term "enhancer" refers to regulatory DNA sequences that, when bound by specific proteins called transcription factors, regulate the expression of an associated gene. Enhancers may be located in the intron of the gene, or 5' or 3' of the coding sequence of the gene. Enhancers may be proximal to the gene (i.e., within a few tens or hundreds of base pairs (bp) of the promoter), or may be located distal to the gene (i.e., thousands of bp, hundreds of thousands of bp, or even millions of bp away from the promoter). A single gene may be regulated by more than one enhancer, all of which are envisaged as within the scope of the instant disclosure.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "enhancers" and "promoters", above).

The term "recombinant polynucleotide" or "recombinant nucleic acid" refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

As used herein, the term "contacting" means establishing a physical connection between two or more entities. For example, contacting a target nucleic acid sequence with a guide nucleic acid means that the target nucleic acid sequence and the guide nucleic acid are made to share a physical connection; e.g., can hybridize if the sequences share sequence similarity.

"Dissociation constant", or "$K_d$", are used interchangeably and mean the affinity between a ligand "L" and a protein "P", i.e., how tightly a ligand binds to a particular protein. It can be calculated using the formula $K_d$=[L][P]/[LP], where [P], [L] and [LP] represent molar concentrations of the protein, ligand and complex, respectively.

The disclosure provides compositions and methods useful for editing a target nucleic acid sequence. As used herein "editing" is used interchangeably with "modifying" and includes but is not limited to cleaving, nicking, deleting, knocking in, knocking out, and the like.

The term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. The term "knock-down" as used herein refers to reduction in the expression of a gene or its gene product(s). As a result of a gene knock-down, the protein activity or function may be attenuated or the protein levels may be reduced or eliminated.

As used herein, "homology-directed repair" (HDR) refers to the form of DNA repair that takes place during repair of double-strand breaks in cells. This process requires nucleotide sequence homology, and uses a donor template to repair or knock-out a target DNA, and leads to the transfer of genetic information from the donor to the target. Homology-directed repair can result in an alteration of the sequence of the target sequence by insertion, deletion, or mutation if the donor template differs from the target DNA sequence and part or all of the sequence of the donor template is incorporated into the target DNA.

As used herein, "non-homologous end joining" (NHEJ) refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

As used herein "micro-homology mediated end joining" (MMEJ) refers to a mutagenic DSB repair mechanism, which always associates with deletions flanking the break sites without the need for a homologous template (in contrast to homology-directed repair, which requires a homologous sequence to guide repair). MMEJ often results in the loss (deletion) of nucleotide sequence near the site of the double-strand break.

A polynucleotide or polypeptide has a certain percent "sequence similarity" or "sequence identity" to another polynucleotide or polypeptide, meaning that, when aligned, that percentage of bases or amino acids are the same, and in the same relative position, when comparing the two sequences. Sequence similarity (sometimes referred to as percent similarity, percent identity, or homology) can be determined in a number of different manners. To determine sequence similarity, sequences can be aligned using the methods and computer programs that are known in the art, including BLAST, available over the world wide web at ncbi.nlm.nih.gov/BLAST. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "polypeptide." and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence.

A "vector" or "expression vector" is a replicon, such as plasmid, phage, virus, or cosmid, to which another DNA segment, i.e., an "insert", may be attached so as to bring about the replication or expression of the attached segment in a cell.

The term "naturally-occurring" or "unmodified" or "wild type" as used herein as applied to a nucleic acid, a polypeptide, a cell, or an organism, refers to a nucleic acid, polypeptide, cell, or organism that is found in nature.

As used herein, a "mutation" refers to an insertion, deletion, substitution, duplication, or inversion of one or more amino acids or nucleotides as compared to a reference amino acid sequence or to a reference nucleotide sequence.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A "host cell," as used herein, denotes a eukaryotic cell, a prokaryotic cell, or a cell from a multicellular organism (e.g., in a cell line), which eukaryotic or prokaryotic cells are used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

The term "antibody," as used herein, encompasses various antibody structures, including but not limited to monoclonal antibodies, polyclonal antibodies, multispecific antibodies (e.g., bispecific antibodies), nanobodies, single domain antibodies such as VHH antibodies, and antibody fragments so long as they exhibit the desired antigen-binding activity or immunological activity. Antibodies represent a large family of molecules that include several types of molecules, such as IgD, IgG, IgA, IgM and IgE.

As used herein, "treatment" or "treating." are used interchangeably herein and refer to an approach for obtaining beneficial or desired results, including but not limited to a therapeutic benefit and/or a prophylactic benefit. By therapeutic benefit is meant eradication or amelioration of the underlying disorder or disease being treated. A therapeutic benefit can also be achieved with the eradication or amelioration of one or more of the symptoms or an improvement in one or more clinical parameters associated with the underlying disease such that an improvement is observed in the subject, notwithstanding that the subject may still be afflicted with the underlying disorder.

The terms "therapeutically effective amount" and "therapeutically effective dose", as used herein, refer to an amount of a drug or a biologic, alone or as a part of a composition, that is capable of having any detectable, beneficial effect on any symptom, aspect, measured parameter or characteristics of a disease state or condition when administered in one or repeated doses to a subject such as a human or an experimental animal. Such effect need not be absolute to be beneficial.

As used herein, "administering" is meant a method of giving a dosage of a compound (e.g., a composition of the disclosure) or a composition (e.g., a pharmaceutical composition) to a subject.

A "subject" is a mammal. Mammals include, but are not limited to, domesticated animals, non-human primates, humans, rabbits, mice, rats and other rodents.

I. General Methods

The practice of the present disclosure employs, unless otherwise indicated, conventional techniques of immunology, biochemistry, chemistry, molecular biology, microbiology, cell biology, genomics and recombinant DNA, which can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 19%); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that endpoints are included, and that each intervening value, to the tenth of the unit of the lower limit unless the context clearly dictates otherwise, between the upper and lower limit of that range and any other stated or intervening value in that stated range, is encompassed. The upper and lower limits of these smaller ranges may independently be included in the smaller ranges, and are also encompassed, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise.

It will be appreciated that certain features of the invention, which are, for clarity, described in the context of separate embodiments, may also be provided in combination in a single embodiment. In other cases, various features of the invention, which are, for brevity, described in the context of a single embodiment, may also be provided separately or in any suitable sub-combination. It is intended that all combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

II. Systems for Genetic Editing of RHO Genes

In a first aspect, the present disclosure provides systems comprising a CRISPR nuclease protein and one or more guide nucleic acids (gNA) for use in modifying a RHO gene (referred to herein as the "target nucleic acid"). The RHO gene to be modified may comprise one or more mutations, including deletions, substitutions or duplications, in the gene region selected from the group consisting of a RHO intron, a RHO exon, a RHO intron-exon junction, a RHO regulatory element, and an intergenic region. The majority of known mutations are substitutions, resulting in defects such as post-Golgi trafficking and OS targeting, misfolding, ER retention and instability, disrupted vesicular traffic and endocytosis, and altered post-translational modifications and reduced stability (Athanasiou, et al. 2018). A non-limiting list of RHO mutations contemplated for editing by the design of the editing systems of the disclosure are presented in Table 4A.

The RHO locus spans 6,706 bp and has of 5 exons. The rhodopsin protein has a molecular weight of approximately 40 kD and spans the membrane of the rod cell or the eye. Rhodopsin absorbs light as it enters the retina and becomes photoexcited, causing it to undergo a change in molecular configuration, and dissociates from the opsin, initiating a process that eventually causes electrical impulses to be sent to the brain along the optic nerve. While more than 80 mutations in the rhodopsin gene have been identified that account for 30% of all Autosomal Dominant Retinitis Pigmentosa (ADRP) cases in humans (Dryja, T P, et al. Invest Opthalmol Vis Sci 41:3124 (2000)), the P23H mutation is the most common in the United States (Olsson, et al. Neuron 9:815)(1992)). Due to problems with protein folding. Pror23His (or P23H) rhodopsin only partially reconstitutes with retinal in vitro (Liu et al. Proc Nat'l Acad Sci 93:4554 (1996)), and mutant rhodopsin expressed in transgenics causes retinal degeneration (Goto, et al. Invest Opthalmol Vis Sci 36:62 (1995)).

The RHO gene is defined as the sequence that spans chr3: 129,528,639-129,535,344 of the human genome (GRCh38.p13) (the notation refers to the chromosome 3 (chr3), starting at the 129,528,639 bp of that chromosome, and extending to the 129,535,344 bp of that chromosome). The human RHO gene (HGNC:10012; see also GenBank Accession No. NM_000539.2) has five exons and encodes a protein having the sequence (SEQ ID NO: 33)
MNGTEGPNFYVPFSNATGVVRSPFEYPQYYLAEPWQFSMLAAYMFLLIVL

GFPINFLTLYVTVQHKKLRTPLNYILLNLAVADLFMVLGGFTSTLYTSLH

GYFVFGPTGCNLEGFFATLGGEIALWSLVVLAIERYVVVCKPMSNFRFGE

NHAIMGVAFTWVMALACAAPPLAGWSRYIPEGLQCSCGIDYYTLKPEVNN

ESFVIYMFVVHFTIPMIIIFFCYGQLVFTVKEAAAQQQESATTQKAEKEV

TRMVIIMVIAFLICWVPYASVAFYIFTHQGSNFGPIFMTIPAFFAKSAAI

YNPVIYIMMNKQFRNCMLTTICCGKNPLGDDEASATVSKTETSQVAPA.

Human rhodopsin contains 348 amino acids. (Nathans J, and Hogness, D, PNAS 81:4851 (1984)). The most frequent mutation leading to retinitis pigmentosa is P23H, resulting in the sequence (SEQ ID NO: 34)
MNGTEGPNFYVPFSNATGVVRS<u>H</u>FEYPQYYLAEPWQFSMLAAYMFLLIVL

GFPINFLTLYVTVQHKKLRTPLNYILLNLAVADLFMVLGGFTSTLYTSLH

GYFVFGPTGCNLEGFFATLGGEIALWSLVVLAIERYVVVCKPMSNFRFGE

NHAIMGVAFTWVMALACAAPPLAGWSRYIPEGLQCSCGIDYYTLKPEVNN

ESFVIYMFVVHFTIPMIIIFFCYGQLVFTVKEAAAQQQESATTQKAEKEV

TRMVIIMVIAFLICWVPYASVAFYIFTHQGSNFGPIFMTIPAFFAKSAAI

YNPVIYIMMNKQFRNCMLTTICCGKNPLGDDEASATVSKTETSQVAPA.

In some embodiments, the disclosure provides systems specifically designed to modify the RHO gene in eukaryotic cells bearing one or more mutations. Generally, any portion of the RHO target nucleic acid can be targeted using the programmable compositions and methods provided herein. In some embodiments, the CRISPR nuclease is a Class 2, Type V nuclease. In some embodiments, the Class 2, Type V nuclease is selected from the group consisting of Cas12a, Cas12b, Cas12c, Cas12d (CasY), Cas12J, and CasX. In some embodiments, the disclosure provides systems comprising one or more CasX proteins and one or more guide nucleic acids (gNA) as a CasX:gNA system designed to target and edit specific locations in the RHO target nucleic acid sequence in order to correct or compensate for the one or more mutations. In other embodiments, the CasX:gNA systems of the disclosure comprise one or more CasX proteins, one or more guide nucleic acids (gNA) and one or more donor template nucleic acids comprising a nucleic acid encoding a portion of a RHO gene wherein the nucleic acid comprises a wild-type sequence, a cDNA sequence encoding a portion of a functional rhodopsin protein, a deletion, an insertion, or a mutation of one or more nucleotides in comparison to a genomic nucleic acid sequence encoding the mutant rhodopsin. The disclosure contemplates use of a donor template of sufficient length in the CasX:gNA system that may also be optimized to contain synthetic intron sequences of shortened length (relative to the genomic intron) between the exons in the donor template to ensure proper expression and processing of the RHO locus. In some embodiments, the donor polynucleotide comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least about 15,000 nucleotides. In other embodiments, the donor polynucleotide comprises at least about 10 to about 15,000 nucleotides, or at least about 100 to about 10,000 nucleotides, or at least about 400 to about 8,000 nucleotides, or at least about 600 to about 5000 nucleotides, or at least about 1000 to about 2000 nucleotides. In some embodiments, the donor template is a single stranded DNA template or a single stranded RNA template. In other embodiments, the donor template is a double stranded DNA template.

In some embodiments, the disclosure provides gene editing pairs of a CasX and a gNA of any of the embodiments described herein that are capable of being bound together prior to their use for gene editing and, thus, are "pre-complexed" as a ribonuclear protein complex (RNP). The use of a pre-complexed RNP confers advantages in the delivery of the system components to a cell or target nucleic acid sequence for editing of the target nucleic acid sequence. In some embodiments, the functional RNP can be delivered ex vivo to a cell by electrophoresis or by chemical means. In other embodiments, the functional RNP can be delivered either ex vivo or in vivo by a vector in their functional form. The gNA can provide target specificity to the complex by including a targeting sequence (or "spacer") having a nucleotide sequence that is complementary to a sequence of the target nucleic acid sequence while the CasX protein of the pre-complexed CasX:gNA provides the site-specific activity such as cleavage or nicking of the target sequence that is guided to a target site (e.g., stabilized at a target site) within a target nucleic acid sequence by virtue of its association with the gNA. The CasX proteins and gNA components of the CasX:gNA systems and their sequences, features and functions are described more fully, below.

The CasX:gNA systems have utility in the treatment of a subject having retinitis pigmentosa. Each of the components of the CasX:gNA systems and their use in the editing of the target nucleic acids in cells is described more fully, below.

III. Guide Nucleic Acids of the Systems for Genetic Editing

In another aspect, the disclosure relates to guide nucleic acids (gNA) comprising a targeting sequence complementary to a target nucleic acid sequence of a RHO gene, wherein the gNA is capable of forming a complex with a CRISPR protein that has specificity to a protospacer adjacent motif (PAM) sequence comprising a TC motif in the complementary non-target strand, and wherein the PAM sequence is located 1 nucleotide 5' of the sequence in the non-target strand that is complementary to the target nucleic acid sequence in the target strand of the target nucleic acid. In some embodiments, the gNA is capable of forming a complex with a Class 2, Type V CRISPR nuclease. In a particular embodiment, the gNA is capable of forming a complex with a CasX nuclease.

In some embodiments, the disclosure provides gNAs utilized in the CasX:gNA systems that have utility in genome editing a RHO gene in a eukaryotic cell. The present disclosure provides specifically-designed gNAs wherein the targeting sequence (or spacer, described more fully, below) of the gNA is complementary to (and are therefore able to hybridize with) target nucleic acid sequences when used as a component of the gene editing CasX:gNA systems. Representative, but non-limiting examples of targeting sequences to the RHO target nucleic acid that can be utilized in the gNA of the embodiments are presented as SEQ ID NOs: SEQ ID NOS: 328-346, 367-376, 382-2100 and 2286-27274. In a particular embodiment, the disclosure provides the targeting sequences presented as SEQ ID NOS: 382-582, which are designed to target known mutations in the RHO gene when utilized in the CasX:gNA systems. In some embodiments, the gNA is a deoxyribonucleic acid molecule ("gDNA"); in some embodiments, the gNA is a ribonucleic acid molecule ("gRNA"); and in other embodiments, the gNA is a chimera, and comprises both DNA and RNA. As used herein, the terms gNA, gRNA, and gDNA cover naturally-occurring molecules, as well as sequence variants.

It is envisioned that in some embodiments, multiple gNAs are delivered in the methods for the modification of a target nucleic acid sequence by use of the CasX:gNA systems which is then edited by host cell repair mechanisms such as non-homologous end joining (NHEJ), homology-directed repair (HDR, which can include, for example, insertion of a donor template to replace all or a portion of the RHO exon), homology-independent targeted integration (HITI), microhomology mediated end joining (MMEJ), single strand annealing (SSA) or base excision repair (BER). For example, when an editing event is designed to delete multiple nucleotides within an exon of the RHO gene is desired, a pair of gNAs can be used in order to bind and cleave at two different sites 5' and 3' of the exon(s) bearing the mutation(s) within the RHO gene. In the context of nucleic acids, cleavage refers to the breakage of the covalent backbone of a nucleic acid molecule; either DNA or RNA, by the nuclease. Both single-stranded cleavage and double-stranded cleavage are possible, and double-stranded cleavage can occur as a result of two distinct single-stranded cleavage events. In some embodiments, small indels introduced by the CasX:gNA systems of the embodiments described herein and cellular repair systems can restore the protein reading frame of the mutant RHO gene ("reframing" strategy). When the reframing strategy is used, the cells may be contacted with a single gNA In other cases, when a deletion or a knock-down/knock-out of the RHO gene is desired, a pair of gNAs with targeting sequences to different or overlapping regions of the target nucleic acid sequence can be used in order to bind and the CasX to cleave at two different or overlapping sites within or proximal to the exon or regulatory element of the gene, which is then edited by non-homologous end joining (NHEJ), homology-directed repair (HDR, which can include, for example, insertion of a donor template to replace all or a portion of a RHO exon), homology-independent targeted integration (HITI), microhomology mediated end joining (MMEJ), single strand annealing (SSA) or base excision repair (BER).

a. Reference gNA and gNA Variants

In some embodiments, a gNA of the present disclosure comprises a wild-type sequence of a naturally-occurring gNA (a "reference gNA"). In other cases, a reference gNA of the disclosure may be subjected to one or more mutagenesis methods, such as the mutagenesis methods described herein, which may include Deep Mutational Evolution (DME), deep mutational scanning (DMS), error prone PCR, cassette mutagenesis, random mutagenesis, staggered extension PCR, gene shuffling, or domain swapping, in order to generate one or more gNA variants with enhanced or varied properties relative to the reference gNA, gNA variants also include variants comprising one or more exogenous sequences, for example fused to either the 5' or 3' end, or inserted internally. The activity of reference gNAs may be used as a benchmark against which the activity of gNA variants are compared, thereby measuring improvements in function or other characteristics of the gNA variants. In other embodiments, a reference gNA may be subjected to one or more deliberate, specifically-targeted mutations in order to produce a gNA variant, for example a rationally designed variant.

The gNAs of the disclosure comprise two segments: a targeting sequence and a protein-binding segment. The targeting segment of a gNA includes a nucleotide sequence (referred to interchangeably as a guide sequence, a spacer, a targeter, or a targeting sequence) that is complementary to (and therefore hybridizes with) a specific sequence (a target site) within the target nucleic acid sequence (e.g., a target ssRNA, a target ssDNA, a strand of a double stranded target DNA, etc.), described more fully below. The targeting sequence of a gNA is capable of binding to a target nucleic acid sequence, including a coding sequence, a complement of a coding sequence, a non-coding sequence, and to regulatory elements. The protein-binding segment (or "activator" or "protein-binding sequence") interacts with (e.g., binds to) a CasX protein as a complex, forming an RNP (described more fully, below). The protein-binding segment is alternatively referred to herein as a "scaffold", which is comprised of several regions, described more fully, below.

In the case of a dual guide RNA (dgRNA), the targeter and the activator portions each have a duplex-forming segment, where the duplex forming segment of the targeter and the duplex-forming segment of the activator have complementarity with one another and hybridize to one another to form a double stranded duplex (dsRNA duplex for a gRNA). When the gNA is a gRNA, the term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together; e.g., by intervening nucleotides). The crRNA has a 5' region that anneals with the tracrRNA followed by the nucleotides of the targeting sequence. Thus, for example, a guide RNA (dgRNA or sgRNA) comprises a guide sequence and a duplex-forming segment of a crRNA, which can also be referred to as a crRNA repeat. A corresponding tracrRNA-like molecule (activator) also comprises a duplex-forming stretch of nucleotides that forms the other half of the dsRNA duplex of the protein-binding segment of the guide RNA. Thus, a targeter and an activator, as a corresponding pair, hybridize to form a dual guide NA, referred to herein as a "dual guide NA", a "dual-molecule gNA", a "dgNA", a "double-molecule guide NA", or a "two-molecule guide NA". Site-specific binding and/or cleavage of a target nucleic acid sequence (e.g., genomic DNA) by the CasX protein can occur at one or more locations (e.g., a sequence of a target nucleic acid) determined by base-pairing complementarity between the targeting sequence of the gNA and the target nucleic acid sequence. Thus, for example, the gNA of the disclosure have sequences complementarity to and therefore can hybridize with the target nucleic acid that is adjacent to a sequence complementary to a TC PAM motif or a PAM sequence, such as ATC, CTC, GTC, or TTC. Because the targeting sequence of a guide sequence hybridizes with a sequence of a target nucleic acid sequence, a targeter can be modified by a user to hybridize with a specific target nucleic acid sequence, so long as the location of the PAM sequence is considered. Thus, in some cases, the sequence of a targeter may be a non-naturally occurring sequence. In other cases, the sequence of a targeter may be a naturally-occurring sequence, derived from the gene to be edited. In other embodiments, the activator and targeter of the gNA are covalently linked to one another (rather than hybridizing to one another) and comprise a single molecule, referred to herein as a "single-molecule gNA," "one-molecule guide NA," "single guide NA", "single guide RNA", a "single-molecule guide RNA," a "one-molecule guide RNA", a "single guide DNA", a "single-molecule DNA", or a "one-molecule guide DNA", ("sgNA", "sgRNA", or a "sgDNA"). In some embodiments, the sgNA includes an "activator" or a "targeter" and thus can be an "activator-RNA" and a "targeter-RNA," respectively.

Collectively, the assembled gNAs of the disclosure comprise four distinct regions, or domains: the RNA triplex, the scaffold stem, the extended stem, and the targeting sequence that, in the embodiments of the disclosure is specific for a target nucleic acid and is located on the 3'end of the gNA. The RNA triplex, the scaffold stem, and the extended stem, together, are referred to as the "scaffold" of the gNA.

b. RNA Triplex

In some embodiments of the guide NAs provided herein (including reference sgNAs), there is a RNA-triplex, and the RNA triplex comprises the sequence of a UUU--nX(~4-15)--UUU stem loop (SEQ ID NO: 19) that ends with an AAAG after 2 intervening stem loops (the scaffold stem loop and the extended stem loop), forming a pseudoknot that may also extend past the triplex into a duplex pseudoknot. The UU-UUU-AAA sequence of the triplex forms as a nexus between the spacer, scaffold stem, and extended stem. In exemplary reference CasX sgNAs, the UUU-loop-UUU region is coded for first, then the scaffold stem loop, and then the extended stem loop, which is linked by the tetraloop, and then an AAAG closes off the triplex before becoming the spacer.

c. Scaffold Stem Loop

In some embodiments of sgNAs of the disclosure, the triplex region is followed by the scaffold stem loop. The scaffold stem loop is a region of the gNA that is bound by CasX protein (such as a reference or CasX variant protein). In some embodiments, the scaffold stem loop is a fairly short and stable stem loop. In some cases, the scaffold stem loop does not tolerate many changes, and requires some form of an RNA bubble. In some embodiments, the scaffold stem is necessary for CasX sgNA function. While it is perhaps analogous to the nexus stem of Cas9 as being a critical stem loop, the scaffold stem of a CasX sgNA, in some embodiments, has a necessary bulge (RNA bubble) that is different from many other stem loops found in CRISPR/Cas systems. In some embodiments, the presence of this bulge is conserved across sgNA that interact with different CasX proteins. An exemplary sequence of a scaffold stem loop sequence of a gNA comprises the sequence CCAGCGAC-UAUGUCGUAUGG (SEQ ID NO: 20). In other embodiments, the disclosure provides gNA variants wherein the scaffold stem loop is replaced with an RNA stem loop sequence from a heterologous RNA source with proximal 5' and 3' ends, such as, but not limited to stem loop sequences selected from MS2, Q β, U1 hairpin II, Uvsx, or PP7 stem loops. In some cases, the heterologous RNA stem loop of the gNA is capable of binding a protein, an RNA structure, a DNA sequence, or a small molecule.

d. Extended Stem Loop

In some embodiments of the CasX sgNAs of the disclosure, the scaffold stem loop is followed by the extended stem loop. In some embodiments, the extended stem comprises a synthetic tracr and crRNA fusion that is largely unbound by the CasX protein. In some embodiments, the extended stem loop can be highly malleable. In some embodiments, a single guide gRNA is made with a GAAA tetraloop linker or a GAGAAA linker between the tracr and crRNA in the extended stem loop. In some cases, the targeter and activator of a CasX sgNA are linked to one another by intervening nucleotides and the linker can have a length of from 3 to 20 nucleotides. In some embodiments of the CasX sgNAs of the disclosure, the extended stem is a large 32-bp loop that sits outside of the CasX protein in the ribonucleoprotein complex. An exemplary sequence of an extended stem loop sequence of a sgNA comprises the sequence GCGC-UUAUUUAUCG-GAGAGAAAUCCGAUAAAUAAGAAGC (SEQ ID NO: 21). In some embodiments, the extended stem loop comprises a GAGAAA spacer sequence. In some embodiments, the disclosure provides gNA variants wherein the extended stem loop is replaced with an RNA stem loop sequence from a heterologous RNA source with proximal 5' and 3' ends, such as, but not limited to stem loop sequences selected from MS2, Qβ, U1 hairpin II, Uvsx, or PP7 stem loops. In such cases, the heterologous RNA stem loop increases the stability of the gNA In other embodiments, the disclosure provides gNA variants having an extended stem loop region comprising at least 10, at least 100, at least 500, at least 1000, or at least 10,000 nucleotides, or at least 10-10,000, at least 10-1000, or at least 10-100 nucleotides.

e. Targeting Sequence

In some embodiments of the gNAs of the disclosure, the extended stem loop is followed by a region that forms part of the triplex, and then the targeting sequence (or "spacer") at the 3' end of the gNA. The targeting sequence targets the CasX ribonucleoprotein holo complex to a specific region of the target nucleic acid sequence of the gene to be modified. Thus, for example, gNA targeting sequences of the disclosure have sequences complementarity to, and therefore can hybridize to, a portion of the RHO gene in a nucleic acid in a eukaryotic cell (e.g., a eukaryotic chromosome, chromosomal sequence, a eukaryotic RNA, etc.) as a component of the RNP when the TC PAM motif or any one of the PAM sequences TTC, ATC, GTC, or CTC is located 1 nucleotide 5' to the non-target strand sequence complementary to the target sequence. The targeting sequence of a gNA can be modified so that the gNA can target a desired sequence of any desired target nucleic acid sequence, so long as the PAM sequence location is taken into consideration. In some embodiments, the gNA scaffold is 5' of the targeting sequence, with the targeting sequence on the 3' end of the gNA. In some embodiments, the PAM motif sequence recognized by the nuclease of the RNP is TC. In other embodiments, the PAM sequence recognized by the nuclease of the RNP is NTC.

In some embodiments, the targeting sequence of the gNA is complementary to a portion of a gene encoding a rhodopsin protein. In some embodiments, the targeting sequence of a gNA is complementary to a RHO exon selected from the group consisting of exons 1-5. In one embodiment, the targeting sequence of a gNA is complementary to RHO exon 1. In another embodiment, the targeting sequence of a gNA is complementary to RHO exon 2. In another embodiment, the targeting sequence of a gNA is complementary to RHO exon 3. In another embodiment, the targeting sequence of a gNA is complementary to RHO exon 4. In another embodiment, the targeting sequence of a gNA is complementary to RHO exon 5. In other embodiments, the targeting sequence of the gNA is complementary to a region within or proximal to an exon comprising a duplication. In other embodiments, the targeting sequence of a gNA is specific for a RHO intronic region, an intron-exon junction of the RHO gene, or an intergenic region. In some embodiments, the targeting sequence of the gNA is complementary to a sequence comprising one or more single nucleotide polymorphisms (SNPs) of the RHO gene or its complement. SNPs that are within a RHO coding sequence or within a RHO non-coding sequence are both within the scope of the instant disclosure. In some embodiments, the targeting sequence of the gNA is complementary to a sequence encoding or proximal to a mutation presented in Table 4A. In some embodiments, the targeting sequence of the gNA is complementary to a region within or proximal to (e.g., within 40 nucleotides of) an exon comprising a deletion. Representative targeting sequences to RHO mutations known or believed to be associated with retinitis pigmentosa that can be used in the editing systems of the disclosure are presented as SEQ ID NOS: 382-582.

In other embodiments, the targeting sequence of a gNA is specific for a junction of the exon, an intron, and/or a regulatory element of the gene. In those cases where the targeting sequence is specific for a regulatory element, such regulatory elements include, but are not limited to promoter regions, enhancer regions, intergenic regions, 5' untranslated regions (5' UTR), 3' untranslated regions (3' UTR), conserved elements, and regions comprising cis-regulatory elements. The promoter region is intended to encompass nucleotides within 5 kb of the initiation point of the encoding sequence or, in the case of gene enhancer elements or conserved elements, can be thousands of bp, hundreds of thousands of bp, or even millions of bp away from the encoding sequence of the gene of the target nucleic acid. In the foregoing, the targets are those in which the encoding gene of the target is intended to be knocked out or knocked down such that the targeted protein is not expressed or is expressed at a lower level in a cell.

In some embodiments, the targeting sequence of the gNA has between 14 and 35 consecutive nucleotides. In some embodiments, the targeting sequence has 14, 15, 16, 18, 18, 19, 20, 21, 22, 23 24, 25, 26, 27, 28, 29, 30, 31, 32, 33, 34 or 35 consecutive nucleotides. In some embodiments, the targeting sequence consists of 20 consecutive nucleotides. In some embodiments, the targeting sequence consists of 19 consecutive nucleotides. In some embodiments, the targeting sequence consists of 18 consecutive nucleotides. In some embodiments, the targeting sequence consists of 17 consecutive nucleotides. In some embodiments, the targeting sequence consists of 16 consecutive nucleotides. In some embodiments, the targeting sequence consists of 15 consecutive nucleotides. In some embodiments, the targeting sequence has 14, 15, 16, 17, 18, 19, 20, 21, 22, 23, 24, 25, 26, 27, 28, 29, 30, 31, 32, 33, 34 or 35 consecutive nucleotides and the targeting sequence can comprise 0 to 5, 0 to 4, 0 to 3, or 0 to 2 mismatches relative to the target nucleic acid sequence and retain sufficient binding specificity such that the RNP comprising the gNA comprising the targeting sequence can form a complementary bond with respect to the target nucleic acid.

Representative, but non-limiting examples of targeting sequences for inclusion in the gNA of the disclosure utilized with the CasX:gNA system for editing of the RHO gene are presented as SEQ ID NOs: 328-346, 367-376, 382-2100 and 2286-27274, representing targeting sequences for targeting a RHO target nucleic acid. In one embodiment, the targeting sequence of the gNA comprises a sequence having at least about 65%, at least about 75%, at least about 85%, or at least about 95% identity to a sequence selected from the group consisting of SEQ ID NOs: 328-346, 367-376, 382-2100 and 2286-27274. In one embodiment, the targeting sequence of the gNA comprises a sequence having at least about 65%, at least about 75%, at least about 85%, or at least about 95% identity to a sequence selected from the group consisting of SEQ ID NOs: 382-582. In another embodiment, the targeting sequence of the gNA consists of a sequence selected from the group consisting of SEQ ID NOs: 328-346, 367-376, 382-2100 and 2286-27274. In another embodiment, the targeting sequence of the gNA consists of a sequence selected from the group consisting of SEQ ID NOs: 382-582. In the foregoing embodiments, thymine (T) nucleotides can be substituted for one or more or all of the uracil (U) nucleotides in any of the targeting sequences such that the gNA can be a gDNA or a gRNA, or a chimera of RNA and DNA. In some embodiments, a targeting sequence of SEQ ID NOs: 328-346, 367-376, 382-2100 and 2286-27274 has at least 1, 2, 3, 4, 5, or 6 or more thymine nucleotides substituted for uracil nucleotides. In other embodiments, a gNA, gRNA, or gDNA of the disclosure comprises 1, 2, 3 or more targeting sequences of SEQ ID NOs: 328-346, 367-376, 382-2100 and 2286-27274, or targeting sequences that are at least 50% identical, at least 55% identical, at least 60% identical, at least 65% identical, at least 70% identical, at least 75% identical, at least 80% identical, at least 85% identical, at least 90% identical, at least 95% identical to one or more sequences of SEQ ID NOs: 328-346, 367-376, 382-2100 and 2286-27274. In some embodiments, a targeting sequence of SEQ ID NOs: 328-582 has at least 1, 2, 3, 4, 5, or 6 or more thymine nucleotides substituted for uracil nucleotides. In other embodiments, a gNA, gRNA, or gDNA of the disclosure comprises 1, 2, 3 or more targeting sequences of SEQ ID NOs: 328-582, or targeting sequences that are at least 50% identical, at least 55% identical, at least 60% identical, at least 65% identical, at least 70% identical, at least 75% identical, at least 80% identical, at least 85% identical, at least 90% identical, at least 95% identical to one or more sequences of SEQ ID NOs: 328-582.

In some embodiments, the CasX:gNA system comprises a first gNA and further comprises a second (and optionally a third, fourth, fifth, or more) gNA, wherein the second gNA or additional gNA has a targeting sequence complementary to a different or overlapping portion of the target nucleic acid sequence compared to the targeting sequence of the first gNA such that multiple points in the target nucleic acid are targeted, and, for example, multiple breaks are introduced in the target nucleic acid by the CasX. It will be understood that in such cases, the second or additional gNA is complexed with an additional copy of the CasX protein. By selection of the targeting sequences of the gNA, defined regions of the target nucleic acid sequence bracketing a particular location within the target nucleic acid can be modified or edited using the CasX:gNA systems described herein, including facilitating the insertion of a donor template or excision of a region or exon comprising a mutation of the RHO gene.

f. gNA Scaffolds

In some embodiments, a CasX reference gRNA comprises a sequence isolated or derived from Deltaproteobacter. In some embodiments, the sequence is a CasX tracrRNA sequence. Exemplary CasX reference tracrRNA sequences isolated or derived from Deltaproteobacter may include:

(SEQ ID NO: 22)
ACAUCUGGCGCGUUUAUUCCAUUACUUUGGAGCCAGUCCCAGCGACUAUG

UCGUAUGGACGAAGCGCUUAUUUAUCGAGA and (SEQ ID NO: 23)
ACAUCUGGCGCGUUUAUUCCAUUACUUUGGAGCCAGUCCCAGCGACUAUG

UCGUAUGGACGAAGCGCUUAUUUAUCGG.

Exemplary crRNA sequences isolated or derived from Deltaproteobacter may comprise a sequence of CCGAUAAGUAAAACGCAUCAAAG (SEQ ID NO: 24). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from Deltaproteobacter.

In some embodiments, a CasX reference guide RNA comprises a sequence isolated or derived from Planctomycetes. In some embodiments, the sequence is a CasX tracrRNA sequence. Exemplary CasX reference tracrRNA sequences isolated or derived from Planctomycetes may include:

(SEQ ID NO: 25)
UACUGGCGCUUUUAUCUCAUUACUUUGAGAGCCAUCACCAGCGACUAUGU

CGUAUGGGUAAAGCGCUUAUUUAUCGGAGA and (SEQ ID NO: 26)
UACUGGCGCUUUUAUCUCAUUACUUUGAGAGCCAUCACCAGCGACUAUGU

CGUAUGGGUAAAGCGCUUAUUUAUCGG.

Exemplary crRNA sequences isolated or derived from Planctomycetes may comprise a sequence of UCUCCGAUAAAUAAGAAGCAUCAAAG (SEQ ID NO: 27). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 980% identical, at least 99% identical, at least 99.5% identical or 100% identical to a sequence isolated or derived from Planctomycetes.

In some embodiments, a CasX reference gNA comprises a sequence isolated or derived from Candidatus Sungbacteria. In some embodiments, the sequence is a CasX tracrRNA sequence. Exemplary CasX reference tracrRNA sequences isolated or derived from Candidatus Sungbacteria may comprise sequences of: GUUUACACACUCCCUCUCAUAGGGU (SEQ ID NO: 28), GUUUACACACUCCCUCUCAUGAGGU (SEQ ID NO: 29), UUUUACAUACCCCCUCUCAUGGGAU (SEQ ID NO: 30) and GUUUACACACUCCCUCUCAUGGGGG (SEQ ID NO: 31). In some embodiments, a CasX reference guide RNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from Candidatus Sungbacteria.

Table 1 provides the sequences of reference gRNAs tracr and scaffold sequences. In some embodiments, the disclosure provides gNA sequences wherein the gNA has a scaffold comprising a sequence having at least one nucleotide modification relative to a reference gNA sequence having a sequence of any one of SEQ ID NOS:4-16 of Table 1. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein, including the sequences of Table 1 and Table 2.

TABLE 1

Reference gRNA sequences

| SEQ ID NO. | Nucleotide Sequence |
|---|---|
| 4 | ACAUCUGGCGCGUUUAUUCCAUUACUUUGGAGCCAGUCCCAGCG ACUAUGUCGUAUGGACGAAGCGCUUAUUUAUCGGAGAGAAACCG AUAAGUAAAACGCAUCAAAG |
| 5 | UACUGGCGCUUUUAUCUCAUUACUUUGAGAGCCAUCACCAGCGA CUAUGUCGUAUGGGUAAAGCGCUUAUUUAUCGGAGAGAAAUCCG AUAAAUAAGAAGCAUCAAAG |
| 6 | ACAUCUGGCGCGUUUAUUCCAUUACUUUGGAGCCAGUCCCAGCG ACUAUGUCGUAUGGACGAAGCGCUUAUUUAUCGGAGA |
| 7 | ACAUCUGGCGCGUUUAUUCCAUUACUUUGGAGCCAGUCCCAGCG ACUAUGUCGUAUGGACGAAGCGCUUAUUUAUCGG |
| 8 | UACUGGCGCUUUUAUCUCAUUACUUUGAGAGCCAUCACCAGCGA CUAUGUCGUAUGGGUAAAGCGCUUAUUUAUCGGAGA |

TABLE 1-continued

Reference gRNA sequences

| SEQ ID NO. | Nucleotide Sequence |
|---|---|
| 9 | UACUGGCGCUUUUAUCUCAUUACUUUGAGAGCCAUCACCAGCGACUAUGUCGUAUGGGUAAAGCGCUUAUUUAUCGG |
| 10 | GUUUACACACUCCCUCUCAUAGGGU |
| 11 | GUUUACACACUCCCUCUCAUGAGGU |
| 12 | UUUUACAUACCCCCUCUCAUGGGAU |
| 13 | GUUUACACACUCCCUCUCAUGGGGG |
| 14 | CCAGCGACUAUGUCGUAUGG |
| 15 | GCGCUUAUUUAUCGGAGAGAAAUCCGAUAAAUAAGAAGC |
| 16 | GGCGCUUUUAUCUCAUUACUUUGAGAGCCAUCACCAGCGACUAUGUCGUAUGGGUAAAGCGCUUAUUUAUCGGA | g. gNA Variants

In another aspect, the disclosure relates to guide nucleic acid variants (referred to herein alternatively as "gNA variant" or "gRNA variant"), which comprise one or more modifications relative to a reference gRNA scaffold. As used herein, "scaffold" refers to all parts to the gNA necessary for gNA function with the exception of the spacer sequence.

In some embodiments, a gNA variant comprises one or more nucleotide substitutions, insertions, deletions, or swapped or replaced regions relative to a reference gRNA sequence of the disclosure. In some embodiments, a mutation can occur in any region of a reference gRNA to produce a gNA variant. In some embodiments, the scaffold of the gNA variant sequence has at least 20%, at least 30%, at least 40%, at least 50%, at least 60%, or at least 70%, at least 80%, at least 85%, at least about 90%, at least about 95%, at least about 96%, at least about 97%, at least about 98%, or at least about 99% identity to the sequence of SEQ ID NO:4 or SEQ ID NO:5.

In some embodiments, a gNA variant comprises one or more nucleotide changes within one or more regions of the reference gRNA that improve a characteristic of the reference gRNA. Exemplary regions include the RNA triplex, the pseudoknot, the scaffold stem loop, and the extended stem loop. In some cases, the variant scaffold stem further comprises a bubble. In other cases, the variant scaffold further comprises a triplex loop region. In still other cases, the variant scaffold further comprises a 5' unstructured region. In one embodiment, the gNA variant scaffold comprises a scaffold stem loop having at least 60% sequence identity to SEQ ID NO:14. In another embodiment, the gNA variant comprises a scaffold stem loop having the sequence of CCAGCGACUAUGUCCUAGUGG (SEQ ID NO: 32). In another embodiment, the disclosure provides a gNA scaffold comprising, relative to SEQ ID NO:5, a C18G substitution, a G55 insertion, a U1 deletion, and a modified extended stem loop in which the original 6 nt loop and 13 most-loop-proximal base pairs (32 nucleotides total) are replaced by a Uvsx hairpin (4 nt loop and 5 loop-proximal base pairs; 14 nucleotides total) and the loop-distal base of the extended stem was converted to a fully base-paired stem contiguous with the new Uvsx hairpin by deletion of the A99 and substitution of G64U. In the foregoing embodiment, the gNA scaffold comprises the sequence (SEQ ID NO: 2238)
ACUGGCGCUUUUAUCUGAUUACUUUGAGAGCCAUCACCAGCGACUAUGUC

GUAGUGGGUAAAGCUCCCUCUUCGGAGGGAGCAUCAAAG.

All gNA variants that have one or more improved functions or characteristics, or add one or more new functions when the variant gNA is compared to a reference gRNA described herein, are envisaged as within the scope of the disclosure. A representative example of such a gNA variant is guide 174 (SEQ ID NO:2238), the design of which is described in the Examples. In some embodiments, the gNA variant adds a new function to the RNP comprising the gNA variant. In some embodiments, the gNA variant has an improved characteristic selected from: improved stability; improved solubility; improved transcription of the gNA; improved resistance to nuclease activity; increased folding rate of the gNA; decreased side product formation during folding; increased productive folding; improved binding affinity to a CasX protein; improved binding affinity to a target DNA when complexed with a CasX protein; improved gene editing when complexed with a CasX protein; improved specificity of editing when complexed with a CasX protein; and improved ability to utilize a greater spectrum of one or more PAM sequences, including ATC, CTC, GTC, or TTC, in the editing of target DNA when complexed with a CasX protein, or any combination thereof. In some cases, the one or more of the improved characteristics of the gNA variant is at least about 1.1 to about 100,000-fold improved relative to the reference gNA of SEQ ID NO:4 or SEQ ID NO:5. In other cases, the one or more improved characteristics of the gNA variant is at least about 1.1, at least about 10, at least about 100, at least about 1000, at least about 10,000, at least about 100,000-fold or more improved relative to the reference gNA of SEQ ID NO:4 or SEQ ID NO:5. In other cases, the one or more of the improved characteristics of the gNA variant is about 1.1 to 100,000-fold, about 1.1 to 10,000-fold, about 1.1 to 1,000-fold, about 1.1 to 500-fold, about 1.1 to 100-fold, about 1.1 to 50-fold, about 1.1 to 20-fold, about 10 to 100,000-fold, about 10 to 10,000-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,000-fold, about 100 to 10,000-fold, about 100 to 1,000-fold, about 100 to 500-fold, about 500 to 100,000-fold, about 500 to 10,000-fold, about 500 to 1,000-fold, about 500 to 750-fold, about 1,000 to 100,000-fold, about 10,000 to 100,000-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference gNA of SEQ ID NO:4 or SEQ ID NO:5. In other cases, the one or more improved characteristics of the gNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475- fold, or 5(K)-fold improved relative to the reference gNA of SEQ ID NO:4 or SEQ ID NO:5.

In some embodiments, a gNA variant can be created by subjecting a reference gRNA to a one or more mutagenesis methods, such as the mutagenesis methods described herein, below, which may include Deep Mutational Evolution (DME), deep mutational scanning (DMS), error prone PCR, cassette mutagenesis, random mutagenesis, staggered extension PCR, gene shuffling, or domain swapping, in order to generate the gNA variants of the disclosure. The activity of reference gRNAs may be used as a benchmark against which the activity of gNA variants are compared, thereby measuring improvements in function of gNA variants. In other embodiments, a reference gRNA may be subjected to one or more deliberate, targeted mutations, substitutions, or domain swaps in order to produce a gNA variant, for example a rationally designed variant. Exemplary gRNA variants produced by such methods are described in the Examples and representative sequences of gNA scaffolds are presented in Table 2 as SEQ ID NOS: 2101-2285.

In some embodiments, the gNA variant comprises one or more modifications compared to a reference guide nucleic acid scaffold sequence, wherein the one or more modification is selected from: at least one nucleotide substitution in a region of the gNA variant; at least one nucleotide deletion in a region of the gNA variant; at least one nucleotide insertion in a region of the gNA variant; a substitution of all or a portion of a region of the gNA variant; a deletion of all or a portion of a region of the gNA variant; or any combination of the foregoing. In some cases, the modification is a substitution of 1 to 15 consecutive or non-consecutive nucleotides in the gNA variant in one or more regions. In other cases, the modification is a deletion of 1 to 10 consecutive or non-consecutive nucleotides in the gNA variant in one or more regions. In other cases, the modification is an insertion of 1 to 10 consecutive or non-consecutive nucleotides in the gNA variant in one or more regions. In other cases, the modification is a substitution of the scaffold stem loop or the extended stem loop with an RNA stem loop sequence from a heterologous RNA source with proximal 5' and 3' ends. In some cases, a gNA variant of the disclosure comprises two or more modifications in one region. In other cases, a gNA variant of the disclosure comprises modifications in two or more regions. In other cases, a gNA variant comprises any combination of the foregoing modifications described in this paragraph.

In some embodiments, a 5' G is added to a gNA variant sequence for expression in vivo, as transcription from a U6 promoter is more efficient and more consistent with regard to the start site when the +1 nucleotide is a G. In other embodiments, two 5' Gs are added to a gNA variant sequence for in vitro transcription to increase production efficiency, as T7 polymerase strongly prefers a G in the +1 position and a purine in the +2 position. In some cases, the 5' G bases are added to the reference scaffolds SEQ ID NOS: 4-16 as set forth in Table 1. In other cases, the 5' G bases are added to the variant scaffolds of SEQ ID NOS: 2101-2285 as set forth in Table 2.

Table 2 provides exemplary gNA variant scaffold sequences. In Table 2, (−) indicates a deletion at the specified position(s) relative to the reference sequence of SEQ ID NO:5, (+) indicates an insertion of the specified base(s) at the position indicated relative to SEQ ID NO:5, (:) indicates the range of bases at the specified start:stop coordinates of a deletion or substitution relative to SEQ ID NO:5, and multiple insertions, deletions or substitutions are separated by commas; e.g., A14C, U17G. In some embodiments, the gNA variant scaffold comprises any one of the sequences listed in Table 2, SEQ ID NOS:2101-2285, or a sequence having at least about 50%, at least about 60%, at least about 70%, at least about 80%, at least about 90%, at least about 95%, at least about 95%, at least about 96%, at least about 97%, at least about 98%, at least about 99% sequence identity thereto. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein.

TABLE 2

Exemplary gNA Scaffold Sequences

| SEQ ID NO: | NAME or Modification | NUCLEOTIDE SEQUENCE |
|---|---|---|
| 2101 | phage replication stable | UACUGGCGCUUUUAUCUCAUUACUUUGAGAGCCAUCACCAGCGACUAUGUCGUAUG GGUAAAGCGCAGGUGGGACGACCUCUCGGUCGUCCUAUCUGAAGCAUCAAAG |
| 2102 | Kissing loop_b1 | UACUGGCGCUUUUAUCUCAUUACUUUGAGAGCCAUCACCAGCGACUAUGUCGUAUG GGUAAAGCGCUGCUCGACGCGUCCUCGAGCAGAAGCAUCAAAG |
| 2103 | Kissing loop_a | UACUGGCGCUUUUAUCUCAUUACUUUGAGAGCCAUCACCAGCGACUAUGUCGUAUG GGUAAAGCGCUGCUCGCUCCGUUCGAGCAGAAGCAUCAAAG |
| 2104 | 32: uvsX hairpin | GUACUGGCGCUUUUAUCUCAUUACUUUGAGAGCCAUCACCAGCGACUAUGUCGUAU GGGUAAAGCGCCCUCUUCGGAGGGAAGCAUCAAAG |
| 2105 | PP7 | UACUGGCGCUUUUAUCUCAUUACUUUGAGAGCCAUCACCAGCGACUAUGUCGUAUG GGUAAAGCGCAGGAGUUUCUAUGGAAACCCUGAAGCAUCAAAG |
| 2106 | 64: trip mut, extended stem truncation | GUACUGGCGCUUUUAUCUCAUUACUUUGAGAGCCAUCACCAGCGACUAUGUCGUAU GGGUAAAGCGCUUACGGACUUCGGUCCGUAAGAAGCAUCAAAG |
| 2107 | hyperstable tetraloop | UACUGGCGCUUUUAUCUCAUUACUUUGAGAGCCAUCACCAGCGACUAUGUCGUAUG GGUAAAGCGCUGCGCUUGCGCAGAAGCAUCAAAG |
| 2108 | C18G | UACUGGCGCUUUUAUCUGAUUACUUUGAGAGCCAUCACCAGCGACUAUGUCGUAUG GGUAAAGCGCUUAUUUAUCGGAGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2109 | U17G | UACUGGCGCUUUUAUCGCAUUACUUUGAGAGCCAUCACCAGCGACUAUGUCGUAUG<br>GGUAAAGCGCUUAUUUAUCGGAGAGAAAUCCGAUAAAUAAGAAGCAUCAAAG |
| 2110 | CUUCGG loop | UACUGGCGCUUUUAUCUCAUUACUUUGAGAGCCAUCACCAGCGACUAUCUCGUAUG<br>GGUAAAGCGCUUAUUUAUCGGAGACUUCGGUCCGAUAAAUAAGAAGCAUCAAAG |
| 2111 | MS2 | UACUGGCGCUUUUAUCUCAUUACUUUGAGAGCCAUCACCAGCGACUAUGUCGUAUG<br>GGUAAAGCGCACAUGAGGAUUACCCAUGUGAAGCAUCAAAG |
| 2112 | -1, A2G, -78, G77U | GCUGGCGCUUUUAUCUCAUUACUUUGAGAGCCAUCACCAGCGACUAUGUCGUAUGG<br>GUAAAGCGCUUAUUUAUCGUGAGAAAUCCGAUAAAUAAGAAGCAUCAAAG |
| 2113 | QB | UACUGGCGCUUUUAUCUCAUUACUUUGAGAGCCAUCACCAGCGACUAUGUCGUAUG<br>GGUAAAGCGCUGCAUGUCUAAGACAGCAGAAGCAUCAAAG |
| 2114 | 45, 44 hairpin | UACUGGCGCUUUUAUCUCAUUACUUUGAGAGCCAUCACCAGCGACUAUGUCGUAUG<br>GGUAAAGCGCAGGGCUUCGGCCGAAGCAUCAAAG |
| 2115 | U1A | UACUGGCGCUUUUAUCUCAUUACUUUGAGAGCCAUCACCAGCGACUAUGUCGUAUG<br>GGUAAAGCGCAAUCCAUUGCACUCCGGAUUGAAGCAUCAAAG |
| 2116 | A14C, U17G | UACUGGCGCUUUUCUCGCAUUACUUUGAGAGCCAUCACCAGCGACUAUGUCGUAUG<br>GGUAAAGCGCUUAUUUAUCGGAGAGAAAUCCGAUAAAUAAGAAGCAUCAAAG |
| 2117 | CUUCGG loop modified | UACUGGCGCUUUUAUCUCAUUACUUUGAGAGCCAUCACCAGCGACUAUGUCGUAUG<br>GGUAAAGCGCUUAUUUAUCGGACUUCGGUCCGAUAAAVAAGAAGCAUCAAAG |
| 2118 | Kissing loop_b2 | UACUGGCGCUUUUAUCUCAUUACUUUGAGAGCCAUCACCAGCGACUAUCUCGUAUG<br>GGUAAAGCGCUGCUCGUUUGCGGCUACGAGCAGAAGCAUCAAAG |
| 2119 | -76:78, -83:87 | UACUGGCGCUUUUAUCUCAUUACUUUGAGAGCCAUCACCAGCGACUAUGUCGUAUG<br>GGUAAAGCGCUUAUUUAUCGAGAGAUAAAUAAGAAGCAUCAAAG |
| 2120 | -4 | UACGGCGCUUUUAUCUCAUUACUUUGAGAGCCAUCACCAGCGACUAUGUCGUAUGG<br>GUAAAGCGCUUAUUUAUCGGAGAGAAAUCCGAUAAAUAAGAAGCAUCAAAG |
| 2121 | extended stem truncation | UACUGGCGCCUUUUAUCUCAUUACUUUGAGAGCCAUCACCAGCGACUAUGUCGUAU<br>GGGUAAAGCGCUUACGGACUUCGGUCCGUAAGAAGCAUCAAAG |
| 2122 | C55 | UACUGGCGCUUUUAUCUCAUUACUUUGAGAGCCAUCACCAGCGACUAUGUCGUAUC<br>GGUAAAGCGCUUAUUUAUCGGAGAGAAAUCCGAUAAAVAAGAAGCAUCAAAG |
| 2123 | trip mut | UACUGGCGCCUUUAUCUCAUUACUUUGAGAGCCAUCACCAGCGACUAUGUCGUAUG<br>GGUAAAGCGCUUAUUUAUCGGACUUCGGUCCGAUAAAUAAGAAGCAUCAAAG |
| 2124 | -76:78 | UACUGGCGCUUUUAUCUCAUUACUUUGAGAGCCAUCACCAGCGACUAUGUCGUAUG<br>GGUAAAGCGCUUAUUUAUCGAGAAAUCCGAUAAAUAAGAAGCAUCAAAG |
| 2125 | -1:5 | GCGCUUUUAUCUCAUUACUUUGAGAGCCAUCACCAGCGACUAUGUCGUAUGGGUAA<br>AGCGCUUAUUUAUCGGAGAGAAAUCCGAUAAAUAAGAAGCAUCAAAG |
| 2126 | -83:87 | UACUGGCGCUUUUAUCUCAUUACUUUGAGAGCCAUCACCAGCGACUAUGUCGUAUG<br>GGUAAAGCGCUUAUUUAUCGGAGAGAGAUAAAUAAGAAGCAUCAAAG |
| 2127 | =+G28, A82U, -84, | UACUGGCGCUUUUAUCUCAUUACUUUGGAGAGCCAUCACCAGCGACUAUGUCGUAU<br>GGGUAAAGCGCUUAUUUAUCGGAGAGUAUCCGAUAAAUAAGAAGCAUCAAAG |
| 2128 | =+51U | UACUGGCGCUUUUAUCUCAUUACUUUGAGAGCCAUCACCAGCGACUAUGUUCGUAU<br>GGGUAAAGCGCUUAUUUAUCGGAGAGAAAUCCGAUAAAUAAGAAGCAUCAAAG |
| 2129 | -1:4, +G5A, +G86, | AGCGCUUUUAUCUCAUUACUUUGAGAGCCAUCACCAGCGACUAUGUCGUAUGGGUA<br>AAGCGCUUAUUUAUCGGAGAGAAAUGCCGAUAAAUAAGAAGCAUCAAAG |
| 2130 | =+A94 | UACUGGCGCUUUUAUCUCAUUACUUUGAGAGCCAUCACCAGCGACUAUGUCGUAUG<br>GGUAAAGCGCUUAUUUAUCGGAGAGAAAUCCGAUAAAUAAGAAGCAUCAAAG |
| 2131 | =+G72 | UACUGGCGCUUUUAUCUCAUUACUUUGAGAGCCAUCACCAGCGACUAUGUCGUAUG<br>GGUAAAGCGCUUAUUUGUAUCGGAGAGAAAUCCGAUAAAUAAGAAGCAUCAAAG |
| 2132 | shorten front, CUUCGG loop modified, extend extended | GCGCUUUUAUCUCAUUACUUUGAGAGCCAUCACCAGCGACUAUGUCGUAUGGGUAA<br>AGCGCUUAUUUAUCGGACUUCGGUCCGAUAAAUAAGCGCAUCAAAG |

TABLE 2-continued

Exemplary gNA Scaffold Sequences

| SEQ ID NO: | NAME or Modification | NUCLEOTIDE SEQUENCE |
|---|---|---|
| 2133 | A14C | UACUGGCGCUUUUCUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAG |
| 2134 | -1:3, +G3 | GUGGCGCUUUUAUCUCAUUACUUUGAGAGCCAUCACCAGCGACUAUGUCGUAUGGG UAAAGCGCUUAUUUAUCGGAGAGAAAUCCGAUAAAUAAGAAGCAUCAAAG |
| 2135 | =+C45, +U46 | UACUGGCGCUUUUAUCUCAUUACUUUGAGAGCCAUCACCAGCGACCUUAUGUCGUA UGGGUAAAGCGCUUAUUUAUCGGAGAGAAAUCCGAUAAAUAAGAAGCAUCAAAG |
| 2136 | CUUCGG loop modified, fun start | GAUGGCGCUUUUAUCUCAUUACUUUGAGAGCCAUCACCAGCGACUAUGUCGUAUGG GUAAAGCGCUUAUUUAUCGGACUUCGGUCCGAUAAAUAAGAASCAUCAAAG |
| 2137 | -93:94 | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAAGAAGCAUCAAAG |
| 2138 | =+U45 | UACUGGCGCUUUUAUCUCAUUACUUUGAGAGCCAUCACCAGCGAUCUAUGUCGUAU GGGUAAAGCGCUUAUUUAUCGGAGAGAAAUCCGAUAAAUAAGAAGCAUCAAAG |
| 2139 | -69, -94 | UACUGGCGCUUUUAUCUCAUUACUUUGAGAGCCAUCACCAGCGACUAUGUCGUAUG GGUAAAGGCUUAUUUAUCGGAGAGAAAUCCGAUAAAAGAAGCAUCAAAG |
| 2140 | -94 | UACUGGCGCUUUUAUCUCAUUACUUUGAGAGCCAUCACCAGCGACUAUGUCGUAUG GGUAAAGCGCUUAUUUAUCGGAGACAAAUCCGAUAAAAAGAAGCAUCAAAG |
| 2141 | modified CUUCGG, minus U in 1st triplex | UACUGGCGCUUUAUCUCAUUACUUUGAGAGCCAUCACCAGCGACUAUGUCGUAUGG GUAAAGCGCUUAUUUAUCGGACUUCGGUCCGAUAAAUAAGAAGCAUCAAAG |
| 2142 | -1:4, +C4, A14C, U17G, +G72, -76:78, -83:87 | CGGCGCUUUUCUCGCAUUACUUUGAGAGCCAUCACCAGCGACUAUGUCGUAUGGGU AAAGCGCUUAUUGUAUCGAGAGAUAAAUAAGAAGCAUCAAAG |
| 2143 | U1C, -73 | CACUGGCGCUUUUAUCUCAUUACUUUGAGAGCCAUCACCAGCGACUAUGUCGUAUG GGUAAAGCGCUAUUUUCGGAGAGAAAUCCGAUAAAUAAGAAGCAUCAAAG |
| 2144 | Scaffold uuCG, stem uuCG. Stem swap, 1 shorten | UACUGGCGCUUUUAUCUCAUUACUUUGAGAGCCAUCACCAGCGACUUCGGUCGUAUG GGUAAAGCGCUUAUGUAUCGGCUUCGGCCGAUACAUAAGAAGCAUCAAAG |
| 2145 | Scaffold uuCG, stem uuCG. Stem swap | UACUGGCGCUUUUAUCUCAUUACUUUGAGAGCCAUCACCAGCGACUUCGGUCGUAU GGGUAAAGCGCUUAUGUAUCGGCUUCGGCCGAUACAUAAGAAGCAUCAAAG |
| 2146 | =+G60 | UACUGGCGCUUUUAUCUCAUUACUUUGAGAGCCAUCACCAGCGACUAUGUCGUAUG GGUGAAAGCGCUUAUUUAUCGGAGAGAAAUCCGAUAAAUAAGAAGCAUCAAAG |
| 2147 | no stem Scaffold uuCG | UACUGGCGCUUUUAUCUCAUUACUUUGAGAGCCAUCACCAGCGACUUCGGUCGUAU GGGUAAAG |
| 2148 | no stem Scaffold uuCG, fun start | GAUGGGCUUUUAUCUCAUUACUUUGAGAGCCAUCACCAGCGACUUCGGUCGUAUGG GUAAAG |
| 2149 | Scaffold uuCG, stem uuCG, fun start | GAUGGGCUUUUAUCUCAUUACUUUGAGAGCCAUCACCAGCGACUUCGGUCGUAUGG CUAAAGCGCUUAUUUAUCGGCUUCGGCCGAUAAAUAAGAAGCAUCAAAG |
| 2150 | Pseudoknots | UACUGGCGCUUUUAUCUCAUUACUUUGAGAGCCAUCACCAGCGACUAUGUCGUAUG GGUAAAGCGCUACACUGGGAUCGCUGAAUUAGAGAUCGGCGUCCUUUCAUUCUAUA UACUUUGGAGUUUUAAAAUGUCUCUAAGUACAGAAGCAUCAAAG |
| 2151 | Scaffold uuCG, stem uuCG | GGCGCUUUAUCUCAUUACUUUGAGAGCCAUCACCAGCGACUUCGGUCGUAUGGGU AAAGCGCUUAUUUAUCGGCUUCGGCCGAUAAAUAAGAAGCAUCAAAG |
| 2152 | Scaffold uuCG, stem uuCG, no start | GCUGGCGCUUUUAUCUCAUUACUUUGAGAGCCAUCACCAGCGACUUCGGUCGUAUG GGUAAAGCCCUUAUUUAUCGGCUUCGGCCGAUAAAUAAGAAGCAUCAAAG |
| 2153 | Scaffold uuCG | UACUGGCGCUUUUAUCUCAUUACUUUGAGAGCCAUCACCAGCGACUUCGGUCGUAU GGGUAAAGCGCUUAUUUAUCGGAGAGAAAUCCGAUAAAUAAGAAGCAUCAAAG |
| 2154 | =+GCUC36 | UACUGGCGCUUUUAUCUCAUUACUUUGAGAGCCAUGCUCCACCAGCGACUAUGUCG UAUGGGUAAAGCGCUUAUUUAUCGGAGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2155 | G quadriplex telomere basket + ends | UACUGGCGCUUUUAUCUCAUUACUUUGAGAGCCAUCACCAGCGACUAUGUCGUAUG GGUAAAGCGGGGUUAGGGUUAGGGUUAGGGAAGCAUCAAAG |
| 2156 | G quadriplex M3q | UACUGGCGCUUUUAUCUCAUUACUUUGAGAGCCAUCACCAGCGACUAUGUCGUAUG GGUAAAGCGGAGGGAGGGAGGGAGAGGGAAAGCAUCAAAG |
| 2157 | G quadriplex telomere basket no ends | UACUGGCGCUUUUAUCUCAUUACUUUGAGAGCCAUCACCAGCGACUAUCUCGUAUG GGUAAAGCGUUGGGUUAGGGUUAGGGUUAGGGAAAAGCAUCAAAG |
| 2158 | 45, 44 hairpin (old version) | UACUGGCGCUUUUAUCUCAUUACUUUGAGAGCCAUCACCAGCGACUAUGUCGUAUG GGUAAAGCGC--------AGGGCUUCGGCCG---------GAAGCAUCAAAG |
| 2159 | Sarcin-ricin loop | UACUGGCGCUUUUAUCUCAUUACUUUGAGAGCCAUCACCAGCGACUAUGUCGUAUG GGUAAAGCGCCUGCUCAGUACGAGAGGAACCGCAGGAAGCAUCAAAG |
| 2160 | uvsX, C18G | UACUGGCGCUUUUAUCUGAUUACUUUGAGAGCCAUCACCAGCGACUAUGUCGUAUG GGUAAAGCGCCCUCUUCGGAGGGAAGCAUCAAAG |
| 2161 | truncated stem loop, C18G, trip mat (U10C) | UACUGGCGCCUUUUAUCUGAUUACUUUGAGAGCCAUCACCAGCGACUAUGUCGUAUG GGUAAAGCGCUUACGGACUUCGGUCCGUAAGAAGCAUCAAAG |
| 2162 | short phage rep, C18G | UACUGGCGCUUUUAUCUGAUUACUUUGAGAGCCAUCACCAGCGACUAUGUCGUAUG GGUAAAGCGCGGACGACCUCUCGGUCGUCCGAAGCAUCAAAG |
| 2163 | phage rep loop, C18G | UACUGGCGCUUUUAUCUGAUUACUUUGAGAGCCAUCACCAGCGACUAUGUCGUAUG GGUAAAGCGCAGGUGGGACGACCUCUCGGUCGUCCUAUCUGAAGCAUCAAAG |
| 2164 | =+G18, stacked onto 64 | UACUGGCGCCUUUUAUCUGCAUUACUUUGAGAGCCAUCACCAGCGACUAUGUCGUAU GGGUAAAGCGCUUACGGACUUCGGUCCGUAAGAAGCAUCAAAG |
| 2165 | truncated stem loop, C18G, -1 A2G | GCUGGCGCUUUUAUCUGAUUACUUUGAGAGCCAUCACCAGCGACUAUGUCGUAUGG GUAAAGCGCUUACGGACUUCGGUCCGUAAGAAGCAUCAAAG |
| 2166 | phage rep loop, C18G, trip mut (U10C) | UACUGGCGCCUUUUAUCUGAUUACUUUGAGAGCCAUCACCAGCGACUAUGUCGUAUG GGUAAAGCGCAGGUGGGACGACCUCUCGGUCGUCCUAUCUGAAGCAUCAAAG |
| 2167 | short phage rep, C18G, trip mut (U10C) | UACUGGCGCCUUUUAUCUGAUUACUUUGAGAGCCAUCACCAGCGACUAUGUCGUAUG GGUAAAGCGCGGACGACCUCUCGGUCGUCCGAAGCAUCAAAG |
| 2168 | avsX, trip mut (U10C) | UACUGGCGCCUUUUAUCUCAUUACUUUGAGAGCCAUCACCAGCGACUAUGUCGUAUG GGUAAAGCGCCCUCUUCGGAGGGAAGCAUCAAAG |
| 2169 | truncated stem loop | UACUGGCGCUUUUAUCUCAUUACUUUGAGAGCCAUCACCAGCGACUAUGUCGUAUG GGUAAAGCGCUUACGGACUUCGGUCCGUAAGAAGCAUCAAAG |
| 2170 | =+A17, stacked onto 64 | UACUGGCGCCUUUAUCAUCAUUACUUUGAGAGCCAUCACCAGCGACUAUGUCGUAU GGGUAAAGCGCUUACGGACUUCGGUCCGUAAGAAGCAUCAAAG |
| 2171 | 3' HDV genomic ribozyme | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGGGCC GGCAUGGUCCCAGCCUCCUCGCUGGCGCCGGCUGGGCAACAUUCCGAGGGGACCGU CCCCUCGGUAAUGGCGAAUGGGACCC |
| 2172 | phage rep loop, top mut (U10C) | UACUGGCGCCUUUAUCUCAUUACUUUGAGAGCCAUCACCAGCGACUAUGUCGUAUG GGUAAAGCGCAGGUGGGACGACCUCUCGGUCGUCCUAUCUGAAGCAUCAAAG |
| 2173 | -79:80 | UACUGGCGCUUUUAUCUCAUUACUUUGAGAGCCAUCACCAGCGACUAUGUCGUAUG GGUAAAGCGCUUAUUUAUCGGAGAAAUCCGAUAAAUAAGAAGCAUCAAAG |
| 2174 | short phage rep, trip mut (U10C) | UACUGGCGCCUUUAUCUCAUUACUUUGAGAGCCAUCACCAGCGACUAUGUCGUAUG GGUAAAGCGCGGACGACCUCUCGGUCGUCCGAAGCAUCAAAG |
| 2175 | extra truncated stem loop | UACUGGCGCUUUUAUCUCAUUACUUUGAGAGCCAUCACCAGCGACUAUGUCGUAUG GGUAAAGCGCCGGACUUCGGUCCGGAAGCAUCAAAG |
| 2176 | U17G, C18G | UACUGGCGCUUUUAUCGGAUUACUUUGAGAGCCAUCACCAGCGACUAUGUCGUAUG GGUAAAGCGCUUAUUUAUCGGAGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2177 | short phage rep | UACUGGCGCUUUUAUCUCAUUACUUUGAGAGCCAUCACCAGCGACUAUGUCGUAUG GGUAAAGCGCGGACGACCUCUCGGUCGUCCGAAGCAUCAAAG |
| 2178 | uvsX, C18G, -1 A2G | GCUGGCGCUUUUAUCUGAUUACUUUGAGAGCCAUCACCAGCGACUAUGUCGUAUGG GUAAAGCGCCCUCUUCGGAGGGAAGCAUCAAAG |
| 2179 | uvsX, C18G, trip mut (U10C), -1 A2G, HDV -99 G65U | GCUGGCGCCUUUAUCUGAUUACUUUGAGAGCCAUCACCAGCGACUAUGUCGUAUGG GUAAAGCUCCCUCUUCGGAGGGAGCAUCAAAG |
| 2180 | 3' HDV antigenomic ribozyme | UAuUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGGGGU CGGCAUGGCAUCUCCACCUCCUCGCGGUCCGACCUGGGCAUCCGAAGGAGGACGCA CGUCCACUCGGAUGGCUAAGGGAGAGCCA |
| 2181 | uvsX, C18G, trip mat (U10C), -1 A2G, HDV AA(98:99)C | GCUGGCGCCUUUAUCUGAUUACUUUGAGAGCCAUCACCAGCGACUAUGUCGUAUGG GUAAAGCGCCCUCUUCGGAGGGCGCAUCAAAG |
| 2182 | 3' HDV ribozyme (Lior Nissim, Timothy Lu) | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGUUUU GGCCGGCAUGGUCCCAGCCUCCUCGCUGGCGCCGGCUGGGCAACAUGCUUCGGCAU GGCGAAUGGGACCCCGGG |
| 2183 | TAC(1:3)GA, stacked onto 64 | GAUGGCGCCUUUAUCUCAUUACUUUGAGAGCCAUCACCAGCGACUAUGUCGUAUGG GUAAAGCGCUUACGGACUUCGGUCCGUAAGAAGCAUCAAAG |
| 2184 | uvsX, -1 A2G | GCUGGCGCUUUUAUCUGAUUACUUUGAGAGCCAUCACCAGCGACUAUGUCGUAUGG GUAAAGCGCCCUCUUCGGAGGGAAGCAUCAAAG |
| 2185 | truncated stem loop, C18G, trip mut (U10C), -1 A2G, HDV -99 G65U | GCUGGCGCCUUUAUCUGAUUACUUUGAGAGCCAUCACCAGCGACUAUGUCGUAUGG GUAAAGCUCUUACGGACUUCGGUCCGUAAGAGCAUCAAAG |
| 2186 | short phage rep, C18G, trip mut (U10C), -1 A2G, HDV -99 G65U | GCUGGCGCCUUUAUCUGAUUACUUUGAGAGCCAUCACCAGCGACUAUGUCGUAUGG GUAAAGCUCGGACGAGCUCUCGGUCGUCCGAGCAUCAAAG |
| 2187 | 3' sTRSV WT viral Hammerhead ribozyme | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCCUG UCACCGGAUGUGCUUUCCGGUCUGAUGAGUCCGUGAGGACGAAACAGG |
| 2188 | short phage rep, C18G, -1 A2G | GCUGGCGCUUUUAUCUGAUUACUUUGAGAGCCAUCACCAGCGACUAUGUCGUAUGG GUAAAGCGCGGACGACCUCUCGGUCGUCCGAAGCAUCAAAG |
| 2189 | short phage rep, C18G, trip mut (U10C), -1 A2G, 3' genomic HDV | GCUGGCGCCUUUAUCUGAUUACUUUGAGAGCCAUCACCAGCGACUAUGUCGUAUGG GUAAAGCGCGGACGACCUCUCGGUCGUCCGAAGCAUCAAAG |
| 2190 | phage rep loop, C18G, trip mut (U10C), -1 A2G, HDV -99 G65U | GCUGGCGCCUUUAUCUGAUUACUUUGAGAGCCAUCACCAGCGACUAUGUCGUAUGG GUAAAGCUCAGGUGGGACGACCUCUCGGUCGUCCUAUCUGAGCAUCAAAG |
| 2191 | 3' HDV ribozyme (Owen Ryan, Jamie Cate) | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGGAUG GCCGGCAUGGUCCCAGCCUCCUCGCUGGCGCCGGCUGGGCAACACCUUCGGGUGGC GAAUGGGAC |
| 2192 | phage rep loop, C18G, -1 A2G | GCUGGCGCUUUUAUCUGAUUACUUUGAGAGCCAUCACCAGCGACUAUGUCGUAUGG GUAAAGCGCAGGUGGGACGACCUCUCGGUCGUCCUAUCUGAAGCAUCAAAG |
| 2193 | 0.14 | UACUGGCGCUUUUAUCUCAUUACUUUGAGAGCCAUCACCAGCGACUAUGUCGUACU GGGUAAAGCGCUUAUUUAUCGGAGAGAAAUCCGAUAAAUAAGAAGCAUCAAAG |
| 2194 | -78, G77U | UACUGGCGCUUUUAUCUCAUUACUUUGAGAGCCAUCACCAGCGACUAUGUCGUAUG GGUAAAGCGCUUAUUUAUCGUGAGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2195 | | GUACUGGCGCUUUUAUCUCAUUACUUUGAGAGCCAUCACCAGCGACUAUGUCGUAU GGGUAAAGCGCUUAUUUAUCGGAGAGAAAUCCGAUAAAUAAGAAGCAUCAAAG |
| 2196 | short phage rep, -1 A2G | GCUGGCGCUUUUAUCUCAUUACUUUGAGAGCCAUCACCAGCGACUAUGUCGUAUGG GUAAAGCGCGGACGACCUCUCGGUCGUCCGAAGCAUCAAAG |
| 2197 | truncated stem loop, C18G, trip mut (U10C), -1 A2G | GCUGGCGCCUUUAUCUGAUUACUUUGAGAGCCAUCACCAGCGACUAUGUCGUAUGG GUAAAGCGCUUACGGACUUCGGUCCGUAAGAAGCAUCAAAG |
| 2198 | -1, A2G | GCUGGCGCUUUUAUCUCAUUACUUUGAGAGCCAUCACCAGCGACUAUGUCGUAUGG GUAAAGCGCUUAUUUAUCGGAGAGAAAUCCGAUAAAUAAGAAGCAUCAAAG |
| 2199 | truncated stem loop, trip mut (U10C), -1 A2G | GCUGGCGCUUUUAUCUCAUUACUUUGAGAGCCAUCACCAGCGACUAUGUCGUAUGG GUAAAGCGCUUACGGACUUCGGUCCGUAAGAAGCAUCAAAG |
| 2200 | uvsX, C18G, trip mut (U10C), -1 A2G | GCUGGCGCCUUUAUCUGAUUACUUUGAGAGCCAUCACCAGCGACUAUGUCGUAUGG GUAAAGCGCCCUCUUCGGAGGGAAGCAUCAAAG |
| 2201 | phage rep loop, -1 A2G | GCUGGCGCUUUUAUCUCAUUACUUUGAGAGCCAUCACCAGCGACUAUGUCGUAUGG GUAAAGCGCAGGUGGGACGACCUCUCGGUCGUCCUAUCUGAAGCAUCAAAG |
| 2202 | phage rep loop, top mut (U10C), -1 A2G | GCUGGCGCUUUUAUCUCAUUACUUUGAGAGCCAUCACCAGCGACUAUGUCGUAUGG GUAAAGCGCAGGUGGGACGACCUCUCGGUCGUCCUAUCUGAAGCAUCAAAG |
| 2203 | phage rep loop, C18G, trip mut (U10C), -1 A2G | GCUGGCGCUUUUAUCUGAUUACUUUGAGAGCCAUCACCAGCGACUAUGUCGUAUGG GUAAAGCGCAGGUGGGACGACCUCUCGGUCGUCCUAUCUGAAGCAUCAAAG |
| 2204 | truncated stem loop, C18G | UACUGGCGCUUUUAUCUGAUUACUUUGAGAGCCAUCACCAGCGACUAUGUCGUAUC GGUAAAGCGCUUACGGACUUCGGUCCGUAAGAAGCAUCAAAG |
| 2205 | uvsX, trip mut (U10C), -1 A2G | GCUGGCGCUUUUAUCUCAUUACUUUGAGAGCCAUCACCAGCGACUAUGUCGUAUGG GUAAAGCGCCCUCUUCGGAGGGAAGCAUCAAAG |
| 2206 | truncated stem loop, -1 A2G | GCUGGCGCUUUUAUCUCAUUACUUUGAGAGCCAUCACCAGCGACUAUGUCGUAUGG GUAAAGCGCUUACGGACUUCGGUCCGUAAGAAGCAUCAAAG |
| 2207 | short phage rep, trip mut (U10C), -1 A2G | GCUGGCGCUUUUAUCUCAUUACUUUGAGAGCCAUCACCAGCGACUAUGUCGUAUGG GUAAAGCGCGGACGACCUCUCGGUCGUCCGAAGCAUCAAAG |
| 2208 | 5'HDV ribozyme (Owen Ryan, Jamie Cate) | GAUGGCCGGCAUGGUCCCAGCCUCCUCGCUGGCGCCGGCUGGGCAACACCUUCGGG UGGCGAAUGGGACUACUGGCGCUUUUAUCUCAUUACUUUGAGAGCCAUCACCAGCG ACUAUGUCGUAUGGGUAAAGCGCUUAUUUAUCGGAGAGAAAUCCGAUAAAUAAGAA GCAUCAAAG |
| 2209 | 5'HDV genomic ribozyme | GGCCGGCAUGGUCCCAGCCUCCUCGCUGGCGCCGGCUGGGCAACAUUCCGAGGGGA CCGUCCCCUCGGUAAUGGCGAAUGGGACCCUACUGGCGCUUUUAUCUCAUUACUUU GAGAGCCAUCACCAGCGACUAUGUCGUAUGGGUAAAGCGCUUAUUUAUCGGAGAGA AAUCCGAUAAAUAAGAAGCAUCAAAG |
| 2210 | truncated stem loop, C18G, trip mut (U10C), -1 A2G, HDV AA(98:99)C | GCUGGCGCCUUUAUCUGAUUACUUUGAGAGCCAUCACCAGCGACUAUGUCGUAUGG GUAAAGCGCUUACGGACUUCGGUCCGUAAGCGCAUCAAAG |
| 2211 | 5'env25 pistol ribozyme (with an added CUUCGG loop) | CGUGGUUAGGGCCACGUUAAAUAGUUGCUUAAGCCCUAAGCGUUGAUCUUCGGAUC AGGUGCAAUACUGGCGCUUUUAUCUCAUUACUUUGAGAGCCAUCACCAGCGACUAU GUCGUAUGGGUAAAGCGCUUAUUUAUCGGAGAGAAAUCCGAUAAAUAAGAAGCAUC AAAG |
| 2212 | 5'HDV antigenomic ribozyme | GGGUCGGCAUGGCAUCUCCACCUCCUCGCGGUCCGACCUGGGCAUCCGAAGGAGGA CGCACGUCCACUCGGAUGGCUAAGGGAGAGCCAUACUGGCGCUUUUAUCUCAUUAC UUUGAGAGCCAUCACCAGCGACUAUGUCGUAUGGGUAAAGCGCUUAUUUAUCGGAG AGAAAUCCGAUAAAUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2213 | 3' Hammerhead ribozyme (Lior Nissim, Timothy Lu) guide scaffold scar | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCCAG UACUGAUGAGUCCGUGAGGACGAAACGAGUAAGCUCGUCUACUGGCGCUUUUAUCU CAU |
| 2214 | =+A27, stacked onto 64 | UACUGGCGCCUUUAUCUCAUUACUUUGAGAGCCAUCACCAGCGACUAUGUCGUAU GGGUAAAGCGCUUACGGACUUCGGUCCGUAAGAAGCAUCAAAG |
| 2215 | 5'Hammerhead ribozyme (Lior Nissim, Timothy Lu) smaller scar | CGACUACUGAUGAGUCCGUGAGGACGAAACGAGUAAGCUCGUCUAGUCGUACUGGC GCUUUUAUCUCAUUACUUUGAGAGCCAUCACCAGCGACUAUGUCGUAUGGGUAAAG CGCUUAUUUAUCGGAGAGAAAUCCGAUAAAUAAGAAGCAUCAAAG |
| 2216 | phage rep loop, C18G, trip mut (U10C), -1 A2G, HDV AA(98:99)C | GCUGGCGCCUUUAUCUGAUUACUUUGAGAGCCAUCACCAGCGACUAUGUCGUAUGG GUAAAGCGCAGGUGGGACGACCUCUCGGUCGUCCUAUCUGCGCAUCAAAG |
| 2217 | -27, stacked onto 64 | UACUGGCGCCUUUAUCUCAUUACUUUGAGAGCCAUCACCAGCGACUAUGUCGUAUGG GUAAAGCGCUUACGGACUUCGGUCCGUAAGAAGCAUCAAAG |
| 2218 | 3' Hatchet | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCAUU CCUCAGAAAAUGACAAACCUGUGGGGCGUAAGUAGAUCUUCGGAUCUAUGAUCGUG CAGACGUUAAAAUGAGGU |
| 2219 | 3' Hammerhead ribozyme (Lior Nissim, Timothy Lu) | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCGAC UACUGAUGAGUCCGUGAGGACGAAACGAGUAAGCUCGUCUAGUCGCGUGUAGCGAA GCA |
| 2220 | 5' Hatchet | CAUUCCUCAGAAAAUGACAAACCUGUGGGGCGUAAGUAGAUCUUCGGAUCUAUGAU CGUGCAGACGUUAAAAUCAGGUUACUGGCGCUUUUAUCUCAUUACUUUGAGAGCCA UCACCAGCGACUAUGUCGUAUGGGUAAAGCGCUUAUUUAUCGGAGAGAAAUCCGAU AAAUAAGAAGCAUCAAAG |
| 2221 | 5' HDV ribozyme (Lior Nissim, Timothy Lu) | UUUUGGCCGGCAUGGUCCCAGCCUCCUCGCUGGCGCCGGCUGGGCAACAUGCUUCG GCAUGGCGAAUGGGACCCCGGUCAUCUGGCGCUUUUAUCUCAUUACUUUGAGAGCCA UCACCAGCGACUAUGUCGUAUGGGUAAAGCGCUUAUUUAUCGGAGAGAAAUCCGAU AAAUAAGAAGCAUCAAAG |
| 2222 | 5' Hammerhead ribozyme (Lior Nissim, Timothy Lu) | CGACUACUGAUGAGUCCGUGAGGACGAAACGAGUAAGCUCGUCUAGUCGCGUGUAG CGAAGCAUACUGGCGCUUUUAUCUCAUUACUUUGAGAGCCAUCACCAGCGACUAUG UCGUAUGGGUAAAGCGCUUAUUUAUCGGAGAGAAAUCCGAUAAAUAAGAAGCAUCA AAG |
| 2223 | 3' HH15 Minimal Hammerhead ribozyme | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGGGGA GCCCCGCUGAUGAGGUCGGGGAGACCGAAAGGGACUUCGGUCCCUACGGGGCUCCC |
| 2224 | 5' RBMX recruiting motif | CCACCCCCACCACCACCCCCACCCCCACCACCACCCUACUGGCGCUUUUAUCUCAU UACUUUGAGAGCCAUCACCAGCGACUAUGUCGUAUGGGUAAAGCGCUUAUUUAUCG GAGAGAAAUCCGAUAAAUAAGAAGCAUCAAAG |
| 2225 | 3' Hammerhead ribozyme (Lior Nissim, Timothy Lu) smaller scar | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCGAC UACUGAUGAGUCCGUGAGGACGAAACGAGUAAGCUCGUCUAGUCG |
| 2226 | 3' env25 pistol ribozyme (with an added CUUCGG loop) | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGCUUG GUUAGGGCCACGUUAAAUAGUUGCUUAAGCCCUAAGCGUUGAUCUUCGGAUCAGGU GCAA |
| 2227 | 3' Env-9 Twister | UACUGGCGCUUUUAUCUCAUUACUUUGAGAGCCAUCACCAGCGACUAUGUCGUAUG GGUAAAGCGCUUAUUUAUCGGAGAGAAAUCCGAUAAAUAAGAAGCAUCAAAGGGCA AUAAGCGGUUACAAGCCCGCAAAAAUAGCAGAGUAAUGUCGCGAUAGCGCGGCAU UAAUGCAGCUUUAUUG |
| 2228 | =+AUUAUCUC AUUACU25 | UACUGGCGCUUUUAUCUCAUUACUAUUAUCUCAUUACUUUGAGAGCCAUCACCAGC GACUAUGUCGUAUGGGUAAAGCGCUUAUUUAUCGGAGAGAAAUCCGAUAAAUAAGA AGCAUCAAAG |

TABLE 2-continued

Exemplary gNA Scaffold Sequences

| SEQ ID NO: | NAME or Modification | NUCLEOTIDE SEQUENCE |
|---|---|---|
| 2229 | 5' Env-9 Twister | GGCAAUAAAGCGGUUACAAGCCCGCAAAAAUAGCAGAGUAAUGUCGCGAUAGCGCGGCAUUAAUGCAGCUUUAUUGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2230 | 3' Twisted Sister 1 | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGACCCGCAAGGCCGACGGCAUCCUUUUCCUCUGGUGLAAGUCUAGCCGUCCCUUCUGGGGCGGGCGCUCAUGGGUAAC |
| 2231 | no stem | UACUGGCGCUUUUAUCUCAUUACUUUGAGAGCCAUCACCAGCGACUAUGUCGUAUGGGUAAAG |
| 2232 | 5' HH15 Minimal Hammerhead ribozyme | GGGAGCCCCGCUGAUGAGGUCGGGGAGACCGAAAGGGACUUCGGUCCCUACGGGGCUCCCUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2233 | 5' Hammerhead ribozyme (Lior Nissim, Timothy Lu) guide scaffold scar | CCAGUACUGAUGAGUCCGUGAGGACGAAACGAGUAAGCUCGUCUACUGGCGCUUUUAUCUCAUUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCA |
| 2234 | 5' Twisted Sister 1 | ACCCGCAAGGCCGACGGCAUCUGCCGCCGCUGGUGCAAGUCCAGCCGCCCCUUCGGGGGCGGGCGCUCAUGGGUAACUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2235 | 5' sTRSV WT viral Hammerhead ribozyme | CCUGUCACCGGAUGUGCUUUCCGGUCUGAUGAGUCCGUGAGGACGAAACAGGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2236 | 148: =+G55, stacked onto 64 | GUACUGGCGCUUUUAUCUCAUUACUUUGAGAGCCAUCACCAGCGACUAUGUCGUAGUGGGUAAAGCGCUUACGGACUUCGGUCCGUAAGAAGCAUCAAAG |
| 2237 | 158: 103 + 148(+G55) -99, G65U | GUACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2238 | 174: Uvsx Extended stem with [A99] G65U), C18G, ^G55, [GU-1] | ACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2239 | 175: extended stem truncation, U10C, [GU-1] | ACUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2240 | 176: 174 with A1G substitution for T7 transcription | GCUGGCGCUUUUAUCUGAUUACUUUGAGAGCCAUCACCAGCGACUAUGUCGUAGUGGGUAAAGCUCCCUCUUCGGAGGGAGCAUCAAAG |
| 2241 | 177: 174 with bubble (+G55) removed | ACUGGCGCUUUUAUCUGAUUACUUUGAGAGCCAUCACCAGCGACUAUGUCGUAUGGGUAAAGCUCCCUCUUCGGAGGGAGCAUCAAAG |
| 2242 | 181: stem 42 (truncated stem loop); U10C, C18G, [GU-1] (95 + [GU-1]) | ACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2243 | 182: stem 42 (truncated stem loop); C18G, [GU-1] | ACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |

TABLE 2-continued

Exemplary gNA Scaffold Sequences

| SEQ ID NO: | NAME or Modification | NUCLEOTIDE SEQUENCE |
|---|---|---|
| 2244 | 183: stem 42 (truncated stem loop); C18G, ^G55, [GU-1] | ACUGGCGCUUUUAUCUGAUUACUUUGAGAGCCAUCACCAGCGACUAUGUCGUAGUG GGUAAAGCGCUUACGGACUUCGGUCCGUAAGAAGCAUCAAAG |
| 2245 | 184: stem 48 (uvsx, -99 g65t); C18G, ^T55, [GU-1] | ACUGGCGCUUUUAUCUGAUUACUUUGAGAGCCAUCACCAGCGACUAUGUCGUAUUG GGUAAAGCUCCCUCUUCGGAGGGAGCAUCAAAG |
| 2246 | 185: stem 42 (truncated stem loop); C18G, ^U55, [GU-1] | ACUGGCGCUUUUAUCUGAUUACUUUGAGAGCCAUCACCAGCGACUAUGUCGUAUUG GGUAAAGCGCUUACGGACUUCGGUCCGUAAGAAGCAUCAAAG |
| 2247 | 186: stem 42 (truncated stem loop); U10C, ^A17, [GU-1] | ACUGGCGCCUUUAUCAUCAUUACUUUGAGAGCCAUCACCAGCGACUAUGUCGUAUG GGUAAAGCGCUUACGGACUUCGGUCCGUAAGAAGCAUCAAAG |
| 2248 | 187: stem 46 (uvsx); C18G, ^G55, [GU-1] | ACUGGCGCUUUUAUCUGAUUACUUUGAGAGCCAUCACCAGCGACUAUGUCGUAGUG GGUAAAGCGCCCUCUUCGGAGGGAAGCAUCAAAG |
| 2249 | 188: stem 50 (ms2 U15C, -99, g65t); C18G, ^G55, [GU-1] | ACUGGCGCUUUUAUCUGAUUACUUUGAGAGCCAJCACCAGCGACUAUGUCGUAGUG GGUAAAGCUCACAUGAGGAUCACCCAUGUGAGCAUCAAAG |
| 2250 | 189: 174 + G8A; U15C; U35A | ACUGGCACUUUUACCUGAUUACUUUGAGAGCCAACACCAGCGACUAUGUCGUAGUG GGUAAAGCUCCCUCUUCGGAGGGAGCAUCAAAG |
| 2251 | 190: 174 + G8A | ACUGGCACUUUUAUCUGAUUACUUUGAGAGCCAUCACCAGCGACUAUGUCGUAGUG GGUAAAGCUCCCUCUUCGGAGGGAGCAUCAAAG |
| 2252 | 191: 174 + G8C | ACUGGCCCUUUUAUCUGAUUACUUUGAGAGCCAUCACCAGCGACUAUGUCGUAGUG GGUAAAGCUCCCUCUUCGGAGGGAGCAUCAAAG |
| 2253 | 192: 174 + U15C | ACUGGCGCUUUUACCUGAUUACUUUGAGAGCCAUCACCAGCGACUAUGUCGUAGUG GGUAAAGCUCCCUCUUCGGAGGGAGCAUCAAAG |
| 2254 | 193, 174 + U35A | ACUGGCGCUUUUAUCUGAUUACUUUGAGAGCCAACACCAGCGACUAUGUCGUAGUG GGUAAAGCUCCCUCUUCGGAGGGAGCAUCAAAG |
| 2255 | 195: 175 + C18G + G8A; U15C; U35A | ACUGGCACCUUUACCUGAUUACUUUGAGAGCCAACACCAGCGACUAUGUCGUAUGG GUAAAGCGCUUACGGACUUCGGUCCGUAAGAAGCAUCAAAG |
| 2256 | 196: 175 + C18G + G8A | ACUGGCACCUUUAUCUGAUUACUUUGAGAGCCAUCACCAGCGACUAUGUCGUAUGG GUAAAGCGCUUACGGACUUCGGUCCGUAAGAAGCAUCAAAG |
| 2257 | 197: 175 + C18G + G8C | ACUGGCCCUUUUAUCUGAUUACUUUGAGAGCCAUCACCAGCGACUAUGUCGUAUGG GUAAAGCGCUUACGGACUUCGGUCCGUAAGAAGCAUCAAAG |
| 2258 | 198: 175 + C18G + U35A | ACUGGCGCUUUUAUCUGAUUACUUUGAGAGCCAACACCAGCGACUAUGUCGUAUGG GUAAAGCGCUUACGGACUUCGGUCCGUAAGAAGCAUCAAAG |
| 2259 | 199: 174 + A2G (test G transcription at start; ccGCT . . . ) | GCUGGCGCUUUUAUCUGAUUACUUUGAGAGCCAUCACCAGCGACUAUGUCGUAGUG GGUAAAGCUCCCUCUUCGGAGGGAGCAUCAAAG |
| 2260 | 200: 174 + ^G1 (ccGACU . . . ) | GACUGGCGCUUUUAUCUGAUUACUUUGAGAGCCAUCACCAGCGACUAUGUCGUAGU GGGUAAAGCUCCCUCUUCGGAGGGAGCAUCAAAG |
| 2261 | 201: 174 + U10C; ^G28 | ACUGGCGCCUUUAUCUGAUUACUUUGGAGAGCCAUCACCAGCGACUAUGUCGUAGU GGGUAAAGCUCCCUCUUCGGAGGGAGCAUCAAAG |

TABLE 2-continued

Exemplary gNA Scaffold Sequences

| SEQ ID NO: | NAME or Modification | NUCLEOTIDE SEQUENCE |
|---|---|---|
| 2262 | 202: 174 + U10A; A28U | ACUGGCGCAUUUAUCUGAUUACUUUGUGAGCCAUCACCAGCGACUAUGUCGUAGUGGGUAAAGCUCCCUCUUCGGAGGGAGCAUCAAAG |
| 2263 | 203: 174 + U10C | ACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2264 | 204: 174 + ^G28 | ACUGGCGCUUUUAUCUGAUUACUUUGGAGAGCCAUCACCAGCGACUAUGUCGUAGUGGGUAAAGCUCCCUCUUCGGAGGGAGCAUCAAAG |
| 2265 | 205: 174 + U10A | ACUGGCGCAUUUAUCUGAUUACUUUGAGAGCCAUCACCAGCGACUAUGUCGUAGUGGGUAAAGCUCCCUCUUCGGAGGGAGCAUCAAAG |
| 2266 | 206, 174 + A28U | ACUGGCGCUUUUAUCUGAUUACUUUGUGAGCCAUCACCAGCGACUAUGUCGUAGUGGGUAAAGCUCCCUCUUCGGAGGGAGCAUCAAAG |
| 2267 | 207: 174 + ^U15 | ACUGGCGCUUUUAUUCUGAUUACUUUGAGAGCCAUCACCAGCGACUAUGUCGUAGUGGGUAAAGCUCCCUCUUCGGAGGGAGCAUCAAAG |
| 2268 | 208: 174 + [U4] | ACGGCGCUUUUAUCUGAUUACUUUGAGAGCCAUCACCAGCGACUAUGUCGUAGUGGUAAAGCUCCCUCUUCGGAGGGAGCAUCAAAG |
| 2269 | 209: 174 + C16A | ACUGGCGCUUUUAUAUGAUUACUUUGAGAGCCAUCACCAGCGACUAUGUCGUAGUGGGUAAAGCUCCCUCUUCGGAGGGAGCAUCAAAG |
| 2270 | 210: 174 + ^U17 | ACUGGCGCUUUUAUCUUGAUUACUUUGAGAGCCAUCACCAGCGACUAUGUCGUAGUGGGUAAAGCUCCCUCUUCGGAGGGAGCAUCAAAG |
| 2271 | 211: 174 + U35G (compare with 174 + U35A above) | ACUGGCGCUUUUAUCUGAUUACUUUGAGAGCCAGCACCAGCGACUAUGUCGUAGUGGGUAAAGCUCCCUCUUCGGAGGGAGCAUCAAAG |
| 2272 | 212: 174 + U11G, A105G (A86G), U26C | ACUGGCGCUGUUAUCUGAUUACUUCGAGAGCCAUCACCAGCGACUAUGUCGUAGUGGGUAAAGCUCCCUCUUCGGAGGGAGCAUCGAAG |
| 2273 | 213: 174 + U11C, A105G (A86G), U26C | ACUGGCGCUCUUAUCUGAUUACUUCGAGAGCCAUCACCAGCGACUAUGUCGUAGUGGGUAAAGCUCCCUCUUCGGAGGGAGCAUCGAAG |
| 2274 | 214: 174 + U12G; A106G (A87G), U25C | ACUGGCGCUUGUAUCUGAUUACUCGAGAGCCAUCACCAGCGACUAUGUCGUAGUGGGUAAAGCUCCCUCUUCGGAGGGAGCAUCAGAG |
| 2275 | 215: 174 + U12C; A106G (A87G), U25C | ACUGGCGCUUCUAUCUGAUUACUCGAGAGCCAUCACCAGCGACUAUGUCGUAGUGGGUAAAGCUCCCUCUUCGGAGGGAGCAUCAGAG |
| 2276 | 216: 174_tx_11.G, 87.G, 22.C | ACUGGCGCUUUGAUCUGAUUACCUUGAGAGCCAUCACCAGCGACUAUGUCGUAGUGGGUAAAGCUCCCUCUUCGGAGGGAGCAUCAAGG |
| 2277 | 217: 174_tx_11.C, 87.G, 22.C | ACUGGCGCUUUCAUCUGAUUACCUUGAGAGCCAUCACCAGCGACUAUGUCGUAGUGGGUAAAGCUCCCUCUUCGGAGGGAGCAUCAAGG |
| 2278 | 218: 174 + U11G | ACUGGCGCUGUUAUCUGAUUACUUUGAGAGCCAUCACCAGCGACUAUGUCGUAGUGGGUAAAGCUCCCUCUUCGGAGGGAGCAUCAAAG |
| 2279 | 219: 174 + A105G (A86G) | ACUGGCGCUUUUAUCUGAUUACUUUGAGAGCCAUCACCAGCGACUAUGUCGUAGUGGGUAAAGCUCCCUCUUCGGAGGGAGCAUCGAAG |
| 2280 | 220; 174 + U26C | ACUGGCGCUUUUAUCUGAUUACUUCGAGAGCCAUCACCAGCGACUAUGUCGUAGUGGGUAAAGCUCCCUCUUCGGAGGGAGCAUCAAAG |
| 2281 | 221: 182 + G8A (196) + 215 mutations + ^C63, A88G | ACUGGCACUUCUAUCUGAUUACUCUGAGAGCCAUCACCAGCGACUAUGUCGUAUGGGUAAAGCCGCUUACGGACUUCGGUCCGUAAGAGGCAUCAGAG |
| 2282 | 222: 174 + G8A (196) + 215 mutations | ACUGGCACUUCUAUCUGAUUACUCUGAGAGCCAUCACCAGCGACUAUGUCGUAGUGGGUAAAGCUCCCUCUUCGGAGGGAGCAUCAGAG |

TABLE 2-continued

Exemplary gNA Scaffold Sequences

| SEQ ID NO: | NAME or Modification | NUCLEOTIDE SEQUENCE |
|---|---|---|
| 2283 | 223: 181 + G8A (196) + ^C63, A88G | ACUGGCACCUUUAUCUGAUUACUUUGAGAGCCAUCACCAGCGACUAUGUCGUAUGG GUAAAGCCGCUUACGGACUUCGGUCCGUAAGAGGCAUCAAAG |
| 2284 | 224: 182 + G8A (196) + 214 mutations + ^C63, A88G | ACUGGCACUUGUAUCUGAUUACUCUGAGAGCCAUCACCAGCGACUAUGUCGUAUGG GUAAAGCCGCUUACGGACUUCGGUUUUUAAGAGGCAUCAGAG |
| 2285 | 225: 174 + G8A (196) + 214 mutations | ACUGGCACUUGUAUCUGAUUACUCUGAGAGCCAUCACCAGCGACUAUGUCGUAGUG GGUAAAGCUCCCUCUUCGGAGGGAGCAUCAGAG |

In some embodiments, the gNA variant comprises a tracrRNA stem loop comprising the sequence -UUU-N4-25-UUU- (SEQ ID NO: 381). For example, the gNA variant comprises a scaffold stem loop or a replacement thereof, flanked by two triplet U motifs that contribute to the triplex region. In some embodiments, the scaffold stem loop or replacement thereof comprises at least 4 nucleotides, at least 5 nucleotides, at least 6 nucleotides, at least 7 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides.

In some embodiments, the gNA variant comprises a crRNA sequence with -AAAG- in a location 5' to the spacer region. In some embodiments, the -AAAG- sequence is immediately 5' to the spacer region.

In some embodiments, the at least one nucleotide modification to a reference gNA to produce a gNA variant comprises at least one nucleotide deletion in the CasX variant gNA relative to the reference gRNA. In some embodiments, a gNA variant comprises a deletion of 1, 2, 3, 4, 5, 6, 7, 8, 9, 10, 11, 12, 13, 14, 15, 16, 17, 18, 19 or 20 consecutive or non-consecutive nucleotides relative to a reference gNA. In some embodiments, the at least one deletion comprises a deletion of 1, 2, 3, 4, 5, 6, 7, 8, 9, 10, 11, 12, 13, 14, 15, 16, 17, 18, 19 or 20 or more consecutive nucleotides relative to a reference gNA. In some embodiments, the gNA variant comprises 2, 3, 4, 5, 6, 7, 8, 9, 10, 11, 12, 13, 14, 15, 16, 17, 18, 19 or 20 or more nucleotide deletions relative to the reference gNA, and the deletions are not in consecutive nucleotides. In those embodiments where there are two or more non-consecutive deletions in the gNA variant relative to the reference gRNA, any length of deletions, and any combination of lengths of deletions, as described herein, are contemplated as within the scope of the disclosure. In some embodiments, a gNA variant comprises at least two deletions in different regions of the reference gRNA. In some embodiments, a gNA variant comprises at least two deletions in the same region of the reference gRNA. For example, the regions may be the extended stem loop, scaffold stem loop, scaffold stem bubble, triplex loop, pseudoknot, triplex, or a 5' end of the gNA variant. The deletion of any nucleotide in a reference gRNA is contemplated as within the scope of the disclosure.

In some embodiments, the at least one nucleotide modification of a reference gRNA to generate a gNA variant comprises at least one nucleotide insertion. In some embodiments, a gNA variant comprises an insertion of 1, 2, 3, 4, 5, 6, 7, 8, 9 or 10 consecutive or non-consecutive nucleotides relative to a reference gRNA. In some embodiments, the at least one nucleotide insertion comprises an insertion of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more insertions relative to the reference gRNA, and the insertions are not consecutive. In those embodiments where there are two or more non-consecutive insertions in the gNA variant relative to the reference gRNA, any length of insertions, and any combination of lengths of insertions, as described herein, are contemplated as within the scope of the disclosure. For example, in some embodiments, a gNA variant may comprise a first insertion of one nucleotide, and a second insertion of two nucleotides and the two insertions are not consecutive. In some embodiments, a gNA variant comprises at least two insertions in different regions of the reference gRNA. In some embodiments, a gNA variant comprises at least two insertions in the same region of the reference gRNA. For example, the regions may be the extended stem loop, scaffold stem loop, scaffold stem bubble, triplex loop, pseudoknot, triplex, or a 5' end of the gNA variant. Any insertion of A, G, C, U (or T, in the corresponding DNA) or combinations thereof at any location in the reference gRNA is contemplated as within the scope of the disclosure.

In some embodiments, the at least one nucleotide modification of a reference gRNA to generate a gNA variant comprises at least one nucleic acid substitution. In some embodiments, a gNA variant comprises 1, 2, 3, 4, 5, 6, 7, 8, 9, 10, 11, 12, 13, 14, 15, 16, 17, 18, 19 or 20 or more consecutive or non-consecutive substituted nucleotides relative to a reference gRNA. In some embodiments, a gNA variant comprises 1-4 nucleotide substitutions relative to a reference gRNA. In some embodiments, the at least one substitution comprises a substitution of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more substitutions relative to the reference gRNA, and the substitutions are not consecutive. In those embodiments where there are two or more non-consecutive substitutions in the gNA variant relative to the reference gRNA, any length of substituted nucleotides, and any combination of lengths of substituted nucleotides, as described herein, are contemplated as within the scope of the disclosure. For example, in some embodiments, a gNA variant may comprise a first substitution of one nucleotide, and a second substitution of two nucleotides and the two substitutions are not consecutive. In some embodiments, a gNA variant comprises at least two substitutions in different regions of the reference gRNA. In some embodiments, a gNA variant comprises at least two substitutions in the same region of the reference gRNA. For example, the regions may be the triplex, the extended stem loop, scaffold stem loop, scaffold stem bubble, triplex loop, pseudoknot, triplex, or a 5' end of the gNA variant. Any substitution of A, G, C. U (or T, in the corresponding DNA) or combinations thereof at any location in the reference gRNA is contemplated as within the scope of the disclosure.

Any of the substitutions, insertions and deletions described herein can be combined to generate a gNA variant of the disclosure. For example, a gNA variant can comprise at least one substitution and at least one deletion relative to a reference gRNA, at least one substitution and at least one insertion relative to a reference gRNA, at least one insertion and at least one deletion relative to a reference gRNA, or at least one substitution, one insertion and one deletion relative to a reference gRNA.

In some embodiments, the gNA variant comprises a scaffold region at least 20% identical, at least 30% identical, at least 40% identical, at least 50% identical, at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to any one of SEQ ID NOS:4-16. In some embodiments, the gNA variant comprises a scaffold region at least 60% homologous (or identical) to any one of SEQ ID NOS:4-16.

In some embodiments, the gNA variant comprises a tracr stem loop at least 60% identical, at least 65% identical, at least 70% identical, at least 75% identical, at least 80% identical, at least 85% identical, at least 90% identical, or at least 95% identical to SEQ ID NO:14. In some embodiments, the gNA variant comprises a tracr stem loop at least 60% homologous (or identical) to SEQ ID NO:14.

In some embodiments, the gNA variant comprises an extended stem loop at least 60% identical, at least 65% identical, at least 70% identical, at least 75% identical, at least 80% identical, at least 85% identical, at least 90% identical, or at least 95% identical to SEQ ID NO:15. In some embodiments, the gNA variant comprises an extended stem loop at least 60% homologous (or identical) to SEQ ID NO:15.

In some embodiments, the gNA variant comprises an exogenous extended stem loop, with such differences from a reference gNA described as follows. In some embodiments, an exogenous extended stem loop has little or no identity to the reference stem loop regions disclosed herein (e.g., SEQ ID NO:15). In some embodiments, an exogenous stem loop is at least 10 bp, at least 20 bp, at least 30 bp, at least 40 bp, at least 50 bp, at least 60 bp, at least 70 bp, at least 80 bp, at least 90 bp, at least 100 bp, at least 200 bp, at least 300 bp, at least 400 bp, at least 500 bp, at least 600 bp, at least 700 bp, at least 800 bp, at least 900 bp, at least 1,000 bp, at least 2,000 bp, at least 3,000 bp, at least 4,000 bp, at least 5,000 bp, at least 6,000 bp, at least 7,000 bp, at least 8,000 bp, at least 9,000 bp, at least 10,000 bp, at least 12,000 bp, at least 15,000 bp or at least 20,000 bp. In some embodiments, the gNA variant comprises an extended stem loop region comprising at least 10, at least 100, at least 500, at least 1000, or at least 10,000 nucleotides. In some embodiments, the heterologous stem loop increases the stability of the gNA. In some embodiments, the heterologous RNA stem loop is capable of binding a protein, an RNA structure, a DNA sequence, or a small molecule. In some embodiments, an exogenous stem loop region replacing the stem loop comprises an RNA stem loop or hairpin in which the resulting gNA has increased stability and, depending on the choice of loop, can interact with certain cellular proteins or RNA. Such exogenous extended stem loops can comprise, for example a thermostable RNA such as MS2 (ACAUGAGGAUUACCCAUGU (SEQ ID NO: 35)), Qβ (UGCAUGUCUAAGACAGCA (SEQ ID NO: 36)), U1 hairpin II (AAUCCAUUGCACUCCGGAUU (SEQ ID NO: 37)), Uvsx (CCUCUUCGGAGG (SEQ ID NO: 38)), PP7 (AGAAGUUUCUAUGGAAACCCU (SEQ ID NO: 39)), Phage replication loop (AGGUGGGACGACCUCUCGGU-CGUCCUAUCU (SEQ ID NO: 40)), Kissing loop_a (UG-CUCGCUCCGUUCGAGCA (SEQ ID NO: 41)), Kissing loop_b1 (UGCUCGACGCGUCCUCGAGCA (SEQ ID NO: 42)), Kissing loop_b2 (UGCUCGUUUGCGGC-UACGAGCA (SEQ ID NO: 43)), G quadriplex M3q (AGG-GAGGGAGGGAGAGG (SEQ ID NO: 44)), G quadriplex telomere basket (GGUUAGGGUUAGGGUUAGG (SEQ ID NO: 45)), Sarcin-ricin loop (CUGCUC-AGUACGAGAGGAACCGCAG (SEQ ID NO: 46)) or Pseudoknots

```
                                    (SEQ ID NO: 47))
(UACACUGGGAUCGCUGAAUUAGAGAUCGGCGUCCUUUCAUUCUAUAU

ACUUUGGAGUUUUAAAAUGUCUCUAAGUACA).
```

In some embodiments, an exogenous stem loop comprises a long non-coding RNA (lncRNA). As used herein, a lncRNA refers to a non-coding RNA that is longer than approximately 200 bp in length. In some embodiments, the 5' and 3' ends of the exogenous stem loop are base paired; i.e., interact to form a region of duplex RNA. In some embodiments, the 5' and 3' ends of the exogenous stem loop are base paired, and one or more regions between the 5' and 3' ends of the exogenous stem loop are not base paired. In some embodiments, the at least one nucleotide modification comprises: (a) substitution of 1 to 15 consecutive or non-consecutive nucleotides in the gNA variant in one or more regions; (b) a deletion of 1 to 10 consecutive or non-consecutive nucleotides in the gNA variant in one or more regions; (c) an insertion of 1 to 10 consecutive or non-consecutive nucleotides in the gNA variant in one or more regions; (d) a substitution of the scaffold stem loop or the extended stem loop with an RNA stem loop sequence from a heterologous RNA source with proximal 5' and 3 ends; or any combination of (a)-(d).

In some embodiments, the gNA variant comprises a scaffold stem loop sequence of CCAGCGACUAUGU-CGUAGUGG (SEQ ID NO: 32). In some embodiments, the gNA variant comprises a scaffold stem loop sequence of CCAGCGACUAUGUCGUAGUGG (SEQ ID NO: 32) with at least 1, 2, 3, 4, or 5 mismatches thereto.

In some embodiments, the gNA variant comprises an extended stem loop region comprising less than 32 nucleotides, less than 31 nucleotides, less than 30 nucleotides, less than 29 nucleotides, less than 28 nucleotides, less than 27 nucleotides, less than 26 nucleotides, less than 25 nucleotides, less than 24 nucleotides, less than 23 nucleotides, less than 22 nucleotides, less than 21 nucleotides, or less than 20 nucleotides. In some embodiments, the gNA variant comprises an extended stem loop region comprising less than 32 nucleotides. In some embodiments, the gNA variant further comprises a thermostable stem loop.

In some embodiments, a sgRNA variant comprises a sequence of SEQ ID NO:2104, SEQ ID NO:2106, SEQ ID NO:2163, SEQ ID NO:2107, SEQ ID NO:2164, SEQ ID NO:2165, SEQ ID NO:2166, SEQ ID NO:2103, SEQ ID NO:2167, SEQ ID NO:2105, SEQ ID NO:2108, SEQ ID NO:2112, SEQ ID NO:2160, SEQ ID NO:2170, SEQ ID NO:2114, SEQ ID NO:2171, SEQ ID NO:2112, SEQ ID NO:2173, SEQ ID NO:2102, SEQ ID NO:2174, SEQ ID NO:2175, SEQ ID NO:2109, SEQ ID NO:2176, SEQ ID NO:2238, SEQ ID NO:2239, SEQ ID NO:2240, SEQ ID NO:2241, SEQ ID NO:2274, SEQ ID NO:2275, or 2279.

In some embodiments, the gNA variant comprises the sequence of any one of SEQ ID NOS:2236, 2237, 2238, 2241, 2244, 2248, 2249, or 2259-2285, or having at least about 80%, at least about 90%, at least about 95%, at least about 96%, at least about 97%, at least about 98%, at least about 99% identity thereto. In some embodiments, the gNA variant comprises one or more additional changes to a sequence of any one of SEQ ID NOs: 2201-2285. In some embodiments, the gNA variant comprises the sequence of any one of SEQ ID NOS:2236, 2237, 2238, 2241, 2244, 2248, 2249, or 2259-2285. In some embodiments, the gNA variant scaffold consists of the sequence of any one of SEQ ID NOS:2236, 2237, 2238, 2241, 2244, 2248, 2249, or 2259-2285, and further comprises a targeting sequence of any of the embodiments described herein.

In some embodiments, a sgRNA variant comprises one or more additional changes to a sequence of SEQ ID N0:2104, SEQ ID NO:2163, SEQ ID NO:2107, SEQ ID NO:2164, SEQ ID NO:2165, SEQ ID NO:2166, SEQ ID NO:2103, SEQ ID NO:2167, SEQ ID NO:2105, SEQ ID NO:2108, SEQ ID NO:2112, SEQ ID NO:2160, SEQ ID NO:2170. SEQ ID NO:2114. SEQ ID NO:2171, SEQ ID NO:2112, SEQ ID NO:2173, SEQ ID NO:2102, SEQ ID NO:2174, SEQ ID NO:2175, SEQ ID NO:2109, SEQ ID NO:2176, SEQ ID NO:2238, SEQ ID NO:2239, SEQ ID NO:2240, SEQ ID NO:2241, SEQ ID NO:2274, SEQ ID NO:2275, or 2279.

In some embodiments of the gNA variants of the disclosure, the gNA variant comprises at least one modification, wherein the at least one modification compared to the reference guide scaffold of SEQ ID NO:5 is selected from one or more of: (a) a C18G substitution in the triplex loop; (b) a G55 insertion in the stem bubble; (c) a U1 deletion; (d) a modification of the extended stem loop wherein (i) a 6 nt loop and 13 loop-proximal base pairs are replaced by a Uvsx hairpin; and (ii) a deletion of A99 and a substitution of G65U that results in a loop-distal base that is fully base-paired. In such embodiments, the gNA variant comprises the sequence of any one of SEQ ID NOS:2236, 2237, 2238, 2241, 2244, 2248, 2249, or 2259-2285.

In the embodiments of the gNA variants, the gNA variant further comprises a targeting sequence (or spacer) region located at the 3' end of the gNA, described more fully, supra, which comprises at least 14 to about 35 nucleotides wherein the targeting sequence is designed with a sequence that is complementary to a target nucleic acid of the RHO gene, including wild-type and sequences having one or more mutations. In some embodiments, the gNA variant comprises a targeting sequence of at least 10 to 30 nucleotides complementary to a target nucleic acid. In some embodiments, the targeting sequence has 14, 15, 16, 17, 18, 19, 20, 21, 22, 23, 24, 25, 26, 27, 28, 29, 30, 31, 32, 33, 34 or 35 nucleotides. In some embodiments, the gNA variant comprises a targeting sequence having 20 nucleotides. In some embodiments, the targeting sequence has 25 nucleotides. In some embodiments, the targeting sequence has 24 nucleotides. In some embodiments, the targeting sequence has 23 nucleotides. In some embodiments, the targeting sequence has 22 nucleotides. In some embodiments, the targeting sequence has 21 nucleotides. In some embodiments, the targeting sequence has 19 nucleotides. In some embodiments, the targeting sequence has 18 nucleotides. In some embodiments, the targeting sequence has 17 nucleotides. In some embodiments, the targeting sequence has 16 nucleotides. In some embodiments, the targeting sequence has 15 nucleotides.

In some embodiments, the targeting sequence of a gNA is complementary to a RHO exon selected from the group consisting of exons 1-5. In other embodiments, the targeting sequence of a gNA is specific for a RHO intronic region, an intron-exon junction of the RHO gene, or an intergenic region. In some embodiments, the targeting sequence of the gNA is complementary to a sequence comprising one or more single nucleotide polymorphisms (SNPs) of the RHO gene or its complement. SNPs that are within a RHO coding sequence or within a RHO non-coding sequence are both within the scope of the instant disclosure. Representative targeting sequences to rhodopsin mutations known or believed to be associated with retinitis pigmentosa and related disorders and that are designed to be utilized in the CasX:gNA systems of the disclosure comprise a sequence of SEQ ID NOS. 382-582, or a sequence that is at least 50% identical, at least 55% identical, at least 60% identical, at least 65% identical, at least 70% identical, at least 75% identical, at least 80% identical, at least 85% identical, at least 90% identical, at least 95% identical thereto. In other embodiments, the disclosure provides targeting sequences for inclusion in the gNA variants of the disclosure comprising a sequence that is at least 50% identical, at least 55% identical, at least 60% identical, at least 65% identical, at least 70% identical, at least 75% identical, at least 80% identical, at least 85% identical, at least 90% identical, at least 95% identical, or 100° % identical to a sequence of SEQ ID NOs: 328-346, 367-376, 382-2100 and 2286-27274. In some embodiments, the targeting sequence of the gNA variant comprises a sequence a sequence of SEQ ID NOs: 328-346, 367-376, 382-2100 and 2286-27274 with a single nucleotide removed from the 3' end of the sequence. In other embodiments, the targeting sequence of the gNA variant comprises a sequence a sequence of SEQ ID NOs: 328-346, 367-376, 382-2100 and 2286-27274 with two nucleotides removed from the 3' end of the sequence. In other embodiments, the targeting sequence of the gNA variant comprises a sequence a sequence of SEQ ID NOs: 328-346, 367-376, 382-2100 and 2286-27274 with three nucleotides removed from the 3' end of the sequence. In other embodiments, the targeting sequence of the gNA variant comprises a sequence a sequence of SEQ ID NOs: 328-346, 367-376, 382-2100 and 2286-27274 with four nucleotides removed from the 3' end of the sequence. In other embodiments, the targeting sequence of the gNA variant comprises a sequence a sequence of SEQ ID NOs: 328-346, 367-376, 382-2100 and 2286-27274 with five nucleotides removed from the 3' end of the sequence. In some embodiments, the targeting sequence of the gNA variant comprises a sequence a sequence of SEQ ID NOs: 382-582 with a single nucleotide removed from the 3' end of the sequence. In other embodiments, the targeting sequence of the gNA variant comprises a sequence a sequence of SEQ ID NOs: 382-582 with two nucleotides removed from the 3' end of the sequence. In other embodiments, the targeting sequence of the gNA variant comprises a sequence a sequence of SEQ ID NOs: 382-582 with three nucleotides removed from the 3' end of the sequence. In other embodiments, the targeting sequence of the gNA variant comprises a sequence a sequence of SEQ ID NOs: 382-582 with four nucleotides removed from the 3' end of the sequence. In other embodiments, the targeting sequence of the gNA variant comprises a sequence a sequence of SEQ ID NOs: 382-582 with five nucleotides removed from the 3' end of the sequence.

In some embodiments, the gNA variant further comprises a targeting sequence region located at the 3' end of the gNA, wherein the targeting sequence is designed with a sequence that is complementary to a target nucleic acid. In some embodiments, the target nucleic acid comprises a PAM sequence located 5' of the targeting sequence with at least a single nucleotide separating the PAM from the first nucleotide of the targeting sequence. In some embodiments, the PAM is located on the non-targeted strand of the target region, i.e. the strand that is complementary to the target nucleic acid. In some embodiments, the PAM sequence is ATC. In some embodiments, the targeting sequence for an ATC PAM comprises SEQ ID NOs: 583-2100 or 2286-5554, or a sequence that is at least 50% identical, at least 55% identical, at least 60% identical, at least 65% identical, at least 70% identical, at least 75% identical, at least 80% identical, at least 85% identical, at least 90% identical, at least 95% identical, or at least 99% identical to SEQ ID NOs: 583-2100 or 2286-5554. In some embodiments, the targeting sequence for an ATC PAM is selected from the group consisting of SEQ ID NOs: 583-2100 or 2286-5554. In some embodiments, the PAM sequence is CTC. In some embodiments, the targeting sequence for a CTC PAM comprises SEQ ID NOs: 367-369, 372, or 10487-19917 or a sequence that is at least 50% identical, at least 55% identical, at least 60% identical, at least 65% identical, at least 70% identical, at least 75% identical, at least 80% identical, at least 85% identical, at least 90% identical, at least 95% identical, or at least 99% identical to SEQ ID NOs: 367-369, 372, or 10487-19917. In some embodiments, the targeting sequence for a CTC PAM is selected from the group consisting of SEQ ID NOs: 367-369, 372, or 10487-19917. In some embodiments, the PAM sequence is GTC. In some embodiments, the targeting sequences for a GTC PAM comprises SEQ ID NOs: 5555-10486 or a sequence that is at least 50% identical, at least 55% identical, at least 60% identical, at least 65% identical, at least 70% identical, at least 75% identical, at least 80% identical, at least 85% identical, at least 90% identical, at least 95% identical, or at least 99% identical to SEQ ID NOs: 5555-10486. In some embodiments, the targeting sequence for a GTC PAM is selected from the group consisting of SEQ ID NOs: 5555-10486. In some embodiments, the PAM sequence is TTC. In some embodiments, a targeting sequences for a TTC PAM comprises SEQ ID NOs: 370-371, 373-376, 19918-27274, or a sequence that is at least 50% identical, at least 55% identical, at least 60% identical, at least 65% identical, at least 70% identical, at least 75% identical, at least 80% identical, at least 85% identical, at least 90% identical, at least 95% identical, or at least 99% identical to SEQ ID NOs: 370-371, 373-376, or 19918-27274. In some embodiments, a targeting sequence for a TTC PAM is selected from the group consisting of SEQ ID NOs: 370-371, 373-376, or 19918-27274.

In some embodiments, the scaffold of the gNA variant is part of an RNP with a CasX variant protein comprising any one of the sequences of SEQ ID NOS: 49-160, 237-239, 243-246, 251-263 or 273-281 as set forth in Tables 3, 6, 7, 8, or 10 or a sequence having at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99% identity thereto. In the foregoing embodiments, the gNA further comprises a targeting sequence.

In some embodiments, the scaffold of the gNA variant is a variant comprising one or more additional changes to a sequence of a reference gRNA that comprises SEQ ID NO:4 or SEQ ID NO:5. In those embodiments where the scaffold of the reference gRNA is derived from SEQ ID NO:4 or SEQ ID NO:5, the one or more improved or added characteristics of the gNA variant are improved compared to the same characteristic in SEQ ID NO:4 or SEQ ID NO:5.

h. Complex Formation with CasX Protein

In some embodiments, a gNA variant has an improved ability to form a complex with a CasX protein (such as a reference CasX or a CasX variant protein) when compared to a reference gRNA. In some embodiments, a gNA variant has an improved affinity for a CasX protein (such as a reference or variant protein) when compared to a reference gRNA, thereby improving its ability to form a ribonucleoprotein (RNP) complex with the CasX protein, as described in the Examples. Improving ribonucleoprotein complex formation may, in some embodiments, improve the efficiency with which functional RNPs are assembled. In some embodiments, greater than 90%, greater than 93%, greater than 95%, greater than 96%, greater than 97%, greater than 98% or greater than 99% of RNPs comprising a gNA variant and its targeting sequence are competent for gene editing of a target nucleic acid.

Exemplary nucleotide changes that can improve the ability of gNA variants to form a complex with CasX protein may, in some embodiments, include replacing the scaffold stem with a thermostable stem loop. Without wishing to be bound by any theory, replacing the scaffold stem with a thermostable stem loop could increase the overall binding stability of the gNA variant with the CasX protein. Alternatively, or in addition, removing a large section of the stem loop could change the gNA variant folding kinetics and make a functional folded gNA easier and quicker to structurally-assemble, for example by lessening the degree to which the gNA variant can get "tangled" in itself. In some embodiments, choice of scaffold stem loop sequence could change with different targeting sequences that are utilized for the gNA. In some embodiments, scaffold sequence can be tailored to the targeting sequence and therefore the target sequence. Biochemical assays can be used to evaluate the binding affinity of CasX protein for the gNA variant to form the RNP, including the assays of the Examples. For example, a person of ordinary skill can measure changes in the amount of a fluorescently tagged gNA that is bound to an immobilized CasX protein, as a response to increasing concentrations of an additional unlabeled "cold competitor" gNA. Alternatively, or in addition, fluorescence signal can be monitored to or seeing how it changes as different amounts of fluorescently labeled gNA are flowed over immobilized CasX protein. Alternatively, the ability to form an RNP can be assessed using in vitro cleavage assays against a defined target nucleic acid sequence.

i. gNA Stability

In some embodiments, a gNA variant has improved stability when compared to a reference gRNA. Increased stability and efficient folding may, in some embodiments, increase the extent to which a gNA variant persists inside a target cell, which may thereby increase the chance of forming a functional RNP capable of carrying out CasX functions such as gene editing. Increased stability of gNA variants may also, in some embodiments, allow for a similar outcome with a lower amount of gNA delivered to a cell, which may in turn reduce the chance of off-target effects during gene editing. Guide RNA stability can be assessed in a variety of ways, including for example in vitro by assembling the guide, incubating for varying periods of time in a solution that mimics the intracellular environment, and then measuring functional activity via the in vitro cleavage assays described herein. Alternatively. or in addition, gNAs can be harvested from cells at varying time points after initial transfection/transduction of the gNA to determine how long gNA variants persist relative to reference gRNAs.

j. Solubility

In some embodiments, a gNA variant has improved solubility when compared to a reference gRNA. In some embodiments, a gNA variant has improved solubility of the CasX protein:gNA RNP when compared to a reference gRNA. In some embodiments, solubility of the CasX protein:gNA RNP is improved by the addition of a ribozyme sequence to a 5' or 3' end of the gNA variant, for example the 5' or 3' of a reference sgRNA. Some ribozymes, such as the M1 ribozyme, can increase solubility of proteins through RNA mediated protein folding. Increased solubility of CasX RNPs comprising a gNA variant as described herein can be evaluated through a variety of means known to one of skill in the art, such as by taking densitometry readings on a gel of the soluble fraction of lysed *E. coli* in which the CasX and gNA variants are expressed.

k. Resistance to Nuclease Activity

In some embodiments, a gNA variant has improved resistance to nuclease activity compared to a reference gRNA that may, for example, increase the persistence of a variant gNA in an intracellular environment, thereby improving gene editing. Resistance to nuclease activity may be evaluated through a variety of methods known to one of skill in the art. For example, in vitro methods of measuring resistance to nuclease activity may include for example contacting reference gNA and variants with one or more exemplary RNA nucleases and measuring degradation. Alternatively, or in addition, measuring persistence of a gNA variant in a cellular environment using the methods described herein can indicate the degree to which the gNA variant is nuclease resistant.

l. Binding Affinity to a Target DNA

In some embodiments, a gNA variant has improved affinity for the target DNA relative to a reference gRNA. In certain embodiments, a ribonucleoprotein complex comprising a gNA variant has improved affinity for the target DNA, relative to the affinity of an RNP comprising a reference gRNA. In some embodiments, the improved affinity of the RNP for the target DNA comprises improved affinity for the target sequence, improved affinity for the PAM sequence, improved ability of the RNP to search DNA for the target sequence, or any combinations thereof. In some embodiments, the improved affinity for the target DNA is the result of increased overall DNA binding affinity.

Without wishing to be bound by theory, it is possible that nucleotide changes in the gNA variant that affect the function of the OBD in the CasX protein may increase the affinity of CasX variant protein binding to the protospacer adjacent motif (PAM), as well as the ability to bind or utilize an increased spectrum of PAM sequences other than the canonical TTC PAM recognized by the reference CasX protein of SEQ ID NO:2, including PAM sequences selected from the group consisting of TTC, ATC, GTC, and CTC, thereby increasing the affinity and diversity of the CasX variant protein for target DNA sequences, resulting in a substantial increase in the target nucleic acid sequences that can be edited and/or bound, compared to a reference CasX. As described more fully, below, increasing the sequences of the target nucleic acid that can be edited, compared to a reference CasX, refers to both the PAM and the protospacer sequence and their directionality according to the orientation of the non-target strand. This does not imply that the PAM sequence of the non-target strand, rather than the target strand, is determinative of cleavage or mechanistically involved in target recognition. For example, when reference is to a TTC PAM, it may in fact be the complementary GAA sequence that is required for target cleavage, or it may be some combination of nucleotides from both strands. In the case of the CasX proteins disclosed herein, the PAM is located 5' of the protospacer with at least a single nucleotide separating the PAM from the first nucleotide of the protospacer. Alternatively, or in addition, changes in the gNA that affect function of the helical I and/or helical II domains that increase the affinity of the CasX variant protein for the target DNA strand can increase the affinity of the CasX RNP comprising the variant gNA for target DNA.

m. Adding or Changing gNA Function

In some embodiments, gNA variants can comprise larger structural changes that change the topology of the gNA variant with respect to the reference gRNA, thereby allowing for different gNA functionality. For example, in some embodiments a gNA variant has swapped an endogenous stem loop of the reference gRNA scaffold with a previously identified stable RNA structure or a stem loop that can interact with a protein or RNA binding partner to recruit additional moieties to the CasX or to recruit CasX to a specific location, such as the inside of a viral capsid, that has the binding partner to the said RNA structure. In other scenarios the RNAs may be recruited to each other, as in Kissing loops, such that two CasX proteins can be co-localized for more effective gene editing at the target DNA sequence. Such RNA structures may include MS2, Qβ, U1 hairpin II, Uvsx, PP7, Phage replication loop, Kissing loop_a. Kissing loop_b1, Kissing loop_b2, G quadriplex M3q, G quadriplex telomere basket, Sarcin-ricin loop, or a Pseudoknot.

In some embodiments, a gNA variant comprises a terminal fusion partner. Exemplary terminal fusions may include fusion of the gRNA to a self-cleaving ribozyme or protein binding motif. As used herein, a "ribozyme" refers to an RNA or segment thereof with one or more catalytic activities similar to a protein enzyme. Exemplary ribozyme catalytic activities may include, for example, cleavage and/or ligation of RNA, cleavage and/or ligation of DNA, or peptide bond formation. In some embodiments, such fusions could either improve scaffold folding or recruit DNA repair machinery. For example, a gRNA may in some embodiments be fused to a hepatitis delta virus (HDV) antigenomic ribozyme, HDV genomic ribozyme, hatchet ribozyme (from metagenomic data), env25 pistol ribozyme (representative from Aliistipes putredinis), HH15 Minimal Hammerhead ribozyme, tobacco ringspot virus (TRSV) ribozyme, WT viral Hammerhead ribozyme (and rational variants), or Twisted Sister 1 or RBMX recruiting motif. Hammerhead ribozymes are RNA motifs that catalyze reversible cleavage and ligation reactions at a specific site within an RNA molecule. Hammerhead ribozymes include type I, type II and type III hammerhead ribozymes. The HDV, pistol, and hatchet ribozymes have self-cleaving activities, gNA variants comprising one or more ribozymes may allow for expanded gNA function as compared to a gRNA reference. For example, gNAs comprising self-cleaving ribozymes can, in some embodiments, be transcribed and processed into mature gNAs as part of polycistronic transcripts. Such fusions may occur at either the 5' or the 3' end of the gNA. In some embodiments, a gNA variant comprises a fusion at both the 5' and the 3' end, w % herein each fusion is independently as described herein. In some embodiments, a gNA variant comprises a phage replication loop or a tetraloop. In some embodiments, a gNA comprises a hairpin loop that is capable of binding a protein. For example, in some embodiments the hairpin loop is an MS2, Qβ, U1 hairpin II, Uvsx, or PP7 hairpin loop.

In some embodiments, a gNA variant comprises one or more RNA aptamers. As used herein, an "RNA aptamer" refers to an RNA molecule that binds a target with high affinity and high specificity. In some embodiments, a gNA variant comprises one or more riboswitches. As used herein, a "riboswitch" refers to an RNA molecule that changes state upon binding a small molecule. In some embodiments, the gNA variant further comprises one or more protein binding motifs. Adding protein binding motifs to a reference gRNA or gNA variant of the disclosure may, in some embodiments, allow a CasX RNP to associate with additional proteins, which can, for example, add the functionality of those proteins to the CasX RNP.

n. Chemically Modified gNA

In some embodiments, the disclosure relates to chemically-modified gNA. In some embodiments, the present disclosure provides a chemically-modified gNA that has guide RNA functionality and has reduced susceptibility to cleavage by a nuclease. A gNA that comprises any nucleotide other than the four canonical ribonucleotides A, C, G, and U, or a deoxynucleotide, is a chemically modified gNA. In some cases, a chemically-modified gNA comprises any backbone or internucleotide linkage other than a natural phosphodiester internucleotide linkage. In certain embodiments, the retained functionality includes the ability of the modified gNA to bind to a CasX of any of the embodiments described herein. In certain embodiments, the retained functionality includes the ability of the modified gNA to bind to a target nucleic acid sequence. In certain embodiments, the retained functionality includes targeting a CasX protein or the ability of a pre-complexed CasX protein-gNA to bind to a target nucleic acid sequence. In certain embodiments, the retained functionality includes the ability to nick a target polynucleotide by a CasX-gNA. In certain embodiments, the retained functionality includes the ability to cleave a target nucleic acid sequence by a CasX-gNA. In certain embodiments, the retained functionality is any other known function of a gNA in a CasX system with a CasX protein of the embodiments of the disclosure.

In some embodiments, the disclosure provides a chemically-modified gNA in which a nucleotide sugar modification is incorporated into the gNA selected from the group consisting of 2'-O—$C_{1-4}$alkyl such as 2'-O-methyl (2'-OMe), 2'-deoxy (2'-H), 2'-O—$C_{1-3}$alkyl-O—$C_{1-3}$alkyl such as 2'-methoxyethyl ("2'-MOE"), 2'-fluoro ("2'-F"), 2'-amino ("2'-NH$_2$"), 2'-arabinosyl ("2'-arabino") nucleotide, 2-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In other embodiments, an internucleotide linkage modification incorporated into the guide RNA is selected from the group consisting of: phosphorothioate "P(S)" (P(S)), phosphonocarboxylate (P(CH$_2$)$_n$COOR) such as phosphonoacetate "PACE" (P(CH$_2$COO—)), thio-phosphonocarboxylate ((S)P(CH$_2$)$_n$COOR) such as thio-phosphonoacetate "thioPACE" ((S)P(CH$_2$)$_n$COO—)), alkylphosphonate (P(C$_{1-3}$alkyl) such as methylphosphonate —P(CH$_3$), boranophosphonate (P(BH$_3$)), and phosphorodithioate (P(S)$_2$).

In certain embodiments, the disclosure provides a chemically-modified gNA in which a nucleobase ("base") modification is incorporated into the gNA selected from the group consisting of: 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dihydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC"), 5-methyl-2-pyrimidine, x(A,G,C,T) and y(A,G,C,T).

In other embodiments, the disclosure provides a chemically-modified gNA in which one or more isotopic modifications are introduced on the nucleotide sugar, the nucleobase, the phosphodiester linkage and/or the nucleotide phosphates, including nucleotides comprising one or more $^{15}$N, $^{13}$C, $^{14}$C, deuterium, $^3$H, $^{32}$P, $^{125}$I, $^{131}$I atoms or other atoms or elements used as tracers.

In some embodiments, an "end" modification incorporated into the gNA is selected from the group consisting of: PEG (polyethyleneglycol), hydrocarbon linkers (including: heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In some embodiments, an "end" modification comprises a conjugation (or ligation) of the gNA to another molecule comprising an oligonucleotide of deoxynucleotides and/or ribonucleotides, a peptide, a protein, a sugar, an oligosaccharide, a steroid, a lipid, a folic acid, a vitamin and/or other molecule. In certain embodiments, the disclosure provides a chemically-modified gNA in which an "end" modification (described above) is located internally in the gNA sequence via a linker such as, for example, a 2-(4-butylamidofluorescein)propane-1,3-diol bis (phosphodiester) linker, which is incorporated as a phosphodiester linkage and can be incorporated anywhere between two nucleotides in the gNA.

In some embodiments, the disclosure provides a chemically-modified gNA having an end modification comprising a terminal functional group such as an amine, a thiol (or sulflhydryl), a hydroxyl, a carboxyl, carbonyl, thionyl, thiocarbonyl, a carbamoyl, a thiocarbamoyl, a phoshoryl, an alkene, an alkyne, an halogen or a functional group-terminated linker that can be subsequently conjugated to a desired moiety selected from the group consisting of a fluorescent dye, a non-fluorescent label, a tag (for $^{14}$C, example biotin, avidin, streptavidin, or moiety containing an isotopic label such as $^{15}$N, $^{13}$C, deuterium, $^3$H, $^{32}$P, $^{125}$I and the like), an oligonucleotide (comprising deoxynucleotides and/or ribonucleotides, including an aptamer), an amino acid, a peptide, a protein, a sugar, an oligosaccharide, a steroid, a lipid, a folic acid, and a vitamin. The conjugation employs standard chemistry well-known in the art, including but not limited to coupling via N-hydroxysuccinimide, isothiocyanate, DCC (or DCI), and/or any other standard method as described in "Bioconjugate Techniques" by Greg T. Hermanson, Publisher Eslsevier Science, $3^{rd}$ed. (2013), the contents of which are incorporated herein by reference in its entirety.

IV. Proteins for Modifying a Target Nucleic Acid

The present disclosure provides systems comprising a CRISPR nuclease that have utility in genome editing of eukaryotic cells. In some embodiments, the CRISPR nuclease employed in the genome editing systems is a Class 2, Type V nuclease. Although members of Class 2, Type V CRISPR-Cas systems have differences, they share some common characteristics that distinguish them from the Cas9 systems. Firstly, the Type V nucleases possess a single RNA-guided RuvC domain-containing effector but no HNH domain, and they recognize T-rich PAM 5' upstream to the target region on the non-targeted strand, which is different from Cas9 systems that rely on G-rich PAM at 3' side of target sequences. Type V nucleases generate staggered double-stranded breaks distal to the PAM sequence, unlike Cas9, which generates a blunt end in the proximal site close to the PAM. In addition. Type V nucleases degrade ssDNA in trans when activated by target dsDNA or ssDNA binding in cis. In some embodiments, the Type V nucleases of the embodiments recognize a 5'-TC PAM motif and produce staggered ends cleaved solely by the RuvC domain. In some embodiments, the Type V nuclease is selected from the group consisting of Cas12a, Cas12b, Cas12c, Cas12d (CasY), Cas12J, and CasX. In some embodiments, the present disclosure provides systems comprising a CasX protein and one or more gNA acids (CasX:gNA system) that are specifically designed to modify a target nucleic acid sequence in eukaryotic cells.

The term "CasX protein", as used herein, refers to a family of proteins, and encompasses all naturally occurring CasX proteins, proteins that share at least 50% identity to naturally occurring CasX proteins, as well as CasX variants exhibiting one or more improved characteristics relative to a naturally-occurring reference CasX protein.

Exemplary improved characteristics of the CasX variant embodiments include, but are not limited to improved folding of the variant, improved binding affinity to the gNA, improved binding affinity to the target nucleic acid, improved ability to utilize a greater spectrum of PAM sequences in the editing and/or binding of target DNA, improved unwinding of the target DNA, increased editing activity, improved editing efficiency, improved editing specificity, increased percentage of a eukaryotic genome that can be efficiently edited, increased activity of the nuclease, increased target strand loading for double strand cleavage, decreased target strand loading for single strand nicking, decreased off-target cleavage, improved binding of the non-target strand of DNA, improved protein stability, improved protein:gNA (RNP) complex stability, improved protein solubility, improved protein:gNA (RNP) complex solubility, improved protein yield, improved protein expression, and improved fusion characteristics, as described more fully, below. In some embodiments, the RNP of the CasX variant and the gNA variant exhibit one or more of the improved characteristics that are at least about 1.1 to about 100,000-fold improved relative to an RNP of the reference CasX protein of SEQ ID NO:1, SEQ ID NO:2, or SEQ ID NO:3 and the gNA of Table 1, when assayed in a comparable fashion. In other cases, the one or more improved characteristics of an RNP of the CasX variant and the gNA variant are at least about 1.1, at least about 10, at least about 100, at least about 1000, at least about 10.000, at least about 100,000-fold or more improved relative to an RNP of the reference CasX protein of SEQ ID NO:1, SEQ ID NO:2, or SEQ ID NO:3 and the gNA of Table 1. In other cases, the one or more of the improved characteristics of an RNP of the CasX variant and the gNA variant are about 1.1 to 100,000-fold, about 1.1 to 10,000-fold, about 1.1 to 1,000-fold, about 1.1 to 500-fold, about 1.1 to 100-fold, about 1.1 to 50-fold, about 1.1 to 20-fold, about 10 to 100,000-fold, about 10 to 10,000-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100.00-fold, about 100 to 10,000-fold, about 100 to 1,000-fold, about 100 to 500-fold, about 500 to 100,000-fold, about 500 to 10,000-fold, about 500 to 1,000-fold, about 500 to 750-fold, about 1,000 to 100,000-fold, about 10,000 to 100,000-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to an RNP of the reference CasX protein of SEQ ID NO:1, SEQ ID NO:2, or SEQ ID NO:3 and the gNA of Table 1, when assayed in a comparable fashion. In other cases, the one or more improved characteristics of an RNP of the CasX variant and the gNA variant are about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to an RNP of the reference CasX protein of SEQ ID NO:1, SEQ ID NO:2, or SEQ ID NO:3 and the gNA of Table 1, when assayed in a comparable fashion.

The term "CasX variant" is inclusive of variants that are fusion proteins, i.e., the CasX is "fused to" a heterologous sequence. This includes CasX variants comprising CasX variant sequences and N-terminal, C-terminal, or internal fusions of the CasX to a heterologous protein or domain thereof.

CasX proteins of the disclosure comprise at least one of the following domains; a non-target strand binding (NTSB) domain, a target strand loading (TSL) domain, a helical I domain, a helical II domain, an oligonucleotide binding domain (OBD), and a RuvC DNA cleavage domain (the last of which may be modified or deleted in a catalytically dead CasX variant), described more fully, below. Additionally, the CasX variant proteins of the disclosure have an enhanced ability to efficiently edit and/or bind target DNA, when complexed with a gNA as an RNP, utilizing PAM TC motif, including PAM sequences selected from TTC, ATC, GTC, or CTC, compared to an RNP of a reference CasX protein and reference gNA. In the foregoing, the PAM sequence is located at least 1 nucleotide 5' to the non-target strand of the protospacer having identity with the targeting sequence of the gNA in a assay system compared to the editing efficiency and/or binding of an RNP comprising a reference CasX protein and reference gNA in a comparable assay system. In one embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is TTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is ATC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is CTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is GTC. In the foregoing embodiments, the increased editing efficiency and/or binding affinity for the one or more PAM sequences is at least 1.5-fold greater or more compared to the editing efficiency and/or binding affinity of an RNP of any one of the CasX proteins of SEQ ID NOS:1-3 and the gNA of Table 1 for the PAM sequences.

In some embodiments, a CasX protein can bind and/or modify (e.g., cleave, nick, methylate, demethylate, etc.) a target nucleic acid and/or a polypeptide associated with target nucleic acid (e.g., methylation or acetylation of a histone tail). In some embodiments, the CasX protein is catalytically dead (dCasX) but retains the ability to bind a target nucleic acid. An exemplary catalytically dead CasX protein comprises one or more mutations in the active site of the RuvC domain of the CasX protein. In some embodiments, a catalytically dead CasX protein comprises substitutions at residues 672, 769 and/or 935 of SEQ ID NO:1. In one embodiment, a catalytically dead CasX protein comprises substitutions of D672A, E769A and/or D935A in a reference CasX protein of SEQ ID NO:1. In other embodiments, a catalytically dead CasX protein comprises substitutions at amino acids 659, 756 and/or 922 in a reference CasX protein of SEQ ID NO:2. In some embodiments, a catalytically dead CasX protein comprises D659A, E756A and/or D922A substitutions in a reference CasX protein of SEQ ID NO:2. In further embodiments, a catalytically dead CasX protein comprises deletions of all or part of the RuvC domain of the CasX protein. It will be understood that the same foregoing substitutions can similarly be introduced into the CasX variants of the disclosure, resulting in a dCasX variant. In one embodiment, all or a portion of the RuvC domain is deleted from the CasX variant, resulting in a dCasX variant. Catalytically inactive dCasX variant proteins can, in some embodiments, be used for base editing or epigenetic modifications. With a higher affinity for DNA, in some embodiments, catalytically inactive dCasX variant proteins can, relative to catalytically active CasX, find their target nucleic acid faster, remain bound to target nucleic acid for longer periods of time, bind target nucleic acid in a more stable fashion, or a combination thereof, thereby improving these functions of the catalytically dead CasX variant protein compared to a CasX variant that retains its cleavage capability.

a. Non-Target Strand Binding Domain

The reference CasX proteins of the disclosure comprise a non-target strand binding domain (NTSBD). The NTSBD is a domain not previously found in any Cas proteins; for example this domain is not present in Cas proteins such as Cas9, Cas12a/Cpf1, Cas13. Cas14, CASCADE, CSM, or CSY. Without being bound to theory or mechanism, a NTSBD in a CasX allows for binding to the non-target DNA strand and may aid in unwinding of the non-target and target strands. The NTSBD is presumed to be responsible for the unwinding, or the capture, of a non-target DNA strand in the unwound state. The NTSBD is in direct contact with the non-target strand in CryoEM model structures derived to date and may contain a non-canonical zinc finger domain. The NTSBD may also play a role in stabilizing DNA during unwinding, guide RNA invasion and R-loop formation. In some embodiments, an exemplary NTSBD comprises amino acids 101-191 of SEQ ID NO:1 or amino acids 103-192 of SEQ ID NO:2. In some embodiments, the NTSBD of a reference CasX protein comprises a four-stranded beta sheet.

b. Target Strand Loading Domain

The reference CasX proteins of the disclosure comprise a Target Strand Loading (TSL) domain. The TSL domain is a domain not found in certain Cas proteins such as Cas9, CASCADE, CSM, or CSY. Without wishing to be bound by theory or mechanism, it is thought that the TSL domain is responsible for aiding the loading of the target DNA strand into the RuvC active site of a CasX protein. In some embodiments, the TSL acts to place or capture the target-strand in a folded state that places the scissile phosphate of the target strand DNA backbone in the RuvC active site. The TSL comprises a cys4 (CXXC, CXXC zinc finger/ribbon domain (SEQ ID NO: 48) that is separated by the bulk of the TSL. In some embodiments, an exemplary TSL comprises amino acids 825-934 of SEQ ID NO:1 or amino acids 813-921 of SEQ ID NO:2.

c. Helical I Domain

The reference CasX proteins of the disclosure comprise a helical I domain. Certain Cas proteins other than CasX have domains that may be named in a similar way. However, in some embodiments, the helical 1 domain of a CasX protein comprises one or more unique structural features, or comprises a unique sequence, or a combination thereof, compared to non-CasX proteins. For example, in some embodiments, the helical I domain of a CasX protein comprises one or more unique secondary structures compared to domains in other Cas proteins that may have a similar name. For example, in some embodiments the helical I domain in a CasX protein comprises one or more alpha helices of unique structure and sequence in arrangement, number and length compared to other CRISPR proteins. In certain embodiments, the helical I domain is responsible for interacting with the bound DNA and targeting sequence of the guide RNA. Without wishing to be bound by theory, it is thought that in some cases the helical I domain may contribute to binding of the protospacer adjacent motif (PAM). In some embodiments, an exemplary helical I domain comprises amino acids 57-100 and 192-332 of SEQ ID NO:1, or amino acids 59-102 and 193-333 of SEQ ID NO:2. In some embodiments, the helical I domain of a reference CasX protein comprises one or more alpha helices.

d. Helical II Domain

The reference CasX proteins of the disclosure comprise a helical II domain. Certain Cas proteins other than CasX have domains that may be named in a similar way. However, in some embodiments, the helical II domain of a CasX protein comprises one or more unique structural features, or a unique sequence, or a combination thereof, compared to domains in other Cas proteins that may have a similar name. For example, in some embodiments, the helical II domain comprises one or more unique structural alpha helical bundles that align along the target DNA:guide RNA channel. In some embodiments, in a CasX comprising a helical II domain, the target strand and guide RNA interact with helical II (and the helical I domain, in some embodiments) to allow RuvC domain access to the target DNA. The helical II domain is responsible for binding to the guide RNA scaffold stem loop as well as the bound DNA. In some embodiments, an exemplary helical II domain comprises amino acids 333-509 of SEQ ID NO:1, or amino acids 334-501 of SEQ ID NO:2.

e. Oligonucleotide Binding Domain

The reference CasX proteins of the disclosure comprise an Oligonucleotide Binding Domain (OBD). Certain Cas proteins other than CasX have domains that may be named in a similar way. However, in some embodiments, the OBD comprises one or more unique functional features, or comprises a sequence unique to a CasX protein, or a combination thereof. For example, in some embodiments the bridged helix (BH), helical I domain, helical II domain, and Oligonucleotide Binding Domain (OBD) together are responsible for binding of a CasX protein to the guide RNA. Thus, for example, in some embodiments the OBD is unique to a CasX protein in that it interacts functionally with a helical I domain, or a helical II domain, or both, each of which may be unique to a CasX protein as described herein. Specifically, in CasX the OBD largely binds the RNA triplex of the guide RNA scaffold. The OBD may also be responsible for binding to the protospacer adjacent motif (PAM). An exemplary OBD domain comprises amino acids 1-56 and 510-660 of SEQ ID NO:1, or amino acids 1-58 and 502-647 of SEQ ID NO:2.

f. RuvC DNA Cleavage Domain

The reference CasX proteins of the disclosure comprise a RuvC domain, that includes 2 partial RuvC domains (RuvC-I and RuvC-II). The RuvC domain is the ancestral domain of all Cas12 CRISPR proteins. The RuvC domain originates from a TNPB (transposase B) like transposase. Similar to other RuvC domains, the CasX RuvC domain has a DED catalytic triad that is responsible for coordinating a magnesium (Mg) ion and cleaving DNA. In some embodiments, the RuvC has a DED motif active site that is responsible for cleaving both strands of DNA (one by one, most likely the non-target strand first at 11-14 nucleotides (nt) into the targeted sequence and then the target strand next at 2-4 nucleotides after the target sequence). Specifically in CasX, the RuvC domain is unique in that it is also responsible for binding the guide RNA scaffold stem loop that is critical for CasX function. An exemplary RuvC domain comprises amino acids 661-824 and 935-986 of SEQ ID NO:1, or amino acids 648-812 and 922-978 of SEQ ID NO:2.

g. Reference CasX Proteins

The disclosure provides naturally-occurring CasX proteins (referred to herein as a "reference CasX protein") that function as an endonuclease that catalyzes a double strand break at a specific sequence in a targeted double-stranded DNA (dsDNA). The sequence specificity is provided by the targeting sequence of the associated gNA to which it is complexed, which hybridizes to a target sequence within the target nucleic acid. For example, reference CasX proteins can be isolated from naturally occurring prokaryotes, such as Deltaproteobacteria, Planctomycetes, or Candidatus Sungbacteria species. A reference CasX protein (sometimes referred to herein as a reference CasX protein) is a Type V CRISPR/Cas endonuclease belonging to the CasX (sometimes referred to as Cas12e) family of proteins that is capable of interacting with a guide NA to form a ribonucleoprotein (RNP) complex. In some embodiments, the RNP complex comprising the reference CasX protein can be targeted to a particular site in a target nucleic acid via base pairing between the targeting sequence (or spacer) of the gNA and a target sequence in the target nucleic acid. In some embodiments, the RNP comprising the reference CasX protein is capable of cleaving target DNA. In some embodiments, the RNP comprising the reference CasX protein is capable of nicking target DNA. In some embodiments, the RNP comprising the reference CasX protein is capable of editing target DNA, for example in those embodiments where the reference CasX protein is capable of cleaving or nicking DNA, followed by non-homologous end joining (NHEJ), homology-directed repair (HDR), homology-independent targeted integration (HITI), micro-homology mediated end joining (MMEJ), single strand annealing (SSA) or base excision repair (BER). In some embodiments, the RNP comprising the CasX protein is a catalytically dead (is catalytically inactive or has substantially no cleavage activity) CasX protein (dCasX), but retains the ability to bind the target DNA, described more fully, supra.

In some cases, a Type V reference CasX protein is isolated or derived from Deltaproteobacteria. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89°% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

(SEQ ID NO: 1)

```
  1  MEKRINKIRK  KLSADNATKP  VSRSGPMKTL  LVRVMTDDLK  KRLEKRRKKP  EVMPQVISNN

61  AANNLRMLLD  DYTKMKEAIL  QVYWQEFKDD  HVGLMCKFAQ  PASKKIDQNK  LKPEMDEKGN

121  LTTAGFACSQ  CGQPLFVYKL  EQVSEKGKAY  TNYFGRCNVA  EHEKLILLAQ  LKPEKDSDEA

181  VTYSLGKFGQ  RALDFYSIHV  TKESTHPVKP  LAQIAGNRYA  SGPVGKALSD  ACMGTIASFL

241  SKYQDIIIEH  QKVVKGNQKR  LESLRELAGK  ENLEYPSVTL  PPQPHTKEGV  DAYNEVIARV
```

```
301 RMWVNLNLWQ KLKLSRDDAK PLLRLKGFPS FPVVERRENE VDWWNTINEV KKLIDAKRDM

361 GRVFWSGVTA EKRNTILEGY NYLPNENDHK KREGSLENPK KPAKRQFGDL LLYLEKKYAG

421 DWGKVFDEAW ERIDKKIAGL TSHIEREEAR NAEDAQSKAV LTDWLRAKAS FVLERIKEMD

481 EKEFYACEIQ LQKWYGDLRG NPFAVEAENR VVDISGESIG SDGHSIQYRN LLAWKYLENG

541 KREFYLLMNY GKKGRIRFTD GTDIKKSGKW QGLLYGGGKA KVIDLTFDPD DEQLIILPLA

601 FGTRQGREFI WNDLLSLETG LIKLANGRVI EKTIYNKKIG RDEPALFVAL TFERREVVDP

661 SNIKPVNLIG VDRGENIPAV IALTDPEGCP LPEFKDSSGG PTDILRIGEG YKEKQRAIQA

721 AKEVEQRRAG GYSRKFASKS RNLADDMVRN SARDLFYHAV THDAVLVFEN LSRGFGRQGK

781 RTFMTERQYT KMEDWLTAKL AYEGLTSKTY LSKTLAQYTS KTCSNCGFTI TTADYDGMLV

841 RLKKTSDGWA TTLNNKELKA EGQITYYNRY KRQTVEKELS AELDRLSEES GNNDISKWTK

901 GRRDEALFLL KKRFSHRPVQ EQFVCLDCGH EVHADEQAAL NIARSWLFLN SNSTEFKSYK

961 SGKQPFVGAW QAFYKRRLKE VWKPNA.
```

In some cases, a Type V reference CasX protein is isolated or derived from Planctomycetes. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

```
                                                             (SEQ. ID NO: 2)
  1 MQEIKRINKI RRRLVKDSNT KKAGKTGPMK TLLVRVMTPD LRERLENLRK KPENIPQPIS

61 NTSRANLNKL LTDYTEMKKA ILHVYKEEFQ KDPVGIMSRV AQPAPKNIDQ RKLIPVKDGN

121 ERLTSSGFAC SQCCQPLYVY KLEQVNDKGK PHTNYFGRCN VSEHERLILL SPHKPEANDE

181 LVTYSLGKFG QRALDFYSIH VTRESNHPVK PLEQIGGNSC ASGPVGKALS DACMGAVASF

241 LTKYQDIILE HQKVIKKNEK RLANLKDIAS ANGLAFPKIT LPPQPHTKEG IEAYNNVVAQ

301 IVIWVNLNLW QKLKIGRDEA KPLQRLKGFP SFPLVERQAN EVDWWDMVCN VKKLINEKKE

361 DGKVFWQNLA GYKRQEALLP YLSSEEDRKK GKKFARYQFG DLLLHLEKKH GEDWGKVYDE

421 AWERIDKKVE GLSKHIKLEE ERRSEDAQSK AALTDWLRAK ASFVIEGLKE ADKDEFCRCE

481 LKLQKWYGDL RGKPFAIEAE NSILDISGFS KQYNCAFIWQ KDGVKKLNLY LIINYFKGGK

541 LRFKKIKPEA FEANPFYTVI NKKSGEIVPM EVNFNFDDPN LIILPLAFGK RQGREFIWND

601 LLSLETGSLK LANGRVIEKT LYNRRTRQDE PALFVALTFE RREVLDSSNI KPMNLIGIDR

661 GENIPAVIAL TDPEGCPLSR FKDSLGNPTH ILRIGESYKE KQRTIQAAKE VEQRRAGGYS

721 RKYASKAKNL ADDMVRNTAR DLLYYAVTQD AMLIFENLSR GFGRQGKRTF MAERQYTRME

781 DWLTAKLAYE GLPSKTYLSK TLAQYTSKTC SNCGFTITSA DYDRVLEKLK KTATGWMTTI

841 NGKELKVEGQ ITYYNRYKRQ NVVKDLSVEL DRLSEESVNN DISSWTKGRS GEALSLIKKR

901 FSHRPVQEKF VCLNCGFETH ADEQAALNIA RSWIFLRSQE YKKYQTNKTT GNTDKRAFVE

961 TWQSFYRKKL KEVWKPAV.
```

In some embodiments, the CasX protein comprises the sequence of SEQ ID NO:2, or at least 60% similarity thereto. In some embodiments, the CasX protein comprises the sequence of SEQ ID NO:2, or at least 80% similarity thereto. In some embodiments, the CasX protein comprises the sequence of SEQ ID NO:2, or at least 90% similarity thereto. In some embodiments, the CasX protein comprises the sequence of SEQ ID NO:2, or at least 95% similarity thereto. In some embodiments, the CasX protein consists of the sequence of SEQ ID NO:2. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:2. These mutations can be insertions, deletions, amino acid substitutions, or any combinations thereof.

In some cases, a Type V reference CasX protein is isolated or derived from Candidatus Sungbacteria. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of sequence of SEQ ID NO:3, or at least 95% similarity thereto. In some embodiments, the CasX protein consists of the sequence of SEQ ID NO:3. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:3. These mutations can be insertions, deletions, amino acid substitutions, or any combinations thereof.

h. CasX Variant Proteins

The present disclosure provides variants of a reference CasX protein (interchangeably referred to herein as "CasX variant" or "CasX variant protein"), wherein the CasX variants comprise at least one modification in at least one domain of the reference CasX protein, including the sequences of SEQ ID NOS:1-3. In some embodiments, the CasX variant exhibits at least one improved characteristic compared to the reference CasX protein. All variants that improve one or more functions or characteristics of the CasX variant protein when compared to a reference CasX protein described herein are envisaged as being within the scope of the disclosure. In some embodiments, the modification is a mutation in one or more amino acids of the reference CasX. In other embodiments, the modification is a substitution of one or more domains of the reference CasX with one or more domains from a different CasX. In some embodiments, insertion includes the insertion of a part or all of a domain from a different CasX protein. Mutations can occur in any one or more domains of the reference CasX protein, and may include, for example, deletion of part or all of one or more domains, or one or more amino acid

```
                                                           (SEQ ID NO: 3)
  1 MDNANKPSTK SLVNTTRISD HFGVTPGQVT RVFSFGIIPT KRQYAIIERW FAAVEAARER

61 LYGMLYAHFQ ENPPAYLKEK FSYETFFKGR PVLNGLRDID PTIMTSAVFT ALRHKAEGAM

121 AAFHTNHRRL FEEARKKMRE YAECLKANEA LLRGAADIDW DKIVNALRTR LNTCLAPEYD

181 AVIADFGALC AFRALIAETN ALKGAYNHAL NQMLPALVKV DEPEEAEESP RLRFFNGRIN

241 DLPKFPVAER ETPPDTETII RQLEDMARVI PDTAEILGYI HRIRHKAARR KPGSAVPLPQ

301 RVALYCAIRM ERNPEEDPST VAGHFLGEID RVCEKRRQGL VRTPFDSQIR ARYMDIISFR

361 ATLAHPDRWT EIQFLPENAA SRRVRPAETIS APFEGFSWTS NRTNPAPQYG MALAK-
    DANAP

421 ADAPELCICL SPSSAAFSVR EKGGDLIYMR PTGGRPGKDN PGKEITWVPG SFDEYPASGV

481 ALKLRLYFGR SQARRMLTNK TWGTLLSDNPR VFAA-
    NAELVG KKRNPQDRWK LFFHMVISGP

541 PPVEYLDFSS DVRSRARTVI GINRGEVNPL AYAVVSVEDG QVLEEGLLGK KEYIDQLIET

601 RRRISEYQSR EQTPPRDLRQ RVRHLQDTVL GSARAKIHSL IAFWKGILAI ERLDDQFHGR

661 EQKIIPKKTY LANKTGFMNA LSFSGAVRVD KKGNPWGGMI EIYPGGISRT CTQCGTVWLA

721 RRPKNPGHRD AMVVIPDIVD DAAATGFDNV DCDAGTVDYG ELFTLSREWV RLTPRYSRVM

781 RGTLGDLERA IRQGDDRKSR QMLELALEPQ PQWGQFFCHR CGFNGQSDVL AATNLARRAI

841 SLIRRLPDTD TPPTP.
```

In some embodiments, the CasX protein comprises the sequence of SEQ ID NO:3, or at least 60% similarity thereto. In some embodiments, the CasX protein comprises the sequence of SEQ ID NO:3, or at least 80% similarity thereto. In some embodiments, the CasX protein comprises the sequence of SEQ ID NO:3, or at least 90% similarity thereto. In some embodiments, the CasX protein comprises the substitutions, deletions, or insertions in any domain of the reference CasX protein. The domains of CasX proteins include the non-target strand binding (NTSB) domain, the target strand loading (TSL) domain, the helical I domain, the helical II domain, the oligonucleotide binding domain (OBD), and the RuvC DNA cleavage domain. Any change in amino acid sequence of a reference CasX protein that leads to an improved characteristic of the CasX protein is considered a CasX variant protein of the disclosure. For example, CasX variants can comprise one or more amino acid substitutions, insertions, deletions, or swapped domains, or any combinations thereof, relative to a reference CasX protein sequence.

In some embodiments, the CasX variant protein comprises at least one modification in at least each of two domains of the reference CasX protein, including the sequences of SEQ ID NOS:1-3. In some embodiments, the CasX variant protein comprises at least one modification in at least 2 domains, in at least 3 domains, at least 4 domains or at least 5 domains of the reference CasX protein. In some embodiments, the CasX variant protein comprises two or more modifications in at least one domain of the reference CasX protein. In some embodiments, the CasX variant protein comprises at least two modifications in at least one domain of the reference CasX protein, at least three modifications in at least one domain of the reference CasX protein or at least four modifications in at least one domain of the reference CasX protein. In some embodiments, wherein the CasX variant comprises two or more modifications compared to a reference CasX protein, each modification is made in a domain independently selected from the group consisting of a NTSBD, TSLD, Helical I domain, Helical II domain, OBD, and RuvC DNA cleavage domain.

In some embodiments, the at least one modification of the CasX variant protein comprises a deletion of at least a portion of one domain of the reference CasX protein, including the sequences of SEQ ID NOS:1-3. In some embodiments, the deletion is in the NTSBD, TSLD, Helical I domain, Helical II domain, OBD, or RuvC DNA cleavage domain.

Suitable mutagenesis methods for generating CasX variant proteins of the disclosure may include, for example, Deep Mutational Evolution (DME), deep mutational scanning (DMS), error prone PCR, cassette mutagenesis, random mutagenesis, staggered extension PCR, gene shuffling, or domain swapping. In some embodiments, the CasX variants are designed, for example by selecting one or more desired mutations in a reference CasX. In certain embodiments, the activity of a reference CasX protein is used as a benchmark against which the activity of one or more CasX variants are compared, thereby measuring improvements in function of the CasX variants. Exemplary improvements of CasX variants include, but are not limited to, improved folding of the variant, improved binding affinity to the gNA, improved binding affinity to the target DNA, altered binding affinity to one or more PAM sequences, improved unwinding of the target DNA, increased activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved protein:gNA complex stability, improved protein solubility, improved protein:gNA complex solubility, improved protein yield, improved protein expression, and improved fusion characteristics, as described more fully, below.

In some embodiments of the CasX variants described herein, the at least one modification comprises: (a) a substitution of 1 to 100 consecutive or non-consecutive amino acids in the CasX variant compared to a reference CasX of SEQ ID NO:1, SEQ ID NO:2, or SEQ ID NO:3; (b) a deletion of 1 to 100 consecutive or non-consecutive amino acids in the CasX variant compared to a reference CasX; (c) an insertion of 1 to 100 consecutive or non-consecutive amino acids in the CasX compared to a reference CasX; or (d) any combination of (a)-(c). In some embodiments, the at least one modification comprises: (a) a substitution of 5-10 consecutive or non-consecutive amino acids in the CasX variant compared to a reference CasX of SEQ ID NO:1, SEQ ID NO:2, or SEQ ID NO:3; (b) a deletion of 1-5 consecutive or non-consecutive amino acids in the CasX variant compared to a reference CasX; (c) an insertion of 1-5 consecutive or non-consecutive amino acids in the CasX compared to a reference CasX: or (d) any combination of (a)-(c).

In some embodiments, the CasX variant protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO:1, SEQ ID NO:2, or SEQ ID NO:3. These mutations can be insertions, deletions, amino acid substitutions, or any combinations thereof.

In some embodiments, the CasX variant protein comprises at least one amino acid substitution in at least one domain of a reference CasX protein. In some embodiments, the CasX variant protein comprises at least about 1-4 amino acid substitutions, 1-10 amino acid substitutions, 1-20 amino acid substitutions, 1-30 amino acid substitutions, 1-40 amino acid substitutions, 1-50 amino acid substitutions, 1-6) amino acid substitutions, 1-70 amino acid substitutions, 1-80 amino acid substitutions, 1-90 amino acid substitutions, 1-100 amino acid substitutions, 2-10 amino acid substitutions, 2-20 amino acid substitutions, 2-30 amino acid substitutions, 3-10 amino acid substitutions, 3-20 amino acid substitutions, 3-30 amino acid substitutions, 4-10 amino acid substitutions, 4-20 amino acid substitutions, 3-300 amino acid substitutions, 5-10 amino acid substitutions, 5-20 amino acid substitutions, 5-30 amino acid substitutions, 10-50 amino acid substitutions, or 20-50 amino acid substitutions, relative to a reference CasX protein, w % hich can be consecutive or non-consecutive, or in different domains. As used herein "consecutive amino acids" refer to amino acids that are contiguous in the primary sequence of a polypeptide. In some embodiments, the CasX variant protein comprises at least about 100 or more amino acid substitutions relative to a reference CasX protein. In some embodiments, the amino acid substitutions are conservative substitutions. In other embodiments, the substitutions are non-conservative; e.g., a polar amino acid is substituted for a non-polar amino acid, or vice versa.

Any amino acid can be substituted for any other amino acid in the substitutions described herein. The substitution can be a conservative substitution (e.g., a basic amino acid is substituted for another basic amino acid). The substitution can be a non-conservative substitution (e.g., a basic amino acid is substituted for an acidic amino acid or vice versa). For example, a proline in a reference CasX protein can be substituted for any of arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine to generate a CasX variant protein of the disclosure.

In some embodiments, a CasX variant protein comprises at least one amino acid deletion relative to a reference CasX protein. In some embodiments, a CasX variant protein comprises a deletion of 1-4 amino acids, 1-10 amino acids, 1-20 amino acids, 1-30 amino acids, 1-40 amino acids, 1-50 amino acids, 1-60 amino acids, 1-70 amino acids, 1-80 amino acids, 1-90 amino acids, 1-100 amino acids, 2-10 amino acids, 2-20 amino acids, 2-30 amino acids, 3-10 amino acids, 3-20 amino acids, 3-30 amino acids, 4-10 amino acids, 4-20 amino acids, 3-300 amino acids, 5-10 amino acids, 5-20 amino acids, 5-30 amino acids, 10-50 amino acids or 20-50 amino acids relative to a reference CasX protein. In some embodiments, a CasX protein comprises a deletion of at least about 100 consecutive amino acids relative to a reference CasX protein. In some embodiments, a CasX variant protein comprises a deletion of at least 1, 2, 3, 4, 5, 6, 7, 8, 9, 10, 20, 30, 40, 50 or 100 consecutive amino acids relative to a reference CasX protein. In some embodiments, a CasX variant protein comprises a deletion of 1, 2, 3, 4, 5, 6, 7, 8, 9 or 10 consecutive amino acids.

In some embodiments, a CasX variant protein comprises two or more deletions relative to a reference CasX protein, and the two or more deletions are not consecutive amino acids. For example, a first deletion may be in a first domain of the reference CasX protein, and a second deletion may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive deletions relative to a reference CasX protein. In some embodiments, a CasX variant protein comprises at least 20 non-consecutive deletions relative to a reference CasX protein. Each non-consecutive deletion may be of any length of amino acids described herein, e.g., 1-4 amino acids, 1-10 amino acids, and the like.

In some embodiments, the CasX variant protein comprises one or more amino acid insertions relative to the sequence of SEQ ID NOS:1, 2, or 3. In some embodiments, a CasX variant protein comprises an insertion of 1 amino acid, an insertion of 2-3 consecutive or non-consecutive amino acids, 2-4 consecutive or non-consecutive amino acids, 2-5 consecutive or non-consecutive amino acids, 2-6 consecutive or non-consecutive amino acids, 2-7 consecutive or non-consecutive amino acids, 2-8 consecutive or non-consecutive amino acids, 2-9 consecutive or non-consecutive amino acids, 2-10 consecutive or non-consecutive amino acids, 2-20 consecutive or non-consecutive amino acids, 2-30 consecutive or non-consecutive amino acids, 2-40 consecutive or non-consecutive amino acids, 2-50 consecutive or non-consecutive amino acids, 2-60 consecutive or non-consecutive amino acids, 2-70 consecutive or non-consecutive amino acids, 2-80 consecutive or non-consecutive amino acids, 2-90 consecutive or non-consecutive amino acids, 2-100 consecutive or non-consecutive amino acids, 3-10 consecutive or non-consecutive amino acids, 3-20 consecutive or non-consecutive amino acids, 3-30 consecutive or non-consecutive amino acids, 4-10 consecutive or non-consecutive amino acids, 4-20 consecutive or non-consecutive amino acids, 3-300 consecutive or non-consecutive amino acids, 5-10 consecutive or non-consecutive amino acids, 5-20 consecutive or non-consecutive amino acids, 5-30 consecutive or non-consecutive amino acids, 10-50 consecutive or non-consecutive amino acids or 20-50 consecutive or non-consecutive amino acids relative to a reference CasX protein. In some embodiments, the CasX variant protein comprises an insertion of 2, 3, 4, 5, 6, 7, 8, 9, 10, 11, 12, 13, 14, 15, 16, 17, 18, 19 or 20 consecutive or non-consecutive amino acids. In some embodiments, a CasX variant protein comprises an insertion of at least about 100 consecutive or non-consecutive amino acids. Any amino acid, or combination of amino acids, can be inserted in the insertions described herein to generate a CasX variant protein.

Any permutation of the substitution, insertion and deletion embodiments described herein can be combined to generate a CasX variant protein of the disclosure. For example, a CasX variant protein can comprise at least one substitution and at least one deletion relative to a reference CasX protein sequence, at least one substitution and at least one insertion relative to a reference CasX protein sequence, at least one insertion and at least one deletion relative to a reference CasX protein sequence, or at least one substitution, one insertion and one deletion relative to a reference CasX protein sequence.

In some embodiments, the CasX variant protein has at least about 60% sequence similarity to SEQ ID NO:2 or a portion thereof. In some embodiments, the CasX variant protein comprises a substitution of Y789T of SEQ ID NO:2, a deletion of P793 of SEQ ID NO:2, a substitution of Y789D of SEQ ID NO:2, a substitution of T72S of SEQ ID NO:2, a substitution of I546V of SEQ ID NO:2, a substitution of E552A of SEQ ID NO:2, a substitution of A636D of SEQ ID NO:2, a substitution of F536S of SEQ ID NO:2, a substitution of A708K of SEQ ID NO:2, a substitution of Y797L of SEQ ID NO:2, a substitution of L792G SEQ ID NO:2, a substitution of A739V of SEQ ID NO:2, a substitution of G791M of SEQ ID NO:2, an insertion of A at position 661 of SEQ ID NO:2, a substitution of A788W of SEQ ID NO:2, a substitution of K390R of SEQ ID NO:2, a substitution of A751S of SEQ ID NO:2, a substitution of E385A of SEQ ID NO:2, an insertion of P at position 696 of SEQ ID NO:2, an insertion of M at position 773 of SEQ ID NO:2, a substitution of G695H of SEQ ID NO:2, an insertion of AS at position 793 of SEQ ID NO:2, an insertion of AS at position 795 of SEQ ID NO:2, a substitution of C477R of SEQ ID NO:2, a substitution of C477K of SEQ ID NO:2, a substitution of C479A of SEQ ID NO:2, a substitution of C479L of SEQ ID NO:2, a substitution of I55F of SEQ ID NO:2, a substitution of K210R of SEQ ID NO:2, a substitution of C233S of SEQ ID NO:2, a substitution of D231N of SEQ ID NO:2, a substitution of Q338E of SEQ ID NO:2, a substitution of Q338R of SEQ ID NO:2, a substitution of L379R of SEQ ID NO:2, a substitution of K390R of SEQ ID NO:2, a substitution of L481Q of SEQ ID NO:2, a substitution of F495S of SEQ ID NO:2, a substitution of D600N of SEQ ID NO:2, a substitution of T886K of SEQ ID NO:2, a substitution of A739V of SEQ ID NO:2, a substitution of K460N of SEQ ID NO:2, a substitution of I199F of SEQ ID NO:2, a substitution of G492P of SEQ ID NO:2, a substitution of T153I of SEQ ID NO:2, a substitution of R591I of SEQ ID NO:2, an insertion of AS at position 795 of SEQ ID NO:2, an insertion of AS at position 796 of SEQ ID NO:2, an insertion of L at position 889 of SEQ ID NO:2, a substitution of E121D of SEQ ID NO:2, a substitution of S270W of SEQ ID NO:2, a substitution of E712Q of SEQ ID NO:2, a substitution of K942Q of SEQ ID NO:2, a substitution of E552K of SEQ ID NO:2, a substitution of K25Q of SEQ ID NO:2, a substitution of N47D of SEQ ID NO:2, an insertion of T at position 696 of SEQ ID NO:2, a substitution of L685I of SEQ ID NO:2, a substitution of N880D of SEQ ID NO:2, a substitution of Q102R of SEQ ID NO:2, a substitution of M734K of SEQ ID NO:2, a substitution of A724S of SEQ ID NO:2, a substitution of T704K of SEQ ID NO:2, a substitution of P224K of SEQ ID NO:2, a substitution of K25R of SEQ ID NO:2, a substitution of M29E of SEQ ID NO:2, a substitution of H152D of SEQ ID NO:2, a substitution of S219R of SEQ ID NO:2, a substitution of E475K of SEQ ID NO:2, a substitution of G226R of SEQ ID NO:2, a substitution of A377K of SEQ ID NO:2, a substitution of E480K of SEQ ID NO:2, a substitution of K416E of SEQ ID NO:2, a substitution of H164R of SEQ ID NO:2, a substitution of K767R of SEQ ID NO:2, a substitution of 17F of SEQ ID NO:2, a substitution of M29R of SEQ ID NO:2, a substitution of H435R of SEQ ID NO:2, a substitution of E385Q of SEQ ID NO:2, a substitution of E385K of SEQ ID NO:2, a substitution of 1279F of SEQ ID NO:2, a substitution of D489S of SEQ ID NO:2, a substitution of D732N of SEQ ID NO:2, a substitution of A739T of SEQ ID NO:2, a substitution of W885R of SEQ ID NO:2, a substitution of E53K of SEQ ID NO:2, a substitution of A238T of SEQ ID NO:2, a substitution of P283Q of SEQ ID NO:2, a substitution of E292K of SEQ ID NO:2, a substitution of Q628E of SEQ ID NO:2, a substitution of R388Q of SEQ ID NO:2, a substitution of G791M of SEQ ID NO:2, a substitution of L792K of SEQ ID NO:2, a substitution of L792E of SEQ ID NO:2, a substitution of M779N of SEQ ID NO:2, a substitution of G27D of SEQ ID NO:2, a substitution of K955R of SEQ ID NO:2, a substitution of S867R of SEQ ID NO:2, a substitution of R693I of SEQ ID NO:2, a substitution of F189Y of SEQ ID NO:2, a substitution of V635M of SEQ ID NO:2, a substitution of F399L of SEQ ID NO:2, a substitution of E498K of SEQ ID NO:2, a substitution of E386R of SEQ ID NO:2, a substitution of V254G of SEQ ID NO:2, a substitution of P793S of SEQ ID NO:2, a substitution of K188E of SEQ ID NO:2, a substitution of QT945KI of SEQ ID NO:2, a substitution of T620P of SEQ ID NO:2, a substitution of T946P of SEQ ID NO:2, a substitution of TT949PP of SEQ ID NO:2, a substitution of N952T of SEQ ID NO:2, a substitution of K682E of SEQ ID NO:2, a substitution of K975R of SEQ ID NO:2, a substitution of L212P of SEQ ID NO:2, a substitution of E292R of SEQ ID NO:2, a substitution of 1303K of SEQ ID NO:2, a substitution of C349E of SEQ ID NO:2, a substitution of E385P of SEQ ID NO:2, a substitution of E386N of SEQ ID NO:2, a substitution of D387K of SEQ ID NO:2, a substitution of L404K of SEQ ID NO:2, a substitution of E466H of SEQ ID NO:2, a substitution of C477Q of SEQ ID NO:2, a substitution of C477H of SEQ ID NO:2, a substitution of C479A of SEQ ID NO:2, a substitution of D659H of SEQ ID NO:2, a substitution of T806V of SEQ ID NO:2, a substitution of K808S of SEQ ID NO:2, an insertion of AS at position 797 of SEQ ID NO:2, a substitution of V959M of SEQ ID N0:2, a substitution of K975Q of SEQ ID NO:2, a substitution of W974G of SEQ ID NO:2, a substitution of A708Q of SEQ ID NO:2, a substitution of V711K of SEQ ID NO:2, a substitution of D733T of SEQ ID NO:2, a substitution of L742W of SEQ ID NO:2, a substitution of V747K of SEQ ID NO:2, a substitution of F755M of SEQ ID NO:2, a substitution of M771A of SEQ ID NO:2, a substitution of M771Q of SEQ ID NO:2, a substitution of W782Q of SEQ ID NO:2, a substitution of G791F, of SEQ ID NO:2 a substitution of L792D of SEQ ID NO:2, a substitution of L792K of SEQ ID NO:2, a substitution of P793Q of SEQ ID NO:2, a substitution of P793G of SEQ ID NO:2, a substitution of Q804A of SEQ ID NO:2, a substitution of Y966N of SEQ ID NO:2, a substitution of Y723N of SEQ ID NO:2, a substitution of Y857R of SEQ ID NO:2, a substitution of S890R of SEQ ID NO:2, a substitution of S932M of SEQ ID NO:2, a substitution of L897M of SEQ ID NO:2, a substitution of R624G of SEQ ID NO:2, a substitution of S603G of SEQ ID NO:2, a substitution of N737S of SEQ ID NO:2, a substitution of L307K of SEQ ID NO:2, a substitution of I658V of SEQ ID NO:2, an insertion of PT at position 688 of SEQ ID NO:2, an insertion of SA at position 794 of SEQ ID NO:2, a substitution of S877R of SEQ ID NO:2, a substitution of N580T of SEQ ID NO:2, a substitution of V335G of SEQ ID NO:2, a substitution of T620S of SEQ ID NO:2, a substitution of W345G of SEQ ID NO:2, a substitution of T280S of SEQ ID NO:2, a substitution of L406P of SEQ ID NO:2, a substitution of A612D of SEQ ID NO:2, a substitution of A751S of SEQ ID NO:2, a substitution of E386R of SEQ ID NO:2, a substitution of V351M of SEQ ID NO:2, a substitution of K210N of SEQ ID NO:2, a substitution of D40A of SEQ ID NO:2, a substitution of E773G of SEQ ID NO:2, a substitution of H207L of SEQ ID NO:2, a substitution of T62A SEQ ID NO:2, a substitution of T287P of SEQ ID NO:2, a substitution of T832A of SEQ ID NO:2, a substitution of A893S of SEQ ID NO:2, an insertion of V at position 14 of SEQ ID NO:2, an insertion of AG at position 13 of SEQ ID NO:2, a substitution of RI IV of SEQ ID NO:2, a substitution of RI2N of SEQ ID NO:2, a substitution of R13H of SEQ ID NO:2, an insertion of Y at position 13 of SEQ ID NO:2, a substitution of R12L of SEQ ID NO:2, an insertion of Q at position 13 of SEQ ID NO:2, an substitution of V15S of SEQ ID NO:2, an insertion of D at position 17 of SEQ ID NO:2 or a combination thereof.

In some embodiments, the CasX variant comprises at least one modification in the NTSB domain.

In some embodiments, the CasX variant comprises at least one modification in the TSL domain. In some embodiments, the at least one modification in the TSL domain comprises an amino acid substitution of one or more of amino acids Y857, S890, or S932 of SEQ ID NO:2.

In some embodiments, the CasX variant comprises at least one modification in the helical I domain. In some embodiments, the at least one modification in the helical I domain comprises an amino acid substitution of one or more of amino acids S219, L249, E259, Q252, E292, L307, or D318 of SEQ ID NO:2.

In some embodiments, the CasX variant comprises at least one modification in the helical 11 domain. In some embodiments, the at least one modification in the helical 11 domain comprises an amino acid substitution of one or more of amino acids D361. L379, E385, E386. D387, F399, L404, R458, C477, or D489 of SEQ ID NO:2.

In some embodiments, the CasX variant comprises at least one modification in the OBD domain. In some embodiments, the at least one modification in the OBD comprises an amino acid substitution of one or more of amino acids F536. E552, T620, or 1658 of SEQ ID NO:2.

In some embodiments, the CasX variant comprises at least one modification in the RuvC DNA cleavage domain. In some embodiments, the at least one modification in the RuvC DNA cleavage domain comprises an amino acid substitution of one or more of amino acids K682, G695, A708, V711, D732, A739, D733, L742, V747, F755, M771, M779, W782, A788, G791, L792, P793, Y797, M799, Q804, S819, or Y857 or a deletion of amino acid P793 of SEQ ID NO:2.

In some embodiments, the CasX variant comprises at least one modification compared to the reference CasX sequence of SEQ ID NO:2 is selected from one or more of: (a) an amino acid substitution of L379R; (b) an amino acid substitution of A708K; (c) an amino acid substitution of T620P; (d) an amino acid substitution of E385P; (e) an amino acid substitution of Y857R; (f) an amino acid substitution of 1658V; (g) an amino acid substitution of F399L; (h) an amino acid substitution of Q252K; (i) an amino acid substitution of L404K; (j) an amino acid substitution of G223Y; (k) an amino acid deletion of P793; and an insertion of R at position 26.

In some embodiments, a CasX variant comprises at least two amino acid changes to the sequence of a reference CasX variant protein selected from the group consisting of: a substitution of Y789T of SEQ ID NO:2, a deletion of P793 of SEQ ID NO:2, a substitution of Y789D of SEQ ID NO:2, a substitution of T72S of SEQ ID NO:2, a substitution of I546V of SEQ ID NO:2, a substitution of E552A of SEQ ID NO:2, a substitution of A636D of SEQ ID NO:2, a substitution of F536S of SEQ ID NO:2, a substitution of A708K of SEQ ID NO:2, a substitution of Y797L of SEQ ID NO:2, a substitution of L792G SEQ ID NO:2, a substitution of A739V of SEQ ID NO:2, a substitution of G791M of SEQ ID NO:2, an insertion of A at position 661 of SEQ ID NO:2, a substitution of A788W of SEQ ID NO:2, a substitution of K390R of SEQ ID NO:2, a substitution of A751S of SEQ ID NO:2, a substitution of E385A of SEQ ID NO:2, an insertion of P at position 696 of SEQ ID NO:2, an insertion of M at position 773 of SEQ ID NO:2, a substitution of G695H of SEQ ID NO:2, an insertion of AS at position 793 of SEQ ID NO:2, an insertion of AS at position 795 of SEQ ID NO:2, a substitution of C477R of SEQ ID NO:2, a substitution of C477K of SEQ ID NO:2, a substitution of C479A of SEQ ID NO:2, a substitution of C479L of SEQ ID NO:2, a substitution of I55F of SEQ ID NO:2, a substitution of K210R of SEQ ID NO:2, a substitution of C233S of SEQ ID NO:2, a substitution of D231N of SEQ ID NO:2, a substitution of Q338E of SEQ ID NO:2, a substitution of Q338R of SEQ ID NO:2, a substitution of L379R of SEQ ID NO:2, a substitution of K390R of SEQ ID NO:2, a substitution of L481Q of SEQ ID NO:2, a substitution of F495S of SEQ ID NO:2, a substitution of D600N of SEQ ID NO:2, a substitution of T886K of SEQ ID NO:2, a substitution of A739V of SEQ ID NO:2, a substitution of K460N of SEQ ID NO:2, a substitution of I199F of SEQ ID NO:2, a substitution of G492P of SEQ ID NO:2, a substitution of T1531 of SEQ ID NO:2, a substitution of R591I of SEQ ID NO:2, an insertion of AS at position 795 of SEQ ID NO:2, an insertion of AS at position 796 of SEQ ID NO:2, an insertion of L at position 889 of SEQ ID NO:2, a substitution of E121D of SEQ ID NO:2, a substitution of S270W of SEQ ID NO:2, a substitution of E712Q of SEQ ID NO:2, a substitution of K942Q of SEQ ID NO:2, a substitution of E552K of SEQ ID NO:2, a substitution of K25Q of SEQ ID NO:2, a substitution of N47D of SEQ ID NO:2, an insertion of T at position 696 of SEQ ID NO:2, a substitution of L685I of SEQ ID NO:2, a substitution of N880D of SEQ ID NO:2, a substitution of Q102R of SEQ ID NO:2, a substitution of M734K of SEQ ID NO:2, a substitution of A724S of SEQ ID NO:2, a substitution of T704K of SEQ ID NO:2, a substitution of P224K of SEQ ID NO:2, a substitution of K25R of SEQ ID NO:2, a substitution of M29E of SEQ ID NO:2, a substitution of H152D of SEQ ID NO:2, a substitution of S219R of SEQ ID NO:2, a substitution of E475K of SEQ ID NO:2, a substitution of G226R of SEQ ID NO:2, a substitution of A377K of SEQ ID NO:2, a substitution of E480K of SEQ ID NO:2, a substitution of K416E of SEQ ID NO:2, a substitution of H164R of SEQ ID NO:2, a substitution of K767R of SEQ ID NO:2, a substitution of I7F of SEQ ID NO:2, a substitution of M29R of SEQ ID NO:2, a substitution of H435R of SEQ ID NO:2, a substitution of E385Q of SEQ ID NO:2, a substitution of E385K of SEQ ID NO:2, a substitution of I279F of SEQ ID NO:2, a substitution of D489S of SEQ ID NO:2, a substitution of D732N of SEQ ID NO:2, a substitution of A739T of SEQ ID NO:2, a substitution of W885R of SEQ ID NO:2, a substitution of E53K of SEQ ID NO:2, a substitution of A238T of SEQ ID NO:2, a substitution of P283Q of SEQ ID NO:2, a substitution of E292K of SEQ ID NO:2, a substitution of Q628E of SEQ ID NO:2, a substitution of R388Q of SEQ ID NO:2, a substitution of G791M of SEQ ID NO:2, a substitution of L792K of SEQ ID NO:2, a substitution of L792E of SEQ ID NO:2, a substitution of M779N of SEQ ID NO:2, a substitution of G27D of SEQ ID NO:2, a substitution of K955R of SEQ ID NO:2, a substitution of S867R of SEQ ID NO:2, a substitution of R693I of SEQ ID NO:2, a substitution of F189Y of SEQ ID NO:2, a substitution of V635M of SEQ ID NO:2, a substitution of F399L of SEQ ID NO:2, a substitution of E498K of SEQ ID NO:2, a substitution of E386R of SEQ ID NO:2, a substitution of V254G of SEQ ID NO:2, a substitution of P793S of SEQ ID NO:2, a substitution of K188E of SEQ ID NO:2, a substitution of QT945KI of SEQ ID NO:2, a substitution of T620P of SEQ ID NO:2, a substitution of T946P of SEQ ID NO:2, a substitution of TT949PP of SEQ ID NO:2, a substitution of N952T of SEQ ID NO:2, a substitution of K682E of SEQ ID NO:2, a substitution of K975R of SEQ ID NO:2, a substitution of L212P of SEQ ID NO:2, a substitution of E292R of SEQ ID NO:2, a substitution of I303K of SEQ ID NO:2, a substitution of C349E of SEQ ID NO:2, a substitution of E385P of SEQ ID NO:2, a substitution of E386N of SEQ ID NO:2, a substitution of D387K of SEQ ID NO:2, a substitution of L404K of SEQ ID NO:2, a substitution of E466H of SEQ ID NO:2, a substitution of C477Q of SEQ ID NO:2, a substitution of C477H of SEQ ID NO:2, a substitution of C479A of SEQ ID NO:2, a substitution of D659H of SEQ ID NO:2, a substitution of T806V of SEQ ID NO:2, a substitution of K808S of SEQ ID NO:2, an insertion of AS at position 797 of SEQ ID NO:2, a substitution of V959M of SEQ ID NO:2, a substitution of K975Q of SEQ ID NO:2, a substitution of W974G of SEQ ID NO:2, a substitution of A708Q of SEQ ID NO:2, a substitution of V711K of SEQ ID NO:2, a substitution of D733T of SEQ ID NO:2, a substitution of L742W of SEQ ID NO:2, a substitution of V747K of SEQ ID NO:2, a substitution of F755M of SEQ ID NO:2, a substitution of M771A of SEQ ID NO:2, a substitution of M771Q of SEQ ID NO:2, a substitution of W782Q of SEQ ID NO:2, a substitution of G791F, of SEQ ID NO:2 a substitution of L792D of SEQ ID NO:2, a substitution of L792K of SEQ ID NO:2, a substitution of P793Q of SEQ ID NO:2, a substitution of P793G of SEQ ID NO:2, a substitution of Q804A of SEQ ID NO:2, a substitution of Y966N of SEQ ID NO:2, a substitution of Y723N of SEQ ID NO:2, a substitution of Y857R of SEQ ID NO:2, a substitution of S890R of SEQ ID NO:2, a substitution of S932M of SEQ ID NO:2, a substitution of L897M of SEQ ID NO:2, a substitution of R624G of SEQ ID NO:2, a substitution of S603G of SEQ ID NO:2, a substitution of N737S of SEQ ID NO:2, a substitution of L307K of SEQ ID NO:2, a substitution of I658V of SEQ ID NO:2, an insertion of PT at position 688 of SEQ ID NO:2, an insertion of SA at position 794 of SEQ ID NO:2, a substitution of S877R of SEQ ID NO:2, a substitution of N580T of SEQ ID NO:2, a substitution of V335G of SEQ ID NO:2, a substitution of T620S of SEQ ID NO:2, a substitution of W345G of SEQ ID NO:2, a substitution of T280S of SEQ ID NO:2, a substitution of L406P of SEQ ID NO:2, a substitution of A612D of SEQ ID NO:2, a substitution of A751S of SEQ ID NO:2, a substitution of E386R of SEQ ID NO:2, a substitution of V351M of SEQ ID NO:2, a substitution of K210N of SEQ ID NO:2, a substitution of D40A of SEQ ID NO:2, a substitution of E773G of SEQ ID NO:2, a substitution of H207L of SEQ ID NO:2, a substitution of T62A SEQ ID NO:2, a substitution of T287P of SEQ ID NO:2, a substitution of T832A of SEQ ID NO:2, a substitution of A893S of SEQ ID NO:2, an insertion of V at position 14 of SEQ ID NO:2, an insertion of AG at position 13 of SEQ ID NO:2, a substitution of RI IV of SEQ ID NO:2, a substitution of R12N of SEQ ID NO:2, a substitution of R13H of SEQ ID NO:2, an insertion of Y at position 13 of SEQ ID NO:2, a substitution of R12L of SEQ ID NO:2, an insertion of Q at position 13 of SEQ ID NO:2, an substitution of V15S of SEQ ID NO:2 and an insertion of D at position 17 of SEQ ID NO:2. In some embodiments, the at least two amino acid changes to a reference CasX protein are selected from the amino acid changes disclosed in the sequences of Table 3. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, a CasX variant protein comprises a substitution of S794R and a substitution of Y797L of SEQ ID NO:2. In some embodiments, a CasX variant protein comprises a substitution of K416E and a substitution of A708K of SEQ ID NO:2. In some embodiments, a CasX variant protein comprises a substitution of A708K and a deletion of P793 of SEQ ID NO:2. In some embodiments, a CasX variant protein comprises a deletion of P793 and an insertion of AS at position 795 SEQ ID NO:2. In some embodiments, a CasX variant protein comprises a substitution of Q367K and a substitution of I425S of SEQ ID NO:2. In some embodiments, a CasX variant protein comprises a substitution of A708K, a deletion of P position 793 and a substitution A793V of SEQ ID NO:2. In some embodiments, a CasX variant protein comprises a substitution of Q338R and a substitution of A339E of SEQ ID NO:2. In some embodiments, a CasX variant protein comprises a substitution of Q338R and a substitution of A339K of SEQ ID NO:2. In some embodiments, a CasX variant protein comprises a substitution of S507G and a substitution of G508R of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of C477K, a substitution of A708K and a deletion of P at position 793 of SEQ ID NO:2. In some embodiments, a CasX variant protein comprises a substitution of L379R, a substitution of C477K, a substitution of A708K and a deletion of P at position of 793 of SEQ ID NO:2. In some embodiments, a CasX variant protein comprises a substitution of L379R, a substitution of A708K, a deletion of P at position 793 and a substitution A739V of SEQ ID NO:2. In some embodiments, a CasX variant protein comprises a substitution of C477K, a substitution of A708K, a deletion of P at position 793 and a substitution of A739V of SEQ ID NO:2. In some embodiments, a CasX variant protein comprises a substitution of L379R, a substitution of C477K, a substitution of A708K, a deletion of P at position 793 and a substitution of A739V of SEQ ID NO:2. In some embodiments, a CasX variant protein comprises a substitution of L379R, a substitution of A708K, a deletion of P at position 793 and a substitution of M779N of SEQ ID NO:2. In some embodiments, a CasX variant protein comprises a substitution of L379R, a substitution of A708K, a deletion of P at position 793 and a substitution of M771N of SEQ ID NO:2. In some embodiments, a CasX variant protein comprises a substitution of L379R, a substitution of 708K, a deletion of P at position 793 and a substitution of D489S of SEQ ID NO:2. In some embodiments, a CasX variant protein comprises a substitution of L379R, a substitution of A708K, a deletion of P at position 793 and a substitution of A739T of SEQ ID NO:2. In some embodiments, a CasX variant protein comprises a substitution of L379R, a substitution of A708K, a deletion of P at position 793 and a substitution of D732N of SEQ ID NO:2. In some embodiments, a CasX variant protein comprises a substitution of L379R, a substitution of A708K, a deletion of P at position 793 and a substitution of G791M of SEQ ID NO:2. In some embodiments, a CasX variant protein comprises a substitution of L379R, a substitution of 708K, a deletion of P at position 793 and a substitution of Y797L of SEQ ID NO:2. In some embodiments, a CasX variant protein comprises a substitution of L379R, a substitution of C477K, a substitution of A708K, a deletion of P at position 793 and a substitution of M779N of SEQ ID NO:2. In some embodiments, a CasX variant protein comprises a substitution of L379R, a substitution of C477K, a substitution of A708K, a deletion of P at position 793 and a substitution of M771N of SEQ ID NO:2. In some embodiments, a CasX variant protein comprises a substitution of L379R, a substitution of C477K, a substitution of A708K, a deletion of P at position 793 and a substitution of D489S of SEQ ID NO:2. In some embodiments, a CasX variant protein comprises a substitution of L379R, a substitution of C477K, a substitution of A708K, a deletion of P at position 793 and a substitution of A739T of SEQ ID NO:2. In some embodiments, a CasX variant protein comprises a substitution of L379R, a substitution of C477K, a substitution of A708K, a deletion of P at position 793 and a substitution of D732N of SEQ ID NO:2. In some embodiments, a CasX variant protein comprises a substitution of L379R, a substitution of C477K, a substitution of A708K, a deletion of P at position 793 and a substitution of G791M of SEQ ID NO:2. In some embodiments, a CasX variant protein comprises a substitution of L379R, a substitution of C477K, a substitution of A708K, a deletion of P at position 793 and a substitution of Y797L of SEQ ID NO:2. In some embodiments, a CasX variant protein comprises a substitution of L379R, a substitution of C477K, a substitution of A708K, a deletion of P at position 793 and a substitution of T620P of SEQ ID NO:2. In some embodiments, a CasX variant protein comprises a substitution of A708K, a deletion of P at position 793 and a substitution of E386S of SEQ ID NO:2. In some embodiments, a CasX variant protein comprises a substitution of E386R, a substitution of F399L and a deletion of P at position 793 of SEQ ID NO:2. In some embodiments, a CasX variant protein comprises a substitution of R581I and A739V of SEQ ID NO:2. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, a CasX variant protein comprises a substitution of A708K, a deletion of P at position 793 and a substitution of A739V of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of C477K, a substitution of A708K and a deletion of P at position 793 of SEQ ID NO:2. In some embodiments, a CasX variant protein comprises a substitution of L379R, a substitution of C477K, a substitution of A708K and a deletion of P at position 793 of SEQ ID NO:2. In some embodiments, a CasX variant protein comprises a substitution of L379R, a substitution of A708K, a deletion of P at position 793 and a substitution of A739V of SEQ ID NO:2. In some embodiments, a CasX variant protein comprises a substitution of C477K, a substitution of A708K, a deletion of P at position 793 and a substitution of A739 of SEQ ID NO:2. In some embodiments, a CasX variant protein comprises a substitution of L379R, a substitution of C477K, a substitution of A708K, a deletion of P at position 793 and a substitution of A739V of SEQ ID NO:2. In some embodiments, a CasX variant protein comprises a substitution of L379R, a substitution of C477K, a substitution of A708K, a deletion of P at position 793 and a substitution of T620P of SEQ ID NO:2. In some embodiments, a CasX variant protein comprises a substitution of M771 A of SEQ ID NO:2. In some embodiments, a CasX variant protein comprises a substitution of L379R, a substitution of A708K, a deletion of P at position 793 and a substitution of D732N of SEQ ID NO:2. In some embodiments, a CasX variant comprises any combination of the foregoing embodiments of this paragraph.

In some embodiments, a CasX variant protein comprises a substitution of W782Q of SEQ ID NO:2. In some embodiments, a CasX variant protein comprises a substitution of M771Q of SEQ ID NO:2. In some embodiments, a CasX variant protein comprises a substitution of R4581 and a substitution of A739V of SEQ ID NO:2. In some embodiments, a CasX variant protein comprises a substitution of L379R, a substitution of A708K, a deletion of P at position 793 and a substitution of M771N of SEQ ID NO:2. In some embodiments, a CasX variant protein comprises a substitution of L379R, a substitution of A708K, a deletion of P at position 793 and a substitution of A739T of SEQ ID NO:2. In some embodiments, a CasX variant protein comprises a substitution of L379R, a substitution of C477K, a substitution of A708K, a deletion of P at position 793 and a substitution of D489S of SEQ ID NO:2. In some embodiments, a CasX variant protein comprises a substitution of L379R, a substitution of C477K, a substitution of A708K, a deletion of P at position 793 and a substitution of D732N of SEQ ID NO:2. In some embodiments, a CasX variant protein comprises a substitution of V711K of SEQ ID NO:2. In some embodiments, a CasX variant protein comprises a substitution of L379R, a substitution of C477K, a substitution of A708K, a deletion of P at position 793 and a substitution of Y797L of SEQ ID NO:2. In some embodiments, a CasX variant protein comprises a substitution of L379R, a substitution of A708K and a deletion of P at position 793 of SEQ ID NO:2. In some embodiments, a CasX variant protein comprises a substitution of L379R, a substitution of C477K, a substitution of A708K, a deletion of P at position 793 and a substitution of M771N of SEQ ID NO:2. In some embodiments, a CasX variant protein comprises a substitution of A708K, a substitution of P at position 793 and a substitution of E386S of SEQ ID NO:2. In some embodiments, a CasX variant protein comprises a substitution of L379R, a substitution of C477K, a substitution of A708K and a deletion of P at position 793 of SEQ ID NO:2. In some embodiments, a CasX variant protein comprises a substitution of L792D of SEQ ID NO:2. In some embodiments, a CasX variant protein comprises a substitution of G791F of SEQ ID NO:2. In some embodiments, a CasX variant protein comprises a substitution of A708K, a deletion of P at position 793 and a substitution of A739V of SEQ ID NO:2. In some embodiments, a CasX variant protein comprises a substitution of L379R, a substitution of A708K, a deletion of P at position 793 and a substitution of A739V of SEQ ID NO:2. In some embodiments, a CasX variant protein comprises a substitution of C477K, a substitution of A708K and a substitution of P at position 793 of SEQ ID NO:2. In some embodiments, a CasX variant protein comprises a substitution of L2491 and a substitution of M771N of SEQ ID NO:2. In some embodiments, a CasX variant protein comprises a substitution of V747K of SEQ ID NO:2. In some embodiments, a CasX variant protein comprises a substitution of L379R, a substitution of C477, a substitution of A708K, a deletion of P at position 793 and a substitution of M779N of SEQ ID NO:2. In some embodiments, a CasX variant protein comprises a substitution of F755M. In some embodiments, a CasX variant comprises any combination of the foregoing embodiments of this paragraph.

In some embodiments, a CasX variant protein comprises at least one modification compared to the reference CasX sequence of SEQ ID NO:2, wherein the at least one modification is selected from one or more of; an amino acid substitution of L379R; an amino acid substitution of A708K; an amino acid substitution of T620P; an amino acid substitution of E385P; an amino acid substitution of Y857R; an amino acid substitution of 1658V; an amino acid substitution of F399L; an amino acid substitution of Q252K; and an amino acid deletion of 1P7931. In some embodiments, a CasX variant protein comprises at least one modification compared to the reference CasX sequence of SEQ ID NO:2, wherein the at least one modification is selected from one or more of: an amino acid substitution of L379R; an amino acid substitution of A708K; an amino acid substitution of T620P; an amino acid substitution of E385P; an amino acid substitution of Y857R; an amino acid substitution of 1658V; an amino acid substitution of F399L; an amino acid substitution of Q252K; an amino acid substitution of L404K; and an amino acid deletion of [P793]. In other embodiments, a CasX variant protein comprises any combination of the foregoing substitutions or deletions compared to the reference CasX sequence of SEQ ID NO:2. In other embodiments, the CasX variant protein can, in addition to the foregoing substitutions or deletions, further comprise a substitution of an NTSB and/or a helical 1b domain from the reference CasX of SEQ ID NO:1.

In some embodiments, the CasX variant protein comprises between 400 and 2000 amino acids, between 500 and 1500 amino acids, between 700 and 1200 amino acids, between 800 and 1100 amino acids, or between 900 and 1000 amino acids.

In some embodiments, the CasX variant protein comprises one or more modifications in a region of non-contiguous residues that form a channel in which gNA:target DNA complexing occurs. In some embodiments, the CasX variant protein comprises one or more modifications comprising a region of non-contiguous residues that form an interface which binds with the gNA. For example, in some embodiments of a reference CasX protein, the helical I, helical II and OBD domains all contact or are in proximity to the gNA:target DNA complex, and one or more modifications to non-contiguous residues within any of these domains may improve function of the CasX variant protein.

In some embodiments, the CasX variant protein comprises one or more modifications in a region of non-contiguous residues that form a channel which binds with the non-target strand DNA. For example, a CasX variant protein can comprise one or more modifications to non-contiguous residues of the NTSBD. In some embodiments, the CasX variant protein comprises one or more modifications in a region of non-contiguous residues that form an interface which binds with the PAM. For example, a CasX variant protein can comprise one or more modifications to non-contiguous residues of the helical I domain or OBD. In some embodiments, the CasX variant protein comprises one or more modifications comprising a region of non-contiguous surface-exposed residues. As used herein, "surface-exposed residues" refers to amino acids on the surface of the CasX protein, or amino acids in which at least a portion of the amino acid, such as the backbone or a part of the side chain is on the surface of the protein. Surface exposed residues of cellular proteins such as CasX, which are exposed to an aqueous intracellular environment, are frequently selected from positively charged hydrophilic amino acids, for example arginine, asparagine, aspartate, glutamine, glutamate, histidine, lysine, serine, and threonine. Thus, for example, in some embodiments of the variants provided herein, a region of surface exposed residues comprises one or more insertions, deletions, or substitutions compared to a reference CasX protein. In some embodiments, one or more positively charged residues are substituted for one or more other positively charged residues, or negatively charged residues, or uncharged residues, or any combinations thereof. In some embodiments, one or more amino acids residues for substitution are near bound nucleic acid, for example residues in the RuvC domain or helical I domain that contact target DNA, or residues in the OBD or helical II domain that bind the gNA, can be substituted for one or more positively charged or polar amino acids.

In some embodiments, the CasX variant protein comprises one or more modifications in a region of non-contiguous residues that form a core through hydrophobic packing in a domain of the reference CasX protein. Without wishing to be bound by any theory, regions that form cores through hydrophobic packing are rich in hydrophobic amino acids such as valine, isoleucine, leucine, methionine, phenylalanine, tryptophan, and cysteine. For example, in some reference CasX proteins, RuvC domains comprise a hydrophobic pocket adjacent to the active site. In some embodiments, between 2 to 15 residues of the region are charged, polar, or base-stacking. Charged amino acids (sometimes referred to herein as residues) may include, for example, arginine, lysine, aspartic acid, and glutamic acid, and the side chains of these amino acids may form salt bridges provided a bridge partner is also present. Polar amino acids may include, for example, glutamine, asparagine, histidine, serine, threonine, tyrosine, and cysteine. Polar amino acids can, in some embodiments, form hydrogen bonds as proton donors or acceptors, depending on the identity of their side chains. As used herein, "base-stacking" includes the interaction of aromatic side chains of an amino acid residue (such as tryptophan, tyrosine, phenylalanine, or histidine) with stacked nucleotide bases in a nucleic acid. Any modification to a region of non-contiguous amino acids that are in close spatial proximity to form a functional part of the CasX variant protein is envisaged as within the scope of the disclosure.

i. CasX Variant Proteins with Domains from Multiple Source Proteins

In certain embodiments, the disclosure provides a chimeric CasX protein comprising protein domains from two or more different CasX proteins, such as two or more reference CasX proteins, or two or more CasX variant protein sequences as described herein. As used herein, a "chimeric CasX protein" refers to a CasX containing at least two domains isolated or derived from different sources, such as two naturally occurring proteins, which may, in some embodiments, be isolated from different species. For example, in some embodiments, a chimeric CasX protein comprises a first domain from a first CasX protein and a second domain from a second, different CasX protein. In some embodiments, the first domain can be selected from the group consisting of the NTSB, TSL, Helical I, Helical II, OBD and RuvC domains. In some embodiments, the second domain is selected from the group consisting of the NTSB, TSL, Helical I, Helical II, OBD and RuvC domains with the second domain being different from the foregoing first domain. For example, a chimeric CasX protein may comprise an NTSB, TSL, Helical I, Helical II, OBD domains from a CasX protein of SEQ ID NO:2, and a RuvC domain from a CasX protein of SEQ ID NO:1, or vice versa. As a further example, a chimeric CasX protein may comprise an NTSB, TSL, Helical II, OBD and RuvC domain from CasX protein of SEQ ID NO:2, and a Helical I domain from a CasX protein of SEQ ID NO:1, or vice versa. Thus, in certain embodiments, a chimeric CasX protein may comprise an NTSB, TSL, Helical II, OBD and RuvC domain from a first CasX protein, and a Helical I domain from a second CasX protein. In some embodiments of the chimeric CasX proteins, the domains of the first CasX protein are derived from the sequences of SEQ ID NO:1, SEQ ID NO:2 or SEQ ID NO:3, and the domains of the second CasX protein are derived from the sequences of SEQ ID NO:1, SEQ ID NO:2 or SEQ ID NO:3, and the first and second CasX proteins are not the same. In some embodiments, domains of the first CasX protein comprise sequences derived from SEQ ID NO:1 and domains of the second CasX protein comprise sequences derived from SEQ ID NO:2. In some embodiments, domains of the first CasX protein comprise sequences derived from SEQ ID NO:1 and domains of the second CasX protein comprise sequences derived from SEQ ID NO:3. In some embodiments, domains of the first CasX protein comprise sequences derived from SEQ ID NO:2 and domains of the second CasX protein comprise sequences derived from SEQ ID NO:3. In some embodiments, the CasX variant is selected of group consisting of CasX variants comprising SEQ ID NOS: 49-160.

In some embodiments, a CasX variant protein comprises at least one chimeric domain comprising a first part from a first CasX protein and a second part from a second, different CasX protein. As used herein, a "chimeric domain" refers to a domain containing at least two parts isolated or derived from different sources, such as two naturally occurring proteins or portions of domains from two reference CasX proteins. The at least one chimeric domain can be any of the NTSB, TSL, helical I, helical II, OBD or RuvC domains as described herein. In some embodiments, the first portion of a CasX domain comprises a sequence of SEQ ID NO:1 and the second portion of a CasX domain comprises a sequence of SEQ ID NO:2. In some embodiments, the first portion of the CasX domain comprises a sequence of SEQ ID NO:1 and the second portion of the CasX domain comprises a sequence of SEQ ID NO:3. In some embodiments, the first portion of the CasX domain comprises a sequence of SEQ ID NO:2 and the second portion of the CasX domain comprises a sequence of SEQ ID NO:3. In some embodiments, the at least one chimeric domain comprises a chimeric RuvC domain. As an example of the foregoing, the chimeric RuvC domain comprises amino acids 661 to 824 of SEQ ID NO:1 and amino acids 922 to 978 of SEQ ID NO:2. As an alternative example of the foregoing, a chimeric RuvC domain comprises amino acids 648 to 812 of SEQ ID NO:2 and amino acids 935 to 986 of SEQ ID NO:1. In some embodiments, a CasX protein comprises a first domain from a first CasX protein and a second domain from a second CasX protein, and at least one chimeric domain comprising at least two parts isolated from different CasX proteins using the approach of the embodiments described in this paragraph. In the foregoing embodiments, the chimeric CasX proteins having domains or portions of domains derived from SEQ ID NOS:1, 2 and 3, can further comprise amino acid insertions, deletions, or substitutions of any of the embodiments disclosed herein.

In some embodiments, a CasX variant protein comprises a sequence of SEQ ID NOS: 49-160, 237-239, 243-246, 251-263 or 273-281 as set forth in Tables 3, 6, 7, 8, or 10. In some embodiments, a CasX variant protein consists of a sequence of SEQ ID NOS: 49-160 as set forth in Table 3. In other embodiments, a CasX variant protein comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 890% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical to a sequence of SEQ ID NOS: 49-160, 237-239, 243-246, 251-263 or 273-281. In other embodiments, a CasX variant protein comprises a sequence of SEQ ID NOS: 49-160 as set forth in Table 3, and further comprises one or more NLS disclosed herein at or near either the N-terminus, the C-terminus, or both. It will be understood that in some cases, the N-terminal methionine of the CasX variants of the Tables is removed from the expressed CasX variant during post-translational modification.

TABLE 3

CasX Variant Sequences

| Description* | Amino Acid Sequence |
|---|---|
| TSL, Helical I, Helical II, OBD and RuvC domains from SEQ ID NO: 2 and an NTSB domain from SEQ ID NO: 1 | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPASKKI DQNKLKPEMDEKGNLTTAGFACSQCGQPLFVYKLEQVSEKGKAYTNYFGRCNVA EHEKLILLAQLKPEKDSDEAVTYSLGKFGQRALDFYSIHVTRESNHPVKPLEQI GGNSCASGPVGKALSDACMGAVASFLTKYQDIILEHQKVIKKNEKRLANLKDIA SANGLAFPKITLPPQPHTKEGIEAYNNVVAQIVIWVNLNLWQKLKIGRDEAKPL QRLKGFPSFPLVERQANEVDWWDMVCNVKKLINEKKEDGKVFWQNLAGYKRQEA LRPYLSSEEDRKKGKKFARYQFGDLLLHLEKKHGEDWGKVYDEAWERIDKKVEG LSKHIKLEEERRSEDAQSKAALTDWLRAKASFVIEGLKEADKDEFCRCELKLQK WYGDLRGKPFAIEAENSILDISGFSKQYNCAFIWQKDGVKKLNLYLIINYFKGG KLRFKKIKPEAFEANRFYTVINKKSGEIVPMEVNFNFDDPNLIILPLAFGKRQG REFIWNDLLSLETGSLKLANGRVIEKTLYNRRTRQDEPALFVALTFERREVLDS SNIKPMNLIGIDRGENIPAVIALTDPEGCPLSRFKDSLGNPTHILRIGESYKEK QRTIQAKKEVEQRRAGGYSRKYASKAKNLADDMVRNTARDLLYYAVTQDAMLIF ENLSRGFGRQGKRTFMAERQYTRMEDWLTAKLAYEGLSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 49) |
| NTSB, Helical I, Helical II, OBD and RuvC domains from SEQ ID NO: 2 and a TSL domain from SEQ ID NO: 1 | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDGKGPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLITNYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITTADYDGMLVRLKKTSDGWATTLNNKELKAEGQITYYNRYKRQTVEKE LSAELDRLSEESGNNDISKWTKGRRDEALFLLKKRFSHRPVQEQFVCLDCGHEV HADEQAALNIARSWLFLRSQEYKKYQTNKTTGNTDKRAFVETWQSFYRKKLKEV WKPAV (SEQ ID NO: 50) |
| TSL, Helical I, Helical II, OBD and RuvC domains from SEQ ID NO: 1 and an NTSB domain from SEQ ID NO: 2 | MEKRINKIRKKLSADNATKPVSRSGPMKTLLVRVMTDDLKKRLEKRRKKPEVMP QVISNNAANNLRMLLDDYTKMKEAILQVYWQEFKDDHVGLMCKFAQPAPKNIDQ RKLIPVKDGNERLTSSGFACSQCCQPLYVYKLEQVNDGKGPHTNYFGRCNVSEH ERLILLSPHKPEANDELVTYSLGKFGQRALDFYSIHVTKESTHPVKPLAQIAGN RYASGPVGKALSDACMGTIASFLSKYQDIIIEHQKVVKGNQKRLESLRELAGKE NLEYPSVTLPPQPHTKEGVDAYNEVIARVRMWVNLNLWQKLKLSRDDAKPLLRL KGFPSFPVVERRENEVDWWNTINEVKKLIDAKRDMGRVFWSGVTAEKRNTILEG YNYLPNENDHKKREGSLENPKKPAKRQFGDLLLYLEKKYAGDWGKVFDEAWERI DKKIAGLTSHIEREEARNAEDAQSKAVLTDWLRAKASFVLERLKEMDEKEFYAC EIQLQKWYGDLRGNPFAVEAENRVVDISGFSIGSDGHSIQYRNLLAWKYLENGK REFYLLMNYGKKGRIRFTDGTDIKKSGKWQGLLYGGGKAKVIDLTFDPDDEQLI ILPLAFGTRQGREFIWNDLLSLETGLIKLANGRVIEKTIYNKKIGRDEPALFVA LTFERREVVDPSNIKPVNLIGVDRGENIPAVLALTDPEGCPLPEFKDSSGGPTD ILRIGEGYKEKQRAIQAAKEVEQRRAGGYSRKFASKSRNLADDMVRNSARDLFY HAVTHDAVLVFENLSRGFGRQGKRTFMTERQYTKMEDWLTAKLAYEGLTSKTYL SKTLAQYTSKTCSNCGFTITTADYDGMLVRLKKTSDGWATTLNNKELKAEGQIT |

TABLE 3-continued

CasX Variant Sequences

| Description* | Amino Acid Sequence |
|---|---|
| | YYNRYKRQTVEKELSAELDRLSEESGNNDISKWTKGRRDEALFLLKKRFSHRPV<br>QEQFVCLDCGHEVHADEQAALNIARSWLFLNSNSTEFKSYKSGKQPFVGAWQAF<br>YKRRLKEVWKPNA (SEQ ID NO: 51) |
| NTSB, Helical I, Helical II, OBD and RuvC domains from SEQ ID NO: 1 and an TSL domain from SEQ ID NO: 2 | MEKRINKIRKKLSADNATKPVSRSGPMKTLLVRVMTDDLKKRLEKRRKKPEVMP<br>QVISNNAANNLRMLLDDYTKMKEAILQVYWQEFKDDHVGLMCKFAQPASKKIDQ<br>NKLKPEMDEKGNLTTAGFACSQCGQPLFVYKLEQVSEKGKAYTNYFGRCNVAEH<br>EKLILLAQLKPEKDSDEAVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPVVERRENEVDWWNTINEVKKLIDAKRDMGRVFWSGVTAEKRNTILE<br>GYNYLPNENDHKKREGSLENPKKPAKRQFGDLLLYLEKKYAGDWGKVFDEAWER<br>IDKKIAGLTSHIEREEARNAEDAQSKAVLTDWLRAKASFVLERLKEMDEKEFYA<br>CEIQLQKWYGDLRGNPFAVEAENRVVDISGFSIGSDGHSIQYRNLLAWKYLENG<br>KREFYLLMNYGKKGRIRFTDGTDIKKSGKWQGLLYGGGKAKVIDLTFDPDDEQL<br>IILPLAFGTRQGREFIWNDLLSLETGLTKLANGRVIEKTIYNKKTGRDEPALFV<br>ALTFERREVVDPSNIKPVNLIGVDRGENIPAVIALTDPEGCPLPEFKDSSGGPT<br>DILRIGEGYKEKQRAIQAAKEVEQRRAGGYSRKFASKSRNLADDMVRNSARDLF<br>YHAVTHDAVLVFENLSRGFGRQGKRTFMTERQYTKMEDWLTAKLAYEGLTSKTY<br>LSKTLAQYTSKTCSNCGFTITSADYDRVLEKLKKTATGWMTTINGKELKVEGQI<br>TYYNRYKRQNVVKDLSVELDRLSEESVNNDISSWTKGRSGEALSLLKKRFSHRP<br>VQEKFVCLNCGFETHADEQAALNIARSWLFLNSNSTEFKSYKSGKQPFVGAWQA<br>FYKRRLKEVWKPNA (SEQ ID NO: 52) |
| NTSB, TSL, Helical I, Helical II and OBD domains SEQ ID NO: 2 and an exogenous RuvC domain or a portion thereof from a second CasX protein. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPVNLIGVDRGENIPAVIALTDPEGCPLPEFKDSSGGPTDILRIGEGYKEKQ<br>RAIQAAKEVEQRRAGGYSRKFASKSRNLADDMVRNSARDLFYHAVTHDAVLVFE<br>NLSRGFGRQGKRTFMTERQYTKMEDWLTAKLAYEGLTSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THA (SEQ ID NO: 53) |
| | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HA (SEQ ID NO: 54) |
| NTSB, TSL, Helical II, OBD and RuvC domains from SEQ ID NO: 2 and a Helical I domain from SEQ ID NO: 1 | MQEIKRINKIRRRLVKDSNTKKAGKTGPMKTLLVRVMTPDLRERLENLRKKPEN<br>IPQPISNNAANNLRMLLDDYTKMKEAILQVYWQEFKDDHVGLMCKFAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVTEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE |

TABLE 3-continued

CasX Variant Sequences

| Description* | Amino Acid Sequence |
|---|---|
| | NLSRGFGRQGKRTFMAERQYTRMEDWLTAKLAYEGLSKTYLSKTLAQYTSKTCS
NCGFTITSADYDRVLEKLKKTATGWMTTINGKELKVEGQITYYNRYKRQNVVKD
LSVELDRLSEESVNNDISSWTKGRSGEALSLLKKRFSHRPVQEKFVCLNCGFET
HADEQAALNIARSWLFLRSQEYKKYQTNKTTGNTDKRAFVETWQSFYRKKLKEV
WKPAV (SEQ ID NO: 55) |
| NTSB, TSL, Helical I, OBD and RuvC domains from SEQ ID NO: 2 and a Helical II domain from SEQ ID NO: 1 | MQEIKRINKIRRRLVKDSNTKKAGKTGPMKTLLVRVMTPDLRERLENLRKKPEN
IPQPISNTSRANLNKLLTDYTEMKKAILHVYWEEFQKDPVGLMSRVAQPAPKNI
DQRKLIPVKDGNERLTSSGFACSQCCQPLYVYKLEQVNDKGKPHTNYFGRCNVS
EHERLILLSPHKPEANDELVTYSLGKFGQRALDFYSIHVTRESNHPVKPLEQIG
GNSCASGPVGKALSDACMGAVASFLTKYQDIILEHQKVIKKNEKRLANLKDIAS
ANGLAFPKITLPPQPHTKEGIEAYNNVVAQIVIWVNLNWQKLKIGRDEAKPLQ
RLKGFPSFPVVERRENEVDWWNTINEVKKLIDAKRDMGRVFWSGVTAEKRNTIL
EGYNYLPNENDHKKREGSLENPKKPAKRQFGDLLLYLEKKYAGDWGKVFDEAWE
RIDKKIAGLTSHIEREEARNAEDAQSKAVLTDWLRAKASFVLERLKEMDEKEFY
ACEIQLQKWYGDLRGNPFAVEAENSILDISGFSKQYNCAFIWQKDGVKKLNLYL
IINYFKGGKLRFKKIKPEAFEANRFYTVINKKSGEIVPMEVNFNFDDPNLIILP
LAFGKRQGREFIWNDLLSLETGSLKLANGRVIEKTLYNRRTRQDEPALFVALTF
ERREVLDSSNIKPMNLIGIDRGENIPAVIALTDPEGCPLSRFKDSLGNPTHILR
IGESYKEKQRTIQAKKEVEQRRAGGYSRKYASKAKNLADDMVRNTARDLLYYAV
TQDAMLIFENLSRGFGRQGKRTFMAERQYTRMEDWLTAKLAYEGLSKTYLSKTL
AQYTSKTCSNCGFTITSADYDRVLEKLKKTATGWMTTINGKELKVEGQITYYNR
YKRQNVVKDLSVELDRLSEESVNNDISSWTKGRSGEALSLLKKRFSHRPVQEKE
VCLNCGFETHADEQAALNIARSWLFLRSQEYKKYQTNKTTGNTDKRAFVETWQS
FYRKKLKEVWKPAV (SEQ ID NO: 56) |
| NTSB, TSL, Helical I, Helical II and RuvC domains from a first CasX protein and an exogenous OBD or a part thereof from a second CasX protein | MISNTSRANLNKLLTDYTEMKKAILEVYWEEFQKDPVGLMSRVAQPAPKNIDQR
KLIPVKDGNERLTSSGFACSQCCQPLYVYKLEQVNDKGKPHTNYFGRCNVSEHE
RLILLSPHKPEANDELVTYSLGKFGQRALDFYSIHVTRESNEPVKPLEQIGGNS
CASGPVGKALSDACMGAVASFLTKYQDIILEHQKVIKKNEKRLANLKDIASANG
LAFPKITLPPQPHTKEGIEAYNNVVAQIVIWVNLNWQKLKIGRDEAKPLQRLK
GFPSFPLVERQANEVDWWDMVCNVKKLINEKKEDGKVFWQNLAGYKRQEALRPY
LSSEEDRKKGKKFARYQFGDLLLELEKKHGEDWGKVYDEAWERIDKKVEGLSKH
IKLEEERRSEDAQSKAALTDWLRAKASFVIEGLKEADKDEFCRCELKLQKWYGD
LRGKPFAIEAENRVVDISGFSIGSDGHSIQYRNLLAWKYLENGKREFYLLMNYG
KKGRIRFTDGTDIKKSGKWQGLLYGGGKAKVIDLTFDPDDEQLIILPLAFGTRQ
GREFIWNDLLSLETGLIKLANGRVIEKTIYNKKIGRDEPALFVALTFERREVVD
PSNIKPMNLIGIDRGENIPAVIALTDPEGCPLSRFKDSLGNPTHILRIGESYKE
KQRTIQAKKEVEQRRAGGYSRKYASKAKNLADDMVRNTARDLLYYAVTQDAMLI
FENLSRGFGRQGKRTFMAERQYTRMEDWLTAKLAYEGLSKTYLSKTLAQYTSKT
CSNCGFTITSADYDRVLEKLKKTATGWMTTINGKELKVEGQITYYNRYKRQNVV
KDLSVELDRLSEESVNNDISSWTKGRSGEALSLLKKRFSHRPVQEKFVCLNCGF
ETHADEQAALNIARSWLFLRSQEYKKYQTNKTTGNTDKRAFVETWQSFYRKKLK
EVWKPAV (SEQ ID NO: 57)

MEKRINKIRKKLSADNATKPVSRSGPMKTLLVRVMTDDLKKRLEKRRKKPEVMP
QVISNTSRANLNKLLTDYTEMKKAILHVYWEEFQKDPVGLMSRVAQPAPKNIDQ
RKLIPVKDGNERLTSSGFACSQCCQPLYVYKLEQVNDKGKPHTNYFGRCNVSEH
ERLILLSPHKPEANDELVTYSLGKFGQRALDFYSIHVTRESNHPVKPLEQIGGN
SCASGPVGKALSDACMGAVASFLTKYQDIILEHQKVIKKNEKRLANLKDIASAN
GLAFPKITLPPQPHTKEGIEAYNNVVAQIVIWVNLNWQKLKIGRDEAKPLQRL
KGFPSFPLVERQANEVDWWDMVCNVKKLINEKKEDGKVFWQNLAGYKRQEALRP
YLSSEEDRKKGKKFARYQFGDLLLHLEKKHGEDWGKVYDEAWERIDKKVEGLSK
HIKLEEERRSEDAQSKAALTDWLRAKASFVIEGLKEADKDEFCRCELKLQKWYG
DLRGKPFAIEAENSILDISGFSKQYNCAFIWQKDGVKKLNLYLIINYFKGGKLR
FKKIKPEAFEANRFYTVINKKSGEIVPMEVNFNFDDPNLIILPLAFGKRQGREF
IWNDLLSLETGSLKLANGRVIEKTLYNRRTRQDEPALFVALTFERREVLDSSNI
KPMNLIGIDRGENIPAVIALTDPEGCPLSRFKDSLGNPTHILRIGESYKEKQRT
IQAKKEVEQRRAGGYSRKYASKAKNLADDMVRNTARDLLYYAVTQDAMLIFENL
SRGFGRQGKRTFMAERQYTRMEDWLTAKLAYEGLSKTYLSKTLAQYTSKTCSNC
GFTITSADYDRVLEKLKKTATGWMTTINGKELKVEGQITYYNRYKRQNVVKDLS
VELDRLSEESVNNDISSWTKGRSGEALSLLKKRFSHRPVQEKFVCLNCGFETHA
DEQAALNIARSWLFLRSQEYKKYQTNKTTGNTDKRAFVETWQSFYRKKLKEVWK
PAV (SEQ ID NO: 58)

MQEIKRINKIRRRLVKDSNTKKAGKTGPMKTLLVRVMTPDLRERLENLRKKPEN
IPQPISNTSRANLNKLLTDYTEMKKAILHVYWEEFQKDPVGLMSRVAQPAPKNI
DQRKLIPVKDGNERLTSSGFACSQCCQPLYVYKLEQVNDKGKPHTNYFGRCNVS
EHERLILLSPHKPEANDELVTYSLGKFGQRALDFYSIHVTRESNHPVKPLEQIG
GNSCASGPVGKALSDACMGAVASFLTKYQDIILEHQKVIKKNEKRLANLKDIAS
ANGLAFPKITLPPQPHTKEGIEAYNNVVAQIVIWVNLNWQKLKIGRDEAKPLQ
RLKGFPSFPLVERQANEVDWWDMVCNVKKLINEKKEDGKVFWQNLAGYKRQEAL
RPYLSSEEDRKKGKKFARYQFGDLLLHLEKKHGEDWGKVYDEAWERIDKKVEGL
SKHIKLEEERRSEDAQSKAALTDWLRAKASFVIEGLKEADKDEFCRCELKLQKW
YGDLRGKPFAIEAENRVVDISGFSIGSDGHSIQYRNLLAWKYLENGKREFYLLM
NYGKKGRIRFTDGTDIKKSGKWQGLLYGGGKAKVIDLTFDPDDEQLIILPLAFG |

TABLE 3-continued

CasX Variant Sequences

| Description* | Amino Acid Sequence |
|---|---|
| | TRQGREFIWNDLLSLETGLIKLANGRVIEKTIYNKKIGRDEPALFVALTFERRE<br>VVDPSNIKPMNLIGIDRGENIPAVIALTDPEGCPLSRFKDSLGNPTHILRIGES<br>YKEKQRTIQAKKEVEQRRAGGYSRKYASKAKNLADDMVRNTARDLLYYAVTQDA<br>MLIFENLSRGFGRQKRTFMAERQYTRMEDWLTAKLAYEGLSKTYLSKTLAQYT<br>SKTCSNCGFTITSADYDRVLEKLKKTATGWMTTINGKELKVEGQITYYNRYKRQ<br>NVVKDLSVELDRLSEESVNNDISSWTKGRSGEALSLLKKRFSHRPVQEKFVCLN<br>CGFETHADEQAALNIARSWLFLRSQEYKKYQTNKTTGNTDKRAFVETWQSFYRK<br>KLKEVWKPAV (SEQ ID NO: 59) |
| substitution of L379R, a substitution of C477K, a substitution of A708K, a deletion of P at position 793 and a substitution of T620P of SEQ ID NO: 2 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 60) |
| substitution of M771A of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFAAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPA (SEQ ID NO: 61) |
| substitution of L379R, a substitution of A708K, a deletion of P at position 793 and a substitution of D732N of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 62) |
| substitution of W782Q of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| | LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFMAERQYTRMEDQLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>WKPAV (SEQ ID NO: 63) |
| substitution of M771Q of SEQ ID NO: 2 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFQAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 64) |
| substitution of R458I and a substitution of A739V of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWIIAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTVRDLLYYAVTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 65) |
| L379R, a substitution of A708K, a deletion of P at position 793 and a substitution of M771N of SEQ ID NO: 2 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFNAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 66) |
| substitution of L379R, a substitution | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS |

TABLE 3-continued

CasX Variant Sequences

| Description* | Amino Acid Sequence |
| --- | --- |
| of A708K, a deletion of P at position 793 and a substitution of A739T of SEQ ID NO: 2 | EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTTRDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 67) |
| substitution of L379R, a substitution of C477K, a substitution of A708K, a deletion of P at position 793 and a substitution of D489S of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLTPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGSLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNTARSWLFLRSQEYKKYQTNKTTGNTDKRAFVETWQSFYRKKLKEV WKPAV (SEQ ID NO: 68) |
| substitution of L379R, a substitution of C477K, a substitution of A708K, a deletion of P at position 793 and a substitution of D732N of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLANDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 69) |
| substitution of V711K of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKEKEQRRAGGYSRKYASKAKNLADDMVRNTARDLLYYAVTQDAMLIFE NLSRGFGRQGKRTFMAERQYTRMEDWLTAKLAYEGLPSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 70) |

TABLE 3-continued

CasX Variant Sequences

| Description* | Amino Acid Sequence |
|---|---|
| substitution of L379R, a substitution of C477K, a substitution of A708K, a deletion of P at position 793 and a substitution of Y797L of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFKRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTLLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 71) |
| 119: substitution of L379R, a substitution of A708K and a deletion of P at position 793 of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASEVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENTPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 72) |
| substitution of L379R, a substitution of C477K, a substitution of A708K, a deletion of P at position 793 and a substitution of M771N of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASEVIEGLKEADKDEFKRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFNAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 73) |
| substitution of A708K, a deletion of P at position 793 and a substitution of E386S of SEQ ID NO: 2. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSESDRKKGKKFARYQFGDLLLHLEKKHGEDWGKVYDEAWERIDKKVEGL SKHIKLEEERRSEDAQSKAALTDWLRAKASFVIEGLKEADKDEFKRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS |

TABLE 3-continued

CasX Variant Sequences

| Description* | Amino Acid Sequence |
|---|---|
| | NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 74) |
| substitution of L379R, a substitution of C477K, a substitution of A708K and a deletion of P at position 793 of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 75) |
| substitution of L792D of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGDPSKTYLSKTLAQYTSKTC<br>SNCGETITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 76) |
| substitution of G791F of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEFLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 77) |
| substitution of A708K, a deletion of P at position 793 and a substitution of A739V of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR |

TABLE 3-continued

CasX Variant Sequences

| Description* | Amino Acid Sequence |
|---|---|
| | EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRPAGGYSRKYASKAKNLADDMVRNTVRDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 78) |
| substitution<br>of L379R, a<br>substitution<br>of A708K, a<br>deletion of P<br>at position<br>793 and a<br>substitution<br>of A739V of<br>SEQ ID<br>NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTVRDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 79) |
| substitution<br>of C477K, a<br>substitution<br>of A708K<br>and a<br>deletion of P<br>at position<br>793 of SEQ<br>ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 80) |
| substitution<br>of L249I and<br>a substitution<br>of M771N of<br>SEQ ID<br>NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIITEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFNAERQYTRMEDWLTAKLAYEGLPSKTYLSKTLAQYTSKTC<br>SNCGFTITSADYDRVLEKLKKTATGWMTTINGKELKVEGQITYYNRYKQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 81) |
| substitution<br>of V747K of<br>SEQ ID<br>NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| | LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAKTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 82) |
| substitution of L379R, a substitution of C477K, a substitution of A708K, a deletion of P at position 793 and a substitution of M779N of SEQ ID NO: 2. | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRNEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSATKGRSGEALSLLKKRFSHRPVQEKFVCLNCGFET<br>HADEQAALNIARSWLFLRS2EYKKYQTNKTTGNTDKRAFVETWQSFYRKKLKEV<br>WKPAV (SEQ ID NO: 83) |
| L379R, F755M | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLTLLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIME<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 84) |
| 429: L379R, A708K, P793_, Y857R | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLITNYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 85) |
| 430: L379R, A708K, | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS |

TABLE 3-continued

CasX Variant Sequences

| Description* | Amino Acid Sequence |
|---|---|
| P793_,<br>Y857R,<br>I658V | EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASEVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 86) |
| 431:<br>L379R,<br>A708K,<br>P793_,<br>Y857R,<br>I658V,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 87) |
| 432:<br>L379R,<br>A708K,<br>P793_,<br>Y857R,<br>I658V,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 88) |
| 433:<br>L379R,<br>A708K,<br>P793_,<br>Y857R,<br>I658V,<br>^V192 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQI<br>GGNSCASGPVGKALSDACMGAVASFLTKYQDIILEHQKVIKKNEKRLANLKDIA<br>SANGLAFPKITLPPQPHTKEGIEAYNNVVAQIVIWVNLNLWQKLKIGRDEAKPL<br>QRLKGFPSFPLVERQANEVDWWDMVCNVKKLINEKKEDGKVFWQNLAGYKRQEA<br>LRPYLSSEEDRKKGKKFARYQFGDLLLHLEKKHGEDWGKVYDEAWERIDKKVEG<br>LSKHIKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRRKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>WKPAV (SEQ ID NO: 89) |

TABLE 3-continued

CasX Variant Sequences

| Description* | Amino Acid Sequence |
|---|---|
| 434:<br>L379R,<br>A708K,<br>P793_,<br>Y857R,<br>I658V,<br>L404K,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLKHLEKKHGEDWGKVYDEAWERIDKKVEGL<br>SKHIKLEEERRSEDAQSKAALTDWLRAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 90) |
| 435:<br>L379R,<br>A708K,<br>P793_,<br>Y857R,<br>I658V,<br>F399L | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 91) |
| 436:<br>L379R,<br>A708K,<br>P793_,<br>Y857R,<br>I658V,<br>F399L,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 92) |
| 437:<br>L379R,<br>A708K,<br>P793_,<br>Y857R,<br>I658V,<br>F399L,<br>C477S | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASEVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS |

TABLE 3-continued

CasX Variant Sequences

| Description* | Amino Acid Sequence |
|---|---|
| | NCGFTITSADYDRVLEKLKKTATGWMTTINGKELKVEGQITYYNRRKQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 93) |
| 438:<br>L379R,<br>A708K,<br>P793_,<br>Y857R,<br>I658V,<br>F399L,<br>L404K | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPPLVERQANEVDWWDMVCNVKKLINEKKEDGKVFWQNLAGYKRQEAL RPYLSSEEDRKKGKKFARYQLGDLLKHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGVDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRRKQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 94) |
| 439:<br>L379R,<br>A708K,<br>P793_,<br>Y857R,<br>I658V,<br>F399L,<br>E386N,<br>C477S,<br>L404K | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPPLVERQANEVDWWDMVCNVKKLINEKKEDGKVFWQNLAGYKRQEAL RPYLSSENDRKKGKKFARYQLGDLLKHLEKKHGEDWGKVYDEAWERIDKKVEGL SKHIKLEEERRSEDAQSKAALTDWLRAKASFVIEGLKEADKDEFSRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGVDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRRKQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 95) |
| 440:<br>L379R,<br>A708K,<br>P793_,<br>Y857R,<br>I658V,<br>F399L,<br>Y797L | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPPLVERQANEVDWWDMVCNVKKLINEKKEDGKVFWQNLAGYKRQEAL RPYLSSEEDRKKGKKFARYQLGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGVDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTLLSKTLAQYTSKTCS NCGFTITSADYDRVLEKLKKTATGWMTTINGKELKVEGQITYYNRRKQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 96) |
| 441:<br>L379R,<br>A708K,<br>P793_,<br>Y857R,<br>I658V,<br>F399L,<br>Y797L,<br>E386N | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPPLVERQANEVDWWDMVCNVKKLINEKKEDGKVFWQNLAGYKRQEAL RPYLSSENDRKKGKKFARYQLGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR |

TABLE 3-continued

CasX Variant Sequences

| Description* | Amino Acid Sequence |
|---|---|
| | EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 97) |
| 442:<br>L379R,<br>A708K,<br>P793_,<br>Y857R,<br>I658V,<br>F399L,<br>Y797L,<br>E386N,<br>C477S,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLHLEKKHGEDWGKVYDEAWERIDKKVEGL<br>SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 98) |
| 443:<br>L379R,<br>A708K,<br>P793_,<br>Y857R,<br>I658V,<br>Y797L | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 99) |
| 444:<br>L379R,<br>A708K,<br>P793_,<br>Y857R,<br>I658V,<br>Y797L,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLKHLEKKHGEDWGKVYDEAWERIDKKVEGL<br>SKHIKLEEERRSEDAQSKAALTDWLRAKASEVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 100) |
| 445:<br>L379R,<br>A708K,<br>P793_,<br>Y857R,<br>I658V,<br>Y797L, | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| E386N | RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 101) |
| 446:<br>L379R,<br>A708K,<br>P793_,<br>Y857R,<br>I658V,<br>Y797L,<br>E386N,<br>C477S,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTLLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 102) |
| 447:<br>L379R,<br>A708K,<br>P793_,<br>Y857R,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 103) |
| 448:<br>L379R,<br>A708K,<br>P793_,<br>Y857R,<br>E386N,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 104) |
| 449:<br>L379R,<br>A708K, | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS |

TABLE 3-continued

CasX Variant Sequences

| Description* | Amino Acid Sequence |
|---|---|
| P793_,<br>D732N,<br>E385P,<br>Y857R | EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 105) |
| 450:<br>L379R,<br>A708K,<br>P793_,<br>D732N,<br>E385P,<br>Y857R,<br>I658V | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRPAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 106) |
| 451:<br>L379R,<br>A708K,<br>P793_,<br>D732N,<br>E385P,<br>Y857R,<br>I658V,<br>F399L | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 107) |
| 452:<br>L379R,<br>A708K,<br>P793_,<br>D732N,<br>E385P,<br>Y857R,<br>I658V,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPNDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 108) |

TABLE 3-continued

CasX Variant Sequences

| Description* | Amino Acid Sequence |
|---|---|
| 453:<br>L379R,<br>A708K,<br>P793_,<br>D732N,<br>E385P,<br>Y857R,<br>I658V,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 109) |
| 454:<br>L379R,<br>A708K,<br>P793_,<br>T620P,<br>E385P,<br>Y857R,<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 110) |
| 455:<br>L379R,<br>A708K,<br>P793_,<br>T620P,<br>E385P,<br>Y857R,<br>I658V,<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 111) |
| 456:<br>L379R,<br>A708K,<br>P793_,<br>T620P,<br>E385P,<br>Y857R,<br>I658V,<br>E386N,<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPNDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENTPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS |

TABLE 3-continued

CasX Variant Sequences

| Description* | Amino Acid Sequence |
|---|---|
| | NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 112) |
| 457:<br>L379R,<br>A708K,<br>P793_,<br>T620P,<br>E385P,<br>Y857R,<br>I658V,<br>F399L,<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNWQKLKIGRDEAKPLQ<br>RLKGFPSFPPLVERQANEVDWWDMVCNVKKLINEKKEDGKVFWQNLAGYKRQEAL<br>RPYLSSPEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLITNYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRPAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 113) |
| 458:<br>L379R,<br>A708K,<br>P793_,<br>T620P,<br>E385P,<br>Y857R,<br>I658V,<br>L404K<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNWQKLKIGRDEAKPLQ<br>RLKGFPSFPPLVERQANEVDWWDMVCNVKKLINEKKEDGKVFWQNLAGYKRQEAL<br>RPYLSSPEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 114) |
| 459:<br>L379R,<br>A708K,<br>P793_,<br>T620P,<br>Y857R,<br>I658V,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 115) |
| 460:<br>L379R,<br>A708K,<br>P793_,<br>T620P,<br>E385P,<br>Q252K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNWQKLKIGRDEAKPLQ<br>RLKGFPSFPPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR |

TABLE 3-continued

CasX Variant Sequences

| Description* | Amino Acid Sequence |
|---|---|
| | EFIWNDLLSLETGSLKLANGRVIEKPLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKGRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 116) |
| 278 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTRESNHPVKPLEQIGG<br>NSCASGPVGKALSDACMGAVASFLTKYQDIILEHQKVIKKNEKRLANLKDIASA<br>NGLAFPKITLPPQPHTKEGIEAYNNVVAQIVIWVNLNLWQKLKIGRDEAKPLQR<br>LKGFPSFPLVERQANEVDWWDMVCNVKKLINEKKEDGKVFWQNLAGYKRQEALR<br>PYLSSEEDRKKGKKFARYQFGDLLLHLEKKHGEDWGKVYDEAWERIDKKVEGLS<br>KHIKLEEERRSEDAQSKAALTDWLRAKASFVIEGLKEADKDEFCRCELKLQKWY<br>GDLRGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVLDSSN<br>IKPMNLIGIDRGENIPAVIALTDPEGCPLSRFKDSLGNPTHILRIGESYKEKQR<br>TIQAKKEVEQRRAGGYSRKYASKAKNLADDMVRNTARDLLYYAVTQDAMLIFEN<br>LSRGFGRQGKRTFMAERQYTRMEDWITAKLAYEGLSKTYLSKTLAQYTSKTCSN<br>CGFTITSADYDRVLEKLKKTATGWMTTINGKELKVEGQITYYNRYKRQNVVKDL<br>SVELDRLSEESVNNDISSWTKGRSGEALSLLKKRFSHRPVQEKFVCLNCGFETH<br>ADEQAALNIARSWLFLRSQEYKKYQTNKTTGNTDKRAFVETWQSFYRKKLKEVW<br>KPAV (SEQ ID NO: 117) |
| 279 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQFALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASEVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 118) |
| 280 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKGRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 119) |
| 285 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| | RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRPAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 120) |
| 286 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 121) |
| 287 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 122) |
| 288 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTMSSGEACSQCCQPLYVYKLEQVNDKGKPHTNYFGRCNV<br>SEHERLILLSPHKPEANDELVTYSLGKFGQRALDFYSIHVTRESNHPVKPLEQI<br>GGNSCASGPVGKALSDACMGAVASFLTKYQDIILEHQKVIKKNEKRLANLKDIA<br>SANGLAFPKITLPPQPHTKEGIEAYNNVVAQIVIWVNLNLWQKLKIGRDEAKPL<br>QRLKGFPSFPLVERQANEVDWWDMVCNVKKLINEKKEDGKVFWQNLAGYKRQEA<br>LRPYLSSEEDRKKGKKFARYQFGDLLLHLEKKHGEDWGKVYDEAWERIDKKVEG<br>LSKHIKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGIDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 123) |
| 290 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS |

TABLE 3-continued

CasX Variant Sequences

| Description* | Amino Acid Sequence |
|---|---|
| | EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFTWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 124) |
| 291 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 125) |
| 293 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 126) |
| 300 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 127) |

TABLE 3-continued

CasX Variant Sequences

| Description* | Amino Acid Sequence |
|---|---|
| 492 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 128) |
| 493 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 129) |
| 387:<br>NTSB swap<br>from SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 130) |
| 395:<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPLVERQANEVDWWDMVCNVKKLINEKKEDGKVFWQNLAGYKRQEALR<br>PYLSSEEDRKKGKKFARYQFGDLLLHLEKKHGEDWGKVYDEAWERIDKKVEGLS<br>KHIKLEEERRSEDAQSKAALTDWLRAKASFVIEGLKEADKDEFCRCELKLQKWY<br>GDLRGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQGRE<br>FIWNDLLSLETGSLKLANGRVIEKTLYNRRTRQDEPALEVALTFERREVIDSSN<br>IKPMNLIGIDRGENIPAVIALTDPEGCPLSRFKDSLGNPTHILRIGESYKEKQR<br>TIQAKKEVEQRRAGGYSRKYASKAKNLADDMVRNTARDLLYYAVTQDAMLIFEN<br>LSRGFGRQGKRTFMAERQYTRMEDWLTAKLAYEGLSKTYLSKTLAQYTSKTCSN |

TABLE 3-continued

CasX Variant Sequences

| Description* | Amino Acid Sequence |
|---|---|
| | CGFTITSADYDRVLEKLKKTATGWMTTINGKELKVEGQITYYNRYKRQNVVKDL<br>SVELDRLSEESVNNDISSWTKGRSGEALSLLKKRFSHRPVQEKFVCLNCGFETH<br>ADEQAALNIARSWLFLRSQEYKKYQTNKTTGNTDKRAFVETWQSFYRKKLKEVW<br>KPAV (SEQ ID NO: 131) |
| 485:<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPLVERQANEVDWWDMVCNVKKLINEKKEDGKVFWQNLAGYKRQEALR<br>PYLSSEEDRKKGKKFARYQLGDLLLHLEKKHGEDWGKVYDEAWERIDKKVEGLS<br>KHIKLEEERRSEDAQSKAALTDWLRAKASFVIEGLKEADKDEFCRCELKLQKWY<br>GDLRGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVLDSSN<br>IKPMNLIGVDRGENIPAVIALTDPEGCPLSRFKDSLGNPTHILRIGESYKEKQR<br>TIQAKKEVEQRRAGGYSRKYASKAKNLADDMVRNTARDLLYYAVTQDAMLIFEN<br>LSRGFGRQGKRTFMAERQYTRMEDWLTAKLAYEGLSKTYLSKTLAQYTSKTCSN<br>CGFTITSADYDRVLEKLKKTATGWMTTINGKELKVEGQITYYNRRKRQNVVKDL<br>SVELDRLSEESVNNDISSWTKGRSGEALSLLKKRFSHRPVQEKFVCLNCGFETH<br>ADEQAALNIARSWLFLRSQEYKKYQTNKTTGNTDKRAFVETWQSFYRKKLKEVW<br>KPAV (SEQ ID NO: 132) |
| 486:<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPLVERQANEVDWWDMVCNVKKLINEKKEDGKVFWQNLAGYKRQEALR<br>PYLSSEEDRKKGKKFARYQLGDLLKHLEKKHGEDWGKVYDEAWERIDKKVEGLS<br>KHIKLEEERRSEDAQSKAALTDWLRAKASFVIEGLKEADKDEFCRCELKLQKWY<br>GDLRGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVLDSSN<br>IKPMNLIGVDRGENIPAVIALTDPEGCPLSRFKDSLGNPTHILRIGESYKEKQR<br>TIQAKKEVEQRRAGGYSRKYASKAKNLADDMVRNTARDLLYYAVTQDAMLIFEN<br>LSRGFGRQGKRTFMAERQYTRMEDWLTAKLAYEGLSKTYLSKTLAQYTSKTCSN<br>CGFTITSADYDRVLEKLKKTATGWMTTINGKELKVEGQITYYNRRKRQNVVKDL<br>SVELDRLSEESVNNDISSWTKGRSGEALSLLKKRFSHRPVQEKFVCLNCGFETH<br>ADEQAALNIARSWLFLRSQEYKKYQTNKTTGNTDKRAFVETWQSFYRKKLKEVW<br>KPAV (SEQ ID NO: 133) |
| 487:<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTKESTHPVKPLAQIAG<br>NRYASGPVGKALSDACMGTIASFLSKYQDIIIEHQKVVKGNQKRLESLRELAGK<br>ENLEYPSVTLPPQPHTKEGVDAYNEVIARVRMWVNLNLWQKLKLSRDDAKPLLR<br>LKGFPSFPLVERQANEVDWWDMVCNVKKLINEKKEDGKVFWQNLAGYKRQEALR<br>PYLSSEEDRKKGKKFARYQLGDLLLHLEKKHGEDWGKVYDEAWERIDKKVEGLS<br>KHIKLEEERRSEDAQSKAALTDWLRAKASFVIEGLKEADKDEFCRCELKLQKWY<br>GDLRGKPFAIEAENSILDISGFSKQYNCAFIWQKDGVKKLNLYLIINYFKGGKL<br>RFKKIKPEAFEANRFYTVINKKSGEIVPMEVNFNFDDPNLIILPLAFGKRQGRE<br>FIWNDLLSLETGSLKLANGRVIEKTLYNRRTRQDEPALFVALTFERREVLDSSN<br>IKPMNLIGVDRGENIPAVIALTDPEGCPLSRFKDSLGNPTHILRIGESYKEKQR<br>TIQAKKEVEQRRAGGYSRKYASKAKNLADDMVRNTARDLLYYAVTQDAMLIFEN<br>LSRGFGRQGKRTFMAERQYTRMEDWLTAKLAYEGLSKTYLSKTLAQYTSKTCSN<br>CGFTITSADYDRVLEKLKKTATGWMTTINGKELKVEGQITYYNRYKRQNVVKDL<br>SVELDRLSEESVNNDISSWTKGRSGEALSLLKKRFSHRPVQEKFVCLNCGFETH<br>ADEQAALNIARSWLFLRSQEYKKYQTNKTTGNTDKRAFVETWQSFYRKKLKEVW<br>KPAV (SEQ ID NO: 134) |
| 488:<br>NTSB and<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR |

TABLE 3-continued

CasX Variant Sequences

| Description* | Amino Acid Sequence |
|---|---|
| | EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 135) |
| 489:<br>NTSB and<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 136) |
| 490:<br>NTSB and<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 137) |
| 491:<br>NTSB and<br>Helical 1B<br>swap from<br>SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 138) |
| 494:<br>NTSB swap<br>from SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTRESNHPVKPLEQIG<br>GNSCASGPVGKALSDACMGAVASFLTKYQDIIIEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| | RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFQRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFERKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 139) |
| 328: S867G | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKKEVEQRRAGGYSRKYASKAKNLADDMVRNTARDLLYYAVTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLGVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 140) |
| 388:<br>L379R + A708R +<br>[P793] +<br>X1<br>Helical2<br>swap | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQFALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPVVERRENEVDWWNTINEVKKLIDAKRDMGRVFWSGVTAEKRNTIL<br>EGYNYLPNENDHKKREGSLENPKKPAKRQFGDLLLYLEKKYAGDWGKVFDEAWE<br>RIDKKIAGLTSHIEREEARNAEDAQSKAVLTDWLRAKASFVLERLKEMDEKEFY<br>ACEIQLQKWYGDLRGNPFAVEAENSILDISGFSKQYNCAFIWQKDGVKKLNLYL<br>IINYFKGGKLRFKKIKPEAFEANRFYTVINKKSGEIVPMEVNFNFDDPNLIILP<br>LAFGKRQGREFIWNDLLSLETGSLKLANGRVIEKTLYNRRTRQDEPALFVALTF<br>ERREVLDSSNIKPMNLIGIDRGENIPAVIALTDPEGCPLSRFKDSLGNPTHILR<br>IGESYKEKQRTIQAKKEVEQRRAGGYSRKYASKAKNLADDMVRNTARDLLYYAV<br>TQDAMLIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQITYYNR<br>YKRQNVVKDLSVELDRLSEESVNNDISSWTKGRSGEALSLLKKRFSHRPVQEKF<br>VCLNCGFETHADEQAALNIARSWLFLRSQEYKKYQTNKTTGNTDKRAFVETWQS<br>FYRKKLKEVWKPAV (SEQ ID NO: 141) |
| 389:<br>L379R + A708K +<br>[P793] +<br>X1 RuvC1<br>swap | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPVNLIGVDRGENIPAVIALTDPEGCPLPEFKDSSGGPTDILRIGEGYKEKQ<br>RAIQAAKEVEQRRAGGYSRKFASKSRNLADDMVRNSARDLFYHAVTHDAVLVFE<br>NLSRGFGRQGKRTFMTERQYTKMEDWLTAKLAYEGLTSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 142) |
| 390:<br>L379R + A708K +<br>[P793] + | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS |

TABLE 3-continued

CasX Variant Sequences

| Description* | Amino Acid Sequence |
|---|---|
| X1 RuvC2 swap | EHERLILLSPHKPEANDELVTYSLGKFGQRALDFYSIHVTRESNHPVKPLEQIG
GNSCASGPVGKALSDACMGAVASFLTKYQDIILEHQKVIKKNEKRLANLKDIAS
ANGLAFPKITLPPQPHTKEGIEAYNNVVAQIVIWVNLNLWQKLKIGRDEAKPLQ
RLKGFPSFPLVERQANEVDWWDMVCNVKKLINEKKEDGKVFWQNLAGYKRQEAL
RPYLSSEEDRKKGKKFARYQFGDLLLHLEKKHGEDWGKVYDEAWERIDKKVEGL
SKHIKLEEERRSEDAQSKAALTDWLRAKASFVIEGLKEADKDEFCRCELKLQKW
YGDLRGKPFAIEAENSILDISGFSKQYNCAFIWQKDGVKKLNLYLIINYFKGGK
LRFKKIKPEAFEANRFYTVINKKSGEIVPMEVNFNFDDPNLIILPLAFGKRQGR
EFIWNDLLSLETGSLKLANGRVIEKTLYNRRTRQDEPALFVALTFERREVLDSS
NIKPMNLIGIDRGENIPAVIALTDPEGCPLSRFKDSLGNPTHILRIGESYKEKQ
RTIQAKKEVEQRRAGGYSRKYASKAKNLADDMVRNTARDLLYYAVTQDAMLIFE
NLSRGFGRQGKRTFMAERQYTRMEDWLTAKLAYEGLSKTYLSKTLAQYTSKTCS
NCGFTITSADYDRVLEKLKKTATGWMTTINGKELKVEGQITYYNRYKRQNVVKD
LSVELDRLSEESVNNDISSWTKGRSGEALSLLKKRFSHRPVQEKFVCLNCGFET
HADEQAALNIARSWLFLNSNSTEFKSYKSGKQPFVGAWQAFYKRRLKEVWKPNA
(SEQ ID NO: 143) |
| 514: ^H817 in 491 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPASKKID
QNKLKPEMDEKGNLTTAGFACSQCGQPLFVYKLEQVSEKGKAYTNYFGRCNVAE
HEKLILLAQLKPEKDSDEAVTYSLGKFGQRALDFYSIHVTKESTHPVKPLAQIA
GNRYASGPVGKALSDACMGTIASFLSKYQDIIIEHQKVVKGNQKRLESLRELAG
KENLEYPSVTLPPQPHTKEGVDAYNEVIARVRMWVNLNLWQKLKLSRDDAKPLL
RLKGFPSFPLVERQANEVDWWDMVCNVKKLINEKKEDGKVFWQNLAGYKRQEAL
RPYLSSEEDRKKGKKFARYQLGDLLLHLEKKHGEDWGKVYDEAWERIDKKVEGL
SKHIKLEEERRSEDAQSKAALTDWLRAKASFVIEGLKEADKDEFCRCELKLQKW
YGDLRGKPFAIEAENSILDISGFSKQYNCAFIWQKDGVKKLNLYLIINYFKGGK
LRFKKIKPEAFEANRFYTVINKKSGEIVPMEVNFNFDDPNLIILPLAFGKRQGR
EFIWNDLLSLETGSLKLANGRVIEKTLYNRRTRQDEPALFVALTFERREVLDSS
NIKPMNLIGVDRGENIPAVIALTDPEGCPLSRFKDSLGNPTHILRIGESYKEKQ
RTIQAKKEVEQRRAGGYSRKYASKAKNLADDMVRNTARDLLYYAVTQDAMLIFE
NLSRGFGRQGKRTFMAERQYTRMEDWLTAKLAYEGLSKTYLSKTLAQYTSKTCS
NCGFTIHTSADYDRVLEKLKKTATGWMTTINGKELKVEGQITYYNRYKRQNVVK
DLSVELDRLSEESVNNDISSWTKGRSGEALSLLKKRFSHRPVQEKFVCLNCGFE
THADEQAALNIARSWLFLRSQEYKKYQTNKTTGNTDKRAFVETWQSFYRKKLKE
VWKPAV (SEQ ID NO: 143) |
| 515: ^P793 in 491 | QEIKRINKIRRRLVKDSNTKKAGKTGPMKTLLVRVMTP4)LRERLENLRKKPEN
IPQPISNTSRANLNKLLTDYTEMKKAILHVYWEEFQKDPVGLMSRVAQPASKKI
DQNKLKPEMDEKGNLTTAGFACSQCGQPLEVYKLEQVSEKGKAYTNYFGRCNVA
EHEKLILLAQLKPEKDSDEAVTYSLGKFGQRALDFYSIHVTKESTHPVKPLAQI
AGNRYASGPVGKALSDACMGTIASFLSKYQDIIIEHQKVVKGNQKRLESLRELA
GKENLEYPSVTLPPQPHTKEGVDAYNEVIARVRMWVNLNLWQKLKLSRDDAKPL
LRLKGFPSFPLVERQANEVDWWDMVCNVKKLINEKKEDGKVFWQNLAGYKRQEA
LRPYLSSEEDRKKGKKFARYQLGDLLLHLEKKHGEDWGKVYDEAWERIDKKVEG
LSKHIKLEEERRSEDAQSKAALTDWLRAKASFVIEGLKEADKDEFCRCELKLQK
WYGDLRGKPFAIEAENSILDISGFSKQYNCAFIWQKDGVKKLNLYLIINYFKGG
KLRFKKIKPEAFEANRFYTVINKKSGEIVPMEVNFNFDDPNLIILPLAFGKRQG
REFIWNDLLSLETGSLKLANGRVIEKTLYNRRTRQDEPALFVALTFERREVLDS
SNIKPMNLIGVDRGENIPAVIALTDPEGCPLSRFKDSLGNPTHILRIGESYKEK
QRTIQAKKEVEQRRAGGYSRKYASKAKNLADDMVRNTARDLLYYAVTQDAMLIF
ENLSRGFGRQGKRTFMAERQYTRMEDWLTAKLAYEGLSKTYLSKTLAQYTSKT
CSNCGFTITSADYDRVLEKLKKTATGWMTTINGKELKVEGQITYYNRYKRQNVV
KDLSVELDRLSEESVNNDISSWTKGRSGEALSLLKKRFSHRPVQEKFVCLNCGF
ETHADEQAALNIARSWLFLRSQEYKKYQTNKTTGNTDKRAFVETWQSFYRKKLK
EVWKPAV (SEQ ID NO: 145) |
| 516: L307H in 491 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPASKKID
QNKLKPEMDEKGNLTTAGFACSQCGQPLFVYKLEQVSEKGKAYTNYFGRCNVAE
HEKLILLAQLKPEKDSDEAVTYSLGKFGQRALDFYSIHVTKESTHPVKPLAQIA
GNRYASGPVGKALSDACMGTIASFLSKYQDIIIEHQKVVKGNQKRLESLRELAG
KENLEYPSVTLPPQPHTKEGVDAYNEVIARVRMWVNHNLWQKLKLSRDDAKPLL
RLKGFPSFPLVERQANEVDWWDMVCNVKKLINEKKEDGKVFWQNLAGYKRQEAL
RPYLSSEEDRKKGKKFARYQLGDLLLHLEKKHGEDWGKVYDEAWERIDKKVEGL
SKHIKLEEERRSEDAQSKAALTDWLRAKASFVIEGLKEADKDEFCRCELKLQKW
YGDLRGKPFAIEAENSILDISGFSKQYNCAFIWQKDGVKKLNLYLIINYFKGGK
LRFKKIKPEAFEANRFYTVINKKSGEIVPMEVNFNFDDPNLIILPLAFGKRQGR
EFIWNDLLSLETGSLKLANGRVIEKTLYNRRTRQDEPALFVALTFERREVLDSS
NIKPMNLIGVDRGENIPAVIALTDPEGCPLSRFKDSLGNPTHILRIGESYKEKQ
RTIQAKKEVEQRRAGGYSRKYASKAKNLADDMVRNTARDLLYYAVTQDAMLIFE
NLSRGFGRQGKRTFMAERQYTRMEDWLTAKLAYEGLSKTYLSKTLAQYTSKTCS
NCGFTITSADYDRVLEKLKKTATGWMTTINGKELKVEGQITYYNRYKRQNVVKD
LSVELDRLSEESVNNDISSWTKGRSGEALSLLKKRFSHRPVQEKFVCLNCGFET
HADEQAALNIARSWLFLRSQEYKKYQTNKTTGNTDKRAFVETWQSFYRKKLKEV
WKPAV (SEQ ID NO: 146) |

TABLE 3-continued

CasX Variant Sequences

| Description* | Amino Acid Sequence |
|---|---|
| 517:<br>^A224 in<br>491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGAPVGKALSDACMGTIASFLSKYQDIIIEHQKVVKGNQKRLESLRELA<br>GKENLEYPSVTLPPQPHTKEGVDAYNEVIARVRMWVNLNLWQKLKLSRDDAKPL<br>LRLKGFPSFPLVERQANEVDWWDMVCNVKKLINEKKEDGKVFWQNLAGYKRQEA<br>LRPYLSSEEDRKKGKKFARYQLGDLLLHLEKKHGEDWGKVYDEAWERIDKKVEG<br>LSKHIKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 147) |
| 518:<br>^R1 in 491 | RQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPASKKI<br>DQNKLKPEMDEKGNLTTAGFACSQCGQPLFVYKLEQVSEKGKAYTNYFGRCNVA<br>EHEKLILLAQLKPEKDSDEAVTYSLGKFGQRALDFYSIHVTKESTHPVKPLAQI<br>AGNRYASGAPVGKALSDACMGTIASFLSKYQDIIIEHQKVVKGNQKRLESLREL<br>AGKENLEYPSVTLPPQPHTKEGVDAYNEVIARVRMWVNLNLWQKLKLSRDDAKP<br>LLRLKGFPSFPLVERQANEVDWWDMVCNVKKLINEKKEDGKVFWQNLAGYKRQE<br>ALRPYLSSEEDRKKGKKFARYQLGDLLLHLEKKHGEDWGKVYDEAWERIDKKVE<br>GLSKHIKLEEERRSEDAQSKAALTDWLRAKASFVIEGLKEADKDEFCRCELKLQ<br>KWYGDLRGKPFAIEAENSILDISGFSKQYNCAFIWQKDGVKKLNLYLIINYFKG<br>GKLRFKKIKPEAFEANRFYTVINKKSGEIVPMEVNFNFDDPNLIILPLAFGKRQ<br>GREFIWNDLLSLETGSLKLANGRVIEKTLYNRRTRQDEPALFVALTFERREVLD<br>SSNIKPMNLIGVDRGENIPAVIALTDPEGCPLSRFKDSLGNPTHILRIGESYKE<br>KQRTIQAKKEVEQRRAGGYSRKYASKAKNLADDMVRNTARDLLYYAVTQDAMLI<br>FENLSRGFGRQGKRTFMAERQYTRMEDWLTAKLAYEGLSKTYLSKTLAQYTSKT<br>CSNCGFTITSADYDRVLEKLKKTATGWMTTINGKELKVEGQITYYNRYKRQNVV<br>KDLSVELDRLSEESVNNDISSWTKGRSGEALSLLKKRFSHRPVQEKFVCLNCGF<br>ETHADEQAALNIARSWLFLRSQEYKKYQTNKTTGNTDKRAFVETWQSFYRKKLK<br>EVWKPAV (SEQ ID NO: 148) |
| 519:<br>^Q692 in<br>491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHIQLRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 149) |
| 520:<br>I705T in 491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTTQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS |

TABLE 3-continued

CasX Variant Sequences

| Description* | Amino Acid Sequence |
|---|---|
| | NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 150) |
| 522:<br>D683R in<br>491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKRSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 151) |
| 523:<br>G26Y in 491 | QEIKRINKIRRRLVKDSNTKKAGKTYPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 152) |
| 524:<br>T817H in<br>491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTIHSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 153) |
| 525;<br>V746A in<br>491 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR |

TABLE 3-continued

CasX Variant Sequences

| Description* | Amino Acid Sequence |
| --- | --- |
| | EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAATQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 154) |
| 526:<br>K708A in<br>491 | QEIKRINKIRRRLVKDSNTKKAGKTGPMKTLLVRVMTPDLRERLENLRKKPENI<br>PQPISNTSRANLNKLLTDYTEMKKAILEVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQKRTFMAERQYTRMEDWLTAKLAYEGLSKTYLSKTLAQYTSKTCS<br>NCGFTITSADYDRVLEKLKKTATGWMTTINGKELKVEGQITYYNRYKQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 155) |
| 527:<br>^R26 in 491 | QEIKRINKIRRRLVKDSNTKKAGKTRGPMKTLLVRVMTPDLRERLENLRKKPEN<br>IPQPISNTSRANLNKLLTDYTEMKKAILHVYWEEFQKDPVGLMSRVAQPASKKI<br>DQNKLKPEMDEKGNLTTAGFACSQCGQPLFVYKLEQVSEKGKAYTNYFGRCNVA<br>EHEKLILLAQLKPEKDSDEAVTYSLGKFGQRALDFYSIHVTKESTHPVKPLAQI<br>AGNRYASGPVGKALSDACMGTIASFLSKYQDIIIEHQKVVKGNQKRLESLRELA<br>GKENLEYPSVTLPPQPHTKEGVDAYNEVIARVRMWVNLNWQKLKLSRDDAKPL<br>LRLKGFPSFPLVERQANEVDWWDMVCNVKKLINEKKEDGKVFWQNLAGYKRQEA<br>LRPYLSSEEDRKKGKKFARYQLGDLLLHLEKKHGEDWGKVYDEAWERIDKKVEG<br>LSKHIKLEEERRSEDAQSKAALTDWLRAKASFVIEGLKEADKDEFQRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRYKQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 156) |
| 528:<br>G223Y in<br>515 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASYPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQKRTFMAERQYTRMEDWLTAKLAYEGLPSKTYLSKTLAQYTSKTCS<br>NCGFTITSADYDRVLEKLKKTATGWMTTINGKELKVEGQITYYNRYKQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 157) |
| 529:<br>G223N in<br>515 | QEIKRINKIRRRLVKDSNTKKAGKTGPMKTLLVRWTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASNPVGKALSDACMGTIASFLSKYQDIIIEHQKVVKGNQKRLESLRELAG<br>KENLEYPSVTLPPQPHTKEGVDAYNEVIARVRMWVNLNWQKLKLSRDDAKPLL<br>RLKGFPSFPLVERQANEVDWWDMVCNVKKLINEKKEDGKVFWQNLAGYKRQEAL |

TABLE 3-continued

CasX Variant Sequences

| Description* | Amino Acid Sequence |
|---|---|
| | RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 158) |
| 530:<br>^W539 in<br>515 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGWG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLPSKTYLSKTLAQYTSKT<br>CSNCGFTITSADYDRVLEKLKKTATGWMTTINGKELKVEGQITYYNRYKRQNVV<br>KDLSVELDRLSEESVNNDISSWTKGRSGEALSLLKKRFSHRPVQEKFVCLNCGF<br>ETHADEQAALNIARSWLFLRSQEYKKYQTNKTTGNTDKRAFVETWQSFYRKKLK<br>EVWKPAV (SEQ ID NO: 159) |
| 531:<br>^Y539 in<br>515 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGYG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLPSKTYLSKTLAQYTSKT<br>CSNCGFTITSADYDRVLEKLKKTATGWMTTINGKELKVEGQITYYNRYKRQNVV<br>KDLSVELDRLSEESVNNDISSWTKGRSGEALSLLKKRFSHRPVQEKFVCLNCGF<br>ETHADEQAALNIARSWLFLRSQEYKKYQTNKTTGNTDKRAFVETWQSFYRKKLK<br>EVWKPAV (SEQ ID NO: 160) |

In some embodiments, the CasX variant protein comprises a sequence selected from the group consisting of SEQ ID NOs: 49-160, 237-239, 243-246, 251-263 or 273-281, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto. In some embodiments, the CasX variant protein comprises a sequence selected from the group consisting of SEQ ID NOs: 49-160, 237-239, 243-246, 251-263 or 273-281.

In some embodiments, the CasX variant protein has one or more improved characteristic of the CasX protein when compared to a reference CasX protein, for example a reference protein of SEQ ID NO:1, SEQ ID NO:2 or SEQ ID NO:3. In some embodiments, the at least one improved characteristic of the CasX variant is at least about 1.1 to about 100,000-fold improved relative to the reference protein. In some embodiments, the at least one improved characteristic of the CasX variant is at least about 1.1 to about 10,000-fold improved, at least about 1.1 to about 1,000-fold improved, at least about 1.1 to about 500-fold improved, at least about 1.1 to about 400-fold improved, at least about 1.1 to about 300-fold improved, at least about 1.1 to about 200-fold improved, at least about 1.1 to about 100-fold improved, at least about 1.1 to about 50-fold improved, at least about 1.1 to about 40-fold improved, at least about 1.1 to about 30-fold improved, at least about 1.1 to about 20-fold improved, at least about 1.1 to about 10-fold improved, at least about 1.1 to about 9-fold improved, at least about 1.1 to about 8-fold improved, at least about 1.1 to about 7-fold improved, at least about 1.1 to about 6-fold improved, at least about 1.1 to about 5-fold improved, at least about 1.1 to about 4-fold improved, at least about 1.1 to about 3-fold improved, at least about 1.1 to about 2-fold improved, at least about 1.1 to about 1.5-fold improved, at least about 1.5 to about 3-fold improved, at least about 1.5 to about 4-fold improved, at least about 1.5 to about 5-fold improved, at least about 1.5 to about 10-fold improved, at least about 5 to about 10-fold improved, at least about 10 to about 20-fold improved, at least 10 to about 30-fold improved, at least 10 to about 50-fold improved or at least 10 to about 100-fold improved than the reference CasX protein. In some embodiments, the at least one improved characteristic of the CasX variant is at least about 10 to about 1000-fold improved relative to the reference CasX protein.

In some embodiments, the one or more improved characteristics of the CasX variant protein is at least about 1.1, at least about 5, at least about 10, at least about 20, at least about 30, at least about 40, at least about 50, at least about 60, at least about 70, at least about 80, at least about 90, at least about 100, at least about 250, at least about 500, or at least about 1000, at least about 5,000, at least about 10.000, or at least about 100.000-fold improved relative to a reference CasX protein of SEQ ID NO:1, SEQ ID NO:2 or SEQ ID NO:3. In other cases, the one or more improved characteristics of the CasX variant is about 1.1 to 100,000-fold, about 1.1 to 10,000-fold, about 1.1 to 1,000-fold, about 1.1 to 500-fold, about 1.1 to 100-fold, about 1.1 to 50-fold, about 1.1 to 20-fold, about 10 to 100,000-fold, about 10 to 10,000-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,000-fold, about 100 to 10,000-fold, about 100 to 1,000-fold, about 100 to 500-fold, about 500 to 100,000-fold, about 500 to 10,000-fold, about 500 to 1,000-fold, about 500 to 750-fold, about 1,000 to 100,000-fold, about 10,000 to 100,000-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference CasX of SEQ ID NO:1, SEQ ID NO:2 or SEQ ID NO:3. In other cases, the one or more improved characteristics of the CasX variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold or more improved relative to the reference CasX of SEQ ID NO: 1, SEQ ID NO: 2 or SEQ ID NO: 3. Exemplary characteristics that can be improved in CasX variant proteins relative to the same characteristics in reference CasX proteins include, but are not limited to, improved folding of the variant, improved binding affinity to the gNA, improved binding affinity to the target DNA, improved ability to utilize a greater spectrum of PAM sequences in the editing and/or binding of target DNA, improved unwinding of the target DNA, increased editing activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved CasX: gNA RNA complex stability, improved protein solubility, improved CasX:gNA RNP complex solubility, improved ability to form cleavage-competent RNP with a gNA, improved protein yield, improved protein expression, and improved fusion characteristics. In some embodiments, the variant comprises at least one improved characteristic. In other embodiments, the variant comprises at least two improved characteristics. In further embodiments, the variant comprises at least three improved characteristics. In some embodiments, the variant comprises at least four improved characteristics. In still further embodiments, the variant comprises at least five, at least six, at least seven, at least eight, at least nine, at least ten, at least eleven, at least twelve, at least thirteen, or more improved characteristics.

Exemplary improved characteristic include, as one example, improved editing efficiency. The CasX variants of the embodiments described herein have the ability to form an RNP complex with the gNA disclosed herein. In some embodiments, an RNP comprising the CasX variant protein and a gNA of the disclosure, at a concentration of 20 pM or less, is capable of cleaving a double stranded DNA target with an efficiency of at least 80%. In some embodiments, the RNP at a concentration of 20 pM or less, is capable of cleaving a double stranded DNA target with an efficiency of at least 40%, at least 50%, at least 60%, at least 70%, at least 80%, at least 85%, at least 90% or at least 95%. In some embodiments, the RNP at a concentration of 50 pM or less, 40 pM or less, 30 pM or less, 20 pM or less, 10 pM or less, or 5 pM or less, is capable of cleaving a double stranded DNA target with an efficiency of at least 40%, at least 50%, at least 60%, at least 70%, at least 80%, at least 85%, at least 9⁰% or at least 95%.

These improved characteristics are described in more detail below.

j. Protein Stability

In some embodiments, the disclosure provides a CasX variant protein with improved stability relative to a reference CasX protein. In some embodiments, improved stability of the CasX variant protein results in expression of a higher steady state of protein, which improves editing efficiency. In some embodiments, improved stability of the CasX variant protein results in a larger fraction of CasX protein that remains folded in a functional conformation and improves editing efficiency or improves purifiability for manufacturing purposes. As used herein, a "functional conformation" refers to a CasX protein that is in a conformation where the protein is capable of binding a gNA and target DNA. In embodiments wherein the CasX variant does not carry one or more mutations rendering it catalytically dead, the CasX variant is capable of cleaving, nicking, or otherwise modifying the target DNA. For example, a functional CasX variant can, in some embodiments, be used for gene-editing, and a functional conformation refers to an "editing-competent" conformation. In some exemplary embodiments, including those embodiments where the CasX variant protein results in a larger fraction of CasX protein that remains folded in a functional conformation, a lower concentration of CasX variant is needed for applications such as gene editing compared to a reference CasX protein. Thus, in some embodiments, the CasX variant with improved stability has improved efficiency compared to a reference CasX in one or more gene editing contexts. Improved stability and efficiency of nuclease activity may be evaluated through a variety of methods known to one of skill in the art.

In some embodiments, the disclosure provides a CasX variant protein having improved thermostability relative to a reference CasX protein. In some embodiments, the CasX variant protein has improved thermostability of the CasX variant protein at a particular temperature range. Without wishing to be bound by any theory, some reference CasX proteins natively function in organisms with niches in groundwater and sediment; thus, some reference CasX proteins may have evolved to exhibit optimal function at lower or higher temperatures that may be desirable for certain applications. For example, one application of CasX variant proteins is gene editing of mammalian cells, which is typically carried out at about 37° C. In some embodiments, a CasX variant protein as described herein has improved thermostability compared to a reference CasX protein at a temperature of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability and functionality compared to a reference CasX protein that results in improved gene editing functionality, such as mammalian gene editing applications, which may include human gene editing applications. Improved thermostability of the nuclease may be evaluated through a variety of methods known to one of skill in the art.

In some embodiments, the disclosure provides a CasX variant protein having improved stability of the CasX variant protein:gNA complex relative to the reference CasX protein:gNA complex such that the RNP remains in a functional form. Stability improvements can include increased thermostability, resistance to proteolytic degradation, enhanced pharmacokinetic properties, stability across a range of pH conditions, salt conditions, and tonicity. Improved stability of the complex may, in some embodiments, lead to improved editing efficiency. In some embodiments, the RNP of the CasX variant and gNA variant has at least a 5%, at least a 10%, at least a 15%, or at least a 20%, or at least a 5-20% higher percentage of cleavage-competent RNP compared to an RNP of the reference CasX of SEQ ID NOS: 1-3 and the gNA of any one of SEQ ID NOS:4-16 of Table 1. Exemplary data of increased cleavage-competent RNP are provided in the Examples.

In some embodiments, the disclosure provides a CasX variant protein having improved thermostability of the CasX variant protein:gNA complex relative to the reference CasX protein:gNA complex. In some embodiments, a CasX variant protein has improved thermostability relative to a reference CasX protein. In some embodiments, the CasX variant protein:gNA complex has improved thermostability relative to a complex comprising a reference CasX protein at temperatures of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability of the CasX variant protein:gNA complex compared to a reference CasX protein:gNA complex, which results in improved function for gene editing applications, such as mammalian gene editing applications, which may include human gene editing applications. Improved thermostability of the RNP may be evaluated through a variety of methods known to one of skill in the art.

In some embodiments, the improved stability and/or thermostability of the CasX variant protein comprises faster folding kinetics of the CasX variant protein relative to a reference CasX protein, slower unfolding kinetics of the CasX variant protein relative to a reference CasX protein, a larger free energy release upon folding of the CasX variant protein relative to a reference CasX protein, a higher temperature at which 50% of the CasX variant protein is unfolded (Tm) relative to a reference CasX protein, or any combination thereof. These characteristics may be improved by a wide range of values: for example, at least 1.1, at least 1.5, at least 10, at least 50, at least 100, at least 500, at least 1,000, at least 5,000, or at least a 10,000-fold improved, as compared to a reference CasX protein. In some embodiments, improved thermostability of the CasX variant protein comprises a higher Tm of the CasX variant protein relative to a reference CasX protein. In some embodiments, the Tm of the CasX variant protein is between about 20° C. to about 30° C., between about 30° C. to about 40° C., between about 40° C. to about 50° C., between about 50° C. to about 60° C., between about 60° C. to about 70° C., between about 70° C. to about 80° C., between about 80° C. to about 90° C. or between about 90° C. to about 100° C. Thermal stability is determined by measuring the "melting temperature" ($T_m$), which is defined as the temperature at which half of the molecules are denatured. Methods of measuring characteristics of protein stability such as Tm and the free energy of unfolding are known to persons of ordinary skill in the art, and can be measured using standard biochemical techniques in vitro. For example, Tm may be measured using Differential Scanning Calorimetry, a thermo-analytical technique in which the difference in the amount of heat required to increase the temperature of a sample and a reference is measured as a function of temperature (Chen et al (2003) Pharm Res 20:1952-60: Ghirlando et al (1999) Immunol Lett 68:47-52). Alternatively, or in addition, CasX variant protein Tm may be measured using commercially available methods such as the ThermoFisher Protein Thermal Shift system. Alternatively, or in addition, circular dichroism may be used to measure the kinetics of folding and unfolding, as well as the Tm (Murray et al. (2002) J. Chromatogr Sci 40:343-9). Circular dichroism (CD) relies on the unequal absorption of left-handed and right-handed circularly polarized light by asymmetric molecules such as proteins. Certain structures of proteins, for example alpha-helices and beta-sheets, have characteristic CD spectra. Accordingly, in some embodiments, CD may be used to determine the secondary structure of a CasX variant protein.

In some embodiments, improved stability and/or thermostability of the CasX variant protein comprises improved folding kinetics of the CasX variant protein relative to a reference CasX protein. In some embodiments, folding kinetics of the CasX variant protein are improved relative to a reference CasX protein by at least about 5, at least about 10, at least about 50, at least about 100, at least about 500, at least about 1,000, at least about 2,000, at least about 3,000, at least about 4,000, at least about 5,000, or at least about a 10,000-fold improvement. In some embodiments, folding kinetics of the CasX variant protein are improved relative to a reference CasX protein by at least about 1 kJ/mol, at least about 5 kJ/mol, at least about 10 kJ/mol, at least about 20 kJ/mol, at least about 30 kJ/mol, at least about 40 kJ/mol, at least about 50 kJ/mol, at least about 60 kJ/mol, at least about 70 k/mol, at least about 80 kJ/mol, at least about 90 kJ/mol, at least about 100 kJ/mol, at least about 150 kJ/mol, at least about 200 k/mol, at least about 250 kJ/mol, at least about 300 kJ/mol, at least about 350 kJ/mol, at least about 400 kJ/mol, at least about 450 kJ/mol, or at least about 500 kJ/mol.

Exemplary amino acid changes that can increase the stability of a CasX variant protein relative to a reference CasX protein may include, but are not limited to, amino acid changes that increase the number of hydrogen bonds within the CasX variant protein, increase the number of disulfide bridges within the CasX variant protein, increase the number of salt bridges within the CasX variant protein, strengthen interactions between parts of the CasX variant protein, increase the buried hydrophobic surface area of the CasX variant protein, or any combinations thereof.

k. Protein Yield

In some embodiments, the disclosure provides a CasX variant protein having improved yield during expression and purification relative to a reference CasX protein. In some embodiments, the yield of CasX variant proteins purified from bacterial or eukaryotic host cells is improved relative to a reference CasX protein. In some embodiments, the bacterial host cells are *Escherichia coli* cells. In some embodiments, the eukaryotic cells are yeast, plant (e.g. tobacco), insect (e.g. *Spodoptera frugiperda* sf9 cells), mouse, rat, hamster, guinea pig, monkey, or human cells. In some embodiments, the eukaryotic host cells are mammalian cells, including, but not limited to human embryonic kidney 293 (HEK293) cells, HEK292T cells, baby hamster kidney (BHK) cells, NS0 cells. SP2/0 cells, YO myeloma cells, P3X63 mouse myeloma cells. PER cells, PER.C6 cells, hybridoma cells, NIH3T3 cells, COS. HeLa, or Chinese hamster ovary (CHO) cells.

In some embodiments, improved yield of the CasX variant protein is achieved through codon optimization. Cells use 64 different codons, 61 of which encode the 20 standard amino acids, while another 3 function as stop codons. In some cases, a single amino acid is encoded by more than one codon. Different organisms exhibit bias towards use of different codons for the same naturally occurring amino acid. Therefore, the choice of codons in a protein, and matching codon choice to the organism in which the protein will be expressed, can, in some cases, significantly affect protein translation and therefore protein expression levels. In some embodiments, the CasX variant protein is encoded by a nucleic acid that has been codon optimized. In some embodiments, the nucleic acid encoding the CasX variant protein has been codon optimized for expression in a bacterial cell, a yeast cell, an insect cell, a plant cell, or a mammalian cell. In some embodiments, the mammal cell is a mouse, a rat, a hamster, a guinea pig, a monkey, or a human. In some embodiments, the CasX variant protein is encoded by a nucleic acid that has been codon optimized for expression in a human cell. In some embodiments, the CasX variant protein is encoded by a nucleic acid from which nucleotide sequences that reduce translation rates in prokaryotes and eukaryotes have been removed. For example, runs of greater than three thymine residues in a row can reduce translation rates in certain organisms or internal polyadenylation signals can reduce translation.

Improved protein yield during expression and purification can be evaluated by methods known in the art. For example, the amount of CasX variant protein can be determined by running the protein on an SDS-page gel, and comparing the CasX variant protein to a either a control whose amount or concentration is known in advance to determine an absolute level of protein. Alternatively. or in addition, a purified CasX variant protein can be run on an SDS-page gel next to a reference CasX protein undergoing the same purification process to determine relative improvements in CasX variant protein yield. Alternatively, or in addition, levels of protein can be measured using immunohistochemical methods such as Western blot or ELISA with an antibody to CasX, or by HPLC. For proteins in solution, concentration can be determined by measuring of the protein's intrinsic UV absorbance, or by methods which use protein-dependent color changes such as the Lowry assay, the Smith copper/bicinchoninic assay or the Bradford dye assay. Such methods can be used to calculate the total protein (such as, for example, total soluble protein) yield obtained by expression under certain conditions. This can be compared, for example, to the protein yield of a reference CasX protein under similar expression conditions.

l. Protein Solubility

In some embodiments, a CasX variant protein has improved solubility relative to a reference CasX protein. In some embodiments, a CasX variant protein has improved solubility of the CasX:gNA ribonucleoprotein complex variant relative to a ribonucleoprotein complex comprising a reference CasX protein.

In some embodiments, an improvement in protein solubility leads to higher yield of protein from protein purification techniques such as purification from *E. coli*. Improved solubility of CasX variant proteins may, in some embodiments, enable more efficient activity in cells, as a more soluble protein may be less likely to aggregate in cells. Protein aggregates can in certain embodiments be toxic or burdensome on cells, and, without wishing to be bound by any theory, increased solubility of a CasX variant protein may ameliorate this result of protein aggregation. Further, improved solubility of CasX variant proteins may allow for enhanced formulations permitting the delivery of a higher effective dose of functional protein, for example in a desired gene editing application. In some embodiments, improved solubility of a CasX variant protein relative to a reference CasX protein results in improved yield of the CasX variant protein during purification of at least about 5, at least about 10, at least about 20, at least about 30, at least about 40, at least about 50, at least about 60, at least about 70, at least about 80, at least about 90, at least about 100, at least about 250, at least about 500, or at least about 1000-fold greater yield. In some embodiments, improved solubility of a CasX variant protein relative to a reference CasX protein improves activity of the CasX variant protein in cells by at least about 1.1, at least about 1.2, at least about 1.3, at least about 1.4, at least about 1.5, at least about 1.6, at least about 1.7, at least about 1.8, at least about 1.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.5, at least about 4, at least about 4.5, at least about 5, at least about 5.5, at least about 6, at least about 6.5, at least about 7.0, at least about 7.5, at least about 8, at least about 8.5, at least about 9, at least about 9.5, at least about 10, at least about 11, at least about 12, at least about 13, at least about 14, or at least about 15-fold greater activity. Improved solubility of the nuclease may be evaluated through a variety of methods known to one of skill in the art, including by taking densitometry readings on a gel of the soluble fraction of lysed Ecoli. Alternatively, or addition, improvements in CasX variant protein solubility can be measured by measuring the maintenance of soluble protein product through the course of a full protein purification. For example, soluble protein product can be measured at one or more steps of gel affinity purification, tag cleavage, cation exchange purification, running the protein on a sizing column. In some embodiments, the densitometry of every band of protein on a gel is read after each step in the purification process. CasX variant proteins with improved solubility may, in some embodiments, maintain a higher concentration at one or more steps in the protein purification process when compared to the reference CasX protein, while an insoluble protein variant may be lost at one or more steps due to buffer exchanges, filtration steps, interactions with a purification column, and the like.

In some embodiments, improving the solubility of CasX variant proteins results in a higher yield in terms of mg/L of protein during protein purification when compared to a reference CasX protein.

In some embodiments, improving the solubility of CasX variant proteins enables a greater amount of editing events compared to a less soluble protein when assessed in editing assays such as the EGFP disruption assays described herein.

m. Protein Affinity for the gNA

In some embodiments, a CasX variant protein has improved affinity for the gNA relative to a reference CasX protein, leading to the formation of the ribonucleoprotein complex. Increased affinity of the CasX variant protein for the gNA may, for example, result in a lower Kn for the generation of a RNP complex, which can, in some cases, result in a more stable ribonucleoprotein complex formation. In some embodiments, increased affinity of the CasX variant protein for the gNA results in increased stability of the ribonucleoprotein complex when delivered to human cells. This increased stability can affect the function and utility of the complex in the cells of a subject, as well as result in improved pharmacokinetic properties in blood, when delivered to a subject. In some embodiments, increased affinity of the CasX variant protein, and the resulting increased stability of the ribonucleoprotein complex, allows for a lower dose of the CasX variant protein to be delivered to the subject or cells while still having the desired activity, for example in vivo or in vitro gene editing.

In some embodiments, a higher affinity (tighter binding) of a CasX variant protein to a gNA allows for a greater amount of editing events when both the CasX variant protein and the gNA remain in an RNP complex. Increased editing events can be assessed using editing assays such as the EGFP disruption assay described herein.

In some embodiments, the $K_d$ of a CasX variant protein for a gNA is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100. In some embodiments, the CasX variant has about 1.1 to about 10-fold increased binding affinity to the gNA compared to the reference CasX protein of SEQ ID NO:2.

Without wishing to be bound by theory, in some embodiments amino acid changes in the Helical I domain can increase the binding affinity of the CasX variant protein with the gNA targeting sequence, while changes in the Helical II domain can increase the binding affinity of the CasX variant protein with the gNA scaffold stem loop, and changes in the oligonucleotide binding domain (OBD) increase the binding affinity of the CasX variant protein with the gRNA triplex.

Methods of measuring CasX protein binding affinity for a gNA include in vitro methods using purified CasX protein and gNA. The binding affinity for reference CasX and variant proteins can be measured by fluorescence polarization if the gNA or CasX protein is tagged with a fluorophore. Alternatively, or in addition, binding affinity can be measured by biolayer interferometry, electrophoretic mobility shift assays (EMSAs), or filter binding. Additional standard techniques to quantify absolute affinities of RNA binding proteins such as the reference CasX and variant proteins of the disclosure for specific gNAs such as reference gNAs and variants thereof include, but are not limited to, isothermal calorimetry (ITC), and surface plasmon resonance (SPR), as well as the methods of the Examples.

n. Affinity for Target DNA

In some embodiments, a CasX variant protein has improved binding affinity for a target nucleic acid relative to the affinity of a reference CasX protein for a target nucleic acid. In some embodiments, the improved affinity for the target nucleic acid comprises improved affinity for the target nucleic acid sequence, improved affinity for the PAM sequence, an improved ability to search DNA for the target nucleic acid sequence, or any combinations thereof. Without wishing to be bound by theory, it is thought that CRISPR/Cas system proteins such as CasX may find their target nucleic acid sequences by one-dimension diffusion along a DNA molecule. The process is thought to include (1) binding of the ribonucleoprotein to the DNA molecule followed by (2) stalling at the target nucleic acid sequence, either of which may be, in some embodiments, affected by improved affinity of CasX proteins for a target nucleic acid sequence, thereby improving function of the CasX variant protein compared to a reference CasX protein.

In some embodiments, a CasX variant protein with improved target nucleic acid affinity has increased overall affinity for DNA. In some embodiments, a CasX variant protein with improved target nucleic acid affinity has increased affinity for specific PAM sequences other than the canonical TTC PAM recognized by the reference CasX protein of SEQ ID NO:2, including binding affinity for PAM sequences selected from the group consisting of TTC, ATC, GTC, and CTC. Without wishing to be bound by theory, it is possible that these protein variants will interact more strongly with DNA overall and will have an increased ability to access and edit sequences within the target DNA due to the ability to bind additional PAM sequences beyond those of wild-type Cas X, thereby allowing for a more efficient search process of the CasX protein for the target sequence. A higher overall affinity for DNA also, in some embodiments, can increase the frequency at which a CasX protein can effectively start and finish a binding and unwinding step, thereby facilitating target strand invasion and R-loop formation, and ultimately the cleavage of a target nucleic acid sequence.

Without wishing to be bound by theory, it is possible that amino acid changes in the NTSBD that increase the efficiency of unwinding, or capture, of a non-target DNA strand in the unwound state, can increase the affinity of CasX variant proteins for target DNA. Alternatively, or in addition, amino acid changes in the NTSBD that increase the ability of the NTSBD to stabilize DNA during unwinding can increase the affinity of CasX variant proteins for target DNA. Alternatively, or in addition, amino acid changes in the OBD may increase the affinity of CasX variant protein binding to the protospacer adjacent motif (PAM), thereby increasing affinity of the CasX variant protein for target nucleic acid. Alternatively, or in addition, amino acid changes in the Helical I and/or II, RuvC and TSL domains that increase the affinity of the CasX variant protein for the target nucleic acid strand can increase the affinity of the CasX variant protein for target nucleic acid.

In some embodiments, the CasX variant protein has increased binding affinity to the target nucleic acid sequence compared to the reference protein of SEQ ID NO: 1. SEQ ID NO:2, or SEQ ID NO:3. In some embodiments, affinity of a CasX variant protein of the disclosure for a target nucleic acid molecule is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100.

In some embodiments, a CasX variant protein has improved binding affinity for the non-target strand of the target nucleic acid. As used herein, the term "non-target strand" refers to the strand of the DNA target nucleic acid sequence that does not form Watson and Crick base pairs with the targeting sequence in the gNA, and is complementary to the target strand.

Methods of measuring CasX protein (such as reference or variant) affinity for a target nucleic acid molecule may include electrophoretic mobility shift assays (EMSAs), filter binding, isothermal calorimetry (ITC), and surface plasmon resonance (SPR), fluorescence polarization and biolayer interferometry (BLI). Further methods of measuring CasX protein affinity for a target include in vitro biochemical assays that measure DNA cleavage events over time.

CasX variant proteins with higher affinity for their target nucleic acid may, in some embodiments, cleave the target nucleic acid sequence more rapidly than a reference CasX protein that does not have increased affinity for the target nucleic acid.

In some embodiments, the CasX variant protein is catalytically dead (dCasX). In some embodiments, the disclosure provides RNP comprising a catalytically-dead CasX protein that retains the ability to bind target DNA. An exemplary catalytically-dead CasX variant protein comprises one or more mutations in the active site of the RuvC domain of the CasX protein. In some embodiments, a catalytically-dead CasX variant protein comprises substitutions at residues 672, 769 and/or 935 of SEQ ID NO:1. In some embodiments, a catalytically-dead CasX variant protein comprises substitutions of D672A, E769A and/or D935A in the reference CasX protein of SEQ ID NO:1. In some embodiments, a catalytically-dead CasX protein comprises substitutions at amino acids 659, 765 and/or 922 of SEQ ID NO:2. In some embodiments, a catalytically-dead CasX protein comprises D659A, E756A and/or D922A substitutions in a reference CasX protein of SEQ ID NO:2. In further embodiments, a catalytically-dead CasX variant protein comprises deletions of all or part of the RuvC domain of the reference CasX protein.

In some embodiments, improved affinity for DNA of a CasX variant protein also improves the function of catalytically inactive versions of the CasX variant protein. In some embodiments, the catalytically inactive version of the CasX variant protein comprises one or mutations in the DED motif in the RuvC. Catalytically dead CasX variant proteins can, in some embodiments, be used for base editing or epigenetic modifications. With a higher affinity for DNA, in some embodiments, catalytically dead CasX variant proteins can, relative to catalytically active CasX, find their target DNA faster, remain bound to target DNA for longer periods of time, bind target DNA in a more stable fashion, or a combination thereof, thereby improving the function of the catalytically dead CasX variant protein.

o. Improved Specificity for a Target Site

In some embodiments, a CasX variant protein has improved specificity for a target DNA sequence relative to a reference CasX protein. As used herein, "specificity," sometimes referred to as "target specificity," refers to the degree to which a CRISPR/Cas system ribonucleoprotein complex cleaves off-target sequences that are similar, but not identical to the target DNA sequence; e.g., a CasX variant RNP with a higher degree of specificity would exhibit reduced off-target cleavage of sequences relative to a reference CasX protein. The specificity, and the reduction of potentially deleterious off-target effects, of CRISPR/Cas system proteins can be vitally important in order to achieve an acceptable therapeutic index for use in mammalian subjects.

In some embodiments, a CasX variant protein has improved specificity for a target site within the target sequence that is complementary to the targeting sequence of the gNA.

Without wishing to be bound by theory, it is possible that amino acid changes in the Helical I and II domains that increase the specificity of the CasX variant protein for the target DNA strand can increase the specificity of the CasX variant protein for the target DNA overall. In some embodiments, amino acid changes that increase specificity of CasX variant proteins for target DNA may also result in decreased affinity of CasX variant proteins for DNA.

Methods of testing CasX protein (such as variant or reference) target specificity may include guide and Circularization for In vitro Reporting of Cleavage Effects by Sequencing (CIRCLE-seq), or similar methods. In brief, in CIRCLE-seq techniques, genomic DNA is sheared and circularized by ligation of stem-loop adapters, which are nicked in the stem-loop regions to expose 4 nucleotide palindromic overhangs. This is followed by intramolecular ligation and degradation of remaining linear DNA. Circular DNA molecules containing a CasX cleavage site are subsequently linearized with CasX, and adapter adapters are ligated to the exposed ends followed by high-throughput sequencing to generate paired end reads that contain information about the off-target site. Additional assays that can be used to detect off-target events, and therefore CasX protein specificity include assays used to detect and quantify indels (insertions and deletions) formed at those selected off-target sites such as mismatch-detection nuclease assays and next generation sequencing (NGS). Exemplary mismatch-detection assays include nuclease assays, in which genomic DNA from cells treated with CasX and sgNA is PCR amplified, denatured and rehybridized to form hetero-duplex DNA, containing one wild type strand and one strand with an indel. Mismatches are recognized and cleaved by mismatch detection nucleases, such as Surveyor nuclease or T7 endonuclease I.

p. Unwinding of DNA

In some embodiments, a CasX variant protein has improved ability of unwinding DNA relative to a reference CasX protein. In some embodiments, a CasX variant protein has enhanced DNA unwinding characteristics. Poor dsDNA unwinding has been shown previously to impair or prevent the ability of CRISPR/Cas system proteins anaCas9 or Cas14s to cleave DNA. Therefore, without wishing to be bound by any theory, it is likely that increased DNA cleavage activity by some CasX variant proteins is due at least in part to an increased ability to find and unwind the dsDNA at a target site.

Without wishing to be bound by theory, it is thought that amino acid changes in the NTSB domain may produce CasX variant proteins with increased DNA unwinding characteristics. Alternatively, or in addition, amino acid changes in the OBD or the helical domain regions that interact with the PAM may also produce CasX variant proteins with increased DNA unwinding characteristics.

Methods of measuring the ability of CasX proteins (such as variant or reference) to unwind DNA include, but are not limited to, in vitro assays that observe increased on rates of dsDNA targets in fluorescence polarization or biolayer interferometry.

q. Catalytic Activity

The ribonucleoprotein complex of the CasX:gNA systems disclosed herein comprise a reference CasX protein or variant thereof that bind to a target nucleic acid sequence and cleaves the target nucleic acid sequence. In some embodiments, a CasX variant protein has improved catalytic activity relative to a reference CasX protein. Without wishing to be bound by theory, it is thought that in some cases cleavage of the target strand can be a limiting factor for Cas12-like molecules in creating a dsDNA break. In some embodiments, CasX variant proteins improve bending of the target strand of DNA and cleavage of this strand, resulting in an improvement in the overall efficiency of dsDNA cleavage by the CasX ribonucleoprotein complex.

In some embodiments, a CasX variant protein has increased nuclease activity compared to a reference CasX protein. Variants with increased nuclease activity can be generated, for example, through amino acid changes in the RuvC nuclease domain. In one embodiment, the CasX variant comprises a nuclease domain having nickase activity. In the foregoing embodiment, the CasX nickase of a CasX:gNA system generates a single-stranded break within 10-18 nucleotides 3' of a PAM site in the non-target strand. In another embodiment, the CasX variant comprises a nuclease domain having double-stranded cleavage activity. In the foregoing embodiment, the CasX of the CasX:gNA system generates a double-stranded break within 18-26 nucleotides 5' of a PAM site on the target strand and 10-18 nucleotides 3' on the non-target strand. Nuclease activity can be assayed by a variety of methods, including those of the Examples. In one embodiment, a CasX variant has a Kcleave constant that is at least 2-fold, or at least 3-fold, or at least 4-fold, or at least 5-fold, or at least 6-fold, or at least 7-fold, or at least 8-fold, or at least 9-fold, or at least 10-fold greater compared to a reference wild-type CasX.

In some embodiments, a CasX variant protein has the improved characteristic of forming RNP with gNA that result in a higher percentage of cleavage-competent RNP compared to an RNP of a reference CasX protein of SEQ ID NO: 1, SEQ ID NO: 2, or SEQ ID NO: 3 and the gNA, as described in the Examples. By cleavage competent, it is meant that the RNP that is formed has the ability to cleave the target nucleic acid. In some embodiments, the RNP of the CasX variant and the gNA exhibit at least a 2% to at least 30%, or at least a 5% to at least a 20%, or at least a 10% to at least a 15% higher percentage of cleavage-competent RNP compared to an RNP of the reference CasX of SEQ ID NO: 1, SEQ ID NO: 2, or SEQ ID NO: 3 and the gNA of Table 1.

In some embodiments, a CasX variant protein has increased target strand loading for double strand cleavage. Variants with increased target strand loading activity can be generated, for example, through amino acid changes in the TLS domain.

Without wishing to be bound by theory, amino acid changes in the TSL domain may result in CasX variant proteins with improved catalytic activity. Alternatively, or in addition, amino acid changes around the binding channel for the RNA:DNA duplex may also improve catalytic activity of the CasX variant protein.

In some embodiments, a CasX variant protein has increased collateral cleavage activity compared to a reference CasX protein. As used herein. "collateral cleavage activity" refers to additional, non-targeted cleavage of nucleic acids following recognition and cleavage of a target nucleic acid sequence. In some embodiments, a CasX variant protein has decreased collateral cleavage activity compared to a reference CasX protein.

In some embodiments, for example those embodiments encompassing applications where target DNA cleavage is not a desired outcome, improving the catalytic activity of a CasX variant protein comprises altering, reducing, or abolishing the catalytic activity of the CasX variant protein. In some embodiments, a ribonucleoprotein complex comprising a CasX variant protein binds to a target DNA and does not cleave the target DNA.

In some embodiments, the CasX ribonucleoprotein complex comprising a CasX variant protein binds a target DNA but generates a single stranded nick in the target DNA In some embodiments, particularly those embodiments wherein the CasX protein is a nickase, a CasX variant protein has decreased target strand loading for single strand nicking. Variants with decreased target strand loading may be generated, for example, through amino acid changes in the TSL domain.

Exemplary methods for characterizing the catalytic activity of CasX proteins may include, but are not limited to, in vitro cleavage assays. In some embodiments, electrophoresis of DNA products on agarose gels can interrogate the kinetics of strand cleavage.

r. Affinity for Target RNA

In some embodiments, variants of a reference CasX protein increase the specificity of the CasX variant protein for a target RHO RNA, and increase the activity of the CasX variant protein with respect to a target RNA when compared to the reference CasX protein. For example, CasX variant proteins can display increased binding affinity for target RNAs, or increased cleavage of target RNAs, when compared to reference CasX proteins. In some embodiments, a ribonucleoprotein complex comprising a CasX variant protein binds to a target RNA and/or cleaves the target RNA. In one embodiment, a CasX variant has at least about two-fold to about 10-fold increased binding affinity to the target nucleic acid sequence compared to the reference protein of SEQ ID NO:1, SEQ ID NO:2, or SEQ ID NO:3.

s. Combinations of Mutations

In some embodiments, the present disclosure provides variants that are a combination of mutations from separate CasX variant proteins. In some embodiments, any variant to any domain described herein can be combined with other variants described herein. In some embodiments, any variant within any domain described herein can be combined with other variants described herein, in the same domain. Combinations of different amino acid changes may in some embodiments produce new optimized variants whose function is further improved by the combination of amino acid changes. In some embodiments, the effect of combining amino acid changes on CasX protein function is linear. As used herein, a combination that is linear refers to a combination whose effect on function is equal to the sum of the effects of each individual amino acid change when assayed in isolation. In some embodiments, the effect of combining amino acid changes on CasX protein function is synergistic. As used herein, a combination of variants that is synergistic refers to a combination whose effect on function is greater than the sum of the effects of each individual amino acid change when assayed in isolation. In some embodiments, combining amino acid changes produces CasX variant proteins in which more than one function of the CasX protein has been improved relative to the reference CasX protein.

t. CasX Fusion Proteins

In some embodiments, the disclosure provides CasX proteins comprising a heterologous protein fused to the CasX. In some cases, the CasX is a reference CasX protein. In other cases, the CasX is a CasX variant of any of the embodiments described herein.

In some embodiments, the CasX variant protein is fused to one or more proteins or domains thereof that has a different activity of interest (i.e., is part of a fusion protein). For example, in some embodiments, the CasX variant protein is fused to a protein (or domain thereof) that inhibits transcription, modifies a target nucleic acid sequence, or modifies a polypeptide associated with a nucleic acid (e.g., histone modification).

In some embodiments, a heterologous polypeptide (or heterologous amino acid such as a cysteine residue or a non-natural amino acid) can be inserted at one or more positions within a CasX protein to generate a CasX fusion protein. In other embodiments, a cysteine residue can be inserted at one or more positions within a CasX protein followed by conjugation of a heterologous polypeptide described below. In some alternative embodiments, a heterologous polypeptide or heterologous amino acid can be added at the N- or C-terminus of the reference or CasX variant protein. In other embodiments, a heterologous polypeptide or heterologous amino acid can be inserted internally within the sequence of the CasX protein.

In some embodiments, the reference CasX or variant fusion protein retains RNA-guided sequence specific target nucleic acid binding and cleavage activity. In some cases, the reference CasX or variant fusion protein has (retains) 50% or more of the activity (e.g., cleavage and/or binding activity) of the corresponding reference CasX or variant protein that does not have the insertion of the heterologous protein. In some cases, the reference CasX or variant fusion protein retains at least about 60%, or at least about 70% or more, at least about 80%, or at least about 90%, or at least about 92%, or at least about 95%, or at least about 98%, or at least about 100% of the activity (e.g., cleavage and/or binding activity) of the corresponding CasX protein that does not have the insertion of the heterologous protein.

In some cases, the reference CasX or variant fusion polypeptide retains (has) target nucleic acid binding activity relative to the activity of the CasX protein without the inserted heterologous amino acid or heterologous polypeptide. For example, in some cases, the reference CasX or variant fusion polypeptide has (retains) 50% or more of the binding activity of the corresponding CasX protein (the CasX protein that does not have the insertion). For example, in some cases, the reference CasX or variant fusion polypeptide has (retains) 60Y % or more (70% or more, 80% or more, 90% or more, 92% or more, 95% or more, 98% or more, or 100%) of the binding activity of the corresponding parent CasX protein (the CasX protein that does not have the insertion).

In some cases, the reference CasX or variant fusion polypeptide retains (has) target nucleic acid binding and/or cleavage activity relative to the activity of the parent CasX protein without the inserted heterologous amino acid or heterologous polypeptide. For example, in some cases, the reference CasX or variant fusion polypeptide has (retains) 50% or more of the binding and/or cleavage activity of the corresponding parent CasX protein (the CasX protein that does not have the insertion). For example, in some cases, the reference CasX or variant fusion polypeptide has (retains) 60% or more (70% or more, 80% or more, 90% or more, 92% or more, 95% or more, 98% or more, or 100%) of the binding and/or cleavage activity of the corresponding CasX parent polypeptide (the CasX protein that does not have the insertion). Methods of measuring cleaving and/or binding activity of a CasX protein and/or a CasX fusion polypeptide will be known to one of ordinary skill in the art and any convenient method can be used.

A variety of heterologous polypeptides are suitable for inclusion in a reference CasX or CasX variant fusion protein of the disclosure. In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion partner has enzymatic activity that modifies a target nucleic acid sequence (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a fusion partner has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used as a fusion partner to increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET domain containing 1A, histone lysine methyltransferase (SET1A), SET domain containing 1B, histone lysine methyltransferase (SET1B), lysine methyltransferase 2A (MLL1 to 5, ASCL1 (ASH1) achaete-scute family bHLH transcription factor 1 (ASH1), SET and MYND domain containing 2 (SYMD2), nuclear receptor binding SET domain protein 1 (NSD1), and the like; histone lysine demethylases such as lysine demethylase 3A (JHDM2a)/Lysine-specific demethylase 3B (JHDM2b), lysine demethylase 6A (UTX), lysine demethylase 6B (JMJD3), and the like; histone acetyltransferases such as lysine acetyltransferase 2A (GCN5), lysine acetyltransferase 2B (PCAF), CREB binding protein (CBP), E1A binding protein p300 (p300), TATA-box binding protein associated factor 1 (TAF1), lysine acetyltransferase 5 (TIP60/PLIP), lysine acetyltransferase 6A (MOZ/MYST3), lysine acetyltransferase 6B (MORF/MYST4), SRC proto-oncogene, non-receptor tyrosine kinase (SRC1), nuclear receptor coactivator 3 (ACTR), MYB binding protein 1a (P160), clock circadian regulator (CLOCK), and the like; and DNA demethylases such as Ten-Eleven Translocation (TET) dioxygenase 1 (TET1CD), tet methylcytosine dioxygenase 1 (TET1), demeter (DME), demeter-like 1 (DML1), demeter-like 2 (DML2), protein ROS1 (ROS1), and the like.

Examples of proteins (or fragments thereof) that can be used as a fusion partner to decrease transcription include but are not limited to: transcriptional repressors such as the Kruppel associated box (KRAB or SKD); KOX1 repression domain: the Mad mSIN3 interaction domain (SID); the ERF repressor domain (ERD), the SRDX repression domain (e.g., for repression in plants), and the like; histone lysine methyltransferases such as PR/SET domain containing protein (Pr-SET7/8), lysine methyltransferase 5B (SUV4-20H1), PR/SET domain 2 (RIZ1), and the like; histone lysine demethylases such as lysine demethylase 4A (JMJD2A/JHDM3A), lysine demethylase 4B (JMJD2B), lysine demethylase 4C (JMJD2C/GASC1), lysine demethylase 4D (JMJD2D), lysine demethylase 5A (JARID1A/RBP2), lysine demethylase 5B (JARID1B/PLU-1), lysine demethylase 5C (JARID 1C/SMCX), lysine demethylase 5D (JARID1D/SMCY), and the like; histone lysine deacetylases such as histone deacetylase 1 (HDAC1), HDAC2, HDAC3, HDAC8, HDAC4, HDAC5, HDAC7, HDAC9, sirtuin 1 (SIRT1). SIRT2, HDAC11, and the like: DNA methylases such as HhaI DNA m5c-methyltransferase (M.HhaI). DNA methyltransferase 1 (DNMT1). DNA methyltransferase 3a (DNMT3a), DNA methyltransferase 3b (DNMT3b), methyltransferase 1 (MET1), S-adenosyl-L-methionine-dependent methyltransferases superfamily protein (DRM3) (plants), DNA cytosine methyltransferase MET2a (ZMET2), chromomethylase 1 (CMT1), chromomethylase 2 (CMT2) (plants), and the like; and periphery recruitment elements such as Lamin A, Lamin B, and the like.

In some cases the fusion partner has enzymatic activity that modifies the target nucleic acid sequence (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants). ZMET2, CMT1, CMT2 (plants), and the like); demethylase activity such as that provided by a demethylase (e.g., Ten-Eleven Translocation (TET) dioxygenase 1 (TET 1 CD). TET1, DME, DML1, DML2, ROS1, and the like), DNA repair activity, DNA damage activity, deamination activity such as that provided by a deaminase (e.g., a cytosine deaminase enzyme, e.g., an APOBEC protein such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y: human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, a reference CasX or Cas X variant protein of the present disclosure is fused to a poly peptide selected from: a domain for increasing transcription (e.g., a VP16 domain, a VP64 domain), a domain for decreasing transcription (e.g., a KRAB domain, e.g., from the Kox1 protein), a core catalytic domain of a histone acetyltransferase (e.g., histone acetyltransferase p300), a protein/domain that provides a detectable signal (e.g., a fluorescent protein such as GFP), a nuclease domain (e.g., a Fok1 nuclease), and a base editor (e.g., cytidine deaminase such as APOBEC1).

In some cases, the fusion partner has enzymatic activity that modifies a protein associated with the target nucleic acid sequence (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB 1, and the like, SET1A. SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDMI A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of suitable fusion partners are (i) a dihydrofolate reductase (DHFR) destabilization domain to generate a chemically controllable subject RNA-guided polypeptide or a conditionally active RNA-guided polypeptide, and (ii) a chloroplast transit peptide.

Suitable chloroplast transit peptides include, but are not limited to:

(SEQ ID NO: 161)
MASMISSSAVTTVSRASRGQSAAMAPFGGLKSMTGFPVRKVNTDIT

SITSNGGRVKCMQVWPPIGKKKFETLSYLPPLTRDSRA;

(SEQ ID NO: 162)
MASMISSSAVTIVSRASRGQSAAMAPFGGLKSMTGFPVRKVNTDIT

SITSNGGRVKS;

(SEQ ID NO: 163)
MASSMLSSATMVASPAQATMVAPFNGLKSSAAFPATRKANNDITSIT

SNGGRVNCMQVWPPIEKKKEETLSYLPDLTDSGGRVNC;

(SEQ ID NO: 164)
MAQVSRICNGVQNPSLISNLSKSSQRKSPLSVSLKTQQHPRAYPISS

WGLKKSGMTLIGSELRPLKVMSSVSTAC;

(SEQ ID NO: 165)
MAQVSRICNGVWNPSLISNLSKSSQRKSPLSVSLKTQQHPRAYPISS

SWGLKKSGMTLIGSELRPLKVMSSVSTAC;

(SEQ ID NO: 166)
MAQINNMAQGIQTLNPNSNFHKPQVPKSSSFLVFGSKKLKNSANSML

VLKKDSITMQLFCSFRISASVATAC;

(SEQ ID NO: 167)
MAALVTSQLATSGTVLSVTDRFRRPGFQGLRPRNPADAALGMRTVGAS

AAPKQSRKPHRFDRRCLSMVV;

(SEQ ID NO: 168)
MAALTTSQLATSATGFGIADRSAPSSLLRHGFQGLKPRSPAGGDATSL

SVTTSARATPKQQRSVQRGSRRFPSVVVC;

(SEQ ID NO: 169)
MASSVLSSAAVATRSNVAQANMVAPFTGLKSAASFPVSRKQNLDITSI

ASNGGRVQC;

(SEQ ID NO: 170)
MESLAATSVFAPSRVAVPAARALVRAGTVVPTRRTSSTSGTSGVKCSA

AVTPQASPVISRSAAAA; and (SEQ ID NO: 171)
MGAAATSMQSLKFSNRLVPPSRRLSPVPNNVTCNNLPKSAAPVRTVKC

CASSWNSTINGAAATTNGASAASS.

In some cases, a reference CasX or variant polypeptide of the present disclosure can include an endosomal escape peptide. In some cases, an endosomal escape polypeptide comprises the amino acid sequence GLFX-ALLXLLXSLWXLLLXA (SEQ ID NO: 172), wherein each X is independently selected from lysine, histidine, and arginine. In some cases, an endosomal escape polypeptide comprises the amino acid sequence GLF-HALLHLLHSLWHLLLHA (SEQ ID NO: 173), or HHHHHHHHH (SEQ ID NO: 174).

Non-limiting examples of fusion partners for use when targeting ssRNA target nucleic acid sequences include (but are not limited to): splicing factors (e.g., RS domains); protein translation components (e.g., translation initiation, elongation, and/or release factors: e.g., eIF4G); RNA methylases: RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

A fusion partner can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PIT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3): proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen): proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI DI and terminal uridylate transferase); proteins and protein domains responsible for RNA localization (for example from IMP1. ZBP1, She2p, She3p, and Bicaudal-D): proteins and protein domains responsible for nuclear retention of RNA (for example Rrp6): proteins and protein domains responsible for nuclear export of RNA (for example TAP, NXF1, THO, TREX, REF, and Aly): proteins and protein domains responsible for repression of RNA splicing (for example PTB, Sam68, and hnRNP A1): proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases: proteins and protein domains capable of stimulating RNA cleavage; Exonucleases: Deadenylases; proteins and protein domains having nonsense mediated RNA decay activity: proteins and protein domains capable of stabilizing RNA: proteins and protein domains capable of repressing translation: proteins and protein domains capable of stimulating translation; proteins and protein domains capable of modulating translation (e.g., translation factors such as initiation factors, elongation factors, release factors, etc., e.g., eIF4G): proteins and protein domains capable of polyadenylation of RNA: proteins and protein domains capable of polyuridinylation of RNA: proteins and protein domains having RNA localization activity; proteins and protein domains capable of nuclear retention of RNA; proteins and protein domains having RNA nuclear export activity; proteins and protein domains capable of repression of RNA splicing: proteins and protein domains capable of stimulation of RNA splicing; proteins and protein domains capable of reducing the efficiency of transcription: and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as a fusion partner have modular organization, with separate sequence-specific RNA binding modules and splicing effector domains. For example, members of the serine/arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived post mitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cc-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pill/Aby1, etc.).

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a subject RNA-guided polypeptide or a conditionally active RNA-guided polypeptide and/or subject CasX fusion polypeptide does not include a NLS so that the protein is not targeted to the nucleus (which can be advantageous, e.g., when the target nucleic acid sequence is an RNA that is present in the cytosol). In some embodiments, a fusion partner can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mcherry, tdTomato, and the like, a histidine tag, e.g., a 6xHis tag; a hemagglutinin (HA) tag; a FLAG tag; a Myc tag; and the like).

In some cases a reference or CasX variant polypeptide includes (is fused to) a nuclear localization signal (NLS) (e.g., in some cases 2 or more, 3 or more, 4 or more, or 5 or more 6 or more, 7 or more, 8 or more NLSs). Thus, in some cases, a reference or CasX variant polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus. In some cases a reference or CasX variant polypeptide includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a reference or CasX variant polypeptide includes (is fused to) between 2 and 5 NLSs (e.g., 2-4, or 2-3 NLSs).

Non-limiting examples of NLSs include sequences derived from: the NLS of the SV40 virus large T-antigen, having the amino acid sequence PKKKRKV (SEQ ID NO: 176); the NLS from nucleoplasmin (e.g., the nucleoplasmin bipartite NLS with the sequence KRPAATKKAGQAKKKK (SEQ ID NO: 177); the c-myc NLS having the amino acid sequence PAAKRVKLD (SEQ ID NO: 178) or RQRR-NELKRSP (SEQ ID NO: 179); the hRNPA1 M9 NLS having the sequence NQSSNFGPMKGGNFG-GRSSGPYGGGGQYFAKPRNQGGY (SEQ ID NO: 180); the sequence RMRIZFKNKGKDTAELRRRRVEVS-VELRKAKKDEQILKRRNV (SEQ ID NO: 181) of the IBB domain from importin-alpha; the sequences VSRKRPRP (SEQ ID NO: 182) and PPKKARED (SEQ ID No: 183) of the myoma T protein; the sequence PQPKKKPL (SEQ ID NO: 184) of human p53; the sequence SALIKKKKKMAP (SEQ ID NO: 185) of mouse c-abl IV; the sequences DRLRR (SEQ ID NO: 186) and PKQKKRK (SEQ ID NO: 187) of the influenza virus NS1; the sequence RKLKK-KIKKL (SEQ ID NO: 188) of the Hepatitis virus delta antigen; the sequence REKKKFLKRR (SEQ ID NO: 189) of the mouse Mx1 protein; the sequence KRKGDEVDGVDEVAKKKSKK (SEQ ID NO: 190) of the human poly(ADP-ribose) polymerase; the sequence RKCLQAGMNLEARKTKK (SEQ ID NO: 191) of the steroid hormone receptors (human) glucocorticoid: the sequence PRPRKIPR (SEQ ID NO: 192) of Borna disease virus P protein (BDV-P1): the sequence PPRKKRTVV (SEQ ID NO: 193) of hepatitis C virus nonstructural protein (HCV-NS5A); the sequence NLSKKKKRKREK (SEQ ID NO: 194) of LEF1; the sequence RRPSRPFRKP (SEQ ID NO: 195) of ORF57 simirae; the sequence KRPRSPSS (SEQ ID NO: 196) of EBV LANA; the sequence KRGIN-DRNFWRGENERKTR (SEQ ID NO: 197) of Influenza A protein; the sequence PRPPKMARYDN (SEQ ID NO: 198) of human RNA helicase A (RHA); the sequence KRSFSKAF (SEQ ID NO: 199) of nucleolar RNA helicase II; the sequence KLKIKRPVK (SEQ ID NO: 200) of TUS-protein; the sequence PKKKRKVPPPPAAKRVKLD (SEQ ID NO: 201) associated with importin-alpha; the sequence PKTRRRPRRSQRKRPPT (SEQ ID NO: 202) from the Rex protein in HTLV-1; the sequence MSRRR-KANPTKLSENAKKLAKEVEN (SEQ ID NO: 203) from the EGL-13 protein of Caenorhabditis elegans; and the sequences KTRRRPRRSQRKRPPT (SEQ ID NO: 204), RRKKRRPRRKKRR (SEQ ID NO: 205), PKKKSRKPKKKSRK (SEQ ID NO: 206), HKKKHP-DASVNFSEFSK (SEQ ID NO: 207), QRPGPY-DRPQRPGPYDRP (SEQ ID NO: 208), LSPSLSPLLSPSL-SPL (SEQ ID NO: 209), RGKGGKGLGKGGAKRHRK (SEQ ID NO: 210), PKRGRGRPKRGRGR (SEQ ID NO: 211), PKKKRKVPPPPAAKRVKLD (SEQ ID NO: 212) and PKKKRKVPPPPKKKRKV (SEQ ID NO: 213). In general, NLS or (multiple NLSs) are of sufficient strength to drive accumulation of a reference or CasX variant fusion protein in the nucleus of a eukaryotic cell. Detection of accumulation in the nucleus may be performed by any suitable technique. For example, a detectable marker may be fused to a reference or CasX variant fusion protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined.

In some cases, a reference or CasX variant fusion protein includes a "Protein Transduction Domain" or PTD (also known as a CPP—cell penetrating peptide), which refers to a protein, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from an extracellular space to an intracellular space, or from the cytosol to within an organelle. In some embodiments, a PTD is covalently linked to the amino terminus of a reference or CasX variant fusion protein. In some embodiments, a PTD is covalently linked to the carboxyl terminus of a reference or CasX variant fusion protein. In some cases, the PTD is inserted internally in the sequence of a reference or CasX variant fusion protein at a suitable insertion site. In some cases, a reference or CasX variant fusion protein includes (is conjugated to, is fused to) one or more PTDs (e.g., two or more, three or more, four or more PTDs). In some cases, a PTD includes one or more nuclear localization signals (NLS). Examples of PTDs include but are not limited to peptide transduction domain of HIV TAT comprising YGRKKRRQRRR (SEQ ID NO: 214), RKKRRQRR (SEQ ID NO: 215); YARAAARQARA (SEQ ID NO: 216); THRLPRRRRRR (SEQ ID NO: 217); and GGRRARRRRRR (SEQ ID NO: 218); a polyarginine sequence comprising a number of arginines sufficient to direct entry into a cell (e.g., 3, 4, 5, 6, 7, 8, 9, 10, or 10-50 arginines (SEQ ID NO: 219)); a VP22 domain (Zender et al. (2002) Cancer Gene Ther. 9(6):489-96); an *Drosophila* Antennapedia protein transduction domain (Noguchi et al. (2003) Diabetes 52(7): 1732-1737); a truncated human calcitonin peptide (Trehin et al. (2004) Pharm. Research 21:1248-1256); polylysine (Wender et al. (2000) Proc. Natl. Acad. Sci. USA 97: 13003-13008); RRQRRTSKLMKR (SEQ ID NO: 220); Transportan GWTLNSAGYLLGKINL-KALAALAKKIL (SEQ ID NO: 221); KALAWEAK-LAKALAKALAKHLAKALAKALKCEA (SEQ ID NO: 222); and RQIKIWFQNRRMKWKK (SEQ ID NO: 223). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, a reference or CasX variant fusion protein can include a CasX protein that is linked to an internally inserted heterologous amino acid or heterologous polypeptide (a heterologous amino acid sequence) via a linker polypeptide (e.g., one or more linker polypeptides). In some embodiments, a reference or CasX variant fusion protein can be linked at the C-terminal and/or N-terminal end to a heterologous polypeptide (fusion partner) via a linker polypeptide (e.g., one or more linker polypeptides) The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. Example linker polypeptides include glycine polymers (G)n, glycine-serine polymer (including, for example, (GS)n, GSGGSn (SEQ ID NO: 224), GGSGGSn (SEQ ID NO: 225), and GGGSn (SEQ ID NO: 226), where n is an integer of at least one), glycine-alanine polymers, alanine-serine polymers, glycine-proline polymers, proline polymers and proline-alanine polymers. Example linkers can comprise amino acid sequences including, but not limited to, GGSG (SEQ ID NO: 227), GGSGG (SEQ ID NO: 228), GSGSG (SEQ ID NO: 229), GSGGG (SEQ ID NO: 230), GGGSG (SEQ ID NO: 231), GSSSG (SEQ ID NO: 232), GPGP (SEQ ID NO: 233), GGP, PPP, PPAPPA (SEQ ID NO: 234), PPPGPPP (SEQ ID NO: 235) and the like. The ordinarily skilled artisan will recognize that design of a peptide conjugated to any elements described above can include linkers that are all or partially flexible, such that the linker can include a flexible linker as well as one or more portions that confer less flexible structure.

V. Systems and Methods for Modification of RHO Nucleic Acids

The CRISPR proteins, guide nucleic acids, and variants thereof provided herein are useful for various applications, including as therapeutics, diagnostics, and for research. To effect the methods of the disclosure for gene editing, resulting in modification of the RHO gene, provided herein are programmable Class 2, Type V CRISPR systems. The programmable nature of the systems provided herein allows for the precise targeting to achieve the desired effect at one or more regions of predetermined interest in the target nucleic acid sequence of the RHO gene. A variety of strategies and methods can be employed to modify the target nucleic acid sequence in a cell using the systems provided herein. As used herein "modifying" includes, but is not limited to, cleaving, nicking, editing, deleting, knocking out, knocking down, mutating, correcting, exon-skipping and the like. Depending on the system components utilized, the editing event may be a cleavage event followed by introducing random insertions or deletions (indels) or other mutations (e.g., a substitution, duplication, or inversion of one or more nucleotides), for example by utilizing the imprecise non-homologous DNA end joining (NHEJ) repair pathway, which may generate, for example, a frame shift mutation. Alternatively, the editing event may be a cleavage event followed by homology-directed repair (HDR), homology-independent targeted integration (HITI), micro-homology mediated end joining (MMEJ), single strand annealing (SSA) or base excision repair (BER), resulting in modification of the target nucleic acid sequence.

In some embodiments, the present disclosure provides methods for the modification of RHO target nucleic acid in a cell having one or more mutations wherein the target nucleic acid is modified to correct or compensate for the one or more mutations such that wild-type rhodopsin (SEQ ID NO:33 or 34) or a functional rhodopsin protein is expressed. In other embodiments, the present disclosure provides methods for the modification of RHO target nucleic acid in a cell having one or more mutations wherein the target nucleic acid is modified to knock-down or knock-out the RHO gene such that expression of the mutant rhodopsin is reduced or eliminated. Non-limiting examples of known mutations of rhodopsin (SEQ ID NO:33) contemplated for modification using the methods and systems of the disclosure are presented in Table 4A.

TABLE 4A

Mutations of rhodopsin relative to SEQ ID NO: 33

| Amino Acid Mutations | Functional Features |
|---|---|
| L328P, T342M, Q344R/P/ter, V345L/M, A346P, P347A/R/Q/L/S/T, Ter349/Q/E | Post-Golgi trafficking and OS targeting |
| N15S, T17M, V20G, P23A/H/L, Q28H, G51R/V, P53R, T58R/M, V87D, G89D, G106R/W, C110F/R/S/Y, E113K, L125R, W161R, A164E/V, C167R/W, P171Q/L/S, Y178N/D/C, E181K, G182S/V, C185R, C187G/Y, G188R/E, D190N/G/Y, H211R/P, C222R, P267R/L, S270R, K296N/E/M | Misfolding, ER retention and instability |
| R135G/L/P/W | Disrupted vesicular traffic and endocytosis |
| T4K, T17M, M39R, N55K, G90V | Altered post-translational modifications and reduced stability |
| M44T, V137M | Altered transducin activation |
| G90D, T94I, A292E, A295V | Constitutive activation |
| F45L, V209M, F220C | Dimerization deficiency |
| P12R, R21C, Q28H, L40R, L46R, L47R, F52Y, F56Y, L57R, Y60ter, Q64ter, R69H, N78I, L79P, V87L, L88P, T92I, T97I, V104F, G109R, G114D/V, E122G, W126L/ter, S127F, L131P, Y136ter, C140S, T160T, M163T, A169P, P170H/R, S176F, P180A/S, Q184P, S186P/W, Y191C, T193M, M207R/K, V210F, I214N, P215L/T, M216R/L/K, R252P, T289P, S297R, A298D, K311E, N315ter, E341K, S343C | No observed biochemical or cellular defect or not studied in detail |

Table 4B sets forth targeting sequences specific to Rho mutants. The ClinVar designation (www.ncbi.nlm.nih.gov/clinvar/) is shown in the left hand column.

TABLE 4B

Targeting sequences directed to RHO mutants

| Clin Var Designation | Sequence | SEQ ID NO: |
|---|---|---|
| VCV000013013 | AAGUGGCUGCGUACCACACC | 382 |
| VCV000013014 | UAGGCAGGUCUUAGGCCAGG | 383 |
| VCV000013014 | UAGGCCAGGGCCACCUGGCU | 384 |
| VCV000013015 | UAGGCCGAGGCCACCUGGCU | 385 |
| VCV000013015 | GCCUAAGACCUGCCUAGGAC | 386 |
| VCV000013016 | ACUUCCUCAGGCUCUACGUC | 387 |
| VCV000013016 | GGCUCUACGUCACCGUCCAG | 388 |
| VCV000013016 | CCAUCAACUUCCUCAGGCUC | 389 |
| VCV000013016 | UCAGGCUCUACGUCACCGUC | 390 |
| VCV000013018 | CCAAUGCGAUGGGUGUGGUA | 391 |
| VCV000013018 | AAUGCGAUGGGUGUGGUACG | 392 |
| VCV000013019 | GCAGAAGCAUGUAGGCGGCC | 393 |
| VCV000013020 | UGGACCUAGGUGGCUUCACC | 394 |
| VCV000013020 | UCAUGGACCUAGGUGGCUUC | 395 |
| VCV000013020 | AUGAAGAGGUCAGCCACGGC | 396 |
| VCV000013021 | UCAUGGUCCUAGAUGGCUUC | 397 |
| VCV000013021 | UAGAUGGCUUCACCAGCACC | 398 |
| VCV000013021 | UGGUCCUAGAUGGCUUCACC | 399 |
| VCV000013021 | AGGACCAUGAAGAGGUCAGC | 400 |
| VCV000013022 | UCUUCUGGCCCACAGGAUGC | 401 |
| VCV000013022 | UGUGGGCCAGAAGACGAAGU | 402 |
| VCV000013022 | UCUGGCCCACAGGAUGCAAU | 403 |
| VCV000013023 | UGUGGAAUCAACUACUACAC | 404 |
| VCV000013024 | UGGCCAUCGAGCUGUACGUG | 405 |
| VCV000013024 | AGCUGUACGUGGUGGUGUGU | 406 |
| VCV000013025 | GGGAUGCACCUGAGGACAGG | 407 |
| VCV000013025 | UCAGGUGCAUCCCCGAGGGC | 408 |
| VCV000013025 | GGUGCAUCCCCGAGGGCCUG | 409 |
| VCV000013026 | UGUGGAAUCGGCUACUACAC | 410 |
| VCV000013026 | GCUACUACACGCUCAAGCCG | 411 |
| VCV000013027 | CCUUCACCAUCCCCAUGAUU | 412 |
| VCV000013027 | ACAUGUUCGUGGUCCCCUUC | 413 |
| VCV000013027 | UGGUCCCCUUCACCAUCCCC | 414 |
| VCV000013027 | UGGGGAUGGUGAAGGGGACC | 415 |
| VCV000013028 | UGGCCAUCGAGUGGUACGUG | 416 |
| VCV000013028 | AGUGGUACGUGGUGGUGUGU | 417 |
| VCV000013029 | AAGACGGAGACGAGCUAGGU | 418 |
| VCV000013029 | UAGGCCGGGGCCACCUAGCU | 419 |
| VCV000013030 | CAGCGUUCUUUGCCGAGAGC | 420 |
| VCV000013030 | GCAAAGAACGCUGGGAUGGU | 421 |

TABLE 4B-continued

Targeting sequences directed to RHO mutants

| Clin Var Designation | Sequence | SEQ ID NO: |
|---|---|---|
| VCV000013030 | CGGCAAAGAACGCUGGGAUG | 422 |
| VCV000013030 | UUGCCGAGAGCGCCGCCAUC | 423 |
| VCV000013032 | UAGGCCCGGGCCACCUGGCU | 424 |
| VCV000013032 | UAGGCAGGUCUUAGGCCCGG | 425 |
| VCV000013033 | CCGAGAGCCUGCAGUGCUCG | 426 |
| VCV000013033 | ACACGAGCACUGCAGGCUCU | 427 |
| VCV000013033 | UCAGGUACAUCCCCGAGAGC | 428 |
| VCV000013033 | CGGGGAUGUACCUGAGGACA | 429 |
| VCV000013033 | GGUACAUCCCCGAGAGCCUG | 430 |
| VCV000013034 | GCUGGGUGCUCUACGCCAGC | 431 |
| VCV000013034 | UGAUCUGCUGGGUGCUCUAC | 432 |
| VCV000013034 | ACGCCAGCGUGGCAUUCUAC | 433 |
| VCV000013035 | AAAUUGUAUCCUGUGGGCCC | 434 |
| VCV000013035 | UCGGGCCCACAGGAUACAAU | 435 |
| VCV000013035 | GGCCCACAGGAUACAAUUUG | 436 |
| VCV000013037 | UGCUGGGCUUCCGCAUCAAC | 437 |
| VCV000013037 | GCAUCAACUUCCUCACGCUC | 438 |
| VCV000013038 | UCAGGCCCACAGGAUGCAAU | 439 |
| VCV000013038 | UCUUCAGGCCCACAGGAUGC | 440 |
| VCV000013038 | UGUGGGCCUGAAGACGAAGU | 441 |
| VCV000013040 | UGUGGAAUCUACUACUACAC | 442 |
| VCV000013042 | ACGUGCCCUUCUCCAGUGCG | 443 |
| VCV000013042 | CACUGGAGAAGGGCACGUAG | 444 |
| VCV000013042 | CCAGUGCGACGGGUGUGGUA | 445 |
| VCV000013042 | AGUGCGACGGGUGUGGUACG | 446 |
| VCV000013043 | ACAGGUUCGUGGUCCACUUC | 447 |
| VCV000013043 | UCUACAGGUUCGUGGUCCAC | 448 |
| VCV000013043 | UUUGUCAUCUACAGGUUCGU | 449 |
| VCV000013044 | UGACCAUCCCAGAGUUCUUU | 450 |
| VCV000013044 | GGGAUGGUCAUGAAGAUGGG | 451 |
| VCV000013044 | UGGCAAAGAACUCUGGGAUG | 452 |
| VCV000013044 | CAGAGUUCUUUGCCAAGAGC | 453 |
| VCV000013044 | UCAUGACCAUCCCAGAGUUC | 454 |
| VCV000013045 | CCUAGGACCAUGAAGAGGUC | 455 |
| VCV000013045 | UAGGUGACUUCACCAGCACC | 456 |
| VCV000013045 | UCAUGGUCCUAGGUGACUUC | 457 |
| VCV000013045 | UGGUCCUAGGUGACUUCACC | 458 |
| VCV000013046 | GCUUCGGGAAGAACCAUGCC | 459 |
| VCV000013046 | CGAAGCGGAAGUUGCUCAUG | 460 |
| VCV000013046 | UCCCGAAGCGGAAGUUGCUC | 461 |
| VCV000013046 | GGAAGAACCAUGCCAUCAUG | 462 |
| VCV000013047 | UGCUGCGCUUCCCCAUCAAC | 463 |
| VCV000013047 | GCUGAUCGUGCUGCGCUUCC | 464 |
| VCV000013048 | UCCAAAUUGCAUCCUGUGGG | 465 |
| VCV000013049 | AUGACCCAGGUGAAGGCAAC | 466 |
| VCV000013049 | UGGAGCUGGCCUGCGCCGCA | 467 |
| VCV000013049 | CCUGGGUCAUGGAGCUGGCC | 468 |
| VCV000013050 | CUCGCCGGCUGGUCCAGGUA | 469 |
| VCV000013051 | UGAUCUGGGGUGCCCUACGCC | 470 |
| VCV000013051 | CUUUCCUGAUCUGGGUGCCC | 471 |
| VCV000013051 | UCGCUUUCCUGAUCUGGGUG | 472 |
| VCV000013051 | GGGUGCCCUACGCCAGCGUG | 473 |
| VCV000013052 | UAGGCCGGGGCCAGCUGGCU | 474 |
| VCV000013053 | UAGGCCUGGGCCACCUGGCU | 475 |
| VCV000013053 | UAGGCAGGUCUUAGGCCUGG | 476 |
| VCV000013054 | CCAGCAUCCUCUACACCUCU | 477 |
| VCV000013054 | UCUACACCUCUCUGCAUGGA | 478 |
| VCV000013055 | AAGGCGCUGCGUACCACACC | 479 |
| VCV000013056 | GGCUCGUCUCCGUCUUGGAC | 480 |
| VCV000013056 | UAGGCCGGGGCCAUCUGGCU | 481 |
| VCV000029875 | CCUAGGUCAUGGCGCUGGCC | 482 |
| VCV000143079 | ACUUCCUCACGCUCUAAGUC | 483 |
| VCV000143079 | CGCUCUAAGUCACCGUCCAG | 484 |
| VCV000143079 | AAGUCACCGUCCAGCACAAG | 485 |
| VCV000143079 | UGUGCUGGACGGUGACUUAG | 486 |
| VCV000143079 | UCACGCUCUAAGUCACCGUC | 487 |
| VCV000143080 | CCAGCUGGUCCAGGUAAUGG | 488 |
| VCV000143081 | AUUCUACACGAGCACUGCAG | 489 |
| VCV000143081 | UGUAGAAUCGACUACUACAC | 490 |
| VCV000143083 | UCACCCAGUUCUUGCCGCAG | 491 |
| VCV000143083 | GCUGCGGCAAGAACUGGGUG | 492 |
| VCV000143083 | CCCAGUUCUUGCCGCAGCAG | 493 |
| VCV000143083 | UCGUCACCCAGUUCUUGCCG | 494 |

TABLE 4B-continued

Targeting sequences directed to RHO mutants

| Clin Var Designation | Sequence | SEQ ID NO: |
|---|---|---|
| VCV000196282 | GGUACAUCCCCAAGGGCCUG | 495 |
| VCV000196282 | UCAGGUACAUCCCCAAGGGC | 496 |
| VCV000196282 | CCAAGGGCCUGCAGUGCUCG | 497 |
| VCV000279882 | AGCUUUACGUGGUGGUGUGU | 498 |
| VCV000279882 | UGGCCAUCGAGCUUUACGUG | 499 |
| VCV000373094 | UUGCCACCCUGGCGGUAUGA | 500 |
| VCV000373094 | UACCGCCAGGGUGGCAAAGA | 501 |
| VCV000381626 | UGGUCCCAGGUGGCUUCACC | 502 |
| VCV000381626 | UCAUGGUCCCAGGUGGCUUC | 503 |
| VCV000381626 | CAGGUGGCUUCACCAGCACC | 504 |
| VCV000417867 | CCUGGGUCAUGGUGCUGGCC | 505 |
| VCV000417867 | UGGUGCUGGCCUGCGCCGCA | 506 |
| VCV000419250 | GGAACGCAUGCUCACCACCA | 507 |
| VCV000419250 | AGUUCCGGAACGCAUGCUCA | 508 |
| VCV000437998 | GCCAGGUAGUACCGUGGGUA | 509 |
| VCV000437998 | AGUACCCACGGUACUACCUG | 510 |
| VCV000493373 | CGGCCAUCGAGCGGUACGUG | 511 |
| VCV000493373 | AUGGCCGGGACCACCAAGGA | 512 |
| VCV000493373 | UUGGUGGUCCCGGCCAUCGA | 513 |
| VCV000523376 | UUGCCAAGAGGGCCGCCAUC | 514 |
| VCV000590911 | ACACGAGCACUGCCAGGCCC | 515 |
| VCV000590911 | CCGAGGGCCUGGCAGUGCUC | 516 |
| VCV000625297 | AAUGCGACGGAUGUGGUACG | 517 |
| VCV000625297 | CCAAUGCGACGGAUGUGGUA | 518 |
| VCV000625297 | GUCGCAUUGGAGAAGGGCAC | 519 |
| VCV000625301 | ACACCUCUCUGCAUGUAUAC | 520 |
| VCV000625301 | CUGCAUGUAUACUUCGUCUU | 521 |
| VCV000625301 | GCAUGUAUACUUCGUCUUCG | 522 |
| VCV000625303 | GUGAUGUACCUGAGGACAGG | 523 |
| VCV000625303 | GGUACAUCACCGAGGGCCUG | 524 |
| VCV000625303 | UCAGGUACAUCACCGAGGGC | 525 |
| VCV000635082 | UGGCCAUCGAGCGGUAAGUG | 526 |
| VCV000635082 | AGCGGUAAGUGGUGGUGUGU | 527 |
| VCV000635416 | UCGGGCCCACAGGAGGCAAU | 528 |
| VCV000635416 | AAAUUGCCUCCUGUGGGCCC | 529 |
| VCV000635416 | UCUUCGGGCCCACAGGAGGC | 530 |
| VCV000635416 | GGCCCACAGGAGGCAAUUUG | 531 |
| VCV000636081 | UAGGCCGGGGCCAACUGGCU | 532 |
| VCV000636082 | AGCACAAGAAGCGGCGCACG | 533 |
| VCV000636083 | UGGUCCUACGUGGCUUCACC | 534 |
| VCV000636083 | UCAUGGUCCUACGUGGCUUC | 535 |
| VCV000636083 | UACGUGGCUUCACCAGCACC | 536 |
| VCV000636084 | GGCGUAGGGCACCCAGCAGA | 537 |
| VCV000636085 | ACAACCGUGUCAUCUAUAUC | 538 |
| VCV000636085 | UCAUGAUAUAGAUGACACGG | 539 |
| VCV000636085 | UGAUAUAGAUGACACGGUUG | 540 |
| VCV000636086 | AUAUCAUGAUGAACAAGUAG | 541 |
| VCV000636086 | UGAUGAACAAGUAGGUGCCU | 542 |
| VCV000802004 | AAGGCGACGGGUGUGGUACG | 543 |
| VCV000802004 | CCAAGGCGACGGGUGUGGUA | 544 |
| VCV000802004 | CCUUGGAGAAGGGCACGUAG | 545 |
| VCV000802004 | ACGUGCCCUUCUCCAAGGCG | 546 |
| VCV000802005 | UGCCCACAGGAUGCAAUUUG | 547 |
| VCV000802005 | UCUUCGUGCCCACAGGAUGC | 548 |
| VCV000802005 | UCGUGCCCACAGGAUGCAAU | 549 |
| VCV000802005 | UGUGGGCACGAAGACGAAGU | 550 |
| VCV000802006 | ACACCAGCACUGCAGGCCCU | 551 |
| VCV000802006 | AUUCCACACCAGCACUGCAG | 552 |
| VCV000802007 | AGCCUCUUGCCUUCCUGUUC | 553 |
| VCV000802007 | GGAACAGGAAGGCAAGAGGC | 554 |
| VCV000802007 | UGUUCCGGAACUGCAUGCUC | 555 |
| VCV000802007 | UGCCUUCCUGUUCCGGAACU | 556 |
| VCV000802008 | UAGGCCGGGGCCGCCUGGCU | 557 |
| VCV000810718 | CCCAGUGUUCUUGCCGCAGC | 558 |
| VCV000810718 | GCUGCGGCAAGAACACUGGG | 559 |
| VCV000810718 | UCGUCACCCAGUGUUCUUGC | 560 |
| VCV000810718 | UCACCCAGUGUUCUUGCCGC | 561 |
| VCV000811432 | UGUGAAAUCGACUACUACAC | 562 |
| VCV000811432 | AUUUCACACGAGCACUGCAG | 563 |
| VCV000811432 | CACGAGCACUGCAGGCCCUC | 564 |
| VCV000812395 | UGGCGCUGGUCUGCGCCGCA | 565 |
| VCV000812395 | GCGCCGCACCCCCACUCGCC | 566 |
| VCV000812396 | GGCUUGAGCGUGUAGUAGUC | 567 |

TABLE 4B-continued

Targeting sequences directed to RHO mutants

| Clin Var Designation | Sequence | SEQ ID NO: |
|---|---|---|
| VCV000812396 | CUGCAGUGCUCGUGUGGAAU | 568 |
| VCV000812396 | UUGUUGACCUCCGGCUUGAG | 569 |
| VCV000812396 | ACACGAGCACUGCAGUGAAG | 570 |
| VCV000812396 | ACUUCACUGCAGUGCUCGUG | 571 |
| VCV000812396 | ACUACUACACGCUCAAGCCG | 572 |
| VCV000812396 | UGGUCCACUUCACUGCAGUG | 573 |
| VCV000812396 | AGCCGGAGGUCAACAACGAG | 574 |
| VCV000812396 | UCUACAUGUUCGUGGUCCAC | 575 |
| VCV000812396 | ACAACGAGUCUUUUGUCAUC | 576 |
| VCV000812396 | ACAUGUUCGUGGUCCACUUC | 577 |
| VCV000812396 | UGUGGAAUCGACUACUACAC | 578 |
| VCV000812396 | UUUGUCAUCUACAUGUUCGU | 579 |
| VCV000812397 | UAUGGAAUCGACUACUACAC | 580 |
| VCV000812397 | AUUCCAUACGAGCACUGCAG | 581 |
| VCV000812397 | AUACGAGCACUGCAGGCCCU | 582 |

Additional targeting sequences to the RHO locus are set forth in Table 4C. Targeting sequences in Table 4C are specific to ATC, TTC, CTC and GTC PAM sites, as indicated in the Table.

TABLE 4C

Additional Rho targeting sequences

| PAM Sequence | Targeting Sequence SEQ ID NO |
|---|---|
| ATCN | 583-2100, 2286-5554 |
| TTCN | 370-371, 373-376, 19918-27274 |
| CTCN | 367-369, 372, 10487-19917 |
| GTCN | 5555-10486 |

In some embodiments, the disclosure provides methods of modifying a RHO target nucleic acid in a cell, the method comprising introducing into the cell a Class 2, Type V CRISPR system. In some embodiments, the disclosure provides methods of modifying a RHO target nucleic acid in a cell, the method comprising introducing into the cell: i) a CasX:gNA system comprising a CasX and a gNA of any one of the embodiments described herein; ii) a CasX:gNA system comprising a CasX, a gNA, and a donor template of any one of the embodiments described herein; iii) one or more nucleic acids encoding the CasX and the gNA, and optionally comprising the donor template; iv) a vector comprising the nucleic acid of (iii), above; v) a VLP comprising the CasX:gNA system of any one of the embodiments described herein; or vi) combinations of two or more of (i) to (v), wherein the target nucleic acid sequence of the cells is modified by the CasX protein and, optionally, the donor template. In some embodiments, the disclosure provides CasX:gNA systems for use in the methods of modifying the RHO gene in a cell, wherein the system comprises a CasX variant of SEQ ID NOs: 49-160, 237-239, 243-246, 251-263 or 273-281 as set forth in Tables 3, 6, 7, 8, or 10, or a variant sequence at least 60% identical, at least 70% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or at least 99.5% identical thereto, the gNA scaffold comprises a sequence of SEQ ID NOS: 2101-2285 as set forth in Table 2 or a sequence at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 990% identical, at least 99.5% identical thereto, and the gNA comprises a targeting sequence selected from the group consisting of SEQ ID NOS: 328-346, 367-376, 382-2100 and 2286-27274 or a sequence at least 65% identical, at least 70% identical, at least 75% identical, at least 80% identical, at least 85% identical, at least 90% identical, or at least 95% identical thereto, and having between 15 and 30 amino acids. In some embodiments, the disclosure provides CasX: gNA systems for use in the methods of modifying the RHO gene in a cell, wherein the system comprises a CasX variant of SEQ ID NOs: 49-160, 237-239, 243-246, 251-263 or 273-281 as set forth in Tables 3, 6, 7, 8, or 10, or a variant sequence at least 60% identical, at least 70% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or at least 99.5% identical thereto, the gNA scaffold comprises a sequence of SEQ ID NOS: 2101-2285 as set forth in Table 2 or a sequence at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical thereto, and the gNA comprises a targeting sequence selected from the group consisting of SEQ ID NOS: 382-582, or a sequence at least 65% identical, at least 70% identical, at least 75% identical, at least 80% identical, at least 85% identical, at least 90% identical, or at least 95% identical thereto, and having between 15 and 30 amino acids.

In those cases where the CasX is delivered to the cell in the protein form and the gNA is delivered in the RNA form, the CasX and gNA can be pre-complexed and delivered as an RNP. Upon hybridization with the target nucleic acid by the CasX and the gNA, the CasX introduces one or more single-strand breaks or double-strand breaks within or near the RHO gene that result in a modification of the target nucleic acid such as a permanent indel (deletion or insertion) or other mutation (a base change, inversion or rearrangement with respect to the genomic sequence) in the target nucleic acid, as described herein. In some embodiments of the method, the RHO target nucleic acid of at least 10% of the cells of the population is modified. In some cases of the foregoing, the modification results in a correction or compensation of the mutation occurs, thereby creating an edited cell such that expression of functional rhodopsin can occur. In other embodiments of the method, the modification comprises altering or suppressing expression of the rhodopsin protein comprising the mutation(s) by a knock-down or knock-out of the gene. In some embodiments, the mutation is a gain of function mutation. In other embodiments, the mutation is a loss of function mutation.

In other embodiments, the method comprises contacting the target nucleic acid sequence with a plurality of gNAs targeted to different or overlapping portions of the RHO gene wherein the CasX protein introduces multiple breaks in the target nucleic acid sequence that result in a permanent indel (deletion or insertion) or other mutation in the target nucleic acid, as described herein. In some cases for the foregoing, the method results in correction of the mutation, thereby creating an edited cell such that expression of wvild-type rhodopsin can occur. In other cases of the foregoing, the method results in the knock-down or knock-out the RHO gene such that the expression of the non-functional rhodopsin is reduced or eliminated. In some embodiments of the methods, the RNP are delivered to the in vitro cell directly by electroporation, injection, nucleofection, delivery via liposomes, delivery by nanoparticles, by encapsidation in a VLP (embodiments of which are described herein), or using a protein transduction domain (PTD) conjugated to one or more components of the CasX:gNA In some cases, the CasX:gNA system for use in the methods of modifying the RHO gene further comprises a donor template nucleic acid of any of the embodiments disclosed herein, wherein the donor template can be inserted by the homology-directed repair (HDR) or homology-independent targeted integration (HITI) repair mechanisms of the host cell. The donor template can be a short single-stranded or double-stranded oligonucleotide, or a long single-stranded or double-stranded oligonucleotide. The donor template may contain one or more single base changes, insertions, deletions, inversions or rearrangements with respect to the genomic sequence, provided that there is sufficient homology with the target nucleic acid sequence to support its integration into the target nucleic acid, which can result in a frame-shift or other mutation, or a replacement of the mutated sequence with wild-type sequence, with a corresponding correction of the mutation such that expression of wild-type or functional rhodopsin can occur. In some embodiments, the donor template sequence comprises a non-homologous sequence flanked by two regions of homology 5' and 3' to the break sites of the target nucleic acid (i.e., homologous arms), facilitating insertion of the non-homologous sequence at the target region which can be mediated by HDR or HITI. The exogenous donor template inserted by HITI can be any length, for example, a relatively short sequence of between 1 and 50 nucleotides in length, or a longer sequence of about 50-1000 nucleotides in length. The lack of homology can be, for example, having no more than 20-50% sequence identity and/or lacking in specific hybridization at low stringency. In other cases, the lack of homology can further include a criterion of having no more than 5, 6, 7, 8, or 9 bp identity. In such cases, the use of homologous arms facilitates the insertion of the non-homologous sequence at the break site(s) introduced by the nuclease. In some embodiments, the donor template polynucleotide comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least about 15,000 nucleotides. In other embodiments, the donor template comprises at least about 10 to about 15,000 nucleotides, or at least about 100 to about 10,000 nucleotides, or at least about 400 to about 8,000 nucleotides, or at least about 600 to about 5000 nucleotides, or at least about 1000) to about 2000 nucleotides. The donor template sequence may comprise certain sequence differences as compared to the genomic sequence; e.g., restriction sites, nucleotide polymorphisms, selectable markers (e.g., drug resistance genes, fluorescent proteins, enzymes etc.), etc., which may be used to assess for successful insertion of the donor nucleic acid at the cleavage site or in some cases may be used for other purposes (e.g., to signify expression at the targeted genomic locus). Alternatively, these sequence differences may include flanking recombination sequences such as FLPs, loxP sequences, or the like, that can be activated at a later time for removal of the marker sequence.

In some embodiments, the method of the disclosure provides CasX protein and gNA pairs that generate site-specific double strand breaks (DSBs) or single strand breaks (SSBs) (e.g., when the CasX protein is a nickase that can cleave only one strand of a target nucleic acid) within double-stranded DNA (dsDNA) target nucleic acids, which can then be repaired either by non-homologous end joining (NHEJ), homology-directed repair (HDR), homology-independent targeted integration (HITI), micro-homology mediated end joining (MMEJ), single strand annealing (SSA) or base excision repair (BER). In some cases, contacting a RHO gene with a gene editing pair occurs under conditions that are permissive for non-homologous end joining or homology-directed repair. Thus, in some cases, the methods provided herein include contacting the RHO gene with a donor template by introducing the donor template (either in vitro outside of a cell, in vitro inside a cell, in vivo inside a cell, or ex vivo), wherein the donor template, a portion of the donor template, a copy of the donor template, or a portion of a copy of the donor template integrates into the RHO gene to replace a portion of the RHO gene such that either the gene is knocked-down/knocked-out, or corrective or compensating sequence is knocked-in such that a functional rhodopsin protein can be expressed.

In some embodiments of the method of modifying a RHO target nucleic acid of a cell in vitro or ex vivo, to induce cleavage or any desired modification to a target nucleic acid, the gNA and/or the CasX protein of the present disclosure and, optionally, the donor template sequence, whether they be introduced as nucleic acids or polypeptides, vectors or VLP, are provided to the cells for about 30 minutes to about 24 hours, or at least about 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days; e.g., every 1.5 days, every 2 days, every 3 days, or any other frequency from about every day to about every four days. The agent(s) may be provided to the subject cells one or more times: e.g., one time, twice, three times, or more than three times, and the cells allowed to incubate with the agent(s) for some amount of time following each contacting event; e.g., 30 minutes to about 24 hours. In the case of in vitro-based methods, after the incubation period with the CasX and gNA (and optionally the donor template), the media is replaced with fresh media and the cells are cultured further. In some embodiments of the method, the cells to be modified by the methods of the disclosure are eukaryotic, which can include rodent cells, mouse cells, rat cells, primate cells, non-human primate cells, and human cells. In some embodiments, the cells are selected from the group consisting of a rod photoreceptor cell, a retinal progenitor cell, a pluripotent stem cell (iPSC), fibroblasts, and Miller glial cells. In some embodiments, the cells are autologous with respect to the subject. In other embodiments, the cells are allogenic with respect to the subject. In some embodiments of the in vitro or ex vivo method, the RHO target nucleic acid of at least 10% of the cells of the population is modified.

In some embodiments of the method of modifying a RHO target nucleic acid in a cell, the method further comprises contacting the target nucleic acid sequence of the cell with: a) an additional CRISPR nuclease and a gNA targeting a different or overlapping portion of the RHO target nucleic acid compared to the first gNA; b) a polynucleotide encoding the additional CRISPR nuclease and the gNA of (a); c) a vector comprising the polynucleotide of (b); or d) a VLP comprising the additional CRISPR nuclease and the gNA of (a), wherein the contacting results in modification of the RHO target nucleic acid at a different location in the sequence compared to the first gNA. In some cases, the additional CRISPR nuclease is a CasX protein having a sequence different from the CasX protein of any of the preceding claims. In other cases, the additional CRISPR nuclease is not a CasX protein. In other cases, the additional CRISPR nuclease is selected from the group consisting of Cas9, Cas12a, Cas12b, Cas12c, Cas12d (CasY), Cas12J, Cas13a, Cas13b, Cas13c, Cas13d, CasX, CasY, Cas14, Cpf1, C2cl, Csn2, and sequence variants thereof.

In those cases where the modification results in a knock-down of the RHO gene, expression of the non-functional rhodopsin protein is reduced by at least about 10%, at least about 20%, at least about 30%, at least about 40%, at least about 50%, at least about 60%, at least about 70%, at least about 80%, or at least about 90% in comparison to cells that have not been modified. In other cases, wherein the modification results in a knock-out of the RHO gene, the target nucleic acid of the cells of the population is modified such that at least about 10%, at least about 20%, at least about 30%, at least about 40%, at least about 50%, at least about 60%, at least about 70%, at least about 80%, or at least about 90% of the cells do not express a detectable level of non-functional rhodopsin protein. Expression of rhodopsin protein can be measured by flow cytometry, ELISA, cell-based assays. Western blot or other methods know in the art or as described in the Examples.

In other embodiments of the method of modifying a target nucleic acid sequence, modifying the RHO gene comprises binding of a CasX to the target nucleic acid sequence without cleavage. In some embodiments, the CasX is a catalytically inactive CasX (dCasX) protein that retains the ability to bind to the gNA and to the RHO target nucleic acid sequence but lacks the ability to cleave the nucleic acid sequence, thereby interfering with transcription of the RHO allele. In some embodiments, the dCasX comprises a mutation at residues D672, E769, and/or D935 corresponding to the CasX protein of SEQ ID NO:1 or D659, E756 and/or D922 corresponding to the CasX protein of SEQ ID NO: 2. In some embodiments, the mutation is a substitution of alanine or glycine for the residue.

In some embodiments, the disclosure provides methods of modifying a RHO target nucleic acid in a population of cells in vivo in a subject. In some embodiments of the method, the modified cells of the population are eukaryotic, which can include rodent cells, mouse cells, rat cells, primate cells, non-human primate cells, and human cells. In some embodiments, the cells are selected from the group consisting of a rod photoreceptor cell or a retinal progenitor cell.

Introducing recombinant expression vectors comprising the components or the nucleic acids encoding the components of the system embodiments into a target cell can be carried out in vivo, in vitro or ex vivo. In some embodiments of the method, vectors may be provided directly to a target host cell. Methods of introducing a nucleic acid (e.g., a nucleic acid comprising a donor polynucleotide sequence, one or more nucleic acids (DNA or RNA) encoding a CasX protein and/or gNA, or a vector comprising same) into a cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, nucleofection, electroporation, direct addition by cell penetrating CasX proteins that are fused to or recruit donor DNA, cell squeezing, calcium phosphate precipitation, direct microinjection, nanoparticle-mediated nucleic acid delivery, and the like. Nucleic acids may be introduced into the cells using well-developed commercially-available transfection techniques such as use of TransMessenger reagents from Qiagen, Stemfect RNA Transfection Kit from Stemgent, and TransIT-mRNA Transfection Kit from Mirus Bio LLC. Lonza nucleofection, Maxagen electroporation and the like. Introducing recombinant expression vectors comprising sequences encoding the CasX:gNA systems (and, optionally, the donor sequences) of the disclosure into cells under in vitro conditions can occur in any suitable culture media and under any suitable culture conditions that promote the survival of the cells. For example, cells may be contacted with vectors comprising the subject nucleic acids (e.g., recombinant expression vectors having the donor template sequence and nucleic acids encoding the CasX and gNA) such that the vectors are taken up by the cells. Vectors used for providing the nucleic acids encoding gNAs and/or CasX proteins to a target host cell can include suitable promoters for driving the expression, that is, transcriptional activation of the nucleic acid of interest. In some cases, the encoding nucleic acid of interest will be operably linked to a promoter. This may include ubiquitously acting promoters, for example, the CMV-beta-actin promoter, or inducible promoters, such as promoters that are active in particular cell populations or that respond to the presence of drugs such as tetracycline or kanamycin. By transcriptional activation, it is intended that transcription will be increased above basal levels in the target host cell comprising the vector by at least about 10-fold, by at least about 100-fold, more usually by at least about 1000-fold. In addition, vectors used for providing a nucleic acid encoding a gNA and/or a CasX protein to a cell may include nucleic acid sequences that encode for selectable markers in the target cells, so as to identify cells that have taken up the CasX protein and/or the gNA.

For viral vector delivery, cells can be contacted with viral particles comprising the subject viral expression vectors and the nucleic acids encoding the CasX and gNA and, optionally, the donor template. In some embodiments, the vector is an Adeno-Associated Viral (AAV) vector, wherein the AAV is selected from AAV1, AAV2, AAV3, AAV4, AAV5, AAV6, AAV7, AAV8, AAV9, AAV10, AAV11, AAV12, AAV 44.9. AAV-Rh74, AAVRh10, or a hybrid, a derivative or variant thereof. In other embodiments, the vector is a retroviral vector, described more fully, below. In other embodiments, the vector is a lentiviral vector. Retroviruses, for example, lentiviruses, may be suitable for use in methods of the present disclosure. Commonly used retroviral vectors are "defective": e.g., are unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, and this envelope protein determines the specificity or tropisms of the viral particle for the cells (ecotropic for murine and rat: amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art, including U.S. Pat. No. 5,173,414; Tratschin et al., Mol. Cell. Biol. 5:3251-3260 (1985): Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Nucleic acids can also be introduced by direct microinjection (e.g., injection of RNA).

VI. Polynucleotides and Vectors

In another aspect, the present disclosure relates to polynucleotides encoding the Class 2, Type V nucleases and gNA that have utility in the editing of the RHO gene comprising one or more mutations. In some embodiments, the disclosure provides polynucleotides encoding the CasX proteins and the polynucleotides of the gNAs (e.g., the gDNAs and gRNAs) of any of the CasX:gNA system embodiments described herein. In some embodiments, the disclosure provides donor template polynucleotides for use with the CasX:gNA systems in modifying the target nucleic acid in the cells having a RHO gene comprising one or more mutations. In yet further embodiments, the disclosure provides vectors comprising polynucleotides encoding the CasX proteins and the gNAs described herein, as well as the donor templates of the embodiments.

In some embodiments, the disclosure provides polynucleotide sequences encoding the reference CasX of SEQ ID NOS: 1-3. In other embodiments, the disclosure provides polynucleotide sequences encoding the CasX variants of any of the embodiments described herein, including the CasX protein variants of SEQ ID NOS: 49-160, 237-239, 243-246, 251-263 or 273-281, or sequences having at least about 50%, at least about 60%, at least about 70%, at least about 80%, or at least about 90%, or at least about 95%, or at least about 96%, or at least about 97%, or at least about 98%, or at least about 99% sequence identity thereto.

In some embodiments, the polynucleotide encodes a gNA scaffold sequence set forth in Table 1 or Table 2, any one of SEQ ID NOS: 2101-2285, or a sequence having at least about 50%, at least about 60%, at least about 70%, at least about 80%, at least about 90%, at least about 95%, at least about 96%, at least about 97%, at least about 98%, at least about 99% sequence identity thereto. In other embodiments, the disclosure provides a targeting sequence polynucleotide selected from the group consisting of SEQ ID NOS: 328-346, 367-376, 382-2100 and 2286-27274, or a sequence having at least about 65%, at least about 75%, at least about 85%, or at least about 95% identity to a sequence selected from the group consisting of SEQ ID NOS: 328-346, 367-376, 382-2100 and 2286-27274. In other embodiments, the disclosure provides a targeting sequence polynucleotide selected from the group consisting of SEQ ID NOS: 382-582, or a sequence having at least about 65%, at least about 75%, at least about 85%, or at least about 95% identity to a sequence selected from the group consisting of SEQ ID NOS: 382-582. In some embodiments, the targeting sequence polynucleotide is, in turn, linked to the gNA scaffold sequence; either as a sgNA or a dgNA, at the 3' end of the scaffold sequence. In other embodiments, the disclosure provides gNAs comprising targeting sequence polynucleotides having one or more single nucleotide polymorphisms (SNP) relative to a sequence selected from the group consisting of SEQ ID NOS: 328-346, 367-376, 382-2100 and 2286-27274, or SEQ ID NOS: 382-582.

The present disclosure provides isolated polynucleotide sequences encoding gNA comprising a targeting sequence that is complementary to, and therefore hybridizes with the RHO gene. In some embodiments, the polynucleotide sequence encodes a gNA comprising a targeting sequence that hybridizes with a RHO exon: e.g., any one of exons 1 to 5. In a particular embodiment, the polynucleotide sequence encodes a gNA comprising a targeting sequence that hybridizes with exon 1 of the RHO gene. In other embodiments, the polynucleotide sequence encodes a gNA comprising a targeting sequence that hybridizes with a RHO intron. In other embodiments, the polynucleotide sequence encodes a gNA comprising a targeting sequence that hybridizes with a RHO intron-exon junction. In other embodiments, the polynucleotide sequence encodes a gNA comprising a targeting sequence that hybridizes with an intergenic region of the RHO gene. In other embodiments, the polynucleotide sequence encodes a gNA comprising a targeting sequence that hybridizes with a RHO regulatory element. In some cases, the RHO regulatory element is 5' of the RHO gene. In other cases, the RHO regulatory element is 3' of the RHO gene. In some cases, the RHO regulatory element is in an intron of the RHO gene. In other cases, the RHO regulatory element comprises the 5' UTR of the RHO gene. In still other cases, the RHO regulatory element comprises the 3'UTR of the RHO gene.

In other embodiments, the disclosure provides donor template nucleic acids, wherein the donor template comprises a nucleotide sequence having homology to a RHO target nucleic acid sequence. In some embodiments, the RHO donor template is intended for gene editing and comprises at least a portion of a RHO gene. In some embodiments, the RHO donor template comprises a sequence that hybridizes with the RHO gene. In other embodiments, the donor template sequence is not identical to the genomic sequence that it replaces and may contain one or more single base changes, insertions, deletions, inversions or rearrangements with respect to the genomic sequence. In some cases of the foregoing embodiment, as the donor template sequence comprises a sequence that is non-homologous relative to the target nucleic acid sequence, the donor template is flanked by two homologous arms such that homology-directed repair between the target DNA region and the two flanking arm sequences results in insertion of the donor template at the target region, resulting in the knock-in of the sequence, such that expression of functional rhodopsin can occur. In some embodiments, the RHO donor sequence comprises a sequence that encodes at least a portion of a RHO exon selected from the group consisting of RHO exons 1-5. In some embodiments, the RHO donor sequence comprises a sequence to correct a mutation of Table 4A. In a particular embodiment, the RHO donor sequence comprises a sequence to correct the P23H mutation. In other embodiments, the RHO donor sequence has a sequence that encodes at least a portion of a RHO intron. In other embodiments, the RHO donor sequence has a sequence that encodes at least a portion of with a RHO intron-exon junction. In other embodiments, the RHO donor sequence has a sequence that encodes at least a portion of an intergenic region of the RHO gene. In other embodiments, the RHO donor sequence has a sequence that encodes at least a portion of a RHO regulatory element. In some cases of the foregoing donor template embodiments, the sequence comprises one or more mutations relative to the wild-type RHO gene such that the gene is knocked-down or knocked out. In some embodiments, the donor polynucleotide comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least about 15,000, or at least about 30.000 nucleotides. In other embodiments, the donor polynucleotide comprises at least about 10 to about 30,000 nucleotides, or at least about 100 to about 15,000 nucleotides, or at least about 400 to about 10,000 nucleotides, or at least about 600 to about 5000 nucleotides, or at least about 1000 to about 2000 nucleotides. In some embodiments, the donor template is a single stranded DNA template or a single stranded RNA template. In other embodiments, the donor template is a double stranded DNA template.

In some embodiments, the disclosure relates to methods to produce polynucleotide sequences encoding the reference CasX, the CasX variants, or the gNA of any of the embodiments described herein, including variants thereof, as well as methods to express the proteins expressed or RNA transcribed by the polynucleotide sequences. In general, the methods include producing a polynucleotide sequence coding for the reference CasX, the CasX variants, or the gNA of any of the embodiments described herein and incorporating the encoding gene into an expression vector appropriate for a host cell. For production of the encoded reference CasX, the CasX variants, or the gNA of any of the embodiments described herein, the method includes transforming an appropriate host cell with an expression vector comprising the encoding polynucleotide, and culturing the host cell under conditions causing or permitting the resulting reference CasX, the CasX variants, or the gNA of any of the embodiments described herein to be expressed or transcribed in the transformed host cell, thereby producing the reference CasX, the CasX variants, or the gNA, which is recovered by methods described herein or by standard purification methods known in the art, including the methods of the Examples. Standard recombinant techniques in molecular biology are used to make the polynucleotides and expression vectors of the present disclosure.

In accordance with the disclosure, polynucleotide sequences that encode the reference CasX, the CasX variants, or the gNA of any of the embodiments described herein are used to generate recombinant DNA molecules that direct the expression in appropriate host cells. Several cloning strategies are suitable for performing the present disclosure, many of which are used to generate a construct that comprises a gene coding for a composition of the present disclosure, or its complement. In some embodiments, the cloning strategy is used to create a gene that encodes a construct that comprises nucleotides encoding the reference CasX, the CasX variants, or the gNA that is used to transform a host cell for expression of the composition.

In one approach, a construct is first prepared containing the DNA sequence encoding a reference CasX, a CasX variant, or a gNA. Exemplary methods for the preparation of such constructs are described in the Examples. The construct is then used to create an expression vector suitable for transforming a host cell, such as a prokaryotic or eukaryotic host cell for the expression and recovery of the polypeptide construct. Where desired, the host cell is an *E. coli* cell. In other embodiments, the host cell is selected from Baby Hamster Kidney fibroblast (BHK) cells, human embryonic kidney 293 (HEK293), human embryonic kidney 293T (HEK293T), NS0 cells, SP2/0 cells, YO myeloma cells, P3X63 mouse myeloma cells, PER cells, PER.C6 cells, hybridoma cells, NIH3T3 cells, CV-1 (simian) in Origin with SV40 genetic material (COS), HeLa. Chinese hamster ovary (CHO), or yeast cells, or other eukaryotic cells known in the art suitable for the production of recombinant products. Exemplary methods for the creation of expression vectors, the transformation of host cells and the expression and recovery of reference CasX, the CasX variants, or the gNA are described in the Examples.

The gene or genes encoding for the reference CasX, the CasX variants, or the gNA constructs can be made in one or more steps, either fully synthetically or by synthesis combined with enzymatic processes, such as restriction enzyme-mediated cloning, PCR and overlap extension, including methods more fully described in the Examples. The methods disclosed herein can be used, for example, to ligate sequences of polynucleotides encoding the various components (e.g., CasX and gNA) genes of a desired sequence. Genes encoding polypeptide compositions are assembled from oligonucleotides using standard techniques of gene synthesis.

In some embodiments, the nucleotide sequence encoding a CasX protein is codon optimized. This type of optimization can entail a mutation of an encoding nucleotide sequence to mimic the codon preferences of the intended host organism or cell while encoding the same CasX protein. Thus, the codons can be changed, but the encoded protein remains unchanged. For example, if the intended target cell of the CasX protein was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX protein variant-encoding nucleotide sequence could be generated. As another non-limiting example, if the intended host cell were an insect cell, then an insect codon-optimized CasX protein-encoding nucleotide sequence could be generated. The gene design can be performed using algorithms that optimize codon usage and amino acid composition appropriate for the host cell utilized in the production of the reference CasX or the CasX variants. In one method of the disclosure, a library of polynucleotides encoding the components of the constructs is created and then assembled, as described above. The resulting genes are then assembled and the resulting genes used to transform a host cell and produce and recover the reference CasX, the CasX variants, or the gNA compositions for evaluation of its properties, as described herein.

In some embodiments, a nucleotide sequence encoding a gNA is operably linked to a control element; e.g., a transcriptional control element, such as a promoter. In some embodiments, a nucleotide sequence encoding a CasX protein is operably linked to a control element; e.g., a transcriptional control element, such as a promoter. In other cases, the nucleotide encoding the CasX and gNA are linked and are operably linked to a single control element. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells; e.g., neurons, spinal motor neurons, medium spiny neurons, cortical neurons, striatal neurons, oligodendrocytes, or glial cells.

Non-limiting examples of eukaryotic promoters (promoters functional in a eukaryotic cell) include EF1alpha, EF1alpha core promoter, those from cytomegalovirus (CMV) immediate early, herpes simplex virus (HSV) thymidine kinase, early and late SV40, long terminal repeats (LTRs) from retrovirus, and mouse metallothionein-I. Further non-limiting examples of eukaryotic promoters include the CMV promoter full-length promoter, the minimal CMV promoter, the chicken β-actin promoter, the hPGK promoter, the HSV TK promoter, the Mini-TK promoter, the human synapsin I promoter which confers neuron-specific expression, the Mecp2 promoter for selective expression in neurons, the minimal IL-2 promoter, the Rous sarcoma virus enhancer/promoter (single), the spleen focus-forming virus long terminal repeat (LTR) promoter, the SV40 promoter, the SV40 enhancer and early promoter, the TBG promoter; promoter from the human thyroxine-binding globulin gene (Liver specific), the PGK promoter, the human ubiquitin C promoter, the UCOE promoter (Promoter of HNRPA2B1-CBX3), the Histone H2 promoter, the Histone H3 promoter, the U1a1 small nuclear RNA promoter (226 nt), the U1b2 small nuclear RNA promoter (246 nt) 26, the TTR minimal enhancer/promoter, the b-kinesin promoter, the human elF4A1 promoter, the ROSA26 promoter and the glyceraldehyde 3-phosphate dehydrogenase (GAPDH) promoter.

Selection of the appropriate vector and promoter is well within the level of ordinary skill in the art, as it related to controlling expression, e.g., for modifying a protein involved in antigen processing, antigen presentation, antigen recognition, and/or antigen response and/or its regulatory element. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, FLAG tag, fluorescent protein, etc.) that can be fused to the CasX protein, thus resulting in a chimeric CasX protein that are used for purification or detection.

In some embodiments, a nucleotide sequence encoding each of a gNA variant or a CasX protein is operably linked to an inducible promoter, a constitutively active promoter, a spatially restricted promoter (i.e., transcriptional control element, enhancer, tissue specific promoter, cell type specific promoter, etc.), or a temporally restricted promoter. In other embodiments, individual nucleotide sequences encoding the gNA or the CasX are linked to one of the foregoing categories of promoters, which are then introduced into the cells to be modified by conventional methods, described below.

In certain embodiments, suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human HI promoter (HI), a POL1 promoter, a 7SK promoter, tRNA promoters and the like.

In some embodiments, a nucleotide sequence encoding a CasX and gNA and, optionally, a donor template, is operably linked to (under the control of) an inducible promoter operable in a eukaryotic cell. Examples of inducible promoters may include, but are not limited to, T7 RNA polymerase promoter, T3 RNA polymerase promoter, isopropyl-beta-D-thiogalactopyranoside (IPTG)-regulated promoter, lactose induced promoter, heat shock promoter, tetracycline-regulated promoter, kanamycin-regulated promoter, steroid-regulated promoter, metal-regulated promoter, estrogen receptor-regulated promoter, etc. Inducible promoters can therefore, in some embodiments, be regulated by molecules including, but not limited to, doxycycline; estrogen and/or an estrogen analog; IPTG; etc. Additional examples of inducible promoters include, without limitation, chemically/biochemically-regulated and physically-regulated promoters such as alcohol-regulated promoters, kanamycin-regulated promoters, tetracycline-regulated promoters (e.g., anhydro-tetracycline (aTc)-responsive promoters and other tetracycline-responsive promoter systems, which include a tetracycline repressor protein (tetR), a tetracycline operator sequence (tetO) and a tetracycline transactivator fusion protein (tTA), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR, etc.), tetracycline regulated promoters, (e.g., promoter systems including Tet Activators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Recombinant expression vectors of the disclosure can also comprise elements that facilitate robust expression of CasX proteins and the gNAs of the disclosure. For example, recombinant expression vectors can include one or more of a polyadenylation signal (PolyA), an intronic sequence or a post-transcriptional regulatory element such as a woodchuck hepatitis post-transcriptional regulatory element (WPRE). Exemplary polyA sequences include hGH poly(A) signal (short), HSV TK poly(A) signal, synthetic polyadenylation signals, SV40 poly(A) signal. D-globin poly(A) signal and the like. A person of ordinary skill in the art will be able to select suitable elements to include in the recombinant expression vectors described herein.

The polynucleotides encoding the reference CasX, the CasX variants, and the gNA sequences can then be individually cloned into one or more expression vectors. In some embodiments, the present disclosure provides vectors comprising the polynucleotides selected from the group consisting of a retroviral vector, a lentiviral vector, an adenoviral vector, an adeno-associated viral (AAV) vector, a virus-like particle (VLP), a herpes simplex virus (HSV) vector, a plasmid, a minicircle, a nanoplasmid, a DNA vector, and an RNA vector. In some embodiments, the vector is a recombinant expression vector that comprises a nucleotide sequence encoding a CasX protein. In other embodiments, the disclosure provides a recombinant expression vector comprising a nucleotide sequence encoding a CasX protein and a nucleotide sequence encoding a gNA. In some cases, the nucleotide sequence encoding the CasX protein variant and/or the nucleotide sequence encoding the gNA are operably linked to a promoter that is operable in a cell type of choice. In other embodiments, the nucleotide sequence encoding the CasX protein variant and the nucleotide sequence encoding the gNA are provided in separate vectors operably linked to a promoter. In other embodiments, the vector can comprise a donor template or a polynucleotide encoding one or more CAR, engineered TCR, one or more engineered TCR subunits, or a separate vector can be utilized to introduce the donor template or the one or more CAR or engineered TCR subunits into the target cell to be modified.

In some embodiments, provided herein are one or more recombinant expression vectors comprising one or more of: (i) a nucleotide sequence of a donor template nucleic acid where the donor template comprises a nucleotide sequence having homology to a target sequence of a target nucleic acid (e.g., a target genome); (ii) a nucleotide sequence that encodes a gNA that hybridizes to a target sequence of the locus of the targeted genome (e.g., configured as a single or dual guide RNA) operably linked to a promoter that is operable in a target cell such as a eukaryotic cell; and (iii) a nucleotide sequence encoding a CasX protein operably linked to a promoter that is operable in a target cell such as a eukaryotic cell. In some embodiments, the sequences encoding the donor template, the gNA and the CasX protein are in different recombinant expression vectors, and in other embodiments one or more polynucleotide sequences (for the donor template, CasX, and the gNA) are in the same recombinant expression vector.

The polynucleotide sequence(s) are inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature. Various vectors are publicly available. The vector may, for example, be in the form of a plasmid, cosmid, viral particle, or phage that may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. Once introduced into a suitable host cell, expression of the protein involved in antigen processing, antigen presentation, antigen recognition, and/or antigen response can be determined using any nucleic acid or protein assay known in the art. For example, the presence of transcribed mRNA of reference CasX or the CasX variants can be detected and/or quantified by conventional hybridization assays (e.g., Northern blot analysis), amplification procedures (e.g. RT-PCR), SAGE (U.S. Pat. No. 5,695,937), and array-based technologies (see e.g., U.S. Pat. Nos. 5,405, 783, 5,412,087 and 5,445,934), using probes complementary to any region of the polynucleotide.

The disclosure provides for the use of plasmid expression vectors containing replication and control sequences that are compatible with and recognized by the host cell and are operably linked to the gene encoding the polypeptide for controlled expression of the polypeptide or transcription of the RNA. Such vector sequences are well known for a variety of bacteria, yeast, and viruses. Useful expression vectors that can be used include, for example, segments of chromosomal, non-chromosomal and synthetic DNA sequences. "Expression vector" refers to a DNA construct containing a DNA sequence that is operably linked to a suitable control sequence capable of effecting the expression of the DNA encoding the polypeptide in a suitable host. The requirements are that the vectors are replicable and viable in the host cell of choice. Low- or high-copy number vectors may be used as desired. The control sequences of the vector include a promoter to effect transcription, an optional operator sequence to control such transcription, a sequence encoding suitable mRNA ribosome binding sites, and sequences that control termination of transcription and translation. The promoter may be any DNA sequence, which shows transcriptional activity in the host cell of choice and may be derived from genes encoding proteins either homologous or heterologous to the host cell.

The polynucleotides and recombinant expression vectors can be delivered to the target host cells by a variety of methods. Such methods include, but are not limited to, viral infection, transfection, lipofection, electroporation, calcium phosphate precipitation, polyethyleneimine (PEI)-mediated transfection, DEAE-dextran mediated transfection, microinjection, liposome-mediated transfection, particle gun technology, nucleofection, direct addition by cell penetrating CasX proteins that are fused to or recruit donor DNA, cell squeezing, calcium phosphate precipitation, direct microinjection, nanoparticle-mediated nucleic acid delivery, and using the commercially available TransMessenger® reagents from Qiagen, Stemfect™ RNA Transfection Kit from Stemgent, and TransIT®-mRNA Transfection Kit from Mirus Bio LLC, Lonza nucleofection, Maxagen electroporation and the like.

A recombinant expression vector sequence can be packaged into a virus or virus-like particle (also referred to herein as a "VLP" or "virion") for subsequent infection and transformation of a cell, ex vivo, in vitro or in vivo. Such VLP or virions will typically include proteins that encapsidate or package the vector genome. Suitable expression vectors may include viral expression vectors based on vaccinia virus; poliovirus; adenovirus; a retroviral vector (e.g., Murine Leukemia Virus), spleen necrosis virus, and vectors derived from retroviruses such as Rous Sarcoma Virus, Harvey Sarcoma Virus, avian leukosis virus, retrovirus, a lentivirus, human immunodeficiency virus, myeloproliferative sarcoma virus, and mammary tumor virus; and the like.

In some embodiments, a recombinant expression vector of the present disclosure is a recombinant adeno-associated virus (AAV) vector. In a particular embodiment, a recombinant expression vector of the present disclosure is a recombinant retrovirus vector. In another particular embodiment, a recombinant expression vector of the present disclosure is a recombinant lentivirus vector.

AAV is a small (20 nm), nonpathogenic virus that is useful in treating human diseases in situations that employ a viral vector for delivery to a cell such as a eukaryotic cell, either in vivo or ex vivo for cells to be prepared for administration to a subject. A construct is generated, for example, encoding any of the CasX proteins and gNA embodiments as described herein, and optionally a donor template, and can be flanked with AAV inverted terminal repeat (ITR) sequences, thereby enabling packaging of the AAV vector into an AAV viral particle.

An "AAV" vector may refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs. In some embodiments, the AAV vector is selected from AAV1, AAV2, AAV3, AAV4, AAV5. AAV6, AAV7, AAV8. AAV9, AAV 10, AAV 44.9. AAV-Rh74 (Rhesus macaque-derived AAV), and AAVRh10, and modified capsids of these serotypes. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped recombinant AAV (rAAV) are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences.

An "AAV virus" or "AAV viral particle" refers to a viral particle composed of at least one AAV capsid protein (preferably by all of the capsid proteins of a wild-type AAV) and an encapsidated polynucleotide. If the particle additionally comprises a heterologous polynucleotide (i.e., a polynucleotide other than a wild-type AAV genome to be delivered to a mammalian cell), it is typically referred to as "rAAV". An exemplary heterologous polynucleotide is a polynucleotide comprising a CasX protein and/or sgNA and, optionally, a donor template of any of the embodiments described herein.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, for example Kotin, R. M. (1994) Human Gene Therapy 5:793-801; Bems, K. I. "Parvoviridae and their Replication" in Fundamental Virology, 2nd Edition, (B. N. Fields and D. M. Knipe, eds.). As used herein, an AAV ITR need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV-Rh74, and AAVRh10, and modified capsids of these serotypes. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Use of AAV serotypes for integration of heterologous sequences into a host cell is known in the art (see, e.g., WO2018195555A1 and US20180258424A1, incorporated by reference herein.)

By "AAV rep coding region" is meant the region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome.

By "AAV cap coding region" is meant the region of the AAV genome which encodes the capsid proteins VP1, VP2, and VP3, or functional homologues thereof. These Cap expression products supply the packaging functions which are collectively required for packaging the viral genome.

In some embodiments, AAV capsids utilized for delivery of the CasX, gNA, and, optionally, donor template nucleotides, to a host cell can be derived from any of several AAV serotypes, including without limitation, AAV1, AAV2. AAV3, AAV4, AAV5. AAV6, AAV7, AAV8, AAV9, AAV10, AAV11, AAV12, AAV 44.9, AAV-Rh74 (Rhesus macaque-derived AAV), and AAVRh10, and the AAV ITRs are derived from AAV serotype 1 or serotype 2. In some embodiments, the AAV vector and the regulatory sequences are selected so that the total size of the vector is below 5 kb, permitting packaging within the AAV capsid. While the AAV vector may be of any AAV serotype, nervous cell tropism varies among AAV capsid serotypes. Thus, use of AAV serotypes compatible with widespread transgene delivery to astrocytes and motoneurons is preferred. In some embodiments, the AAV vector is of serotype 9 or of serotype 6, which have been demonstrated to effectively deliver polynucleotides to motor neurons and glia throughout the spinal cord in preclinical models of ALS (Foust, K D. et al. Therapeutic AAV9-mediated suppression of mutant RHO slows disease progression and extends survival in models of inherited ALS. Mol Ther. 21(12):2148 (2013)). In some embodiments, the methods provide use of AAV9 or AAV6 for targeting of neurons via intraparenchymal brain injection. In some embodiments, the methods provide use of AAV9 for intravenous administering of the vector wherein the AAV9 has the ability to penetrate the blood-brain barrier and drive gene expression in the nervous system via both neuronal and glial tropism of the vector. In order to produce rAAV viral particles, an AAV expression vector is introduced into a suitable host cell using known techniques, such as by transfection. Packaging cells are typically used to form virus particles; such cells include HEK293 or HEK293T cells (and other cells described herein or known in the art), which package adenovirus. A number of transfection techniques are generally known in the art; see, e.g., Sambrook et al. (1989) Molecular Cloning, a laboratory manual, Cold Spring Harbor Laboratories, New York. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In some embodiments, host cells transfected with the above-described AAV expression vectors are rendered capable of providing AAV helper functions in order to replicate and encapsidate the nucleotide sequences flanked by the AAV ITRs to produce rAAV viral particles. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs (open reading frames), encoding the rep and cap coding regions, or functional homologues thereof. Accessory functions can be introduced into and then expressed in host cells using methods known to those of skill in the art. Commonly, accessory functions are provided by infection of the host cells with an unrelated helper virus. In some embodiments, accessory functions are provided using an accessory function vector. Depending on the host/vector system utilized, any of a number of suitable transcription and translation control elements, including constitutive and inducible promoters, transcription enhancer elements, transcription terminators, etc., may be used in the expression vector.

In other embodiments, suitable vectors may include virus-like particles (VLP). Virus-like particles (VLPs) are particles that closely resemble viruses, but do not contain viral genetic material and are therefore non-infectious. In some embodiments, VLPs comprise a polynucleotide encoding a transgene of interest, for example any of the CasX protein and/or a gNA embodiments, and, optionally, donor template polynucleotides described herein, packaged with one or more viral structural proteins.

In other embodiments, the disclosure provides VLPs produced in vitro that comprise a CasX:gNA RNP complex and, optionally, a donor template. Combinations of structural proteins from different viruses can be used to create VLPs, including components from virus families including Parvoviridae (e.g., adeno-associated virus), Retroviridae (e.g., HIV and Alpharetrovirus), Flaviviridae (e.g., Hepatitis C virus), Paramyxoviridae (e.g., Nipah) and bacteriophages (e.g., Qβ, AP205). In some embodiments, the disclosure provides VLP systems designed using components of retrovirus, including lentiviruses such as HIV and Alpharetrovirus, in which individual plasmids comprising polynucleotides encoding the various components are introduced into a packaging cell that, in turn, produce the VLP. In some embodiments, the disclosure provides VLP comprising one or more components of i) protease, ii) a protease cleavage site, iii) one or more components of a gag poly protein selected from matrix protein (MA), nucleocapsid protein (NC), capsid protein (CA), or p1-p6 protein, v) CasX; vi) gNA, and vi) targeting glycoproteins or antibody fragments wherein the resulting VLP particle encapsidates a CasX:gNA RNP. The targeting glycoproteins or antibody fragments on the surface that provides tropism of the VLP to the target cell, wherein upon administration and entry into the target cell, the RNP molecule is free to be transported into the nucleus of the cell. In other embodiments, the disclosure provides VLP of the foregoing and further comprises one or more components of a pol polyprotein (e.g. a protease), and, optionally, a second CasX or a donor template. The foregoing offers advantages over other vectors in the art in that viral transduction to dividing and non-dividing cells is efficient and that the VLP delivers potent and short-lived RNP that escape a subject's immune surveillance mechanisms that would otherwise detect a foreign protein. In some embodiments, a system to make VLP in a host cell comprises polynucleotides encoding one or more components selected from i) one or more components of a gag polyprotein; ii) a CasX protein of any of the embodiments described herein: iii) a protease cleavage site; iv) a protease: v) a guide RNA of any of the embodiments described herein; vi) a pol polyprotein or portions thereof (e.g., a protease): vii) a pseudotyping glycoprotein or antibody fragment that provides for binding and fusion of the VLP to a target cell; and viii) a donor template. The disclosure contemplates multiple configurations of the arrangement of the encoded components, including duplicates of some of the encoded components. The envelope glycoprotein can be derived from any enveloped viruses known in the art to confer tropism to VLP, including but not limited to the group consisting of Argentine hemorrhagic fever virus, Australian bat virus, *Autographa californica* multiple nucleopolyhedrovirus, Avian leukosis virus, baboon endogenous virus, Bolivian hemorrhagic fever virus, Boma disease virus, Breda virus, Bunyamwera virus, Chandipura virus, Chikungunya virus, Crimean-Congo hemorrhagic fever virus, Dengue fever virus, Duvenhage virus, Eastern equine encephalitis virus, Ebola hemorrhagic fever virus. Ebola Zaire virus, enteric adenovirus, Ephemerovirus, Epstein-Bar virus (EBV), European bat virus 1. European bat virus 2, Fug Synthetic gP Fusion, Gibbon ape leukemia virus, Hantavirus, Hendra virus, hepatitis A virus, hepatitis B virus, hepatitis C virus, hepatitis D virus, hepatitis E virus, hepatitis G Virus (GB virus C), herpes simplex virus type 1, herpes simplex virus type 2, human cytomegalovirus (HHV5), human foamy virus, human herpesvirus (HHV), human Herpesvirus 7, human herpesvirus type 6, human herpesvirus type 8, human immunodeficiency virus 1 (HIV-1), human metapneumovirus, human T-lymphotropic virus 1, influenza A, influenza B, influenza C virus, Japanese encephalitis virus, Kaposi's sarcoma-associated herpesvirus (HHV8), Kaysanur Forest disease virus, La Crosse virus, Lagos bat virus, Lassa fever virus, lymphocytic choriomeningitis virus (LCMV), Machupo virus, Marburg hemorrhagic fever virus, measles virus, Middle eastern respiratory syndrome-related coronavirus, Mokola virus, Moloney murine leukemia virus, monkey pox, mouse mammary tumor virus, mumps virus, murine gammaherpesvirus, Newcastle disease virus, Nipah virus, Nipah virus, Norwalk virus, Omsk hemorrhagic fever virus, papilloma virus, parvovirus, pseudorabies virus, Quaranfil virus, rabies virus, RD114 Endogenous Feline Retrovirus, respiratory syncytial virus (RSV), Rift Valley fever virus, Ross River virus, rRotavirus. Rous sarcoma virus, rubella virus, Sabia-associated hemorrhagic fever virus, SARS-associated coronavirus (SARS-CoV), Sendai virus, Tacaribe virus, Thogotovirus, tick-borne encephalitis causing virus, varicella zoster virus (HHV3), varicella zoster virus (HHV3), variola major virus, variola minor virus, Venezuelan equine encephalitis virus, Venezuelan hemorrhagic fever virus, vesicular stomatitis virus (VSV), VSV-G, Vesiculovirus, West Nile virus, western equine encephalitis virus, and Zika Virus. In some embodiments, the packaging cell used for the production of VLP is selected from the group consisting of HEK293 cells, Lenti-X HEK293T cells, BHK cells, HepG2 cells, Saos-2 cells, HuH7 cells, NS0 cells, SP2/0 cells, YO myeloma cells, A549 cells, P3X63 mouse myeloma cells, PER cells, PER.C6 cells, hybridoma cells, VERO cells, NIH3T3 cells, COS cells, W138 cells, MRC5 cells, A549 cells, HeLa cells, CHO cells, or HT1080 cells.

VII. Cells

In another aspect, the present disclosure relates to a population of cells having one or more mutations in the RHO gene that has been modified by the systems and methods disclosed herein.

In some embodiments, the present disclosure provides populations of cells that have been modified to correct or compensate for the one or more mutations in the RHO gene such that wild-type rhodopsin (SEQ ID NO:33) or a functional rhodopsin protein is expressed. Cells that have been genetically modified in this way may be administered to a subject for purposes such as gene therapy; e.g., to treat a disease associated with a defect in the RHO gene. Non-limiting examples of mutations of rhodopsin contemplated for modification in populations of cells using the systems of the disclosure are presented in Table 4A. For example, patient-specific autologous induced pluripotent stem cells (iPSC), fibroblasts, or Müller glial cells can be isolated from the subject and then the target nucleic acid bearing the mutation of these iPSC cells can be edited using the CasX:gNA systems by the methods described herein. For example, the method can comprise editing within or near a P23H mutation in a RHO gene of the iPSC, then the genome-edited cells can be differentiated into cells such as photoreceptor cells or retinal progenitor cells and propagated into a population of cells that can be administered into the subject. The differentiating step may be performed according to any method known in the art. For example, iPSCs can be used to generate retinal organioids and photoreceptors as described in the art (Phillips et al., Stem Cells, June 2014, 32(6): pgs. 1480-1492: Zhong et al. Nat. Commun., 2014, 5: pg 4047; Tucker et al., PLoS One, April 2011, 6(4): e18992). In some embodiments of the foregoing, the administration is via an intraocular, intravitreal, subretinal, or suprachoroidal injection or implantation.

In some embodiments, the population of cells are modified by a Class 2, Type V Cas nuclease and one or more guides targeted to the one or more mutations of the RHO gene. In some embodiments, the disclosure provides methods and populations of cells modified by introducing into the cells of the population: i) a CasX:gNA system comprising a CasX and a gNA of any one of the embodiments described herein; ii) a CasX:gNA system comprising a CasX, a gNA, and a donor template of any one of the embodiments described herein: iii) one or more nucleic acids encoding the CasX and the gNA, and optionally comprising the donor template; iv) a vector selected from the group consisting of a retroviral vector, a lentiviral vector, an adenoviral vector, an adeno-associated viral (AAV) vector, and a herpes simplex virus (HSV) vector and comprising the nucleic acid of (iii), above: v) a VLP comprising the CasX:gNA system of any one of the embodiments described herein; or vi) combinations of two or more of (i) to (v), wherein the RHO target nucleic acid sequence of the cells targeted by the gNA is modified by the CasX protein and, optionally, the donor template.

In some embodiments, the gNA of the CasX:gNA system is targeted to a mutation in the RHO gene, including, but not limited to the mutations of Table 4A, wherein the NHEJ repair mechanisms of the cell can correct or compensate for the mutation in the cells of the population such that a functional rhodopsin protein can be expressed. In another embodiment, two or more gNA are used in the CasX:gNA system to modify the cells of the population wherein the gNA are targeted to different or overlapping portion of the RHO gene target nucleic acid. In one embodiment of the foregoing, the two or more gNA are targeted to sequences that flank (5' and 3' to) a portion or the entirety of the mutation. In a particular embodiment, the mutation in the cells of the population to be modified is the P23H mutation. In some cases of the foregoing, the NHEJ repair mechanisms of the cell can correct or compensate for the mutation. In some embodiments, the disclosure provides a population of cells wherein the cells have been modified such that at least 60%, at least 70%, at least 75%, at least 80%, at least 85%, at least 90%, or at least 95% of the modified cells express a detectable level of functional rhodopsin protein. In other embodiments, the disclosure provides a population of cells wherein the cells have been modified by the systems and methods of any of the embodiments described herein such that the expression of rhodopsin protein is increased by at least about 10%, at least about 20%, at least about 30%, at least about 40%, at least about 50%, at least about 60%, at least about 70%, at least about 80%, or at least about 90% in comparison to a cell where the RHO gene has not been modified. Expression of the rhodopsin protein can be determined by ELISA, Western blot, electrochemiluminescence assays or other methods know in the art, or as described in the Examples.

In some embodiments, the disclosure provides a method of preparing cells for treatment of a subject having retinitis pigmentosa comprising modifying cells having one or more mutations in the RHO gene by editing the target nucleic acid with a CasX:gNA system or by introducing into the cells a polynucleotide or vector encoding the CasX:gNA system of any of the embodiments described herein, wherein the modification results in the cells ability to produce a wild-type or a functional rhodopsin protein. In some embodiments, the cell has been modified such that expression of functional rhodopsin is increased by at least about 10%, at least about 20%, at least about 30%, at least about 40%, at least about 50%, at least about 60%, at least about 70%, at least about 80%, or at least about 90% in comparison to a cell where the RHO gene has not been modified. In other embodiments of the method, the cells have been modified such that at least about 50%, at least about 60%, at least about 70%, at least about 75%, at least about 80%, at least about 85%, at least about 90%, or at least about 95% of the modified cells express a detectable level of functional rhodopsin. Such modified cells altered in this manner are useful for therapy applications, for example for ex vivo preparation of cells for use in a subject having retinitis pigmentosa. In other embodiments, the disclosure provides compositions of cells modified to express functional rhodopsin for use as a medicament in the treatment of retinitis pigmentosa.

In some cases of the method, the cells of the population are contacted with a CasX and a gNA wherein the gNA is a guide RNA (gRNA). In other cases, the cells of the population are contacted with a CasX and a gNA wherein the gNA is a guide DNA (gDNA). In other cases, the cells of the populations are contacted with a CasX and a gNA wherein the gNA is a chimera comprising DNA and RNA. As described herein, in embodiments of any of the combinations, each of said gNA molecules (a combination of the scaffold and targeting sequence, w % bich can be configured as a sgRNA or a dgRNA) can be provided as an RNP complexed with a CasX molecule described herein, such that the RNP can then modify the target gene. In some embodiments, the cells of the population are contacted with an RNP of a CasX comprising a sequence of SEQ ID NOs: 49-160, 237-239, 243-246, 251-263 or 273-281, or a sequence at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, or at least 99.5% identical thereto, the gNA scaffold comprises a sequence of SEQ ID NOS: 2101-2285 or a sequence at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least $^{990}$% identical, at least 99.5% identical thereto, and the gNA comprises a targeting sequence of SEQ ID NOs: 328-346, 367-376, 382-2100 and 2286-27274, or SEQ ID NOS: 382-582 or a sequence at least 65% identical, at least 70% identical, at least 75% identical, at least 80% identical, at least 85% identical, at least 90% identical, or at least 95% identical thereto and having between 15 and 30 amino acids. Upon hybridization with the target nucleic acid by the CasX and the gNA, the CasX introduces one or more single-strand breaks or double-strand breaks within the RHO gene that results in a modification of the target nucleic acid such as a permanent indel (deletion or insertion) or a mutation (e.g., substitution, duplication, or inversion) in the target nucleic acid that, in connection with the repair mechanisms of the host cell, results in a correction or a compensation of the mutation with a corresponding expression of functional rhodopsin protein, thereby creating the modified population of cells.

In some embodiments of the method, the target nucleic acid of the cells of the population is modified using a plurality of gNAs (e.g., two, three, four or more) targeted to different or overlapping portions of the RHO gene wherein the CasX protein introduces multiple breaks in the target nucleic acid sequence that result in a permanent indel (deletion or insertion) or corrective mutation (e.g., a substitution, duplication, or inversion of one or more nucleotides), or is used in conjunction with a donor template, as described, supra.

An RNP can be introduced into the cells to be modified via any suitable method, including via electroporation, injection, nucleofection, delivery via liposomes, delivery by nanoparticles, or using a protein transduction domain (PTD) conjugated to one or more components of the CasX:gNA. In other cases, the CasX and the one or more gNA are introduced into the population of cells as encoding polynucleotides using a vector; embodiments of which are described herein. Additional methods of modification of the cells using the CasX:gNA system components include viral infection, transfection, conjugation, protoplast fusion, particle gun technology, calcium phosphate precipitation, direct microinjection, and the like. The choice of method is generally dependent on the type of cell being transformed and the circumstances under which the transformation is taking place; e.g., in vitro, ex vivo, or in vivo. A general discussion of these methods can be found in Ausubel, et al, Short Protocols in Molecular Biology, 3rd ed., Wiley & Sons, 1995.

In some embodiments of the method of modify the population of cells, the method further comprises contacting the RHO gene target nucleic acid sequence of the population of cells with: i) an additional CRISPR nuclease and a gNA targeting a different or overlapping portion of the RHO target nucleic acid compared to the first gNA; ii) a polynucleotide encoding the additional CRISPR nuclease and the gNA of (i); iii) a vector selected from the group consisting of a retroviral vector, a lentiviral vector, an adenoviral vector, an adeno-associated viral (AAV) vector, a herpes simplex virus (HSV) vector and comprising the polynucleotide of (ii): or iv) a VLP comprising the additional CRISPR nuclease and the gNA of (i), wherein the contacting results in modification of the RHO gene at a different location in the sequence compared to the sequence targeted by the first gNA. In one embodiment of the foregoing, the additional CRISPR nuclease is a CasX protein having a sequence different from the CasX protein of the previous embodiments. In another embodiment of the foregoing, the additional CRISPR nuclease is not a CasX protein and is selected from the group consisting of Cas9, Cas12a. Cas12b, Cas12c. Cas12d (CasY), Cas12J. Cas13a, Cas13b, Cas13c. Cas13d, CasX, CasY, Cas14, Cpf1, C2cl, Csn2, and sequence variants thereof.

In some embodiments, the population of modified cells are animal cells, for example, derived from a rodent, rat, mouse, rabbit or dog cell. In some embodiments, the cell is a human cell. In some embodiments, the cell is a non-human primate cell; e.g., a cynomolgus monkey cell. In some embodiments, the cells are selected from the group consisting of a rod photoreceptor cell, a retinal progenitor cell, a pluripotent stem cell (iPSC), a fibroblast, and Miller glial cells.

In some embodiments of the method, the modifying of the RHO gene target nucleic acid sequence of the population of cells occurs in vitro or ex vivo. The method provides that the cells can be obtained from a unit of blood or a biopsy collected from a subject using any number of techniques known to the skilled artisan. The cells collected may be washed and filtered or centrifuged to remove the desired cells from other cells or tissue and, optionally, to place the cells in an appropriate buffer or media for subsequent processing steps. The method may include one or more steps of i) introducing into the cells the CasX:gNA system components for the editing of the target nucleic acids: ii) introducing into the cells one or more nucleic acids encoding the CasX:gNA system components to the cells: iii) expansion of the cells, and iv) cryopreservation of the cells for subsequent administration to the subject.

VIII. Therapeutic Methods

In another aspect, the present disclosure relates to methods of treating a subject having a disease associated with mutations in the RHO gene, such as retinitis pigmentosa. In some cases, the allele related to the disease associated with mutations in the RHO gene (RHO-related disease) of the subject to be modified comprises one or more mutations, including, but not limited to the mutations presented in Table 4A. A number of therapeutic strategies have been used to design the compositions for use in the methods of treatment of a subject with a RHO-related disease. Additionally, the methods can be used to treat a subject in advance of any symptom of retinitis pigmentosa, e.g., prior to the development of loss of or changes in vision, visual acuity, nyctalopia, color vision, peripheral vision, loss of the mid-peripheral visual field, photophobia, contrast sensitivity, gaze tracking, light aversion, macular sensitivity, and depth perception. Accordingly, the prophylactic administration of a modified cell population or a therapeutically effective amount of the CasX:gNA system composition(s) or the polynucleic acids encoding the CasX:gNA systems of the embodiments can serve to prevent or reduce the progression of a RHO-related disease.

As described herein, the methods of treatment can prevent, treat and/or ameliorate a RHO-related disease of a subject. In some embodiments, the disclosure provides a method of treating a RHO-related disease in a subject in need thereof, comprising modifying a RHO gene having one or more mutations in eye cells of the subject. In some embodiments, the modifying comprises contacting said cells of one or both eyes of the subject with a therapeutically effective dose of i) a CasX:gNA system comprising a CasX and a gNA of any one of the embodiments described herein; ii) a CasX:gNA system comprising a CasX, a gNA, and a donor template of any one of the embodiments described herein; iii) one or more nucleic acids encoding the CasX and the gNA, and optionally comprising the donor template, iv) a vector selected from the group consisting of a retroviral vector, a lentiviral vector, an adenoviral vector, an adeno-associated viral (AAV) vector, and a herpes simplex virus (HSV) vector and comprising the nucleic acid of (iii), above; v) a VLP comprising the CasX:gNA system of any one of the embodiments described herein; or vi) combinations of two or more of (i) to (v), wherein the RHO target nucleic acid sequence of the cells targeted by the gNA is modified by the CasX protein and, optionally, the donor template. In some embodiments of the method, a second gNA is utilized, wherein the second gNA has a targeting sequence complementary to a different or overlapping portion of the target nucleic acid compared to the first gNA, resulting in an additional break in the RHO target nucleic acid of the cells of the subject. In some embodiments of the foregoing, the gene can be modified by the NHEJ host repair mechanisms, or the CasX:gNA system is utilized in conjunction with a donor template that is inserted by HDR or HITI mechanisms, wherein at least about 10%, at least about 20%, at least about 30%, at least about 40%, at least about 50%, at least about 60%, at least about 70%, at least about 80%, or at least about 90% of the targeted cells are modified. In some embodiments, the modification corrects or compensates for the mutation, resulting in the expression of a functional rhodopsin in the subject. In some cases, expression of a wild-type or functional rhodopsin protein is increased in the eye of a subject by at least about 10%, at least about 20%, at least about 30%, at least about 40%, at least about 50%, at least about 60%, at least about 70%, at least about 80%, or at least about 90% in comparison to a subject wherein the RHO gene of the cells has not been modified. In other embodiments of the foregoing, the gene can be modified by the NHEJ host repair mechanisms, or utilized in conjunction with a donor template that is inserted by HDR or HITI mechanisms to knock-down or knock-out the RHO gene, resulting in the reduction or elimination of the expression of the mutant rhodopsin in the cells of the subject. In some cases, expression of the mutant rhodopsin protein is decreased in the cells of the subject by at least about 10%, at least about 20%, at least about 30%, at least about 40%, at least about 50%, at least about 60%, at least about 70%, at least about 80%, or at least about 90% in comparison to cells of a subject wherein the RHO gene has not been modified. The embodiments of the paragraph are more fully detailed, below, while the methods employed in the modification of the RHO gene have been described, supra. In some embodiments of the method of treatment, the subject is selected from the group consisting of a rodent, a mouse, a rat, and a non-human primate. In other embodiments of the method of treatment, the subject is a human. In some embodiments, the eye cells of the subject to be modified are selected from the group consisting of a neuron, a rod photoreceptor cell, a retinal progenitor cell, a pluripotent stem cell (iPSC), a fibroblast, and Miller glial cell.

In some embodiments of the method of treatment, the method comprises administering to one or both eyes of the subject a therapeutically effective dose of a vector comprising or encoding the CasX protein and the gNA and, optionally, the donor template (described, supra), wherein the contacting of the cells of the subject with the vector results in modification of the target nucleic acid of the cells by the components of the CasX:gNA system. In some embodiments, the method comprises administration of the vector comprising or encoding a CasX and a plurality of gNAs targeted to different locations in the RHO gene, wherein the contacting of the cells of the subject with the CasX:gNA RNP complexes results in modification of the target nucleic acid of the cells. In one particular embodiment, the vector is an AAV. The AAV utilized can be selected from the group consisting of AAV1, AAV2, AAV3, AAV4, AAV5, AAV6, AAV7, AAV8, AAV9, AAV10, AAV11, AAV12, AAV 44.9, AAV-Rh74, and AAVRh10, or mutated variants thereof. The vector of the embodiments are administered to the subject at a therapeutically effective dose. In some embodiments, the vector is administered to the subject at a dose of at least about $1 \times 10^5$ vector genomes (vg), at least about $1 \times 10^6$ vg, at least about $1 \times 10^7$ vg, at least about $1 \times 10^8$ vg, at least about $1 \times 10^9$ vg, at least about $1 \times 10^{10}$ vg, at least about $1 \times 10^{11}$ vg, at least about $1 \times 10^{12}$ vg, at least about $1 \times 10^{13}$ vg, at least about $1 \times 10^{14}$ vg, at least about $1 \times 10^{15}$ vg, at least about $1 \times 10^{16}$ vg. In other embodiments, the vector is administered to the subject at a dose of at least about $1 \times 10^5$ vg to about $1 \times 10^{16}$ vg, or at least about $1 \times 10^6$ vg to about $1 \times 10^{15}$ vg, or at least about $1 \times 10^7$ vg to about $1 \times 10^{14}$ vg, or at least about $1 \times 10^8$ vg to about $1 \times 10^{13}$ vg, or at least about $1 \times 10^9$ vg to about $1 \times 10^{12}$ vg, or at least about $1 \times 10^{10}$ vg to about $1 \times 10^{11}$ vg. In some embodiments, the vector is administered to the subject at a dose of at least about $1 \times 10^5$ vector genomes (vg)/kg, at least about $1 \times 10^6$ vg/kg, at least about $1 \times 10^7$ vg/kg, at least about $1 \times 10^8$ vg/kg, at least about $1 \times 10^9$ vg/kg, at least about $1 \times 10^{10}$ vg/kg, at least about $1 \times 10^{11}$ vg/kg, at least about $1 \times 10^{12}$ vg/kg, at least about $1 \times 10^{13}$ vg/kg, at least about $1 \times 10^{14}$ vg/kg, at least about $1 \times 10^{15}$ vg/kg, at least about $1 \times 10^{16}$ vg/kg. In other embodiments, the vector is administered to the subject at a dose of at least about $1 \times 10^5$ vg/kg to about $1 \times 10^{16}$ vg/kg, or at least about $1 \times 10^6$ vg/kg to about $1 \times 10^{15}$ vg/kg, or at least about $1 \times 10^7$ vg/kg to about $1 \times 10^{14}$ vg/kg, or at least about $1 \times 10^8$ vg/kg to about $1 \times 10^{13}$ vg/kg, or at least about $1 \times 10^9$ vg/kg to about $1 \times 10^{12}$ vg/kg, or at least about $1 \times 10^{10}$ vg/kg to about $1 \times 10^{11}$ vg/kg.

In other cases, the vector is a VLP of any of the embodiments described herein wherein the VLP is administered to the subject at a dose of at least about $1 \times 10^5$ particles, at least about $1 \times 10^6$ particles, at least about $1 \times 10^7$ particles, at least about $1 \times 10^8$ particles, at least about $1 \times 10^9$ particles, at least about $1 \times 10^{10}$ particles, at least about $1 \times 10^{11}$ particles, at least about $1 \times 10^{12}$ particles, at least about $1 \times 10^{13}$ particles, at least about $1 \times 10^{14}$ particles, at least about $1 \times 10^{15}$ particles, at least about $1 \times 10^{16}$ particles. In still other cases, the VLP is administered to the subject at a dose of at least about $1 \times 10^5$ particles to about $1 \times 10^{16}$ particles, or at least about $1 \times 10^6$ particles to about $1 \times 10^{15}$ particles, or at least about $1 \times 10^7$ particles to about $1 \times 10^{14}$ particles, or at least about $1 \times 10^8$ particles to about $1 \times 10^{13}$ particles, or at least about $1 \times 10^9$ particles to about $1 \times 10^{12}$ particles, or at least about $1 \times 10^{10}$ particles to about $1 \times 10^{11}$ particles.

In other cases, the vector is a VLP of any of the embodiments described herein wherein the VLP is administered to the subject at a dose of at least about $1 \times 10^5$ particles/kg, at least about $1 \times 10^6$ particles/kg, at least about $1 \times 10^7$ particles/kg, at least about $1 \times 10^6$ particles/kg, at least about $1 \times 10^9$ particles/kg, at least about $1 \times 10^{10}$ particles/kg, at least about $1 \times 10^{11}$ particles/kg, at least about $1 \times 10^{12}$ particles/kg, at least about $1 \times 10^{13}$ particles/kg, at least about $1 \times 10^{14}$ particles/kg, at least about $1 \times 10^{15}$ particles/kg, at least about $1 \times 10^{16}$ particles/kg. In still other cases, the VLP is administered to the subject at a dose of at least about $1 \times 10^5$ particles/kg to about $1 \times 10^{16}$ particles/kg, or at least about $1 \times 10^6$ particles/kg to about $1 \times 10^{15}$ particles/kg, or at least about $1 \times 10^7$ particles/kg to about $1 \times 10^{14}$ particles/kg, or at least about $1 \times 10^8$ particles/kg to about $1 \times 10^{13}$ particles/kg, or at least about $1 \times 10^9$ particles/kg to about $1 \times 10^{12}$ particles/kg, or at least about $1 \times 10^{10}$ particles/kg to about $1 \times 10^{11}$ particles/kg.

The vector or VLP can be administered according to any of the treatment regimens disclosed herein, below, and are administered to one or both eyes of the subject by a route of administration selected from intraocular, intravitreal, subretinal, or suprachoroidal injection or implantation.

In some embodiments, the treatment results in the improvement of one or more clinical parameters or endpoints associated with the disease in the subject, wherein the clinical parameter or endpoint is selected from one or any combination of the group consisting of: mean change or mean rate of change in 1) best corrected visual acuity (BCVA); 2) visual field sensitivity (including analysis of hill of vision volumes); 3) retinal sensitivity measured by full-field stimulus testing (FST) 67; 4) multiluminance mobility tests: 5) electrophysiological measures of retinal function: 6) optical coherence tomography (OCT) documenting the rate of photoreceptor loss: and 7) hypo- or hyperfluorescent lesion size on fundus autofluorescence; 8) color vision; 9) contrast sensitivity: 10) gaze tracking: 11) light aversion; 12) macular sensitivity.

In other embodiments, the disclosure provides methods of treating a subject having a RHO-related disease, the method comprising administering to one or both eyes of the subject of a therapeutically effective amount of the modified population of cells of any one of the embodiments described herein, wherein the administration can produce a beneficial effect in helping to treat (e.g., reduce the severity) or prevent the progression of the disease or results in an improvement in one or more clinical parameters or endpoints associated with the disease in the subject. In the foregoing, clinical parameters or endpoints are selected from one or any combination of the group consisting of; mean change or mean rate of change in 1) best corrected visual acuity (BCVA); 2) visual field sensitivity (including analysis of hill of vision volumes); 3) retinal sensitivity measured by full-field stimulus testing (FST); 4) multiluminance mobility tests: 5) electrophysiological measures of retinal function; 6) optical coherence tomography (OCT) documenting the rate of photoreceptor loss; and 7) hypo- or hyperfluorescent lesion size on fundus autofluorescence; 8) color vision; 9) contrast sensitivity; 10) gaze tracking; I1) light aversion: 12) macular sensitivity. In the embodiments, the population of cells are modified in vitro or ex vivo by CasX:gNA system composition(s) or the nucleic acids encoding the CasX:gNA system of the embodiments described herein, supra. The cells to be modified are selected from the group consisting of a rod photoreceptor cell, a retinal progenitor cell, a pluripotent stem cell (iPSC), fibroblasts, and Miller glial cells. In some cases, the CasX and gNA is delivered to the cells of the population as an RNP (embodiments of which are described herein, supra), wherein the target nucleic acid is modified such that a wild-type or a functional rhodopsin protein is expressed. In other cases, the CasX and gNA is delivered to the cell in a vector (embodiments of which are described herein, supra), wherein the target nucleic acid is modified such that a wild-type or a functional rhodopsin protein is expressed. In some embodiments, the method of treatment comprises the administration to the subject of a population of the modified cells such that, upon administration, a wild-type or a functional rhodopsin protein is expressed. Embodiments of such populations of modified cells are described herein, supra. In some cases, the cells have been modified such that expression of a wild-type or functional rhodopsin protein is increased by at least about 10%, at least about 20%, at least about 30%, at least about 40%, at least about 50%, at least about 60%, at least about 70%, at least about 80%, or at least about 90% in comparison to a cell where the RHO gene has not been modified. In other cases, the cells have been modified such that at least about 50%, at least about 60%, at least about 70%, at least about 75%, at least about 80%, at least about 85%, at least about 90%, or at least about 95% of the modified cells express a detectable level of functional rhodopsin protein. In some embodiments, the modified cells administered to the subject, or their progeny, persist in the subject for at least one month, two month, three months, four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the modified cells to the subject. In some embodiments of the method of treatment, the dose of total cells is within a range of between at or about $10^4$ and at or about $10^9$ cells, such as between $10^5$ and $10^6$ cells body weight, for example, at or about $1\times10^5$ cells, $1.5\times10^5$ cells, $2\times10^5$ cells, or $1\times10^6$ cells body weight. For example, in some embodiments, the cells are administered at, or within a certain range of error of, between at or about $10^4$ and at or about $10^9$ cells, such as between $10^5$ and $10^6$ cells body weight, for example, at or about $1\times10^5$ cells, $1.5\times10^5$ cells, $2\times10^5$ cells, or $1\times10^6$ cells. In some embodiments, the cells are selected from the group consisting of rodent cells, mouse cells, rat cells, and non-human primate cells. In other embodiments, the cells are human cells. In some embodiments, the cells are selected from the group consisting of a rod photoreceptor cell, a retinal progenitor cell, a pluripotent stem cell (iPSC), fibroblasts, and Müller glial cells. In one embodiment, the cells are autologous with respect to the subject to be administered the cells. In another embodiment, the cells are allogeneic with respect to the subject to be administered the cells. In some embodiments, the cells are administered to one or both eyes of the subject by a route of administration selected from intraocular, intravitreal, subretinal, or suprachoroidal injection or implantation.

In another embodiment, the invention provides a method of treatment of a subject having a RHO-related disease according to a treatment regimen comprising one or more consecutive doses using a therapeutically effective dose of a population of the modified cells. In one embodiment of the treatment regimen, the therapeutically effective dose of the cells is administered as a single dose. In another embodiment of the treatment regimen, the therapeutically effective dose of the cells is administered to the subject as two or more doses over a period of at least two weeks, or at least one month, or at least two months, or at least three months, or at least four months, or at least five months, or at least six months, or once a year, or every 2 or 3 years. In some embodiments, the dose of total cells and/or dose of individual sub-populations of cells is within a range of between at or about $10^4$ and at or about $10^9$ cells per dose, such as between $10^5$ and $10^6$ cells, for example, at or about $1\times10^5$ cells, $1.5\times10^5$ cells, $2\times10^5$ cells, or $1\times10^6$ cells per dose. For example, in some embodiments, the cells are administered at, or within a certain range of error of, between at or about $10^4$ and at or about $10^9$ cells per dose, such as between $10^5$ and $10^6$ cells, for example, at or about $1\times10^5$ cells, $1.5\times10^5$ cells, $2\times10^5$ cells, or $1\times10^6$ cells per dose. The cells can be administered to one or both eyes of the subject by a route of administration selected from intraocular, intravitreal, subretinal, or suprachoroidal injection or implantation.

In another embodiment, the invention provides a method of treatment of a subject having a RHO-related disease according to a treatment regimen comprising one or more consecutive doses using a therapeutically effective dose of a CasX:gNA system, or a polynucleotide encoding the CasX:gNA system, or a vector of any of the embodiments described herein. In one embodiment of the treatment regimen, the therapeutically effective dose is administered as a single dose. In another embodiment of the treatment regimen, the therapeutically effective dose is administered to the subject as two or more doses over a period of at least two weeks, or at least one month, or at least two months, or at least three months, or at least four months, or at least five months, or at least six months, or once a year, or every 2 or 3 years. The doses can be administered to one or both eyes of the subject by a route of administration selected from intraocular, intravitreal, subretinal, or suprachoroidal injection or implantation.

In some embodiments, the treatment regimen results in the improvement of one, two, or more clinical parameters or endpoints associated with the disease in the subject, wherein the clinical parameter or endpoint is selected from one or any combination of the group consisting of: mean change or mean rate of change in 1) best corrected visual acuity (BCVA); 2) visual field sensitivity (including analysis of hill of vision volumes); 3) retinal sensitivity measured by full-field stimulus testing (FST) 67: 4) multiluminance mobility tests: 5) electrophysiological measures of retinal function; 6) optical coherence tomography (OCT) documenting the rate of photoreceptor loss; and 7) hypo- or hyperfluorescent lesion size on fundus autofluorescence: 8) color vision: 9) contrast sensitivity; 10) gaze tracking; 11) light aversion; 12) macular sensitivity.

In some embodiments, the disclosure provides compositions comprising CasX and gNA gene editing pairs, for use as a medicament for the treatment of a subject having a neurologic disease, such as retinitis pigmentosa. In the foregoing, the CasX can be a CasX variant of SEQ ID NOs: 49-160, 237-239, 243-246, 251-263 or 273-281 and the gNA can be a gNA variant comprising a sequence of SEQ ID NOS: 2101 having a targeting sequence of SEQ ID NOs: SEQ ID NOs: 49-160, 237-239, 243-246, 251-263 or 273-281, or SEQ ID NOS: 382-582. In other embodiments, the disclosure provides compositions of vectors comprising or encoding the gene editing pairs of CasX and gNA for use as a medicament for the treatment of a subject having a disease, such as retinitis pigmentosa.

IX. Kits and Articles of Manufacture

In another aspect, provided herein are kits comprising the compositions of the embodiments described herein. In some embodiments, the kit comprises a CasX protein and one or a plurality of gNA of any of the embodiments of the disclosure comprising a targeting sequence complementary to a target nucleic acid of the RHO gene, an excipient and a suitable container (for example a tube, vial or plate). In other embodiments, the kit comprises a nucleic acid encoding a CasX protein and one or a plurality of gNA of any of the embodiments of the disclosure comprising a targeting sequence complementary to a target nucleic acid of the RHO gene, an excipient and a suitable container. In other embodiments, the kit comprises a vector comprising a nucleic acid encoding a CasX protein and one or a plurality of gNA of any of the embodiments of the disclosure comprising a targeting sequence complementary to a target nucleic acid of the RHO gene, an excipient and a suitable container. In still other embodiments, the kit comprises a VLP comprising a CasX protein and one or a plurality of gNA of any of the embodiments of the disclosure comprising a targeting sequence complementary to a target nucleic acid of the RHO gene an excipient and a suitable container. In still other embodiments, the kit comprises a plurality of cells edited using the Class 2 Type V Crispr systems described herein.

In some embodiments, the kit further comprises a buffer, a nuclease inhibitor, a protease inhibitor, a liposome, a therapeutic agent, a label, a label visualization reagent, or any combination of the foregoing. In some embodiments, the kit further comprises a pharmaceutically acceptable carrier, diluent or excipient.

In some embodiments, the kit comprises appropriate control compositions for gene modifying applications, and instructions for use.

In another aspect, the disclosure relates to compositions comprising a Class 2 Type V CRISPR protein and a first guide nucleic acid (gNA), wherein the gNA comprises a targeting sequence complementary to a non-target strand sequence located 1 nucleotide 3' of a protospacer adjacent motif (PAM) sequence of a RHO gene target nucleic acid sequence, wherein the RHO gene comprises one or more mutations. In one embodiment, the PAM sequence comprises a TC motif. In another embodiment, the PAM sequence comprises ATC, GTC, CTC or TTC. In another embodiment, the Class 2 Type V CRISPR protein comprises a RuvC domain. In the foregoing embodiments, the RuvC domain generates a staggered double-stranded break in the target nucleic acid sequence and the Class 2 Type V CRISPR protein does not comprise an HNH nuclease domain.

ENUMERATED EMBODIMENTS

The invention may be defined by reference to the following sets of enumerated, illustrative embodiments:

Set I

1. A CasX:gNA system comprising a CasX protein and a guide nucleic acid (gNA), wherein the gNA comprises a targeting sequence complementary to a target nucleic acid sequence comprising a rhodopsin (RHO) gene.

2. The CasX:gNA system of Set I embodiment 1, wherein the RHO gene comprises a protein coding sequence comprising a mutation.

3. The CasX:gNA system of any one of Set I embodiments 1-2, wherein the RHO gene comprises a regulatory region, optionally comprising a mutation.

4. The CasX:gNA system of any one of Set I embodiments 1 and 3, wherein the RHO gene comprises a wild-type protein coding sequence.

5. The CasX:gNA system of Set I embodiment 2, wherein the RHO gene comprising a mutation encodes a rhodopsin protein comprising a mutation compared to a wild-type rhodopsin protein sequence of SEQ ID NO:100.

6. The CasX:gNA system of any one of Set I embodiments 2 and 5, wherein the RHO gene comprising a mutation encodes a protein comprising the sequence of SEQ ID NO:101.

7. The CasX:gNA system of any one of Set I embodiments 2 and 5-6, wherein the RHO gene comprising a mutation encodes a protein comprising a P23 or P23H substitution compared to a wild-type rhodopsin protein sequence of SEQ ID NO:100.

8. The CasX:gNA system of any one of Set I embodiments 1-7, wherein the gNA is a guide RNA (gRNA).

9. The CasX:gNA system of any one of Set I embodiments 1-7, wherein the gNA is a guide DNA (gDNA).

10. The CasX:gNA system of any one of Set I embodiments 1-7, wherein the gNA is a chimera comprising DNA and RNA.

11. The CasX:gNA system of any one of Set I embodiments 1-10, wherein the gNA is a single-molecule gNA (sgNA).

12. The CasX:gNA system of any one of Set I embodiments 1-10, wherein the gNA is a dual-molecule gNA (dgNA).

13. The CasX:gNA system of any one of Set I embodiments 1-12, wherein the gNA comprises a targeting sequence consisting of 14, 15, 16, 17, 18, 19, 20, 21, 22, 23, 24, 25, 26, 27, 28, 29, or 30 consecutive nucleotides.

14. The CasX:gNA system of Set I embodiment 13, wherein the targeting sequence of the gNA consists of 20 nucleotides.

15. The CasX:gNA system of any one of Set I embodiments 7-14, wherein the targeting sequence of the gNA is complementary to a sequence comprising the P23H substitution.

16. The CasX:gNA system of any one of Set I embodiments 1-15, wherein the targeting sequence of the gNA comprises a sequence of AAGUGGCUGCGUACCACACC (SEQ ID NO: 382).

17. The CasX:gNA system of any one of Set I embodiments 1-16, wherein the targeting sequence of the gNA consists of a sequence of AAGUGGCUGCGUACCACACC (SEQ ID NO: 382).

18. The CasX:gNA system of any one of Set I embodiments 1-16, wherein the targeting sequence of the gNA consists of a sequence of AAGUGGCUGCGUACCACAC (SEQ ID NO: 27275).

19. The CasX:gNA system of any one of Set I embodiments 1-16, wherein the targeting sequence of the gNA consists of a sequence of AAGUGGCUGCGUACCACA (SEQ ID NO: 27276).

20. The CasX:gNA system of any one of Set I embodiments 1-16, wherein the targeting sequence of the gNA consists of a sequence of AAGUGGCUGCGUACCAC (SEQ ID NO: 27277).

21. The CasX:gNA system of any one of Set I embodiments 1-16, wherein the targeting sequence of the gNA consists of a sequence of AAGUGGCUGCGUACCA (SEQ ID NO: 27278).

22. The CasX:gNA system of any one of Set I embodiments 1-16, wherein the targeting sequence of the gNA consists of a sequence of AAGUGGCUGCGUACC (SEQ ID NO: 27279).

23. The CasX:gNA system of any one Set I embodiments 1-22, further comprising a second gNA, wherein the second gNA has a targeting sequence complementary a different or overlapping portion of the target nucleic acid sequence compared to the targeting sequence of the gNA of any one of the preceding Set I embodiments.

24. The CasX:gNA system of any one of Set I embodiments 1-23, wherein the gNA has a scaffold comprising a sequence having at least about 50%, at least about 60%, at least about 70%, at least about 80%, at least about 90%, at least about 95%, at least about 96%, at least about 97%, at least about 98%, at least about 99%, or 100% sequence identity to a sequence selected from the group consisting of sequences set forth in Table 1 and Table 2.

25. The CasX:gNA system of any one of Set I embodiments 1-24, wherein the gNA has a scaffold comprising a sequence having at least one nucleotide modification relative to a reference gNA sequence having a sequence of any one of SEQ ID NOS: 4-16 of Table 1.

26. The CasX:gNA system of Set I embodiment 25, wherein the at least one modification of the reference gNA comprises at least one substitution, deletion, or substitution of a nucleotide of the gNA sequence.

27. The CasX:gNA system of any one Set I embodiments 1-26, wherein the gNA is chemically modified.

28. The CasX:gNA system of any one Set I embodiments 1-27, wherein the CasX protein comprises a reference CasX protein having a sequence of any one of SEQ ID NOS: 1-3 a CasX variant protein having a sequence selected from those presented in Table 3, or a sequence having at least about 50%, at least about 60%, at least about 70%, at least about 80%, at least about 90%, or at least about 95%, or at least about 96%, or at least about 97%, or at least about 98%, or at least about 99% sequence identity to a sequence presented in Table 3.

29. The CasX:gNA system of Set I embodiment 28, wherein the CasX protein has binding affinity for a protospacer adjacent motif (PAM) sequence selected from the group consisting of TTC, ATC, GTC, and CTC.

30. The CasX:gNA system of Set I embodiment 28 or Set I embodiment 29, wherein the CasX variant protein comprises at least one amino acid modification relative to a reference CasX protein having a sequence of any one of SEQ ID NOS:1-3.

31. The CasX:gNA system of Set I embodiment 30, wherein the at least one amino acid modification comprises an amino acid substitution, deletion, or substitution in a domain of the CasX variant protein relative to the reference CasX protein.

32. The CasX:gNA system of Set I embodiment 31, wherein the domain is selected from the group consisting of a non-target strand binding (NTSB) domain, a target strand loading (TSL) domain, a helical I domain, a helical II domain, an oligonucleotide binding domain (OBD), and a RuvC DNA cleavage domain.

33. The CasX:gNA system of any one of Set I embodiments 28-32, wherein the CasX protein is fused to one or more nuclear localization signals (NLS).

34. The CasX:gNA system of Set I embodiment 33, wherein the one or more NLS are selected from the group of sequences consisting of PKKKRKV (SEQ ID NO: 176), KRPAATKKAGQAKKKK (SEQ ID NO: 177), PAAKRVKLD (SEQ ID NO: 178), RQRRNELKRSP (SEQ ID NO: 179), NQSSNFGPMKGGNFGGRSSGPYGGGGQYFAKPRNQGGY (SEQ ID NO: 180), RMRIZFKNKGKDTAELRRRRVEVSVELRKAKKDEQILKRRNV (SEQ ID NO: 181), VSRKRPRP (SEQ ID NO: 182), PPKKARED (SEQ ID NO: 183), PQPKKKPL (SEQ ID NO: 184), SALIKKKKKMAP (SEQ ID NO: 185), DRLRR (SEQ ID NO: 186), PKQKKRK (SEQ ID NO: 187), RKLKKKIKKL (SEQ ID NO: 188), REKKKFLKRR (SEQ ID NO: 189), KRKGDEVDGVDEVAKKKSKK (SEQ ID NO: 190), RKCLQAGMNLEARKTKK (SEQ ID NO: 191), PRPRKIPR (SEQ ID NO: 192), PPRKKRTVV (SEQ ID NO: 193), NLSKKKKRKREK (SEQ ID NO: 194), RRPSRPFRKP (SEQ ID NO: 195), KRPRSPSS (SEQ ID NO: 196), KRGINDRNFWRGENERKTR (SEQ ID NO: 197), PRPPKMARYDN (SEQ ID NO: 198), KRSFSKAF (SEQ ID NO: 199), KLKIKRPVK (SEQ ID NO: 200), PKTRRRPRRSQRKRPPT (SEQ ID NO: 202), RRKKRRPRRKKRR (SEQ ID NO: 205), PKKKSRKPKKKSRK (SEQ ID NO: 206), HKKKHPDASVNFSEFSK (SEQ ID NO: 207), QRPGPYDRPQRPGPYDRP (SEQ ID NO: 208), LSPSLSPLLSPSLSPL (SEQ ID NO: 209), RGKGGKGLGKGGAKRHRK (SEQ ID NO: 210), PKRGRGRPKRGRGR (SEQ ID NO: 322), and MSRRRKANPTKLSENAKKLAKEVEN (SEQ ID NO: 203).

35. The CasX:gNA system of Set I embodiment 33 or Set I embodiment 34, wherein the one or more NLS are fused at the C-terminus of the CasX protein.

36. The CasX:gNA system of Set I embodiment 33 or Set I embodiment 34, wherein the one or more NLS are fused at the N-terminus of the CasX protein.

37. The CasX:gNA system of Set I embodiment 33 or Set I embodiment 34, wherein the one or more NLS are fused at the N-terminus and C-terminus of the CasX protein.

38. The CasX:gNA system of any one of Set I embodiments 28-37, wherein the CasX variant protein exhibits one or more improved characteristics as compared to a reference CasX protein.

39. The CasX:gNA system of Set I embodiment 38, wherein the one or more improved characteristics are selected from the group consisting of improved folding of the CasX protein, improved binding affinity of the CasX protein to the guide RNA, improved RNP complex formation, improved binding affinity to the target nucleic acid sequence, altered binding affinity to one or more PAM sequences, improved unwinding of the target nucleic acid sequence, increased activity, increased target nucleic acid sequence cleavage rate, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved CasX protein stability, improved protein:guide RNA complex stability, improved protein solubility, improved protein:guide RNA complex solubility, improved protein yield, improved protein expression, and improved fusion characteristics.

40. The CasX:gNA system of Set I embodiment 38 or Set I embodiment 39, wherein the improved characteristic of the CasX variant protein is at least about 1.1 to about 100,000-fold improved relative to the reference CasX protein of SEQ ID NO: 1, SEQ ID NO: 2, or SEQ ID NO: 3.

41. The CasX:gNA system of Set I embodiment 38 or Set I embodiment 39, wherein the improved characteristic of the CasX variant protein is at least about 10-fold, at least about 100-fold, at least about 1,000-fold, or at least about 10,000-fold improved relative to the reference CasX protein of SEQ ID NO: 1. SEQ ID NO: 2, or SEQ ID NO: 3.

42. The CasX:gNA system of any one of Set I embodiments 39-41, wherein the improved characteristic is improved binding affinity to the target nucleic acid sequence.

43. The CasX:gNA system of any one of Set I embodiments 39-41, wherein the improved characteristic is increased target nucleic acid sequence cleavage rate.

44. The CasX:gNA system of any one of Set I embodiments 39-41, wherein the improved characteristic is improved CasX protein stability.

45. The CasX:gNA system of any one of Set I embodiments 39-41, wherein the improved characteristic is increased binding affinity to one or more PAM sequences wherein the one or more PAM sequences are selected from the group consisting of TTC, ATC, GTC, and CTC.

46. The CasX:gNA system of any one of Set I embodiments 28-45, wherein the CasX variant protein and the gNA are associated together in a ribonucleoprotein (RNP) complex.

47. The CasX:gNA system of any one of Set I embodiments 28-46, wherein the CasX variant protein comprises a nuclease domain having nickase activity.

48. The CasX:gNA system of any one of Set I embodiments 28-46, wherein the CasX variant protein comprises a nuclease domain having double-stranded cleavage activity.

49. The CasX:gNA system of any one of Set I embodiments 1-37, wherein the CasX protein is a catalytically inactive CasX (dCasX) protein, and wherein the dCasX and the gNA retain the ability to bind to the target nucleic acid sequence.

50. The CasX:gNA system of Set I embodiment 49, wherein the dCasX comprises a mutation at residues:
a. D672, E769, and/or D935 corresponding to the CasX protein of SEQ ID NO:1, or
b. D659, E756 and/or D922 corresponding to the CasX protein of SEQ ID NO: 2.

51. The CasX:gNA system of Set I embodiment 50, wherein the mutation is a substitution of alanine for the residue.

52. The CasX:gNA system of any one of Set I embodiments 1-51, further comprising a donor template nucleic acid.

53. The CasX:gNA system of Set I embodiment 52, wherein the donor template comprises a nucleic acid comprising at least a portion of a RHO gene, wherein the RHO gene portion is selected from the group consisting of a RHO exon, a RHO intron, and a RHO intron-exon junction.

54. The CasX:gNA system of Set I embodiment 52 or Set I embodiment 53, wherein the donor template ranges in size from 10-10,000 nucleotides.

55. The CasX:gNA system of any one of Set I embodiments 52-54, wherein the donor template is a single-stranded DNA template or a single stranded RNA template.

56. The CasX:gNA system of any one of Set I embodiments 52-54, wherein the donor template is a double-stranded DNA template.

57. The CasX:gNA system of any one of Set I embodiments 52-56, wherein the donor template comprises at least a portion of the sequence that encodes SEQ ID NO: 100.

58. The CasX:gNA system of Set I embodiment 57, wherein the donor template encodes a protein comprising P23 of SEQ ID NO:100.

59. A nucleic acid comprising a sequence that encodes components of the CasX:gNA system of any one of Set I embodiments 1-51.

60. The nucleic acid of Set I embodiment 59, wherein the nucleic acid encoding the CasX protein or the gNA is codon optimized for expression in a eukaryotic cell.

61. A vector comprising the nucleic acid of Set I embodiment 59 or Set I embodiment 60.

62. The vector of Set I embodiment 61, wherein the vector further comprises a promoter.

63. A vector comprising a donor template for use in a CasX:gNA system, wherein the donor template comprises a nucleic acid comprising at least a portion of a RHO gene, and wherein the RHO gene portion is selected from the group consisting of a RHO exon, a RHO intron, and a RHO intron-exon junction.

64. The vector of Set I embodiment 63, wherein the donor template comprises a sequence that encodes at least a portion of the sequence that encodes SEQ ID NO: 100.

65. The vector of Set I embodiment 63 or Set I embodiment 64, further comprising the nucleic acid of Set I embodiment 59 or Set I embodiment 60.

66. The vector of any one of Set I embodiments 63-65, wherein the vector is selected from the group consisting of a retroviral vector, a lentiviral vector, an adenoviral vector, an adeno-associated viral (AAV) vector, a herpes simplex virus (HSV) vector, a virus-like particle (VLP), a plasmid, a minicircle, a nanoplasmid, and an RNA vector.

67. The vector of Set I embodiment 66, wherein the vector is an AAV vector.

68. The vector of Set I embodiment 67, wherein the AAV vector is selected from AAV1, AAV2, AAV3, AAV4, AAV5, AAV6, AAV7, AAV8, AAV9, AAV10, AAV-Rh74, or AAVRh10.

69. The vector of Set I embodiment 66, wherein the vector is a retroviral vector.

70. The vector of Set I embodiment 66, wherein the vector encoding the VLP comprises one or more nucleic acids encoding a gag polyprotein, the CasX protein of any one of Set I embodiments 28-48, and the gNA of any one of Set I embodiments 8-27.

71. A method of modifying a RHO target nucleic acid sequence comprising a RHO gene in a cell, the method comprising contacting the RHO target nucleic acid sequence with a CasX protein and a guide nucleic acid (gNA) comprising a targeting sequence, wherein said contacting comprises introducing into the cell:
a. the CasX protein of any one of Set I embodiments 28-48 or a nucleic acid encoding the CasX protein; and
b. the gNA of any one of Set I embodiments 1-27, or a nucleic acid encoding the gNA, wherein said contacting results in modification of the RHO target nucleic acid sequence by the CasX protein.

72. The method of Set I embodiment 71, wherein the CasX protein and the gNA are associated together in a RNP complex.

73. The method of Set I embodiment 71 or Set I embodiment 72, further comprising a second gNA or a nucleic acid encoding the second gNA, wherein the second gNA has a targeting sequence complementary to a different or overlapping portion of the RHO target nucleic acid sequence.

74. The method of any one of Set I embodiments 71-73, wherein the RHO regulatory region comprises a mutation.

75. The method of any one of Set I embodiments 71-74, wherein the RHO gene comprise a mutation and wherein the modifying comprises introducing a single-stranded break in the RHO target nucleic acid sequence.

76. The method of any one of Set I embodiments 71-74, wherein the RHO gene comprises a mutation and wherein the modifying comprises introducing a double-stranded break in the RHO target nucleic acid sequence.

77. The method of Set I embodiment 75 or Set I embodiment 76, wherein the mutation encodes a P23 substitution or a P23H substitution as compared to the wild-type rhodopsin protein sequence.

78. The method of Set I embodiment 77, wherein the modifying of the RHO target nucleic acid sequence results in correction of the P23H substitution.

79. The method of any one of Set I embodiments 71-78, wherein the modifying of the RHO target nucleic acid sequence results in the RHO target nucleic acid sequence encoding the wild-type rhodopsin protein sequence of SEQ ID NO:100.

80. The method of any one of Set I embodiments 71-79, wherein the modifying of the RHO target nucleic acid sequence occurs in vitro.

81. The method of any one of Set I embodiments 71-80, wherein the modifying of the RHO target nucleic acid sequence occurs in vivo.

82. The method of any one of Set I embodiments 71-81, wherein the cell is a eukaryotic cell.

83. The method of Set I embodiment 82, wherein the eukaryotic cell is selected from the group consisting of a 84. The method of Set I embodiment 83, wherein the eukaryotic cell is a human cell.

85. The method of any one of Set I embodiments 71-84, wherein the cell is a photoreceptor cell.

86. The method of any one of Set I embodiments 71-84, wherein the cell is a retinal progenitor cell, 87. The method of any one of Set I embodiments 71-84, wherein the cell is an induced pluripotent stem cell (iPSC).

88. The method of any one of Set I embodiment 71-87, wherein the method further comprises contacting the RHO target nucleic acid sequence with a donor template complementary to at least a portion of a RHO gene and/or a RHO regulatory region comprising one or more mutations, wherein the donor template is inserted into the RHO target nucleic acid sequence to correct the one or more mutations or is inserted to replace the target nucleic acid sequence.

89. The method of Set I embodiment 88, wherein the donor template ranges in size from 10-10,000 nucleotides.

90. The method of Set I embodiment 88, wherein the donor template ranges in size from 100-1,000 nucleotides.

91. The method of any one of Set I embodiments 88-90, wherein the donor template is a single-stranded DNA template or a single stranded RNA template.

92. The method of any one of Set I embodiments 88-90, wherein the donor template is a double-stranded DNA template.

93. The method of any one of Set I embodiments 88-92, wherein the donor template is inserted by homology directed repair (HDR).

94. The method of any one of Set I embodiments 82-93, wherein the method comprises contacting the eukaryotic cell with a vector encoding the CasX protein and the gNA, and optionally further comprising the donor template.

95. The method of Set I embodiment 94, wherein the vector is an Adeno-Associated Viral (AAV) vector.

96. The method of Set I embodiment 95, wherein the AAV is AAV1, AAV2, AAV3, AAV4, AAV5, AAV6, AAV7, AAV8, AAV9, AAV10, AAV-Rh74, or AAVRh10.

97. The method of Set I embodiment 94, wherein the vector is a lentiviral vector.

98. The method of any one of Set I embodiments 82-93, wherein the method comprises contacting the eukaryotic cell with a VLP vector, wherein the VLP vector comprises the RNP of Set I embodiment 46.

99. The method of any one of Set I embodiments 94-98, wherein the vector is administered to a subject at a therapeutically effective dose.

100. The method of Set I embodiment 99, wherein the subject is selected from the group consisting of mouse, rat, dog, pig, non-human primate, and human.

101. The method of Set I embodiment 100, wherein the subject is a human.

102. The method of any one of Set I embodiments 99-101, wherein the vector is administered at a dose of at least about $1\times10^5$ vector genomes (vg), or at least about $1\times10^6$ vg, or at least about $1\times10^7$ vg, or at least about $1\times10^8$ vg, or at least about $1\times10^9$ vg, or at least about $1\times10^{10}$ vg, or at least about $1\times10^{11}$ vg, or at least about $1\times10^{12}$ vg.

103. The method of any one of Set I embodiments 99-102, wherein the vector is administered by a route of administration selected from the group consisting of intraocular, intravitreal, and sub-retinal routes.

104. The method of any one of Set I embodiments 71-103, comprising further contacting the target nucleic acid sequence with an additional CRISPR protein, or a polynucleotide encoding the additional CRISPR protein.

105. The method of Set I embodiment 104, wherein the additional CRISPR protein is a CasX protein having a sequence different from the CasX of any one of Set I embodiments 28-51.

106. The method of Set I embodiment 104, wherein the additional CRISPR protein is not a CasX protein.

107. A method of modifying a RHO target nucleic acid sequence of a cell, wherein the nucleic acid encodes a protein having the sequence of SEQ ID NO: 101, the method comprising contacting said cell with: a) CasX:gNA system of any one of Set I embodiments 1-58: b) the nucleic acid of Set I embodiment 59 or Set I embodiment 60; c) the vector as in any one of Set I embodiments 94-103; or combinations thereof.

108. The method of Set I embodiment 107, wherein the cell is modified such that expression of the protein of SEQ ID: 101 is reduced by at least about 50%, at least about 60%, at least about 70%, at least about 80%, at least about 90%, or at least about 95% in comparison to a cell that has not been modified.

109. The method of Set I embodiment 107 or Set I embodiment 108, wherein the cell has been modified such that the cell does not express a detectable level of the protein of SEQ ID NO:101.

110. The method of Set I embodiment 107, wherein the cell has been modified such that it expresses RHO protein having the sequence of SEQ ID NO:100.

111. A population of cells modified by the method of Set I embodiment 107 or Set I embodiment 108, wherein the cells have been modified such that at least 70%, at least 75%, at least 80%, at least 85%, at least 90%, or at least 95% of the modified cells do not express a detectable level of the protein of SEQ ID NO:101.

112. A population of cells modified by the method of Set I embodiment 110, wherein the cells have been modified such that at least 70%, at least 75%, at least 80%, at least 85%, at least 90%, or at least 95% of the modified cells express a detectable level of RHO protein having the sequence of SEQ ID NO:100.

113. The population of cells of Set I embodiment 111 or Set I embodiment 112, wherein the cell is a non-primate mammalian cell, a non-human primate cell, or a human cell.

114. The population of cells of any one of Set I embodiments 111-113, wherein the cell is selected from the group consisting of a photoreceptor cell, a retinal progenitor cell, or a pluripotent stem cell (iPSC).

115. A method of treating a RHO-related disorder in a subject in need thereof, comprising modifying in a cell of the subject a RHO gene, wherein the RHO gene has one or more mutations, the modifying comprising either contacting said cell with;
  a. CasX:gNA system of any one of Set I embodiments 1-58;
  b. the nucleic acid of Set I embodiment 59 or Set I embodiment 60.
  c. the vector of any one of Set I embodiments 61-70: or
  d. combinations thereof.

116. The method of Set I embodiment 115, further comprising a second gNA or a nucleic acid encoding the second gNA, wherein the second gNA has a targeting sequence complementary to a different or overlapping portion of the target nucleic acid sequence.

117. The method of Set I embodiment 115 or Set I embodiment 116, wherein the modifying corrects the one or more mutations, or wherein expression of the RHO having the one or more mutations is inhibited or suppressed.

118. The method of any one of Set I embodiments 115-117, wherein the RHO-related disorder is retinitis pigmentosa.

119. The method of any one of Set I embodiments 115-118, wherein the method comprises contacting the cell with the vector.

120. The method of Set I embodiment 119, wherein the vector is an Adeno-Associated Viral (AAV) vector.

121. The method of Set I embodiment 120, wherein the AAV is AAV1, AAV2, AAV3, AAV4, AAV5, AAV6, AAV7, AAV8, AAV9, AAV10, AAV-Rh74, or AAVRh10.

122. The method of Set I embodiment 120, wherein the vector is a lentiviral vector.

123. The method of any one of Set I embodiments 115-119, wherein the method comprises contacting the eukaryotic cell with a VLP vector, wherein the VLP vector comprises the RNP of Set I embodiment 46.

124. The method of any one of Set I embodiments 115-123, wherein the vector is administered to a subject at a therapeutically effective dose.

125. The method of Set I embodiment 124, wherein the subject is selected from the group consisting of mouse, rat, dog, pig, non-human primate, and human.

126. The method of Set I embodiment 126, wherein the subject is a human.

127. The method of any one of Set I embodiments 115-126, wherein the vector is administered to the subject at a dose of at least about $1\times10^5$ vector genomes (vg), or at least about $1\times10^6$ vg, or at least about $1\times10^7$ vg, or at least about $1\times10^8$ vg, or at least about $1\times10^9$ vg, or at least about $1\times10^{10}$ vg, or at least about $1\times10^{11}$ vg, or at least about $1\times10^{12}$ vg.

128. The method of any one of Set I embodiments 115-127, wherein the vector is administered by a route of administration selected from the group consisting of intraocular, intravitreal, and sub-retinal routes.

129. The method of any one of Set I embodiments 115-128, comprising further contacting the target nucleic acid sequence with an additional CRISPR protein, or a polynucleotide encoding the additional CRISPR protein.

130. The method of Set I embodiment 129, wherein the additional CRISPR protein is a CasX protein having a sequence different from the CasX of any of the preceding Set I embodiments.

131. The method of Set I embodiment 130, wherein the additional CRISPR protein is not a CasX protein.

132. The method of any one of Set I embodiments 115-131, wherein the method results in improvement in at least one clinically-relevant endpoint selected from the group consisting of change in the mean retinal sensitivity of the central 2° of the ocular fundus, visual acuity, contrast sensitivity, multiluminance mobility test (MLMT), full-field light sensitivity threshold (FST), health-related quality of life using a questionnaire on visual function, duration of response, and time-to-treatment failure.

133. The method of any one of Set I embodiments 115-132, wherein the method results in improvement in at least one clinically-relevant endpoint selected from the group consisting of change in the mean retinal sensitivity of the central 2° of the ocular fundus, visual acuity, contrast sensitivity, multiluminance mobility test (MLMT), full-field light sensitivity threshold (FST), health-related quality of life using a questionnaire on visual function, duration of response, and time-to-treatment failure.

Set II

1. A composition comprising a Class 2 Type V CRISPR protein and a first guide nucleic acid (gNA), wherein the gNA comprises a targeting sequence complementary to a rhodopsin (RHO) gene target nucleic acid sequence, w % herein the RHO gene comprises one or more mutations.

2. The composition of Set II embodiment 1, wherein the RHO gene comprises one or more mutations in a region selected from the group consisting of;
   a. a RHO intron;
   b. a RHO exon;
   c. a RHO intron-exon junction;
   d. a RHO regulatory element; and
   e. an intergenic region.

3. The composition of any one of Set II embodiment 1 or Set II embodiment 2, wherein the mutation is an insertion, deletion, substitution, duplication, or inversion of one or more nucleotides as compared to the wild-type RHO gene sequence.

4. The composition of any one of Set II embodiments 1-3, wherein the mutation is a gain of function mutation.

5. The composition of any one of Set II embodiments 1-3, wherein the RHO gene comprises a mutation set forth in Table 4A.

6. The composition of any one of Set II embodiments 1-5, wherein the RHO gene comprising a mutation encodes a protein comprising a P23 or P23H substitution compared to a wild-type rhodopsin protein sequence of SEQ ID NO:100.

7. The composition of any one of Set II embodiments 1-6, wherein the RHO gene encodes a non-functional rhodopsin protein.

8. The composition of any one of Set II embodiments 1-6, wherein the gNA is a guide RNA (gRNA).

9. The composition of any one of Set II embodiments 1-6, wherein the gNA is a guide DNA (gDNA).

10. The composition of any one of Set II embodiments 1-6, wherein the gNA is a chimera comprising DNA and RNA.

11. The composition of any one of Set II embodiments 1-10, wherein the gNA is a single-molecule gNA (sgNA).

12. The composition of any one of Set II embodiments 1-10, wherein the gNA is a dual-molecule gNA (dgNA).

13. The composition of any one of Set I1 embodiments 1-12, wherein the targeting sequence of the gNA comprises a sequence selected from the group consisting of the sequences of SEQ ID NOS:328-346, 367-376, 382-2100 and 2286-27274, or a sequence having at least about 65%, at least about 75%, at least about 85%, or at least about 95% identity thereto.

14. The composition of any one of Set II embodiments 1-12, wherein the targeting sequence of the gNA comprises a sequence selected from the group consisting of the sequences of SEQ ID NOs:328-346, 367-376, 382-2100 and 2286-27274.

15. The composition of any one of Set I1 embodiments 1-12, wherein the targeting sequence of the gNA comprises a sequence of SEQ ID NOs: 328-346, 367-376, 382-2100 and 2286-27274 with a single nucleotide removed from the 3' end of the sequence.

16. The composition of any one of Set II embodiments 1-12, wherein the targeting sequence of the gNA comprises a sequence of SEQ ID NOs: 2328-346, 367-376, 382-2100 and 2286-27274 with two nucleotides removed from the 3' end of the sequence.

17. The composition of any one of Set II embodiments 1-12, wherein the targeting sequence of the gNA comprises a sequence of SEQ ID NOs: 328-346, 367-376, 382-2100 and 2286-27274 with three nucleotides removed from the 3' end of the sequence.

18. The composition of any one of Set II embodiments 1-12, wherein the targeting sequence of the gNA comprises a sequence of SEQ ID NOs: 328-346, 367-376, 382-2100 and 2286-27274 with four nucleotides removed from the 3' end of the sequence.

19. The composition of any one of Set II embodiments 1-12, wherein the targeting sequence of the gNA comprises a sequence of SEQ ID NOs: 328-346, 367-376, 382-2100 and 2286-27274 with five nucleotides removed from the 3' end of the sequence.

20. The composition of any one of Set II embodiments 1-19, wherein the targeting sequence of the gNA comprises a sequence having one or more single nucleotide polymorphisms (SNP) relative to a sequence of SEQ ID NOS: 328-346, 367-376, 382-2100 and 2286-27274.

21. The composition of any one of Set II embodiments 1-19, wherein the targeting sequence of the gNA is complementary to a sequence of a RHO exon.

22. The composition of any one of Set II embodiments 1-21, wherein the targeting sequence of the gNA is complementary to a sequence of RHO exon 1.

23. The composition of Set II embodiment 21 or Set II embodiment 22, wherein the targeting sequence of the gNA is complementary to a target nucleic acid sequence encoding the P23H substitution.

24. The CasX:gNA system of any one of Set II embodiments 21-23, wherein the targeting sequence of the gNA comprises a sequence of AAGUGGCUGCGUACCACACC (SEQ ID NO: 382).

25. The CasX:gNA system of any one of Set II embodiments 21-23, wherein the targeting sequence of the gNA consists of a sequence of AAGUGGCUGCGUACCACACC (SEQ ID NO: 382).

26. The CasX:gNA system of any one of Set II embodiments 21-23, wherein the targeting sequence of the gNA consists of a sequence of AAGUGGCUGCGUACCACAC (SEQ ID NO: 27275).

27. The CasX:gNA system of any one of Set II embodiments 21-23, wherein the targeting sequence of the gNA consists of a sequence of AAGUGGCUGCGUACCACA (SEQ ID NO: 27276).

28. The CasX:gNA system of any one of Set II embodiments 21-23, wherein the targeting sequence of the gNA consists of a sequence of AAGUGGCUGCGUACCAC (SEQ ID NO: 27277).

29. The CasX:gNA system of any one of Set II embodiments 21-23, wherein the targeting sequence of the gNA consists of a sequence of AAGUGGCUGCGUACCA (SEQ ID NO: 27278).

30. The CasX:gNA system of any one of Set II embodiments 21-23, wherein the targeting sequence of the gNA consists of a sequence of AAGUGGCUGCGUACC (SEQ ID NO: 27279).

31. The composition of any one of Set II embodiments 1-19, wherein the targeting sequence of the gNA is complementary to a sequence of a RHO intron.

32. The composition of any one of Set I1 embodiments 1-19, wherein the targeting sequence of the gNA is complementary to a sequence of a RHO intron-exon junction.

33. The composition of any one of Set II embodiments 1-19, wherein the targeting sequence of the gNA is complementary to a sequence of a RHO regulatory element.

34. The composition of any one of Set II embodiments 1-19, wherein the targeting sequence of the gNA is complementary to a sequence comprising one or more single nucleotide polymorphisms (SNPs) of the RHO gene.

35. The composition of any one of Set I1 embodiments 1-19, wherein the targeting sequence of the gNA is complementary to a sequence of an intergenic region of the RHO gene.

36. The composition of any one of Set II embodiments 1-35, further comprising a second gNA, wherein the second gNA has a targeting sequence complementary to a different or overlapping portion of the RHO target nucleic acid compared to the targeting sequence of the first gNA.

37. The composition of Set II embodiment 36, wherein the second gNA has a targeting sequence complementary to the same exon targeted by the first gNA.

38. The composition of Set II embodiment 36, wherein the second gNA has a targeting sequence complementary to a different exon targeted by the first gNA.

39. The composition of Set II embodiment 36, wherein the second gNA has a targeting sequence complementary to an intron 3' to the exon targeted by the first gNA.

40. The composition of any one of Set II embodiments 1-39, wherein the first or second gNA has a scaffold comprising a sequence having at least about 50%, at least about 60%, at least about 70%, at least about 80%, at least about 90%, at least about 95%, at least about 96%, at least about 97%, at least about 98%, at least about 99%, or 100% sequence identity to a sequence selected from the group consisting of SEQ ID NOS: 2201-2285.

41. The composition of any one of Set II embodiments 1-39, wherein the first or second gNA has a scaffold comprising a sequence selected from the group consisting of SEQ ID NOS: 2201-2285.

42. The composition of any one of Set II embodiments 1-39, wherein the first or second gNA scaffold comprises a sequence having at least one modification relative to a reference gNA sequence selected from the group consisting of SEQ ID NOS: 4-16.

43. The composition of Set II embodiment 42, wherein the at least one modification of the reference gNA comprises at least one substitution, deletion, or substitution of a nucleotide of the reference gNA sequence.

44. The composition of any one of Set II embodiments 1-43, wherein the first or second gNA is chemically modified.

45. The composition of any one of Set II embodiments 1-44, wherein the Class 2 Type V CRISPR protein is a reference CasX protein having a sequence of any one of SEQ ID NOS: 1-3, a CasX variant protein having a sequence of SEQ ID NOs: 49-160, 237-239, 243-246, 251-263 or 273-281, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto.

46. The composition of any one of Set II embodiments 1-44, wherein the Class 2 Type V CRISPR protein is a CasX variant protein having a sequence of SEQ ID NOs: 49-160, 237-239, 243-246, 251-263 or 273-281

47. The composition of Set II embodiment 45, wherein the CasX variant protein comprises at least one modification relative to a reference CasX protein having a sequence selected from SEQ ID NOS:1-3.

48. The composition of Set II embodiment 47, wherein the at least one modification comprises at least one amino acid substitution, deletion, or substitution in a domain of the CasX variant protein relative to the reference CasX protein.

49. The composition of Set II embodiment 48, w-herein the domain is selected from the group consisting of a non-target strand binding (NTSB) domain, a target strand loading (TSL) domain, a helical I domain, a helical II domain, an oligonucleotide binding domain (OBD), and a RuvC DNA cleavage domain.

50. The composition of any one of Set II embodiments 45-49, wherein the CasX protein further comprises one or more nuclear localization signals (NLS).

51. The composition of Set II embodiment 50, wherein the one or more NLS are selected from the group of sequences consisting of SEQ ID NOS: 176-213.

52. The composition of Set II embodiment 50 or Set II embodiment 51, wherein the one or more NLS are expressed at or near the C-terminus of the CasX protein.

53. The composition of Set II embodiment 50 or Set II embodiment 51, wherein the one or more NLS are expressed at or near the N-terminus of the CasX protein.

54. The composition of Set II embodiment 50 or Set II embodiment 51, comprising one or more NLS located at or near the N-terminus and at or near the C-terminus of the CasX protein.

55. The composition of any one of Set II embodiments 45-54, wherein the Class 2 Type V CRISPR protein is capable of forming a ribonuclear protein complex (RNP) with the gNA.

56. The composition of Set II embodiment 55, wherein an RNP comprising the CasX variant protein and the gNA exhibit at least one or more improved characteristics as compared to an RNP comprising the reference CasX protein of SEQ ID NO: 1, SEQ ID NO: 2, or SEQ ID NO: 3 and a gNA comprising a sequence of any one of SEQ ID NOS: 4-16.

57. The composition of Set II embodiment 56, wherein the improved characteristic is selected from one or more of the group consisting of improved folding of the CasX variant; improved binding affinity to a guide nucleic acid (gNA); improved binding affinity to a target DNA; improved ability to utilize a greater spectrum of one or more PAM sequences, including ATC, CTC, GTC, or TTC, in the editing of target DNA; improved unwinding of the target DNA: increased editing activity; improved editing efficiency; improved editing specificity; increased nuclease activity: increased target strand loading for double strand cleavage; decreased target strand loading for single strand nicking; decreased off-target cleavage; improved binding of non-target DNA strand; improved protein stability; improved protein solubility; improved protein:gNA complex (RNP) stability; improved protein:gNA complex solubility; improved protein yield; improved protein expression: and improved fusion characteristics.

58. The composition of Set II embodiment 56 or Set II embodiment 57, wherein the improved characteristic of the RNP of the CasX variant protein and the gNA variant is at least about 1.1 to about 100-fold or more improved relative to the RNP of the reference CasX protein of SEQ ID NO: 1, SEQ ID NO: 2, or SEQ ID NO: 3 and the gNA comprising a sequence of any one of SEQ ID NOS: 4-16.

59. The composition of Set II embodiment 56 or Set II embodiment 57, wherein the improved characteristic of the CasX variant protein is at least about 1.1, at least about 2, at least about 10, at least about 100-fold or more improved relative to the reference CasX protein of SEQ ID NO: 1, SEQ ID NO: 2, or SEQ ID NO: 3 and the gNA comprising a sequence of any one of SEQ ID NOS: 4-16.

60. The composition of any one of Set II embodiments 56-59, wherein the improved characteristic comprises editing efficiency, and the RNP of the CasX variant protein and the gNA variant comprises a 1.1 to I00-fold improvement in editing efficiency compared to the RNP of the reference CasX protein of SEQ ID NO: 2 and the gNA of any one of SEQ ID NOS: 4-16.

61. The composition of any one of Set II embodiments 56-60, wherein the RNP comprising the CasX variant and the gNA variant exhibits greater editing efficiency and/or binding of a target sequence in the target nucleic acid when any one of the PAM sequences TTC, ATC, GTC, or CTC is located 1 nucleotide 5' to the non-target strand sequence having identity with the targeting sequence of the gNA in a cellular assay system compared to the editing efficiency and/or binding of an RNP comprising a reference CasX protein and a reference gNA in a comparable assay system.

62. The composition of Set II embodiment 61, wherein the PAM sequence is TTC.

63. The composition of Set II embodiment 62, wherein the targeting sequence of the gNA comprises a sequence selected from the group consisting of SEQ ID NOs: 370-371, 373-376, and 19918-27274.

64. The composition of Set II embodiment 61, wherein the PAM sequence is ATC

65. The composition of Set II embodiment 64, wherein the targeting sequence of the gNA comprises a sequence selected from the group consisting of SEQ ID NOs: 583-2100, and 2286-5554.

66. The composition of Set II embodiment 61, wherein the PAM sequence is CTC.

67. The composition of Set II embodiment 66, wherein the targeting sequence of the gNA comprises a sequence selected from the group consisting of SEQ ID NOs: 367-369, 372, and 10487-19917.

68. The composition of Set II embodiment 61, wherein the PAM sequence is GTC.

69. The composition of Set II embodiment 68, wherein the targeting sequence of the gNA comprises a sequence selected from the group consisting of SEQ ID NOs: 5555-10486.

70. The composition of any one of Set II embodiments 61-69, wherein the increased binding affinity for the one or more PAM sequences is at least 1.5-fold greater compared to the binding affinity of any one of the reference CasX proteins of SEQ ID NOS: 1-3 for the PAM sequences.

71. The composition of any one of Set II embodiments 56-70, wherein the RNP has at least a 5%, at least a 10%, at least a 15%, or at least a 20% higher percentage of cleavage-competent RNP compared to an RNP of the reference CasX proteins of SEQ ID NOS: 1-3 and the gNA of SEQ ID NOS: 4-16.

72. The composition of any one of Set II embodiments 45-71, wherein the CasX variant protein comprises a RuvC DNA cleavage domain having nickase activity.

73. The composition of any one of Set II embodiments 45-71, wherein the CasX variant protein comprises a RuvC DNA cleavage domain having double-stranded cleavage activity.

74. The composition of any one of Set I1 embodiments 45-71, wherein the CasX protein is a catalytically inactive CasX (dCasX) protein, and wherein the dCasX and the gNA retain the ability to bind to the RHO target nucleic acid.

75. The composition of Set II embodiment 74, wherein the dCasX comprises a mutation at residues:

a. D672, E769, and/or D935 corresponding to the CasX protein of SEQ ID NO:1; or b. D659, E756 and/or D922 corresponding to the CasX protein of SEQ ID NO: 2.

76. The composition of Set II embodiment 75, wherein the mutation is a substitution of alanine for the residue.

77. The composition of any one of Set II embodiments 1-73, further comprising a donor template nucleic acid.

78. The composition of Set II embodiment 77, wherein the donor template comprises a nucleic acid comprising at least a portion of a RHO gene selected from the group consisting of a RHO exon, a RHO intron, a RHO intron-exon junction, and a RHO regulatory element.

79. The composition of Set II embodiment 78, wherein the donor template comprises a wild-type nucleic acid sequence.

80. The composition of Set II embodiment 78, wherein the donor template comprises a nucleic acid sequence having one or more mutations relative to the wild-type RHO gene sequence.

81. The composition of any one of Set II embodiments 77-80, wherein the donor template ranges in size from 10-10,000 nucleotides.

82. The composition of any one of Set II embodiments 77-81, wherein the donor template is a single-stranded DNA template or a single stranded RNA template.

83. The composition of any one of Set II embodiments 77-81, wherein the donor template is a double-stranded DNA template.

84. The composition of any one of Set II embodiments 77-83, wherein the donor template comprises homologous arms at or near the 5' and 3' ends of the donor template that are complementary to sequences flanking cleavage sites in the RHO target nucleic acid introduced by the Class 2 Type V CRISPR protein.

85. A nucleic acid comprising the donor template of any one of Set II embodiments 77-84.

86. A nucleic acid comprising a sequence that encodes the CasX of any one of Set II embodiments 45-76.

87. A nucleic acid comprising a sequence that encodes the gNA of any one of Set II embodiments 1-44.

88. The nucleic acid of Set II embodiment 86, wherein the sequence that encodes the CasX protein is codon optimized for expression in a eukaryotic cell.

89. A vector comprising the gNA of any one of Set II embodiments 1-44, the CasX protein of any one of Set II embodiments 45-76, or the nucleic acid of any one of Set II embodiments 85-88.

90. The vector of Set II embodiment 89, wherein the vector further comprises a promoter.

91. The vector of Set II embodiment 89 or Set II embodiment 90, wherein the vector is selected from the group consisting of a retroviral vector, a lentiviral vector, an adenoviral vector, an adeno-associated viral (AAV) vector, a herpes simplex virus (HSV) vector, a virus-like particle (VLP), a plasmid, a minicircle, a nanoplasmid, a DNA vector, and an RNA vector.

92. The vector of Set II embodiment 91, wherein the vector is an AAV vector.

93. The vector of Set II embodiment 92, wherein the AAV vector is selected from AAV1, AAV2, AAV3, AAV4, AAV5. AAV6, AAV7, AAV8, AAV9, AAV10. AAV11, AAV12, AAV 44.9, AAV-Rh74, or AAVRh10.

94. The vector of Set II embodiment 93, wherein the AAV vector is selected from AAV1. AAV2, AAV5, AAV8, or AAV9.

95. The vector of Set II embodiment 91, wherein the vector is a retroviral vector.

96. The vector of Set II embodiment 91, wherein the vector is a VLP vector comprising one or more components of a gag polyprotein.

97. The vector of Set II embodiment 96, wherein the one or more components of the gag polyprotein are selected from the group consisting of matrix protein (MA), nucleocapsid protein (NC), capsid protein (CA), p1-p6 protein, and protease cleavage site.

98. The vector of Set II embodiment 96 or Set II embodiment 97, comprising the CasX protein and the gNA.

99. The vector of Set II embodiment 98, wherein the CasX protein and the gNA are associated together in an RNP.

100. The vector of any one of Set II embodiments 96-99, further comprising the donor template.

101. The vector of any one of Set II embodiments 96-1I0, further comprising a pseudotyping viral envelope glycoprotein or antibody fragment that provides for binding and fusion of the VLP to a target cell.

102. A host cell comprising the vector of any one of Set II embodiments 89-101.

103. The host cell of Set II embodiment 101, wherein the host cell is selected from the group consisting of BHK, HEK293. HEK293T, NS0, SP2/0, YO myeloma cells. P3X63 mouse myeloma cells, PER, PER.C6. NIH3T3, COS. HeLa, CHO, and yeast cells.

104. A method of modifying a RHO target nucleic acid sequence in a population of cells, wherein the RHO target nucleic acid comprises one or more mutations, the method comprising introducing into cells of the population:
  a. the composition of any one of Set II embodiments 1-84;
  b. the nucleic acid of any one of Set II embodiments 85-88;
  c. the vector of any one of Set II embodiments 89-101; or
  d. combinations of two or more of (a)-(c), wherein the RHO target nucleic acid sequence of the cells targeted by the first gNA is modified by the CasX protein.

105. The method of Set II embodiment 104, wherein the modifying comprises introducing a single-stranded break in the RHO target nucleic acid sequence of the cells of the population.

106. The method of Set II embodiment 104, wherein the modifying comprises introducing a double-stranded break in the RHO target nucleic acid sequence of the cells of the population.

107. The method of any one of Set II embodiments 104-106, further comprising introducing into the cells of the population a second gNA or a nucleic acid encoding the second gNA, wherein the second gNA has a targeting sequence complementary to a different or overlapping portion of the RHO target nucleic acid compared to the first gNA, resulting in an additional break in the RHO target nucleic acid of the cells of the population.

108. The method of any one of Set II embodiments 104-107, wherein the modifying comprises introducing an insertion, deletion, substitution, duplication, or inversion of one or more nucleotides in the RHO target nucleic acid of the cells of the population.

109. The method of any one of Set II embodiments 104-108, wherein the RHO target nucleic acid of at least 10% of the cells of the population is modified.

110. The method of Set I1 embodiment 108, wherein the modifying results in a knocking down or knocking out of the RHO gene in the cells of the population such that expression of non-functional rhodopsin protein is decreased by at least about 10%, at least about 20%, at least about 30%, at least about 40%, at least about 50%, at least about 60%, at least about 70%, at least about 80%, or at least about 90% in comparison to a cell where the RHO gene has not been modified.

111. The method of Set II embodiment 108, wherein the RHO gene of the cells of the population is modified such that at least about 10% f, at least about 20%, at least about 30% r, at least about 40%, at least about 50%, at least about 60%, at least about 70%, at least about 80%, or at least about 90% of the modified cells do not express a detectable level of non-functional rhodopsin protein.

112. The method of Set II embodiment 108, wherein the modifying results in a correction or compensation of the mutation of the RHO gene in the cells of the population such that functional rhodopsin protein is expressed by the cells.

113. The method of Set II embodiment 108, wherein expression of the functional rhodopsin protein by the cells of the population is increased by at least about 10%, at least about 20%, at least about 30%, at least about 40%, at least about 50%, at least about 60%, at least about 70%, at least about 80%, or at least about 90% in comparison to a cell where the RHO gene has not been modified.

114. The method of any one of Set II embodiments 104-107, wherein the method comprises insertion of the donor template into the break site(s) of the RHO gene target nucleic acid sequence of the cells of the population.

115. The method of Set II embodiment 114, wherein insertion of the donor template is mediated by homology-directed repair (HDR) or homology-independent targeted integration (HITI).

116. The method of Set I1 embodiment 114 or Set II embodiment 115, wherein insertion of the donor template results in a correction or compensation of the RHO gene in the cells of the population such that functional rhodopsin protein is expressed by the cells.

117. The method of Set II embodiment 114, wherein expression of the functional rhodopsin protein by the cells of the population is increased by at least about 10%, at least about 20%, at least about 30%, at least about 40%, at least about 50%, at least about 60%, at least about 70%, at least about 80%, or at least about 90% in comparison to a cell where the RHO gene has not been modified.

118. The method of any one of Set II embodiments 114-116, wherein the RHO gene of the cells of the population is modified such that at least about 50%, at least about 60%, at least about 70%, at least about 75%, at least about 80%, at least about 85%, at least about 90%, or at least about 95% of the modified cells express a detectable level of functional rhodopsin.

119. The method of Set II embodiment 114 or Set II embodiment 115, wherein insertion of the donor template results in a knocking down or knocking out the RHO gene in the cells of the population such that expression of a non-functional rhodopsin protein is decreased by at least about 10%, at least about 20%, at least about 30%, at least about 40%, at least about 50%, at least about 60%, at least about 70%, at least about 80%, or at least about 90% in comparison to a cell where the RHO gene has not been modified of the RHO gene in the cells of the population.

120. The method of Set II embodiment 114 or Set II embodiment 115, wherein the RHO gene of the cells of the population is modified such that at least about 10%, at least about 20%, at least about 30%, at least about 40%, at least about 50%, at least about 60%, at least about 70%, at least about 80%, or at least about 90% of the modified cells do not express a detectable level of non-functional rhodopsin protein.

121. The method of any one of Set II embodiments 104-120, wherein the cells are eukaryotic.

122. The method of Set II embodiment 121, wherein the eukaryotic cells are selected from the group consisting of rodent cells, mouse cells, rat cells, and non-human primate cells.

123. The method of Set II embodiment 121, wherein the eukaryotic cells are human cells.

124. The method of Set II embodiment 121-123, wherein the eukaryotic cells are selected from the group consisting of a neuron, a rod photoreceptor cell, a retinal progenitor cell, a pluripotent stem cell (iPSC), a fibroblast, and a Miller glial cell.

125. The method of any one of Set II embodiment 104-124, wherein the modifying of the RHO gene target nucleic acid sequence of the population of cells occurs in vitro or ex vivo.

126. The method of Set II embodiments 104-124, wherein the modifying of the RHO gene target nucleic acid sequence of the population of cells occurs in vivo in a subject.

127. The method of Set II embodiment 126, wherein the subject is selected from the group consisting of a rodent, a mouse, a rat, and a non-human primate.

128. The method of Set I1 embodiment 126, wherein the subject is a human.

129. The method of any one of Set II embodiments 126-128, wherein the method comprises administering a therapeutically effective dose of an AAV vector to the subject.

130. The method of Set II embodiment 129, wherein the AAV vector is administered to the subject at a dose of at least about $1\times10^5$ vector genomes (vg), at least about $1\times10^5$ vector genomes (vg)/kg, at least about $1\times106$ vg/kg, at least about $1\times10^7$ vg/kg, at least about $1\times10^8$ vg/kg, at least about $1\times109$ vg/kg, at least about $1\times10^{10}$ vg/kg, at least about $1\times10^{11}$ vg/kg, at least about $1\times10^{12}$ vg/kg, at least about $1\times10^{13}$ vg/kg, at least about $1\times10^{14}$ vg/kg, at least about $1\times10^{15}$ vg/kg, or at least about $1\times10^{16}$ vg/kg.

131. The method of Set II embodiment 129, wherein the AAV vector is administered to the subject at a dose of at least about $1\times10^5$ vg/kg to about $1\times10^{16}$ vg/kg, at least about $1\times10^6$ vg/kg to about $1\times10^{15}$ vg/kg, at least about $1\times10^7$ vg/kg to about $1\times10^{14}$ vg/kg, at least about $1\times10^8$ vg/kg to about $1\times10^{13}$ vg/kg, at least about $1\times10^9$ vg/kg to about $1\times10^{12}$ vg/kg, or at least about $1\times10^{10}$ vg/kg to about $1\times10^{11}$ vg/kg.

132. The method of any one of Set II embodiments 126-128, wherein the method comprises administering a therapeutically effective dose of a VLP to the subject.

133. The method of Set II embodiment 132, wherein the VLP is administered to the subject at a dose of at least about $1\times10^5$ particles/kg, at least about $1\times10^6$ particles/kg, at least about $1\times10^7$ particles/kg, at least about $1\times10^8$ particles/kg, at least about $1\times10^9$ particles/kg, at least about $1\times10^{10}$ particles/kg, at least about $1\times10^{11}$ particles/kg, at least about $1\times10^{12}$ particles/kg, at least about $1\times10^{13}$ particles/kg, at least about $1\times10^{14}$ particles/kg, at least about $1\times10^{15}$ particles/kg, at least about $1\times10^{16}$ particles/kg.

134. The method of Set II embodiment 132, wherein the VLP is administered to the subject at a dose of at least about $1\times10^5$ particles/kg to about $1\times10^{16}$ particles/kg, at least about $1\times10^6$ particles/kg to about $1\times10^{15}$ particles/kg, at least about $1\times10^7$ particles/kg to about $1\times10^9$ particles/kg, at least about $1\times10^{12}$ particles/kg to about $1\times10^{10}$ particles/kg, at least about $1\times10^9$ particles/kg to about $1\times10^{12}$ particles/kg, at least about $1\times10^{10}$ particles/kg to about $1\times10^{11}$ particles/kg.

135. The method of any one of Set II embodiments 127-134 wherein the vector or VLP is administered to one or both eyes of the subject by a route of administration selected from intraocular, intravitreal, subretinal, or suprachoroidal injection or implantation.

136. The method of any one of Set II embodiments 104-134, further comprising contacting the RHO target nucleic acid sequence of the population of cells with:
  a. an additional CRISPR nuclease and a gNA targeting a different or overlapping portion of the RHO target nucleic acid compared to the first gNA;
  b. a polynucleotide encoding the additional CRISPR nuclease and the gNA of (a);
  c. a vector comprising the polynucleotide of (b); or
  d. a VLP comprising the additional CRISPR nuclease and the gNA of (a);
wherein the contacting results in modification of the RHO gene at a different location in the sequence compared to the sequence targeted by the first gNA.

137. The method of Set II embodiment 136, wherein the additional CRISPR nuclease is a CasX protein having a sequence different from the CasX protein of any of the preceding Set 11 embodiments.

138. The method of Set II embodiment 136, wherein the additional CRISPR nuclease is not a CasX protein.

139. The method of Set I embodiment 138, wherein the additional CRISPR nuclease is selected from the group consisting of Cas9, Cas12a, Cas12b, Cas12c, Cas12d (CasY), Cas12J, Cas13a. Cas13b, Cas13c. Cas13d, CasX, CasY, Cas14, Cpf1, C2cl, Csn2, Cas Phi, and sequence variants thereof.

140. A population of cells modified by the method of any one of Set II embodiments 104-139, wherein the cells have been modified such that at least 70%, at least 75%, at least 80%, at least 85%, at least 90%, or at least 95% of the modified cells do not express a detectable level of non-functional rhodopsin protein.

141. A population of cells modified by the method of any one of Set II embodiments 104-139, wherein the mutation of the RHO target nucleic acid is corrected or compensated for in the modified cells of the population, resulting in expression of a functional rhodopsin protein by the modified cells.

142. The population of cells of Set II embodiment 141, wherein the cells have been modified such that expression of a functional rhodopsin protein is increased by at least about 10%, at least about 20%, at least about 30%, at least about 40%, at least about 50%, at least about 60%, at least about 70%, at least about 80%, or at least about 90% in comparison to a cell where the RHO gene has not been modified.

143. The population of cells of any one of Set II embodiment 140-142, wherein the cells are selected from the group consisting of a neuron, a rod photoreceptor cell, a retinal progenitor cell, a pluripotent stem cell (iPSC), a fibroblast, and a Miller glial cell.

144. A method of treating a RHO-related disease in a subject in need thereof, the method comprising administering to one or both eyes of the subject a therapeutically effective amount of the cells of any one of Set II embodiments 140-143.

145. The method of Set II embodiment 144, wherein the RHO-related disease is retinitis pigmentosa.

146. The method of Set I1 embodiment 144 or Set II embodiment 145, wherein the subject is selected from the group consisting of a rodent, a mouse, a rat, and a non-human primate.

147. The method of any one of Set II embodiments 144-146, wherein the subject is a human.

148. The method of any one of Set II embodiments 144-147, wherein the cells are autologous with respect to the subject to be administered the cells.

149. The method of any one of Set II embodiments 144-147 wherein the cells are allogeneic with respect to the subject to be administered the cells.

150. The method of any one of Set II embodiments 144-149, wherein the cells are administered by a route of administration selected from intraocular, intravitreal, subretinal, or suprachoroidal injection or implantation.

151. A method of treating a RHO-related disease in a subject in need thereof, comprising modifying a RHO gene having one or more mutations in eye cells of the subject, the modifying comprising contacting said cells in one or both eyes with a therapeutically effective dose of;
  a. the composition of any one of Set II embodiments 1-84;
  b. the nucleic acid of any one of Set II embodiments 85-88;
  c. the vector as in any one of Set II embodiments 89-95;
  d. the VLP of any one of Set II embodiments 96-101: or
  e. combinations of two or more of (a)-(d),
wherein the RHO gene of the cells targeted by the first gNA is modified by the CasX protein.

152. The method of Set II embodiment 151, wherein the modifying comprises introducing a single-stranded break in the RHO gene of the cells.

153. The method of Set II embodiment 151, wherein the modifying comprises introducing a double-stranded break in the RHO gene of the cells.

154. The method of any one of Set II embodiments 151-153, further comprising introducing into the cells of the subject a second gNA or a nucleic acid encoding the second gNA, wherein the second gNA has a targeting sequence complementary to a different or overlapping portion of the target nucleic acid compared to the first gNA, resulting in an additional break in the RHO target nucleic acid of the cells of the subject.

155. The method of any one of Set II embodiments 151-153, wherein the modifying comprises introducing an insertion, deletion, substitution, duplication, or inversion of one or more nucleotides in the RHO gene of the cells.

156. The method of any one of Set II embodiments 151-154, wherein the modifying comprises insertion of the donor template into the break site(s) of the RHO gene target nucleic acid sequence of the cells.

157. The method of Set II embodiment 156, wherein the insertion of the donor template is mediated by homology-directed repair (HDR) or homology-independent targeted integration (HITI).

158. The method of any one of Set II embodiments 151-157, wherein the modifying results in a correction of or compensation for the mutation(s) in the RHO gene in the modified cells of the subject.

159. The method of Set II embodiment 158, wherein correction of the mutation results in expression of functional rhodopsin protein by the modified cells of the subject.

160. The method of Set II embodiment 158 or Set II embodiment 159, wherein the RHO gene of the modified cells express increased levels of a functional rhodopsin protein, wherein the increase is at least about 10%, at least about 20%, at least about 30%, at least about 40%, at least about 50%, at least about 60%, at least about 70%, at least about 80%, or at least about 90% in comparison to a cell with a RHO gene that has not been modified.

161. The method of any one of Set II embodiments 151-157, wherein the modifying results in a knocking down or knocking out the RHO gene in the modified cells of the subject such that at least about 10%, at least about 20%, at least about 30%, at least about 40%, at least about 50%, at least about 60%, at least about 70%, at least about 80%, or at least about 90% of the modified cells do not express a detectable level of non-functional rhodopsin protein.

162. The method of any one of Set II embodiments 151-157, wherein the modifying results in a knocking down or knocking out the RHO gene in the modified cells of the subject such that expression of non-functional rhodopsin protein in the subject is decreased by at least about 10%, at least about 20%, at least about 30%, at least about 40%, at least about 50%, at least about 60%, at least about 70%, at least about 80%, or at least about 90% in comparison to a subject where the RHO gene has not been modified.

163. The method of any one of Set II embodiments 151-162, wherein the subject is selected from the group consisting of rodent, mouse, rat, and non-human primate.

164. The method of any one of Set II embodiments 151-162, wherein the subject is a human.

165. The method of any one of Set II embodiments 151-162, wherein the cells that are modified are selected from the group consisting of a neuron, a rod photoreceptor cell, a retinal progenitor cell, a pluripotent stem cell (iPSC), a fibroblast, and a Müller glial cell.

166. The method of any one of Set II embodiments 151-164, wherein the RHO-related disease is retinitis pigmentosa.

167. The method of any one of Set II embodiments 151-166, wherein the vector is administered to the subject at a therapeutically-effective dose.

168. The method of any one of Set II embodiments 151-167, wherein the vector is an AAV, and is administered to the subject at a dose of at least $1 \times 10^5$ vector genomes (vg), at least about $1 \times 10^5$ vector genomes (vg)/kg, at least about $1 \times 10^6$ vg/kg, at least about $1 \times 10^7$ vg/kg, at least about $1 \times 10^8$ vg/kg, at least about $1 \times 10^9$ vg/kg, at least about $1 \times 10^{10}$ vg/kg, at least about $1 \times 10^{11}$ vg/kg, at least about $1 \times 10^{12}$ vg/kg, at least about $1 \times 10^{13}$ vg/kg, at least about $1 \times 10^{14}$ vg/kg, at least about $1 \times 10^{15}$ vg/kg, or at least about $1 \times 10^{16}$ vg/kg.

169. The method of any one of Set II embodiments 151-167, wherein the vector is an AAV, and is administered to the subject at a dose of at least about $1 \times 10^5$ vg/kg to about $1 \times 10^{16}$ vg/kg, at least about $1 \times 10^6$ vg/kg to about $1 \times 10^{15}$ vg/kg, at least about $1 \times 10^7$ vg/kg to about $1 \times 10^{14}$ vg/kg, at least about $1 \times 10^8$ vg/kg to about $1 \times 10^{13}$ vg/kg, at least about $1 \times 10^9$ vg/kg to about $1 \times 10^{12}$ vg/kg, or at least about $1 \times 10^{10}$ vg/kg to about $1 \times 10^{11}$ vg/kg.

170. The method of any one of Set II embodiments 151-166, wherein the VLP is administered to the subject at a therapeutically-effective dose.

171. The method of Set II embodiment 170, wherein the VLP is administered to the subject at a dose of at least about $1 \times 10^7$ particles/kg, at least about $1 \times 10^6$ particles/kg, at least about $1 \times 10^7$ particles/kg, at least about $1 \times 10^8$ particles/kg, at least about $1 \times 10^9$ particles/kg, at least about $1 \times 10^{10}$ particles/kg, at least about $1 \times 10^{11}$ particles/kg, at least about $1 \times 10^{12}$ particles/kg, at least about $1 \times 10^{13}$ particles/kg, at least about $1 \times 10^{14}$ particles/kg, at least about $1 \times 10^{15}$ particles/kg, at least about $1 \times 10^{16}$ particles/kg.

172. The method of Set II embodiment 170, wherein the VLP is administered to the subject at a dose of at least about $1 \times 10^5$ particles/kg to about $1 \times 10^{16}$ particles/kg, at least about $1 \times 10^6$ particles/kg to about $1 \times 10^{15}$ particles/kg, at least about $1 \times 10^7$ particles/kg to about $1 \times 10^{14}$ particles/kg, at least about $1 \times 10^8$ particles/kg to about $1 \times 10^{13}$ particles/kg, at least about $1 \times 10^9$ particles/kg to about $1 \times 10^{12}$ particles/kg, at least about $1 \times 10^{10}$ particles/kg to about $1 \times 10^{11}$ particles/kg.

173. The method of any one of Set II embodiments 167-172, wherein the vector or VLP is administered to one or both eyes of the subject by a route of administration selected from intraocular, intravitreal, subretinal, or suprachoroidal injection or implantation.

174. The method of any one of Set II embodiments 151-173, wherein the method results in improvement in at least one clinically-relevant endpoint selected from the group consisting of mean change or mean rate of change in: 1) best corrected visual acuity (BCVA); 2) visual field sensitivity (including analysis of hill of vision volumes); 3) retinal sensitivity measured by full-field stimulus testing (FST): 4) multiluminance mobility tests; 5) electrophysiological measures of retinal function; 6) optical coherence tomography (OCT) documenting the rate of photoreceptor loss; and 7) hypo- or hyperfluorescent lesion size on fundus autofluorescence: 8) color vision; 9) contrast sensitivity: 10) gaze tracking: 11) light aversion: 12) macular sensitivity.

175. The method of any one of Set II embodiments 151-173, wherein the method results in improvement in at least two clinically-relevant endpoints selected from the group consisting of mean change or mean rate of change in: 1) best corrected visual acuity (BCVA): 2) visual field sensitivity (including analysis of hill of vision volumes): 3) retinal sensitivity measured by full-field stimulus testing (FST): 4) multiluminance mobility tests; 5) electrophysiological measures of retinal function: 6) optical coherence tomography (OCT) documenting the rate of photoreceptor loss; and 7) hypo- or hyperfluorescent lesion size on fundus autofluorescence; 8) color vision: 9) contrast sensitivity; 10) gaze tracking; I I) light aversion: 12) macular sensitivity.

176. The composition of Set II embodiment 1, wherein the target nucleic acid sequence is complementary to a non-target strand sequence located 1 nucleotide 3' of a protospacer adjacent motif (PAM) sequence.

177. The composition of Set II embodiment 176, wherein the PAM sequence comprises a TC motif.

178. The composition of Set II embodiment 177, wherein the PAM sequence comprises ATC, GTC, CTC or TTC.

179. The composition of any one of Set II embodiments 176-178, wherein the Class 2 Type V CRISPR protein comprises a RuvC domain.

180. The composition of Set II embodiment 179, wherein the RuvC domain generates a staggered double-stranded break in the target nucleic acid sequence.

181. The composition of any one of Set II embodiments 176-180, wherein the Class 2 Type V CRISPR protein does not comprise an HNH nuclease domain.

182. A composition of any one of Set II embodiments 1-84 or Set II embodiments 176-181; a nucleic acid of any one of Set II embodiments 85-88; a vector of any one of Set II embodiments 89-95: a VLP of any one of Set II embodiments %-101; or combinations thereof, for use as a medicament for the treatment of a RHO-related disease.

The present description sets forth numerous exemplary configurations, methods, parameters, and the like. It should be recognized, however, that such description is not intended as a limitation on the scope of the present disclosure, but is instead provided as a description of exemplary embodiments.

EXAMPLES

Example 1: Creation, Expression and Purification of CasX Stx2

1. Growth and Expression

An expression construct for CasX Stx2 (also referred to herein as CasX2), derived from Planctomycetes (having the amino acid sequence of SEQ ID NO: 2 and encoded by the sequence of the Table 5, below), was constructed from gene fragments (Twist Biosciences) that were codon optimized for *E. coli*. The assembled construct contains a TEV-cleavable, C-terminal, TwinStrep tag and was cloned into a pBR322-derivative plasmid backbone containing an ampicillin resistance gene. The expression construct was transformed into chemically competent BL21* (DE3) *E. coli* and a starter culture was grown overnight in LB broth supplemented with carbenicillin at 37° C., 200 RPM, in UltraYield Flasks (Thomson Instrument Company). The following day, this culture was used to seed expression cultures at a 1:100 ratio (starter culture:expression culture). Expression cultures were Terrific Broth (Novagen) supplemented with carbenicillin and grown in UltraYield flasks at 37C, 200 RPM. Once the cultures reached an OD of 2, they were chilled to 16-C and IPTG (isopropyl β-D-1-thiogalactopyranoside) was added to a final concentration of 1 mM, from a 1 M stock. The cultures were induced at 16 C, 200 RPM for 20 hours before being harvested by centrifugation at 4,000×g for 15 minutes, 4° C. The cell paste was weighed and resuspended in lysis buffer (50 mM HEPES-NaOH, 250 mM NaCl, 5 mM $MgCl_2$, 1 mM TCEP, 1 mM benzamidine-HCL, 1 mM PMSF, 0.5% CHAPS, 10% glycerol, pH 8) at a ratio of 5 mL of lysis buffer per gram of cell paste. Once resuspended, the sample was frozen at −80° C. until purification.

TABLE 5

DNA sequence of CasX Stx2 construct

| Construct | DNA Sequence |
|---|---|
| SV40 NLS-CasX-SV40 NILS-TEV cleavage site - TwinStrep tag | (SEQ ID NO: 236) |

2. Purification

Frozen samples were thawed overnight at 4° C. with magnetic stirring. The viscosity of the resulting lysate was reduced by sonication and lysis was completed by homogenization in three passes at 17 k PSI using an Emulsiflex C3 (Avestin). Lysate was clarified by centrifugation at 50,000× g, 4° C., for 30 minutes and the supernatant was collected. The clarified supernatant was applied to a Heparin 6 Fast Flow column (GE Life Sciences) by gravity flow. The column was washed with 5 CV of Heparin Buffer A (50 mM HEPES-NaOH, 250 mM NaCl, 5 mM $MgCl_2$, 1 mM TCEP, 10% glycerol. pH 8), then with 5 CV of Heparin Buffer B (Buffer A with the NaCl concentration adjusted to 500 mM). Protein was eluted with 5 CV of Heparin Buffer C (Buffer A with the NaCl concentration adjusted to 1 M), collected in fractions. Fractions were assayed for protein by Bradford Assay and protein-containing fractions were pooled. The pooled heparin eluate was applied to a Strep-Tactin XT Superflow column (IBA Life Sciences) by gravity flow. The column was washed with 5 CV of Strep Buffer (50 mM HEPES-NaOH, 500 mM NaCl, 5 mM $MgCl_2$, 1 mM TCEP, 10% glycerol, pH 8). Protein was eluted from the column using 5 CV of Strep Buffer with 50 mM D-Biotin added and collected in fractions. CasX-containing fractions were pooled, concentrated at 4° C. using a 30 kDa cut-off spin concentrator, and purified by size exclusion chromatography on a Superdex 200 pg column (GE Life Sciences). The column was equilibrated with SEC Buffer (25 mM sodium phosphate, 300 mM NaCl, 1 mM TCEP, 10% glycerol, pH 7.25) operated by an AKTA Pure FPLC system (GE Life Sciences). CasX-containing fractions that eluted at the appropriate molecular weight were pooled, concentrated at 4° C. using a 30 kDa cut-off spin concentrator, aliquoted, and snap-frozen in liquid nitrogen before being stored at −80° C.

3. Results

Figure 2:
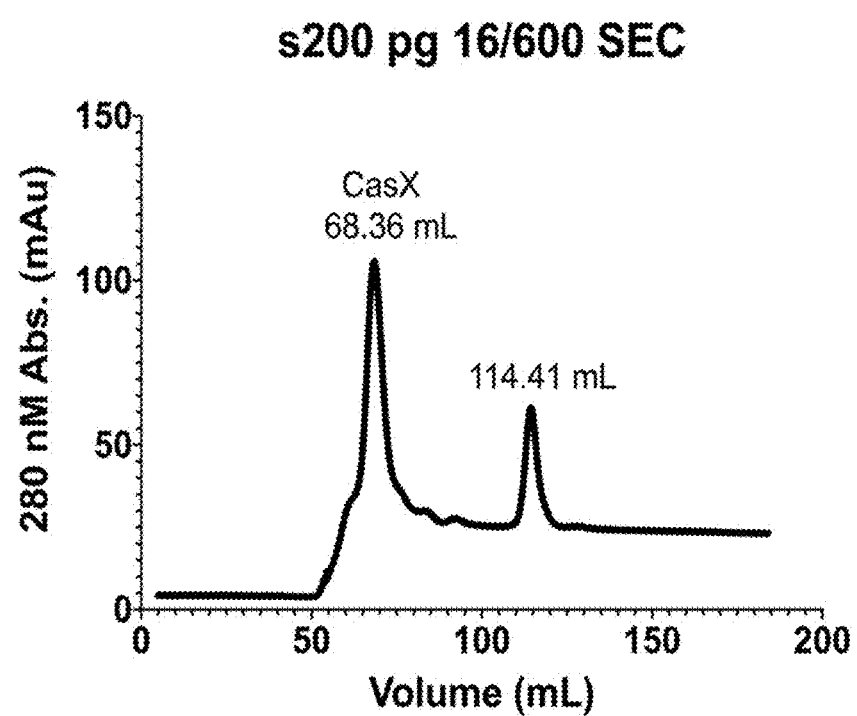
FIG. 2 shows the chromatogram from a size exclusion chromatography assay of the StX2, using of Superdex 200 16/600 pg Gel Filtration, as described in Example 1.
Figure 3:
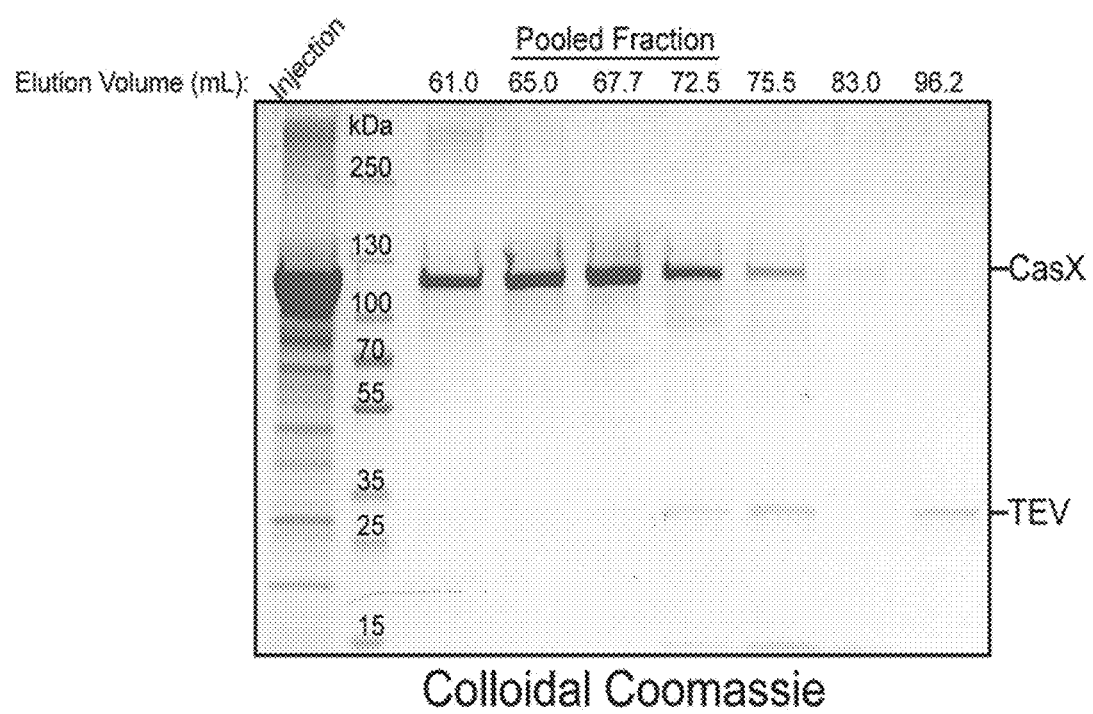
FIG. 3 shows an SDS-PAGE gel of StX2 purification fractions visualized by colloidal Coomassie staining, as described in Example 1.

Samples from throughout the purification were resolved by SDS-PAGE and visualized by colloidal Coomassie staining, as shown in FIG. 1 and FIG. 3. In FIG. 1, the lanes, from left to right, are: molecular weight standards, Pellet: insoluble portion following cell lysis, Lysate: soluble portion following cell lysis, Flow Thru: protein that did not bind the Heparin column, Wash: protein that eluted from the column in wash buffer, Elution: protein eluted from the heparin column with elution buffer, Flow Thru: Protein that did not bind the StrepTactinXT column, Elution: protein eluted from the StrepTactin XT column with elution buffer, Injection: concentrated protein injected onto the s200 gel filtration column, Frozen: pooled fractions from the s200 elution that have been concentrated and frozen. In FIG. 3, the lanes from right to left, are the injection (sample of protein injected onto the gel filtration column,) molecular weight markers, lanes 3-9 are samples from the indicated elution volumes. Results from the gel filtration are shown in FIG. 2. The 68.36 mL peak corresponds to the apparent molecular weight of CasX and contained the majority of CasX protein. The average yield was 0.75 mg of purified CasX protein per liter of culture, with 75% purity, as evaluated by colloidal Coomassie staining.

Example 2: Generation of CasX 119, 438, and 457

Figure 4:
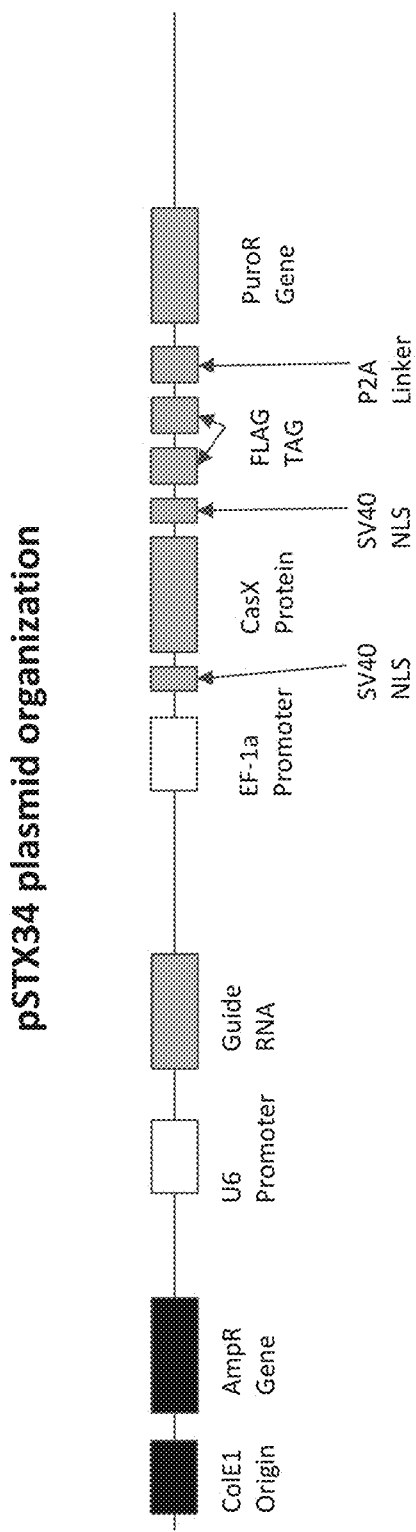
FIG. 4 is a schematic showing the organization of the components in the pSTX34 plasmid used to assemble the CasX constructs, as described in Example 2.

In order to generate the CasX 119, 438, and 457 constructs (sequences in Table 6), the codon-optimized CasX 37 construct (based on the CasX Stx2 construct of Example 1, encoding Planctomycetes CasX SEQ ID NO: 2, with a A708K substitution and a [P793] deletion with fused NLS, and linked guide and non-targeting sequences) was cloned into a mammalian expression plasmid (pStX; see FIG. 4) using standard cloning methods. To build CasX 119, the CasX 37 construct DNA was PCR amplified in two reactions using Q5 DNA polymerase (New England BioLabs Cat #M0491L) according to the manufacturer's protocol, using primers oIC539 and oIC88 as well as oIC87 and oIC540 respectively (see FIG. 5). To build CasX 457, the CasX 365 construct DNA was PCR amplified in four reactions using Q5 DNA polymerase (New England BioLabs Cat #M0491L) according to the manufacturer's protocol, using primers oIC539 and oIC212, oIC21 I and oIC376, oIC375 and oIC551, and oIC550 and oIC540 respectively. To build CasX 438, the CasX 119 construct DNA was PCR amplified in four reactions using Q5 DNA polymerase according to the manufacturer's protocol, using primers oIC539 and oIC689, oIC688 and oIC376, oIC375 and oIC551, and oIC550 and oIC540 respectively. The resulting PCR amplification products were then purified using Zymoclean™ DNA clean and concentrator (Zymo Research Cat #4014) according to the manufacturer's protocol. The pStX backbone was digested using XbaI and SpeI in order to remove the 2931 base pair fragment of DNA between the two sites in plasmid pStx34. The digested backbone fragment was purified by gel extraction from a 1% agarose gel (Gold Bio Cat #A-201-500) using Zymoclean™ Gel DNA Recovery Kit (Zymo Research Cat #D4002) according to the manufacturer's protocol. The three fragments were then pieced together using Gibson Assembly® (New England BioLabs Cat #E2621S) following the manufacturer's protocol. Assembled products in the pStx34 were transformed into chemically-competent or electro-competent Turbo Competent E. coli bacterial cells, plated on LB-Agar plates (LB: Teknova Cat #L9315, Agar: Quartzy Cat #214510) containing carbenicillin. Individual colonies were picked and miniprepped using Qiagen spin Miniprep Kit (Qiagen Cat #27104) following the manufacturer's protocol. The resultant plasmids were sequenced using Sanger sequencing to ensure correct assembly, pStX34 includes an EF-1α promoter for the protein as well as a selection marker for both puromycin and carbenicillin. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent E. coli (NEB Cat #C29841), plated on LB-Agar plates containing carbenicillin. Individual colonies were picked and miniprepped using Qiagen spin Miniprep Kit and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX 119, 438 and 457 proteins was performed using the general methodologies of Example 1 (however the DNA sequences were codon optimized for expression in E. coli).

Figure 6:
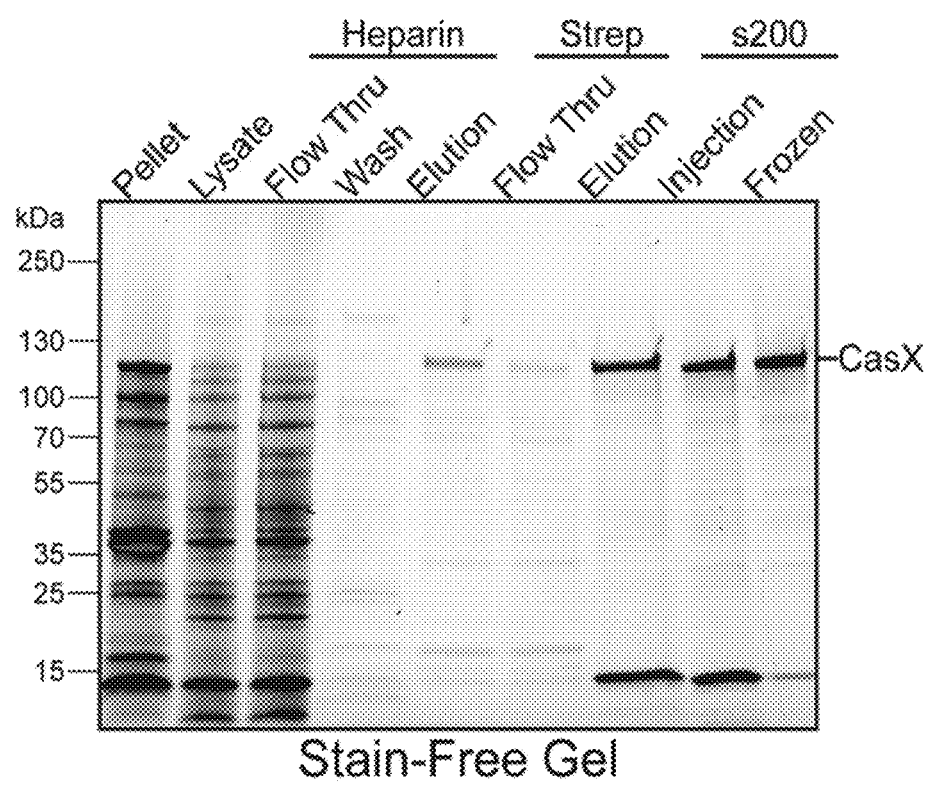
FIG. 6 shows an SDS-PAGE gel of purification samples, visualized on a Bio-Rad Stain-Free™ gel, as described in Example 2.
Figure 7:
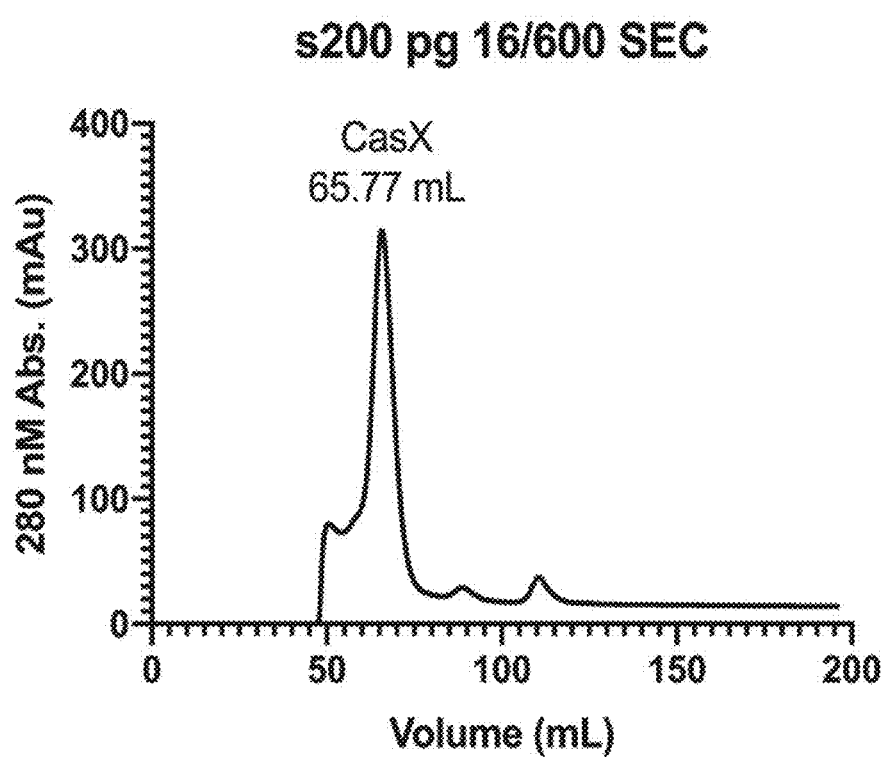
FIG. 7 shows the chromatogram of Superdex 200 16/600 pg Gel Filtration, as described in Example 2.
Figure 8:
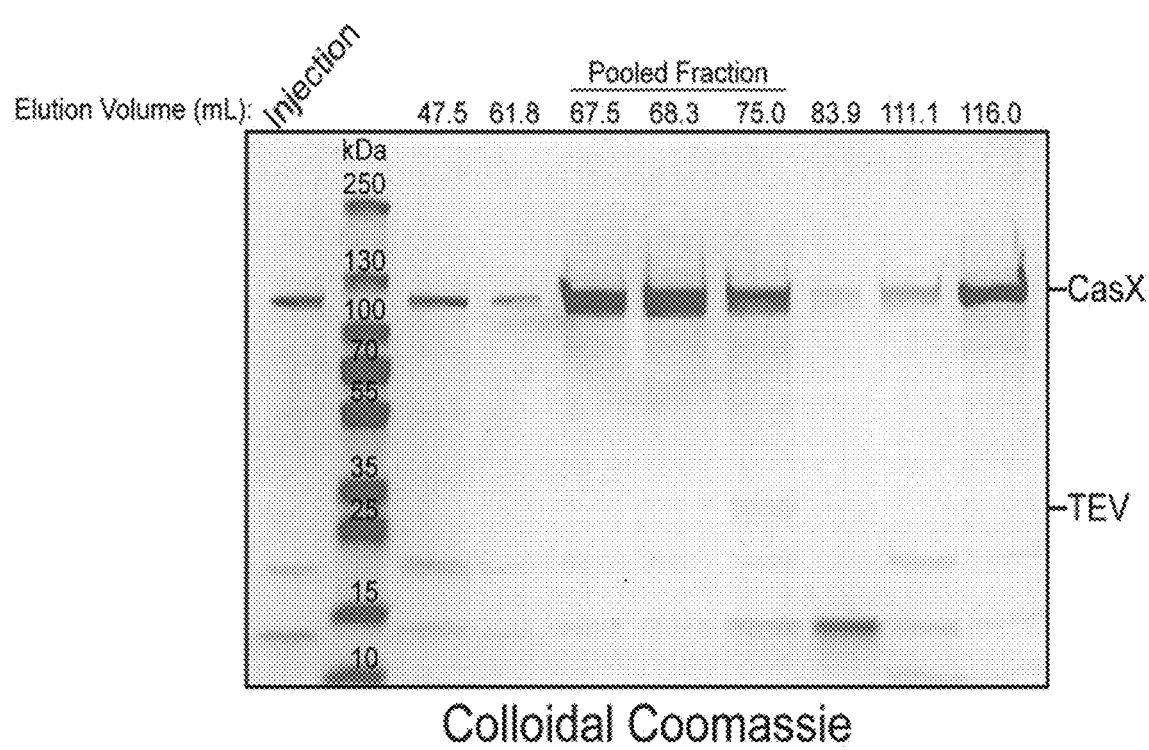
FIG. 8 shows an SDS-PAGE gel of gel filtration samples, stained with colloidal Coomassie, as described in Example 2.

CasX Variant 119: following the same expression and purification scheme for WT CasX, the following results were obtained for CasX variant 119. Samples from throughout the purification procedure were resolved by SDS-PAGE and visualized by colloidal Coomassie staining, as shown in FIG. 6 and FIG. 8. Results from the gel filtration are shown in FIG. 7. The average yield was 11.7 mg of purified CasX protein per liter of culture at 95% purity, as evaluated by colloidal Coomassie staining.

Figure 9:
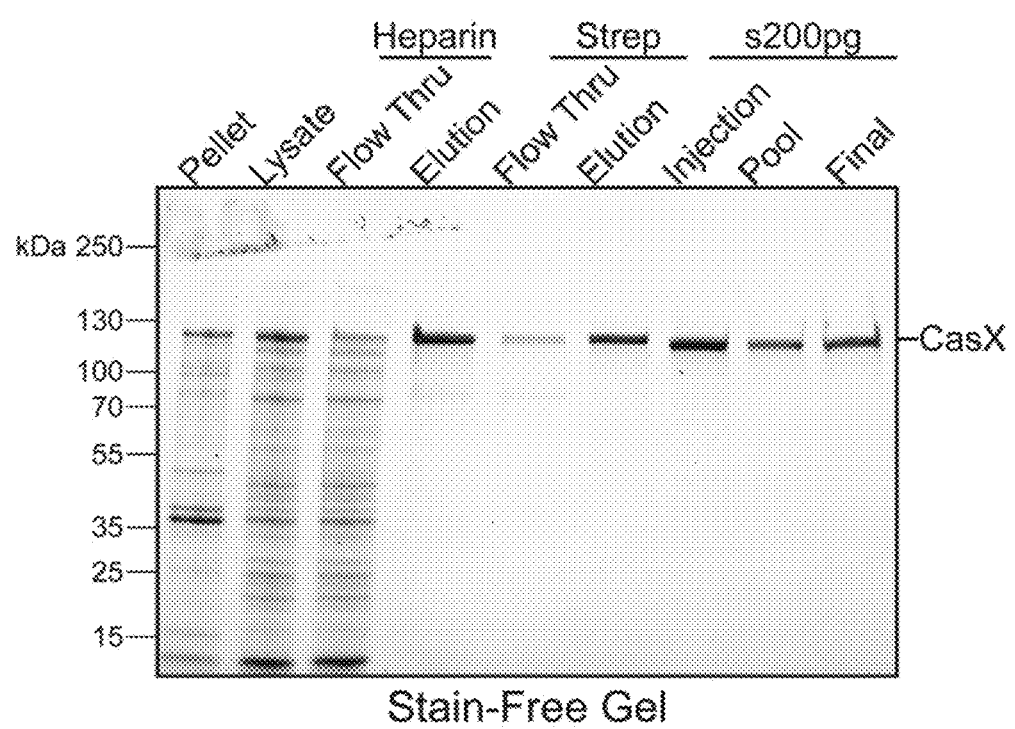
FIG. 9 shows an SDS-PAGE gel of purification samples of CasX 438, visualized on a Bio-Rad Stain-Free™ gel, as described in Example 2.
Figure 10:
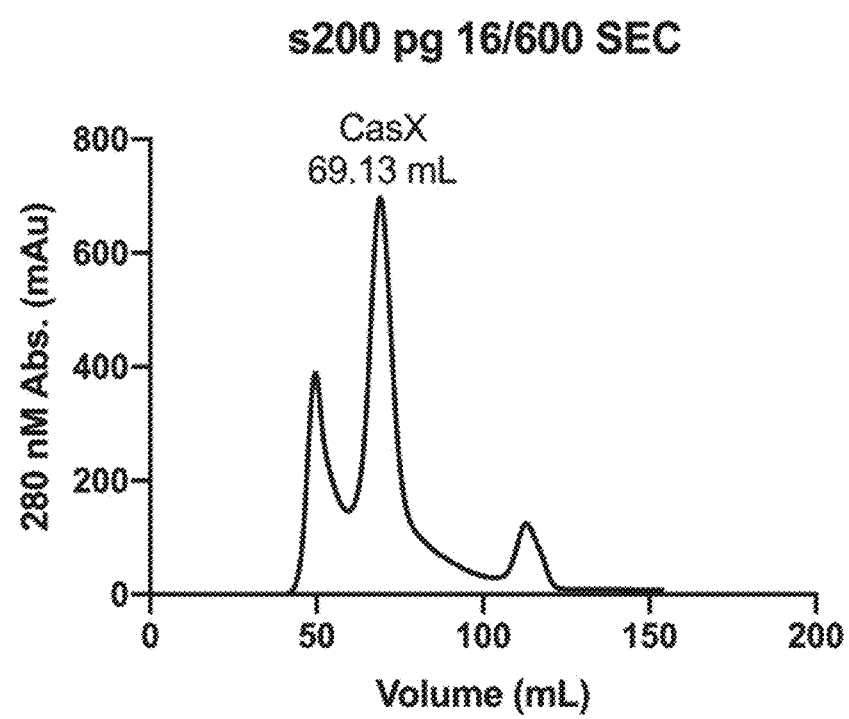
FIG. 10 shows the chromatogram from a size exclusion chromatography assay of the CasX 438, using of Superdex 200 16/600 pg gel filtration, as described in Example 2.
Figure 11:
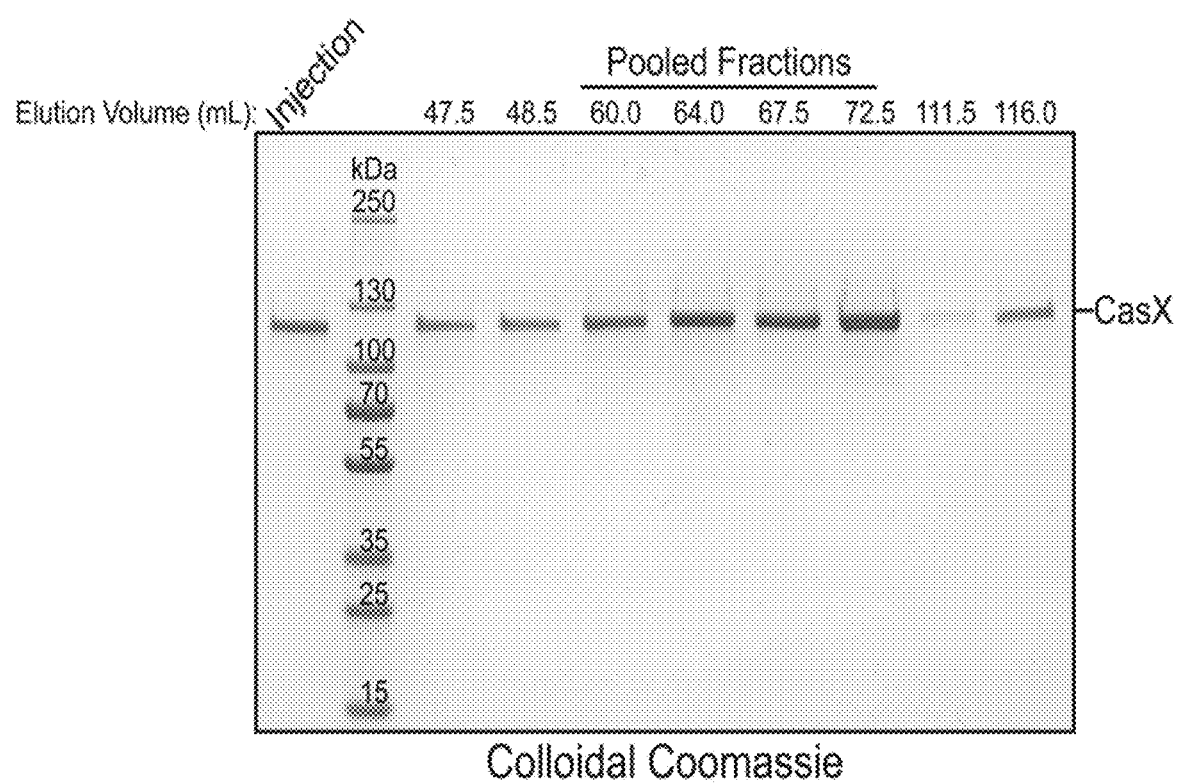
FIG. 11 shows an SDS-PAGE gel of CasX 438 purification fractions visualized by colloidal Coomassie staining, as described in Example, as described in Example 2.

CasX Variant 438: Following the same expression and purification scheme for WT CasX, the following results were obtained for CasX variant 438. Samples from throughout the purification procedure were resolved by SDS-PAGE and visualized by colloidal Coomassie staining, as shown in FIGS. 9 and 11. Results from the gel filtration are shown in FIG. 10. The average yield was 13.1 mg of purified CasX protein per liter of culture at 97.5% purity, as evaluated by colloidal Coomassie staining.

Figure 12:
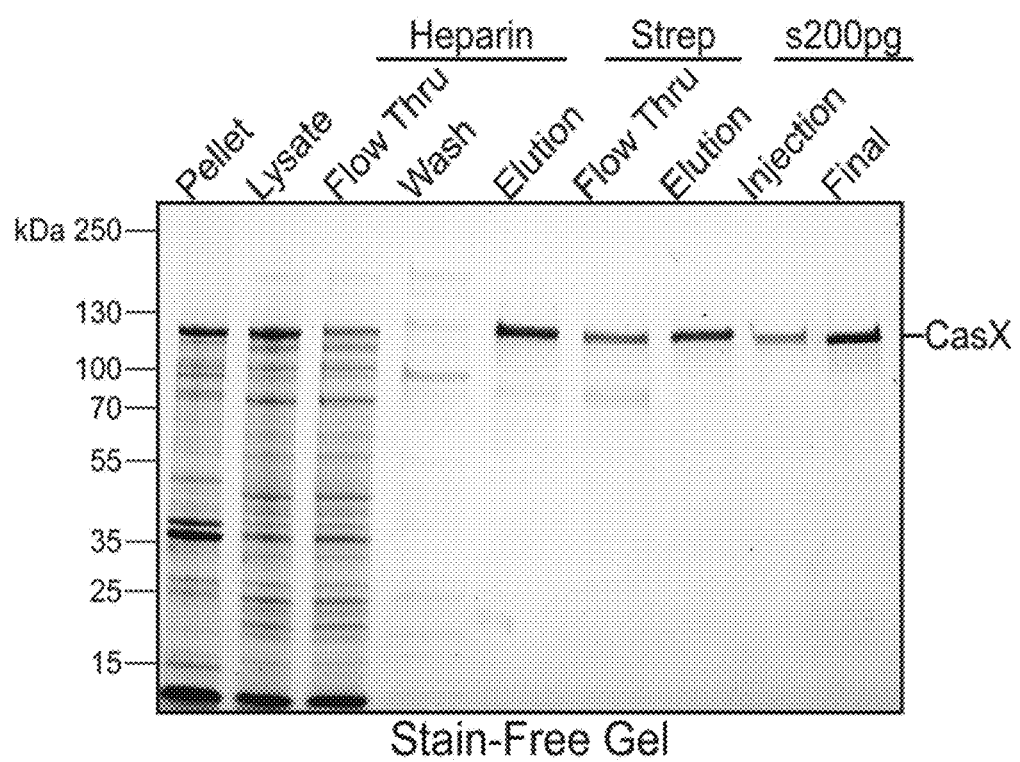
FIG. 12 shows an SDS-PAGE gel of purification samples of CasX 457, visualized on a Bio-Rad Stain-Free™ gel, as described in Example 2.
Figure 13:
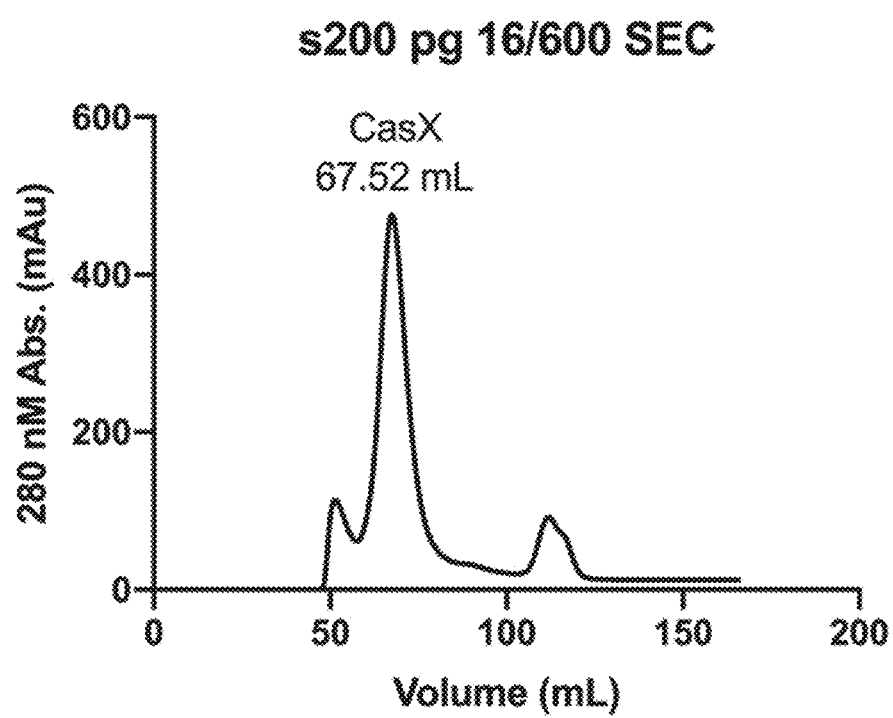
FIG. 13 shows the chromatogram from a size exclusion chromatography assay of the CasX 457, using of Superdex 200 16/600 pg gel filtration, as described in Example 2.
Figure 14:
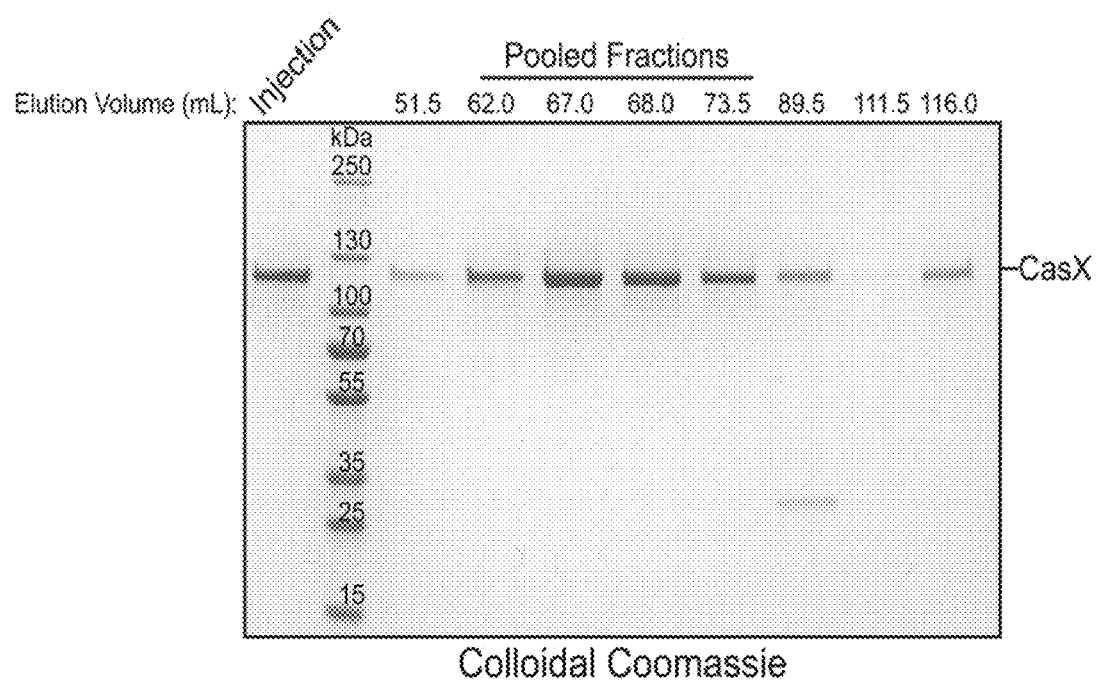
FIG. 14 shows an SDS-PAGE gel of CasX 457 purification fractions visualized by colloidal Coomassie staining, as described in Example 2.
Figure 15:
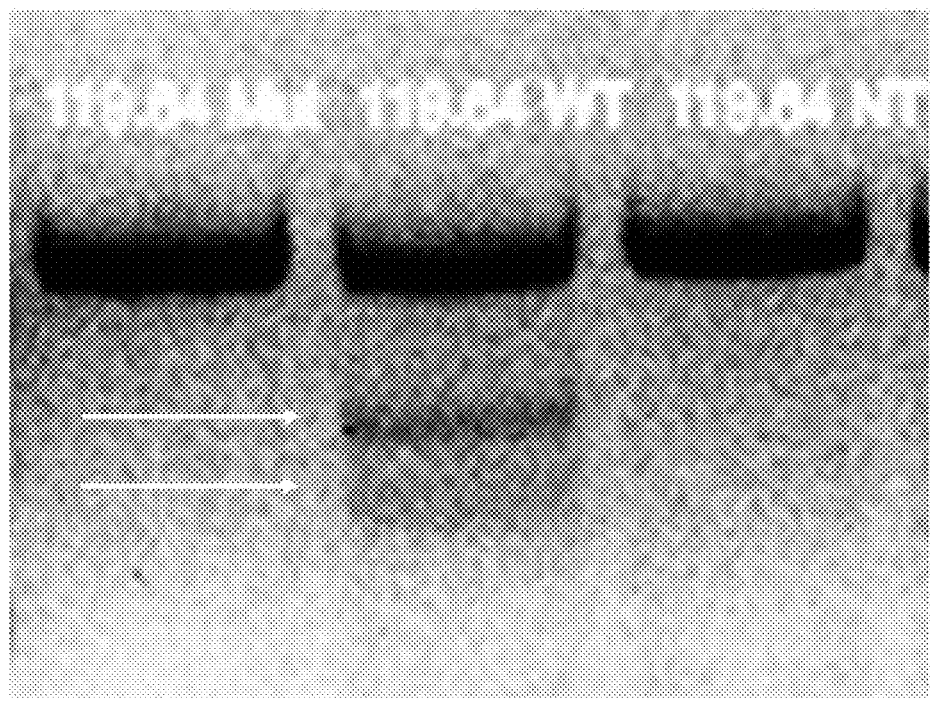
FIG. 15 is a gel image from a T7E1 assay demonstrating allele-specific editing at the wild-type RHO p23 locus in HEK293T cells (arrows, center lane), while the construct targeting the P23H mutation (left lane) as well as a non-targeting negative control (right lane) show no evidence of editing, as described in Example 18.
Figure 16:
FIG. 16 is a gel image from a T7E1 assay demonstrating allele-specific editing at the wild-type RHO p23 locus in HEK293T cells by CasX 119, guide 174 and spacer 11.1 (second lane), while the construct having the 11.2 spacer targeting the P23H mutation (third lane) shows no evidence of editing, as described in Example 18. Similarly, Cas9 constructs with appropriate WT spacers showed evidence of editing (lanes 5 and 6) while Cas9 constructs with spacers to the mutation show no evidence of editing (lanes 4 and 7).
Figure 17:
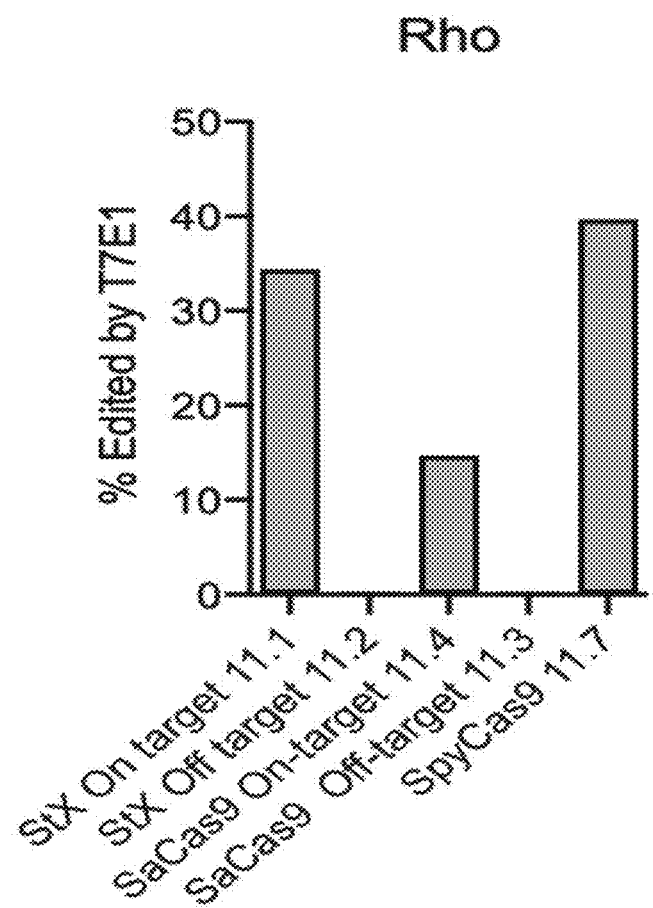
FIG. 17 is a graph quantifying the results of the T7E1 assay.

CasX Variant 457: Following the same expression and purification scheme for WT CasX, the following results were obtained for CasX variant 457. Samples from throughout the purification procedure were resolved by SDS-PAGE and visualized by colloidal Coomassie staining, as shown in FIGS. 12 and 14 and gel filtration, as shown in FIG. 13. The average yield was 9.76 mg of purified CasX protein per liter of culture at 91.6% purity, as evaluated by colloidal Coomassie staining.

Overall, the results support that CasX variants can be produced and recovered at high levels of purity sufficient for experimental assays and evaluation.

TABLE 6

Sequences of CasX 119, 438 and 457

| Construct | DNA Sequence | Amino Acid Sequence |
|---|---|---|
| CasX 119 | (SEQ ID NO: 240) | QEIKRINKIRRRLVKDSNTKKAGKTGPMKTLLVRVMTPDLR ERLENLRKKPENIPQPISNTSRANLNKLLTDYTEMKKAILHV YWEEFQKDPVGLMSRVAQPAPKNIDQRKLIPVKDGNERLTS SGFACSQCCQPLYVYKLEQVNDKGKPHTNYFGRCNVSEHER LILLSPHKPEANDELVTYSLGKFGQRALDFYSIHVTRESNHPV KPLEQIGGNSCASGPVGKALSDACMGAVASFLTKYQDIILEH QKVIKKNEKRLANLKDIASANGLAFPKITLPPQPHTKEGIEAY NNVVAQIVIWVNLNLWQKLKIGRDEAKPLQRLKGFPSFPLV ERQANEVDWWDMVCNVKKLINEKKEDGKVFWQNLAGYK RQEALRPYLSSEEDRKKGKKFARYQFGDLLLHLEKKHGED WGKVYDEAWERIDKKVEGLSKHIKLEEERRSEDAQSKAALT DWLRAKASFVIEGLKEADKDEFCRCELKLQKWYGDLRGKP FAIEAENSILDISGFSKQYNCAFIWQKDGVKKLNLYLIINYFK GGKLRFKKIKPEAFEANRFYTVINKKSGEIVPMEVNFNFDDP NLIILPLAFGKRQGREFIWNDLLSLETGSLKLANGRVIEKTLY NRRTRQDEPALFVALTFERREVLDSSNIKPMNLIGIDRGENIP AVIALTDPEGCPLSRFKDSLGNPTHILRIGESYKEKQRTIQAK KEVEQRRAGGYSRKYASKAKNLADDMVRNTARDLLYYAV TQDAMLIFENLSRGFGRQGKRTFMAERQYTRMEDWLTAKL AYEGLSKTYLSKTLAQYTSKTCSNCGFTITSADYDRVLEKLK KTATGWMTTINGKELKVEGQITYYNRYKRQNVVKDLSVEL DRLSEESVNNDISSWTKGRSGEALSLLKKRFSHRPVQEKFVC LNCGFETHADEQAALNIARSWLFLRSQEYKKYQTNKTTGNT DKRAFVETWQSFYRKKLKEVWKPAV (SEQ ID NO: 237) |

TABLE 6-continued

Sequences of CasX 119, 438 and 457

| Construct | DNA Sequence | Amino Acid Sequence |
|---|---|---|
| CasX 457 | (SEQ ID NO: 241) | QEIKRINKIRRRLVKDSNTKKAGKTGPMKTLLVRVMTPDLR ERLENLRKKPENIPQPISNTSRANLNKLLTDYTEMKKAILHV YWEEFQKDPVGLMSRVAQPAPKNIDQRKLIPVKDGNERLTS SGFACSQCCQPLYVYKLEQVNDKGKPHTNYFGRCNVSEHER LILLSPHKPEANDELVTYSLGKFGQRALDFYSIHVTRESNHPV KPLEQIGGNSCASGPVGKALSDACMGAVASFLTKYQDIILEH KKVIKKNEKRLANLKDIASANGLAFPKITLPPQPHTKEGIEAY NNVVAQIVIWVNLNLWQKLKIGRDEAKPLQRLKGFPSFPLV ERQANEVDWWDMVCNVKKLINEKKEDGKVFWQNLAGYK RQEALRPYLSSPEDRKKGKKFARYQLGDLLLHLEKKHGED WGKVYDEAWERIDKKVEGLSKHIKLEEERRSEDAQSKAALT DWLRAKASFVIEGLKEADKDEFCRCELKLQKWYGDLRGKP FAIEAENSILDISGFSKQYNCAFIWQKDGVKKLNLYLIINYFK GGKLRFKKIKPEAFEANRFYTVINKKSGEIVPMEVNFNFDDP NLIILPLAFGKRQGREFIWNDLLSLETGSLKLANGRVIEKPLY NRRTRQDEPALFVALTFERREVLDSSNIKPMNLIGVDRGENIP AVIALTDPEGCPLSRFKDSLGNPTHILRIGESYKEKQRTIQAK KEVEQRRAGGYSRKYASKAKNLADDMVRNTARDLLYYAV TQDAMLIFENLSRGFGRQGKRTFMAERQYTRMEDWLTAKL AYEGLSKTYLSKTLAQYTSKTCSNCGFTITSADYDRVLEKLK KTATGWMTTINGKELKVEGQITYYNRRKRQNVVKDLSVEL DRLSEESVNNDISSWTKGRSGEALSLLKKRFSHRPVQEKFVC LNCGFETHADEQAALNIARSWLFLRSQEYKKYQTNKTTGNT DKRAFVETWQSFYRKKLKEVWKPAV (SEQ ID NO: 238) |
| CasX 438 | (SEQ ID NO: 242) | QEIKRINKIRRRLVKDSNTKKAGKTGPMKTLLVRVMTPDLR ERLENLRKKPENIPQPISNTSRANLNKLLTDYTEMKKAILHV YWEEFQKDPVGLMSRVAQPAPKNIDQRKLIPVKDGNERLTS SGFACSQCCQPLYVYKLEQVNDKGKPHTNYFGRCNVSEHER LILLSPHKPEANDELVTYSLGKFGQRALDFYSIHVTRESNHPV KPLEQIGGNSCASGPVGKALSDACMGAVASFLTKYQDIILEH QKVIKKNEKRLANLKDIASANGLAFPKITLPPQPHTKEGIEAY NNVVAQIVIWVNLNLWQKLKIGRDEAKPLQRLKGFPSFPLV ERQANEVDWWDMVCNVKKLINEKKEDGKVFWQNLAGYK RQEALRPYLSSEEDRKKGKKFARYQLGDLLKHLEKKHGED WGKVYDEAWERIDKKVEGLSKHIKLEEERRSEDAQSKAALT DWLRAKASFVIEGLKEADKDEFCRCELKLQKWYGDLRGKP FAIEAENSILDISGFSKQYNCAFIWQKDGVKKLNLYLIINYFK GGKLRFKKIKPEAFEANRFYTVINKKSGEIVPMEVNFNFDDP NLIILPLAFGKRQGREFIWNDLLSLETGSLKLANGRVIEKTLY NRRTRQDEPALFVALTFERREVLDSSNIKPMNLIGVDRGENIP AVIALTDPEGCPLSRFKDSLGNPTHILRIGESYKEKQRTIQAK KEVEQRRAGGYSRKYASKAKNLADDMVRNTARDLLYYAV TQDAMLIFENLSRGFGRQGKRTFMAERQYTRMEDWLTAKL AYEGLSKTYLSKTLAQYTSKTCSNCGFTITSADYDRVLEKLK KTATGWMTTINGKELKVEGQITYYNRRKRQNVVKDLSVEL DRLSEESVNNDISSWTKGRSGEALSLLKKRFSHRPVQEKFVC LNCGFETHADEQAALNIARSWLFLRSQEYKKYQTNKTTGNT DKRAFVETWQSFYRKKLKEVWKPAV (SEQ ID NO: 239) |

Example 3: CasX Construct 488, 491, 515 and 527

In order to generate the CasX 488 construct (sequences in Table 7), the codon-optimized CasX 119 construct (based on the CasX Stx2 construct of Example 1, encoding Planctomycetes CasX SEQ ID NO: 2, with a A708K substitution, a L379R substitution, and a [P793] deletion with fused NLS, and linked guide and non-targeting sequences) was cloned into a destination plasmid (pStX: see FIG. 4) using standard cloning methods. In order to generate the CasX 491 construct (sequences in Table 7), the codon-optimized CasX 484 construct (based on the CasX Stx2 construct of Example 1, encoding Planctomycetes CasX SEQ ID NO: 2, with a A708K substitution, a L379R substitution, a [P793] deletion, a 1658V substitution, and a F399L substitution with fused NLS, and linked guide and non-targeting sequences) was cloned into a destination plasmid (pStX; see FIG. 4) using standard cloning methods. Construct CasX 1 (CasX SEQ ID NO: 1) was cloned into a destination vector using standard cloning methods. To build CasX 488, the CasX 119 construct DNA was PCR amplified using Q5 DNA polymerase according to the manufacturer's protocol, using primers oIC765 and oIC762 (see FIG. 5). To build CasX 491, the codon optimized CasX 484 construct DNA was PCR amplified using Q5 DNA polymerase according to the manufacturer's protocol, using primers oIC765 and oIC762 (see FIG. 5). The CasX 1 construct was PCR amplified using Q5 DNA polymerase according to the manufacturer's protocol, using primers oIC766 and oIC784. Each of the PCR products were purified by gel extraction from a 1% agarose gel (Gold Bio Cat #A-201-500) using Zymoclean™ Gel DNA Recovery Kit according to the manufacturer's protocol. The corresponding fragments were then pieced together using Gibson Assembly® (New England BioLabs Cat #E2621S) following the manufacturer's protocol. Assembled products in pStx1 were transformed into chemically-competent Turbo Competent *E. coli* bacterial cells, plated on LB-Agar plates containing kanamycin. Individual colonies were picked and miniprepped using Qiagen spin Miniprep Kit following the manufacturer's protocol. The resultant plasmids were sequenced using Sanger sequencing to ensure correct assembly. The correct clones were then subcloned into the mammalian expression vector pStx34 using restriction enzyme cloning. The pStx34 backbone and the CasX 488 and 491 clones in pStx1 were digested with XbaI and BamHI respectively. The digested backbone and respective insert fragments were purified by gel extraction from a 1% agarose gel (Gold Bio Cat #A-201-500) using Zymoclean™ Gel DNA Recovery Kit according to the manufacturer's protocol. The clean backbone and insert were then ligated together using T4 Ligase (New England Biolabs Cat #M0202L) according to the manufacturer's protocol. The ligated products were transformed into chemically-competent Turbo Competent *E. coli* bacterial cells, plated on LB-Agar plates containing carbenicillin. Individual colonies were picked and miniprepped using Qiagen spin Miniprep Kit following the manufacturer's protocol. The resultant plasmids were sequenced using Sanger sequencing to ensure correct assembly.

Figure 5:
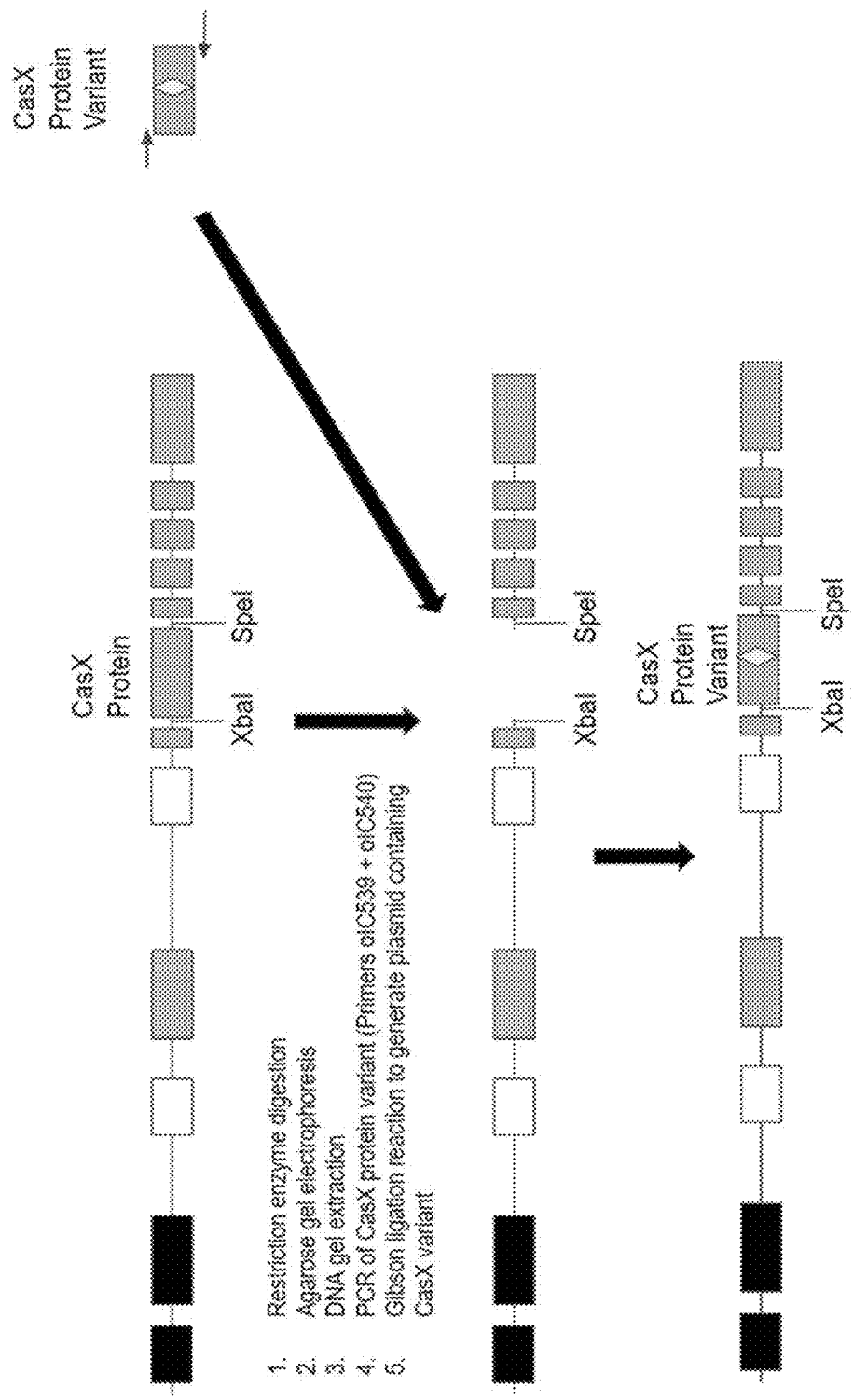
FIG. 5 is a schematic showing the steps of generating the CasX 119 variant, as described in Example 1.

To build CasX 515 (sequences in Table 7), the CasX 491 construct DNA was PCR amplified in two reactions using Q5 DNA polymerase according to the manufacturer's protocol, using primers oIC539 and oSH556 as well as oSH555 and oIC540 respectively (see FIG. 5). To build CasX 527 (sequences in Table 7), the CasX 491 construct DNA was PCR amplified in two reactions using Q5 DNA polymerase according to the manufacturer's protocol, using primers oIC539 and oSH584 as well as oSH583 and oIC540 respectively. The PCR products were purified by gel extraction from a 1% agarose gel using Zymoclean™ Gel DNA Recovery Kit according to the manufacturer's protocol. The pStX backbone was digested using XbaI and SpeI in order to remove the 2931 base pair fragment of DNA between the two sites in plasmid pStx56. The digested backbone fragment was purified by gel extraction from a 1% agarose gel using Zymoclean™ Gel DNA Recovery Kit according to the manufacturer's protocol. The insert and backbone fragments were then pieced together using Gibson Assembly® (New England BioLabs Cat #E2621S) following the manufacturer's protocol. Assembled products in the pStx56 were transformed into chemically-competent Turbo Competent *E. coli* bacterial cells, plated on LB-Agar plates containing kanamycin. Individual colonies were picked and miniprepped using Qiagen spin Miniprep Kit following the manufacturer's protocol. The resultant plasmids were sequenced using Sanger sequencing to ensure correct assembly, pStX34 includes an EF-1α promoter for the protein as well as a selection marker for both puromycin and carbenicillin, pStX56 includes an EF-1α promoter for the protein as well as a selection marker for both puromycin and kanamycin Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase and an appropriate restriction enzyme for the plasmid. Golden Gate products were transformed into chemically or electro-competent cells such as NEB Turbo competent *E. coli* (NEB Cat #C2984I), plated on LB-Agar plates containing the appropriate antibiotic. Individual colonies were picked and miniprepped using QIAprep® Spin Miniprep Kit and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX constructs was performed using the general methodologies of Example 1 and are summarized as follows:

CasX variant 488: following the same expression and purification scheme for WT CasX, the following results were obtained for CasX variant 488. Samples from throughout the purification procedure were resolved by SDS-PAGE and visualized by colloidal Coomassie staining, as well as resolved by gel filtration. The average yield was 2.7 mg of purified CasX protein per liter of culture at 98.8% purity, as evaluated by colloidal Coomassie staining.

CasX Variant 491: following the same expression and purification scheme for WT CasX, the following results were obtained for CasX variant 488. Samples from throughout the purification procedure were resolved by SDS-PAGE and visualized by colloidal Coomassie staining, as well as resolved by gel filtration. The average yield was 12.4 mg of purified CasX protein per liter of culture at 99.4% purity, as evaluated by colloidal Coomassie staining.

CasX variant 515: following the same expression and purification scheme for WT CasX, the following results were obtained for CasX variant 488. Samples from throughout the purification procedure were resolved by SDS-PAGE and visualized by colloidal Coomassie staining, as well as resolved by gel filtration. The average yield was 7.8 mg of purified CasX protein per liter of culture at 87.2% purity, as evaluated by colloidal Coomassie staining.

TABLE 7

Sequences of CasX 488, 491, 515 and 527

| Construct Sequence | DNA Sequence | Amino Acid |
|---|---|---|
| CasX 488 | CAAGAGATCAAGAGAATCAACAAGATCAGAAGG | QEIKRINKIRRRL |
| | AGACTGGTCAAGGACAGCAACACAAAGAAGGCC | VKDSNTKKAGK |
| | GGCAAGACAGGCCCCATGAAaACCCTGCTCGTCA | TGPMKTLLVRV |
| | GAGTGATGACCCCTGACCTGAGAGAGCGGCTGG | MTPDLRERLENL |
| | AAAACCTGAGAAAGAAGCCCGAGAACATCCCTC | RKKPENIPQPISN |
| | AGCCTATCAGCAACACCAGCAGGGCCAACCTGA | TSRANLNKLLTD |
| | ACAAGCTGCTGACCGACTACACCGAGATGAAGA | YTEMKKAILHV |
| | AAGCCATCCTGCACGTGTACTGGGAAGAGTTCCA | YWEEFQKDPVG |
| | GAAAGACCCCGTGGGCCTGATGAGCAGAGTTGCT | LMSRVAQPASK |
| | CAGCCTGCCAGCAAGAAGATCGACCAGAACAAG | KIDQNKLKPEMD |

TABLE 7-continued

Sequences of CasX 488, 491, 515 and 527

| Construct Sequence | DNA Sequence | Amino Acid |
|---|---|---|
| | CTGAAGCCCGAGATGGACGAGAAGGGCAATCTG | EKGNLTTAGFAC |
| | ACCACAGCCGGCTTTGCCTGCTCTCAGTGTGGCC | SQCGQPLFVYKL |
| | AGCCTCTGTTCGTGTACAAGCTGGAACAGGTGTC | EQVSEKGKAYT |
| | CGAGAAAGGCAAGGCCTACACCAACTACTTCGG | NYFGRCNVAEH |
| | CAGATGTAACGTGGCCGAGCACGAGAAGCTGAT | EKLILLAQLKPE |
| | TCTGCTGGCCCAGCTGAAACCTGAGAAGGACTCT | KDSDEAVTYSLG |
| | GATGAGGCCGTGACCTACAGCCTGGGCAAGTTTG | KFGQRALDFYSI |
| | GACAGAGAGCCCTGGACTTCTACAGCATCCACGT | HVTKESTHPVKP |
| | GACCAAAGAAAGCACACACCCCGTGAAGCCCCT | LAQIAGNRYASG |
| | GGCTCAGATCGCCGGCAATAGATACGCCTCTGGA | PVGKALSDACM |
| | CCTGTGGGCAAAGCCCTGTCCGATGCCTGCATGG | GTIASFLSKYQDI |
| | GAACAATCGCCAGCTTCCTGAGCAAGTACCAGGA | IIEHQKVVKGNQ |
| | CATCATCATCGAGCACCAGAAGGTGGTCAAGGG | KRLESLRELAGK |
| | CAACCAGAAGAGACTGGAAAGCCTGAGGGAGCT | ENLEYPSVTLPP |
| | GGCCGGCAAAGAGAACCTGGAATACCCCAGCGT | QPHTKEGVDAY |
| | GACCCTGCCTCCTCAGCCTCACACAAAAGAAGGC | NEVIARVRMWV |
| | GTGGACGCCTACAACGAAGTGATCGCCAGAGTG | NLNLWQKLKLS |
| | AGAATGTGGGTCAACCTGAACCTGTGGCAGAAG | RDDAKPLLRLKG |
| | CTGAAACTGTCCAGGGACGACGCCAAGCCTCTGC | FPSFPLVERQAN |
| | TGAGACTGAAGGGCTTCCCTAGCTTCCCTCTGGT | EVDWWDMVCN |
| | GGAAAGACAGGCCAATGAAGTGGATTGGTGGGA | VKKLINEKKEDG |
| | CATGGTCTGCAACGTGAAGAAGCTGATCAACGA | KVFWQNLAGYK |
| | GAAGAAAGAGGATGGCAAGGTTTTCTGGCAGAA | RQEALRPYLSSE |
| | CCTGGCCGGCTACAAGAGACAAGAAGCCCTGAG | EDRKKGKKFAR |
| | GCCTTACCTGAGCAGCGAAGAGGACCGGAAGAA | YQFGDLLLHLEK |
| | GGGCAAGAAGTTCGCCAGATACCAGTTCGGCGA | KHGEDWGKVYD |
| | CCTGCTGCTGCACCTGGAAAAGAAGCACGGCGA | EAWERIDKKVE |
| | GGACTGGGGCAAAGTGTACGATGAGGCCTGGGA | GLSKHIKLEEER |
| | GAGAATCGACAAGAAGGTGGAAGGCCTGAGCAA | RSEDAQSKAALT |
| | GCACATTAAGCTGGAAGAGGAAAGAAGGAGCGA | DWLRAKASFVIE |
| | GGACGCCCAATCTAAAGCCGCTCTGACCGATTGG | GLKEADKDEFCR |
| | CTGAGAGCCAAGGCCAGCTTTGTGATCGAGGGCC | CELKLQKWYGD |
| | TGAAAGAGGCCGACAAGGACGAGTTCTGCAGAT | LRGKPFAIEAEN |
| | GCGAGCTGAAGCTGCAGAAGTGGTACGGCGATC | SILDISGFSKQYN |
| | TGAGAGGCAAGCCCTTCGCCATTGAGGCCGAGA | CAFIWQKDGVK |
| | ACAGCATCCTGGACATCAGCGGCTTCAGCAAGCA | KLNLYLIINYFK |
| | GTACAACTGCGCCTTCATTTGGCAGAAAGACGGC | GGKLRFKKIKPE |
| | GTCAAGAAACTGAACCTGTACCTGATCATCAATT | AFEANRFYTVIN |
| | ACTTCAAAGGCGGCAAGCTGCGGTTCAAGAAGA | KKSGEIVPMEVN |
| | TCAAACCCGAGGCCTTCGAGGCTAACAGATTCTA | FNFDDPNLIILPL |
| | CACCGTGATCAACAAAAAGTCCGGCGAGATCGT | AFGKRQGREFIW |
| | GCCCATGGAAGTGAACTTCAACTTCGACGACCCC | NDLLSLETGSLK |
| | AACCTGATTATCCTGCCTCTGGCCTTCGGCAAGA | LANGRVIEKTLY |
| | GACAGGGCAGAGAGTTCATCTGGAACGATCTGCT | NRRTRQDEPALF |
| | GAGCCTGGAAACCGGCTCTCTGAAGCTGGCCAAT | VALTFERREVLD |
| | GGCAGAGTGATCGAGAAAACCCTGTACAACAGG | SSNIKPMNLIGID |
| | AGAACCAGACAGGACGAGCCTGCTCTGTTTGTGG | RGENIPAVIALTD |
| | CCCTGACCTTCGAGAGAAGAGAGGTGCTGGACA | PEGCPLSRFKDS |
| | GCAGCAACATCAAGCCCATGAACCTGATCGGCAT | LGNPTHILRIGES |
| | CGACCGGGGCGAGAATATCCCTGCTGTGATCGCC | YKEKQRTIQAKK |
| | CTGACAGACCCTGAAGGATGCCCACTGAGCAGAT | EVEQRRAGGYS |
| | TCAAGGACTCCCTGGGCAACCCTACACACATCCT | RKYASKAKNLA |
| | GAGAATCGGCGAGAGCTACAAAGAGAAGCAGAG | DDMVRNTARDL |
| | GACAATCCAGGCCAAGAAAGAGGTGGAACAGAG | LYYAVTQDAML |
| | AAGAGCCGGCGGATACTCTAGGAAGTACGCCAG | IFENLSRGFGRQ |
| | CAAGGCCAAGAATCTGGCCGACGACATGGTCCG | GKRTFMAERQY |
| | AAACACCGCCAGAGATCTGCTGTACTACGCCGTG | TRMEDWLTAKL |
| | ACACAGGACGCCATGCTGATCTTCGAGAATCTGA | AYEGLSKTYLSK |
| | GCAGAGGCTTCGGCCGGCAGGGCAAGAGAACCT | TLAQYTSKTCSN |
| | TTATGGCCGAGAGGCAGTACACCAGAATGGAAG | CGFTITSADYDR |
| | ATTGGCTCACAGCTAAACTGGCCTACGAGGGACT | VLEKLKKTATG |
| | GAGCAAGACCTACCTGTCCAAAACACTGGCCCAG | WMTTINGKELK |
| | TATACCTCCAAGACCTGCAGCAATTGCGGCTTCA | VEGQITYYNRYK |
| | CCATCACCAGCGCCGACTACGACAGAGTGCTGGA | RQNVVKDLSVE |
| | AAAGCTCAAGAAAACCGCCACCGGCTGGATGAC | LDRLSEESVNND |
| | CACCATCAACGGCAAAGAGCTGAAGGTTGAGGG | ISSWTKGRSGEA |
| | CCAGATCACCTACTACAACAGGTACAAGAGGCA | LSLLKKRFSHRP |
| | GAACGTCGTGAAGGATCTGAGCGTGGAACTGGA | VQEKFVCLNCGF |
| | CAGACTGAGCGAAGAGAGCGTGAACAACGACAT | ETHADEQAALNI |
| | CAGCAGCTGGACAAAGGGCAGATCAGGCGAGGC | ARSWLFLRSQEY |
| | TCTGAGCCTGCTGAAGAAGAggTTTAGCCACAGA | KKYQTNKTTGN |
| | CCTGTGCAAGAAGTTCGTGTGCCTGAACTGCG | TDKRAFVETWQ |
| | GCTTCGAGACACACGCCGATGAACAGGCTGCCCT | SFYRKKLKEVW |
| | GAACATTGCCAGAAGCTGGCTGTTCCTGAGAAGC | KPAV (SEQ ID |
| | CAAGAGTACAAGAAGTACCAGACCAACAAGACC | NO: 243) |

TABLE 7-continued

Sequences of CasX 488, 491, 515 and 527

| Construct Sequence | DNA Sequence | Amino Acid |
|---|---|---|
| | ACCGGCAACACCGACAAGAGGGCCTTTGTGGAA ACCTGGCAGAGCTTCTACAGAAAAAAGCTGAAA GAAGTCTGGAAGCCCGCCGTG(SEQ ID NO: 247) | |
| CasX 491 | CAAGAGATCAAGAGAATCAACAAGATCAGAAGG AGACTGGTCAAGGACAGCAACACAAAGAAGGCC GGCAAGACAGGCCCCATGAAaACCCTGCTCGTCA GAGTGATGACCCCTGACCTGAGAGAGCGGCTGG AAAACCTGAGAAAGAAGCCCGAGAACATCCCTC AGCCTATCAGCAACACCAGCAGGGCCAACCTGA ACAAGCTGCTGACCGACTACACCGAGATGAAGA AAGCCATCCTGCACGTGTACTGGGAAGAGTTCCA GAAAGACCCCGTGGGCCTGATGAGCAGAGTTGCT CAGCCTGCCAGCAAGAAGATCGACCAGAACAAG CTGAAGCCCGAGATGGACGAGAAGGGCAATCTG ACCACAGCCGGCTTTGCCTGCTCTCAGTGTGGCC AGCCTCTGTTCGTGTACAAGCTGGAACAGGTGTC CGAGAAAGGCAAGGCCTACACCAACTACTTCGG CAGATGTAACGTGGCCGAGCACGAGAAGCTGAT TCTGCTGGCCCAGCTGAAACCTGAGAAGGACTCT GATGAGGCCGTGACCTACAGCCTGGGCAAGTTTG GACAGAGAGCCCTGGACTTCTACAGCATCCACGT GACCAAAGAAAGCACACACCCCGTGAAGCCCCT GGCTCAGATCGCCGGCAATAGATACGCCTCTGGA CCTGTGGGCAAAGCCCTGTCCGATGCCTGCATGG GAACAATCGCCAGCTTCCTGAGCAAGTACCAGGA CATCATCATCGAGCACCAGAAGGTGGTCAAGGG CAACCAGAAGAGACTGGAAAGCCTGAGGGAGCT GGCCGGCAAAGAGAACCTGGAATACCCCAGCGT GACCCTGCCTCCTCAGCCTCACACAAAAGAAGGC GTGGACGCCTACAACGAAGTGATCGCCAGAGTG AGAATGTGGGTCAACCTGAACCTGTGGCAGAAG CTGAAACTGTCCAGGGACGACGCCAAGCCTCTGC TGAGACTGAAGGGCTTCCCTAGCTTCCCTCTGGT GGAAAGACAGGCCAATGAAGTGGATTGGTGGGA CATGGTCTGCAACGTGAAGAAGCTGATCAACGA GAAGAAAGAGGATGGCAAGGTTTTCTGGCAGAA CCTGGCCGGCTACAAGAGACAAGAAGCCCTGAG GCCTTACCTGAGCAGCGAAGAGGACCGGAAGAA GGGCAAGAAGTTCGCCAGATACCAGCTGGGCGA CCTGCTGCTGCACCTGGAAAAGAAGCACGGCGA GGACTGGGGCAAAGTGTACGATGAGGCCTGGGA GAGAATCGACAAGAAGGTGGAAGGCCTGAGCAA GCACATTAAGCTGGAAGAGGAAAGAAGGAGCGA GGACGCCCAATCTAAAGCCGCTCTGACCGATTGG GTGGACATTAAGCTGGAAGAGGAAAGAAGGAGCGA GGACGCCCAATCTAAAGCCGCTCTGACCGATTGG CTGAGAGCCAAGGCCAGCTTTGTGATCGAGGGCC TGAAAGAGGCCGACAAGGACGAGTTCTGCAGAT GCGAGCTGAAGCTGCAGAAGTGGTACGGCGATC TGAGAGGCAAGCCCTTCGCCATTGAGGCCGAGA ACAGCATCCTGGACATCAGCGGCTTCAGCAAGCA GTACAACTGCGCCTTCATTTGGCAGAAAGACGGC GTCAAGAAACTGAACCTGTACCTGATCATCAATT ACTTCAAAGGCGGCAAGCTGCGGTTCAAGAAGA TCAAACCCGAGGCCTTCGAGGCTAACAGATTCTA CACCGTGATCAACAAAAAGTCCGGCGAGATCGT GCCCATGGAAGTGAACTTCAACTTCGACGACCCC AACCTGATTATCCTGCCTCTGGCCTTCGGCAAGA GACAGGGCAGAGAGTTCATCTGGAACGATCTGCT GAGCCTGGAAACCGGCTCTCTGAAGCTGGCCAAT GGCAGAGTGATCGAGAAAACCCTGTACAACAGG AGAACCAGACAGGACGAGCCTGCTCTGTTTGTGG CCCTGACCTTCGAGAGGAAGAGGTGCTGGACA GCAGCAACATCAAGCCCATGAACCTGATCGGCGT GGACCGGGGCGAGAATATCCCTGCTGTGATCGCC CTGACAGACCCTGAAGGATGCCCACTGAGCAGAT TCAAGGACTCCCTGGGCAACCCTACACACATCCT GAGAATCGGCGAGAGCTACAAAGAGAAGCAGAG GACAATCCAGGCCAAGAAAGAGGTGGAACAGAG AAGAGCCGGCGGATACTCTAGGAAGTACGCCAG CAAGGCCAAGAATCTGGCCGACAAGAATGGTCCG AAACACCGCCAGAGATCTGCTGTACTACGCCGTG ACACAGGACGCCATGCTGATCTTCGAGAATCTGA GCAGAGGCTTCGGCCGGCAGGGCAAGAGAACCT TTATGGCCGAGAGGCAGTACACCAGAATGGAAG ATTGGCTCACAGCTAAACTGGCCTACGAGGGACT | QEIKRINKIRRRL VKDSNTKKAGK TGPMKTLLVRV MTPDLRERLENL RKKPENIPQPISN TSRANLNKLLTD YTEMKKAILHV YWEEFQKDPVG LMSRVAQPASK KIDQNKLKPEMD EKGNLTTAGFAC SQCGQPLFVYKL EQVSEKGKAYT NYFGRCNVAEH EKLILLAQLKPE KDSDEAVTYSLG KFGQRALDFYSI HVTKESTHPVKP LAQIAGNRYASG PVGKALSDACM GTIASFLSKYQDI IIEHQKVVKGNQ KRLESLRELAGK ENLEYPSVTLPP QPHTKEGVDAY NEVIARVRMWV NLNLWQKLKLS RDDAKPLLRLKG FPSFPLVERQAN EVDWWDMVCN VKKLINEKKEDG KVFWQNLAGYK RQEALRPYLSSE EDRKKGKKFAR YQLGDLLLHLEK KHGEDWGKVYD EAWERIDKKVE GLSKHIKLEEER RSEDAQSKAALT DWLRAKASFVIE GLKEADKDEFCR CELKLQKWYGD LRGKPFAIEAEN SILDISGFSKQYN CAFIWQKDGVK KLNLYLIINYFK GGKLRFKKIKPE AFEANRFYTVIN KKSGEIVPMEVN FNFDDPNLIILPL AFGKRQGREFIW NDLLSLETGSLK LANGRVIEKTLY NRRTRQDEPALF VALTFERREVLD SSNIKPMNLIGV DRGENIPAVIALT DPEGCPLSRFKD SLGNPTHILRIGE SYKEKQRTIQAK KEVEQRRAGGY SRKYASKAKNL ADDMVRNTARD LLYYAVTQDAM LIFENLSRGFGRQ GKRTFMAERQY TRMEDWLTAKL AYEGLSKTYLSK TLAQYTSKTCSN CGFTITSADYDR VLEKLKKTATG |

TABLE 7-continued

Sequences of CasX 488, 491, 515 and 527

| Construct Sequence | DNA Sequence | Amino Acid |
|---|---|---|
| | GAGCAAGACCTACCTGTCCAAAACACTGGCCCAG<br>TATACCTCCAAGACCTGCAGCAATTGCGGCTTCA<br>CCATCACCAGCGCCGACTACGACAGAGTGCTGGA<br>AAAGCTCAAGAAAACCGCCACCGGCTGGATGAC<br>CACCATCAACGGCAAAGAGCTGAAGGTTGAGGG<br>CCAGATCACCTACTACAACAGGTACAAGAGGCA<br>GAACGTCGTGAAGGATCTGAGCGTGGAACTGGA<br>CAGACTGAGCGAAGAGAGCGTGAACAACGACAT<br>CAGCAGCTGGACAAAGGGCAGATCAGGCGAGGC<br>TCTGAGCCTGCTGAAGAAGAggTTTAGCCACAGA<br>CCTGTGCAAGAGAAGTTCGTGTGCCTGAACTGCG<br>GCTTCGAGACACACGCCGATGAACAGGCTGCCCT<br>GAACATTGCCGAAGCTGGCTGTTCCTGAGAAGC<br>CAAGAGTACAAGAAGTACCAGACCAACAAGACC<br>ACCGGCAACACCGACAAGAGGGCCTTTGTGGAA<br>ACCTGGCAGAGCTTCTACAGAAAAAAGCTGAAA<br>GAAGTCTGGAAGCCCGCCGTG (SEQ ID NO: 248) | WMTTINGKELK<br>VEGQITYYNRYK<br>RQNVVKDLSVE<br>LDRLSEESVNND<br>ISSWTKGRSGEA<br>LSLLKKRFSHRP<br>VQEKFVCLNCGF<br>ETHADEQAALNI<br>ARSWLFLRSQEY<br>KKYQTNKTTGN<br>TDKRAFVETWQ<br>SFYRKKLKEVW<br>KPAV (SEQ ID NO: 244) |
| CasX 515 | CAAGAGATCAAGAGAATCAACAAGATCAGAAGG<br>AGATGGTCAAGGACAGCAACACAAAGAAGGCC<br>GGCAAGACAGGCCCCATGAAaCCCTGCTCGTCA<br>GAGTGATGACCCCTGACCTGAGAGAGCGGCTGG<br>AAAACCTGAGAAAGAAGCCCGAGAACATCCCTC<br>AGCCTATCAGCAACACCAGCAGGGCCAACCTGA<br>ACAAGCTGCTGACCGACTACACCGAGATGAAGA<br>AAGCCATCCTGCACGTGTACTGGGAAGAGTTCCA<br>GAAAGACCCCGTGGGCCTGATGAGCAGAGTTGCT<br>CAGCCTGCCAGCAAGAAGATCGACCAGAACAAG<br>CTGAAGCCCGAGATGGACGAGAAGGGCAATCTG<br>ACCACAGCCGGCTTTGCCTGCTCTCAGTGTGGCC<br>AGCCTCTGTTCGTGTACAAGCTGGAACAGGTGTC<br>CGAGAAAGGCAAGGCCTACACCAACTACTTCGG<br>CAGATGTAACGTGGCCGAGCACGAGAAGCTGAT<br>TCTGCTGGCCCAGCTGAAACCTGAGAAGGACTCT<br>GATGAGGCCGTGACCTACAGCCTGGGCAAGTTTG<br>GACAGAGAGCCCTGGACTTCTACAGCATCCACGT<br>GACCAAAGAAAGCACACACCCCGTGAAGCCCCT<br>GGCTCAGATCGCCGGCAATAGATACGCCTCTGGA<br>CCTGTGGGCAAAGCCCTGTCCGATGCCTGCATGG<br>GAACAATCGCCAGCTTCCTGAGCAAGTACCAGGA<br>CATCATCATCGAGCACCAGAAGGTGGTCAAGGG<br>CAACCAGAAGAGACTGGAAAGCCTGAGGGAGCT<br>GGCCGGCAAAGAGAACCTGGAATACCCCAGCGT<br>GACCCTGCCTCCTCAGCCTCACACAAAAGAAGGC<br>GTGGACGCCTACAACGAAGTGATCGCCAGAGTG<br>AGAATGTGGGTCAACCTGAACCTGTGGCAGAAG<br>CTGAAACTGTCCAGGGACGACGCCAAGCCTCTGC<br>TGAGACTGAAGGGCTTCCCTAGCTTCCCTCTGGT<br>GGAAAGACAGGCCAATGAAGTGGATTGGTGGGA<br>CATGGTCTGCAACGTGAAGAAGCTGATCAACGA<br>GAAGAAAGAGGATGGCAAGGTTTTCTGGCAGAA<br>CCTGGCCGGCTACAAGAGACAAGAAGCCCTGAG<br>GCCTTACCTGAGCAGCGAAGAGGACCGGAAGAA<br>GGGCAAGAAGTTCGCCAGATACCAGCTGGGCGA<br>CCTGCTGCTGCACCTGGAAAAGAAGCACGGCGA<br>GGACTGGGGCAAAGTGTACGATGAGGCCTGGGA<br>GAGAATCGACAAGAAGGTGGAAGGCCTGAGCAA<br>GCACATTAAGCTGGAAGAGGAAAGAAGGAGCGA<br>GGACGCCCAATCTAAAGCCGCTCTGACCGATTGG<br>CTGAGAGCCAAGGCCAGCTTTGTGATCGAGGGCC<br>TGAAAGAGGCCGACAAGGACGAGTTCTGCAGAT<br>GCGAGCTGAAGCTGCAGAAGTGGTACGGCGATC<br>TGAGAGGCAAGCCCTTCGCCATTGAGGCCGAGA<br>ACAGCATCCTGGACATCAGCGGCTTCAGCAAGCA<br>GTACAACTGCGCCTTCATTTGGCAGAAAGACGGC<br>GTCAAGAAACTGAACCTGTACCTGATCATCAATT<br>ACTTCAAAGGCGGCAAGCTGCGGTTCAAGAAGA<br>TCAAACCCGAGGCCTTCGAGGCTAACAGATTCTA<br>CACCGTGATCAACAAAAGTCCGGCGAGATCGT<br>GCCCATGGAAGTGAACTTCAACTTCGACGACCCC<br>AACCTGATTATCCTGCCTCTGGCCTTCGGCAAGA<br>GACAGGGCAGAGAGTTCATCTGGAACGATCTGCT<br>GAGCCTGGAAACCGGCTCTCTGAAGCTGGCCAAT<br>GGCAGAGTGATCGAGAAACCCTGTACAACAGG<br>AGAACCAGACAGGACGAGCCTGCTCTGTTTGTGG | QEIKRINKIRRRL<br>VKDSNTKKAGK<br>TGPMKTLLVRV<br>MTPDLRERLENL<br>RKKPENIPQPISN<br>TSRANLNKLLTD<br>YTEMKKAILHV<br>YWEEFQKDPVG<br>LMSRVAQPASK<br>KIDQNKLKPEMD<br>EKGNLTTAGFAC<br>SQCGQPLFVYKL<br>EQVSEKGKAYT<br>NYFGRCNVAEH<br>EKLILLAQLKPE<br>KDSDEAVTYSLG<br>KFGQRALDFYSI<br>HVTKESTHPVKP<br>LAQIAGNRYASG<br>PVGKALSDACM<br>GTIASFLSKYQDI<br>IIEHQKVVKGNQ<br>KRLESLRELAGK<br>ENLEYPSVTLPP<br>QPHTKEGVDAY<br>NEVIARVRMWV<br>NLNLWQKLKLS<br>RDDAKPLLRLKG<br>FPSFPLVERQAN<br>EVDWWDMVCN<br>VKKLINEKKEDG<br>KVFWQNLAGYK<br>RQEALRPYLSSE<br>EDRKKGKKFAR<br>YQLGDLLLHLEK<br>KHGEDWGKVYD<br>EAWERIDKKVE<br>GLSKHIKLEEER<br>RSEDAQSKAALT<br>DWLRAKASFVIE<br>GLKEADKDEFCR<br>CELKLQKWYGD<br>LRGKPFAIEAEN<br>SILDISGFSKQYN<br>CAFIWQKDGVK<br>KLNLYLIINYFK<br>GGKLRFKKIKPE<br>AFEANRFYTVIN<br>KKSGEIVPMEVN<br>FNFDDPNLIILPL<br>AFGKRQGREFIW<br>NDLLSLETGSLK<br>LANGRVIEKTLY<br>NRRTQDEPALF<br>VALTFERREVLD<br>SSNIKPMNLIGV<br>DRGENIPAVIALT |

TABLE 7-continued

Sequences of CasX 488, 491, 515 and 527

| Construct Sequence | DNA Sequence | Amino Acid |
|---|---|---|
| | CCCTGACCTTCGAGAGAAGAGAGGTGCTGGACA GCAGCAACATCAAGCCCATGAACCTGATCGGCGT GGACCGGGGCGAGAATATCCCTGCTGTGATCGCC CTGACAGACCCTGAAGGATGCCCACTGAGCAGAT TCAAGGACTCCCTGGGCAACCCTACACACATCCT GAGAATCGGCGAGAGCTACAAAGAGAAGCAGAG GACAATCCAGGCCAAGAAAGAGGTGGAACAGAG AAGAGCCGGCGGATACTCTAGGAAGTACGCCAG CAAGGCCAAGAATCTGGCCGACGACATGGTCCG AAACACCGCCAGAGATCTGCTGTACTACGCCGTG ACACAGGACGCCATGCTGATCTTCGAGAATCTGA GCAGAGGCTTCGGCCGGCAGGGCAAGAGAACCT TTATGGCCGAGAGGCAGTACACCAGAATGGAAG ATTGGCTCACAGCTAAACTGGCCTACGAGGGACT GCCCAGCAAGACCTACCTGTCCAAAACACTGGCC CAGTATACCTCCAAGACCTGCAGCAATTGCGGCT TCACCATCACCAGCGCCGACTACGACAGAGTGCT GGAAAAGCTCAAGAAAACCGCCACCGGCTGGAT GACCACCATCAACGGCAAAGAGCTGAAGGTTGA GGGCCAGATCACCTACTACAACAGGTACAAGAG GCAGAACGTCGTGAAGGATCTGAGCGTGGAACT GGACAGACTGAGCGAAGAGAGCGTGAACAACGA CATCAGCAGCTGGACAAAGGGCAGATCAGGCGA GGCTCTGAGCCTGCTGAAGAAGAggTTTAGCCAC AGACCTGTGCAAGAGAAGTTCGTGTGCCTGAACT GCGGCTTCGAGACACACGCCGATGAACAGGCTG CCCTGAACATTGCCAGAAGCTGGCTGTTCCTGAG AAGCCAAGAGTACAAGAAGTACCAGACCAACAA GACCACCGGCAACACCGACAAGAGGGCCTTTGT GGAAACCTGGCAGAGCTTCTACAGAAAAAAGCT GAAAGAAGTCTGGAAGCCCGCCGTG (SEQ ID NO: 249) | DPEGCPLSRFKD SLGNPTHILRIGE SYKEKQRTIQAK KEVEQRRAGGY SRKYASKAKNL ADDMVRNTARD LLYYAVTQDAM LIFENLSRGFGRQ GKRTFMAERQY TRMEDWLTAKL AYEGLPSKTYLS KTLAQYTSKTCS NCGFTITSADYD RVLEKLKKTATG WMTTINGKELK VEGQITYYNRYK RQNVVKDLSVE LDRLSEESVNND ISSWTKGRSGEA LSLLKKRFSHRP VQEKFVCLNCGF ETHADEQAALNI ARSWLFLRSQEY KKYQTNKTTGN TDKRAFVETWQ SFYRKKLKEVW KPAV (SEQ ID NO: 245) |
| CasX 527 | CAAGAGATCAAGAGAATCAACAAGATCAGAAGG AGACTGGTCAAGGACAGCAACACAAAGAAGGCC GGCAAGACAcggGGCCCCATGAAaACCCTGCTCGT CAGAGTGATGACCCCTGACCTGAGAGAGCGGCT GGAAAACCTGAGAAAGAAGCCCGAGAACATCCC TCAGCCTATCAGCAACACCAGCAGGGCCAACCTG AACAAGCTGCTGACCGACTACACCGAGATGAAG AAAGCCATCCTGCACGTGTACTGGGAAGAGTTCC AGAAAGACCCCGTGGGCCTGATGAGCAGAGTTG CTCAGCCTGCCAGCAAGAAGATCGACCAGAACA AGCTGAAGCCCGAGATGGACGAGAAGGGCAATC TGACCACAGCCGGCTTTGCCTGCTCTCAGTGTGG CCAGCCTCTGTTCGTGTACAAGCTGGAACAGGTG TCCGAGAAAGGCAAGGCCTACACCAACTACTTCG GCAGATGTAACGTGGCCGAGCACGAGAAGCTGA TTCTGCTGGCCCAGCTGAAACCTGAGAAGGACTC TGATGAGGCCGTGACCTACAGCCTGGGCAAGTTT GGACAGAGAGCCCTGGACTTCTACAGCATCCACG TGACCAAAGAAAGCACACACCCCGTGAAGCCCC TGGCTCAGATCGCCGGCAATAGATACGCCTCTGG ACCTGTGGGCAAAGCCCTGTCCGATGCCTGCATG GGAACAATCGCCAGCTTCCTGAGCAAGTACCAGG ACATCATCATCGAGCACCAGAAGGTGGTCAAGG GCAACCAGAAGAGACTGGAAAGCCTGAGGGAGC TGGCCGGCAAAGAGAACCTGGAATACCCCAGCG TGACCCTGCCTCCTCAGCCTCACACAAAAGAAGG CGTGGACGCCTACAACGAAGTGATCGCCAGAGT GAGAATGTGGGTCAACCTGAACCTGTGGCAGAA GCTGAAACTGTCCAGGGACGACGCCAAGCCTCTG CTGAGACTGAAGGGCTTCCCTAGCTTCCCTCTGG TGGAAAGACAGGCCAATGAAGTGGATTGGTGGG ACATGGTCTGCAACGTGAAGAAGCTGATCAACG AGAAGAAAGAGGATGGCAAGGTTTTCTGGCAGA ACCTGGCCGGCTACAAGAGACAAGAAGCCCTGA GGCCTTACCTGAGCAGCGAAGAGGACCGGAAGA AGGGCAAGAAGTTCGCCAGATACCAGCTGGGCG ACCTGCTGCTGCACCTGGAAAAGAAGCACGGCG AGGACTGGGGCAAAGTGTACGATGAGGCCTGGG AGAGAATCGACAAGAAGGTGGAAGCCTGAGCA AGCACATTAAGCTGGAAGAGGAAAGAAGGAGCG AGGACGCCCAATCTAAAGCCGCTCTGACCGATTG GCTGAGAGCCAAGGCCAGCTTTGTGATCGAGGGC | QEIKRINKIRRRL VKDSNTKKAGK TRGPMKTLLVR VMTPDLRERLEN LRKKPENIPQPIS NTSRANLNKLLT DYTEMKKAILH VYWEEFQKDPV GLMSRVAQPAS KKIDQNKLKPEM DEKGNLTTAGFA CSQCGQPLFVYK LEQVSEKGKAYT NYFGRCNVAEH EKLILLAQLKPE KDSDEAVTYSLG KFGQRALDFYSI HVTKESTHPVKP LAQIAGNRYASG PVGKALSDACM GTIASFLSKYQDI IIEHQKVVKGNQ KRLESLRELAGK ENLEYPSVTLPP QPHTKEGVDAY NEVIARVRMWV NLNLWQKLKLS RDDAKPLLRLKG FPSFPLVERQAN EVDWWDMVCN VKKLINEKKEDG KVFWQNLAGYK RQEALRPYLSSE EDRKKGKKFAR YQLGDLLLHLEK KHGEDWGKVYD EAWERIDKKVE GLSKHIKLEEER RSEDAQSKAALT DWLRAKASFVIE GLKEADKDEFCR CELKLQKWYGD |

TABLE 7-continued

Sequences of CasX 488, 491, 515 and 527

| Construct Sequence | DNA Sequence | Amino Acid |
|---|---|---|
| | CTGAAAGAGGCCGACAAGGACGAGTTCTGCAGA | LRGKPFAIEAEN |
| | TGCGAGCTGAAGCTGCAGAAGTGGTACGGCGAT | SILDISGFSKQYN |
| | CTGAGAGGCAAGCCCTTCGCCATTGAGGCCGAGA | CAFIWQKDGVK |
| | ACAGCATCCTGGACATCAGCGGCTTCAGCAAGCA | KLNLYLIINYFK |
| | GTACAACTGCGCCTTCATTTGGCAGAAAGACGGC | GGKLRFKKIKPE |
| | GTCAAGAAACTGAACCTGTACCTGATCATCAATT | AFEANRFYTVIN |
| | ACTTCAAAGGCGGCAAGCTGCGGTTCAAGAAGA | KKSGEIVPMEVN |
| | TCAAACCCGAGGCCTTCGAGGCTAACAGATTCTA | FNFDDPNLIILPL |
| | CACCGTGATCAACAAAAAGTCCGGCGAGATCGT | AFGKRQGREFIW |
| | GCCCATGGAAGTGAACTTCAACTTCGACGACCCC | NDLLSLETGSLK |
| | AACCTGATTATCCTGCCTCTGGCCTTCGGCAAGA | LANGRVIEKTLY |
| | GACAGGGCAGAGAGTTCATCTGGAACGATCTGCT | NRRTRQDEPALF |
| | GAGCCTGGAAACCGGCTCTCTGAAGCTGGCCAAT | VALTFERREVLD |
| | GGCAGAGTGATCGAGAAAACCCTGTACAACAGG | SSNIKPMNLIGV |
| | AGAACCAGACAGGACGAGCCTGCTCTGTTTGTGG | DRGENIPAVIALT |
| | CCCTGACCTTCGAGAGAAGAGAGGTGCTGGACA | DPEGCPLSRFKD |
| | GCAGCAACATCAAGCCCATGAACCTGATCGGCGT | SLGNPTHILRIGE |
| | GGACCGGGGCGAGAATATCCCTGCTGTGATCGCC | SYKEKQRTIQAK |
| | CTGACAGACCCTGAAGGATGCCCACTGAGCAGAT | KEVEQRRAGGY |
| | TCAAGGACTCCCTGGGCAACCCTACACACATCCT | SRKYASKAKNL |
| | GAGAATCGGCGAGAGCTACAAAGAGAAGCAGAG | ADDMVRNTARD |
| | GACAATCCAGGCCAAGAAAGAGGTGGAACAGAG | LLYYAVTQDAM |
| | AAGAGCCGGCGGATACTCTAGGAAGTACGCCAG | LIFENLSRGFGRQ |
| | CAAGGCCAAGAATCTGGCCGACGACATGGTCCG | GKRTFMAERQY |
| | AAACACCGCCAGAGATCTGCTGTACTACGCCGTG | TRMEDWLTAKL |
| | ACACAGGACGCCATGCTGATCTTCGAGAATCTGA | AYEGLSKTYLSK |
| | GCAGAGGCTTCGGCCGGCAGGGCAAGAGAACCT | TLAQYTSKTCSN |
| | TTATGGCCGAGAGGCAGTACACCAGAATGGAAG | CGFTITSADYDR |
| | ATTGGCTCACAGCTAAACTGGCCTACGAGGGACT | VLEKLKKTATG |
| | GAGCAAGACCTACCTGTCCAAAACACTGGCCCAG | WMTTINGKELK |
| | TATACCTCCAAGACCTGCAGCAATTGCGGCTTCA | VEGQITYYNRYK |
| | CCATCACCAGCGCCGACTACGACAGAGTGCTGGA | RQNVVKDLSVE |
| | AAAGCTCAAGAAAACCCACCGGCTGGATGAC | LDRLSEESVNND |
| | CACCATCAACGGCAAAGAGCTGAAGGTTGAGGG | ISSWTKGRSGEA |
| | CCAGATCACCTACTACAACAGGTACAAGAGGCA | LSLLKKRFSHRP |
| | GAACGTCGTGAAGGATCTGAGCGTGGAACTGGA | VQEKFVCLNCGF |
| | CAGACTGAGCGAAGAGAGCGTGAACAACGACAT | ETHADEQAALNI |
| | CAGCAGCTGGACAAAGGGCAGATCAGGCGAGGC | ARSWLFLRSQEY |
| | TCTGAGCCTGCTGAAGAAGAggTTTAGCCACAGA | KKYQTNKTTGN |
| | CCTGTGCAAGAGAAGTTCGTGTGCCTGAACTGCG | TDKRAFVETWQ |
| | GCTTCGAGACACACGCCGATGAACAGGCTGCCCT | SFYRKKLKEVW |
| | GAACATTGCCAGAAGCTGGCTGTTCCTGAGAAGC | KPAV (SEQ ID |
| | CAAGAGTACAAGAAGTACCAGACCAACAAGACC | NO: 246) |
| | ACCGGCAACACCGACAAGAGGGCCTTTGTGGAA | |
| | ACCTGGCAGAGCTTCTACAGAAAAAAGCTGAAA | |
| | GAAGTCTGGAAGCCCGCCGTG (SEQ ID NO: 250) | |

Example 4: Design and Generation of CasX Constructs 278-280, 285-288, 290, 291, 293, 300, 492, and 493

In order to generate the CasX 278-280, 285-288, 290, 291, 293, 300, 492, and 493 constructs (sequences in Table 8), the N- and C-termini of the codon-optimized CasX 119 construct (based on the CasX Stx37 construct of Example 2, encoding Planctomycetes CasX SEQ ID NO: 2, with a A708K substitution and a [P793] deletion with fused NLS, and linked guide and non-targeting sequences) in a mammalian expression vector were manipulated to delete or add NLS sequences (sequences in Table 9). Constructs 278, 279, and 280 were manipulations of the N- and C-termini using only an SV40 NLS sequence. Construct 280 had no NLS on the N-terminus and added two SV40 NLS' on the C-terminus with a triple proline linker in between the two SV40 NLS sequences. Constructs 278, 279, and 280 were made by amplifying pStx34.119.174.NT with Q5 DNA polymerase according to the manufacturer's protocol, using primers oIC527 and oIC528, oIC730 and oIC522, and oIC730 and oIC530 for the first fragments each and using oIC529 and oIC520, oIC519 and oIC731, and oIC529 and oIC731 to create the second fragments each. These fragments were purified by gel extraction from a 1% agarose gel using Zymoclean™ Gel DNA Recovery Kit according to the manufacturer's protocol. The respective fragments were cloned together using Gibson Assembly® (New England BioLabs Cat #E2621S) following the manufacturer's protocol. Assembled products in the pStx34 were transformed into chemically-competent Turbo Competent E. coli bacterial cells, plated on LB-Agar plates containing carbenicillin and incubated at 37° C. Individual colonies were picked and miniprepped using Qiagen spin Miniprep Kit following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically- or electro-competent cells such as NEB Turbo competent *E. coli* (NEB Cat #C29841), plated on LB-Agar plates containing carbenicillin and incubated at 37° C. Individual colonies were picked and miniprepped using Qiagen spin Miniprep Kit and following the manufacturer's protocol. The resultant plasmids were sequenced using Sanger sequencing to ensure correct ligation.

In order to generate constructs 285-288, 290, 291, 293, and 300, a nested PCR method was used for cloning. The backbone vector and PCR template used was construct pStx34 279.119.174.NT, having the CasX 119, guide 174, and non-targeting spacer (see Examples 8 and 9 and Tables therein for sequences). Construct 278 has the configuration SV40NLS-CasX119. Construct 279 has the configuration CasX119-SV40NLS. Construct 280 has the configuration CasX119-SV40NLS-PPP linker-SV40NLS. Construct 285 has the configuration CasX119-SV40NLS-PPP linker-SynthNLS3. Construct 286 has the configuration CasX119-SV40NLS-PPP linker-SynthNLS4. Construct 287 has the configuration CasX119-SV40NLS-PPP linker-SynthNLS5. Construct 288 has the configuration CasX119-SV40NLS-PPP linker-SynthNLS6. Constrict 290 has the configuration CasX119-SV40NLS-PPP linker-EGL-13 NLS. Construct 291 has the configuration CasX119-SV40NLS-PPP linker-c-Myc NLS. Construct 293 has the configuration CasX119-SV40NLS-PPP linker-Nucleolar RNA Helicase II NLS. Construct 300 has the configuration CasX119-SV40NLS-PPP linker-Influenza A protein NLS. Construct 492 has the configuration SV40NLS-CasX119-SV40NLS-PPP linker-SV40NLS. Construct 493 has the configuration SV40NLS-CasX119-SV40NLS-PPP linker-c-Myc NLS. Each variant had a set of three PCRs: two of which were nested, were purified by gel extraction, digested, and then ligated into the digested and purified backbone. Assembled products in the pStx34 were transformed into chemically-competent Turbo Competent *E. coli* bacterial cells, plated on LB-Agar plates containing carbenicillin and incubated at 37° C. Individual colonies were picked and miniprepped using Qiagen spin Miniprep Kit following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence.

These two oligos were annealed together and cloned into the resulting pStX individually or in bulk by Golden Gate assembly using T4 DNA Ligase (New England BioLabs Cat #M0202L) and an appropriate restriction enzyme for the plasmid. Golden Gate products were transformed into chemically- or electro-competent cells such as NEB Turbo competent *E. coli* (NEB Cat #C29841), plated on LB-Agar plates containing carbenicillin and incubated at 37° C. Individual colonies were picked and miniprepped using Qiagen spin Miniprep Kit and following the manufacturer's protocol. The resultant plasmids were sequenced using Sanger sequencing to ensure correct ligation.

In order to generate constructs 492 and 493, constructs 280 and 291 were digested using XbaI and BamHI (NEB #R0145S and NEB #R3136S) according to the manufacturer's protocol. Next, they were purified by gel extraction from a 1% agarose gel using Zymoclean™ Gel DNA Recovery Kit according to the manufacturer's protocol. Finally, they were ligated using T4 DNA ligase (NEB #M0202S) according to the manufacturer's protocol into the digested and purified pStx34.119.174.NT using XbaI and BamHI and Zymoclean™ Gel DNA Recovery Kit. Assembled products in the pStx34 were transformed into chemically-competent Turbo Competent *E. coli* bacterial cells, plated on LB-Agar plates containing carbenicillin and incubated at 37° C. Individual colonies were picked and miniprepped using Qiagen spin Miniprep Kit following the manufacturer's protocol. The resultant plasmids were sequenced using Sanger sequencing to ensure correct assembly. Sequences encoding the targeting spacer sequences that target the gene of interest were designed based on CasX PAM locations. Targeting sequence DNA was ordered as single-stranded DNA (ssDNA) oligos (Integrated DNA Technologies) consisting of the targeting spacer sequence and the reverse complement of this sequence. These two oligos were annealed together and cloned into each pStX individually or in bulk by Golden Gate assembly using T4 DNA Ligase (New England BioLabs Cat #M0202L) and an appropriate restriction enzyme for the respective plasmids. Golden Gate products were transformed into chemically- or electro-competent cells such as NEB Turbo competent *E. coli* (NEB Cat #C29841), plated on LB-Agar plates containing carbenicillin and incubated at 37° C. Individual colonies were picked and miniprepped using Qiagen spin Miniprep Kit and following the manufacturer's protocol. The resultant plasmids were sequenced using Sanger sequencing to ensure correct ligation. The plasmids would be used to produce and recover CasX protein utilizing the general methodologies of Examples 1 and 2.

TABLE 8

CasX 278-280, 285-288, 290, 291, 293, 300, 492, and 493 sequences

| Construct | Amino Acid Sequence |
|---|---|
| 278 | MAPKKKRKVSRQEIKRINKIRRRLVKDSNTKKAGKTGPMKTLLVRVMTP<br>DLRERLENLRKKPENIPQPISNTSRANLNKLLTDYTEMKKAILHVYWEEF<br>QKDPVGLMSRVAQPAPKNIDQRKLIPVKDGNERLTSSGFACSQCCQPLYV<br>YKLEQVNDKGKPHTNYFGRCNVSEHERLILLSPHKPEANDELVTYSLGKF<br>GQRALDFYSIHVTRESNHPVKPLEQIGGNSCASGPVGKALSDACMGAVAS<br>FLTKYQDIILEHQKVIKKNEKRLANLKDIASANGLAFPKITLPPQPHTKEGI<br>EAYNNVVAQIVIWVNLNLWQKLKIGRDEAKPLQRLKGFPSFPLVERQAN<br>EVDWWDMVCNVKKLINEKKEDGKVFWQNLAGYKRQEALRPYLSSEED<br>RKKGKKFARYQFGDLLLHLEKKHGEDWGKVYDEAWERIDKKVEGLSKH<br>IKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYF<br>KGGKLRFKKIKPEAFEANRFYTVINKKSGEIVPMEVNFNFDDPNLIILPLAF<br>GKRQGREFIWNDLLSLETGSLKLANGRVIEKTLYNRRTRQDEPALFVALT<br>FERREVLDSSNIKPMNLIGIDRGENIPAVIALTDPEGCPLSRFKDSLGNPTHI |

TABLE 8-continued

CasX 278-280, 285-288, 290, 291, 293, 300, 492, and 493 sequences

| Construct | Amino Acid Sequence |
|---|---|
| | LRIGESYKEKQRTIQAKKEVEQRRAGGYSRKYASKAKNLADDMVRNTAR DLLYYAVTQDAMLIFENLSRGFGRQGKRTFMAERQYTRMEDWLTAKLA YEGLSKTYLSKTLAQYTSKTCSNCGFTITSADYDRVLEKLKKTATGWMT TINGKELKVEGQITYYNRYKRQNVVKDLSVELDRLSEESVNNDISSWTKG RSGEALSLLKKRFSHRPVQEKFVCLNCGFETHADEQAALNIARSWLFLRS QEYKKYQTNKTTGNTDKRAFVETWQSFYRKKLKEVWKPAV (SEQ ID NO: 251) |
| 279 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIHV TRESNHPVKPLEQIGGNSCASGPVGKALSDACMGAVASFLTKYQDIILEHQ KVIKKNEKRLANLKDIASANGLAFPKITLPPQPHTKEGIEAYNNVVAQIVI WVNLNLWQKLKIGRDEAKPLQRLKGFPSFPLVERQANEVDWWDMVCNV KKLINEKKEDGKVFWQNLAGYKRQEALRPYLSSEEDRKKGKKFARYQFG DLLLHLEKKHGEDWGKVYDEAWERIDKKVEGLSKHIKLEEERRSEDAQS KAALTDWLRAKASFVIEGLKEADKDEFCRCELKLQKWYGDLRGKPFAIE AENSILDISGFSKQYNCAFIWQKDGVKKLNLYLIINYFKGGKLRFKKIKPE AFEANRFYTVINKKSGEIVPMEVNFNFDDPNLIILPLAFGKRQGREFIWNDL LSLETGSLKLANGRVIEKTLYNRRTRQDEPALFVALTFERREVLDSSNIKP MNLIGIDRGENIPAVIALTDPEGCPLSRFKDSLGNPTHILRIGESYKEKQRTI QAKKEVEQRRAGGYSRKYASKAKNLADDMVRNTARDLLYYAVTQDAM LIFENLSRGFGRQGKRTFMAERQYTRMEDWLTAKLAYEGLSKTYLSKTL AQYTSKTCSNCGFTITSADYDRVLEKLKKTATGWMTTINGKELKVEGQIT YYNRYKRQNVVKDLSVELDRLSEESVNNDISSWTKGRSGEALSLLKKRFS HRPVQEKFVCLNCGFETHADEQAALNIARSWLFLRSQEYKKYQTNKTTG NTDKRAFVETWQSFYRKKLKEVWKPAVTSPKKKRKV (SEQ ID NO: 252) |
| 280 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIHV TRESNHPVKPLEQIGGNSCASGPVGKALSDACMGAVASFLTKYQDIILEHQ KVIKKNEKRLANLKDIASANGLAFPKITLPPQPHTKEGIEAYNNVVAQIVI WVNLNLWQKLKIGRDEAKPLQRLKGFPSFPLVERQANEVDWWDMVCNV KKLINEKKEDGKVFWQNLAGYKRQEALRPYLSSEEDRKKGKKFARYQFG DLLLHLEKKHGEDWGKVYDEAWERIDKKVEGLSKHIKLEEERRSEDAQS KAALTDWLRAKASFVIEGLKEADKDEFCRCELKLQKWYGDLRGKPFAIE AENSILDISGFSKQYNCAFIWQKDGVKKLNLYLIINYFKGGKLRFKKIKPE AFEANRFYTVINKKSGEIVPMEVNFNFDDPNLIILPLAFGKRQGREFIWNDL LSLETGSLKLANGRVIEKTLYNRRTRQDEPALFVALTFERREVLDSSNIKP MNLIGIDRGENIPAVIALTDPEGCPLSRFKDSLGNPTHILRIGESYKEKQRTI QAKKEVEQRRAGGYSRKYASKAKNLADDMVRNTARDLLYYAVTQDAM LIFENLSRGFGRQGKRTFMAERQYTRMEDWLTAKLAYEGLSKTYLSKTL AQYTSKTCSNCGFTITSADYDRVLEKLKKTATGWMTTINGKELKVEGQIT YYNRYKRQNVVKDLSVELDRLSEESVNNDISSWTKGRSGEALSLLKKRFS HRPVQEKFVCLNCGFETHADEQAALNIARSWLFLRSQEYKKYQTNKTTG NTDKRAFVETWQSFYRKKLKEVWKPAVTSPKKKRKVPPPPKKKRKV (SEQ ID NO: 253) |
| 285 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKGK PHTNYFGRCNVSEHERLILLSPHKPEANDELVTYSLGKFGQRALDFYSIHV TRESNHPVKPLEQIGGNSCASGPVGKALSDACMGAVASFLTKYQDIILEHQ KVIKKNEKRLANLKDIASANGLAFPKITLPPQPHTKEGIEAYNNVVAQIVI WVNLNLWQKLKIGRDEAKPLQRLKGFPSFPLVERQANEVDWWDMVCNV KKLINEKKEDGKVFWQNLAGYKRQEALRPYLSSEEDRKKGKKFARYQFG DLLLHLEKKHGEDWGKVYDEAWERIDKKVEGLSKHIKLEEERRSEDAQS KAALTDWLRAKASFVIEGLKEADKDEFCRCELKLQKWYGDLRGKPFAIE AENSILDISGFSKQYNCAFIWQKDGVKKLNLYLIINYFKGGKLRFKKIKPE AFEANRFYTVINKKSGEIVPMEVNFNFDDPNLIILPLAFGKRQGREFIWNDL LSLETGSLKLANGRVIEKTLYNRRTRQDEPALFVALTFERREVLDSSNIKP MNLIGIDRGENIPAVIALTDPEGCPLSRFKDSLGNPTHILRIGESYKEKQRTI QAKKEVEQRRAGGYSRKYASKAKNLADDMVRNTARDLLYYAVTQDAM LIFENLSRGFGRQGKRTFMAERQYTRMEDWLTAKLAYEGLSKTYLSKTL AQYTSKTCSNCGFTITSADYDRVLEKLKKTATGWMTTINGKELKVEGQIT YYNRYKRQNVVKDLSVELDRLSEESVNNDISSWTKGRSGEALSLLKKRFS HRPVQEKFVCLNCGFETHADEQAALNIARSWLFLRSQEYKKYQTNKTTG NTDKRAFVETWQSFYRKKLKEVWKPAVTSPKKKRKVPPPHKKKHPDASV NFSEFSK (SEQ ID NO: 254) |
| 286 | MQEIKRINKIRRRLVKDSNTKKAGKTGPMKTLLVRVMTPDLRERLENLRK KPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKGK |

TABLE 8-continued

CasX 278-280, 285-288, 290, 291, 293, 300, 492, and 493 sequences

| Construct | Amino Acid Sequence |
|---|---|
|  | PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENL SRGF GRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPQRPGPYDRPQ<br>RPGPYDRP (SEQ ID NO: 255) |
| 287 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPLSPSLSPLLSPS<br>LSPL (SEQ ID NO: 256) |
| 288 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTMSSGFACSQCCQPLYVYKLEQVNDKG<br>KPHTNYFGRCNVSEHERLILLSPHKPEANDELVTYSLGKFGQRALDFYSIH<br>VTRESNHPVKPLEQIGGNSCASGPVGKALSDACMGAVASFLTKYQDIILEH<br>QKVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPRGKGGKGLG<br>KGGAKRHRK (SEQ ID NO: 257) |
| 290 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP |

TABLE 8-continued

CasX 278-280, 285-288, 290, 291, 293, 300, 492, and 493 sequences

| Construct | Amino Acid Sequence |
|---|---|
| | MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPSRRRKANPTK<br>LSENAKKLAKEVEN (SEQ ID NO: 258) |
| 291 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPPAAKRVKLD<br>(SEQ ID NO: 259) |
| 293 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPKRSFSKAF<br>(SEQ ID NO: 260) |
| 300 | MQEIKRINKIRRRLVKDSNTKKAGKTGPMKTLLVRVMTPDLRERLENLRK<br>KPENIPQPISNTSRANLNKLLTDYTEMKKAILHVYWEEFQKDPVGLMSRV<br>AQPAPKNIDQRKLIPVKDGNERLTSSGFACSQCCQPLYVYKLEQVNDKGK<br>PHTNYFGRCNVSEHERLILLSPHKPEANDELVTYSLGKFGQRALDFYSIHV<br>TRESNHPVKPLEQIGGNSCASGPVGKALSDACMGAVASFLTKYQDIILEHQ<br>KVIKKNEKRLANLKDIASANGLAFPKITLPPQPHTKEGIEAYNNVVAQIVI<br>WVNLNLWQKLKIGRDEAKPLQRLKGFPSFPLVERQANEVDWWDMVCNV<br>KKLINEKKEDGKVFWQNLAGYKRQEALRPYLSSEEDRKKGKKFARYQFG<br>DLLLHLEKKHGEDWGKVYDEAWERIDKKVEGLSKHIKLEEERRSEDAQS<br>KAALTDWLRAKASFVIEGLKEADKDEFCRCELKLQKWYGDLRGKPFAIE<br>AENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDL<br>LSLETGSLKLANGRVIEKTLYNRRTRQDEPALFVALTFERREVLDSSNIKP<br>MNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAM<br>LIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQIT<br>YYNRYKRQNVVKDLSVELDRLSEESVNNDISSWTKGRSGEALSLLKKRFS<br>HRPVQEKFVCLNCGFETHADEQAALNIARSWLFLRSQEYKKYQTNKTTG<br>NTDKRAFVETWQSFYRKKLKEVWKPAVTSPKKKRKVPPPKRGINDRNFW<br>RGENERKTR (SEQ ID NO: 261) |

TABLE 8-continued

CasX 278-280, 285-288, 290, 291, 293, 300, 492, and 493 sequences

| Construct | Amino Acid Sequence |
|---|---|
| 492 | MAPKKKRKVSRMQEIKRINKIRRRLVKDSNTKKAGKTGPMKTLLVRVMT<br>PDLRERLENLRKKPENIPQPISNTSRANLNKLLTDYTEMKKAILHVYWEEF<br>QKDPVGLMSRVAQPAPKNIDQRKLIPVKDGNERLTSSGFACSQCCQPLYV<br>YKLEQVNDKGKPHTNYFGRCNVSEHERLILLSPHKPEANDELVTYSLGKF<br>GQRALDFYSIHVTRESNHPVKPLEQIGGNSCASGPVGKALSDACMGAVAS<br>FLTKYQDIILEHQKVIKKNEKRLANLKDIASANGLAFPKITLPPQPHTKEGI<br>EAYNNVVAQIVIWVNLNLWQKLKIGRDEAKPLQRLKGFPSFPLVERQANE<br>VDWWDMVCNVKKLINEKKEDGKVFWQNLAGYKRQEALRPYLSSEEDR<br>KKGKKFARYQFGDLLLHLEKKHGEDWGKVYDEAWERIDKKVEGLSKHI<br>KLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYF<br>KGGKLRFKKIKPEAFEANRFYTVINKKSGEIVPMEVNFNFDDPNLIILPLAF<br>GKRQGREFIWNDLLSLETGSLKLANGRVIEKTLYNRRTRQDEPALFVALTF<br>ERREVLDSSNIKPMNLIGIDRGENIPAVIALTDPEGCPLSRFKDSLGNPTHIL<br>RIGESYKEKQRTIQAKKEVEQRRAGGYSRKYASKAKNLADDMVRNTARD<br>LLYYAVTQDAMLIFENLSRGFGRQGKRTFMAERQYTRMEDWLTAKLAY<br>EGLSKTYLSKTLAQYTSKTCSNCGFTITSADYDRVLEKLKKTATGWMTTI<br>NGKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQE<br>YKKYQTNKTTGNTDKRAFVETWQSFYRKKLKEVWKPAVTSPKKKRKVP<br>PPPKKKRKV (SEQ ID NO: 262) |
| 493 | MAPKKKRKVSRMQEIKRINKIRRRLVKDSNTKKAGKTGPMKTLLVRVMT<br>PDLRERLENLRKKPENIPQPISNTSRANLNKLLTDYTEMKKAILHVYWEEF<br>QKDPVGLMSRVAQPAPKNIDQRKLIPVKDGNERLTSSGFACSQCCQPLYV<br>YKLEQVNDKGKPHTNYFGRCNVSEHERLILLSPHKPEANDELVTYSLGKF<br>GQRALDFYSIHVTRESNHPVKPLEQIGGNSCASGPVGKALSDACMGAVAS<br>FLTKYQDIILEHQKVIKKNEKRLANLKDIASANGLAFPKITLPPQPHTKEGI<br>EAYNNVVAQIVIWVNLNLWQKLKIGRDEAKPLQRLKGFPSFPLVERQANE<br>VDWWDMVCNVKKLINEKKEDGKVFWQNLAGYKRQEALRPYLSSEEDR<br>KKGKKFARYQFGDLLLHLEKKHGEDWGKVYDEAWERIDKKVEGLSKHI<br>KLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYF<br>KGGKLRFKKIKPEAFEANRFYTVINKKSGEIVPMEVNFNFDDPNLIILPLAF<br>GKRQGREFIWNDLLSLETGSLKLANGRVIEKTLYNRRTRQDEPALFVALTF<br>ERREVLDSSNIKPMNLIGIDRGENIPAVIALTDPEGCPLSRFKDSLGNPTHIL<br>RIGESYKEKQRTIQAKKEVEQRRAGGYSRKYASKAKNLADDMVRNTARD<br>LLYYAVTQDAMLIFENLSRGFGRQGKRTFMAERQYTRMEDWLTAKLAY<br>EGLSKTYLSKTLAQYTSKTCSNCGFTITSADYDRVLEKLKKTATGWMTTI<br>NGKELKVEGQITYYNRYKRQNVVKDLSVELDRLSEESVNNDISSWTKGRS<br>GEALSLLKKRFSHRPVQEKFVCLNCGFETHADEQAALNIARSWLFLRSQE<br>YKKYQTNKTTGNTDKRAFVETWQSFYRKKLKEVWKPAVTSPKKKRKVP<br>PPPAAKRVKLD (SEQ ID NO: 263) |

TABLE 9

Nuclear localization sequence list

| CasX | NLS | DNA Sequence | Amino Acid Sequence |
|---|---|---|---|
| 278, 279, 280, 492, 493 | SV40 | CCAAAGAAGAAGCGGAAGG TC (SEQ ID NO: 264) | PKKKRKV (SEQ ID NO: 176) |
| 285 | SynthNLS3 | CACAAGAAGAAACATCCAGA CGCATCAGTCAACTTTAGCG AGTTCAGTAAA (SEQ ID NO: 265) | HKKKHPDASVNFSE FSK (SEQ ID NO: 207) |
| 286 | SynthNLS4 | CAGCGCCCTGGGCCTTACGA TAGGCCGCAAAGACCCGGAC CGTATGATCGCCCT (SEQ ID NO: 266) | QRPGPYDRPQRPGP YDRP (SEQ ID NO: 208) |
| 287 | SynthNLS5 | CTCAGCCCGAGTCTTAGTCC ACTGCTTTCCCCGTCCCTGTC TCCACTG (SEQ ID NO: 267) | LSPSLSPLLSPSLSPL (SEQ ID NO: 209) |
| 288 | SynthNLS6 | CGGGGCAAGGGTGGCAAGG GGCTTGGCAAGGGGGGGCA AGAGGCACAGGAAG (SEQ ID NO: 268) | RGKGGKGLGKGGA KRHRK (SEQ ID NO: 210) |

TABLE 9-continued

Nuclear localization sequence list

| CasX | NLS | DNA Sequence | Amino Acid Sequence |
|---|---|---|---|
| 290 | EGL-13 | AGCCGCCGCAGAAAAGCCAA TCCTACAAAACTGTCAGAAA ATGCGAAAAAACTTGCTAAG GAGGTGGAAAAC (SEQ ID NO: 269) | SRRRKANPTKLSEN AKKLAKEVEN (SEQ ID NO: 203) |
| 291 | c-Myc | CCTGCCGCAAAGCGAGTGAA ATTGGAC (SEQ ID NO: 270) | PAAKRVKLD (SEQ ID NO: 178) |
| 293 | Nucleolar RNA Helicase II | AAGCGGTCCTTCAGTAAGGC CTTT (SEQ ID NO: 271) | KRSFSKAF (SEQ ID NO: 199) |
| 300 | Influenza A protein | AAACGGGGAATAAACGACC GGAACTTCTGGCGCGGGGAA AACGAGCGCAAAACCCGA (SEQ ID NO: 272) | KRGINDRNFWRGEN ERKTR (SEQ ID NO: 197) |

Example 5: Design and Generation of CasX Constructs 387,395,485-491, and 494

In order to generate CasX 395, CasX 485, CasX 486, CasX 487, the codon optimized CasX 119 (based on the CasX 37 construct of Example 2, encoding Planctomycetes CasX SEQ ID NO: 2, with a A708K substitution and a [P793] deletion with fused NLS, and linked guide and non-targeting sequences), CasX 435, CasX 438, and CasX 484 (each based on CasX 119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector comprising a KanR marker, colE1 ori, and CasX with fused NLS (pStx1) using standard cloning methods. Gibson primers were designed to amplify the CasX SEQ ID NO: 1 Helical I domain from amino acid 192-331 in its own vector to replace this corresponding region (aa 193-332) on CasX 119, CasX 435, CasX 438, and CasX 484 in pStx1 respectively. The Helical I domain from CasX SEQ ID NO: I was amplified with primers oIC768 and oIC784 using Q5 DNA polymerase according to the manufacturer's protocol. The destination vector containing the desired CasX variant was amplified with primers oIC765 and oIC764 using Q5 DNA polymerase according to the manufacturer's protocol. The two fragments were purified by gel extraction from a 1% agarose gel using Zymoclean™ Gel DNA Recovery Kit according to the manufacturer's protocol. The insert and backbone fragments were then pieced together using Gibson Assembly® (New England BioLabs Cat #E2621S) following the manufacturer's protocol. Assembled products in the pStx1 staging vector were transformed into chemically-competent Turbo Competent E. coli bacterial cells, plated on LB-Agar plates (LB: Teknova Cat #L9315, Agar: Quartzy Cat #214510) containing kanamycin and incubated at 37° C. Individual colonies were picked and miniprepped using Qiagen spin Miniprep Kit following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly.

Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent E. coli (NEB Cat #C29841), plated on LB-Agar plates (LB: Teknova Cat #L9315, Agar: Quartzy Cat #214510) containing carbenicillin and incubated at 37° C. Individual colonies were picked and miniprepped using Qiagen spin Miniprep Kit following the manufacturer's protocol. The resultant plasmids were sequenced using Sanger sequencing to ensure correct ligation.

In order to generate CasX 488, CasX 489, CasX 490, and CasX 491 (sequences in Table 10), the codon optimized CasX 119 (based on the CasX 37 construct of Example 2, encoding Planctomycetes CasX SEQ ID NO: 2, with a A708K substitution and a [P793] deletion with fused NLS, and linked guide and non-targeting sequences), CasX 435, CasX 438, and CasX 484 (each based on CasX119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector that was made up of a KanR marker, colE1 ori, and STX with fused NLS (pStx1) using standard cloning methods. Gibson primers were designed to amplify the CasX Stx1 NTSB domain from amino acid 101-191 and Helical 1 domain from amino acid 192-331 in its own vector to replace this similar region (aa 103-332) on CasX 119. CasX 435, CasX 438, and CasX 484 in pStx1 respectively. The NTSB and Helical I domain from CasX SEQ ID NO: I were amplified with primers oIC766 and oIC784 using Q5 DNA polymerase according to the manufacturer's protocol. The destination vector containing the desired CasX variant was amplified with primers oIC762 and oIC765 using Q5 DNA polymerase according to the manufacturer's protocol. The two fragments were purified by gel extraction from a 1% agarose gel using Zymoclean™ Gel DNA Recovery Kit according to the manufacturer's protocol. The insert and backbone fragments were then pieced together using Gibson Assembly® (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and miniprepped using Qiagen spin Miniprep Kit following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C29841), plated on LB-Agar plates (LB: Teknova Cat #L9315, Agar: Quartzy Cat #214510) containing carbenicillin and incubated at 37° C. Individual colonies were picked and miniprepped using Qiagen spin Miniprep Kit and following the manufacturer's protocol. The resultant plasmids were sequenced using Sanger sequencing to ensure correct ligation.

In order to generate CasX 387 and CasX 494 (sequences in Table 10), the codon optimized CasX 119 (based on the CasX 37 construct of Example 2, encoding Planctomycetes CasX SEQ ID NO: 2, with a A708K substitution and a [P793] deletion with fused NLS, and linked guide and non-targeting sequences) and CasX 484 (based on CasX119 construct of Example 2 encoding Planctomycetes CasX SEQ ID NO: 2, with a L379R substitution, a A708K substitution, and a [P793] deletion with fused NLS, and linked guide and non-targeting sequences) were cloned respectively into a 4 kb staging vector that was made up of a KanR marker, colE1 on, and STX with fused NLS (pStx1) using standard cloning methods. Gibson primers were designed to amplify the CasX Stx1 NTSB domain from amino acid 101-191 in its own vector to replace this similar region (aa 103-192) on CasX 119 and CasX 484 in pStx1 respectively. The NTSB domain from CasX Stx1 was amplified with primers oIC766 and oIC767 using Q5 DNA polymerase according to the manufacturer's protocol. The destination vector containing the desired CasX variant was amplified with primers oIC763 and oIC762 using Q5 DNA polymerase according to the manufacturer's protocol. The two fragments were purified by gel extraction from a 1% agarose gel using Zymoclean™ Gel DNA Recovery Kit according to the manufacturer's protocol. The insert and backbone fragments were then pieced together using Gibson Assembly® (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and miniprepped using Qiagen spin Miniprep Kit following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C29841), plated on LB-Agar plates (LB: Teknova Cat #L9315, Agar: Quartzy Cat #214510) containing carbenicillin and incubated at 37° C. Individual colonies were picked and miniprepped using Qiagen spin Miniprep Kit and following the manufacturer's protocol. The resultant plasmids were sequenced using Sanger sequencing to ensure correct ligation. Sequences of the resulting constructs are listed in Table 10.

TABLE 10

Sequences of CasX 395 and 485-491

| Construct | DNA Sequence | Amino Acid Sequence |
|---|---|---|
| CasX 387 | (SEQ ID NO: 283) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTRE SNHPVKPLEQIGGNSCASGPVGKALSDACMGAVASFLTKYQDII LEHQKVIKKNEKRLANLKDIASANGLAFPKITLPPQPHTKEGIEA YNNVVAQIVIWVNLNLWQKLKIGRDEAKPLQRLKGFPSFPLVE RQANEVDWWDMVCNVKKLINEKKEDGKVFWQNLAGYKRQE ALRPYLSSEEDRKKGKKFARYQFGDLLLHLEKKHGEDWGKVY DEAWERIDKKVEGLSKHIKLEEERRSEDAQSKAALTDWLRAKA SFVIEGLKEADKDEFCRCELKLQKWYGDLRGKPFAIEAENSILDI SGFSKQYNCAFIWQKDGVKKLNLYLIINYFKGGKLRFKKIKPEA FEANRFYTVINKKSGEIVPMEVNFNFDDPNLIILPLAFGKRQGRE FIWNDLLSLETGSLKLANGRVIEKTLYNRRTRQDEPALFVALTF ERREVLDSSNIKPMNLIGIDRGENIPAVIALTDPEGCPLSRFKDSL GNPTHILRIGESYKEKQRTIQAKKEVEQRRAGGYSRKYASKAK NLADDMVRNTARDLLYYAVTQDAMLIFENLSRGFGRQGKRTF |

TABLE 10-continued

Sequences of CasX 395 and 485-491

| Construct | DNA Sequence | Amino Acid Sequence |
|---|---|---|
| | | MAERQYTRMEDWLTAKLAYEGLSKTYLSKTLAQYTSKTCSNC
GFTITSADYDRVLEKLKKTATGWMTTINGKELKVEGQITYYNR
YKRQNVVKDLSVELDRLSEESVNNDISSWTKGRSGEALSLLKK
RFSHRPVQEKFVCLNCGFETHADEQAALNIARSWLFLRSQEYK
KYQTNKTTGNTDKRAFVETWQSFYRKKLKEVWKPAVTSPKKK
RKV (SEQ ID NO: 273) |
| CasX 395 | (SEQ ID NO: 284) | MAPKKKRKVSRQEIKRINKIRRRLVKDSNTKKAGKTGPMKTLL
VRVMTPDLRERLENLRKKPENIPQPISNTSRANLNKLLTDYTEM
KKAILHVYWEEFQKDPVGLMSRVAQPAPKNIDQRKLIPVKDGN
ERLTSSGFACSQCCQPLYVYKLEQVNDGKPHTNYFGRCNVSE
HERLILLSPHKPEANDELVTYSLGKFGQRALDFYSIHVTKESTHP
VKPLAQIAGNRYASGPVGKALSDACMGTIASFLSKYQDIIIEHQ
KVVKGNQKRLESLRELAGKENLEYPSVTLPPQPHTKEGVDAYN
EVIARVRMWVNLNLWQKLKLSRDDAKPLLRLKGFPSFPLVERQ
ANEVDWWDMVCNVKKLINEKKEDGKVFWQNLAGYKRQEAL
RPYLSSEEDRKKGKKFARYQFGDLLLHLEKKHGEDWGKVYDE
AWERIDKKVEGLSKHIKLEEERRSEDAQSKAALTDWLRAKASF
VIEGLKEADKDEFCRCELKLQKWYGDLRGKPFAIEAAENSILDIS
GFSKQYNCAFIWQKDGVKKLNLYLIINYFKGGKLRFKKIKPEAF
EANRFYTVINKKSGEIVPMEVNFNFDDPNLIILPLAFGKRQGREF
IWNDLLSETGSLKLANGRVIEKTLYNRRTRQDEPALFVALTFE
RREVLDSSNIKPMNLIGIDRGENIPAVIALTDPEGCPLSRFKDSLG
NPTHILRIGESYKEKQRTIQAKKEVEQRRAGGYSRKYASKAKN
LADDMVRNTARDLLYYAVTQDAMLIFENLSRGFGRQGKRTFM
AERQYTRMEDWLTAKLAYEGLSKTYLSKTLAQYTSKTCSNCG
FTITSADYDRVLEKLKKTATGWMTTINGKELKVEGQITYYNRY
KRQNVVKDLSVELDRLSEESVNNDISSWTKGRSGEALSLLKKR
FSHRPVQEKFVCLNCGFETHADEQAALNIARSWLFLRSQEYKK
YQTNKTTGNTDKRAFVETWQSFYRKKLKEVWKPAVTSPKKKR
KVTSPKKKRKV (SEQ ID NO: 274) |
| CasX 485 | (SEQ ID NO: 285) | MAPKKKRKVSRQEIKRINKIRRRLVKDSNTKKAGKTGPMKTLL
VRVMTPDLRERLENLRKKPENIPQPISNTSRANLNKLLTDYTEM
KKAILHVYWEEFQKDPVGLMSRVAQPAPKNIDQRKLIPVKDGN
ERLTSSGFACSQCCQPLYVYKLEQVNDGKPHTNYFGRCNVSE
HERLILLSPHKPEANDELVTYSLGKFGQRALDFYSIHVTKESTHP
VKPLAQIAGNRYASGPVGKALSDACMGTIASFLSKYQDIIIEHQ
KVVKGNQKRLESLRELAGKENLEYPSVTLPPQPHTKEGVDAYN
EVIARVRMWVNLNLWQKLKLSRDDAKPLLRLKGFPSFPLVERQ
ANEVDWWDMVCNVKKLINEKKEDGKVFWQNLAGYKRQEAL
RPYLSSEEDRKKGKKFARYQLGDLLLHLEKKHGEDWGKVYDE
AWERIDKKVEGLSKHIKLEEERRSEDAQSKAALTDWLRAKASF
VIEGLKEADKDEFCRCELKLQKWYGDLRGKPFAIEAAENSILDIS
GFSKQYNCAFIWQKDGVKKLNLYLIINYFKGGKLRFKKIKPEAF
EANRFYTVINKKSGEIVPMEVNFNFDDPNLIILPLAFGKRQGREF
IWNDLLSETGSLKLANGRVIEKTLYNRRTRQDEPALFVALTFE
RREVLDSSNIKPMNLIGVDRGENIPAVIALTDPEGCPLSRFKDSL
GNPTHILRIGESYKEKQRTIQAKKEVEQRRAGGYSRKYASKAK
NLADDMVRNTARDLLYYAVTQDAMLIFENLSRGFGRQGKRTF
MAERQYTRMEDWLTAKLAYEGLSKTYLSKTLAQYTSKTCSNC
GFTITSADYDRVLEKLKKTATGWMTTINGKELKVEGQITYYNR
RKRQNVVKDLSVELDRLSEESVNNDISSWTKGRSGEALSLLKK
RFSHRPVQEKFVCLNCGFETHADEQAALNIARSWLFLRSQEYK
KYQTNKTTGNTDKRAFVETWQSFYRKKIKEVWKPAVTSPKKK
RKV (SEQ ID NO: 275) |
| CasX 486 | (SEQ ID NO: 286) | MAPKKKRKVSRQEIKRINKIRRRLVKDSNTKKAGKTGPMKTLL
VRVMTPDLRERLENLRKKPENIPQPISNTSRANLNKLLTDYTEM
KKAILHVYWEEFQKDPVGLMSRVAQPAPKNIDQRKLIPVKDGN
ERLTSSGFACSQCCQPLYVYKLEQVNDGKPHTNYFGRCNVSE
HERLILLSPHKPEANDELVTYSLGKFGQRALDFYSIHVTKESTHP
VKPLAQIAGNRYASGPVGKALSDACMGTIASFLSKYQDIIIEHQ
KVVKGNQKRLESLRELAGKENLEYPSVTLPPQPHTKEGVDAYN
EVIARVRMWVNLNLWQKLKLSRDDAKPLLRLKGFPSFPLVERQ
ANEVDWWDMVCNVKKLINEKKEDGKVFWQNLAGYKRQEAL
RPYLSSEEDRKKGKKFARYQLGDLLKHLEKKHGEDWGKVYDE
AWERIDKKVEGLSKHIKLEEERRSEDAQSKAALTDWLRAKASF
VIEGLKEADKDEFCRCELKLQKWYGDLRGKPFAIEAAENSILDIS
GFSKQYNCAFIWQKDGVKKLNLYLIINYFKGGKLRFKKIKPEAF
EANRFYTVINKKSGEIVPMEVNFNFDDPNLIILPLAFGKRQGREF
IWNDLLSETGSLKLANGRVIEKTLYNRRTRQDEPALFVALTFE
RREVLDSSNIKPMNLIGVDRGENIPAVIALTDPEGCPLSRFKDSL
GNPTHILRIGESYKEKQRTIQAKKEVEQRRAGGYSRKYASKAK
NLADDMVRNTARDLLYYAVTQDAMLIFENISRGFGRQGKRTF |

TABLE 10-continued

Sequences of CasX 395 and 485-491

| Construct | DNA Sequence | Amino Acid Sequence |
|---|---|---|
| | | MAERQYTRMEDWLTAKLAYEGLSKTYLSKTLAQYTSKTCSNC GFTITSADYDRVLEKLKKTATGWMTTINGKELKVEGQITYYNR RKRQNVVKDLSVELDRLSEESVNNDISSWTKGRSGEALSLLKK RFSHRPVQEKFVCLNCGFETHADEQAALNIARSWLFLRSQEYK KYQTNKTTGNTDKRAFVETWQSFYRKKLKEVWKPAVTSPKKK RKV (SEQ ID NO: 276) |
| CasX 487 | (SEQ ID NO: 287) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPAPKNIDQRKLIPVKDGN ERLTSSGFACSQCCQPLYVYKLEQVNDGKPHTNYFGRCNVSE HERLILLSPHKPEANDELVTYSLGKFGQRALDFYSIHVTKESTHP VKPLAQIAGNRYASGPVGKALSDACMGTIASFLSKYQDIIIEHQ KVVKGNQKRLESLRELAGKENLEYPSVTLPPQPHTKEGVDAYN EVIARVRMWVNLNLWQKLKLSRDDAKPLLRLKGFPSFPLVERQ ANEVDWWDMVCNVKKLINEKKEDGKVFWQNLAGYKRQEAL RPYLSSEEDRKKGKKFARYQLGDLLLHLEKKHGEDWGKVYDE AWERIDKKVEGLSKHIKLEEERRSEDAQSKAALTDWLRAKASF VIEGLKEADKDEFCRCELKLQKWYGDLRGKPFAIEAENSILDIS GFSKQYNCAFIWQKDGVKKLNLYLIINYFKGGKLRFKKIKPEAF EANRFYTVINKKSGEIVPMEVNFNFDDPNLIILPLAFGKRQGREF IWNDLLSLETGSLKLANGRVIEKTLYNRRTRQDEPALFVALTFE RREVLDSSNIKPMNLIGVDRGENIPAVIALTDPEGCPLSRFKDSL GNPTHILRIGESYKEKQRTIQAKKEVEQRRAGGYSRKYASKAK NLADDMVRNTARDLLYYAVTQDAMLIFENLSRGFGRQGKRTF MAERQYTRMEDWLTAKLAYEGLSKTYLSKTLAQYTSKTCSNC GFTITSADYDRVLEKLKKTATGWMTTINGKELKVEGQITYYNR YKRQNVVKDLSVELDRLSEESVNNDISSWTKGRSGEALSLLKK RFSHRPVQEKFVCLNCGFETHADEQAALNIARSWLFLRSQEYK KYQTNKTTGNTDKRAFVETWQSFYRKKLKEVWKPAVTSPKKK RKV (SEQ ID NO: 277) |
| CasX 488 | (SEQ ID NO: 288) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTKE STHPVKPLAQIAGNRYASGPVGKALSDACMGTIASFLSKYQDIII EHQKVVKGNQKRLESLRELAGKENLEYPSVTLPPQPHTKEGVD AYNEVIARVRMWVNLNLWQKLKLSRDDAKPLLRLKGFPSFPL VERQANEVDWWDMVCNVKKLINEKKEDGKVFWQNLAGYKR QEALRPYLSSEEDRKKGKKFARYQFGDLLLHLEKKHGEDWGK VYDEAWERIDKKVEGLSKHIKLEEERRSEDAQSKAALTDWLRA KASFVIEGLKEADKDEFCRCELKLQKWYGDLRGKPFAIEAENSI LDISGFSKQYNCAFIWQKDGVKKLNLYLIINYFKGGKLRFKKIK PEAFEANRFYTVINKKSGEIVPMEVNFNFDDPNLIILPLAFGKRQ GREFIWNDLLSLETGSLKLANGRVTEKTLYNRRTRQDEPALFVA LTFERREVLDSSNIKPMNLIGIDRGENIPAVIALTDPEGCPLSRFK DSLGNPTHILRIGESYKEKQRTIQAKKEVEQRRAGGYSRKYASK AKNLADDMVRNTARDLLYYAVTQDAMLIFENLSRGFGRQGKR TFMAERQYTRMEDWLTAKLAYEGLSKTYLSKTLAQYTSKTCS NCGFTITSADYDRVLEKLKKTATGWMTTINGKELKVEGQITYY NRYKRQNVVKDLSVELDRLSEESVNNDISSWTKGRSGEALSLL KKRFSHRPVQEKFVCLNCGFETHADEQAALNIARSWLFLRSQE YKKYQTNKTTGNTDKRAFVETWQSFYRKKLKEVWKPAVTSPK KKRKV (SEQ ID NO: 278) |
| CasX 489 | (SEQ ID NO: 289) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTKE STHPVKPLAQIAGNRYASGPVGKALSDACMGTIASFLSKYQDIII EHQKVVKGNQKRLESLRELAGKENLEYPSVTLPPQPHTKEGVD AYNEVIARVRMWVNLNLWQKLKLSRDDAKPLLRLKGFPSFPL VERQANEVDWWDMVCNVKKLINEKKEDGKVFWQNLAGYKR QEALRPYLSSEEDRKKGKKFARYQLGDLLLHLEKKHGEDWGK VYDEAWERIDKKVEGLSKHIKLEEERRSEDAQSKAALTDWLRA KASFVIEGLKEADKDEFCRCELKLQKWYGDLRGKPFAIEAENSI LDISGISKQYNCAFIWQKDGVKKINLYLIINYFKGGKLRFKKIK PEAFEANRFYTVINKKSGEIVPMEVNFNFDDPNLIILPLAFGKRQ GREFIWNDLLSLETGSLKLANGRVIEKTLYNRRTRQDEPALFVA LTFERREVLDSSNIKPMNLIGVDRGENIPAVIALTDPEGCPLSRF KDSLGNPTHILRIGESYKEKQRTIQAKKEVEQRRAGGYSRKYAS KAKNLADDMVRNTARDLLYYAVTQDAMLIFENLSRGFGRQGK |

TABLE 10-continued

Sequences of CasX 395 and 485-491

| Construct | DNA Sequence | Amino Acid Sequence |
|---|---|---|
| | | RTFMAERQYTRMEDWLTAKLAYEGLSKTYLSKTLAQYTSKTC SNCGFTITSADYDRVLEKLKKTATGWMTTINGKELKVEGQITY YNRRKRQNVVKDLSVELDRLSEESVNNDISSWTKGRSEALSL LKKRFSHRPVQEKFVCLNCGFETHADEQAALNIARSWLFLRSQ EYKKYQTNKTTGNTDKRAFVETWQSFYRKKLKEVWKPAVTSP KKKRKV (SEQ ID NO: 279) |
| CasX 490 | (SEQ ID NO: 290) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTKE STHPVKPLAQIAGNRYASGPVGKALSDACMGTIASFLSKYQDIII EHQKVVKGNQKRLESLRELAGKENLEYPSVTLPPQPHTKEGVD AYNEVIARVRMWVNLNLWQKLKLSRDDAKPLLRLKGFPSFPL VERQANEVDWWDMVCNVKKLINEKKEDGKVFWQNLAGYKR QEALRPYLSSEEDRKKGKKFARYQLGDLLKHLEKKHGEDWGK VYDEAWERIDKKVEGLSKHIKLEEERRSEDAQSKAALTDWLRA KASFVIEGLKEADKDEFCRCELKLQKWYGDLRGKPFAIEAENSI LDISGFSKQYNCAFIWQKDGVKKLNLYLIINYFKGGKLRFKKIK PEAFEANRFYTVINKKSGEIVPMEVNFNFDDPNLIILPLAFGKRQ GREFIWNDLLSLETGSLKLANGRVIEKTLYNRRTRQDEPALFVA LTFERREVLDSSNIKPMNLIGVDRGENIPAVIALTDPEGCPLSRF KDSLGNPTHILRIGESYKEKQRTIQAKKEVEQRRAGGYSRKYAS KAKNLADDMVRNTARDLLYYAVTQDAMLIFENLSRGFGRQGK RTFMAERQYTRMEDWLTAKLAYEGLSKTYLSKTLAQYTSKTC SNCGFTITSADYDRVLEKLKKTATGWMTTINGKELKVEGQITY YNRRKRQNVVKDLSVELDRLSEESVNNDISSWTKGRSEALSL LKKRFSHRPVQEKFVCLNCGFETHADEQAALNIARSWLFLRSQ EYKKYQTNKTTGNTDKRAFVETWQSFYRKKLKEVWKPAVTSP KKKRKV (SEQ ID NO: 280) |
| CasX 491 | (SEQ ID NO: 291) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTKE STHPVKPLAQIAGNRYASGPVGKALSDACMGTIASFLSKYQDIII EHQKVVKGNQKRLESLRELAGKENLEYPSVTLPPQPHTKEGVD AYNEVIARVRMWVNLNLWQKLKLSRDDAKPLLRLKGFPSFPL VERQANEVDWWDMVCNVKKLINEKKEDGKVFWQNLAGYKR QEALRPYLSSEEDRKKGKKFARYQLGDLLLHLEKKHGEDWGK VYDEAWERIDKKVEGLSKHIKLEEERRSEDAQSKAALTDWLRA KASFVIEGLKEADKDEFCRCELKLQKWYGDLRGKPFAIEAENSI LDISGFSKQYNCAFIWQKDGVKKLNLYLIINYFKGGKLRFKKIK PEAFEANRFYTVINKKSGEIVPMEVNFNFDDPNLIILPLAFGKRQ GREFIWNDLLSLETGSLKLANGRVIEKTLYNRRTRQDEPALFVA LTFERREVLDSSNIKPMNLIGVDRGENIPAVIALTDPEGCPLSRF KDSLGNPTHILRIGESYKEKQRTIQAKKEVEQRRAGGYSRKYAS KAKNLADDMVRNTARDLLYYAVTQDAMLIFENLSRGFGRQGK RTFMAERQYTRMEDWLTAKLAYEGLSKTYLSKTLAQYTSKTC SNCGFTITSADYDRVLEKLKKTATGWMTTINGKELKVEGQITY YNRYKRQNVVKDLSVELDRLSEESVNNDISSWTKGRSEALSL LKKRFSHRPVQEKFVCLNCGFETHADEQAALNIARSWLFLRSQ EYKKYQTNKTTGNTDKRAFVETWQSFYRKKLKEVWKPAVTSP KKKRKV (SEQ ID NO: 281) |
| CasX 494 | (SEQ ID NO: 292) | MAPKKKRKVSRQEIKRINKIRRRLVKDSNTKKAGKTGPMKTLL VRVMTPDLRERLENLRKKPENIPQPISNTSRANLNKLLTDYTEM KKAILHVYWEEFQKDPVGLMSRVAQPASKKIDQNKLKPEMDE KGNLTTAGFACSQCGQPLFVYKLEQVSEKGKAYTNYFGRCNV AEHEKLILLAQLKPEKDSDEAVTYSLGKFGQRALDFYSIHVTRE SNHPVKPLEQIGGNSCASGPVGKALSDACMGAVASFLTKYQDII LEHQKVIKKNEKRLANLKDIASANGLAFPKITLPPQPHTKEGIEA YNNVVAQIVIWVNLNLWQKLKIGRDEAKPLQRLKGFPSFPLVE RQANEVDWWDMVCNVKKLINEKKEDGKVFWQNLAGYKRQE ALRPYLSSEEDRKKGKKFARYQLGDLLLHLEKKHGEDWGKVY DEAWERIDKKVEGLSKHIKLEEERRSEDAQSKAALTDWLRAKA SFVIEGLKEADKDEFCRCELKLQKWYGDLRGKPFAIEAENSILDI SGFSKQYNCAFIWQKDGVKKLNLYLIINYFKGGKLRFKKIKPEA FEANRFYTVINKKSGEIVPMEVNFNFDDPNLIILPLAFGKRQGRE FIWNDLLSLETGSLKLANGRVIEKTLYNRRTRQDEPALFVALTF ERREVLDSSNIKPMNLIGVDRGENIPAVIALTDPEGCPLSRFKDS LGNPTHILRIGESYKEKQRTIQAKKEVEQRRAGGYSRKYASKA KNLADDMVRNTARDLLYYAVTQDAMLIFENLSRGFGRQGKRT |

TABLE 10-continued

Sequences of CasX 395 and 485-491

| Construct | DNA Sequence | Amino Acid Sequence |
|---|---|---|
| | | FMAERQYTRMEDWLTAKLAYEGLSKTYLSKTLAQYTSKTCSN CGFTITSADYDRVLEKLKKTATGWMTTINGKELKVEGQITYYN RYKRQNVVKDLSVELDRLSEESVNNDISSWTKGRSGEALSLLK KRFSHRPVQEKFVCLNCGFETHADEQAALNIARSWLFLRSQEY KKYQTNKTTGNTDKRAFVETWQSFYRKKLKEVWKPAVTSPKK KRKV (SEQ ID NO: 282) |

Example 6: Generation of RNA Guides

For the generation of RNA single guides and spacers, templates for in vitro transcription were generated by performing PCR with Q5 polymerase (NEB M0491) according to the recommended protocol, with template oligos for each backbone and amplification primers with the T7 promoter and the spacer sequence. The DNA primer sequences for the T7 promoter, guide and spacer for guides and spacers are presented in Table 11, below. The template oligos, labeled "backbone fwd" and "backbone rev" for each scaffold, were included at a final concentration of 20 nM each, and the amplification primers (T7 promoter and the unique spacer primer) were included at a final concentration of 1 uM each. The sg2, sg32, sg64, and sg174 guides correspond to SEQ ID NOS: 5, 2104, 2106, and 2238, respectively, with the exception that sg2, sg32, and sg64 were modified with an additional 5' G to increase transcription efficiency (compare sequences in Table 11 to Table 2). The 7.37 spacer targets beta2-microglobulin (B2M). Following PCR amplification, templates were cleaned and isolated by phenol-chloroform-isoamyl alcohol extraction followed by ethanol precipitation.

In vitro transcriptions were carried out in buffer containing 50 mM Tris pH 8.0, 30 mM $MgCl_2$, 0.01% Triton X-100, 2 mM spermidine, 20 mM DTT, 5 mM NTPs, 0.5 µM template, and 100 µg/mL T7 RNA polymerase. Reactions were incubated at 37° C. overnight. 20 units of DNase I (Promega #M6101) were added per 1 mL of transcription volume and incubated for one hour. RNA products were purified via denaturing PAGE, ethanol precipitated, and resuspended in IX phosphate buffered saline. To fold the sgRNAs, samples were heated to 70° C. for 5 min and then cooled to room temperature. The reactions were supplemented to 1 mM final $MgCl_2$ concentration, heated to 50° C. for 5 min and then cooled to room temperature. Final RNA guide products were stored at −80° C.

TABLE 11

Sequences for generation of guide RNA

| Primer | Primer sequence | RNA product |
|---|---|---|
| T7 promoter primer | GAAATTAATACGACTCACTATA (SEQ ID NO: 293) | Used for all |
| sg2 backbone fwd | GAAATTAATACGACTCACTATAGGTACTGG CGCTTTTATCTCATTACTTTGAGAGCCATCA CCAGCGACTATGTCGTATGGGTAAAG (SEQ ID NO: 294) | GGUACUGGCGCUU UUAUCUCAUUACU UUGAGAGCCAUCA CCAGCGACUAUGU |
| sg2 backbone rev | CTTTGATGCTTCTTATTTATCGGATTTCTCTC CGATAAATAAGCGCTTTACCCATACGACAT AGTCGCTGGTGATGGC (SEQ ID NO: 295) | CGUAUGGGUAAA GCGCUUAUUUAUC GGAGAGAAAUCCG |
| sg2.7.37 spacer primer | CGGAGCGAGACATCTCGGCCCTTTGATGCT TCTTATTTATCGGATTTCTCTCCG (SEQ ID NO: 296) | AUAAAUAAGAAG CAUCAAAGGGCCG AGAUGUCUCGCUC CG (SEQ ID NO: 306) |
| sg32 backbone fwd | GAAATTAATACGACTCACTATAGGTACTGG CGCTTTTATCTCATTACTTTGAGAGCCATCA CCAGCGACTATGTCGTATGGGTAAAGCGC (SEQ ID NO: 297) | GGUACUGGCGCUU UUAUCUCAUUACU UUGAGAGCCAUCA CCAGCGACUAUGU |
| sg32 backbone rev | CTTTGATGCTTCCCTCCGAAGAGGGCGCTTT ACCCATACGACATAG (SEQ ID NO: 298) | CGUAUGGGUAAA GCGCCCUCUUCGG |
| sg32.7.37 spacer primer | CGGAGCGAGACATCTCGGCCCTTTGATGCT TCCCTCCGAAGAG (SEQ ID NO: 299) | AGGGAAGCAUCAA AGGGCCGAGAUGU CUCG (SEQ ID NO: 307) |
| sg64 backbone fwd | GAAATTAATACGACTCACTATAGGTACTGG CGCCTTTATCTCATTACTTTGAGAGCCATCA CCAGCGACTATGTCGTATGGGTAAAGCGC (SEQ ID NO: 300) | GGUACUGGCGCCU UUAUCUCAUUACU UUGAGAGCCAUCA CCAGCGACUAUGU |
| sg64 backbone rev | CTTTGATGCTTCTTACGGACCGAAGTCCGTA AGCGCTTTACCCATACGACATAG (SEQ ID NO: 301) | CGUAUGGGUAAA GCGCUUACGGACU UCGGUCCGUAAGA |

TABLE 11-continued

Sequences for generation of guide RNA

| Primer | Primer sequence | RNA product |
|---|---|---|
| sg64.7.37 spacer primer | CGGAGCGAGACATCTCGGCCCTTTGATGCT TCTTACGGACCGAAG (SEQ ID NO: 302) | AGCAUCAAAGGGC CGAGAUGUCUCGC UCCG (SEQ ID NO: 308) |
| sg174 backbone fwd | GAAATTAATACGACTCACTATAACTGGCGC TTTTATCTGATTACTTTGAGAGCCATCACCA GCGACTATGTCGTAGTGGGTAAAGCT (SEQ ID NO: 303) | ACUGGCGCUUUUA UCUgAUUACUUUG AGAGCCAUCACCA GCGACUAUGUCGU |
| sg174 backbone rev | CTTTGATGCTCCCTCCGAAGAGGGAGCTTT ACCCACTACGACATAGTCGC (SEQ ID NO: 304) | AgUGGGUAAAGCU CCCUCUUCGGAGG GAGCAUCAAAGGG |
| sg174.7.37 spacer primer | CGGAGCGAGACATCTCGGCCCTTTGATGCT CCCTCC (SEQ ID NO: 305) | CCGAGAUGUCUCG CUCCG (SEQ ID NO: 309) |

Example 7: RNP Assembly

Purified wild-type and RNP of CasX and single guide RNA (sgRNA) were either prepared immediately before experiments or prepared and snap-frozen in liquid nitrogen and stored at −80° C. for later use. To prepare the RNP complexes, the CasX protein was incubated with sgRNA at 1:1.2 molar ratio. Briefly, sgRNA was added to Buffer #1 (25 mM NaPi, 150 mM NaCl, 200 mM trehalose, 1 mM $MgCl_2$), then the CasX was added to the sgRNA solution, slowly with swirling, and incubated at 37° C. for 10 min to form RNP complexes. RNP complexes were filtered before use through a 0.22 µm Costar 8160 filters that were pre-wet with 200 µl Buffer #1. If needed, the RNP sample was concentrated with a 0.5 ml Ultra 100-Kd cutoff filter, (Millipore part #UFC510096), until the desired volume was obtained. Formation of competent RNP was assessed as described in Example 11.

Example 8: Assessing Binding Affinity to the Guide RNA

Purified wild-type and improved CasX will be incubated with synthetic single-guide RNA containing a 3' Cy7.5 moiety in low-salt buffer containing magnesium chloride as well as heparin to prevent non-specific binding and aggregation. The sgRNA will be maintained at a concentration of 10 pM, while the protein will be titrated from 1 pM to 100 µM in separate binding reactions. After allowing the reaction to come to equilibrium, the samples will be run through a vacuum manifold filter-binding assay with a nitrocellulose membrane and a positively charged nylon membrane, which bind protein and nucleic acid, respectively. The membranes will be imaged to identify guide RNA, and the fraction of bound vs unbound RNA will be determined by the amount of fluorescence on the nitrocellulose vs nylon membrane for each protein concentration to calculate the dissociation constant of the protein-sgRNA complex. The experiment will also be carried out with improved variants of the sgRNA to determine if these mutations also affect the affinity of the guide for the wild-type and mutant proteins. We will also perform electromobility shift assays to qualitatively compare to the filter-binding assay and confirm that soluble binding, rather than aggregation, is the primary contributor to protein-RNA association.

Example 9: Assessing Binding Affinity to the Target DNA

Purified wild-type and improved CasX will be complexed with single-guide RNA bearing a targeting sequence complementary to the target nucleic acid. The RNP complex will be incubated with double-stranded target DNA containing a PAM and the appropriate target nucleic acid sequence with a 5' Cy7.5 label on the target strand in low-salt buffer containing magnesium chloride as well as heparin to prevent non-specific binding and aggregation. The target DNA will be maintained at a concentration of 1 nM, while the RNP will be titrated from 1 pM to 100 µM in separate binding reactions. After allowing the reaction to come to equilibrium, the samples will be run on a native 5% polyacrylamide gel to separate bound and unbound target DNA. The gel will be imaged to identify mobility shifts of the target DNA, and the fraction of bound vs unbound DNA will be calculated for each protein concentration to determine the dissociation constant of the RNP-target DNA ternary complex.

Example 10: Assessing Differential PAM Recognition In Vitro

Purified wild-type and engineered CasX variants will be complexed with single-guide RNA bearing a fixed targeting sequence. The RNP complexes will be added to buffer containing $MgCl_2$ at a final concentration of 100 nM and incubated with 5' Cy7.5-labeled double-stranded target DNA at a concentration of 10 nM. Separate reactions will be carried out with different DNA substrates containing different PAMs adjacent to the target nucleic acid sequence. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the rate of cleavage of the non-canonical PAMs by the CasX variants will be determined.

Example 11: CasX:gNA In Vitro Cleavage Assays

1. Determining Cleavage-Competent Fractions for Protein Variants Compared to Wild-Type Reference CasX The ability of CasX variants to form active RNP compared to reference CasX was determined using an n vitro cleavage assay. The beta-2 microglobulin (B2M) 7.37 target for the cleavage assay was created as follows. DNA oligos with the sequence (SEQ ID NO: 310)
TGAAGCTGACAGCATTCGGGCCGAGATGTCTCGCTCCGTGGCCTT AGCTGTGCTCGCGCT (non-target strand, NTS) and (SEQ ID NO: 311)
TGAAGCTGACAGCATTCGGGCCGAGATGTCTCGCTCCGTGGCCTT AGCTGTGCTCGCGCT (target strand, TS)

were purchased with 5' fluorescent labels (LI-COR IRDye 700 and 800, respectively), dsDNA targets were formed by mixing the oligos in a 1:1 ratio in 1× cleavage buffer (20 mM Tris HCl pH 7.5, 150 mM NaCl, 1 mM TCEP, 5% glycerol, 10 mM $MgCl_2$), heating to 95° C. for 10 minutes, and allowing the solution to cool to room temperature.

CasX RNPs were reconstituted with the indicated CasX and guides (see graphs) at a final concentration of 1 µM with 1.5-fold excess of the indicated guide unless otherwise specified in 1× cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. The 7.37 target was used, along with sgRNAs having spacers complementary to the 7.37 target.

Figure 18:
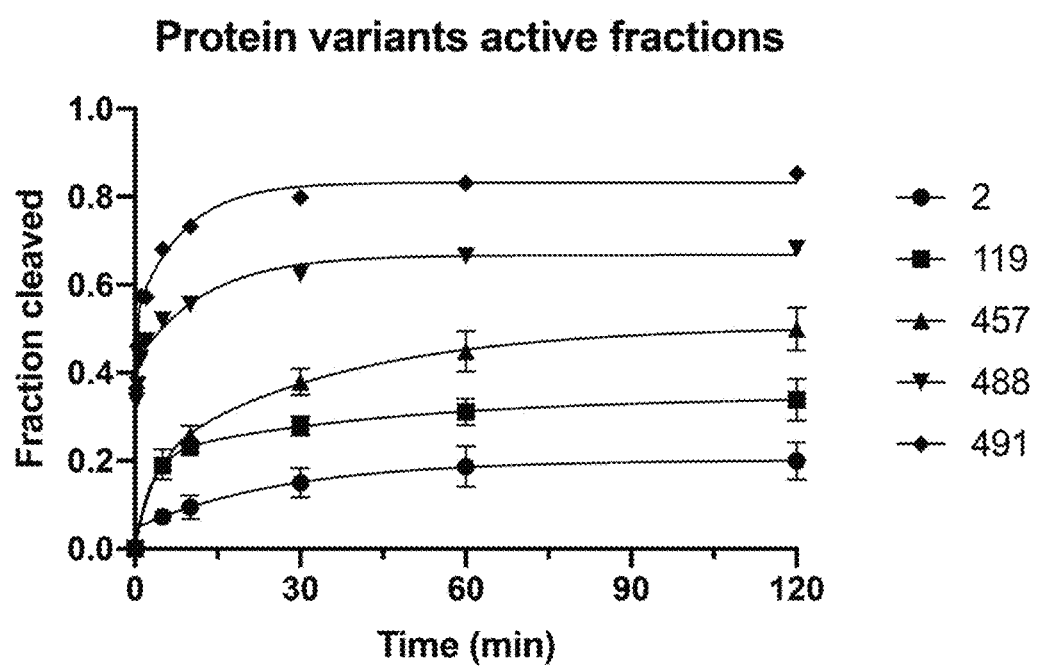
FIG. 18 is a graph of the results of an assay for the quantification of active fractions of RNP formed by sgRNA174 and the CasX variants, as described in Example 11. Equimolar amounts of RNP and target were co-incubated and the amount of cleaved target was determined at the indicated timepoints. Mean and standard deviation of three independent replicates are shown for each timepoint. The biphasic fit of the combined replicates is shown. "2" refers to the reference CasX protein of SEQ ID NO:2.

Cleavage reactions were prepared with final RNP concentrations of 100 nM and a final target concentration of 100 nM. Reactions were carried out at 37° C., and initiated by the addition of the 7.37 target DNA. Aliquots were taken at 5, 10, 30, 60, and 120 minutes and quenched by adding to 95% formamide, 20 mM EDTA. Samples were denatured by heating at 95° C. for 10 minutes and run on a 10% urea-PAGE gel. The gels were either imaged with a LI-COR Odyssey CLx and quantified using the LI-COR Image Studio software or imaged with a Cytiva Typhoon and quantified using the Cytiva IQTL software. The resulting data were plotted and analyzed using Prism. We assumed that CasX acts essentially as a single-turnover enzyme under the assayed conditions, as indicated by the observation that sub-stoichiometric amounts of enzyme fail to cleave a greater-than-stoichiometric amount of target even under extended time-scales and instead approach a plateau that scales with the amount of enzyme present. Thus, the fraction of target cleaved over long time-scales by an equimolar amount of RNP is indicative of what fraction of the RNP is properly formed and active for cleavage. The cleavage traces were fit with a biphasic rate model, as the cleavage reaction clearly deviates from monophasic under this concentration regime, and the plateau was determined for each of three independent replicates. The mean and standard deviation were calculated to determine the active fraction (Table 12). The graph is shown in FIG. 18.

Apparent active (competent) fractions were determined for RNPs formed for CasX2+guide 174+7.37 spacer, CasX119+guide 174+7.37 spacer, CasX457+guide 174+7.37 spacer, CasX488+guide 174+7.37 spacer, and CasX491+guide 174+7.37 spacer. The determined active fractions are shown in Table 12. All CasX variants had higher active fractions than the wild-type CasX2, indicating that the engineered CasX variants form significantly more active and stable RNP with the identical guide under tested conditions compared to wild-type CasX. This may be due to an increased affinity for the sgRNA, increased stability or solubility in the presence of sgRNA, or greater stability of a cleavage-competent conformation of the engineered CasX: sgRNA complex. An increase in solubility of the RNP was indicated by a notable decrease in the observed precipitate formed when CasX457, CasX488, or CasX491 was added to the sgRNA compared to CasX2.

Figure 19:
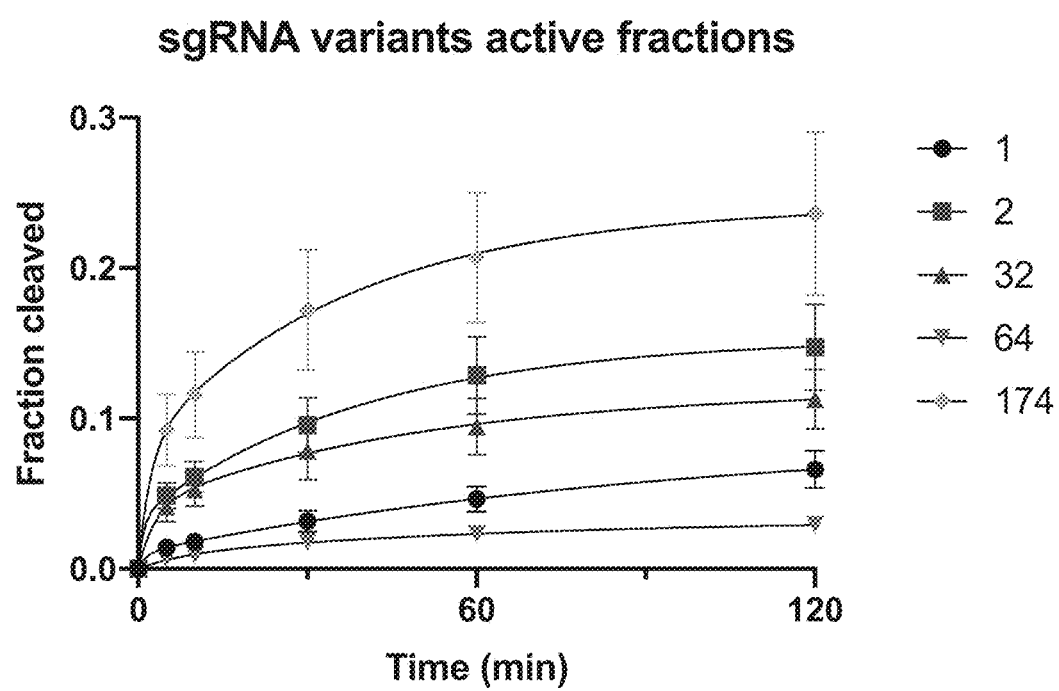
FIG. 19 shows the quantification of active fractions of RNP formed by CasX2 (reference CasX protein of SEQ ID NO:2) and the modified sgRNAs, as described in Example 11. Equimolar amounts of RNP and target were co-incubated and the amount of cleaved target was determined at the indicated timepoints. Mean and standard deviation of three independent replicates are shown for each timepoint. The biphasic fit of the combined replicates is shown.

2. In vitro Cleavage Assays—Determining $k_{cleave}$ for CasX Variants Compared to Wild-Type Reference CasX Cleavage-competent fractions were also determined using the same protocol for CasX2.2.7.37, CasX2.32.7.37, CasX2.64.7.37, and CasX2.174.7.37 to be 16±3%, 13±3%, 5±2%, and 22±5%, as shown in FIG. 19 and Table 12.

Figure 20:
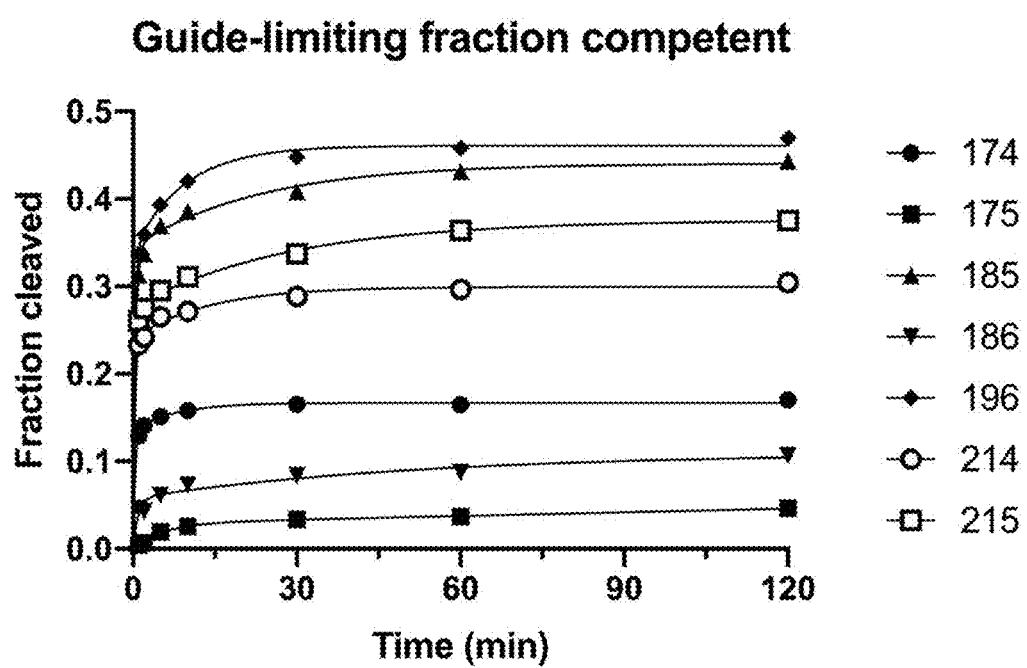
FIG. 20 shows the quantification of active fractions of RNP formed by CasX 491 and the modified sgRNAs under guide-limiting conditions, as described in Example 11. Equimolar amounts of RNP and target were co-incubated and the amount of cleaved target was determined at the indicated timepoints. The biphasic fit of the data is shown.

A second set of guides were tested under different conditions to better isolate the contribution of the guide to RNP formation. 174, 175, 185, 186, 196, 214, and 215 guides with 7.37 spacer were mixed with CasX491 at final concentrations of 1 µM for the guide and 1.5 µM for the protein, rather than with excess guide as before. Results are shown in FIG. 20 and Table 12. Many of these guides exhibited additional improvement over 174, with 185 and 196 achieving 44% and 46% competent fractions, respectively, compared with 17% for 174 under these guide-limiting conditions.

The data indicate that both CasX variants and sgRNA variants are able to form a higher degree of active RNP with guide RNA compare to wild-type CasX and wild-type sgRNA.

The apparent cleavage rates of CasX variants 119, 457, 488, and 491 compared to wild-type reference CasX were determined using an in vitro fluorescent assay for cleavage of the target 7.37.

CasX RNPs were reconstituted with the indicated CasX (see FIG. 21) at a final concentration of 1 µM with 1.5-fold excess of the indicated guide in 1× cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. Cleavage reactions were set up with a final RNP concentration of 200 nM and a final target concentration of 10 nM. Reactions were carried out at 37° C. except where otherwise noted and initiated by the addition of the target DNA. Aliquots were taken at 0.25, 0.5, 1, 2, 5, and 10 minutes and quenched by adding to 95% formamide, 20 mM EDTA. Samples were denatured by heating at 95° C. for 10 minutes and run on a 10% urea-PAGE gel. The gels were imaged with a LI-COR Odyssey CLx and quantified using the LI-COR Image Studio software or imaged with a Cytiva Typhoon and quantified using the Cytiva IQTL software. The resulting data were plotted and analyzed using Prism, and the apparent first-order rate constant of non-target strand cleavage ($k_{cleave}$) was determined for each CasX:sgRNA combination replicate individually. The mean and standard deviation of three replicates with independent fits are presented in Table 12, and the cleavage traces are shown in FIG. 22.

Figure 21:
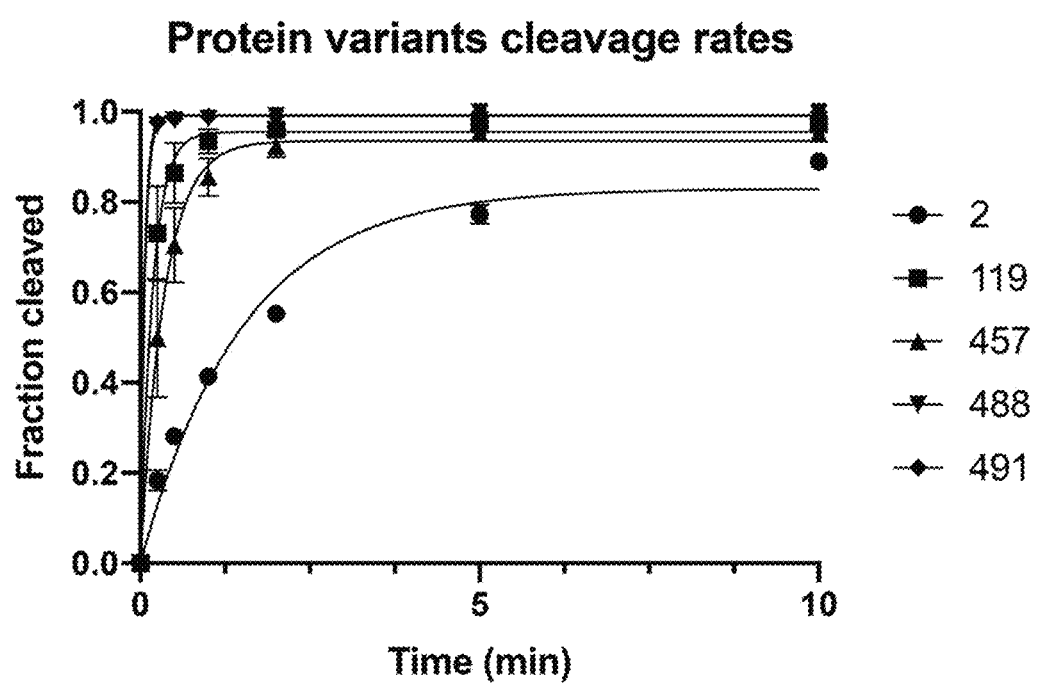
FIG. 21 shows the quantification of cleavage rates of RNP formed by sgRNA174 and the CasX variants, as described in Example 11. Target DNA was incubated with a 20-fold excess of the indicated RNP and the amount of cleaved target was determined at the indicated time points. Mean and standard deviation of three independent replicates are shown for each timepoint, except for 488 and 491 where a single replicate is shown. The monophasic fit of the combined replicates is shown.
Figure 22:
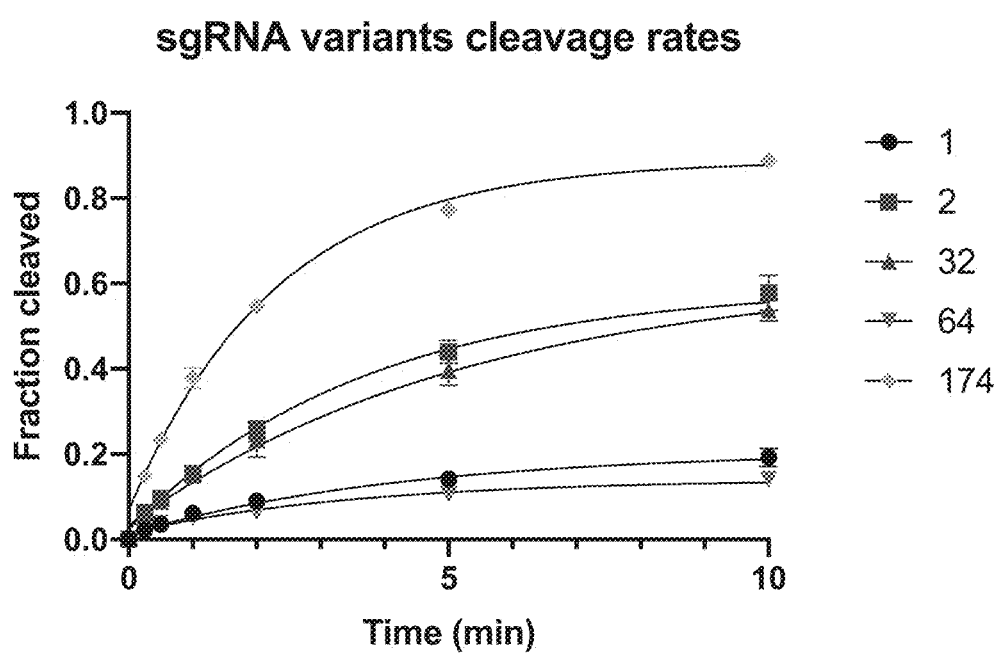
FIG. 22 shows the quantification of cleavage rates of RNP formed by CasX2 and the sgRNA variants, as described in Example 11. Target DNA was incubated with a 20-fold excess of the indicated RNP and the amount of cleaved target was determined at the indicated time points. Mean and standard deviation of three independent replicates are shown for each timepoint. The monophasic fit of the combined replicates is shown.

Apparent cleavage rate constants were determined for wild-type CasX2, and CasX variants 119, 457, 488, and 491 with guide 174 and spacer 7.37 utilized in each assay (see Table 12 and FIG. 21). All CasX variants had improved cleavage rates relative to the wild-type CasX2. CasX457 cleaved more slowly than 119, despite having a higher competent fraction as determined above. CasX488 and CasX491 had the highest cleavage rates by a large margin: as the target was almost entirely cleaved in the first time-point, the true cleavage rate exceeds the resolution of this assay, and the reported $k_{cleave}$ should be taken as a lower bound.

The data indicate that the CasX variants have a higher level of activity, with $k_{cleave}$ rates reaching at least 30-fold higher compared to wild-type CasX2.

3. In Vitro Cleavage Assays: Comparison of Guide Variants to Wild-Type Guides

Cleavage assays were also performed with wild-type reference CasX2 and reference guide 2 compared to guide variants 32, 64, and 174 to determine whether the variants improved cleavage. The experiments were performed as described above. As many of the resulting RNPs did not approach full cleavage of the target in the time tested, we determined initial reaction velocities ($V_0$) rather than first-order rate constants. The first two timepoints (15 and 30 seconds) were fit with a line for each CasX:sgRNA combination and replicate. The mean and standard deviation of the slope for three replicates were determined.

Figure 23:
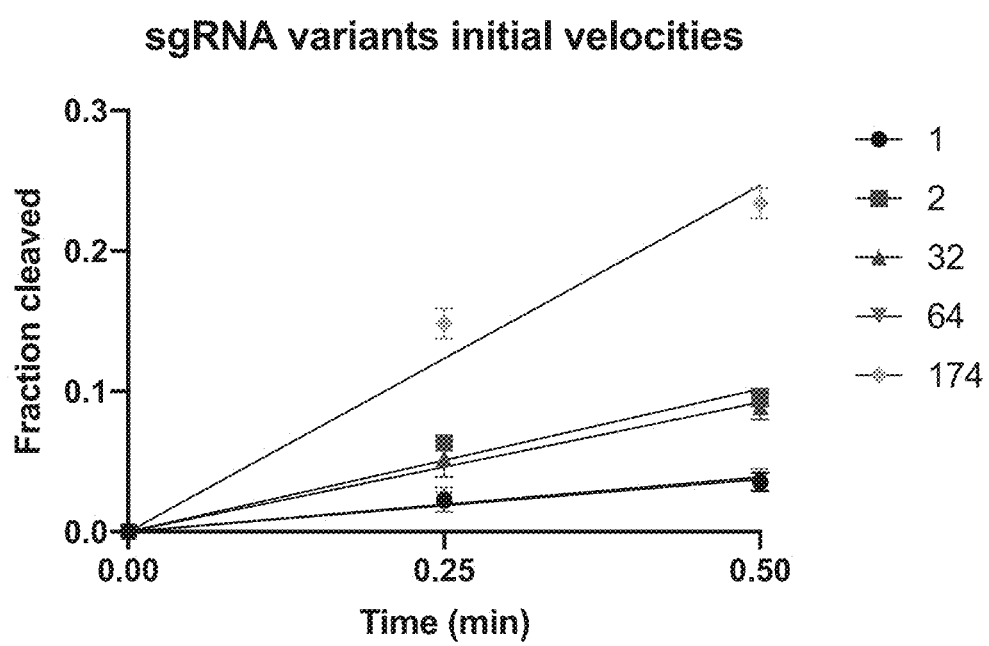
FIG. 23 shows the quantification of initial velocities of RNP formed by CasX2 and the sgRNA variants, as described in Example 11. The first two time-points of the previous cleavage experiment were fit with a linear model to determine the initial cleavage velocity.

Under the assayed conditions, the W for CasX2 with guides 2, 32, 64, and 174 were 20.4±1.4 nM/min, 18.4±2.4 nM/min, 7.8±1.8 nM/min, and 49.3±1.4 nM/mm (see Table 12 and FIG. 22 and FIG. 23). Guide 174 showed substantial improvement in the cleavage rate of the resulting RNP (~2.5-fold relative to 2, see FIG. 23), while guides 32 and 64 performed similar to or worse than guide 2. Notably, guide 64 supports a cleavage rate lower than that of guide 2 but performs much better in vivo (data not shown). Some of the sequence alterations to generate guide 64 likely improve in vivo transcription at the cost of a nucleotide involved in triplex formation. Improved expression of guide 64 likely explains its improved activity in vivo, while its reduced stability may lead to improper folding in vitro.

Additional experiments were carried out with guides 174, 175, 185, 186, 196, 214, and 215 with spacer 7.37 and CasX491 to determine relative cleavage rates. To reduce cleavage kinetics to a range measurable with our assay, the cleavage reactions were incubated at 10° C. Results are in FIG. 24 and Table 12. Under these conditions, 215 was the only guide that supported a faster cleavage rate than 174, 196, which exhibited the highest active fraction of RNP under guide-limiting conditions, had kinetics essentially the same as 174, again highlighting that different variants result in improvements of distinct characteristics.

The data support that, under the conditions of the assay, use of the majority of the guide variants with CasX results in RNP with a higher level of activity than one with the wild-type guide, with improvements in initial cleavage velocity ranging from ~2-fold to >6-fold. Numbers in Table 12 indicate, from left to right, CasX variant, sgRNA scaffold, and spacer sequence of the RNP construct. In the RNP construct names in the table below, CasX protein variant, guide scaffold and spacer are indicated from left to right.

TABLE 12

Results of cleavage and RNP formation assays

| RNP Construct | $k_{cleave}$* | Initial velocity* | Competent fraction |
|---|---|---|---|
| 2.2.7.37 | | 20.4 ± 1.4 nM/min | 16 ± 3% |
| 2.32.7.37 | | 18.4 ± 2.4 nM/min | 13 ± 3% |
| 2.64.7.37 | | 7.8 ± 1.8 nM/min | 5 ± 2% |
| 2.174.7.37 | 0.51 ± 0.01 min$^{-1}$ | 49.3 ± 1.4 nM/min | 22 ± 5% |
| 119.174.7.37 | 6.29 ± 2.11 min$^{-1}$ | | 35 ± 6% |
| 457.174.7.37 | 3.01 ± 0.90 min$^{-1}$ | | 53 ± 7% |
| 488.174.7.37 | 15.19 min$^{-1}$ | | 67% |
| 491.174.7.37 | 16.59 min$^{-1}$/ 0.293 min$^{-1}$ (10° C.) | | 83%/17% (guide-limited) |
| 491.175.7.37 | 0.089 min$^{-1}$ (10° C.) | | 5% (guide-limited) |
| 491.185.7.37 | 0.227 min$^{-1}$ (10° C.) | | 44% (guide-limited) |
| 491.186.7.37 | 0.099 min$^{-1}$ (10° C.) | | 11% (guide-limited) |
| 491.196.7.37 | 0.292 min$^{-1}$ (10° C.) | | 46% (guide-limited) |
| 491.214.7.37 | 0.284 min$^{-1}$ (10° C.) | | 30% (guide-limited) |

TABLE 12-continued

Results of cleavage and RNP formation assays

| RNP Construct | $k_{cleave}$* | Initial velocity* | Competent fraction |
|---|---|---|---|
| 491.215.7.37 | 0.398 min$^{-1}$ (10° C.) | | 38% (guide-limited) |

*Mean and standard deviation

Example 12: Identification of Nicking Variants

Purified modified CasX variants will be complexed with single-guide RNA bearing a fixed targeting sequence. The RNP complexes will be added to buffer containing $MgCl_2$ at a final concentration of 100 nM and incubated with double-stranded target DNA with a 5' fluorescein label on the target strand and a 5' Cy5 label on the non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. Efficient cleavage of one strand but not the other would be indicative that the variant possessed single-strand nickase activity.

Example 13: Assessing Improved Expression and Solubility Characteristics of CasX Variants for RNP Production Wild-type and modified CasX variants will be expressed in BL21 (DE3) *E. coli* under identical conditions. All proteins will be under the control of an IPTG-inducible T7 promoter. Cells will be grown to an OD of 0.6 in TB media at 37° C., at which point the growth temperature will be reduced to 16° C., and expression will be induced by the addition of 0.5 mM IPTG. Cells will be harvested following 18 hours of expression. Soluble protein fractions will be extracted and analyzed on an SDS-PAGE gel. The relative levels of soluble CasX expression will be identified by Coomassie staining. The proteins will be purified in parallel according to the protocol above, and final yields of pure protein will be compared. To determine the solubility of the purified protein, the constructs will be concentrated in storage buffer until the protein begins to precipitate. Precipitated protein will be removed by centrifugation and the final concentration of soluble protein will be measured to determine the maximum solubility for each variant. Finally, the CasX variants will be complexed with single guide RNA and concentrated until precipitation begins. Precipitated RNP will be removed by centrifugation and the final concentration of soluble RNP will be measured to determine the maximum solubility of each variant when bound to guide RNA.

Example 14: Assays Used to Measure sgNA and CasX Protein Activity

Several assays were used to carry out initial screens of CasX protein and sgNA Deep Mutational Evolution (DME) libraries and modified mutants, and to measure the activity of select protein and sgNA variants relative to CasX reference sgNAs and proteins.

*E. coli* CRISPRi Screen:
Briefly, biological triplicates of dead CasX DME Libraries on a chloramphenicol (CM) resistant plasmid with a GFP gNA on a carbenicillin (Carb) resistant plasmid were transformed (at >5× library size) into MG1655 with genetically integrated and constitutively expressed GFP and RFP. Cells were grown overnight in EZ-RDM+Carb, CM and Anhydrotetracycline (aTc) inducer. E. coli were FACS sorted based on gates for the top 1% of GFP but not RFP repression, collected, and resorted immediately to further enrich for highly functional CasX molecules. Double sorted libraries were then grown out and DNA was collected for deep sequencing on a highseq. This DNA was also re-transformed onto plates and individual clones were picked for further analysis.

E. coli Toxin Selection:

Briefly carbenicillin resistant plasmid containing an arabinose inducible toxin were transformed into E. coli cells and made electrocompetent. Biological triplicates of CasX DME Libraries with a toxin targeted gNA on a chloramphenicol resistant plasmid were transformed (at >5× library size) into said cells and grown in LB+CM and arabinose inducer. E. coli that cleaved the toxin plasmid survived in the induction media and were grown to mid log and plasmids with functional CasX cleavers were recovered. This selection was repeated as needed. Selected libraries were then grown out and DNA was collected for deep sequencing on a highseq. This DNA was also re-transformed onto plates and individual clones were picked for further analysis and testing.

Figure 25:
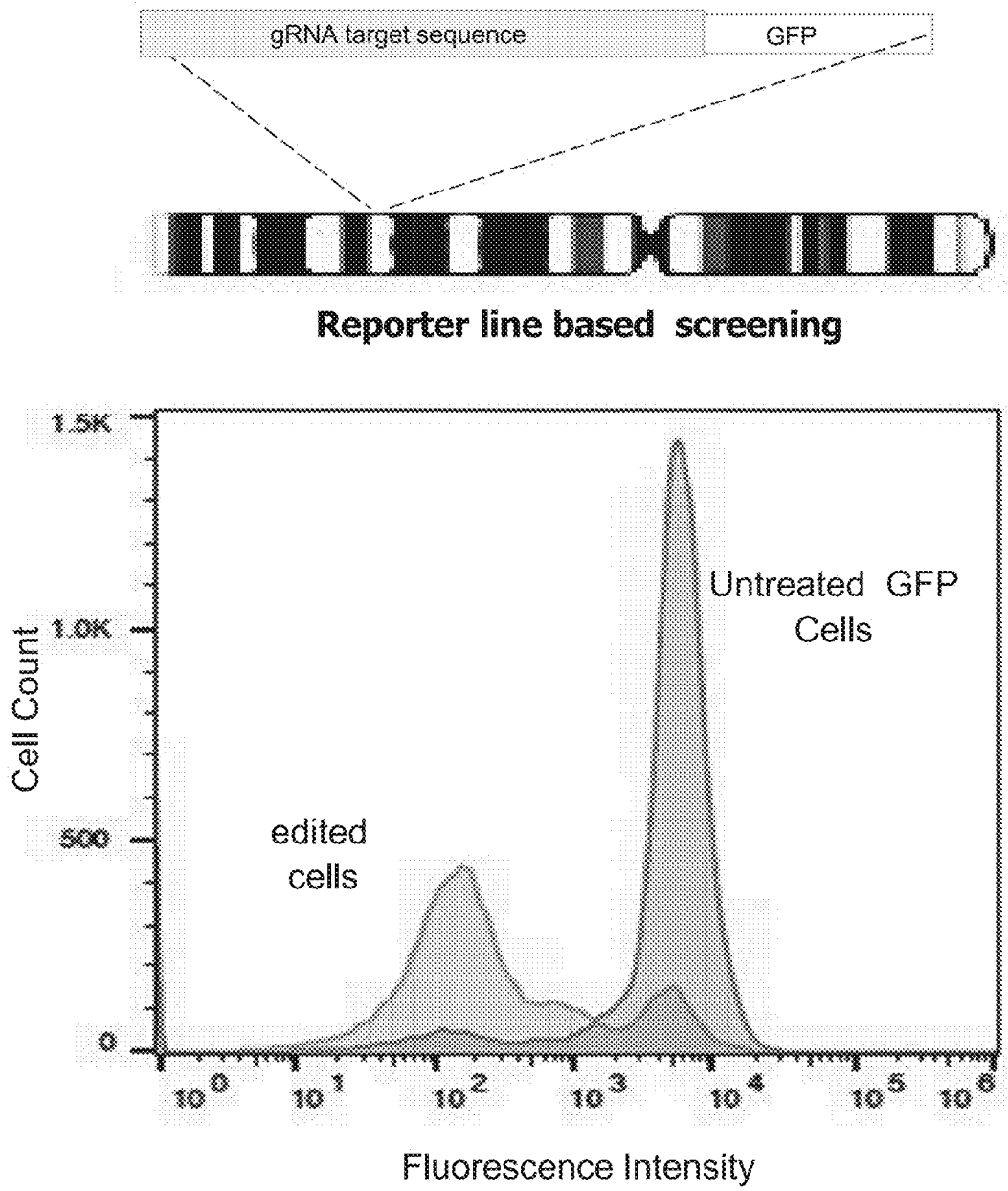
FIG. 25 is a diagram and an example fluorescence activated cell sorting (FACS) plot illustrating an exemplary method for assaying the effectiveness of a reference CasX protein or single guide RNA (sgRNA), or variants thereof, as described in Example 14. A reporter (e.g., GFP reporter) coupled to a gRNA target sequence, complementary to the gRNA spacer, is integrated into a reporter cell line. Cells are transformed or transfected with a CasX protein and/or sgRNA variant, with the spacer motif of the sgRNA complementary to and targeting the gRNA target sequence of the reporter. Ability of the CasX:sgRNA ribonucleoprotein complex to cleave the target sequence is assayed by FACS. Cells that lose reporter expression indicate occurrence of CasX:sgRNA ribonucleoprotein complex-mediated cleavage and indel formation.

Lentiviral Based Screen EGFP Screen:

Lentiviral particles were produced in HEK293 cells at a confluency of 70%-90% at time of transfection. Cells were transfected using polyethylenimine based transfection of plasmids containing a CasX DME library. Lentiviral vectors were co-transfected with the lentiviral packaging plasmid and the VSV-G envelope plasmids for particle production. Media was changed 12 hours post-transfection, and virus harvested at 36-48 hours post-transfection. Viral supernatants were filtered using 0.45 mm membrane filters, diluted in cell culture media if appropriate, and added to target cells HEK cells with an Integrated GFP reporter. Polybrene was supplemented to enhance transduction efficiency, if necessary. Transduced cells were selected for 24-48 hours post-transduction using puromycin and grown for 7-10 days. Cells were then sorted for GFP disruption & collected for highly functional CasX sgNA or protein variants (see FIG. 25). Libraries were then Amplified via PCR directly from the genome and collected for deep sequencing on a highseq. This DNA could also be re-cloned and re-transformed onto plates and individual clones were picked for further analysis.

Example 15: Assaying Editing Efficiency of an HEK EGFP Reporter

To assay the editing efficiency of CasX reference sgNAs and proteins and variants thereof, EGFP HEK293T reporter cells were seeded into 96-well plates and transfected according to the manufacturer's protocol with Lipofectamine™ 3000 (Life Technologies) and 100-200 ng plasmid DNA encoding a reference or CasX variant protein, P2A-puromycin fusion and the reference or variant sgNA. The next day cells were selected with 1.5 pg/ml puromycin for 2 days and analyzed by fluorescence-activated cell sorting (FACS) 7 days after selection to allow for clearance of EGFP protein from the cells. EGFP disruption via editing was traced using an Attune NxT Flow Cytometer and high-throughput autosampler.

Example 16: Cleavage Efficiency of CasX Reference sgRNA

The reference CasX sgRNA of SEQ ID NO:4 (below) is described in WO 2018064371 and U.S. Ser. No. 10/570,415B2, the contents of which are incorporated herein by reference:

(SEQ ID NO: 4)
ACAUCUGGCGCGUUUAUUCCAUUACUUUGGAGCCAGUCCCAGCGACUAU

GUCGUAUGGACGAAGCGCUUAUUUAUCGGAGAGAAACCGAUTAAGUAAA

ACGCAUCAAAG.

It was found that alterations to the sgRNA reference sequence of SEQ ID NO:4, producing SEQ ID NO:5 (below) were able to improve CasX cleavage efficiency. The sequence (SEQ ID NO: 5)
UACUGGCGCUUUUAUCUCAUUACUUUGAGAGCCAUCACCAGCGACUA

UGUCGUAUGGGUAAGCGCUUAUUUAUCGGAGAGAAAUCCGAUAAAUA

AGAAGCAUCAAAG.

To assay the editing efficiency of CasX reference sgRNAs and variants thereof, EGFP HEK293T reporter cells were seeded into 96-well plates and transfected according to the manufacturer's protocol with Lipofectamine™ 3000 (Life Technologies) and 100-200 ng plasmid DNA encoding a reference CasX protein, P2A-puromycin fusion and the sgRNA. The next day cells were selected with 1.5 pg/ml puromycin for 2 days and analyzed by fluorescence-activated cell sorting (FACS) 7 days after selection to allow for clearance of EGFP protein from the cells. EGFP disruption via editing was traced using an Attune NxT Flow Cytometer and high-throughput autosampler.

When testing cleavage of an EGFP reporter by CasX reference and sgNA variants, the following spacer target sequences were used: E6 (TGTGGTCGGGGTAGCGGCTG (SEQ ID NO: 17)) and E7 (TCAAGTCCGC-CATGCCCGAA (SEQ ID NO: 18)).

Figure 26:
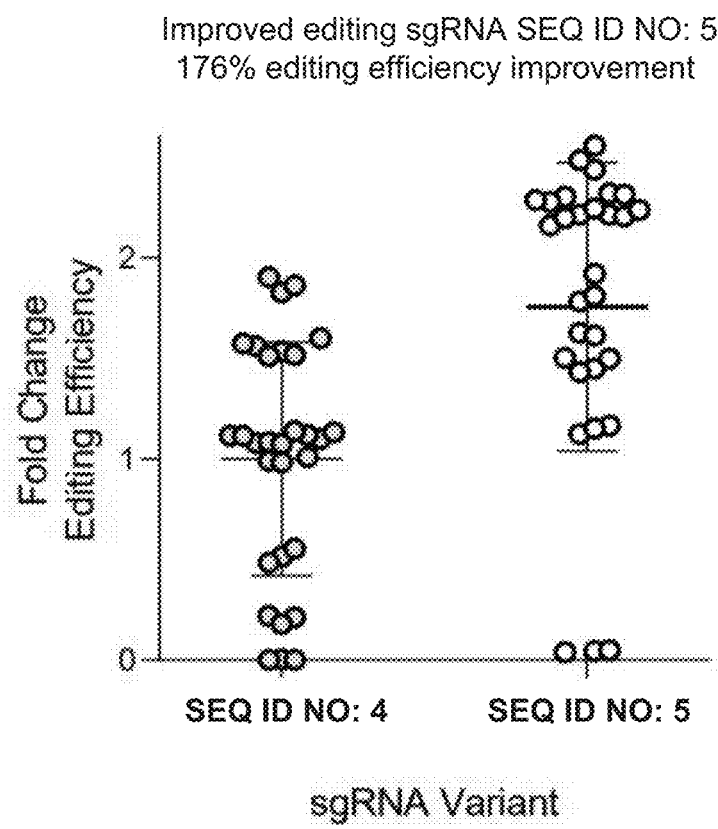
FIG. 26 shows results of gene editing in an EGFP disruption assay, as described in Example 16. Editing was measured by indel formation and GFP disruption in HEK293 cells carrying a GFP reporter.
Figure 27:
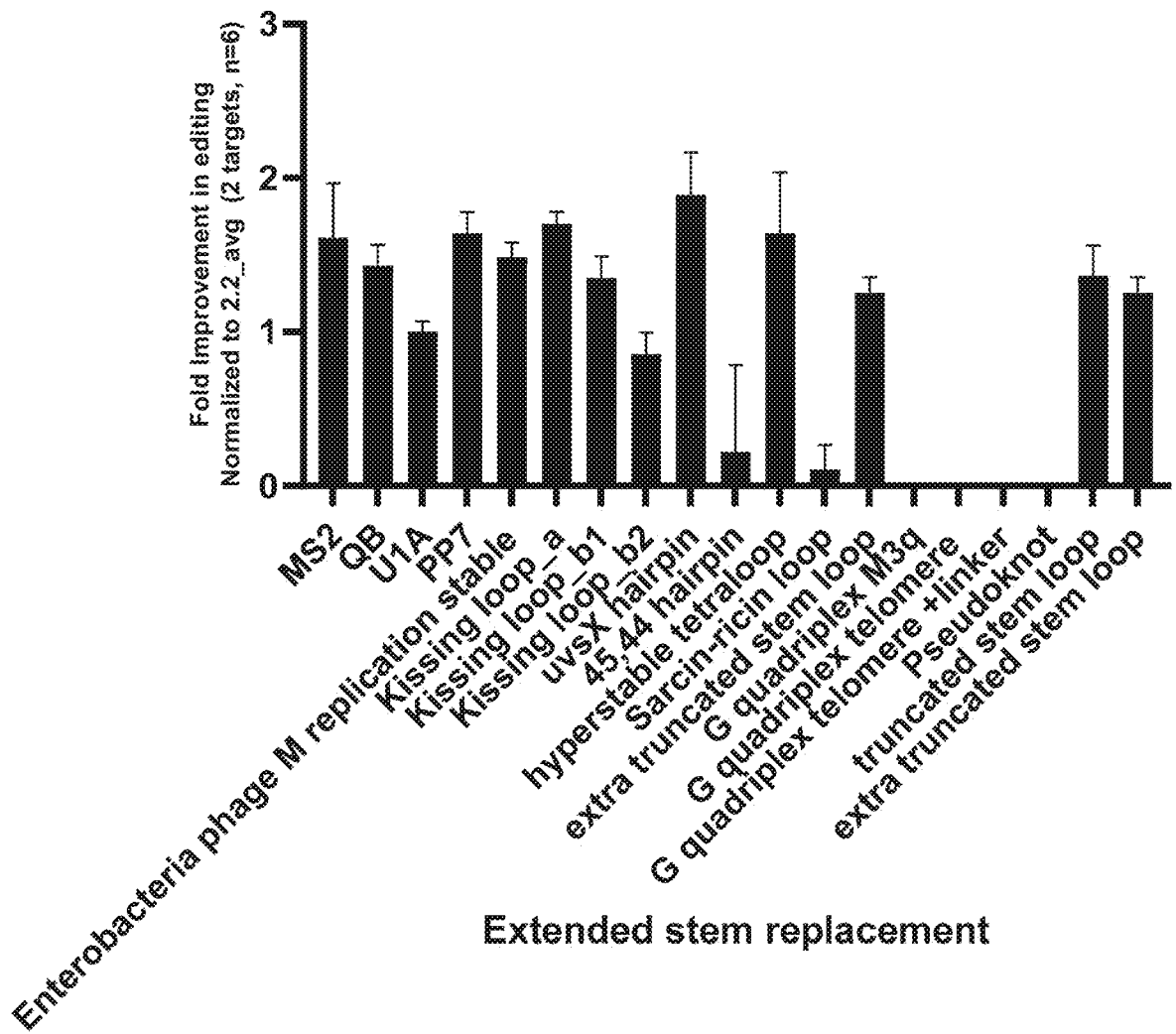
FIG. 27 shows results of gene editing in an EGFP disruption assay where further editing improvements were obtained in the sgRNA scaffold of SEQ ID NO:5 by swapping the extended stem loop sequence (indicated in the X-axis) for additional sequences to generate the scaffolds whose sequences are shown in Table 2, as described in Example 17.

An example of the increased cleavage efficiency of the sgRNA of SEQ ID NO:5 compared to the sgRNA of SEQ ID NO:4 is shown in FIG. 26. Editing efficiency of SEQ ID NO: 5 was improved 176% compared to SEQ ID NO: 4. Accordingly, SEQ ID NO: 5 was chosen as reference sgRNA for DME and additional sgNA variant design, described below.

Example 17: Design, Creation and Evaluation of gNA Variants with Improved Target Cleavage Guide nucleic acid (gNA) variants were designed and tested in order to assess improvements in cleavage activity relative to reference gNAs. These guides were discovered via DME or rational design and replacement or addition of guide parts such as the extended stem or the addition of ribozymes at the termini, as described herein.

Experimental design: All guides were tested In HEK293T or a HEK293T reporter line as follows. Mammalian cells were maintained in a 37° C. incubator, at 5% C02. HEK293T Human kidney cells and derivatives thereof were grown in Dulbecco's Modified Eagle Medium (DMEM; Corning Cellgro, #10-013-CV) supplemented with 10% fetal bovine serum (FBS; Seradigm, #1500-500), and 100 Units/ml penicillin and 100 mg/ml streptomycin (100×-Pen- Strep; GIBCO #15140-122), and can additionally include sodium pyruvate (100×, Thermofisher #11360070), Non-essential amino acids (100× Thermofisher #11140050). HEPES buffer (100× Thermofisher #15630080), and 2-mercaptoethanol (1000× Thermofisher #21985023). Cells were seeded at 20-30 thousand cells per well into 96-well plates and transfected using 0.25-1 uL of Lipofectamine™ 3000 (Thermo Fisher Scientific #L3000008), 50-500 ng of a plasmid containing CasX and the reference or variant CasX guide targeting the reporter or target gene following the manufacturer's protocol. 24-72 hours later the media was changed and 0.3-3.0 ug/ml puromycin (Sigma #P8833) was added to select for transformation. 24-96 hours following selection the cells were analyzed by flow cytometry and gated for the appropriate forward and side scatter, selected for single cells and then gated for green fluorescent protein (GFP) or antibody reporter expression (Attune Nxt Flow Cytometer, Thermo Fisher Scientific) to quantify the expression levels of fluorophores. At least 10,000 events were collected for each sample. For the HEK293T-GFP genome editing reporter cell line, flow cytometry was used to quantify the percentage of GFP-negative (edited) cells and the number of cells with GFP disruption for each variant was compared to the reference guide to generate a fold change measurement.

Figure 24:
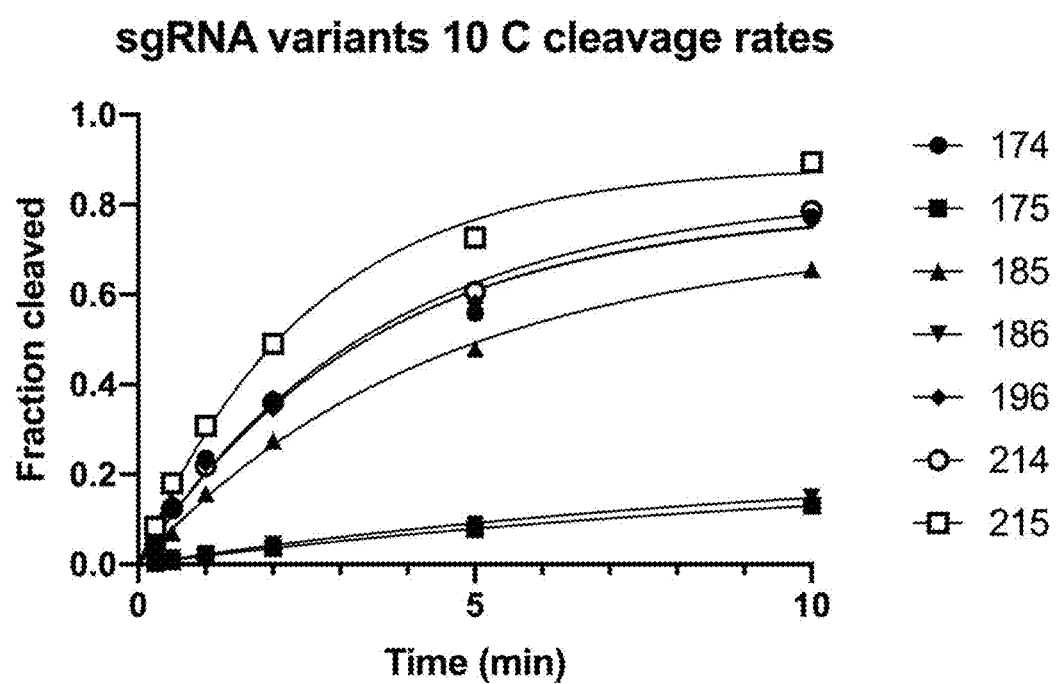
FIG. 24 shows the quantification of cleavage rates of RNP formed by CasX491 and the sgRNA variants, as described in Example 11. Target DNA was incubated with a 20-fold excess of the indicated RNP at 10° C., and the amount of cleaved target was determined at the indicated time points. The monophasic fit of the timepoints is shown.
Figure 28:
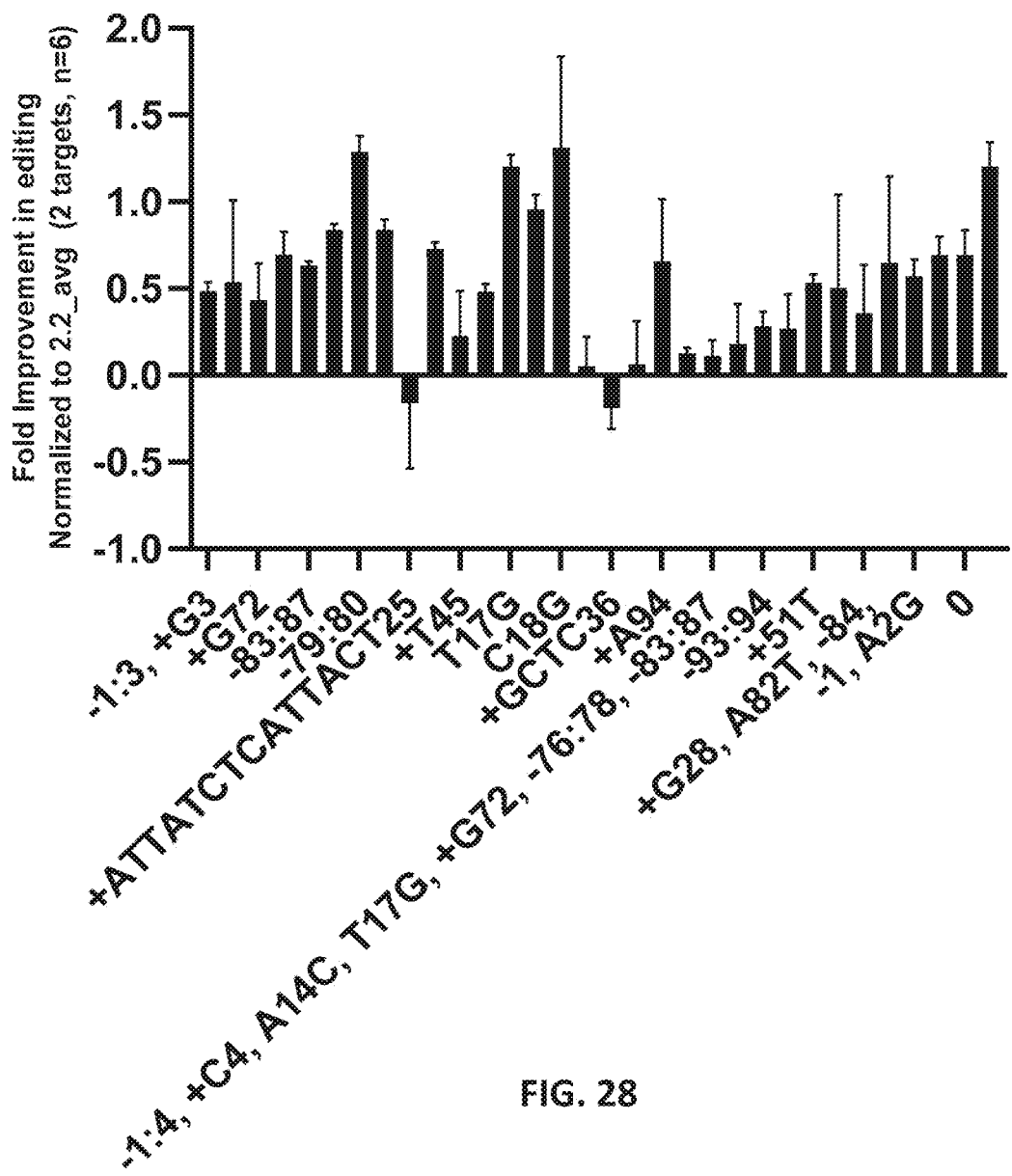
FIG. 28 is a graph showing the fold improvement of sgRNA variants (ATTATCTCATTACT; SEQ ID NO: 27301) generated by DME mutations normalized to SEQ ID NO:5 as the CasX reference sgRNA, as described in Example 17.
Figure 29:
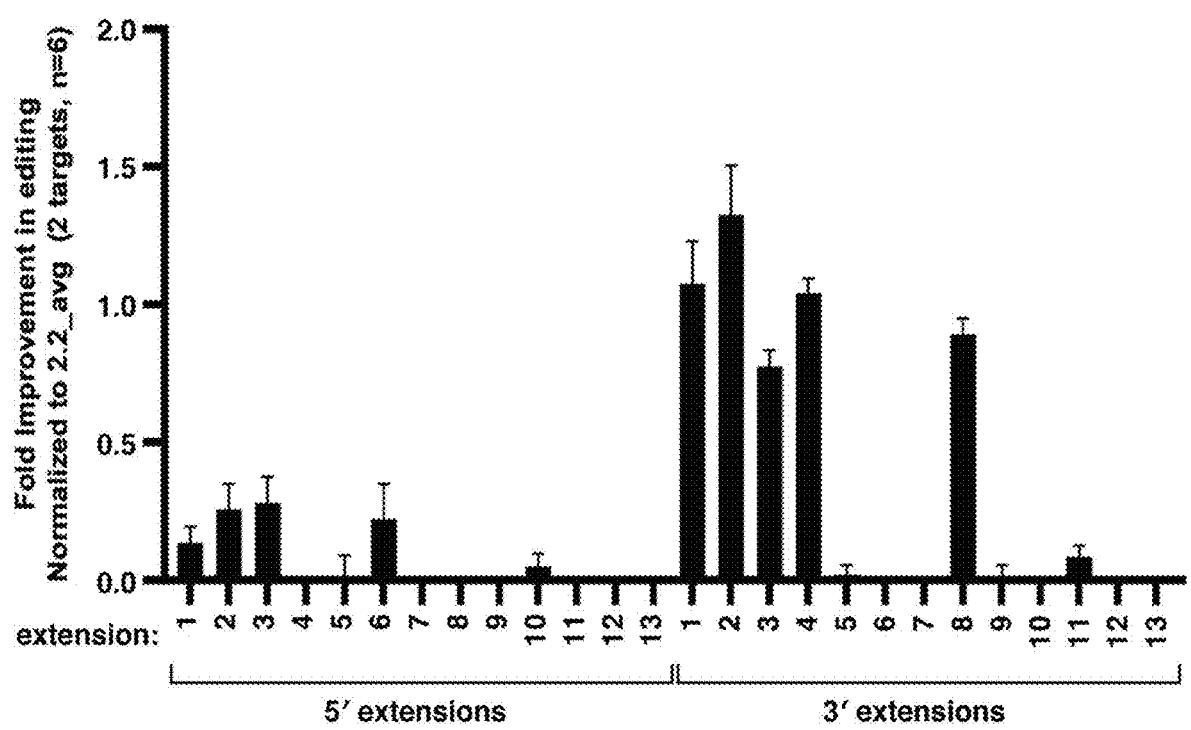
FIG. 29 is a graph showing the fold improvement normalized to the SEQ ID NO:5 reference CasX sgRNA of variants created by both combining (stacking) scaffold stem mutations showing improved cleavage, DME mutations showing improved cleavage, and using ribozyme appendages showing improved cleavage (the appendages and their sequences are listed in Table 13 in Example 17). The resulting sgRNA variants yield 2-fold or greater improvement in cleavage compared to SEQ ID NO:5 in this assay. EGFP editing assays were performed with spacer target sequences of E6 (TGTGGTCGGGGTAGCGGCTG (SEQ ID NO: 17)) and E7(TCAAGTCCGCCATGCCCGAA (SEQ ID NO: 18)) described in Example 16.

Results: Results from the sgNA variants generated via DME were measured and compared to the reference gNA of SEQ ID NO: 4. These results are presented in FIG. 28, with most variants showing improvements from 0.1 to nearly 1.5-fold compared to the reference gNA. Results of the variants generated via rational design and replacement or addition of guide parts (such as the extended stem or the addition of ribozymes at the termini) are shown in FIGS. 28 and 24 respectively; again showing improvements with many of the constructs. The additions to the variants, along with their encoding sequences, portrayed by number in FIG. 29 are listed in Table 13, below. We observed that single mutations such as the C18G improve guide activity when compared to the reference. Additionally, rationally swapping in different stem loops for the extended stem loop, such as MS2, QB, PP7, UvsX, etc. improved activity when compared to the reference guide, as does truncating the original extended stem loop. Finally, we demonstrate that while most ribozymes disrupt activity, the addition of a 3' HDV to the reference guide RNA can improve activity up to 20-50%.

TABLE 13

Extensions added to 3' and 5' ends of gNA

| Exten. Numb. | Extension Name | Extension Encoding Sequence |
| --- | --- | --- |
| 1 | HDV antigenomic ribozyme | GGGTCGGCATGGCATCTCCACCTCCTCGCGGTCCGACCT GGGCATCCGAAGGAGGACGCACGTCCACTCGGATGGCT AAGGGAGAGCCA (SEQ ID NO: 312) |
| 2 | HDV genomic ribozyme | GGCCGGCATGGTCCCAGCCTCCTCGCTGGCGCCGGCTGG GCAACATTCCGAGGGGACCGTCCCCTCGGTAATGGCGA ATGGGACCC (SEQ ID NO: 313) |
| 3 | HDV ribozyme (v1) | GATGGCCGGCATGGTCCCAGCCTCCTCGCTGGCGCCGGC TGGGCAACACCTTCGGGTGGCGAATGGGAC (SEQ ID NO: 314) |
| 4 | HDV ribozyme (v2) | TTTTGGCCGGCATGGTCCCAGCCTCCTCGCTGGCGCCGG CTGGGCAACATGCTTCGGCATGGCGAATGGGACCCCGG G (SEQ ID NO: 315) |
| 5 | Hatchet | CATTCCTCAGAAAATGACAAACCTGTGGGGCGTAAGTA GATCTTCGGATCTATGATCGTGCAGACGTTAAAATCAGG T (SEQ ID NO: 316) |
| 6 | env25 pistol ribozyme (with CUUCGG loop) | CGTGGTTAGGGCCACGTTAAATAGTTGCTTAAGCCCTAA GCGTTGATCTTCGGATCAGGTGCAA (SEQ ID NO: 317) |
| 7 | HH15 Minimal Hammerhead ribozyme | GGGAGCCCCGCTGATGAGGTCGGGGAGACCGAAAGGGA CTTCGGTCCCTACGGGGCTCCC (SEQ ID NO: 318) |
| 8 | sTRSV WT viral Hammerhead ribozyme | CCTGTCACCGGATGTGCTTTCCGGTCTGATGAGTCCGTG AGGACGAAACAGG (SEQ ID NO: 319) |
| 9 | Hammerhead ribozyme | CGACTACTGATGAGTCCGTGAGGACGAAACGAGTAAGC TCGTCTAGTCGCGTGTAGCGAAGCA (SEQ ID NO: 320) |
| 10 | Hammerhead ribozyme, smaller scar | CGACTACTGATGAGTCCGTGAGGACGAAACGAGTAAGC TCGTCTAGTCG (SEQ ID NO: 321) |
| 11 | Hammerhead ribozyme, guide scaffold scar | CCAGTACTGATGAGTCCGTGAGGACGAAACGAGTAAGC TCGTCTACTGGCGCTTTTATCTCAT (SEQ ID NO: 322) |
| 12 | Twisted Sister 1 | ACCCGCAAGGCCGACGGCATCCGCCGCCGCTGGTGCAA GTCCAGCCGCCCCTTCGGGGCGGGCGCTCATGGGTAAC (SEQ ID NO: 323) |

TABLE 13-continued

Extensions added to 3' and 5' ends of gNA

| Exten. Numb. | Extension Name | Extension Encoding Sequence |
|---|---|---|
| 13 | Env-9 Twister | GGCAATAAAGCGGTTACAAGCCCGCAAAAATAGCAGAG TAATGTCGCGATAGCGCGGCATTAATGCAGCTTTATTG (SEQ ID NO: 324) |
| 14 | RBMX recruiting motif | CCACCCCCACCACCACCCCCACCCCCACCACCACCC (SEQ ID NO: 325) |

The results support the conclusion that DME and rational design can be used to improve the performance of the gNAs and that many of these variant RNAs can now be used with the targeting sequences as a component of the CasX:gNA systems described herein to edit target nucleic acid sequences.

Example 18: CasX Edits P23 RHO in an Allele-Specific Manner

The goal of this experiment was to show that CasX variant 119 and scaffold variants 64 and 174 can edit the human RHO locus around amino acid residue P23, while native CasX variant 2 and scaffold 2 cannot. HEK293T cells with both wild-type alleles should be editable by the WT CasX spacer (11.1, having the sequence AAGGGGCTGCGTAC-CACACC, SEQ ID NO: 367), but not by the mutant CasXspacer (11.2 having the sequence AAGTGGCTGCGTACCACACC, SEQ ID NO: 368). This experiment additionally demonstrates the ability of CasX spacers to distinguish between on-target and off-target alleles that differ by a single nucleotide.

Materials and Methods:

HEK293T cells were seeded at 20-40 k cells/well in a 96 well plate in 100 µL of Fibroblast (FB) medium and cultured in a 37° C. incubator with 5% C02. The following day, confluence of seeded cells was checked to ensure that cells were at ~75% confluence at time of transfection. If cells were at the right confluence, transfection was carried out. Each CasX and guide construct (119.174, see Table for sequence) was transfected into the HEK293T cells at 100-500 ng per well using Lipofectamine™ 3000 following the manufacturer's protocol, using 3 wells per construct as replicates. SaCas9 and SpyCas9 targeting RHO were used as benchmarking controls. For each Cas protein type, a non-targeting plasmid was used as a negative control. Cells were selected for successful transfection with puromycin at 0.3-3 pg/ml for 24-48 hours followed by 24-48 hours of recovery in FB medium. A subset of cells for each sample from the experiment was lysed, and the genome was extracted using a Quick extract solution following the manufacturer's protocol. Editing was analyzed using a T7E1 assay. Briefly, the genomic locus at the targeted edit site was amplified using primers (e.g., a 500 bp region around the intended target) using a PCR program on a thermocycler. The PCR amplicon was then hybridized following a hybridization program on a thermocycler, and then treated with T7 Endonuclease for 30 mins at 37° C. The sample was then analyzed on a 2% agarose gel to visualize the DNA bands.

Figure 30:
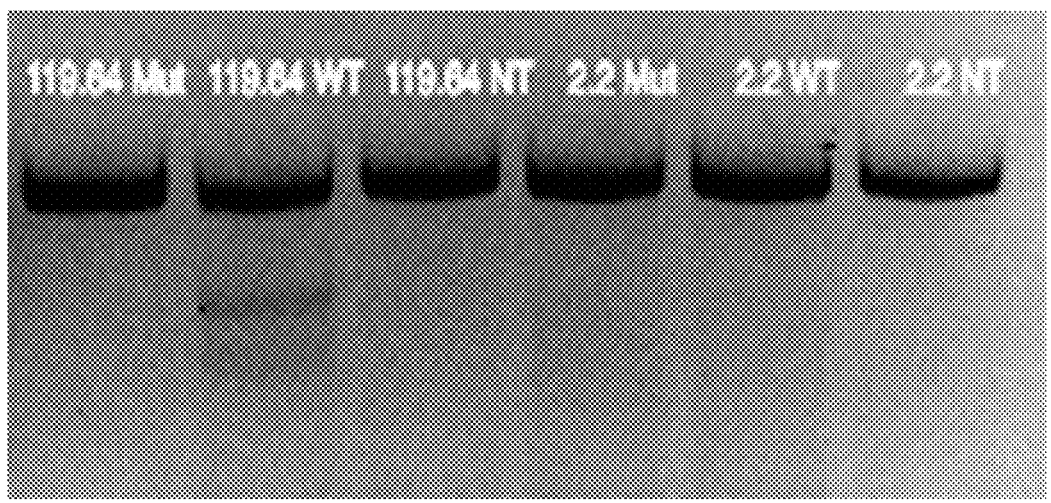
FIG. 30 shows a gel image from the T7E1 assay demonstrating allele-specific editing by CasX variant 119 and scaffold 64 at the WIT RHO P23 locus in HEK293T cells, as described in Example 18. Genomic DNA from HEK293T cells lipofected with CasX and guide constructs are: (from left to right in the gel) CasX 119 and guide scaffold 64 with spacer targeting mutant allele, CasX 119 and guide scaffold 64 with spacer targeting WT allele (demonstrating editing), CasX 119 and guide scaffold 64 with non-targeting spacer. CasX 2 and guide scaffold 2 with spacer targeting mutant allele, CasX 2 and guide scaffold 2 with spacer targeting WT allele, CasX 2 and guide scaffold 2 with non-targeting spacer) were assayed for editing at the RHO locus by a T7E1 assay.

Results:

As shown in FIG. 30, results from the T7E1 assay performed to assess editing demonstrated that the CasX construct, 119.64, was able to edit the WT RHO locus in HEK293T cells when targeted to the P23 locus using a spacer that targets the WT sequence (119.64.WT, second lane). A CasX construct with a spacer that targets the mutant sequence (119.64.Mut), or a non-targeting sequence (119.64.NT), was not able to edit the WT locus in these cells.

Figure 31:
FIG. 31 shows a gel image of the T7E1 assay results assessing editing by CasX, SaCas9 and SpyCa9 at the WT RHO P23 locus in HEK293T cells, as described in Example 18.
Figure 32:
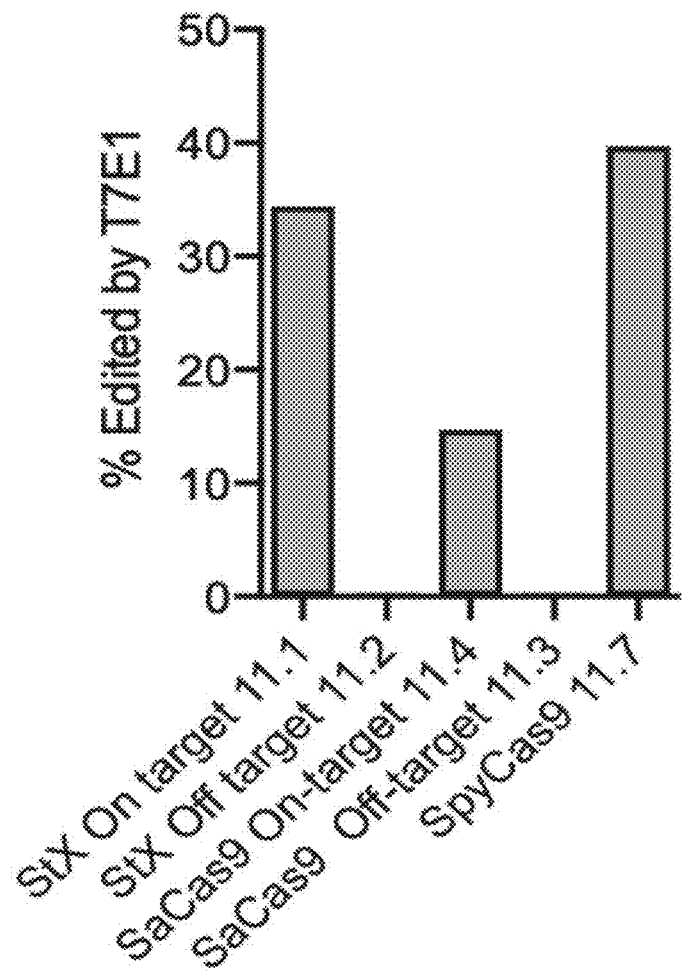
FIG. 32 is a graph with the quantification of the editing results of the gel in FIG. 31, as described in Example 18.

FIG. 31 (T7E1 gel) and FIG. 32 (quantification of gel) shows that CasX variant 119 and scaffold variant 174 with spacer 11.1 was able to edit the on-target wild type RHO locus at 34.4% efficiency, while CasX variant and scaffold 174 with the off-target spacer 11.2 showed no activity at the WT locus. In comparison, the on-target SaCas9 construct showed 14.7% editing. SpyCas9 showed 39.9% efficiency at editing the RHO locus in general, but not at the P23H locus due to the absence of a nearby PAM.

This example demonstrates that CasX with appropriate guides was able to edit the P23 RHO locus in an allele-specific manner, and that the engineered CasX variant 119 and scaffold 64 (as opposed to native CasX variant 2 and scaffold 2) was able to edit P23 RHO locus at a non-canonical CTCN PAM. Additionally, CasX variant 119 and scaffold 174 maintains the ability to edit P23 RHO locus in an allele-specific manner, and edits on target with higher efficiency than SaCas9. SpyCas9 cannot edit allele-specifically at the P23 RHO locus due to unavailability of a PAM sequence. Thus, CasX is uniquely positioned to edit the P23 RHO locus in an allele-specific manner.

Example 19. Engineered CasX Variants Edit P23 RHO in an Allele Specific Manner

The purpose of this experiment was to assess the ability of engineered CasX variants to edit the human P23 RHO locus in an allele-specific manner. The ability to edit on target with high specificity and minimum off target activity is important for an allele-specific therapeutic approach to address AdRP.

Materials and Methods:

An ARPE19 dual reporter cell line (WT.RHO.GFP mut.RHO.mscarlet) was first generated by knocking into ARPE19 cells a transgene cassette that constitutively expresses exon 1 of the human RHO gene linked to GFP and exon 1 of the human P23H.RHO gene linked to mscarlet. The modified cells were expanded by serial passage every 3-5 days and maintained in Fibroblast (FB) medium, consisting of Dulbecco's Modified Eagle Medium (DMEM: Corning Cellgro, #10-013-CV) supplemented with 10% fetal bovine serum (FBS; Seradigm, #1500-500), and 100 Units/mL penicillin and 100 mg/mL streptomycin (100×-Pen-Strep; GIBCO #15140-122), and can additionally include sodium pyruvate (100×, Thermofisher #11360070), non-essential amino acids (100× Thermofisher #11140050). HEPES buffer (100× Thermofisher #15630080), and 2-mercaptoethanol (1000× Thermofisher #21985023). The cells were incubated at 37° C., and 5% CO2. After 1-2 weeks, GFP+/mscarlet+ cells were bulk sorted into FB medium. The reporter lines were expanded by serial passage every 3-5 days and maintained in FB medium in an incubator at 37° C., and 5% CO2. Reporter clones were generated by a limiting dilution method. The clonal lines were characterized via flow cytometry, genomic sequencing, and functional modification of the RHO locus using a previously validated RHO targeting CasX molecule. The optimal reporter lines were identified as ones that i) had single copies of WTRHO.GFP and mutRHO.mscarlet correctly integrated per cell, ii) maintained doubling times equivalent to unmodified cells, and iii) resulted in reduction in GFP/mscarlet fluorescence upon disruption of the RHO gene when assayed using the methods described below.

ARPE19 dual reporter cells, constructed using cell line generation methods described above were used for this experiment. Cells were seeded at 20-40 k cells/well in a 96 well plate in 100 µL of FB medium and cultured in a 37° C. incubator with 5% CO2. The following day, lentiviral vectors packaging each CasX and guide construct (spacer sequences were 11.1 and 11.2) were used to transduce cells at a high multiplicity of infection (MOI 300), using 3 wells per construct as replicates. A lentivirus packaging a non-targeting construct (spacer 11.2) was used as a negative control. Cells were selected for successful transduction with puromycin at 0.3-3 µg/ml for 24-48 hours followed by recovery in FB medium. Edited cells were analyzed by flow cytometry 14 days after transduction. Briefly, cells were sequentially gated for live cells, single cells, and fraction of GFP-negative and mscarlet-negative cells.

Figure 33:
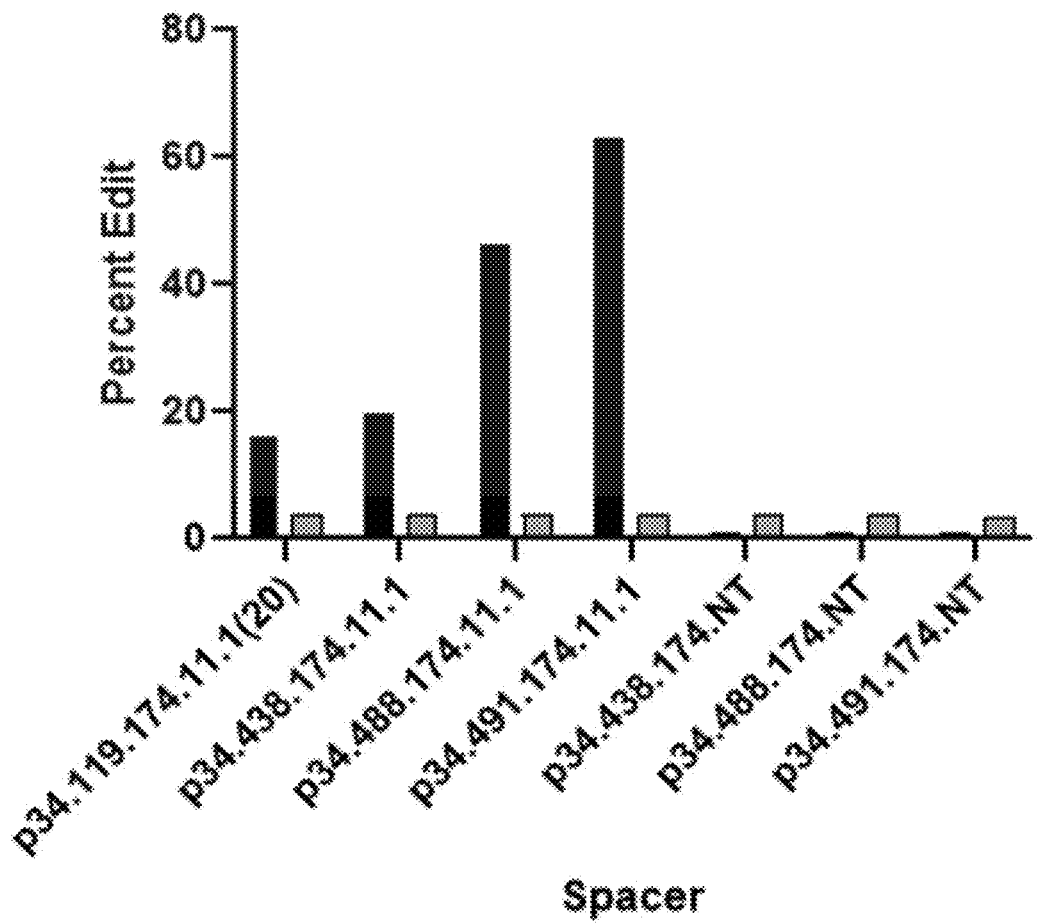
FIG. 33 shows results of an editing experiment in which CasX protein variants 119, 438, 488, and 491 with scaffold 174 were used to edit the RHO locus in ARPE19 dual reporter cells (WT.RHO-GFP P23H.RHO-mscarlet) cells in an allele-specific manner, as described in Example 19. ARPE19 dual reporter cells were transduced at MOI 300 with lentivirus packaging CasX constructs with spacer 11.1 targeting the WT.RHO allele, and editing was analyzed at the WT allele (GFP– cells, black bars) and the mutant allele (mscarlet-cells, gray bars) by flow cytometry 14 days post-transduction. Data are presented as average editing from n=3 replicates.
Figure 34:
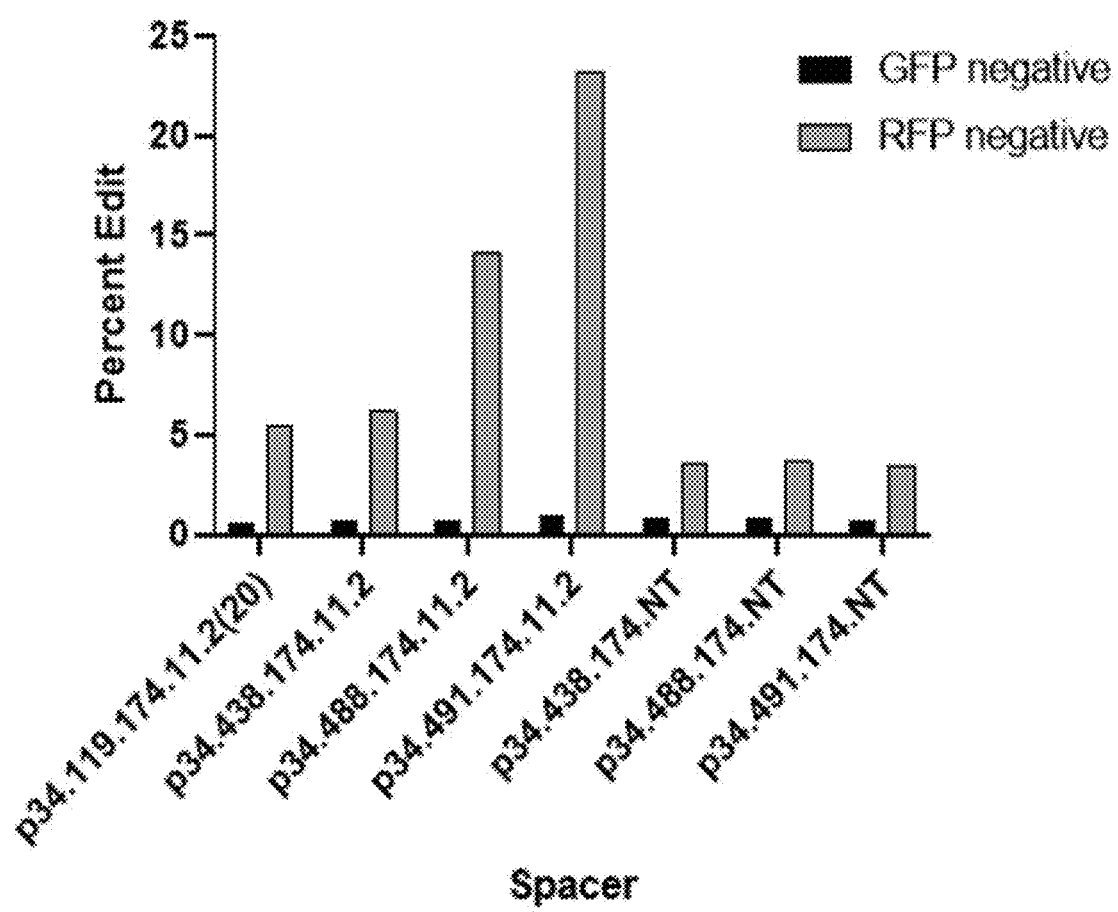
FIG. 34 shows results of an editing experiments in which CasX protein variants 119, 438, 488, and 491 with scaffold 174 edit the RHO locus in ARPE 19 dual reporter cells (WT.RHO-GFP P23H.RHO-mscarlet) cells in an allele-specific manner, as described in Example 19. ARPE19 dual reporter cells were transduced at MOI 300 with lentivirus packaging CasX constructs with spacer 11.2 targeting the mut.RHO allele, and editing was analyzed at the WT allele (GFP– cells, black bars) and the mutant allele (mscarlet-cells, gray bars) by flow cytometry 14 days post-transduction. Data are presented as average editing from n=3 replicates.

Results:

The graph in FIG. 33 shows that CasX variants 119, 438, 488 and 491 and scaffold 174 with spacer 11.1 targeting the WT RHO allele are able to edit on target with minimal off-target activity at the mutant RHO allele. Improved CasX variants show increasingly higher levels of editing on target (GFP– cells, black bars), with no appreciable gain in off-target activity at the P23 RHO locus (mscarlet– cells, gray bars). Similarly, the graph in FIG. 34 shows that CasX variants 119, 438, 488 and 491 and scaffold 174 with spacer 11.2 targeting the mutant RHO allele are able to edit on target with minimal off-target activity at the WT RHO allele. The CasX variants show increasingly higher levels of editing on target at the mutant RHO locus (mscarlet-cells, gray bars)(491>488>438>119), with no appreciable gain in off-target activity at the WT RHO locus (GFP– cells, black bars).

Under conditions of the assays, the results demonstrates that improved, engineered CasX variants edit the P23 RHO locus at higher efficiencies while maintaining allele-specificity.

Example 20: CasX Edits the RHO Gene at Many Different Loci in HEK293T Cells

The purpose of the experiment was to demonstrate the ability of CasX to edit the human RHO locus using the CasX variants 438, 488 and 491, guide 174 variant, and spacers (See Table 1 for sequences) targeting exon 1 of the human RHO gene.

Materials and Methods:

To facilitate assessment of editing outcomes, a HEK293T dual reporter cell line was first generated by knocking into HEK293T cells two transgene cassettes that constitutively expressed exon 1 of the human RHO gene linked to GFP and exon 1 of the human P23H.RHO gene linked to mscarlet. The modified cells were expanded by serial passage every 3-5 days and maintained in Fibroblast (FB) medium, consisting of Dulbecco's Modified Eagle Medium (DMEM; Corning Cellgro, #10-013-CV) supplemented with 10% fetal bovine serum (FBS; Seradigm, #1500-500), and 100 Units/mL penicillin and 100 mg/mL streptomycin (100×-Pen-Strep; GIBCO #15140-122), and can additionally include sodium pyruvate (100×, Thermofisher #11360070), non-essential amino acids (100× Thermofisher #11140050), HEPES buffer (100× Thermofisher #15630080), and 2-mercaptoethanol (1000× Thermofisher #21985023). The cells were incubated at 37° C., and 5% CO2. After 1-2 weeks, GFP+/mscarlet+ cells were bulk sorted into FB medium. The reporter lines were expanded by serial passage every 3-5 days and maintained in FB medium in an incubator at 37° C., and 5% C02. Reporter clones were generated by a limiting dilution method. The clonal lines were characterized via flow cytometry, genomic sequencing, and functional modification of the RHO locus using a previously validated RHO targeting CasX molecule. The optimal reporter lines were identified as ones that i) had a single copies of WTRHO.GFP and mutRHO.mscarlet correctly integrated per cell, ii) maintained doubling times equivalent to unmodified cells, and iii) resulted in reduction in GFP and mscarlet fluorescence upon disruption of the RHO gene when assayed using the methods described below.

Spacers for the guides were chosen based on PAM availability without prior knowledge of potential activity (see Table 14 for sequences). HEK293T dual reporter cells were seeded at 20-40 k cells/well in a 96 well plate in 100 µL of FB medium and cultured in a 37° C. incubator with 5% C02. The following day, cells were transfected at ~75% confluence. Each CasX and guide construct with spacers (see table for spacer and guide sequences) was transfected into the HEK293T dual reporter cells at 100-500 ng per well using Lipofectamine™ 3000 following the manufacturer's protocol, using 3 wells per construct as replicates. A non-targeting plasmid was used as a negative control. Cells were selected for successful transfection with puromycin at 0.3-3 µg/ml for 24-48 hours followed by recovery in FB medium. Edited cells were analyzed by flow cytometry 14 days after transfection. Briefly, cells were sequentially gated for live cells, single cells, and fraction of GFP-negative and/or mscarlet-negative cells.

Figure 35:
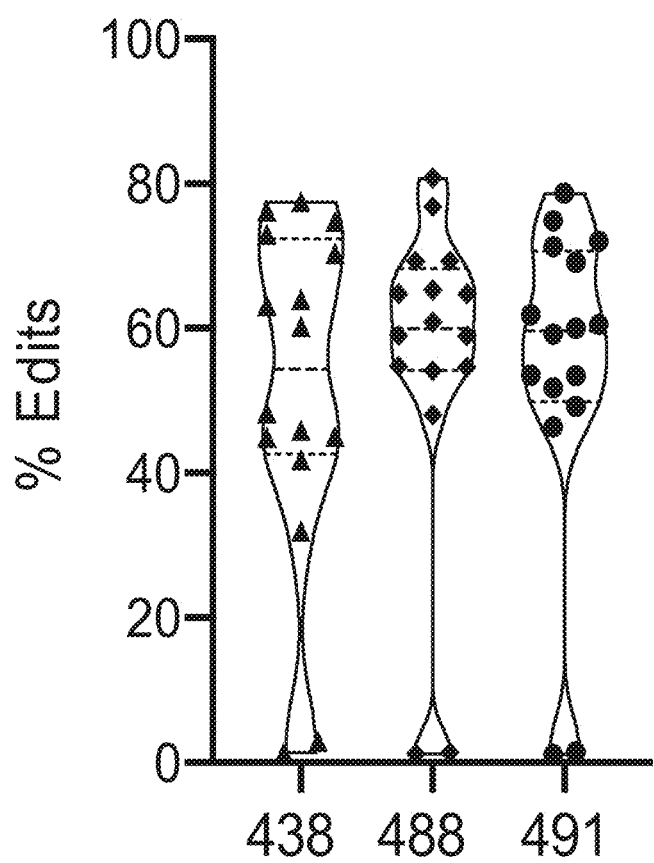
FIG. 35 shows the results of an editing experiment in which CasX protein variants 438, 488, and 491 with scaffold 174 edit the RHO locus in HEK293T dual reporter cells (WT.RHO-GFP P23H.RHO-mscarlet) cells, as described in Example 20. HEK293T dual reporter cells were transduced at MOI 300 with lentivirus packaging CasX constructs targeting the RHO gene and editing was analyzed by flow cytometry 14 days post-transduction. Data are presented as violin plots where each individual data point represents average editing (from n=3 replicates) generated by a single spacer.

Results:

The graph in FIG. 35 shows the results of flow cytometry analysis of Cas-mediated editing at the RHO locus in the HEK293T APRE19 dual dual reporter cells 14 days post-transfection. Eighteen different spacers (indicated by the individual data points) targeting the RHO exon 1 locus were used for each of the different CasX variants (438, 488, and 491) used in this experiment. Each data point is an average measurement of 3 replicates for an individual spacer. The results indicate that CasX and guides with several different spacers were able to edit the RHO locus with an average editing of 20%. The construct with non-targeting spacer resulted in no editing (data not shown).

Under conditions of the assays, the results demonstrate that, under the conditions of the assay, CasX variants 438, 488 and 491 with appropriate guides were able to successfully edit the RHO gene at many different loci in HEK293T dual reporter cells.

TABLE 14

RHO Guide sequences

| SSpacer | SSpacer Sequence | 174 Scaffold Sequence | Scaffold + Spacer Sequence |
|---|---|---|---|
| 11.13 | CAGCATTCT TGGGTGGGA GC (SEQ ID NO: 328) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGCAGCA TTCTTGGGTGGGAGC (SEQ ID NO: 348) |
| 11.14 | TGGGTGGGA GCAGCCACG GG (SEQ ID NO: 329) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTGGGT GGGAGCAGCCACGGG (SEQ ID NO: 349) |
| 11.15 | TGGCTGTGG CCCTTGTGG CT (SEQ ID NO: 330) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTGGCT GTGGCCCTTGTGGCT (SEQ ID NO: 350) |
| 11.16 | GTGCCATTC ATGGCTGTG GC (SEQ ID NO: 331 | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGGTGCC ATTCATGGCTGTGGC (SEQ ID NO: 351) |
| 11.17 | ACGTGCCCT TCTCCAATG CG (SEQ ID NO: 332) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGACGTG CCCTTCTCCAATGCG (SEQ ID NO: 352) |
| 11.18 | CCAATGCGA C GGGTGTGG TA (SEQ ID NO: 333) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGCCAAT GCGACGGGTGTGGTA (SEQ ID NO: 353) |
| 11.19 | AGTACCCAC AGTACTACC TG (SEQ ID NO: 334) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGAGTAC CCACAGTACTACCTG (SEQ ID NO: 354) |
| 11.20 | CCATGCTGG CCGCCTACA TG (SEQ ID NO: 335) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGCCATG CTGGCCGCCTACATG (SEQ ID NO: 355) |
| 11.21 | GCTGATCGT GCTGGGCTT CC (SEQ ID NO: 336) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGGCTGA TCGTGCTGGGCTTCC (SEQ ID NO: 356) |
| 11.22 | CCATCAACT TCCTCACGC TC (SEQ ID | ACTGGCGCTTTTATCT GATTACTTTGAGAGC CATCACCAGCGACTA | ACTGGCGCTTTTATCTGAT TACTTTGAGAGCCATCACC AGCGACTATGTCGTAGTGG |

TABLE 14-continued

RHO Guide sequences

| SSpacer | SSpacer Sequence | 174 Scaffold Sequence | Scaffold + Spacer Sequence |
|---|---|---|---|
| | NO: 337) | TGTCGTAGTGGGTAA AGCTCCCTCTTCGGA GGGAGCAT CAAAG (SEQ ID NO: 347) | GTAAAGCTCCCTCTTCGGA GGGAGCATCAAAGCCATC AACTTCCTCACGCTC (SEQ ID NO: 357) |
| 11.23 | TCACGCTCT ACGTCACCG TC (SEQ ID NO: 338) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTCACG CTCTACGTCACCGTC (SEQ ID NO: 358) |
| 11.24 | TGTGCTGGA CGGTGACGT AG (SEQ ID NO: 339) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTGTGC TGGACGGTGACGTAG (SEQ ID NO: 359) |
| 11.25 | TGGTCCTAG GTGGCTTCA CC (SEQ ID NO: 340) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTGGTC CTAGGTGGCTTCACC (SEQ ID NO: 360) |
| 11.26 | CCAGCACCC TCTACACCT CT (SEQ ID NO: 341) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGCCAGC ACCCTCTACACCTCT (SEQ ID NO: 361) |
| 11.27 | TCTTCGGGC CCACAGGAT GC (SEQ ID NO: 342) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTCTTC GGGCCCACAGGATGC (SEQ ID NO: 362) |
| 11.28 | GGCCCACAG GATGCAATT TG (SEQ ID NO: 343) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGGGCCC ACAGGATGCAATTTG (SEQ ID NO: 363) |
| 11.29 | TTGCCACCC TGGGCGGIA TG (SEQ ID NO: 344) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGTTGCC ACCCTGGGCGGTATG (SEQ ID NO: 364) |
| 11.1 | AAGGGGCT GCGTACCAC ACC (SEQ ID NO: 345) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGAAGGG GCTGCGTACCACACC (SEQ ID NO: 365) |

TABLE 14-continued

RHO Guide sequences

| SSpacer | SSpacer Sequence | 174 Scaffold Sequence | Scaffold + Spacer Sequence |
|---|---|---|---|
| 11.2 | AAGTGGG CTGCGTAC CACACC (SEQ ID NO: 346) | ACTGGCGCTTTTATCT GATTACTTTGAGAGC CATCACCAGCGACTA TGTCGTAGTGGGTAA AGCTCCCTCTTCGGA GGGAGCATCAAAG (SEQ ID NO: 347) | ACTGGCGCTTTTATCTGAT TACTTTGAGAGCCATCACC AGCGACTATGTCGTAGTGG GTAAAGCTCCCTCTTCGGA GGGAGCATCAAAGAAGTG GGCTGCGTACCACACC (SEQ ID NO: 366) |

Example 21: CasX Targeted to P23 RHO Shows No Detectable Editing at Predicted Off-Target Locations in the Human Genome A key aspect to evaluate targeted RNP of CasX and guide RNA is to ensure specific cleavage at on-target sites in the genome, with limited or no detectable edits at possible off-targets. The purpose of these experiments was to evaluate whether we could detect off-target editing of the RNP targeted to the human RHO P23H spacer (see Table 15 for spacer sequences).

To achieve this goal, a set of predicted off targets for the human RHO P23H spacer (11.2) in the human genome were generated computationally, and then assessed for detectable editing when treated with a targeted CasX RNP.

Materials and Methods:

Off-Target Site Prediction

Off-targets of the spacer sequence 11.2 were predicted for the entire human genome (hg38). Off-targets were required to have a competent PAM (here, TTC or CTC), and sufficient similarity to the spacer 11.2 sequence. A position-weight-matrix (PWM) was generated to model the PAM-spacer sequence, with a requirement for more stringent sequence matching in the PAM and in the PAM-proximal region of the spacer. Every sequence across the genome was compared to this PWM to generate a score. A score threshold was determined to include every single and double mutation within the spacer sequence, the large majority of triple and quadruple mutants (excluding only those sequences with all mutations occurring in the 7 PAM-proximal nucleotides), and a subset of higher order mutations (5 or more mutations). Regions of the genome with a score greater than or equal to the score threshold were identified for the experiments.

Cell Treatment

HEK293T cells were seeded at 20-40 k cells/well in a 96 well plate in 100 µL of Fibroblast (FB) medium and cultured in a 37° C. incubator with 5% CO2. The following day, confluence of seeded cells was checked to ensure that cells were at ~75% confluence at time of transfection. If cells were at the right confluence, transfection was carried out. Each CasX and guide construct (119.174, see Table 15 for spacer sequences) was transfected into the HEK293T cells at 100-500 ng per well using Lipofectamine™ 3000 following the manufacturer's protocol, using 3 wells per construct as replicates. SaCas9 and SpyCas9 targeting RHO were used as benchmarking controls. For each Cas protein type, a non-targeting plasmid was used as a negative control. Cells were selected for successful transfection with puromycin at 0.3-3 µg/ml for 24-48 hours followed by 24-48 hours of recovery in FB medium. A subset of cells for each sample from the experiment was lysed, and the genome was extracted using a Quick extract solution following the manufacturer's protocol.

An ARPE19 dual reporter cell line (WT.RHO.GFP mut.RHO.mscarlet) was first generated by knocking into ARPE19 cells a transgene cassette that constitutively expresses exon 1 of the human RHO gene linked to GFP and exon 1 of the human P23H.RHO gene linked to mscarlet. The modified cells were expanded by serial passage every 3-5 days and maintained in Fibroblast (FB) medium, consisting of Dulbecco's Modified Eagle Medium (DMEM: Corning Cellgro, #10-013-CV) supplemented with 10% fetal bovine serum (FBS; Seradigm, #1500-500), and 100 Units/mL penicillin and 100 mg/mL streptomycin (100×-Pen-Strep: GIBCO #15140-122), and can additionally include sodium pyruvate (100×, Thermofisher #11360070), non-essential amino acids (100× Thermofisher #11140050). HEPES buffer (100× Thermofisher #15630080), and 2-mercaptoethanol (1000× Thermofisher #21985023). The cells were incubated at 37° C., and 5% CO2. After 1-2 weeks, GFP+ cells were bulk sorted into FB medium. The reporter lines were expanded by serial passage every 3-5 days and maintained in FB medium in an incubator at 37° C., and 5% CO2. Reporter clones were generated by a limiting dilution method. The clonal lines were characterized via flow cytometry, genomic sequencing, and functional modification of the RHO locus using a previously validated RHO targeting CasX molecule. The optimal reporter lines were identified as ones that i) had a single copy of GFP correctly integrated per cell, ii) maintained doubling times equivalent to unmodified cells, and iii) resulted in reduction in GFP fluorescence upon disruption of the RHO gene when assayed using the methods described below.

ARPE19 dual reporter cells, constructed using cell line generation methods described above, were used for this experiment. Cells were seeded at 20-40 k cells/well in a 96 well plate in 100 µL of FB medium and cultured in a 37° C. incubator with 5% CO2. The following day, lentiviral vectors packaging each CasX and guide construct (e.g., see table for sequences) were used to transduce cells at a high multiplicity of infection (MOI 300), using 3 wells per construct as replicates. A lentivirus packaging a non-targeting construct was used as a negative control. Cells were selected for successful transduction with puromycin at 0.3-3 µg/ml for 24-48 hours followed by recovery in FB medium. Cells from the experiment were lysed, and the genome was extracted using a Quick extract solution following the manufacturer's protocol.

NGS Prep and Analysis

Genomic DNA was amplified via PCR with primers specific to the target genomic location of interest to form a target amplicon. These primers contain additional sequence at the 5' ends to introduce Illumina read and 2 sequences (see table for sequences). Typical PCR conditions would be: 1× Kapa Hifi buffer, 300 nM dNTPs, 300 nM each primer, 0.75 ul of Kapa Hifi Hotstart DNA polymerase in a 50 d reaction. On a thermal cycler, cycle for 95° C. for 5 min; then 16-25 cycles of 98° C. for 15 s, 60° C. for 20 s, 72° C. for 1 min; with a final extension of 2 min at 72° C. Amplified DNA product was purified with Ampure XP DNA cleanup kit, with elution in 30 µl of water.

A second PCR step was done with indexing adapters to allow multiplexing on the Illumina platform. 20 µl of the purified product from the previous step was combined with 1× Kapa GC buffer, 300 nM dNTPs, 200 nM each primer, 0.75 ul of Kapa Hifi Hotstart DNA polymerase in a 50 µl reaction. On a thermal cycler, cycle for 95° C. for 5 min; then 18 cycles of 98° C. for 15 s, 65° C. for 15 s, 72° C. for 30 s; with a final extension of 2 min at 72° C. Amplified DNA product was purified with Ampure XP DNA cleanup kit, with elution in 30 µl of water. Quality and quantification of the amplicon was assessed using a Fragment Analyzer DNA analyzer kit (Agilent, dsDNA 35-1500 bp). Amplicons were sequenced on the Illumina Miseq™ according to the manufacturer's instructions.

Raw fastq files from sequencing were processed as follows: (1) The sequences were trimmed for quality and for adapter sequences; (2) the sequences from read 1 and read 2 were merged into a single insert sequence: (3) each sequence was quantified for containing an insertion or deletion (indel) relative to the reference sequence, in a window around the 3' end of the spacer (30 bp window centered at −3 bp from 3' end of spacer). The activity of the StX molecule was quantified as the total percent of reads that contain an indel for each sample.

Results:

Two different experiments were conducted to test for off-target cleavage by X-editing RNP. In brief, two different cell lines were each edited by CasX RNP targeted to the human WT or P23H RHO Locus (using spacers 11.1 and 11.2 respectively), or were treated with an non-targeting control RNP (NT). The genomic DNA from each cell experiment was isolated and prepped for NGS sequencing by targeted amplification of the RHO locus ("On-target") and 8 other loci across the genome that were predicted to be off-targets, based on having a competent PAM (TTC or CTC) and were sufficiently similar to spacer 11.2.

Figure 36:
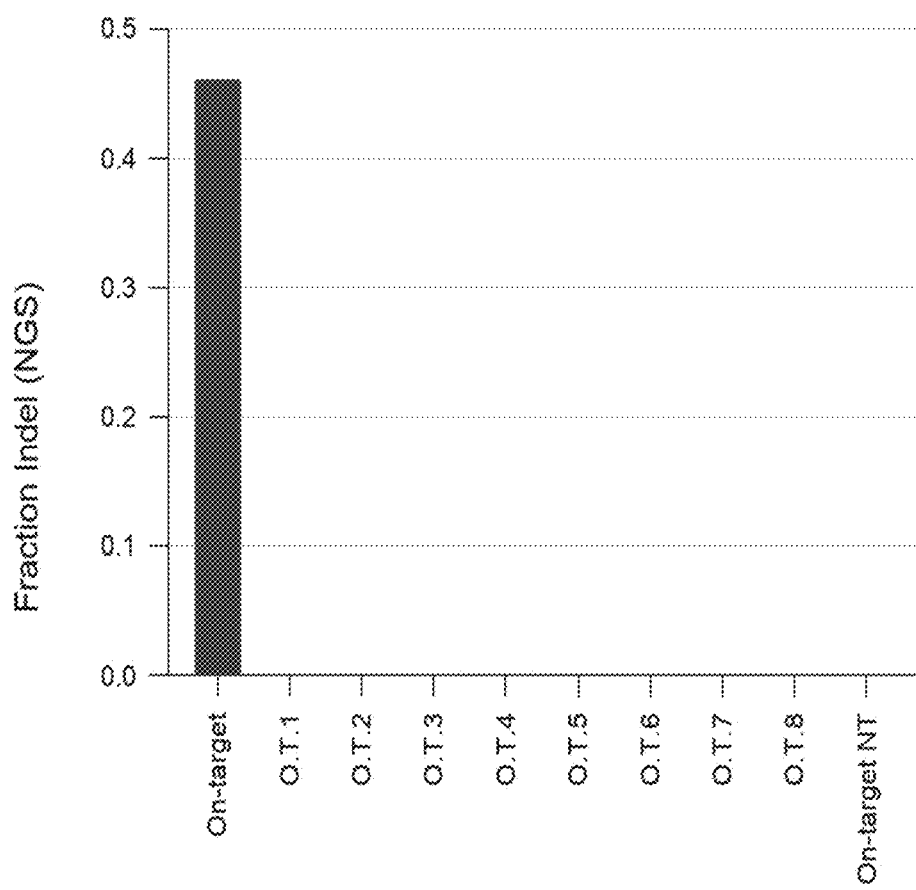
FIG. 36 shows results of editing in the HEK293 cell line, treated by transfection of p34.119.174.11.1 (or NT-last bar), assessing for indel formation, as described in Example 21.
Figure 37:
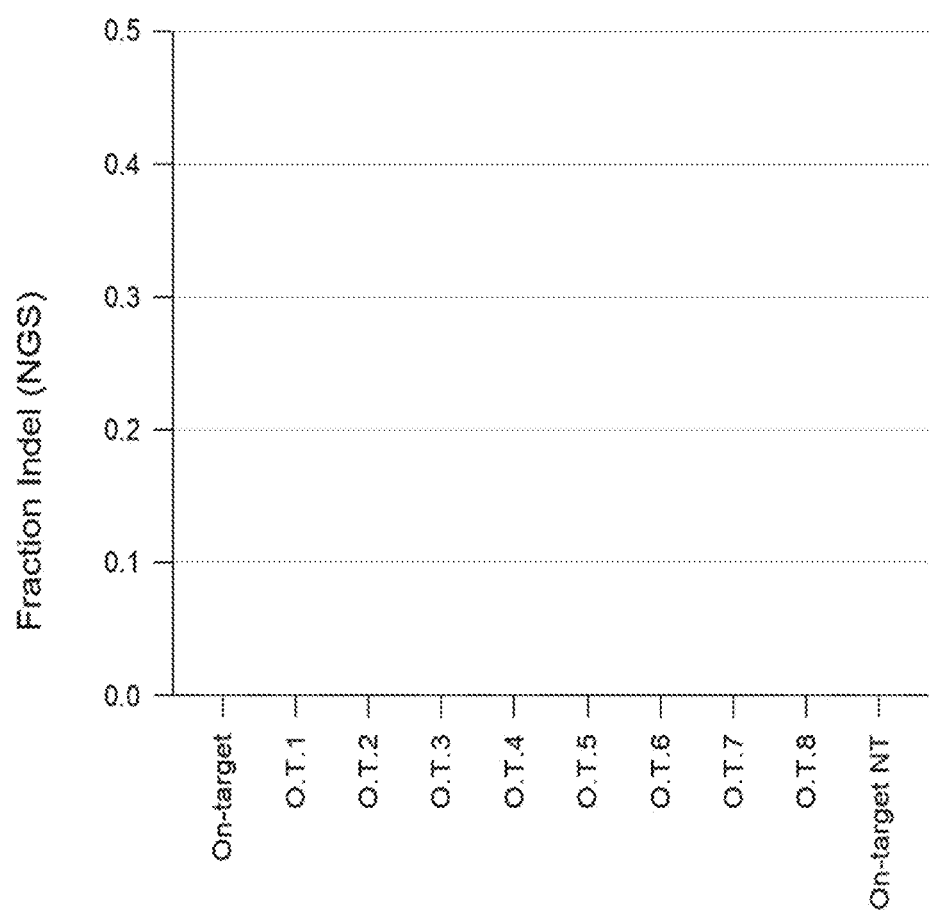
FIG. 37 shows results of editing in the HEK293 cell line, treated by transfection of p34.119.174.11.2 (or NT—last bar), assessing for indel formation, as described in Example 21.

In the first experiment (FIG. 36), a HEK293T cell line was treated with XE-119.174.11.1, XE-119.174.11.2, or XE-119.174.NT by transfection. None of the predicted off-target sites of spacer 11.2 showed any detectable indel formation when treated with RNP targeted with spacers 11.1 (targeting the WT RHO exon 1) or 11.2 (targeting the P23H mutation in Rho Exon 1; FIG. 37). The on-target site of the RHO exon 1 was appreciably edited by spacer 11.1, with approximately 45% of cells showing indel formation. No editing was observed by spacer 11.2 at the WT RHO Exon1 (FIG. 37), which was expected given that this cell type does not contain a P23H mutated allele.

Figure 38:
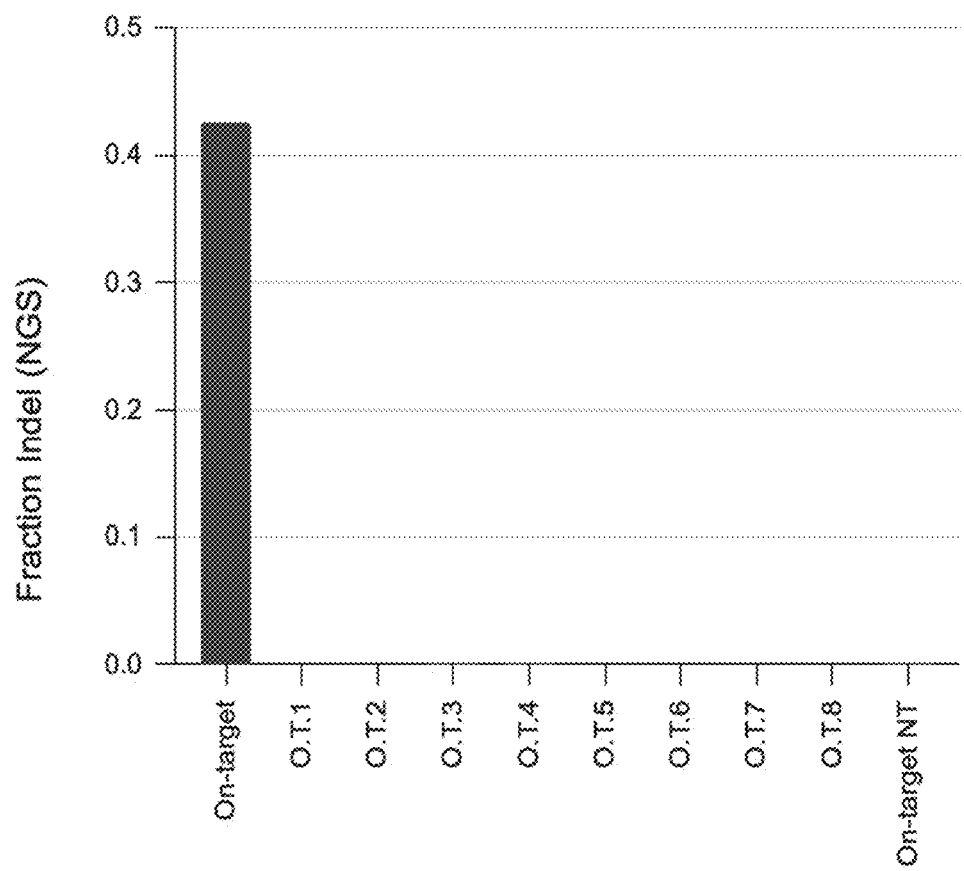
FIG. 38 shows results of editing in the ARPE cell line (with P23H dual reporter), treated by lentiviral delivery of p56.491.174.11.1 (or NT—last bar), assessing for indel formation, as described in Example 21.

In the second experiment (FIG. 38), an ARPE-derived cell line was treated with XE-491.174.11.1 or XE-119.174.NT by lentiviral transduction. None of the predicted off-target sites of spacer 11.2 showed any detectable indel formation when treated with RNP targeted with spacer 11.1. The on-target site of the RHO exon 1 was appreciably edited by spacer 11.1, with approximately 42% of cells showing indel formation.

Under conditions of the assay, the results show consistent editing of the on-target site and undetected editing at off-target sites, across multiple cell types and delivery modalities. Thus, the CasX-RNP targeted to Rho are highly specific with no evidence of genotoxicity.

TABLE 15

Sequences for on target at the P23 RHO locus, and predicted off-targets in the human genome

| Spacer | PAM | Sequence | SEQ ID NO: |
|---|---|---|---|
| On-target, 11.1 | CTC | AAGGGGCTGCGTACCACACC | 367 |
| On-target, 11.2 | CTC | AAGTGGCTGCGTACCACACC | 368 |
| O.T.1 | CTC | AAGTGGCTGCCCTCCACAGA | 369 |
| O.T.2 | TTC | AAGTGGCTGCATTCTACACC | 370 |
| O.T.3 | TTC | AAGTGGCTATGAACAACAGC | 371 |
| O.T.4 | CTC | AAGTGGCTGCCAGCCACCCC | 372 |
| O.T.5 | TTC | AAGTGGCTGCTGACAGCACT | 373 |
| O.T.6 | TTC | AAGTGGCTGCCTCCCTCAGT | 374 |
| O.T.7 | TTC | AAGTGGCTGTGAACCATGGC | 375 |
| O.T.8 | TTC | AAGTGGCTGCTTATCTAAGC | 376 |

Example 22: CasX Edits the P23 RHO Locus in Vivo in C57BL/6J Mice

The purpose of this experiment was to demonstrate the ability of CasX to edit in vivo the endogenous RHO locus in the mouse retina, with a spacer targeting the P23 residue at a therapeutically relevant level, to generate proof-of-concept data that will justify and inform experiments in the P23H mouse disease model. Here, we assessed whether CasX variant 491 and guide variant 174, and a spacer targeting the P23 locus of the mouse RHO gene can generate significant, detectable in the retina when injected subretinally, and evaluate efficacy and safety of two different viral doses (1.0e+9 and 1.0e+10 vg). Rescue of 10% of rod photoreceptors can restore vision in cases of AdRP. Therefore, editing 10% of the RHO loci in rod photoreceptors in the retina may provide a therapeutic benefit in a disease context by reducing the levels of the mutant rhodopsin protein and preventing rod photoreceptor degeneration.

Materials and Methods:

Generation of AAV Plasmids and Viral Vectors

The CasX variant 491 under the control of the CMV promoter and RNA guide variant 174/spacer 11.30 (AAGGGGCCCGCACCACGCC (SEQ ID NO: 377), targeting mouse RHO exon 1 at P23 residues) under the U6 promoter were cloned into a pAAV plasmid flanked with AAV2 ITR AAV.491.174.11.30 vectors were produced in HEK293 cells using the triple-transfection method.

Subretinal Injections

C57BL/6J mice were obtained from the Jackson Laboratories and maintained in a normal 12 hours light/dark cycle. Subretinal injections were performed on 5-6 weeks old mice. Mice were anesthetized with isoflurane inhalation. Proparacaine (0.5%) was applied topically on the cornea and the eyes were dilated with drops of tropicamide (1%) and phenylephrine (2.5%). Eyes were kept lubricated with genteal gel during the surgery. Under a surgical microscope, an ultrafine 30½-gauge disposable needle was passed through the sclera, at the equator and next to the limbus, to create a small hole into the vitreous cavity. Using a blunt-end needle, 1-1.5 µL of virus was injected directly into the subretinal space, between the RPE and retinal layer. Each experimental group (n=5) were injected in one eye with 1e+9 vg or 1e+10 viral genome (vg)/eye, and the contralateral eye injected with the AAV formulation buffer.

NGS Analysis 3 weeks post-injection, animals were sacrificed and the eyes enucleated in fresh PBS. Whole retinae were isolated from the eye cups and processed for gDNA extraction using the DNeasy Blood & Tissue Kit (Qiagen) according to the manufacturer's instructions. Amplicons were amplified from 200 ng of gDNA with a set of primers (Fwd 5'-

(SEQ ID NO: 378)
(Fwd 5'-
ACACTCTTTCCCTACACGACGCTCTTCCGATCTNNNNNNNNGCAGCCTTGG

TCTCTGTCTACG-3;

(SEQ ID NO: 379)
Rev 5'-
GTGACTGGAGTTCAGACGTGTGCTCTTCCGATCTGCCCCAGTCTCTCTGC

TCATACC-3')

targeting the mouse RHO, exon 1 locus, bead-purified (Beckman coulter, Agencourt Ampure XP) and then re-amplified to incorporate illumina adapter sequence. Specifically, these primers contained an additional sequence at the 5' ends to introduce Illumina read and 2 sequences as well as a 16 nt random sequence that functions as a unique molecular identifier (UMI). Quality and quantification of the amplicon was assessed using a Fragment Analyzer DNA analyzer kit (Agilent, dsDNA 35-1500 bp). Amplicons were sequenced on the Illumina Miseq™ according to the manufacturer's instructions. Raw fastq files from sequencing were processed as follows: (1) the sequences were trimmed for quality and for adapter sequences using the program cutadapt (v. 2.1); (2) the sequences from read 1 and read 2 were merged into a single insert sequence using the program flash2 (v2.2.00); and (3) the consensus insert sequences were run through the program CRISPResso2 (v 2.0.29), along with the expected amplicon sequence and the spacer sequence. This program quantifies the percent of reads that were modified in a window around the 3' end of the spacer (30 bp window centered at −3 bp from 3' end of spacer). The activity of the CasX molecule was quantified as the total percent of reads that contain insertions, substitutions and/or deletions anywhere within this window.

Immunohistology

Mice were euthanized 3-4 weeks post-injection. Enucleated eyes were placed in 10% formalin overnight at 4° C. Retinae were dissected out from the eye cups, rinsed in PBS thoroughly and immersed in 15%-30% sucrose gradient. Tissues were embedded in optimal cutting temperature (OCT), froze on dry ice before being transferred to −80'C storage. 20 µM sections were cut using a cryostat. The sections were blocked for ≥1 hour at room temperature in blocking buffer (2% normal goat serum, 1% BSA, 0, 1% Triton-X 100) before antibody labeling. The antibodies used were anti-mouse HA (abcam, 1:500) and Alexa Fluor 488 rabbit anti-mouse (Invitrogen, 1:2000). Sections were counterstained with DAPI to label nuclei, mounted on slides and imaged on a fluorescent microscope.

Figure 39:
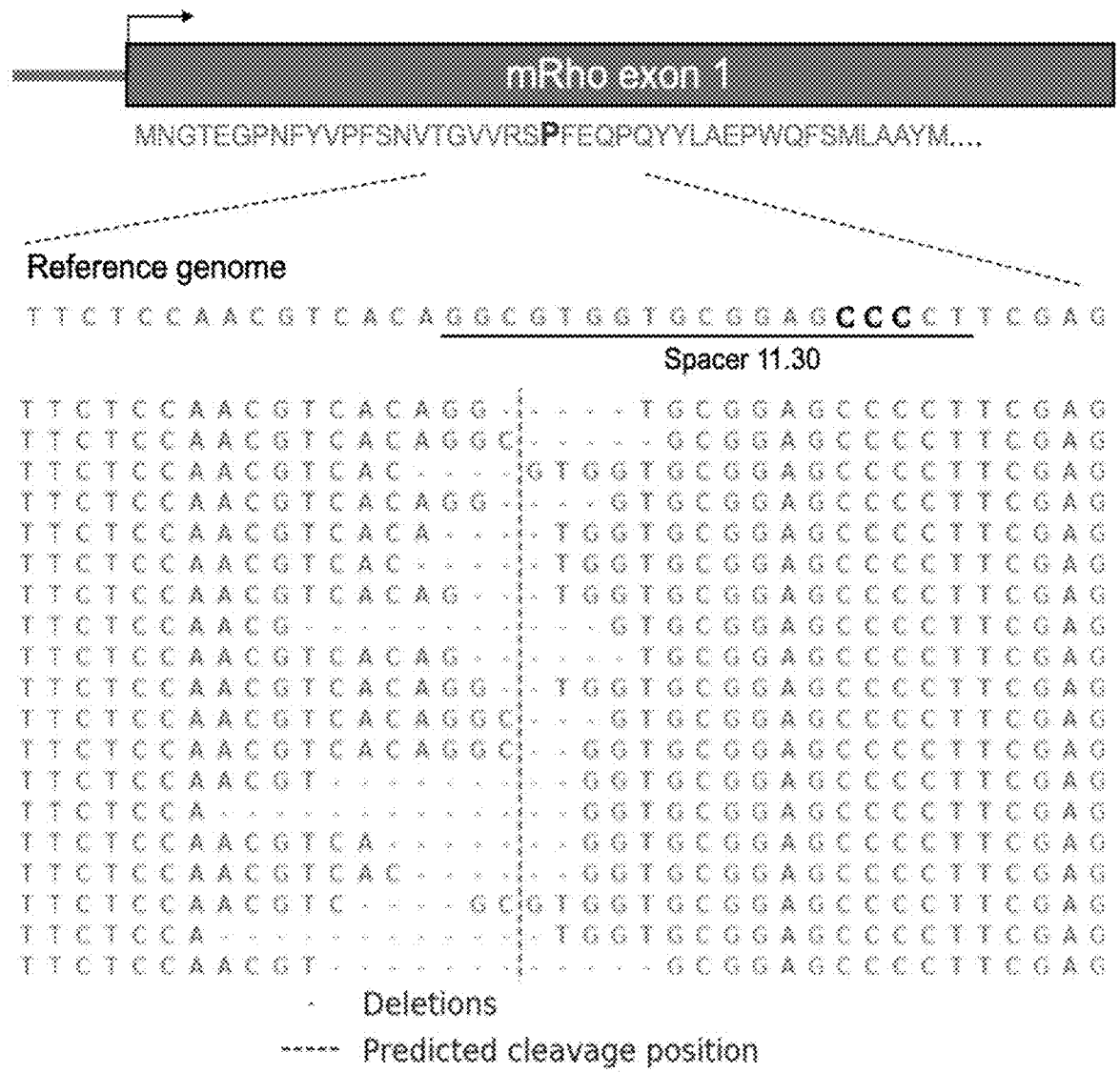
FIG. 39 is an illustration of reference mRHO exon 1 locus (SEQ ID NOs: 27280 and 27281) and target amino acid residue P23 (CCC) sequence (highlighted in bold), showing spacer 11.30 target sequence and expected CasX-mediated cleavage, as described in Example 22. The most common predicted edits quantified in CRISPResso edits (substitution/deletions (SEQ ID NOs: 27282-27300)) are displayed under the reference genome).
Figure 40:
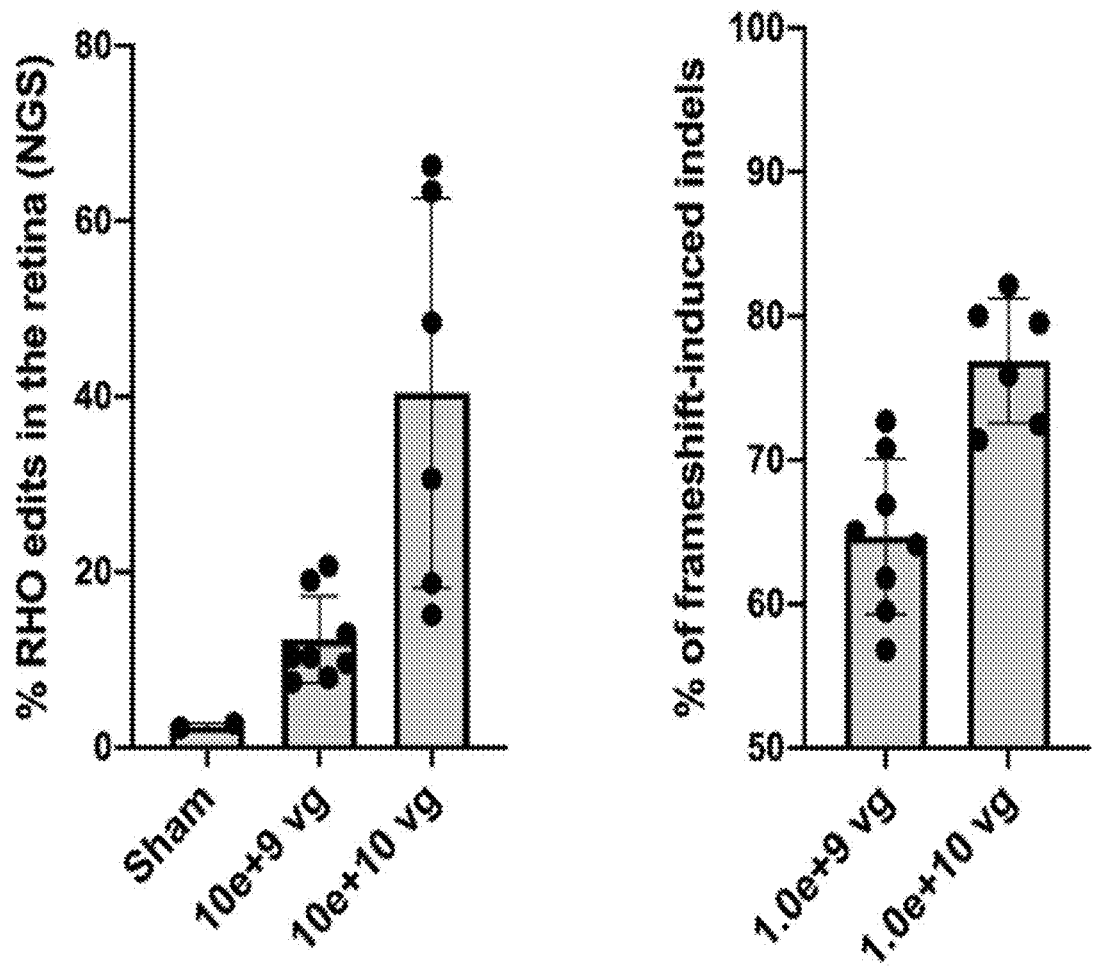
FIG. 40 shows results of in vivo AAV CasX-mediated editing of the mRHO P23 locus in retinae in C57BL6J (n=6-8) mice, as described in Example 22. Retinae were harvested 3 weeks post-injection, gDNA extracted, amplified and indel rates analyzed via NGS and CRISPResso analysis. Left panel shows the quantification in % of total indels detected by NGS at the mouse P23 RHO locus in AAV-CasX or sham-injected retinae compared to the mouse reference genome. Right panel shows the fraction (%) of edits predicted to lead to frameshift mutations in RHO protein. Data are presented as average of NGS readouts of editing outcomes from the entire retina, from six to eight animals per experimental cohort.

Results:

We assessed the ability of CasX to edit the P23 RHO locus in the mouse retina. Two therapeutically relevant doses, 1.0e+9 and 1.0E+10 vg of AAV-CasX.491.174.11.30 were administered in the subretinal space of 5-6 weeks old C57BL/6J mice. Three weeks post-injections, retinae were harvested and editing levels quantified via NGS and the CRISPResso analysis pipeline. The spacer 11.30 targets the WT P23 genomic locus (FIG. 39) located at the beginning of the first exon of RHO. Overexpression of CasX-491.174.11.30 led to significant, dose-dependent, editing of mRHO exon 1 locus in treated—compared to sham-injected retinae (FIG. 40). The left panel shows the quantification in % of total indels detected by NGS at the mouse P23 RHO locus in AAV-CasX or sham-injected retinae compared to the mouse reference genome. The right panel shows the fraction (%) of edits predicted to lead to frameshift mutations in RHO protein. Data are presented as average of NGS readouts of editing outcomes from the entire retina, from six to eight animals per experimental cohort. The highest AAV dose, 1e+10 vg/eye, increased indels rate by 4-fold compared to the 1.0e+9 vg dose, with 40.3±22% versus 12.3±5% RHO editing detected respectively. The majority of indels generated by CasX.491 were deletions (left panel), predicted to translate to a high frequency of frameshift-mutations (64.7 versus 76.9% for 1.0e+9 and 1.0e+10 vg/dose respectively), and hypothetically high levels of RHO protein knock down. These results suggest that with a spacer driving allele-specific target of mutant P23H locus in the P23H+/− mouse model, CasX could efficiently editing 10% of rod photoreceptor, with the majority of edits translating to a knocking-down the mutant P23H Rho and significantly delay photoreceptor degeneration.

Figure 41:
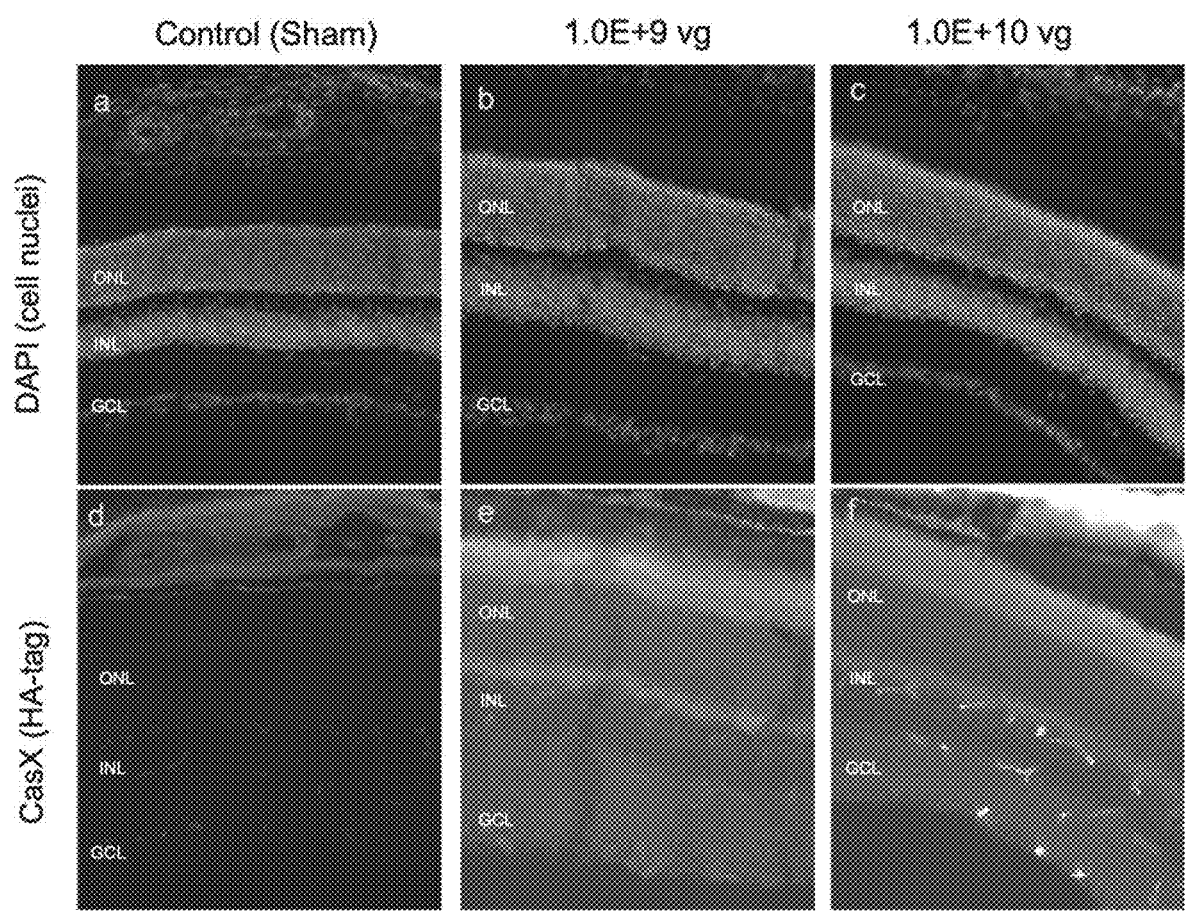
FIG. 41 shows representative fluorescence imaging of retinas from AAV-CasX treated mice or negative controls and stained, as described in Example 22. Cell nuclei were counterstained with DAPI (top row.

Immunohistochemistry performed on injected retinal cross-sectioned confirmed CasX expression in the photoreceptors layers, but also showed spread of the virus to the inner layers as show in in FIGS. 41A-F. The treatment groups were 1.0e+9 vg of AAV-CasX (FIG. 41B and e), 1.0e+10 vg AAV-CasX (FIG. 41 c and f); or PBS (FIGS. 41A and 41D). Levels of HA-tagged CasX was assessed by Anti-HA antibody staining (lower panels of FIGS. 41E, and 41F) in the photoreceptor cell bodies in the located in the outer nuclear layer (ONL) as well as outer segments, in retinas injected with both the 1e9 vg (FIGS. 41B and 41E) and 1e10 vg (FIGS. 41C and 41F). The control retinas that received a sham (FIGS. 41A and 41C) injection only showed background levels of signal for HA staining (FIG. 41D) in the RPE/sclera and had no detectable level in the ONL/INL layer. Additionally, gross histological analysis showed that the retinal structure was maintained after subretinal administration of AAV packaging CasX constructs.

Under the conditions of the experiments, the results demonstrate proof-of-concept that CasX 491, scaffold 174, and a spacer targeting the mouse P23 RHO locus can achieve therapeutically-relevant levels of edits at the P23 mouse locus when subretinally delivered via AAV in the murine retina.

Example 23: Use of CasX:gNA System to Alleviate Disease Symptoms in a P23H Disease Model The mouse RHO$^{P23H}$ model is a well-established disease model for AdRP. The purpose of this experiment will be to demonstrate that CasX and a guide RNA with a spacer targeting the P23H RHO locus in RHO$^{P23H}$ mice can alleviate disease symptoms by preventing rod photoreceptor degeneration.

Materials and Methods: AAV packaging CasX, guide and a spacer targeting the mouse P23H RHO locus (AAGTFFCTCCGCACCACGCC, SEQ ID NO: 380) will be subretinally administered in 4-6 week old RHO$^{P23H}$ mice at doses ranging from 1e8 viral genomes (vg) to 1e10 vg using injection volumes of 1-1.5 µL. As controls, AAV formulation buffer (e.g., phosphate buffered saline) will be injected in the contralateral eye for experimental animals. As pre-determined time point, for example once before injection and then biweekly starting at 4 weeks post-injection and until 12 weeks post-injection, retinal health and function will be assessed by Optical Coherence Tomography (OCT) and Electroretinography (ERG). Additionally, also at pre-determined time points, for example at 4 weeks post injection and at 12 weeks post injection, a subset of animals will be sacrificed and retinas collected for editing assessment by NGS, WB, and RNAseq.

This experiment is expected to show that the CasX and guide with a spacer targeting the mouse P23H RHO locus, when delivered by subretinal AAV injection to RHO$^{P23H}$ mice, can edit the target genomic locus (as measured by NGS analysis) and result in reduction of the mutant rhodopsin protein (as measured by WB analysis). Immunohistology is expected to show the maintenance of rod photoreceptors and absence of retinal degeneration. RNAseq is expected to show reduction in the transcript levels of mutant RHO, with no detectable effect on the levels of the WT RHO transcript. OCT and ERG is expected to show that retinal integrity and function are maintained in the eyes that receive AAV.CasX, while the sham treated eyes follow the natural progression of retinal degeneration and loss of function.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11535835B1). An electronic copy of the "Sequence Listing" will also be available from the USPTO upon request and payment of the fee set forth in 37 CFR 1.19(b)(3).

The invention claimed is:

1. A composition comprising a CasX variant protein comprising the sequence of SEQ ID NO: 138, or a sequence having at least 90% sequence identity thereto, and a first guide ribonucleic acid (gRNA), wherein the CasX variant protein is a chimeric CasX protein comprising protein domains from two or more different CasX proteins and wherein the gRNA comprises a targeting sequence complementary to a rhodopsin (RHO) gene target nucleic acid sequence comprising one or more mutations.

2. The composition of claim 1, wherein the one or more mutations are in a region selected from the group consisting of:
   a) a RHO intron;
   b) a RHO exon;
   c) a RHO intron-exon junction;
   d) a RHO regulatory element; and
   e) an intergenic region.

3. The composition of claim 1, wherein the one or more mutations comprise an insertion, deletion, substitution, duplication, or inversion of one or more nucleotides as compared to a wild-type RHO gene sequence.

4. The composition of claim 3, wherein the one or more mutations comprise a gain of function mutation.

5. The composition of claim 1, wherein the one or more mutations in the RHO gene target nucleic acid sequence encode a mutation selected from the group consisting of: T4K, P12R, N15S, T17M, V20G, R21C, P23A/H/L, Q28H, M39R, L40R, M44T, L46R, L47R, G51R/V, F52Y, P53R, N55K, F56Y, L57R, T58R/M, Y60ter, Q64ter, R69H, N78I, L79P, V87L, V87D, L88P, G89D, G90V, G90D, T92I, T94I, T97I, V104F, G106R/W, G109R, C110F/R/S/Y, E113K, G114D/V, E122G, L125R, W126L/ter, S127F, L131P, R135G/UP/W, Y136ter, V137M, C140S, T160T, W161R, M163T, A164E/V, C167R/W, A169P, P170H/R, P171Q/US, S176F, Y178N/D/C, P180A/S, E181K, G182S/V, Q184P, C185R, S186P/W, C187G/Y, G188R/E, D190N/G/Y, Y191C, T193M, M207R/K, V210F, H211R/P, I214N, P215L/T, M216L/K, C222R, R252P, P267R/L, S270R, T289P, A292E, A295V, K296N/E/M, S297R, A298D, K311E, N315ter, L328P, E341K, S343C, T342M, Q344R/P/ter, V345L/M, A346P, P347A/R/Q/L/S/T, and Ter349/Q/E relative to the wild-type rhodopsin protein sequence of SEQ ID NO: 33.

6. The composition of claim 1, wherein the RHO gene encodes a protein comprising a P23H substitution compared to the wild-type rhodopsin protein sequence of SEQ ID NO: 33.

7. The composition of claim 1, wherein the RHO gene encodes a non-functional rhodopsin protein.

8. The composition of claim 1, wherein the gRNA is a single-molecule gRNA (sgRNA).

9. The composition of claim 1, wherein the targeting sequence of the gRNA comprises a ribonucleic acid (RNA) sequence encoded by a sequence selected from the group consisting of the sequences of SEQ ID NOS: 328-344, 367, and 368, or a sequence having at least 90% identity thereto.

10. The composition of claim 1, wherein the targeting sequence of the gRNA comprises a ribonucleic acid (RNA) sequence encoded by a sequence selected from the group consisting of the sequences of SEQ ID NOS: 328-344 367, and 368.

11. The composition of claim 1, wherein the targeting sequence of the gRNA is complementary to a sequence of a RHO exon, to a sequence of a RHO intron, to a sequence of a RHO intron-exon junction, to a sequence of a RHO regulatory element, to a sequence of an intergenic region of the RHO gene or to a sequence comprising one or more single nucleotide polymorphisms (SNPs) of the RHO gene.

12. The composition of claim 1, wherein the targeting sequence of the gRNA is complementary to a sequence of RHO exon 1 or complementary to a target nucleic acid sequence encoding a P23H substitution compared to the wild-type rhodopsin protein sequence of SEQ ID NO: 33.

13. The composition of claim 1, further comprising a second gRNA, wherein the second gRNA has a targeting sequence complementary to a different or overlapping portion of the RHO target nucleic acid compared to the targeting sequence of the first gRNA.

14. The composition of claim 13, wherein the first or second gRNA has a scaffold comprising the sequence of SEQ ID NO: 2238, or a sequence having at least 70% identity thereto.

15. The composition of claim 1, wherein the CasX variant protein further comprises one or more nuclear localization signals (NLS).

16. The composition of claim 10, further comprising a donor template nucleic acid.

17. The composition of claim 1, wherein the chimeric CasX protein comprising protein domains from two or more different CasX proteins, comprises proteins domains from two or more different reference CasX proteins.

18. The composition of claim 1, wherein the chimeric CasX protein comprising protein domains from two or more different CasX proteins, comprises proteins domains from two or more different CasX variant proteins.

19. A composition comprising a CasX variant protein and a first guide ribonucleic acid (gRNA), wherein the CasX variant protein comprises the sequence of SEQ ID NO: 138, or a sequence having at least 90% sequence identity thereto, wherein the gRNA has a scaffold comprising a sequence having at least 70% sequence identity to the sequence of SEQ ID NO: 2238, and wherein the gRNA comprises a targeting sequence complementary to a rhodopsin (RHO) gene target nucleic acid sequence comprising one or more mutations.

20. The composition of claim 19, wherein the one or more mutations are in a region selected from the group consisting of:
  a) a RHO intron;
  b) a RHO exon;
  c) a RHO intron-exon junction;
  d) a RHO regulatory element; and
  e) an intergenic region.

21. The composition of claim 19, wherein the RHO gene comprising a mutation encodes a protein comprising a P23H substitution compared to the wild-type rhodopsin protein sequence of SEQ ID NO: 33.

22. The composition of claim 19, wherein the targeting sequence of the gRNA comprises a ribonucleic acid (RNA) sequence encoded by a sequence selected from the group consisting of the sequences of SEQ ID NOS: 328-344, 367, and 368 or a sequence having at least 90% identity thereto.

23. A nucleic acid vector:
  (a) encoding a CasX variant protein, the CasX variant protein comprising the sequence of SEQ ID NO: 138 or a sequence having at least 90% sequence identity thereto; and
  (b) encoding a guide ribonucleic acid (gRNA), wherein the gRNA has a scaffold comprising a sequence having at least 70% sequence identity to the sequence of SEQ ID NO: 2238 and wherein the gRNA comprises a targeting sequence complementary to a rhodopsin (RHO) gene target nucleic acid sequence comprising one or more mutations.

24. The nucleic acid vector of claim 23, wherein the targeting sequence of the gRNA comprises a ribonucleic acid (RNA) sequence encoded by a sequence selected from the group consisting of the sequences of SEQ ID NOs: 328-344, 367, and 368 or a sequence having at least 90% identity thereto.

25. The nucleic acid vector of claim 23, wherein the nucleic acid vector is as an adeno-associated viral (AAV) vector.

26. A method of treating autosomal dominant retinitis pigmentosa in a subject in need thereof with a P23H mutation relative to the wild-type rhodopsin protein sequence of SEQ ID NO: 33, comprising modifying a RHO gene encoding the mutation in eye cells of the subject, the modifying comprising contacting said cells in one or both eyes with a therapeutically effective dose of the nucleic acid vector of claim 25, wherein the contacting is by intravitreal or subretinal injection, and wherein the targeting sequence complementary to the RHO gene target nucleic acid sequence is encoded by the sequence of SEQ ID NO: 368.

* * * * *

UNITED STATES PATENT AND TRADEMARK OFFICE
CERTIFICATE OF CORRECTION

PATENT NO. : 11,535,835 B1
APPLICATION NO. : 17/483681
DATED : December 27, 2022
INVENTOR(S) : Oakes et al.

It is certified that error appears in the above-identified patent and that said Letters Patent is hereby corrected as shown below:

In the Claims

At Claim 1, Column 287, Line 37, please replace "proteins and" with --proteins, and--.

At Claim 5, Column 287, Line 64, please replace "R135G/UP/W" with --R135G/L/P/W--.

At Claim 5, Column 287, Line 65, please replace "P171Q/US" with --P171Q/L/S--.

At Claim 5, Column 288, Line 32, please replace "M216L/K" with --M216R/L/K--.

Signed and Sealed this
Sixth Day of June, 2023

Katherine Kelly Vidal
*Director of the United States Patent and Trademark Office*